United States Patent
Jia et al.

(10) Patent No.: US 9,382,246 B2
(45) Date of Patent: Jul. 5, 2016

(54) INHIBITORS OF BRUTON'S TYROSINE KINASE

(71) Applicant: Pharmacyclics LLC, Sunnyvale, CA (US)

(72) Inventors: Zhaozhong J. Jia, San Mateo, CA (US); Wei Chen, Fremont, CA (US); William D. Thomas, San Jose, CA (US)

(73) Assignee: Pharmacyclics LLC, Sunnyvale, CA (US)

( * ) Notice: Subject to any disclaimer, the term of this patent is extended or adjusted under 35 U.S.C. 154(b) by 0 days.

(21) Appl. No.: 14/559,889

(22) Filed: Dec. 3, 2014

(65) Prior Publication Data

US 2015/0158865 A1    Jun. 11, 2015

Related U.S. Application Data

(60) Provisional application No. 61/912,483, filed on Dec. 5, 2013.

(51) Int. Cl.

| C07D 401/04 | (2006.01) |
|---|---|
| C07D 401/14 | (2006.01) |
| C07D 403/04 | (2006.01) |
| C07D 403/14 | (2006.01) |
| A61K 31/4025 | (2006.01) |
| A61K 31/445 | (2006.01) |
| A61K 31/397 | (2006.01) |
| A61K 31/497 | (2006.01) |
| C07D 471/04 | (2006.01) |
| C07D 401/12 | (2006.01) |
| C07D 405/14 | (2006.01) |
| C07D 409/14 | (2006.01) |
| C07D 413/14 | (2006.01) |
| C07D 417/14 | (2006.01) |
| C07D 403/12 | (2006.01) |

(52) U.S. Cl.
CPC ............ C07D 471/04 (2013.01); A61K 31/397 (2013.01); A61K 31/4025 (2013.01); A61K 31/445 (2013.01); A61K 31/497 (2013.01); C07D 401/04 (2013.01); C07D 401/12 (2013.01); C07D 401/14 (2013.01); C07D 403/12 (2013.01); C07D 405/14 (2013.01); C07D 409/14 (2013.01); C07D 413/14 (2013.01); C07D 417/14 (2013.01)

(58) Field of Classification Search
CPC .. C07D 401/04; C07D 401/14; C07D 403/04; C07D 403/14; A61K 31/497; A61K 31/445; A61K 31/397; A61K 31/4025
USPC ..................... 544/407; 514/255.05
See application file for complete search history.

(56) References Cited

U.S. PATENT DOCUMENTS

| 7,884,108 | B2 | 2/2011 | Blomgren et al. |
| 8,877,760 | B2 | 11/2014 | Song et al. |
| 2012/0040968 | A1 | 2/2012 | Shimada et al. |
| 2012/0108566 | A1 | 5/2012 | Bauer et al. |
| 2013/0131040 | A1 | 5/2013 | Song et al. |
| 2014/0113931 | A1 | 4/2014 | Song et al. |
| 2014/0309209 | A1 | 10/2014 | Song et al. |

FOREIGN PATENT DOCUMENTS

| CA | 2860765 | A1 | 7/2013 |
| CN | 102311389 | A | 1/2012 |
| CN | 103664878 | A | 3/2014 |
| CN | 104262328 | A | 1/2015 |
| EP | 2762476 | A1 | 8/2014 |
| KR | 2010097077 | | 9/2010 |
| WO | WO-9931073 | A1 | 6/1999 |
| WO | WO-0075113 | | 12/2000 |
| WO | WO-0076980 | A1 | 12/2000 |
| WO | WO-03099796 | | 12/2003 |
| WO | WO-2004002964 | A1 | 1/2004 |
| WO | WO-2006099075 | A2 | 9/2006 |
| WO | WO-2008009458 | A1 | 1/2008 |
| WO | WO-2008/024978 | A2 | 2/2008 |
| WO | WO-2008024963 | A1 | 2/2008 |
| WO | WO-2008033858 | A2 | 3/2008 |
| WO | WO-2009039397 | A2 | 3/2009 |
| WO | WO-2009114470 | A2 | 9/2009 |
| WO | WO-2009122034 | A2 | 10/2009 |
| WO | WO-2009131687 | A2 | 10/2009 |
| WO | WO-2009136995 | A2 | 11/2009 |
| WO | WO-2009137596 | A1 | 11/2009 |
| WO | WO-2009145856 | A1 | 12/2009 |
| WO | WO-2009158571 | A1 | 12/2009 |
| WO | WO-2010058846 | A1 | 5/2010 |
| WO | WO-2010128659 | A1 | 11/2010 |
| WO | WO-2010129802 | A1 | 11/2010 |

(Continued)

OTHER PUBLICATIONS

Whang et al., Drug Discovery Today, pp. 1-5, 2014.*

(Continued)

*Primary Examiner* — Venkataraman Balasubramanian

(74) *Attorney, Agent, or Firm* — Foley Hoag LLP

(57) ABSTRACT

Disclosed herein are reversible and irreversible inhibitors of Bruton's tyrosine kinase (Btk). Also disclosed are pharmaceutical compositions that include the compounds. Methods of using the Btk inhibitors are described, alone or in combination with other therapeutic agents, for the treatment of autoimmune diseases or conditions, heteroimmune diseases or conditions, cancer, including lymphoma, and inflammatory diseases or conditions.

20 Claims, No Drawings

(56) References Cited

FOREIGN PATENT DOCUMENTS

| | | |
|---|---|---|
| WO | WO-2010144345 A1 | 12/2010 |
| WO | WO-2010144647 A1 | 12/2010 |
| WO | WO-2012002577 A1 | 1/2012 |
| WO | WO-2012053606 A1 | 4/2012 |
| WO | WO-2012061415 A1 | 5/2012 |
| WO | WO-2012061418 A2 | 5/2012 |
| WO | WO-2012100135 A1 | 7/2012 |
| WO | WO-2012145569 A1 | 10/2012 |
| WO | WO-2013010380 A1 | 1/2013 |
| WO | WO-2013047813 A1 | 4/2013 |
| WO | WO-2013054351 A1 | 4/2013 |
| WO | WO-2013078466 A1 | 5/2013 |
| WO | WO-2013078468 A1 | 5/2013 |
| WO | WO-2013099041 A1 | 7/2013 |
| WO | WO-2013108754 A1 | 7/2013 |
| WO | WO-2013192046 A2 | 12/2013 |
| WO | WO-2013192049 A2 | 12/2013 |
| WO | WO-2014058921 A2 | 4/2014 |
| WO | WO-2014111031 A1 | 7/2014 |
| WO | WO-2014124230 A2 | 8/2014 |
| WO | WO-2014157687 A1 | 10/2014 |

OTHER PUBLICATIONS

Akinleye et al. Journal of Hematology & Oncology 2013, 6:59.*
Chakravarty et al. Clinical Immunology (2013) 148, 66-78.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
PCT/US2014/068434 International Search Report and Written Opinion dated Feb. 26, 2015.

\* cited by examiner

INHIBITORS OF BRUTON'S TYROSINE KINASE

CROSS-REFERENCE

This application claims the benefit of U.S. Provisional Application No. 61/912,483, filed Dec. 5, 2013 which is incorporated herein by reference in its entirety.

FIELD OF THE INVENTION

Described herein are compounds, methods of making such compounds, pharmaceutical compositions and medicaments containing such compounds, and methods of using such compounds and compositions to inhibit the activity of tyrosine kinases.

BACKGROUND OF THE INVENTION

Bruton's tyrosine kinase (Btk), a member of the Tec family of non-receptor tyrosine kinases, is a key signaling enzyme expressed in all hematopoietic cells types except T lymphocytes and natural killer cells. Btk plays an essential role in the B-cell signaling pathway linking cell surface B-cell receptor (BCR) stimulation to downstream intracellular responses.

Btk is a key regulator of B-cell development, activation, signaling, and survival (Kurosaki, *Curr Op Imm,* 2000, 276-281; Schaeffer and Schwartzberg, *Curr Op Imm* 2000, 282-288). In addition, Btk plays a role in a number of other hematopoetic cell signaling pathways, e.g., Toll like receptor (TLR) and cytokine receptormediated TNF-α production in macrophages, IgE receptor (FcepsilonRI) signaling in Mast cells, inhibition of Fas/APO-1 apoptotic signaling in B-lineage lymphoid cells, and collagen-stimulated platelet aggregation. See, e.g., C. A. Jeffries, et al., (2003), *Journal of Biological Chemistry* 278:26258-26264; N. J. Horwood, et al., (2003), *The Journal of Experimental Medicine* 197:1603-1611; Iwaki et al. (2005), *Journal of Biological Chemistry* 280(48):40261-40270; Vassilev et al. (1999), *Journal of Biological Chemistry* 274(3):1646-1656, and Quek et al. (1998), *Current Biology* 8(20):1137-1140.

SUMMARY OF THE INVENTION

Described herein are inhibitors of Bruton's tyrosine kinase (Btk). Also described herein are irreversible inhibitors of Btk. Also described herein are reversible inhibitors of Btk. Further described are irreversible inhibitors of Btk that form a covalent bond with a cysteine residue on Btk. Further described herein are irreversible inhibitors of other tyrosine kinases, wherein the other tyrosine kinases share homology with Btk by having a cysteine residue (including a Cys 481 residue) that can form a covalent bond with the irreversible inhibitor (such tyrosine kinases, are referred herein as "Btk tyrosine kinase cysteine homologs").

Also described herein are methods for synthesizing such reversible or irreversible inhibitors, methods for using such reversible or irreversible inhibitors in the treatment of diseases (including diseases wherein irreversible inhibition of Btk provides therapeutic benefit to a patient having the disease). Further described are pharmaceutical formulations that include a reversible or irreversible inhibitor of Btk.

In one aspect, provided herein is a compound of Formula (IA) having the structure:

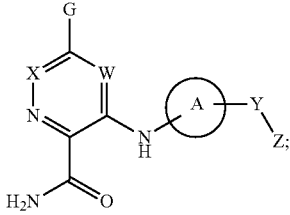

Formula (IA)

wherein:
ring A is substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;
W is —C($R_2$)— or —N—;
X is —C($R_2$)— or —N—;
Y is optionally present and when present is —$CH_2$O—, —$OCH_2$—, —$OCH_2CH_2$O—, —O—, —N($R_3$)—, —C(O)—, —N($R_3$)C(O)—, —C(O)N($R_3$)—, —N($R_3$)C(O)N($R_3$)—, —S(O)—, —S(O)$_2$—, —N($R_3$)S(O)$_2$—, —S(O)$_2$N($R_3$)—, —C(=NH)—, —C(=NH)N($R_3$)—, —C(=NH)N($R_3$)—, or substituted or unsubstituted $C_1$-$C_4$alkylene;
Z is optionally present and when present is substituted or unsubstituted $C_1$-$C_3$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;
G is

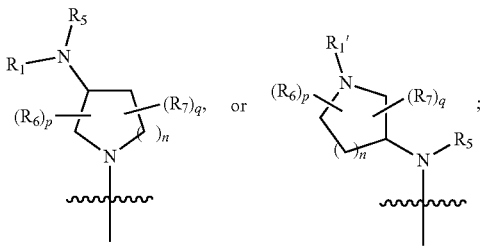

$R_1$ is —$R_4$, —$CH_2R_4$, —C(O)$R_9$, —C(O)C(O)$R_9$, —C(O)O$R_4$, —C(O)N($R_3$)($R_4$), or —S(O)$_2R_9$;
$R_1'$ is —C(O)$R_9$, —C(O)C(O)$R_9$, —C(O)O$R_4$, —C(O)N($R_3$)($R_4$), or —S(O)$_2R_9$;
each $R_2$ is independently H, substituted or unsubstituted $C_1$-$C_4$alkyl, —CN, or halogen;
each $R_3$ is independently is H, or substituted or unsubstituted $C_1$-$C_4$alkyl;
each $R_4$ is independently H, substituted or unsubstituted $C_1$-$C_6$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;
$R_5$ is H, substituted or unsubstituted $C_1$-$C_4$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;
or $R_1$ and $R_5$ together with the nitrogen atom to which they are attached are combined to form a substituted or unsubstituted $C_2$-$C_9$heterocycloalkyl ring;

each $R_6$ is independently halogen, —CN, —OH, —NH$_2$, substituted or unsubstituted C$_1$-C$_4$alkoxy, substituted or unsubstituted C$_1$-C$_4$alkyl, substituted or unsubstituted C$_3$-C$_6$cycloalkyl, substituted or unsubstituted C$_2$-C$_6$heterocycloalkyl, or —N(R$_3$)$_2$; or R$_1$ and R$_6$ are combined to form a substituted or unsubstituted C$_2$-C$_9$heterocycloalkyl ring;

each $R_7$ is independently halogen, —CN, —OH, —NH$_2$, substituted or unsubstituted C$_1$-C$_4$alkoxy, substituted or unsubstituted C$_1$-C$_4$alkyl, substituted or unsubstituted C$_3$-C$_6$cycloalkyl, substituted or unsubstituted C$_2$-C$_6$heterocycloalkyl, or —N(R$_3$)$_2$;

$R_9$ is —R$_4$, or

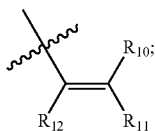

$R_{10}$ is H, halogen, —CN, or -L$_1$-L$_2$;
$R_{11}$ and $R_{12}$ are independently H, halogen, —CN, or -L$_1$-L$_2$; or R$_{11}$ and R$_{12}$ taken together form a bond;
each L$_1$ is optionally present and when present each L$_1$ is independently substituted or unsubstituted C$_1$-C$_6$alkyl, substituted or unsubstituted C$_3$-C$_6$cycloalkyl, substituted or unsubstituted C$_1$-C$_6$heteroalkyl, substituted or unsubstituted C$_2$-C$_7$heterocycloalkyl, substituted or unsubstituted C$_6$-C$_{12}$aryl, substituted or unsubstituted C$_1$-C$_{12}$heteroaryl, —C(=O)—, —O—, or —S—;
each L$_2$ is independently H, substituted or unsubstituted C$_1$-C$_6$alkyl, substituted or unsubstituted C$_3$-C$_6$cycloalkyl, substituted or unsubstituted C$_1$-C$_6$heteroalkyl, substituted or unsubstituted C$_2$-C$_7$heterocycloalkyl, substituted or unsubstituted C$_6$-C$_{12}$aryl, substituted or unsubstituted C$_1$-C$_{12}$heteroaryl or —N(R$_{13}$)$_2$;
each $R_{13}$ is independently H, C$_1$-C$_6$alkyl, C$_3$-C$_6$cycloalkyl, C$_1$-C$_6$heteroalkyl, C$_2$-C$_7$ heterocycloalkyl, C$_6$-C$_{12}$aryl, or C$_1$-C$_{12}$heteroaryl;
n is 0-3;
p is 0-3; and
q is 0-3;
or a pharmaceutically acceptable solvate, pharmaceutically acceptable salt, or pharmaceutically acceptable prodrug thereof;
provided that
i) when W is N, and R$_1$ is H, t-Boc, or C(O)—CH=CH$_2$; then X is other than C-Et or N; and
ii) when W is N,

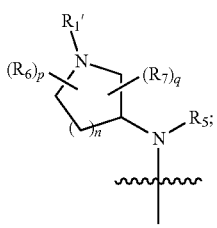

then X is CH or N;
iii) when W is N, and X is CH; then R$_1$' is other than —C(O)Me, or t-Boc; and
iv) when n is 0; then each of p and q is independently 0, 1, or 2.

In another aspect, provided herein is a compound of Formula (I) having the structure:

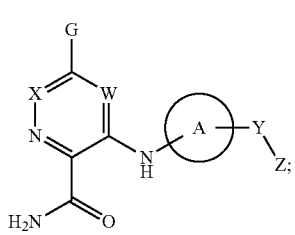

Formula (I)

wherein:
ring A is substituted or unsubstituted C$_3$-C$_6$cycloalkyl, substituted or unsubstituted C$_2$-C$_7$heterocycloalkyl, substituted or unsubstituted C$_6$-C$_{12}$aryl, or substituted or unsubstituted C$_1$-C$_{12}$heteroaryl;
W is —C(R$_2$)— or —N—;
X is —C(R$_2$)— or —N—;
Y is optionally present and when present is —CH$_2$O—, —OCH$_2$—, —OCH$_2$CH$_2$O—, —O—, —N(R$_3$)—, —C(O)—, —N(R$_3$)C(O)—, —C(O)N(R$_3$)—, —N(R$_3$)C(O)N(R$_3$)—, —S(O)—, —S(O)$_2$—, —N(R$_3$)S(O)$_2$—, —S(O)$_2$N(R$_3$)—, —C(=NH)—, —C(=NH)N(R$_3$)—, or substituted or unsubstituted C$_1$-C$_4$alkylene;
Z is optionally present and when present is substituted or unsubstituted C$_1$-C$_3$alkyl, substituted or unsubstituted C$_3$-C$_6$cycloalkyl, substituted or unsubstituted C$_2$-C$_7$heterocycloalkyl, substituted or unsubstituted C$_6$-C$_{12}$aryl, or substituted or unsubstituted C$_1$-C$_{12}$heteroaryl;
G is

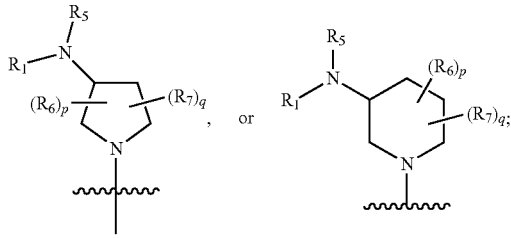

$R_1$ is —R$_4$, —CH$_2$R$_4$, —C(O)R$_9$, —C(O)C(O)R$_9$, —C(O)OR$_4$, —C(O)N(R$_3$)(R$_4$), or —S(O)$_2$R$_9$;
each $R_2$ is independently H, —CN, or halogen;
each $R_3$ is independently is H, or substituted or unsubstituted C$_1$-C$_4$alkyl;
each $R_4$ is independently H, substituted or unsubstituted C$_1$-C$_6$alkyl, substituted or unsubstituted C$_3$-C$_6$cycloalkyl, substituted or unsubstituted C$_2$-C$_7$heterocycloalkyl, substituted or unsubstituted C$_6$-C$_{12}$aryl, or substituted or unsubstituted C$_1$-C$_{12}$heteroaryl;
$R_5$ is H, substituted or unsubstituted C$_1$-C$_4$alkyl, substituted or unsubstituted C$_3$-C$_6$cycloalkyl, substituted or unsubstituted C$_2$-C$_7$heterocycloalkyl, C$_6$-C$_{12}$aryl, or substituted or unsubstituted C$_1$-C$_{12}$heteroaryl;
or R$_1$ and R$_5$ together with the nitrogen atom to which they are attached are combined to form a substituted or unsubstituted C$_2$-C$_9$heterocycloalkyl ring;
each $R_6$ is independently halogen, —CN, —OH, —NH$_2$, substituted or unsubstituted C$_1$-C$_4$alkoxy, substituted or unsubstituted C$_1$-C$_4$alkyl, substituted or unsubstituted C$_3$-C$_6$cycloalkyl, substituted or unsubstituted $C_2$-$C_6$heterocycloalkyl, or —N($R_3$)$_2$; or $R_1$ and $R_6$ are combined to form a substituted or unsubstituted $C_2$-$C_9$heterocycloalkyl ring;

each $R_7$ is independently halogen, —CN, —OH, —NH$_2$, substituted or unsubstituted $C_1$-$C_4$alkoxy, substituted or unsubstituted $C_1$-$C_4$alkyl, substituted or unsubstituted $C_3$-$C_6$cycloalkyl, substituted or unsubstituted $C_2$-$C_6$heterocycloalkyl, or —N($R_3$)$_2$;

$R_9$ is —$R_4$, or

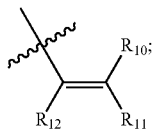

$R_{10}$ is H, halogen, —CN, or -$L_1L_2$;
$R_{11}$ and $R_{12}$ are independently H, halogen, —CN, or -$L_1$-$L_2$; or $R_{11}$ and $R_{12}$ taken together form a bond;
each $L_1$ is optionally present and when present each $L_1$ is independently substituted or unsubstituted $C_1$-$C_6$alkyl, substituted or unsubstituted $C_3$-$C_6$cycloalkyl, substituted or unsubstituted $C_1$-$C_6$heteroalkyl, substituted or unsubstituted $C_2$-$C_7$heterocycloalkyl, substituted or unsubstituted $C_6$-$C_{12}$aryl, substituted or unsubstituted $C_1$-$C_{12}$heteroaryl, —C(=O)—, —O—, or —S—;
each $L_2$ is independently H, substituted or unsubstituted $C_1$-$C_6$alkyl, substituted or unsubstituted $C_3$-$C_6$cycloalkyl, substituted or unsubstituted $C_1$-$C_6$heteroalkyl, substituted or unsubstituted $C_2$-$C_7$heterocycloalkyl, substituted or unsubstituted $C_6$-$C_{12}$aryl, substituted or unsubstituted $C_1$-$C_{12}$heteroaryl or —N($R_{13}$)$_2$;
each $R_{13}$ is independently H, $C_3$-$C_6$cycloalkyl, $C_1$-$C_6$heteroalkyl, $C_2$-$C_7$ heterocycloalkyl, $C_6$-$C_{12}$aryl, or $C_1$-$C_{12}$heteroaryl;
p is 0-3; and
q is 0-3;
or a pharmaceutically acceptable solvate, pharmaceutically acceptable salt, or pharmaceutically acceptable prodrug thereof.

In one embodiment is a compound of Formula (IA) or (I) wherein ring A is substituted or unsubstituted $C_6$-$C_{12}$aryl. In another embodiment is a compound of Formula (IA) or (I) wherein ring A is phenyl. In another embodiment is a compound of Formula (IA) or (I) wherein Y is absent, —CH$_2$O—, —OCH$_2$—, —O—, —N($R_3$)—, —C(O)—, —N($R_3$)C(O)—, —C(O)N($R_3$)—, or substituted or unsubstituted $C_1$-$C_4$alkylene. In another embodiment is a compound of Formula (IA) or (I) wherein Y is absent, —C(O)—, or —C(O)N($R_3$)—. In another embodiment is a compound of Formula (IA) or (I) wherein Z is substituted or unsubstituted $C_2$-$C_7$heterocycloalkyl, substituted or unsubstituted $C_6$-$C_{12}$aryl, or substituted or unsubstituted $C_1$-$C_{12}$heteroaryl. In another embodiment is a compound of Formula (IA) or (I) wherein $R_1$ is —C(O)$R_9$. In another embodiment is a compound of Formula (IA) or (I) wherein $R_9$ is —$R_4$, and $R_4$ is substituted or unsubstituted $C_6$-$C_{12}$aryl, or substituted or unsubstituted $C_1$-$C_{12}$heteroaryl.

In another embodiment is a compound of Formula (IA) or (I) wherein ring A is substituted or unsubstituted $C_1$-$C_{12}$heteroaryl. In another embodiment is a compound of Formula (IA) or (I) wherein ring A is pyridyl. In another embodiment is a compound of Formula (IA) or (I) wherein Y is absent, —CH$_2$O—, —OCH$_2$—, —O—, —N($R_3$)—, —N($R_3$)C(O)—, —C(O)N($R_3$)—, or substituted or unsubstituted $C_1$-$C_4$alkylene. In another embodiment is a compound of Formula (IA) or (I) wherein Y is absent, —C(O)—, or —C(O)N($R_3$)—. In another embodiment is a compound of Formula (IA) or (I) wherein Z is substituted or unsubstituted $C_2$-$C_7$heterocycloalkyl, substituted or unsubstituted $C_6$-$C_{12}$aryl, or substituted or unsubstituted $C_1$-$C_{12}$heteroaryl. In another embodiment is a compound of Formula (IA) or (I) wherein $R_1$ is —C(O)$R_9$. In another embodiment is a compound of Formula (IA) or (I) wherein $R_9$ is —$R_4$, and $R_4$ is substituted or unsubstituted $C_6$-$C_{12}$aryl, or substituted or unsubstituted $C_1$-$C_{12}$heteroaryl.

In a further embodiment of the aforementioned embodiments is a compound of Formula (IA) or (I) wherein X is —C(H)—. In a further embodiment of the aforementioned embodiments is a compound of Formula (IA) or (I) wherein X is —N—. In a further embodiment of the aforementioned embodiments is a compound of Formula (IA) or (I) wherein W is —C(H)—. In a further embodiment of the aforementioned embodiments is a compound of Formula (IA) or (I) wherein W is —N—.

In another aspect is a pharmaceutical composition comprising a therapeutically effective amount of a compound of Formula (IA) or (I) or a pharmaceutically acceptable salt, pharmaceutically acceptable solvate, or pharmaceutically acceptable prodrug thereof, and a pharmaceutically acceptable excipient. In one embodiment, the pharmaceutical composition comprising the compound of Formula (IA) or (I) or a pharmaceutically acceptable salt, pharmaceutically acceptable solvate, or pharmaceutically acceptable prodrug thereof, is formulated for a route of administration selected from oral administration, parenteral administration, buccal administration, nasal administration, topical administration, or rectal administration.

In another aspect is a method for treating an autoimmune disease or condition comprising administering to a patient in need a therapeutically effective amount of a compound of Formula (IA) or (I) or a pharmaceutically acceptable salt, pharmaceutically acceptable solvate, or pharmaceutically acceptable prodrug thereof. In one embodiment the autoimmune disease is selected from rheumatoid arthritis or lupus. In a further aspect is a method for treating a heteroimmune disease or condition comprising administering to a patient in need a therapeutically effective amount of a compound of Formula (IA) or (I) or a pharmaceutically acceptable salt, pharmaceutically acceptable solvate, or pharmaceutically acceptable prodrug thereof. In yet another embodiment is a method for treating a cancer comprising administering to a patient in need a therapeutically effective amount of a compound of Formula (IA) or (I) or a pharmaceutically acceptable salt, pharmaceutically acceptable solvate, or pharmaceutically acceptable prodrug thereof. In one embodiment the cancer is a B-cell proliferative disorder. In another embodiment the B-cell proliferative disorder is diffuse large B cell lymphoma, follicular lymphoma, mantel cell lymphoma, or chronic lymphocytic leukemia.

In yet a further aspect is a method for treating mastocytosis comprising administering to a patient in need a therapeutically effective amount of a compound of Formula (I) or a pharmaceutically acceptable salt, pharmaceutically acceptable solvate, or pharmaceutically acceptable prodrug thereof.

In another aspect is a method for treating osteoporosis or bone resorption disorders comprising administering to a patient in need a therapeutically effective amount of a compound of Formula (I) or a pharmaceutically acceptable salt, pharmaceutically acceptable solvate, or pharmaceutically acceptable prodrug thereof.

In a further aspect is a method for treating an inflammatory disease or condition comprising administering to a patient in need a therapeutically effective amount of a compound of Formula (I) or a pharmaceutically acceptable salt, pharmaceutically acceptable solvate, or pharmaceutically acceptable prodrug thereof.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

In a further aspect are provided pharmaceutical compositions, which include a therapeutically effective amount of at least one of any of the compounds herein, or a pharmaceutically acceptable salt, pharmaceutically acceptable prodrug, or pharmaceutically acceptable solvate. In certain embodiments, compositions provided herein further include a pharmaceutically acceptable diluent, excipient and/or binder.

Pharmaceutical compositions formulated for administration by an appropriate route and means containing effective concentrations of one or more of the compounds provided herein, or pharmaceutically effective derivatives thereof, that deliver amounts effective for the treatment, prevention, or amelioration of one or more symptoms of diseases, disorders or conditions that are modulated or otherwise affected by tyrosine kinase activity, or in which tyrosine kinase activity is implicated, are provided. The effective amounts and concentrations are effective for ameliorating any of the symptoms of any of the diseases, disorders or conditions disclosed herein.

In certain embodiments, provided herein is a pharmaceutical composition containing: i) a physiologically acceptable carrier, diluent, and/or excipient; and ii) one or more compounds provided herein.

In one aspect, provided herein are methods for treating a patient by administering a compound provided herein. In some embodiments, provided herein is a method of inhibiting the activity of tyrsoine kinase(s), such as Btk, or of treating a disease, disorder, or condition, which would benefit from inhibition of tyrosine kinase(s), such as Btk, in a patient, which includes administering to the patient a therapeutically effective amount of at least one of any of the compounds herein, or pharmaceutically acceptable salt, pharmaceutically acceptable prodrug, or pharmaceutically acceptable solvate.

In another aspect, provided herein is the use of a compound disclosed herein for inhibiting Bruton's tyrosine kinase (Btk) activity or for the treatment of a disease, disorder, or condition, which would benefit from inhibition of Bruton's tyrosine kinase (Btk) activity.

In some embodiments, compounds provided herein are administered to a human.

In some embodiments, compounds provided herein are orally administered.

In other embodiments, compounds provided herein are used for the formulation of a medicament for the inhibition of tyrosine kinase activity. In some other embodiments, compounds provided herein are used for the formulation of a medicament for the inhibition of Bruton's tyrosine kinase (Btk) activity.

Articles of manufacture including packaging material, a compound or composition or pharmaceutically acceptable derivative thereof provided herein, which is effective for inhibiting the activity of tyrosine kinase(s), such as Btk, within the packaging material, and a label that indicates that the compound or composition, or pharmaceutically acceptable salt, pharmaceutically acceptable prodrug, or pharmaceutically acceptable solvate thereof, is used for inhibiting the activity of tyrosine kinase(s), such as Btk, are provided.

In a further aspect, provided herein is a method for inhibiting Bruton's tyrosine kinase in a subject in need thereof by administering to the subject thereof a composition containing a therapeutically effective amount of at least one compound having the structure of Formula (IA), (I), (Ia), (II), (III), (IV), (Va)-(Vh), or (VIa)-(VIb). In some embodiments, the subject in need is suffering from an autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, *scleroderma*, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, *scleroderma*, or vulvodynia.

In other embodiments, the subject in need is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis.

In certain embodiments, the subject in need is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In further embodiments, the subject in need is suffering from a cancer. In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In further embodiments, the subject in need is suffering from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a further aspect, provided herein is a method for treating an autoimmune disease by administering to a subject in need thereof a composition containing a therapeutically effective amount of at least one compound having the structure of Formula (IA), Formula (I), Formula (Ia), Formula (II), Formula (III), Formula (IV), Formula (Va)-(Vh), or Formula (VIa)-(VIb). In one embodiment, the autoimmune disease is arthritis. In another embodiment, the autoimmune disease is lupus. In some embodiments, the autoimmune disease is inflammatory bowel disease (including Crohn's disease and ulcerative colitis), rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, *scleroderma*, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, *scleroderma*, or vulvodynia.

In a further aspect, provided herein is a method for treating a heteroimmune condition or disease by administering to a subject in need thereof a composition containing a therapeutically effective amount of at least one compound having the structure of Formula (IA), Formula (I), Formula (Ia), Formula (II), Formula (III), Formula (IV), Formula (Va)-(Vh), or Formula (VIa)-(VIb). In some embodiments, the heteroimmune condition or disease is graft versus host disease, transplantation, transfusion, anaphylaxis, allergy, type I hypersensitivity, allergic conjunctivitis, allergic rhinitis, or atopic dermatitis.

In a further aspect, provided herein is a method for treating an inflammatory disease by administering to a subject in need thereof a composition containing a therapeutically effective amount of at least one compound having the structure of Formula (IA), Formula (I), Formula (Ia), Formula (II), Formula (III), Formula (IV), Formula (Va)-(Vh), or Formula (VIa)-(VIb). In some embodiments, the inflammatory disease is asthma, inflammatory bowel disease (including Crohn's disease and ulcerative colitis), appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In yet another aspect, provided herein is a method for treating a cancer by administering to a subject in need thereof a composition containing a therapeutically effective amount of at least one compound having the structure of Formula (IA), Formula (I), Formula (Ia), Formula (II), Formula (III), Formula (IV), Formula (Va)-(Vh), or Formula (VIa)-(VIb). In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In another aspect, provided herein is a method for treating a thromboembolic disorder by administering to a subject in need thereof a composition containing a therapeutically effective amount of at least one compound having the structure of Formula (IA), Formula (I), Formula (Ia), Formula (II), Formula (III), Formula (IV), Formula (Va)-(Vh), or Formula (VIa)-(VIb). In some embodiments, the thromboembolic disorder is myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a further aspect, provided herein is a method for treating an autoimmune disease by administering to a subject in need thereof a composition containing a therapeutically effective amount of a compound that forms a covalent bond with Bruton's tyrosine kinase. In one embodiment, the compound forms a covalent bond with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase.

In a further aspect, provided herein is a method for treating a heteroimmune condition or disease by administering to a subject in need thereof a composition containing a therapeutically effective amount of a compound that forms a covalent bond with Bruton's tyrosine kinase. In one embodiment, the compound forms a covalent bond with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase.

In a further aspect, provided herein is a method for treating an inflammatory disease by administering to a subject in need thereof a composition containing a therapeutically effective amount of a compound that forms a covalent bond with Bruton's tyrosine kinase. In one embodiment, the compound forms a covalent bond with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase. In yet another aspect, provided herein is a method for treating a cancer by administering to a subject in need thereof a composition containing a therapeutically effective amount of a compound that forms a covalent bond with Bruton's tyrosine kinase. In one embodiment, the compound forms a covalent bond with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase.

In another aspect, provided herein is a method for treating a thromboembolic disorder by administering to a subject in need thereof a composition containing a therapeutically effective amount of a compound that forms a covalent bond with Bruton's tyrosine kinase. In one embodiment, the compound forms a covalent bond with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase.

In another aspect are methods for modulating, including irreversibly inhibiting the activity of Btk or other tyrosine kinases, wherein the other tyrosine kinases share homology with Btk by having a cysteine residue (including a Cys 481 residue) that can form a covalent bond with at least one irreversible inhibitor described herein, in a mammal comprising administering to the mammal at least once an effective amount of at least one compound having the structure of Formula (IA), Formula (I), Formula (Ia), Formula (II), Formula (III), Formula (IV), Formula (Va)-(Vh), or Formula (VIa)-(VIb). In another aspect are methods for modulating, including including reversibly or irreversibly inhibiting, the activity of Btk in a mammal comprising administering to the mammal at least once an effective amount of at least one compound having the structure of Formula (IA), Formula (I), Formula (Ia), Formula (II), Formula (III), Formula (IV), Formula (Va)-(Vh), or Formula (VIa)-(VIb). In another aspect are methods for treating Btk-dependent or Btk mediated conditions or diseases, comprising administering to the mammal at least once an effective amount of at least one compound having the structure of Formula (IA), Formula (I), Formula (Ia), Formula (II), Formula (III), Formula (IV), Formula (Va)-(Vh), or Formula (VIa)-(VIb).

In another aspect are methods for treating inflammation comprising administering to the mammal at least once an effective amount of at least one compound having the structure of Formula (IA), Formula (I), Formula (Ia), Formula (II), Formula (III), Formula (IV), Formula (Va)-(Vh), or Formula (VIa)-(VIb).

A further aspect are methods for the treatment of cancer comprising administering to the mammal at least once an effective amount of at least one compound having the structure of Formula (IA), Formula (I), Formula (Ia), Formula (II), Formula (III), Formula (IV), Formula (Va)-(Vh), or Formula (VIa)-(VIb). The type of cancer may include, but is not limited to, pancreatic cancer and other solid or hematological tumors.

In another aspect are methods for treating respiratory diseases comprising administering to the mammal at least once an effective amount of at least one compound having the structure of Formula (IA), Formula (I), Formula (Ia), Formula (II), Formula (III), Formula (IV), Formula (Va)-(Vh), or Formula (VIa)-(VIb). In a further embodiment of this aspect, the respiratory disease is asthma. In a further embodiment of this aspect, the respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, and seasonal asthma.

In another aspect are methods for preventing rheumatoid arthritis and osteoarthritis comprising administering to the mammal at least once an effective amount of at least one compound having the structure of Formula (IA), Formula (I), Formula (Ia), Formula (II), Formula (III), Formula (IV), Formula (Va)-(Vh), or Formula (VIa)-(VIb).

In another aspect are methods for treating inflammatory responses of the skin comprising administering to the mammal at least once an effective amount of at least one compound having the structure of Formula (IA), Formula (I), Formula (Ia), Formula (II), Formula (III), Formula (IV), Formula (Va)-(Vh), or Formula (VIa)-(VIb). Such inflammatory responses of the skin include, by way of example, dermatitis, contact dermatitis, eczema, urticaria, rosacea, and scarring. In another aspect are methods for reducing psoriatic lesions in the skin, joints, or other tissues or organs, comprising administering to the mammal an effective amount of a first compound having the structure of Formula (IA), Formula (I), Formula (Ia), Formula (II), Formula (III), Formula (IV), Formula (Va)-(Vh), or Formula (VIa)-(VIb).

In another aspect is the use of a compound of Formula (IA), Formula (I), Formula (Ia), Formula (II), Formula (III), Formula (IV), Formula (Va)-(Vh), or Formula (VIa)-(VIb), in the manufacture of a medicament for treating an inflammatory disease or condition in an animal in which the activity of Btk or other tyrosine kinases, wherein the other tyrosine kinases share homology with Btk by having a cysteine residue (including a Cys 481 residue) that can form a covalent bond with at least one irreversible inhibitor described herein, contributes to the pathology and/or symptoms of the disease or condition. In one embodiment of this aspect, the tyrosine kinase protein is Btk. In another or further embodiment of this aspect, the inflammatory disease or conditions are respiratory, cardiovascular, or proliferative diseases.

In any of the aforementioned aspects are further embodiments in which administration is enteral, parenteral, or both, and wherein (a) the effective amount of the compound is systemically administered to the mammal; (b) the effective amount of the compound is administered orally to the mammal; (c) the effective amount of the compound is intravenously administered to the mammal; (d) the effective amount of the compound administered by inhalation; (e) the effective amount of the compound is administered by nasal administration; or (f) the effective amount of the compound is administered by injection to the mammal; (g) the effective amount of the compound is administered topically (dermal) to the mammal; (h) the effective amount of the compound is administered by ophthalmic administration; or (i) the effective amount of the compound is administered rectally to the mammal.

In any of the aforementioned aspects are further embodiments comprising single administrations of the effective amount of the compound, including further embodiments in which (i) the compound is administered to the mammal once; (ii) the compound is administered to the mammal multiple times over the span of one day; (iii) the compound is administered to the mammal continually; or (iv) the compound is administered to the mammal continuously.

In any of the aforementioned aspects are further embodiments comprising multiple administrations of the effective amount of the compound, including further embodiments in which (i) the compound is administered in a single dose; (ii) the time between multiple administrations is every 6 hours; (iii) the compound is administered to the mammal every 8 hours. In further or alternative embodiments, the method comprises a drug holiday, wherein the administration of the compound is temporarily suspended or the dose of the compound being administered is temporarily reduced; at the end of the drug holiday, dosing of the compound is resumed. The length of the drug holiday can vary from 2 days to 1 year.

In any of the aforementioned aspects involving the treatment of proliferative disorders, including cancer, are further embodiments comprising administering at least one additional agent selected from the group consisting of alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclitaxel™, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In any of the aforementioned aspects involving the prevention or treatment of Btk-dependent or tyrosine kinase mediated diseases or conditions are further embodiments comprising identifying patients by screening for a tyrosine kinase gene haplotype. In further or alternative embodiments the tyrosine kinase gene haplotype is a tyrosine kinase pathway gene, while in still further or alternative embodiments, the tyrosine kinase gene haplotype is a Btk haplotype.

In a further or alternative embodiments, the compounds of Formula (IA), (I), (Ia), (II), (III), (IV), (Va)-(Vh), or (VIa)-(VIb) are reversible inhibitors of Bruton's tyrosine kinase (Btk), while in still further or alternative embodiments, such reversible inhibitors are selective for Btk. In even further or alternative embodiments, such inhibitors have an $IC_{50}$ below 10 microM in enzyme assay. In one embodiment, a Btk reversible inhibitor has an $IC_{50}$ of less than 1 microM, and in another embodiment, less than 0.25 microM.

In further or alternative embodiments, the compounds of Formula (IA), (I), (Ia), (II), (III), (IV), (Va)-(Vh), or (VIa)-(VIb) are selective reversible inhibitors for Btk over Itk. In further or alternative embodiments, the compounds of Formula (IA), (I), (Ia), (II), (III), (IV), (Va)-(Vh), or (VIa)-(VIb) are selective reversible inhibitors for Btk over Lck. In further or alternative embodiments, the compounds of Formula (IA), (I), (Ia), (II), (III), (IV), (Va)-(Vh), or (VIa)-(VIb) are selective reversible inhibitors for Btk over ABL. In further or alternative embodiments, the compounds of Formula (IA), (I), (Ia), (II), (III), (IV), (Va)-(Vh), or (VIa)-(VIb) are selective reversible inhibitors for Btk over CMET. In further or alternative embodiments, the compounds of Formula (IA), (I), (Ia), (II), (III), (IV), (Va)-(Vh), or (VIa)-(VIb) are selective reversible inhibitors for Btk over EGFR. In further or alternative embodiments, the compounds of Formula (IA), (I), (Ia), (II), (III), (IV), (Va)-(Vh), or (VIa)-(VIb) are selective reversible inhibitors for Btk over Lyn.

In further or alternative embodiments, the reversible Btk inhibitors are also inhibitors of EGFR.

In a further or alternative embodiment, the compound of Formula (IA), Formula (I), Formula (Ia), Formula (II), Formula (III), Formula (IV), Formula (Va)-(Vh), or Formula (VIa)-(VIb), are irreversible inhibitors of Bruton's tyrosine kinase (Btk), while in still further or alternative embodiments, such irreversible inhibitors are selective for Btk. In even further or alternative embodiments, such inhibitors have an $IC_{50}$ below 10 microM in enzyme assay. In one embodiment, a Btk irreversible inhibitor has an $IC_{50}$ of less than 1 microM, and in another embodiment, less than 0.25 microM.

In further or alternative embodiment, the compound of Formula (IA), Formula (I), Formula (Ia), Formula (II), Formula (III), Formula (IV), Formula (Va)-(Vh), or Formula (VIa)-(VIb) are selective irreversible inhibitors for Btk over Itk. In further or alternative embodiment, the compound of Formula (IA), Formula (I), Formula (Ia), Formula (II), Formula (III), Formula (IV), Formula (Va)-(Vh), or Formula (VIa)-(VIb) are selective irreversible inhibitors for Btk over Lck. In further or alternative embodiment, the compound of Formula (IA), Formula (I), Formula (Ia), Formula (II), Formula (III), Formula (IV), Formula (Va)-(Vh), or Formula (VIa)-(VIb) are selective irreversible inhibitors for Btk over ABL. In further or alternative embodiment, the compound of Formula (IA), Formula (I), Formula (Ia), Formula (II), Formula (III), Formula (IV), Formula (Va)-(Vh), or Formula (VIa)-(VIb) are selective irreversible inhibitors for Btk over CMET. In further or alternative embodiment, the compound of Formula (IA), Formula (I), Formula (Ia), Formula (II), Formula (III), Formula (IV), Formula (Va)-(Vh), or Formula (VIa)-(VIb), are selective irreversible inhibitors for Btk over EGFR. In further or alternative embodiment, the compound of Formula (IA), Formula (I), Formula (Ia), Formula (II), Formula (III), Formula (IV), Formula (Va)-(Vh), or Formula (VIa)-(VIb), are selective irreversible inhibitors for Btk over Lyn.

In further or alternative embodiments, the irreversible Btk inhibitors are also inhibitors of EGFR.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Certain Terminology

Unless defined otherwise, all technical and scientific terms used herein have the same meaning as is commonly understood by one of skill in the art to which the claimed subject matter belongs. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of the following substituents: halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t$$R^a$ (where t is 1 or 2), —S(O)$_t$O$R^a$ (where t is 1 or 2) and —S(O)$_t$N($R^a$)$_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

The alkyl group could also be a "lower alkyl" having 1 to 6 carbon atoms.

As used herein, $C_1$-$C_x$ includes $C_1$-$C_2$, $C_1$-$C_3$ ... $C_1$-$C_x$.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t$$R^a$ (where t is 1 or 2), —S(O)$_t$O$R^a$ (where t is 1 or 2) and —S(O)$_t$N($R^a$)$_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t$$R^a$ (where t is 1 or 2), —S(O)$_t$O$R^a$ (where t is 1 or 2) and —S(O)$_t$N($R^a$)$_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain is optionally substituted by one or more of the following substituents: halo, cyano, nitro, aryl, cycloalkyl, heterocyclyl, heteroaryl, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t$$R^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. Aryl groups include, but are not limited to, groups such as phenyl, fluorenyl, and naphthyl. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is optionally saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—SR$^a$, —R$^b$—OC(O)—R$^a$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Halo" or "halogen" refers to bromo, chloro, fluoro or iodo substituents.

The terms "haloalkyl," "haloalkenyl," "haloalkynyl" and "haloalkoxy" include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical is optionally substituted as defined above for an alkyl group.

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. The radicals may be fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

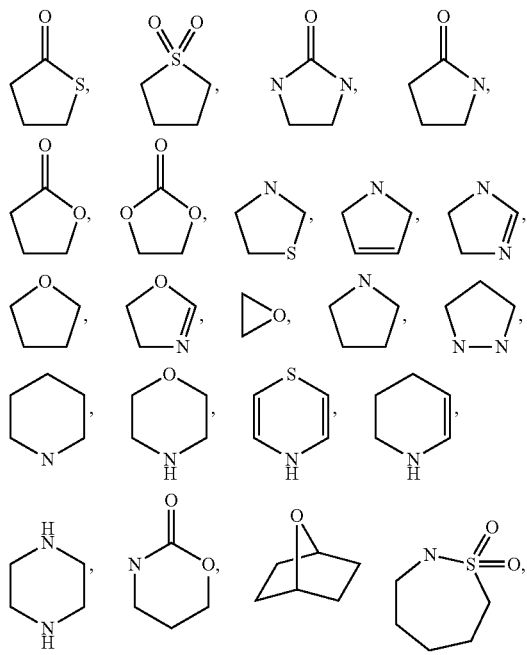

-continued

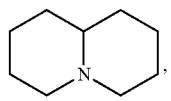 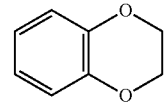

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

"Heteroaryl" refers to a radical derived from a 3- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula $R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Sulfanyl" refers to the —S— radical.
"Sulfinyl" refers to the —S(=O)— radical.
"Sulfonyl" refers to the —S(=O)$_2$— radical.
"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Imino" refers to the =NH radical.
"Thioxo" refers to the =S radical.

An "alkoxy" group refers to a (alkyl)O— group, where alkyl is as defined herein.

An "aryloxy" group refers to an (aryl)O— group, where aryl is as defined herein.

"Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

As used herein, the terms "heteroalkyl" "heteroalkenyl" and "heteroalkynyl" include optionally substituted alkyl, alkenyl and alkynyl radicals in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and CH=CH—N(CH$_3$)—CH$_3$. In addition, up to two heteroatoms may be consecutive, such as, by way of example, —CH$_2$—NH—OCH$_3$ and CH$_2$—O—Si(CH$_3$)$_3$.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond" or "single bond" refers to a chemical bond between two atoms, or two moieties when the atoms joined by the bond are considered to be part of larger substructure.

An "isocyanato" group refers to a —NCO group.
An "isothiocyanato" group refers to a —NCS group.

The term "moiety" refers to a specific segment or functional group of a molecule. Chemical moieties are often recognized chemical entities embedded in or appended to a molecule.

A "thioalkoxy" or "alkylthio" group refers to a —S-alkyl group.

A "alkylthioalkyl" group refers to an alkyl group substituted with a —S-alkyl group.

As used herein, the term "O-carboxy" or "acyloxy" refers to a group of formula RC(=O)O—.

"Carboxy" means a —C(O)OH radical.

As used herein, the term "acetyl" refers to a group of formula —C(=O)CH$_3$.

"Acyl" refers to the group —C(O)R.

As used herein, the term "trihalomethanesulfonyl" refers to a group of formula X$_3$CS(=O)$_2$— where X is a halogen.

"Cyanoalkyl" means an alkyl radical, as defined herein, substituted with at least one cyano group.

As used herein, the term "N-sulfonamido" or "sulfonylamino" refers to a group of formula RS(=O)$_2$NH—.

As used herein, the term "O-carbamyl" refers to a group of formula —OC(=O)NR$_2$.

As used herein, the term "N-carbamyl" refers to a group of formula ROC(=O)NH—.

As used herein, the term "O-thiocarbamyl" refers to a group of formula —OC(=S)NR$_2$.

As used herein, "N-thiocarbamyl" refers to a group of formula ROC(=S)NH—.

As used herein, the term "C-amido" refers to a group of formula —C(=O)NR$_2$.

"Aminocarbonyl" refers to a —CONH$_2$ radical.

As used herein, the term "N-amido" refers to a group of formula RC(=O)NH—.

As used herein, the substituent "R" appearing by itself and without a number designation refers to a substituent selected from among from alkyl, cycloalkyl, aryl, heteroaryl (bonded through a ring carbon) and non-aromatic heterocycle (bonded through a ring carbon).

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

An "alkenyloxy" group refers to a (alkenyl)O— group, where alkenyl is as defined herein.

The term "alkylamine" refers to the N(alkyl)$_x$H$_y$ group, where x and y are selected from among x=1, y=1 and x=2, y=0. When x=2, the alkyl groups, taken together with the N atom to which they are attached, can optionally form a cyclic ring system.

"Alkylaminoalkyl" refers to an alkyl radical, as defined herein, substituted with an alkylamine, as defined herein.

An "amide" is a chemical moiety with the formula —C(O)NHR or —NHC(O)R, where R is selected from among alkyl, cycloalkyl, aryl, heteroaryl (bonded through a ring carbon) and heteroalicyclic (bonded through a ring carbon). An amide moiety may form a linkage between an amino acid or a peptide molecule and a compound described herein, thereby forming a prodrug. Any amine, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, acyl, nitro, haloalkyl, fluoroalkyl, haloalkoxy, amino, including mono- and di-substituted amino groups, and the N-oxide and protected derivatives thereof; or "optionally substituted" or "substituted" may be -L$_s$R$_s$, wherein each L$_s$ is independently selected from a bond, —O—, —C(=O)—, —S—, —S(=O)—, —S(=O)$_2$—, —NH—, —N(CH$_3$)—, —NHC(O)—, —N(CH$_3$)C(O)—, —C(O)NH—, —C(O)N(CH$_3$)—, S(=O)$_2$NH—, —NHS(=O)$_2$, —OC(O)NH—, —NHC(O)O—, -(substituted or unsubstituted C$_1$-C$_6$ alkyl)-, or -(substituted or unsubstituted C$_2$-C$_6$ alkenyl)-; and each R$_s$ is independently selected from H, C$_1$-C$_6$alkyl, C$_2$-C$_6$ alkenyl, C$_3$-C$_6$cycloalkyl, C$_2$-C$_7$heterocycloalkyl, heteroaryl, or heteroalkyl. The protecting groups that may form the protective derivatives of the above substituents are known to those of skill in the art and may be found in references such as Greene and Wuts, above.

The term "nucleophile" or "nucleophilic" refers to an electron rich compound, or moiety thereof. An example of a nucleophile includes, but in no way is limited to, a cysteine residue of a molecule, such as, for example Cys 481 of Btk.

The term "electrophile", or "electrophilic" refers to an electron poor or electron deficient molecule, or moiety thereof. Examples of electrophiles include, but in no way are limited to, Micheal acceptor moieties.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, the term "agonist" refers to a compound, the presence of which results in a biological activity of a protein that is the same as the biological activity resulting from the presence of a naturally occurring ligand for the protein, such as, for example, Btk.

As used herein, the term "partial agonist" refers to a compound the presence of which results in a biological activity of a protein that is of the same type as that resulting from the presence of a naturally occurring ligand for the protein, but of a lower magnitude.

As used herein, the term "antagonist" refers to a compound, the presence of which results in a decrease in the magnitude of a biological activity of a protein. In certain embodiments, the presence of an antagonist results in complete inhibition of a biological activity of a protein, such as, for example, Btk. In certain embodiments, an antagonist is an inhibitor.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of the weight of compounds disclosed herein, such as, compounds of any of Formula (IA), Formula (I), Formula (Ia), Formula (II), Formula (III), Formula (IV), Formula (Va)-(Vh), or Formula (VIa)-(VIb), dosed that is delivered into the general circulation of the animal or human being studied. The total exposure (AUC$_{(0-\infty)}$) of a drug when administered intravenously is usually defined as 100% bioavailable (F %). "Oral bioavailability" refers to the extent to which compounds disclosed herein, such as, compounds of any of Formula (IA), Formula (I), Formula (Ia), Formula (II), Formula (III), Formula (IV), Formula (Va)-(Vh), or Formula (VIa)-(VIb), are absorbed into the general circulation when the pharmaceutical composition is taken orally as compared to intravenous injection.

"Blood plasma concentration" refers to the concentration of compounds disclosed herein, such as, compounds of any of Formula (IA), Formula (I), Formula (Ia), Formula (II), Formula (III), Formula (IV), Formula (Va)-(Vh), or Formula (VIa)-(VIb), in the plasma component of blood of a subject. It is understood that the plasma concentration of compounds of any of Formula (IA), Formula (I), Formula (Ia), Formula (II), Formula (III), Formula (IV), Formula (Va)-(Vh), or Formula (VIa)-(VIb), may vary significantly between subjects, due to variability with respect to metabolism and/or possible interactions with other therapeutic agents. In accordance with one embodiment disclosed herein, the blood plasma concentration of the compounds of any of Formula (IA), Formula (I), Formula (Ia), Formula (II), Formula (III), Formula (IV), Formula (Va)-(Vh), or Formula (VIa)-(VIb), may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of a compound of any of Formula (IA), Formula (I), Formula (Ia), Formula (II), Formula (III), Formula (IV), Formula (Va)-(Vh), or Formula (VIa)-(VIb), may vary from subject to subject.

The term "Bruton's tyrosine kinase," as used herein, refers to Bruton's tyrosine kinase from *Homo sapiens*, as disclosed in, e.g., U.S. Pat. No. 6,326,469 (GenBank Accession No. NP_000052).

The term "Bruton's tyrosine kinase homolog," as used herein, refers to orthologs of Bruton's tyrosine kinase, e.g., the orthologs from mouse (GenBank Accession No. AAB47246), dog (GenBank Accession No. XP_549139.), rat (GenBank Accession No. NP_001007799), chicken (GenBank Accession No. NP_989564), or zebra fish (GenBank Accession No. XP_698117), and fusion proteins of any of the foregoing that exhibit kinase activity towards one or more substrates of Bruton's tyrosine kinase (e.g. a peptide substrate having the amino acid sequence "AVLESEEELYSSARQ").

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound of any of Formula (IA), Formula (I), Formula (Ia), Formula (II), Formula (III), Formula (IV), Formula (Va)-(Vh), or Formula (VIa)-(VIb), age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "homologous cysteine," as used herein refers to a cysteine residue found with in a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys 350.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75-100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75-100 nucleic acids in length, over a region that is about 50 nucleic acids in length, or, where not specified, across the entire sequence of a polynucleotide sequence.

The terms "inhibits", "inhibiting", or "inhibitor" of a kinase, as used herein, refer to inhibition of enzymatic phosphotransferase activity.

The term "irreversible inhibitor," as used herein, refers to a compound that, upon contact with a target protein (e.g., a kinase) causes the formation of a new covalent bond with or within the protein, whereby one or more of the target protein's biological activities (e.g., phosphotransferase activity) is diminished or abolished notwithstanding the subsequent presence or absence of the irreversible inhibitor. In contrast, a reversible inhibitor compound upon contact with a target protein does not cause the formation of a new covalent bond with or within the protein and therefore can associate and dissociate from the target protein.

The term "irreversible Btk inhibitor," as used herein, refers to an inhibitor of Btk that can form a covalent bond with an amino acid residue of Btk. In one embodiment, the irreversible inhibitor of Btk can form a covalent bond with a Cys residue of Btk; in particular embodiments, the irreversible inhibitor can form a covalent bond with a Cys 481 residue (or a homolog thereof) of Btk or a cysteine residue in the homologous corresponding position of another tyrosine kinase.

The term "isolated," as used herein, refers to separating and removing a component of interest from components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "prophylactically effective amount," as used herein, refers that amount of a composition applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

As used herein, the term "selective binding compound" refers to a compound that selectively binds to any portion of one or more target proteins.

As used herein, the term "selectively binds" refers to the ability of a selective binding compound to bind to a target protein, such as, for example, Btk, with greater affinity than it binds to a non-target protein. In certain embodiments, specific binding refers to binding to a target with an affinity that is at least 10, 50, 100, 250, 500, 1000 or more times greater than the affinity for a non-target.

As used herein, the term "selective modulator" refers to a compound that selectively modulates a target activity relative to a non-target activity. In certain embodiments, specific modulator refers to modulating a target activity at least 10, 50, 100, 250, 500, 1000 times more than a non-target activity.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

As used herein, the term "target protein" refers to a molecule or a portion of a protein capable of being bound by a selective binding compound. In certain embodiments, a target protein is Btk.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the $IC_{50}$ refers to an amount, concentration or dosage of a particular test compound that achieves a 50% inhibition of a maximal response, such as inhibition of Btk, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

DETAILED DESCRIPTION OF THE INVENTION

The methods described herein include administering to a subject in need a composition containing a therapeutically effective amount of one or more reversible or irreversible Btk inhibitor compounds described herein. Without being bound by theory, the diverse roles played by Btk signaling in various hematopoietic cell functions, e.g., B-cell receptor activation, suggests that small molecule Btk inhibitors are useful for reducing the risk of or treating a variety of diseases affected by or affecting many cell types of the hematopoetic lineage including, e.g., autoimmune diseases, heteroimmune conditions or diseases, inflammatory diseases, cancer (e.g., B-cell proliferative disorders), and thromboembolic disorders. Further, the irreversible Btk inhibitor compounds described herein can be used to inhibit a small subset of other tyrosine kinases that share homology with Btk by having a cysteine residue (including a Cys 481 residue) that can form a covalent bond with the irreversible inhibitor. Thus, a subset of tyrosine kinases other than Btk are also expected to be useful as therapeutic targets in a number of health conditions.

In some embodiments, the methods described herein can be used to treat an autoimmune disease, which includes, but is not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, *scleroderma*, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, *scleroderma*, and vulvodynia.

In some embodiments, the methods described herein can be used to treat heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In further embodiments, the methods described herein can be used to treat an inflammatory disease, which includes, but is not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

In yet other embodiments, the methods described herein can be used to treat a cancer, e.g., B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

In further embodiments, the methods described herein can be used to treat thromboembolic disorders, which include, but are not limited to myocardial infarct, angina pectoris (including unstable angina), reocclusions or restenoses after angioplasty or aortocoronary bypass, stroke, transitory ischemia, peripheral arterial occlusive disorders, pulmonary embolisms, and deep venous thromboses.

Symptoms, diagnostic tests, and prognostic tests for each of the above-mentioned conditions are known in the art. See, e.g., *Harrison's Principles of Internal Medicine©*" 16th ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models of are useful for establishing a range of therapeutically effective doses of reversible or irreversible Btk inhibitor compounds for treating any of the foregoing diseases.

For example, dosing of reversible or irreversible Btk inhibitor compounds for treating an autoimmune disease can be assessed in a mouse model of rheumatoid arthritis. In this model, arthritis is induced in Balb/c mice by administering anti-collagen antibodies and lipopolysaccharide. See Nandakumar et al. (2003), *Am. J. Pathol* 163:1827-1837.

In another example, dosing of reversible or irreversible Btk inhibitors for the treatment of B-cell proliferative disorders can be examined in, e.g., a human-to-mouse xenograft model in which human B-cell lymphoma cells (e.g. Ramos cells) are implanted into immunodeficient mice (e.g., "nude" mice) as described in, e.g., Pagel et al. (2005), Clin Cancer Res 11(13): 4857-4866.

Animal models for treatment of thromboembolic disorders are also known.

The therapeutic efficacy of the compound for one of the foregoing diseases can be optimized during a course of treatment. For example, a subject being treated can undergo a diagnostic evaluation to correlate the relief of disease symptoms or pathologies to inhibition of in vivo Btk activity achieved by administering a given dose of an irreversible Btk inhibitor. Cellular assays known in the art can be used to determine in vivo activity of Btk in the presence or absence of an irreversible Btk inhibitor. For example, since activated Btk is phosphorylated at tyrosine 223 (Y223) and tyrosine 551 (Y551), phospho-specific immunocytochemical staining of P-Y223 or P-Y551-positive cells can be used to detect or quantify activation of Bkt in a population of cells (e.g., by FACS analysis of stained vs unstained cells). See, e.g., Nisitani et al. (1999), *Proc. Natl. Acad. Sci*, USA 96:2221-2226. Thus, the amount of the Btk inhibitor compound that is administered to a subject can be increased or decreased as needed so as to maintain a level of Btk inhibition optimal for treating the subject's disease state.

Compounds

In the following description of reversible or irreversible Btk compounds suitable for use in the methods described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the ordinary skill of the art are employed. In addition, nucleic acid and amino acid sequences for Btk (e.g., human Btk) are known in the art as disclosed in, e.g., U.S. Pat. No. 6,326,469. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

The Btk inhibitor compounds described herein are selective for Btk and kinases having a cysteine residue in an amino acid sequence position of the tyrosine kinase that is homologous to the amino acid sequence position of cysteine 481 in Btk Inhibitor compounds described herein include a Michael acceptor moiety.

Generally, a reversible or irreversible inhibitor compound of Btk used in the methods described herein is identified or characterized in an in vitro assay, e.g., an acellular biochemical assay or a cellular functional assay. Such assays are useful to determine an in vitro $IC_{50}$ for a reversible or irreversible Btk inhibitor compound.

For example, an acellular kinase assay can be used to determine Btk activity after incubation of the kinase in the absence or presence of a range of concentrations of a candidate irreversible Btk inhibitor compound. If the candidate compound is in fact an irreversible Btk inhibitor, Btk kinase activity will not be recovered by repeat washing with inhibitor-free medium. See, e.g., J. B. Smaill, et al. (1999), *J. Med. Chem.* 42(10):1803-1815. Further, covalent complex formation between Btk and a candidate irreversible Btk inhibitor is a useful indicator of irreversible inhibition of Btk that can be readily determined by a number of methods known in the art (e.g., mass spectrometry). For example, some irreversible Btk-inhibitor compounds can form a covalent bond with Cys 481 of Btk (e.g., via a Michael reaction).

Cellular functional assays for Btk inhibition include measuring one or more cellular endpoints in response to stimulating a Btk-mediated pathway in a cell line (e.g., BCR activation in Ramos cells) in the absence or presence of a range of concentrations of a candidate irreversible Btk inhibitor compound. Useful endpoints for determining a response to BCR activation include, e.g., autophosphorylation of Btk, phosphorylation of a Btk target protein (e.g., PLC-γ), and cytoplasmic calcium flux.

High throughput assays for many acellular biochemical assays (e.g., kinase assays) and cellular functional assays (e.g., calcium flux) are well known to those of ordinary skill in the art. In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. Automated systems thereby allow the identification and characterization of a large number of reversible or irreversible Btk compounds without undue effort.

Reversible or irreversible Btk inhibitor compounds can be used for the manufacture of a medicament for treating any of the foregoing conditions (e.g., autoimmune diseases, inflammatory diseases, allergy disorders, B-cell proliferative disorders, or thromboembolic disorders).

In some embodiments, the reversible or irreversible Btk inhibitor compound used for the methods described herein inhibits Btk or a Btk homolog kinase activity with an in vitro $IC_{50}$ of less than about 10 μM. (e.g., less than about 1 μM, less than about 0.5 μM, less than about 0.4 μM, less than about 0.3 μM, less than about 0.1, less than about 0.08 μM, less than about 0.06 μM, less than about 0.05 μM, less than about 0.04 μM, less than about 0.03 μM, less than about 0.02 μM, less than about 0.01, less than about 0.008 μM, less than about 0.006 μM, less than about 0.005 μM, less than about 0.004 μM, less than about 0.003 μM, less than about 0.002 μM, less than about 0.001, less than about 0.00099 μM, less than about 0.00098 μM, less than about 0.00097 μM, less than about 0.00096 μM, less than about 0.00095 μM, less than about 0.00094 μM, less than about 0.00093 μM, less than about 0.00092, or less than about 0.00090 μM).

In one embodiment, the irreversible Btk inhibitor compound selectively and irreversibly inhibits an activated form of its target tyrosine kinase (e.g., a phosphorylated form of the tyrosine kinase). For example, activated Btk is transphosphorylated at tyrosine 551. Thus, in these embodiments the irreversible Btk inhibitor inhibits the target kinase in cells only once the target kinase is activated by the signaling events.

Described herein are compounds of any of Formula (IA), Formula (I), Formula (Ia), Formula (II), Formula (III), Formula (IV), Formula (Va)-(Vh), or Formula (VIa)-(VIb). Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided. In some embodiments, when compounds disclosed herein contain an oxidizable nitrogen atom, the nitrogen atom can be converted to an N-oxide by methods well known in the art. In certain embodiments, isomers and chemically protected forms of compounds having a structure represented by any of Formula (IA), Formula (I), Formula (Ia), Formula (II), Formula (III), Formula (IV), Formula (Va)-(Vh), or Formula (VIa)-(VIb) are also provided.

In another embodiment are compounds having the structure of Formula (IA):

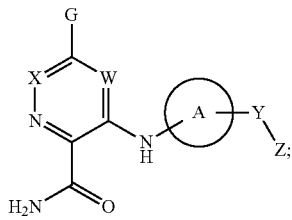

Formula (IA)

wherein:
ring A is substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;
W is —C($R_2$)— or —N—;
X is —C($R_2$)— or —N—;
Y is optionally present and when present is —CH$_2$O—, —OCH$_2$—, —OCH$_2$CH$_2$O—, —O—, —N($R_3$)—, —C(O)—, —N($R_3$)C(O)—, —C(O)N($R_3$)—, —N($R_3$)C(O)N($R_3$)—, —S(O)—, —S(O)$_2$—, —N($R_3$)S(O)$_2$—, —S(O)$_2$N($R_3$)—, —C(=NH)—, —C(=NH)N($R_3$)—, —C(=NH)N($R_3$)—, or substituted or unsubstituted $C_1$-$C_4$alkylene;
Z is optionally present and when present is substituted or unsubstituted $C_1$-$C_3$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;
G is

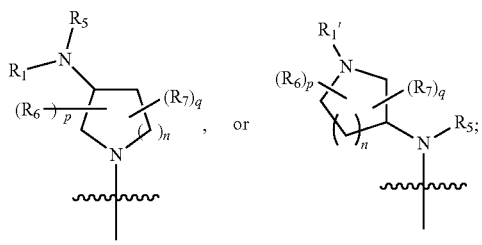

, or $R_1$ is —$R_4$, —CH$_2R_4$, —C(O)$R_9$, —C(O)C(O)$R_9$, —C(O)O$R_4$, —C(O)N($R_3$)($R_4$), or —S(O)$_2R_9$;
$R_{1'}$ is —C(O)$R_9$, —C(O)C(O)$R_9$, —C(O)O$R_4$, —C(O)N($R_3$)($R_4$), or —S(O)$_2R_9$;
each $R_2$ is independently H, substituted or unsubstituted $C_1$-$C_4$alkyl, —CN, or halogen;
each $R_3$ is independently is H, or substituted or unsubstituted $C_1$-$C_4$alkyl;
each $R_4$ is independently H, substituted or unsubstituted $C_1$-$C_6$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;
$R_5$ is H, substituted or unsubstituted $C_1$-$C_4$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;
or $R_1$ and $R_5$ together with the nitrogen atom to which they are attached are combined to form a substituted or unsubstituted $C_2$-$C_9$heterocycloalkyl ring;

each $R_6$ is independently halogen, —CN, —OH, —NH$_2$, substituted or unsubstituted $C_1$-$C_4$alkoxy, substituted or unsubstituted $C_1$-$C_4$alkyl, substituted or unsubstituted $C_3$-$C_6$cycloalkyl, substituted or unsubstituted $C_2$-$C_6$heterocycloalkyl, or —N($R_3$)$_2$; or $R_1$ and $R_6$ are combined to form a substituted or unsubstituted $C_2$-$C_9$heterocycloalkyl ring;
each $R_7$ is independently halogen, —CN, —OH, —NH$_2$, substituted or unsubstituted $C_1$-$C_4$alkoxy, substituted or unsubstituted $C_1$-$C_4$alkyl, substituted or unsubstituted $C_3$-$C_6$cycloalkyl, substituted or unsubstituted $C_2$-$C_6$heterocycloalkyl, or —N($R_3$)$_2$;
$R_9$ is —$R_4$, or

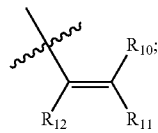

$R_{10}$ is H, halogen, —CN, or -$L_1$-$L_2$;
$R_{11}$ and $R_{12}$ are independently H, halogen, —CN, or -$L_1$-$L_2$; or $R_{11}$ and $R_{12}$ taken together form a bond;
each $L_1$ is optionally present and when present each $L_1$ is independently substituted or unsubstituted $C_1$-$C_6$alkyl, substituted or unsubstituted $C_3$-$C_6$cycloalkyl, substituted or unsubstituted $C_1$-$C_6$heteroalkyl, substituted or unsubstituted $C_2$-$C_7$heterocycloalkyl, substituted or unsubstituted $C_6$-$C_{12}$aryl, substituted or unsubstituted $C_1$-$C_{12}$heteroaryl, —C(=O)—, —O—, or —S—;
each $L_2$ is independently H, substituted or unsubstituted $C_1$-$C_6$alkyl, substituted or unsubstituted $C_3$-$C_6$cycloalkyl, substituted or unsubstituted $C_1$-$C_6$heteroalkyl, substituted or unsubstituted $C_2$-$C_7$heterocycloalkyl, substituted or unsubstituted $C_6$-$C_{12}$aryl, substituted or unsubstituted $C_1$-$C_{12}$heteroaryl or —N($R_{13}$)$_2$;
each $R_{13}$ is independently H, $C_1$-$C_6$alkyl, $C_3$-$C_6$cycloalkyl, $C_1$-$C_6$heteroalkyl, $C_2$-$C_7$ heterocycloalkyl, $C_6$-$C_{12}$aryl, or $C_1$-$C_{12}$heteroaryl;
n is 0-3;
p is 0-3; and
q is 0-3;
or a pharmaceutically acceptable solvate, pharmaceutically acceptable salt, or pharmaceutically acceptable prodrug thereof;
provided that
i) when W is N, and $R_1$ is H, t-Boc, or —C(O)—CH=CH$_2$; then X is other than C-Et or N; and
ii) when W is N, G is

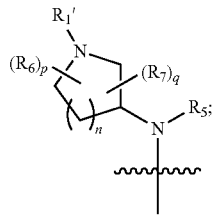

then X is CH or N;
iii) when W is N, and X is CH; then $R_{1'}$ is other than —C(O) Me, or t-Boc; and
iv) when n is 0; then each of p and q is independently 0, 1, or 2.

In one embodiment, each R₂ is independently H, —CN, or halogen.

In another embodiment, each of W and X is N. In another embodiment, each of W and X is N, ring A is phenyl, Y is —C(O)—, and Z is morpholinyl.

In another embodiment, each of W and X is N, and R₁' is —C(O)R₉, —C(O)C(O)R₉, —C(O)OR₄, —C(O)N(R₃)(R₄), or —S(O)₂R₉.

In another embodiment, each of W and X is N, and R₁' is —C(O)R₉, —C(O)OR₄, —C(O)N(R₃)(R₄), or —S(O)₂R₉.

In another embodiment, X is CH.

In another embodiment, W is N, X is CH, and R₁' is —C(O)R₉, —C(O)C(O)R₉, —C(O)OR₄, —C(O)N(R₃)(R₄), or —S(O)₂R₉.

In another embodiment, W is N, X is CH, and R₁' is —C(O)R₉, —C(O)OR₄, —C(O)N(R₃)(R₄), or —S(O)₂R₉.

In another embodiment are compounds having the structure of Formula (I):

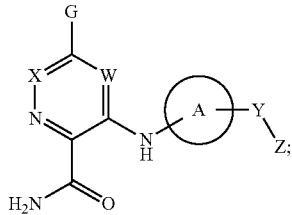

Formula (I)

wherein:
ring A is substituted or unsubstituted C₃-C₆cycloalkyl, substituted or unsubstituted C₂-C₇heterocycloalkyl, substituted or unsubstituted C₆-C₁₂aryl, or substituted or unsubstituted C₁-C₁₂heteroaryl;
W is —C(R₂)— or —N—;
X is —C(R₂)— or —N—;
Y is optionally present and when present is —CH₂O—, —OCH₂—, —OCH₂CH₂O—, —O—, —N(R₃)—, —C(O)—, —N(R₃)C(O)—, —C(O)N(R₃)—, —N(R₃)C(O)N(R₃)—, —S(O)—, —S(O)₂—, —N(R₃)S(O)₂—, —S(O)₂N(R₃)—, —C(=NH)—, —C(=NH)N(R₃)—, or substituted or unsubstituted C₁-C₄alkylene;
Z is optionally present and when present is substituted or unsubstituted C₁-C₃alkyl, substituted or unsubstituted C₃-C₆cycloalkyl, substituted or unsubstituted C₂-C₇heterocycloalkyl, substituted or unsubstituted C₆-C₁₂aryl, or substituted or unsubstituted C₁-C₁₂heteroaryl;
G is

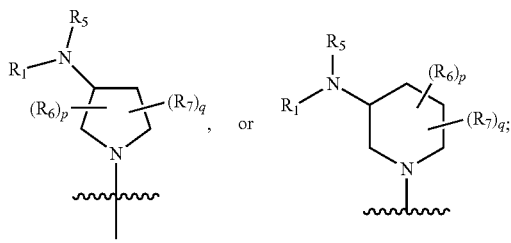

R₁ is —R₄, —CH₂R₄, —C(O)R₉, —C(O)C(O)R₉, —C(O)OR₄, —C(O)N(R₃)(R₄), or —S(O)₂R₉;
each R₂ is independently H, —CN, or halogen;
each R₃ is independently is H, or substituted or unsubstituted C₁-C₄alkyl;

each R₄ is independently H, substituted or unsubstituted C₁-C₆alkyl, substituted or unsubstituted C₃-C₆cycloalkyl, substituted or unsubstituted C₂-C₇heterocycloalkyl, substituted or unsubstituted C₆-C₁₂aryl, or substituted or unsubstituted C₁-C₁₂heteroaryl;
R₅ is H, substituted or unsubstituted C₁-C₄alkyl, substituted or unsubstituted C₃-C₆cycloalkyl, substituted or unsubstituted C₂-C₇heterocycloalkyl, substituted or unsubstituted C₆-C₁₂aryl, or substituted or unsubstituted C₁-C₁₂heteroaryl;
or R₁ and R₅ together with the nitrogen atom to which they are attached are combined to form a substituted or unsubstituted C₂-C₉heterocycloalkyl ring;
each R₆ is independently halogen, —CN, —OH, —NH₂, substituted or unsubstituted C₁-C₄alkoxy, substituted or unsubstituted C₁-C₄alkyl, substituted or unsubstituted C₃-C₆cycloalkyl, substituted or unsubstituted C₂-C₆heterocycloalkyl, or —N(R₃)₂; or R₁ and R₆ are combined to form a substituted or unsubstituted C₂-C₉heterocycloalkyl ring;
each R₇ is independently halogen, —CN, —OH, —NH₂, substituted or unsubstituted C₁-C₄alkoxy, substituted or unsubstituted C₁-C₄alkyl, substituted or unsubstituted C₃-C₆cycloalkyl, substituted or unsubstituted C₂-C₆heterocycloalkyl, or —N(R₃)₂;
R₉ is —R₄, or

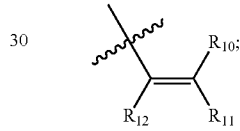

R₁₀ is H, halogen, —CN, or -L₁-L₂;
R₁₁ and R₁₂ are independently H, halogen, —CN, or -L₁-L₂; or R₁₁ and R₁₂ taken together form a bond;
each L₁ is optionally present and when present each L₁ is independently substituted or unsubstituted C₁-C₆alkyl, substituted or unsubstituted C₃-C₆cycloalkyl, substituted or unsubstituted C₁-C₆heteroalkyl, substituted or unsubstituted C₂-C₇heterocycloalkyl, substituted or unsubstituted C₆-C₁₂aryl, substituted or unsubstituted C₁-C₁₂heteroaryl, —C(=O)—, —O—, or —S—;
each L₂ is independently H, substituted or unsubstituted C₁-C₆alkyl, substituted or unsubstituted C₃-C₆cycloalkyl, substituted or unsubstituted C₁-C₆heteroalkyl, substituted or unsubstituted C₂-C₇heterocycloalkyl, substituted or unsubstituted C₆-C₁₂aryl, substituted or unsubstituted C₁-C₁₂heteroaryl or —N(R₁₃)₂;
each R₁₃ is independently H, C₁-C₆alkyl, C₃-C₆cycloalkyl, C₁-C₆heteroalkyl, C₂-C₇ heterocycloalkyl, C₆-C₁₂aryl, or C₁-C₁₂heteroaryl;
p is 0-3; and q is 0-3;
or a pharmaceutically acceptable solvate, pharmaceutically acceptable salt, or pharmaceutically acceptable prodrug thereof.

In one embodiment is a compound of Formula (IA) or (I) wherein Formula (IA) or (I) wherein ring A is substituted or unsubstituted C₃-C₆cycloalkyl. In another embodiment is a compound of Formula (IA) or (I) wherein Formula (IA) or (I) wherein ring A is substituted or unsubstituted C₂-C₇heterocycloalkyl. In another embodiment is a compound of Formula (IA) or (I) wherein Formula (IA) or (I) wherein ring A is substituted or unsubstituted C₆-C₁₂aryl. In another embodiment is a compound of Formula (IA) or (I)

wherein Formula (IA) or (I) wherein ring A is substituted or unsubstituted $C_1$-$C_{12}$heteroaryl.

In another embodiment is a compound of Formula (IA) or (I) wherein Formula (IA) or (I) wherein ring A is substituted or unsubstituted phenyl. In another embodiment is a compound of Formula (IA) or (I) wherein Formula (IA) or (I) wherein ring A is substituted or unsubstituted phenyl, Y is absent, and Z is substituted or unsubstituted $C_1$-$C_3$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl. In another embodiment is a compound of Formula (IA) or (I) wherein Formula (IA) or (I) wherein ring A is substituted or unsubstituted phenyl, Y is absent, and Z is substituted or unsubstituted $C_1$-$C_3$alkyl. In another embodiment is a compound of Formula (IA) or (I) wherein Formula (IA) or (I) wherein ring A is substituted or unsubstituted phenyl, Y is absent, and Z is substituted or unsubstituted $C_3$-$C_6$cycloalkyl. In another embodiment is a compound of Formula (IA) or (I) wherein Formula (IA) or (I) wherein ring A is substituted or unsubstituted phenyl, Y is absent, and Z is substituted or unsubstituted $C_2$-$C_7$heterocycloalkyl. In another embodiment is a compound of Formula (IA) or (I) wherein Formula (IA) or (I) wherein ring A is substituted or unsubstituted phenyl, Y is absent, and Z is substituted or unsubstituted $C_6$-$C_{12}$aryl. In another embodiment is a compound of Formula (IA) or (I) wherein Formula (IA) or (I) wherein ring A is substituted or unsubstituted phenyl, Y is absent, and Z is substituted or unsubstituted $C_1$-$C_{12}$heteroaryl. In another embodiment is a compound of Formula (IA) or (I) wherein Formula (IA) or (I) wherein ring A is substituted or unsubstituted phenyl, Y is absent, and Z is a substituted or unsubstituted pyrimidine. In another embodiment is a compound of Formula (IA) or (I) wherein Formula (IA) or (I) wherein ring A is substituted or unsubstituted phenyl, Y is absent, and Z is a substituted or unsubstituted oxazole.

In another embodiment is a compound of Formula (IA) or (I) wherein Formula (IA) or (I) wherein ring A is substituted or unsubstituted phenyl, Y is —C(O)—, and Z is substituted or unsubstituted $C_1$-$C_3$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl. In another embodiment is a compound of Formula (IA) or (I) wherein Formula (IA) or (I) wherein ring A is substituted or unsubstituted phenyl, Y is —C(O)—, and Z is substituted or unsubstituted $C_1$-$C_3$alkyl. In another embodiment is a compound of Formula (IA) or (I) wherein Formula (IA) or (I) wherein ring A is substituted or unsubstituted phenyl, Y is —C(O)—, and Z is substituted or unsubstituted $C_3$-$C_6$cycloalkyl. In another embodiment is a compound of Formula (IA) or (I) wherein Formula (IA) or (I) wherein ring A is substituted or unsubstituted phenyl, Y is —C(O)—, and Z is substituted or unsubstituted $C_2$-$C_7$heterocycloalkyl. In another embodiment is a compound of Formula (IA) or (I) wherein Formula (IA) or (I) wherein ring A is substituted or unsubstituted phenyl, Y is —C(O)—, and Z is substituted or unsubstituted morpholine. In another embodiment is a compound of Formula (IA) or (I) wherein Formula (IA) or (I) wherein ring A is substituted or unsubstituted phenyl, Y is —C(O)—, and Z is substituted or unsubstituted $C_6$-$C_{12}$aryl. In another embodiment is a compound of Formula (IA) or (I) wherein Formula (IA) or (I) wherein ring A is substituted or unsubstituted phenyl, Y is —C(O)—, and Z is substituted or unsubstituted $C_1$-$C_{12}$heteroaryl.

In another embodiment is a compound of Formula (IA) or (I) wherein Formula (IA) or (I) wherein G is

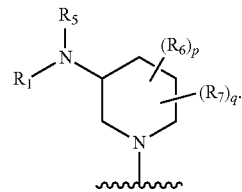

In another embodiment is a compound of Formula (IA) or (I) wherein Formula (IA) or (I) wherein G is

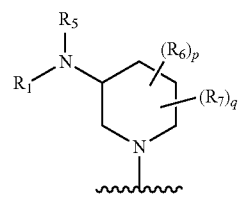

and $R_5$ is H. In another embodiment is a compound of Formula (IA) or (I) wherein Formula (IA) or (I) wherein G is

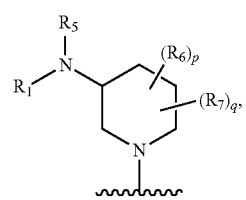

$R_5$ is H, and p and q are 0. In another embodiment is a compound of Formula (IA) or (I) wherein G is

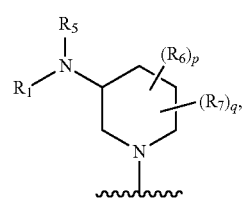

$R_5$ is H, p and q are 0, $R_1$ is —C(O)$R_9$, $R_9$ is —$R_4$, and $R_4$ is substituted or unsubstituted $C_6$-$C_{12}$aryl. In another embodiment is a compound of Formula (IA) or (I) wherein G is

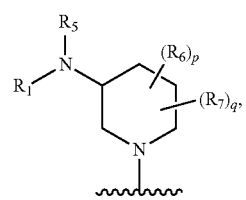

$R_5$ is H, p and q are 0, $R_1$ is —C(O)$R_9$, $R_9$ is —$R_4$, and $R_4$ is substituted or unsubstituted phenyl. In another embodiment is a compound of Formula (IA) or (I) wherein G is

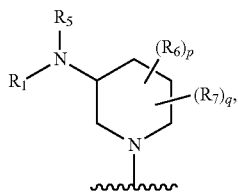

$R_5$ is H, p and q are 0, $R_1$ is —C(O)$R_9$, $R_9$ is —$R_4$, and $R_4$ is substituted or unsubstituted $C_1$-$C_{12}$heteroaryl. In another embodiment is a compound of Formula (IA) or (I) wherein G is

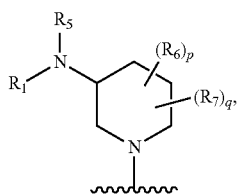

$R_5$ is H, p and q are 0, $R_t$ is —C(O)$R_9$, $R_9$ is —$R_4$, and $R_4$ is substituted or unsubstituted pyridine. In another embodiment is a compound of Formula (IA) or (I) wherein G is

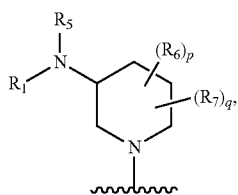

$R_5$ is H, p and q are 0, $R_t$ is —C(O)$R_9$, $R_9$ is —$R_4$, and $R_4$ is substituted or unsubstituted pyrimidine. In another embodiment is a compound of Formula (IA) or (I) wherein G is

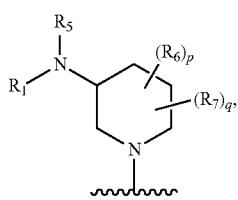

$R_5$ is H, p and q are 0, $R_t$ is —C(O)$R_9$, $R_9$ is —$R_4$, and $R_4$ is substituted or unsubstituted thiazole. In another embodiment is a compound of Formula (IA) or (I) wherein G is

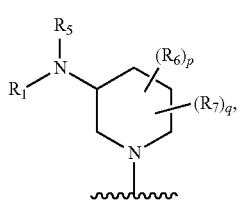

$R_5$ is H, p and q are 0, $R_t$ is —C(O)$R_9$, $R_9$ is —$R_4$, and $R_4$ is substituted or unsubstituted thiophene. In another embodiment is a compound of Formula (IA) or (I) wherein G is

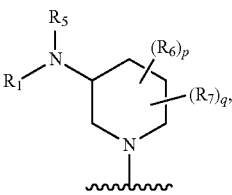

$R_5$ is H, p and q are 0, $R_t$ is —C(O)$R_9$, $R_9$ is —$R_4$, and $R_4$ is substituted or unsubstituted quinoline. In another embodiment is a compound of Formula (IA) or (I) wherein G is

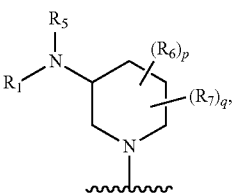

$R_5$ is H, p and q are 0, $R_1$ is —C(O)$R_9$, $R_9$ is —$R_4$, and $R_4$ is substituted or unsubstituted imidazopyridine. In another embodiment is a compound of Formula (IA) or (I) wherein G is

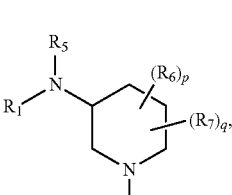

$R_5$ is H, p and q are 0, $R_1$ is —C(O)$R_9$, $R_9$ is —$R_4$, and $R_4$ is substituted or unsubstituted $C_1$-$C_6$alkyl. In another embodiment is a compound of Formula (IA) or (I) wherein G is

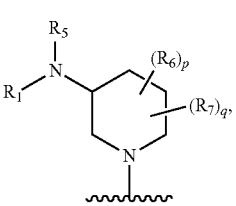

$R_5$ is H, p and q are 0, $R_t$ is —C(O)$R_9$, $R_9$ is —$R_4$, and $R_4$ is substituted or unsubstituted $C_3$-$C_6$cycloalkyl. In another embodiment is a compound of Formula (IA) or (I) wherein G is

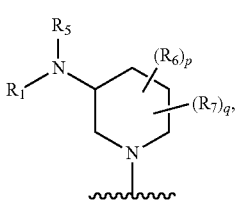

$R_5$ is H, p and q are 0, $R_1$ is —C(O)$R_9$, $R_9$ is —$R_4$, and $R_4$ is substituted or unsubstituted $C_2$-$C_7$heterocycloalkyl. In another embodiment is a compound of Formula (IA) or (I) wherein G is

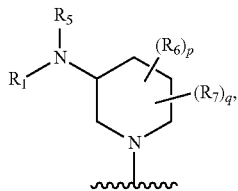

$R_5$ is H, p and q are 0, $R_1$ is —C(O)$R_9$, and $R_9$ is

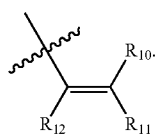

In another embodiment is a compound of Formula (IA) or (I) wherein G is

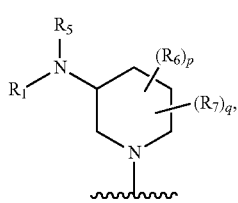

$R_5$ is H, p and q are 0, $R_1$ is —C(O)$R_9$, $R_9$ is

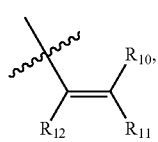

and $R_{10}$, $R_{11}$, and $R_{12}$ are each H. In another embodiment is a compound of Formula (IA) or (I) wherein G is

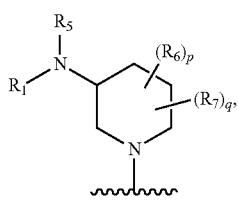

$R_5$ is H, p and q are 0, $R_1$ is —C(O)$R_9$, $R_9$ is

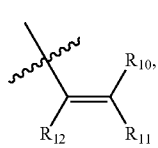

and $R_{11}$ and $R_{12}$ taken together form a bond.

In another embodiment is a compound of Formula (IA) or (I) wherein G is

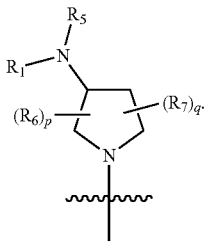

In another embodiment is a compound of Formula (IA) or (I) wherein G is

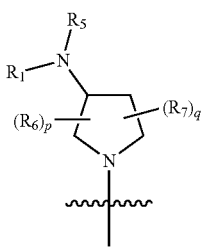

and $R_5$ is H. In another embodiment is a compound of Formula (IA) or (I) wherein G is

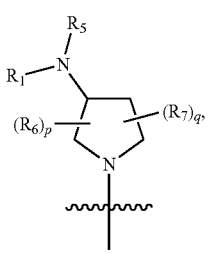

$R_5$ is H, and p and q are 0. In another embodiment is a compound of Formula (IA) or (I) wherein G is

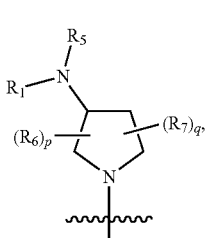

$R_5$ is H, p and q are 0, $R_1$ is —C(O)$R_9$, $R_9$ is —$R_4$, and $R_4$ is substituted or unsubstituted $C_6$-$C_{12}$aryl. In another embodiment is a compound of Formula (IA) or (I) wherein G is

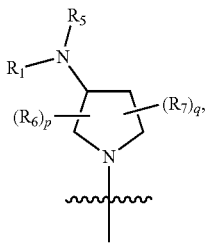

$R_5$ is H, p and q are 0, $R_1$ is —C(O)$R_9$, $R_9$ is —$R_4$, and $R_4$ is substituted or unsubstituted phenyl. In another embodiment is a compound of Formula (IA) or (I) wherein G is

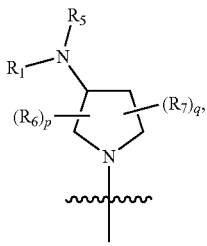

$R_5$ is H, p and q are 0, $R_1$ is —C(O)$R_9$, $R_9$ is —$R_4$, and $R_4$ is substituted or unsubstituted $C_1$-$C_{12}$heteroaryl. In another embodiment is a compound of Formula (IA) or (I) wherein G is

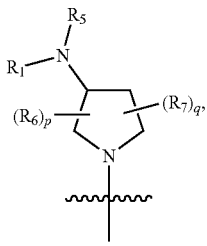

$R_5$ is H, p and q are 0, $R_1$ is —C(O)$R_9$, $R_9$ is —$R_4$, and $R_4$ is substituted or unsubstituted pyridine. In another embodiment is a compound of Formula (IA) or (I) wherein G is

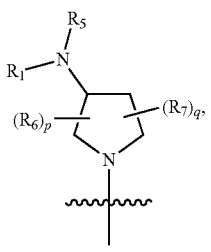

$R_5$ is H, p and q are 0, $R_1$ is —C(O)$R_9$, $R_9$ is —$R_4$, and $R_4$ is substituted or unsubstituted pyrimidine. In another embodiment is a compound of Formula (IA) or (I) wherein G is

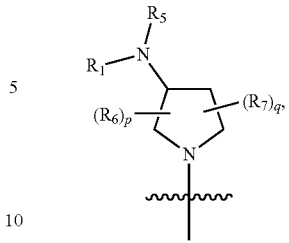

$R_5$ is H, p and q are 0, $R_1$ is —C(O)$R_9$, $R_9$ is —$R_4$, and $R_4$ is substituted or unsubstituted thiazole. In another embodiment is a compound of Formula (IA) or (I) wherein G is

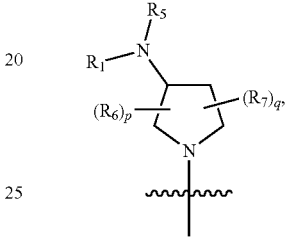

$R_5$ is H, p and q are 0, $R_1$ is —C(O)$R_9$, $R_9$ is —$R_4$, and $R_4$ is substituted or unsubstituted thiophene. In another embodiment is a compound of Formula (IA) or (I) wherein G is

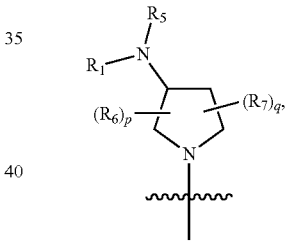

$R_5$ is H, p and q are 0, $R_1$ is —C(O)$R_9$, $R_9$ is —$R_4$, and $R_4$ is substituted or unsubstituted quinoline. In another embodiment is a compound of Formula (IA) or (I) wherein G is

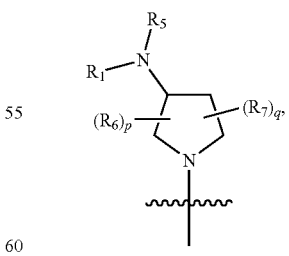

$R_5$ is H, p and q are 0, $R_1$ is —C(O)$R_9$, $R_9$ is —$R_4$, and $R_4$ is substituted or unsubstituted imidazopyridine. In another embodiment is a compound of Formula (IA) or (I) wherein G is

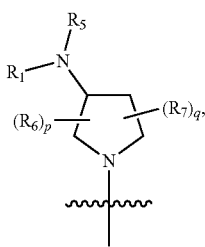

$R_5$ is H, p and q are 0, $R_1$ is —C(O)$R_9$, $R_9$ is —$R_4$, and $R_4$ is substituted or unsubstituted $C_1$-$C_6$alkyl. In another embodiment is a compound of Formula (IA) or (I) wherein G is

$R_5$ is H, p and q are 0, $R_1$ is —C(O)$R_9$, $R_9$ is —$R_4$, and $R_4$ is substituted or unsubstituted $C_3$-$C_6$cycloalkyl. In another embodiment is a compound of Formula (IA) or (I) wherein G is

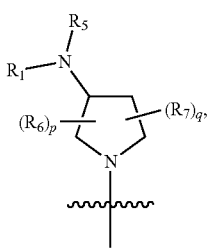

$R_5$ is H, p and q are 0, $R_1$ is —C(O)$R_9$, $R_9$ is —$R_4$, and $R_4$ is substituted or unsubstituted $C_2$-$C_7$heterocycloalkyl. In another embodiment is a compound of Formula (IA) or (I) wherein G is

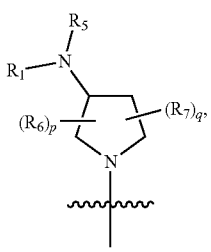

$R_5$ is H, p and q are 0, $R_1$ is —C(O)$R_9$, and $R_9$ is

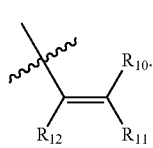

In another embodiment is a compound of Formula (IA) or (I) wherein G is

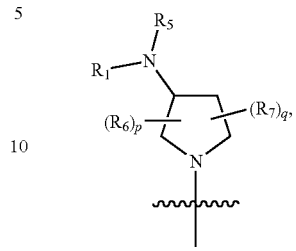

$R_5$ is H, p and q are 0, $R_1$ is —C(O)$R_9$, $R_9$ is

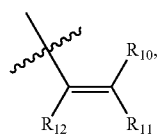

and $R_{10}$, $R_{11}$, and $R_{12}$ are each H. In another embodiment is a compound of Formula (IA) or (I) wherein G is

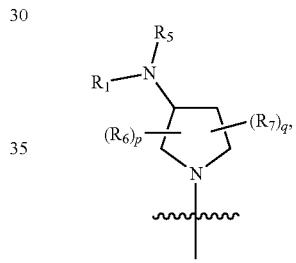

$R_5$ is H, p and q are 0, $R_1$ is —C(O)$R_9$, $R_9$ is

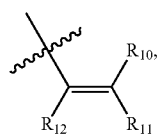

and $R_{11}$ and $R_{12}$ taken together form a bond.

In another embodiment are compounds having the structure of Formula (Ia):

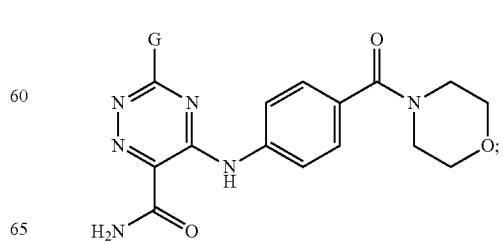

Formula (Ia)

wherein:
G is

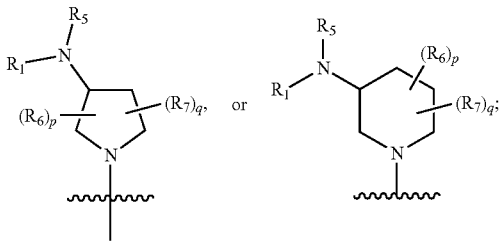

$R_1$ is —$R_4$, —$CH_2R_4$, —$C(O)R_9$, —$C(O)C(O)R_9$, —$C(O)OR_4$, —$C(O)N(R_3)(R_4)$, or —$S(O)_2R_9$;

each $R_3$ is independently is H, or substituted or unsubstituted $C_1$-$C_4$alkyl;

each $R_4$ is independently H, substituted or unsubstituted $C_1$-$C_6$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;

$R_5$ is H, substituted or unsubstituted $C_1$-$C_4$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl; or $R_1$ and $R_5$ together with the nitrogen atom to which they are attached are combined to form a substituted or unsubstituted $C_2$-$C_9$heterocycloalkyl ring;

each $R_6$ is independently halogen, —CN, —OH, —$NH_2$, substituted or unsubstituted $C_1$-$C_4$alkoxy, substituted or unsubstituted $C_1$-$C_4$alkyl, substituted or unsubstituted $C_3$-$C_6$cycloalkyl, substituted or unsubstituted $C_2$-$C_6$heterocycloalkyl, or —$N(R_3)_2$; or $R_1$ and $R_6$ are combined to form a substituted or unsubstituted $C_2$-$C_9$heterocycloalkyl ring;

each $R_7$ is independently halogen, —CN, —OH, —$NH_2$, substituted or unsubstituted $C_1$-$C_4$alkoxy, substituted or unsubstituted $C_1$-$C_4$alkyl, substituted or unsubstituted $C_3$-$C_6$cycloalkyl, substituted or unsubstituted $C_2$-$C_6$heterocycloalkyl, or —$N(R_3)_2$;

$R_9$ is —$R_4$, or

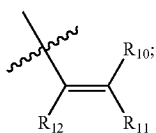

$R_{10}$ is H, halogen, —CN, or -$L_1$-$L_2$;

$R_{11}$ and $R_{12}$ are independently H, halogen, —CN, or -$L_1$-$L_2$; or $R_{11}$ and $R_{12}$ taken together form a bond;

each $L_1$ is optionally present and when present each $L_1$ is independently substituted or unsubstituted $C_1$-$C_6$alkyl, substituted or unsubstituted $C_3$-$C_6$cycloalkyl, substituted or unsubstituted $C_1$-$C_6$heteroalkyl, substituted or unsubstituted $C_2$-$C_7$heterocycloalkyl, substituted or unsubstituted $C_6$-$C_{12}$aryl, substituted or unsubstituted $C_1$-$C_{12}$heteroaryl, —C(=O)—, —O—, or —S—;

each $L_2$ is independently H, substituted or unsubstituted $C_1$-$C_6$alkyl, substituted or unsubstituted $C_3$-$C_6$cycloalkyl, substituted or unsubstituted $C_1$-$C_6$heteroalkyl, substituted or unsubstituted $C_2$-$C_7$heterocycloalkyl, substituted or unsubstituted $C_6$-$C_{12}$aryl, substituted or unsubstituted $C_1$-$C_{12}$heteroaryl or —$N(R_{13})_2$;

each $R_{13}$ is independently H, $C_1$-$C_6$alkyl, $C_3$-$C_6$cycloalkyl, $C_1$-$C_6$heteroalkyl, $C_2$-$C_7$ heterocycloalkyl, $C_6$-$C_{12}$aryl, or $C_1$-$C_{12}$heteroaryl;

p is 0-3; and q is 0-3;

or a pharmaceutically acceptable solvate, pharmaceutically acceptable salt, or pharmaceutically acceptable prodrug thereof.

In another embodiment is a compound of Formula (Ia) wherein G is

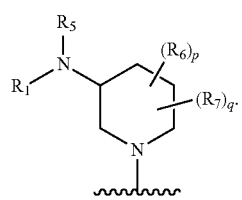

In another embodiment is a compound of Formula (Ia) wherein G is

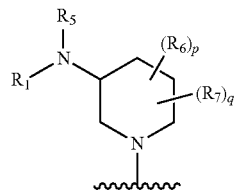

and $R_5$ is H. In another embodiment is a compound of Formula (Ia) wherein G is

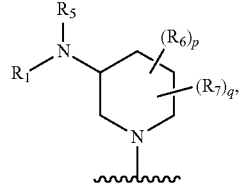

$R_5$ is H, and p and q are 0. In another embodiment is a compound of Formula (Ia) wherein G is

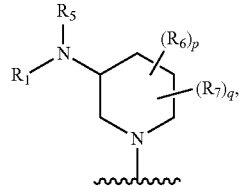

$R_5$ is H, p and q are 0, $R_1$ is —$C(O)R_9$, $R_9$ is —$R_4$, and $R_4$ is substituted or unsubstituted $C_6$-$C_{12}$aryl. In another embodiment is a compound of Formula (Ia) wherein G is

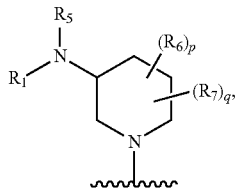

$R_5$ is H, p and q are 0, $R_1$ is —C(O)$R_9$, $R_9$ is —$R_4$, and $R_4$ is substituted or unsubstituted phenyl. In another embodiment is a compound of Formula (Ia) wherein G is

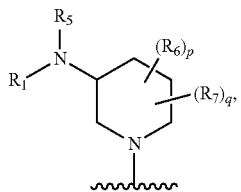

$R_5$ is H, p and q are 0, $R_1$ is —C(O)$R_9$, $R_9$ is —$R_4$, and $R_4$ is substituted or unsubstituted $C_1$-$C_{12}$heteroaryl. In another embodiment is a compound of Formula (Ia) wherein G is

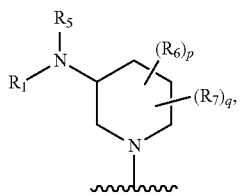

$R_5$ is H, p and q are 0, $R_1$ is —C(O)$R_9$, $R_9$ is —$R_4$, and $R_4$ is substituted or unsubstituted pyridine. In another embodiment is a compound of Formula (Ia) wherein G is

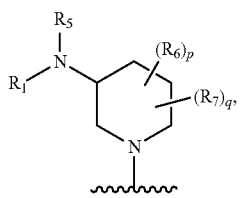

$R_5$ is H, p and q are 0, $R_1$ is —C(O)$R_9$, $R_9$ is —$R_4$, and $R_4$ is substituted or unsubstituted pyrimidine. In another embodiment is a compound of Formula (Ia) wherein G is

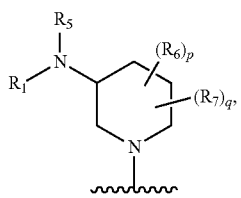

$R_5$ is H, p and q are 0, $R_1$ is —C(O)$R_9$, $R_9$ is —$R_4$, and $R_4$ is substituted or unsubstituted thiazole. In another embodiment is a compound of Formula (Ia) wherein G is

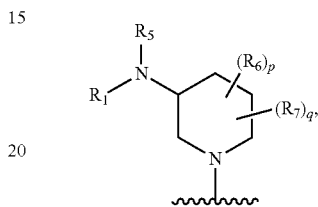

$R_5$ is H, p and q are 0, $R_1$ is —C(O)$R_9$, $R_9$ is —$R_4$, and $R_4$ is substituted or unsubstituted thiophene. In another embodiment is a compound of Formula (Ia) wherein G is

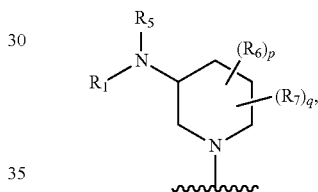

$R_5$ is H, p and q are 0, $R_1$ is —C(O)$R_9$, $R_9$ is —$R_4$, and $R_4$ is substituted or unsubstituted quinoline. In another embodiment is a compound of Formula (Ia) wherein G is

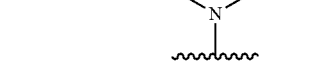

$R_5$ is H, p and q are 0, $R_1$ is —C(O)$R_9$, $R_9$ is —$R_4$, and $R_4$ is substituted or unsubstituted imidazopyridine. In another embodiment is a compound of Formula (Ia) wherein G is

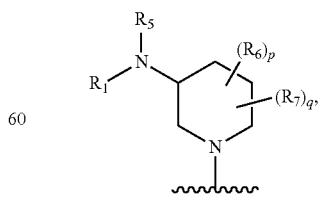

$R_5$ is H, p and q are 0, $R_1$ is —C(O)$R_9$, $R_9$ is —$R_4$, and $R_4$ is substituted or unsubstituted $C_1$-$C_6$alkyl. In another embodiment is a compound of Formula (Ia) wherein G is $R_5$ is H, p and q are 0, $R_1$ is —C(O)$R_9$, $R_9$ is —$R_4$, and $R_4$ is substituted or unsubstituted $C_3$-$C_6$cycloalkyl. In another embodiment is a compound of Formula (Ia) wherein G is

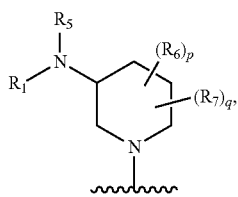

$R_5$ is H, p and q are 0, $R_1$ is —C(O)$R_9$, $R_9$ is —$R_4$, and $R_4$ is substituted or unsubstituted $C_2$-$C_7$heterocycloalkyl. In another embodiment is a compound of Formula (Ia) wherein G is

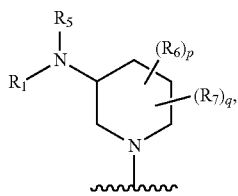

$R_5$ is H, p and q are 0, $R_1$ is —C(O)$R_9$, and $R_9$ is

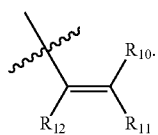

In another embodiment is a compound of Formula (Ia) wherein G is

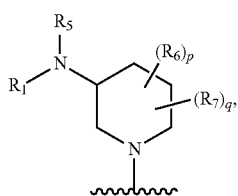

$R_5$ is H, p and q are 0, $R_1$ is —C(O)$R_9$, $R_9$ is

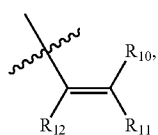

and $R_{10}$, $R_{11}$, and $R_{12}$ are each H. In another embodiment is a compound of Formula (Ia) wherein

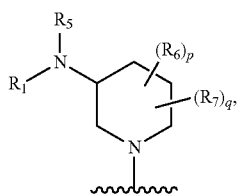

$R_5$ is H, p and q are 0, $R_1$ is —C(O)$R_9$, $R_9$ is

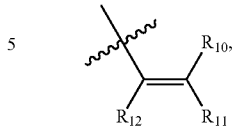

and $R_{11}$ and $R_{12}$ taken together form a bond.

In another embodiment is a compound of Formula (Ia) wherein G is

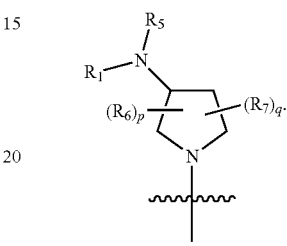

In another embodiment is a compound of Formula (Ia) wherein G is

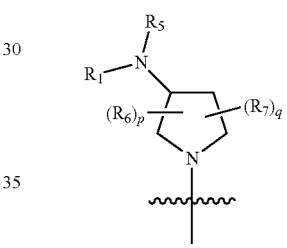

and $R_5$ is H. In another embodiment is a compound of Formula (Ia) wherein G is

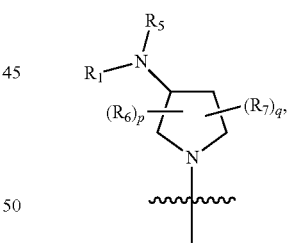

$R_5$ is H, and p and q are 0. In another embodiment is a compound of Formula (Ia) wherein G is

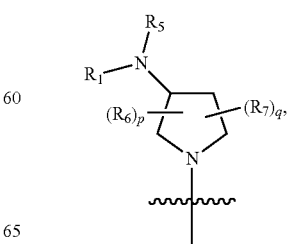

$R_5$ is H, p and q are 0, $R_1$ is —C(O)$R_9$, $R_9$ is —$R_4$, and $R_4$ is substituted or unsubstituted $C_6$-$C_{12}$aryl. In another embodiment is a compound of Formula (Ia) wherein G is

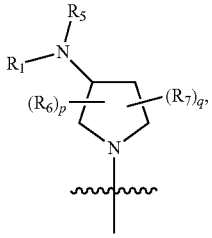

$R_5$ is H, p and q are 0, $R_1$ is —C(O)$R_9$, $R_9$ is —$R_4$, and $R_4$ is substituted or unsubstituted phenyl. In another embodiment is a compound of Formula (Ia) wherein G is

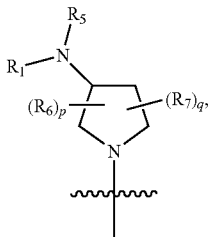

$R_5$ is H, p and q are 0, $R_1$ is —C(O)$R_9$, $R_9$ is —$R_4$, and $R_4$ is substituted or unsubstituted $C_1$-$C_{12}$heteroaryl. In another embodiment is a compound of Formula (Ia) wherein G is

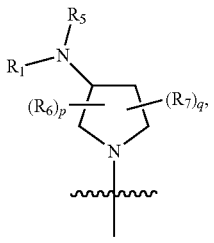

$R_5$ is H, p and q are 0, $R_1$ is —C(O)$R_9$, $R_9$ is —$R_4$, and $R_4$ is substituted or unsubstituted pyridine. In another embodiment is a compound of Formula (Ia) wherein G is

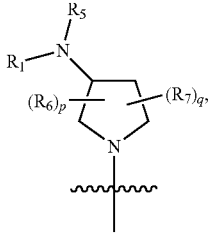

$R_5$ is H, p and q are 0, $R_1$ is —C(O)$R_9$, $R_9$ is —$R_4$, and $R_4$ is substituted or unsubstituted pyrimidine. In another embodiment is a compound of Formula (Ia) wherein G is

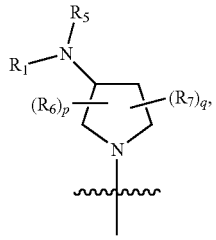

$R_5$ is H, p and q are 0, $R_1$ is —C(O)$R_9$, $R_9$ is —$R_4$, and $R_4$ is substituted or unsubstituted thiazole. In another embodiment is a compound of Formula (Ia) wherein G is

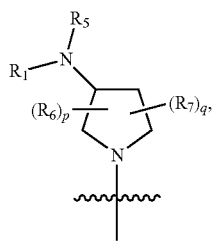

$R_5$ is H, p and q are 0, $R_1$ is —C(O)$R_9$, $R_9$ is —$R_4$, and $R_4$ is substituted or unsubstituted thiophene. In another embodiment is a compound of Formula (Ia) wherein G is

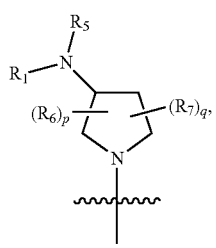

$R_5$ is H, p and q are 0, $R_1$ is —C(O)$R_9$, $R_9$ is —$R_4$, and $R_4$ is substituted or unsubstituted quinoline. In another embodiment is a compound of Formula (Ia) wherein G is

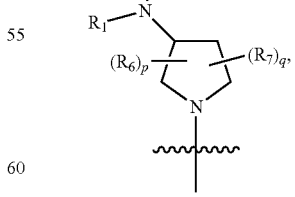

$R_5$ is H, p and q are 0, $R_1$ is —C(O)$R_9$, $R_9$ is —$R_4$, and $R_4$ is substituted or unsubstituted imidazopyridine. In another embodiment is a compound of Formula (Ia) wherein G is

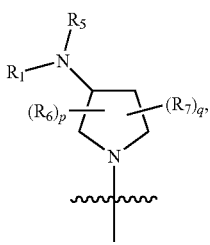

$R_5$ is H, p and q are 0, $R_1$ is —C(O)$R_9$, $R_9$ is —$R_4$, and $R_4$ is substituted or unsubstituted $C_1$-$C_6$alkyl. In another embodiment is a compound of Formula (Ia) wherein G is

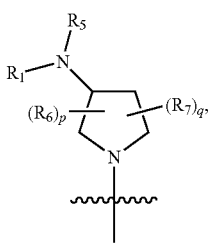

$R_5$ is H, p and q are 0, $R_1$ is —C(O)$R_9$, $R_9$ is —$R_4$, and $R_4$ is substituted or unsubstituted $C_3$-$C_6$cycloalkyl. In another embodiment is a compound of Formula (Ia) wherein G is

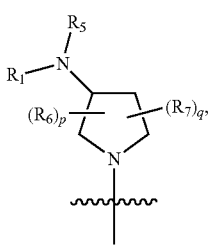

$R_5$ is H, p and q are 0, $R_1$ is —C(O)$R_9$, $R_9$ is —$R_4$, and $R_4$ is substituted or unsubstituted $C_2$-$C_7$heterocycloalkyl. In another embodiment is a compound of Formula (Ia) wherein G is

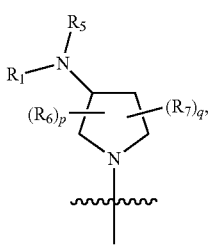

$R_5$ is H, p and q are 0, $R_1$ is —C(O)$R_9$, and $R_9$ is

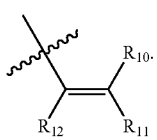

In another embodiment is a compound of Formula (Ia) wherein G is

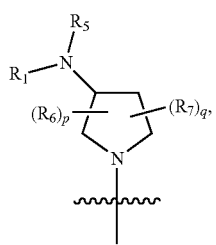

$R_5$ is H, p and q are 0, $R_1$ is —C(O)$R_9$, $R_9$ is

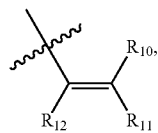

and $R_{10}$, $R_{11}$, and $R_{12}$ are each H. In another embodiment is a compound of Formula (Ia) wherein G is

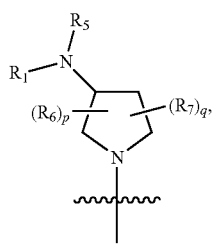

$R_5$ is H, p and q are 0, $R_1$ is —C(O)$R_9$, $R_9$ is

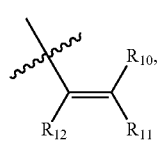

and $R_{11}$ and $R_{12}$ taken together form a bond.

In another embodiment are compounds having the structure of Formula (II):

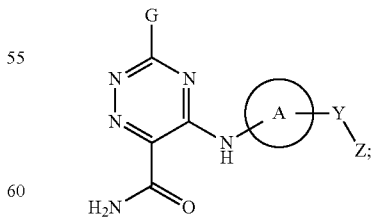

Formula (II)

wherein:
ring A is substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;

Y is optionally present and when present is —CH$_2$O—, —OCH$_2$—, —OCH$_2$CH$_2$O—, —O—, —N(R$_3$)—, —C(O)—, —N(R$_3$)C(O)—, —C(O)N(R$_3$)—, —N(R$_3$)C(O)N(R$_3$)—, —S(O)—, —S(O)$_2$—, —N(R$_3$)S(O)$_2$—, —S(O)$_2$N(R$_3$)—, —C(=NH)—, —C(=NH)N(R$_3$)—, or substituted or unsubstituted C$_1$-C$_4$alkylene;

Z is optionally present and when present is substituted or unsubstituted C$_1$-C$_3$alkyl, substituted or unsubstituted C$_3$-C$_6$cycloalkyl, substituted or unsubstituted C$_2$-C$_7$heterocycloalkyl, substituted or unsubstituted C$_6$-C$_{12}$aryl, or substituted or unsubstituted C$_1$-C$_{12}$heteroaryl;

G is

[Chemical structures shown]

R$_1$ is —C(O)R$_9$, —C(O)OR$_4$, —C(O)N(R$_3$)(R$_4$), or —S(O)$_2$R$_9$;

each R$_3$ is independently is H, or substituted or unsubstituted C$_1$-C$_4$alkyl;

R$_4$ is substituted or unsubstituted C$_1$-C$_4$alkyl, substituted or unsubstituted C$_3$-C$_6$cycloalkyl, substituted or unsubstituted C$_2$-C$_7$heterocycloalkyl, substituted or unsubstituted C$_6$-C$_{12}$aryl, or substituted or unsubstituted C$_1$-C$_{12}$heteroaryl;

R$_5$ is H, substituted or unsubstituted C$_1$-C$_4$alkyl, substituted or unsubstituted C$_3$-C$_6$cycloalkyl, substituted or unsubstituted C$_2$-C$_7$heterocycloalkyl, substituted or unsubstituted C$_6$-C$_{12}$aryl, or substituted or unsubstituted C$_1$-C$_{12}$heteroaryl;

each R$_6$ and R$_7$ is independently halogen, —CN, —OH, —NH$_2$, substituted or unsubstituted C$_1$-C$_4$alkoxy, substituted or unsubstituted C$_1$-C$_4$alkyl, substituted or unsubstituted C$_3$-C$_6$cycloalkyl, substituted or unsubstituted C$_2$-C$_6$heterocycloalkyl, or —N(R$_3$)$_2$;

R$_9$ is substituted or unsubstituted C$_1$-C$_6$alkyl, substituted or unsubstituted C$_3$-C$_6$cycloalkyl, substituted or unsubstituted C$_2$-C$_7$heterocycloalkyl, substituted or unsubstituted C$_6$-C$_{12}$aryl, substituted or unsubstituted C$_1$-C$_{12}$heteroaryl, or

[Chemical structure shown with R$_{10}$, R$_{11}$, R$_{12}$]

R$_{10}$ is H, halogen, —CN, or -L$_1$-L$_2$;

R$_{11}$ and R$_{12}$ are independently H, halogen, —CN, or -L$_1$-L$_2$; or R$_{11}$ and R$_{12}$ taken together form a bond;

each L$_1$ is optionally present and when present each L$_1$ is independently substituted or unsubstituted C$_1$-C$_6$alkyl, substituted or unsubstituted C$_3$-C$_6$cycloalkyl, substituted or unsubstituted C$_1$-C$_6$heteroalkyl, substituted or unsubstituted C$_2$-C$_7$heterocycloalkyl, substituted or unsubstituted C$_6$-C$_{12}$aryl, substituted or unsubstituted C$_1$-C$_{12}$heteroaryl, —C(=O)—, —O—, or —S—;

each L$_2$ is independently H, substituted or unsubstituted C$_1$-C$_6$alkyl, substituted or unsubstituted C$_3$-C$_6$cycloalkyl, substituted or unsubstituted C$_1$-C$_6$heteroalkyl, substituted or unsubstituted C$_2$-C$_7$heterocycloalkyl, substituted or unsubstituted C$_6$-C$_{12}$aryl, substituted or unsubstituted C$_1$-C$_{12}$heteroaryl or —N(R$_{13}$)$_2$;

each R$_{13}$ is independently H, C$_1$-C$_6$alkyl, C$_3$-C$_6$cycloalkyl, C$_1$-C$_6$heteroalkyl, C$_2$-C$_7$heterocycloalkyl, C$_6$-C$_{12}$aryl, or C$_1$-C$_{12}$heteroaryl;

p is 0-3; and q is 0-3;

or a pharmaceutically acceptable solvate, pharmaceutically acceptable salt, or pharmaceutically acceptable prodrug thereof.

In another embodiment is a compound of Formula (II) wherein ring A is substituted or unsubstituted C$_3$-C$_6$cycloalkyl. In another embodiment is a compound of Formula (II) wherein ring A is substituted or unsubstituted C$_2$-C$_7$heterocycloalkyl. In another embodiment is a compound of Formula (II) wherein ring A is substituted or unsubstituted C$_6$-C$_{12}$aryl. In another embodiment is a compound of Formula (II) wherein ring A is substituted or unsubstituted C$_1$-C$_{12}$heteroaryl.

In another embodiment is a compound of Formula (II) wherein ring A is substituted or unsubstituted phenyl. In another embodiment is a compound of Formula (II) wherein ring A is substituted or unsubstituted phenyl, Y is absent, and Z is substituted or unsubstituted C$_1$-C$_3$alkyl, substituted or unsubstituted C$_3$-C$_6$cycloalkyl, substituted or unsubstituted C$_2$-C$_7$heterocycloalkyl, substituted or unsubstituted C$_6$-C$_{12}$aryl, or substituted or unsubstituted C$_1$-C$_{12}$heteroaryl. In another embodiment is a compound of Formula (II) wherein ring A is substituted or unsubstituted phenyl, Y is absent, and Z is substituted or unsubstituted C$_1$-C$_3$alkyl. In another embodiment is a compound of Formula (II) wherein ring A is substituted or unsubstituted phenyl, Y is absent, and Z is substituted or unsubstituted C$_3$-C$_6$cycloalkyl. In another embodiment is a compound of Formula (II) wherein ring A is substituted or unsubstituted phenyl, Y is absent, and Z is substituted or unsubstituted C$_2$-C$_7$heterocycloalkyl. In another embodiment is a compound of Formula (II) wherein ring A is substituted or unsubstituted phenyl, Y is absent, and Z is substituted or unsubstituted C$_6$-C$_{12}$aryl. In another embodiment is a compound of Formula (II) wherein ring A is substituted or unsubstituted phenyl, Y is absent, and Z is substituted or unsubstituted C$_1$-C$_{12}$heteroaryl. In another embodiment is a compound of Formula (II) wherein ring A is substituted or unsubstituted phenyl, Y is absent, and Z is a substituted or unsubstituted pyrimidine. In another embodiment is a compound of Formula (II) wherein ring A is substituted or unsubstituted phenyl, Y is absent, and Z is a substituted or unsubstituted oxazole.

In another embodiment is a compound of Formula (II) wherein ring A is substituted or unsubstituted phenyl, Y is —C(O)—, and Z is substituted or unsubstituted C$_1$-C$_3$alkyl, substituted or unsubstituted C$_3$-C$_6$cycloalkyl, substituted or unsubstituted C$_2$-C$_7$heterocycloalkyl, substituted or unsubstituted C$_6$-C$_{12}$aryl, or substituted or unsubstituted C$_1$-C$_{12}$heteroaryl. In another embodiment is a compound of Formula (II) wherein ring A is substituted or unsubstituted phenyl, Y is —C(O)—, and Z is substituted or unsubstituted C$_1$-C$_3$alkyl. In another embodiment is a compound of Formula (II) wherein ring A is substituted or unsubstituted phenyl, Y is —C(O)—, and Z is substituted or unsubstituted C$_3$-C$_6$cycloalkyl. In another embodiment is a compound of Formula (II) wherein ring A is substituted or unsubstituted phenyl, Y is —C(O)—, and Z is substituted or unsubstituted C$_2$-C$_7$heterocycloalkyl. In another embodiment is a compound of Formula (II) wherein ring A is substituted or unsubstituted phenyl, Y is —C(O)—, and Z is substituted or unsubstituted morpholine. In another embodiment is a compound of Formula (II) wherein ring A is substituted or unsubstituted phenyl, Y is —C(O)—, and Z is substituted or unsubstituted $C_6$-$C_{12}$aryl. In another embodiment is a compound of Formula (II) wherein ring A is substituted or unsubstituted phenyl, Y is —C(O)—, and Z is substituted or unsubstituted $C_1$-$C_{12}$heteroaryl.

In another embodiment is a compound of Formula (II) wherein G is

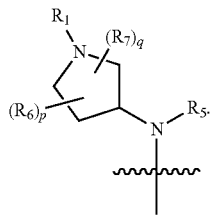

In another embodiment is a compound of Formula (II) wherein G is

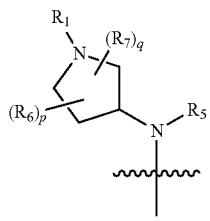

and $R_5$ is H. In another embodiment is a compound of Formula (II) wherein G is

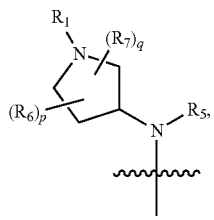

$R_5$ is H, and p and q are 0. In another embodiment is a compound of Formula (II) wherein G is

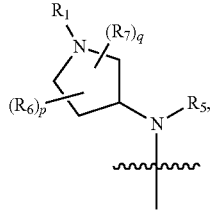

$R_5$ is H, p and q are 0, $R_1$ is —C(O)$R_9$, $R_9$ is substituted or unsubstituted $C_6$-$C_{12}$aryl. In another embodiment is a compound of Formula (II) wherein G is

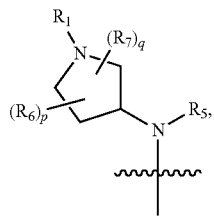

$R_5$ is H, p and q are 0, $R_1$ is —C(O)$R_9$, $R_9$ is substituted or unsubstituted phenyl. In another embodiment is a compound of Formula (II) wherein G is

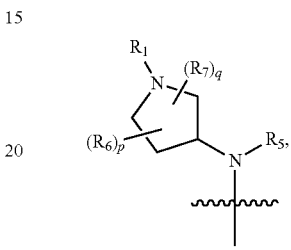

$R_5$ is H, p and q are 0, $R_1$ is —C(O)$R_9$, $R_9$ is substituted or unsubstituted $C_1$-$C_{12}$heteroaryl. In another embodiment is a compound of Formula (II) wherein G is

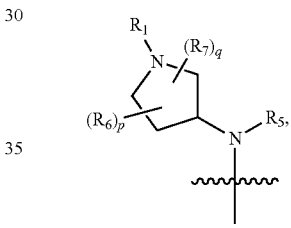

$R_5$ is H, p and q are 0, $R_1$ is —C(O)$R_9$, and $R_9$ is substituted or unsubstituted $C_1$-$C_6$alkyl. In another embodiment is a compound of Formula (II) wherein G is

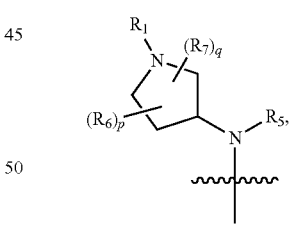

$R_5$ is H, p and q are 0, $R_1$ is —C(O)$R_9$, $R_9$ is substituted or unsubstituted $C_3$-$C_6$cycloalkyl. In another embodiment is a compound of Formula (II) wherein G is

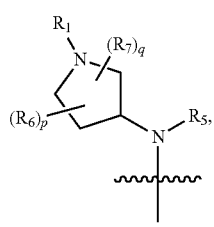

$R_5$ is H, p and q are 0, $R_1$ is —C(O)$R_9$, $R_9$ is substituted or unsubstituted $C_2$-$C_7$heterocycloalkyl. In another embodiment is a compound of Formula (II) wherein G is

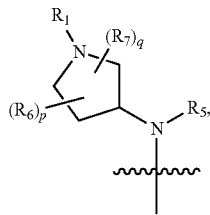

$R_5$ is H, p and q are 0, $R_1$ is —C(O)$R_9$, and $R_9$ is

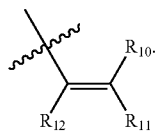

In another embodiment is a compound of Formula (II) wherein G is

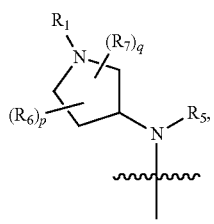

$R_5$ is H, p and q are 0, $R_1$ is —C(O)$R_9$, $R_9$ is

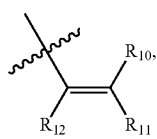

and $R_{10}$, $R_{11}$, and $R_{12}$ are each H. In another embodiment is a compound of Formula (II) wherein G is

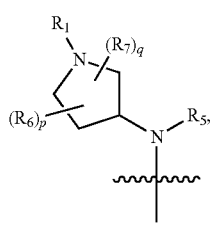

$R_5$ is H, p and q are 0, $R_1$ is —C(O)$R_9$, $R_9$ is

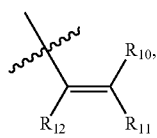

$R_{10}$ and $R_{12}$ are each H, $R_{11}$ is -$L_1$-$L_2$, $L_1$ is —CH$_2$—, and $L_2$ is —N(CH$_3$)$_2$. In another embodiment is a compound of Formula (II) wherein G is

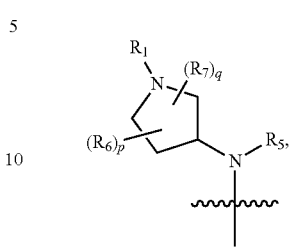

$R_5$ is H, p and q are 0, $R_1$ is —C(O)$R_9$, $R_9$ is

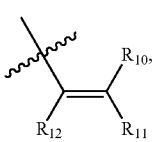

and $R_{11}$ and $R_{12}$ taken together form a bond.
In another embodiment is a compound of Formula (II) wherein G is

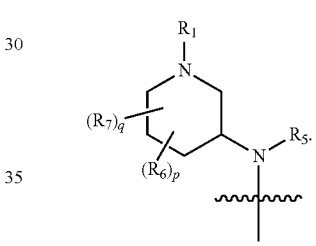

In another embodiment is a compound of Formula (II) wherein G is

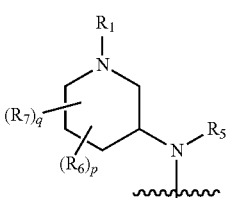

and $R_5$ is H. In another embodiment is a compound of Formula (II) wherein G is

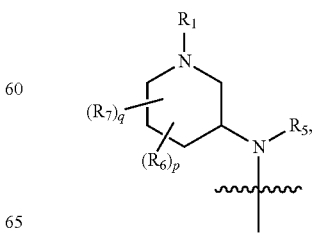

$R_5$ is H, and p and q are 0. In another embodiment is a compound of Formula (II) wherein G is

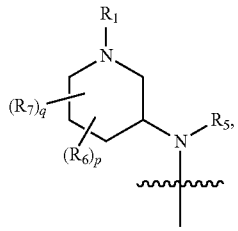

$R_5$ is H, p and q are 0, $R_1$ is —C(O)$R_9$, $R_9$ is substituted or unsubstituted $C_6$-$C_{12}$aryl. In another embodiment is a compound of Formula (II) wherein G is

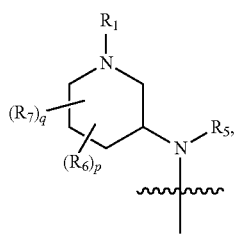

$R_5$ is H, p and q are 0, $R_1$ is —C(O)$R_9$, $R_9$ is substituted or unsubstituted phenyl. In another embodiment is a compound of Formula (II) wherein G is

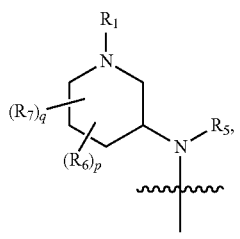

$R_5$ is H, p and q are 0, $R_1$ is —C(O)$R_9$, $R_9$ is substituted or unsubstituted $C_1$-$C_{12}$heteroaryl. In another embodiment is a compound of Formula (II) wherein G is

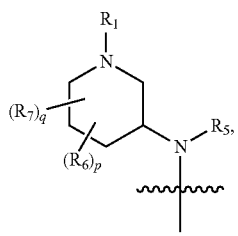

$R_5$ is H, p and q are 0, $R_1$ is —C(O)$R_9$, and $R_9$ is substituted or unsubstituted $C_1$-$C_6$alkyl. In another embodiment is a compound of Formula (II) wherein G is

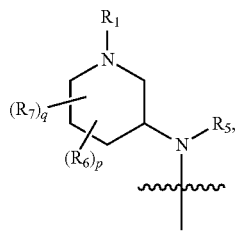

$R_5$ is H, p and q are 0, $R_1$ is —C(O)$R_9$, $R_9$ is substituted or unsubstituted $C_3$-$C_6$cycloalkyl. In another embodiment is a compound of Formula (II) wherein G is

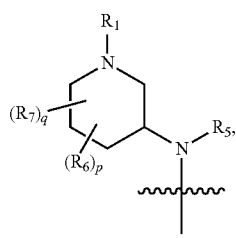

$R_5$ is H, p and q are 0, $R_1$ is —C(O)$R_9$, $R_9$ is substituted or unsubstituted $C_2$-$C_7$heterocycloalkyl. In another embodiment is a compound of Formula (II) wherein G is

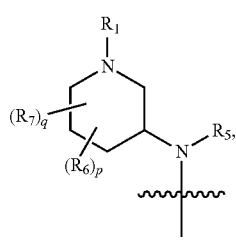

$R_5$ is H, p and q are 0, $R_1$ is —C(O)$R_9$, and $R_9$ is

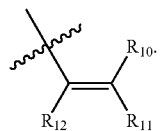

In another embodiment is a compound of Formula (II) wherein G is

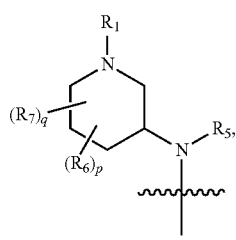

$R_5$ is H, p and q are 0, $R_1$ is —C(O)$R_9$, $R_9$ is

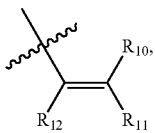

and $R_{10}$, $R_{11}$, and $R_{12}$ are each H. In another embodiment is a compound of Formula (II) wherein G is

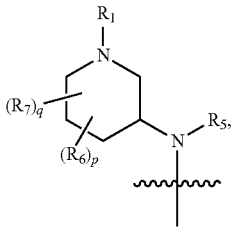

$R_5$ is H, p and q are 0, $R_1$ is —C(O)$R_9$, $R_9$ is

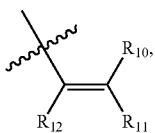

$R_{10}$ and $R_{12}$ are each H, $R_{11}$ is -$L_1$-$L_2$, $L_1$ is —CH$_2$—, and $L_2$ is —N(CH$_3$)$_2$. In another embodiment is a compound of Formula (II) wherein G is

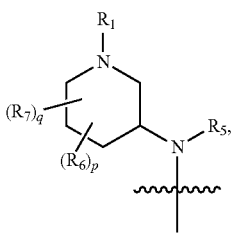

$R_5$ is H, p and q are 0, $R_1$ is —C(O)$R_9$, $R_9$ is

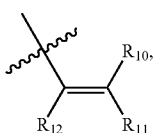

and $R_{11}$ and $R_{12}$ taken together form a bond.

In another embodiment are compounds having the structure of Formula (III):

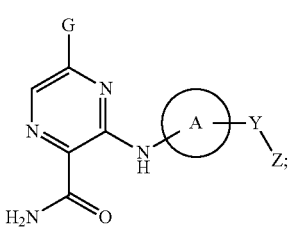

Formula (III)

wherein:
ring A is substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;
Y is optionally present and when present is —CH$_2$O—, —OCH$_2$—, —O—, —N(R$_3$)—, —C(O)—, —N(R$_3$)C(O)—, —C(O)N(R$_3$)—, —N(R$_3$)C(O)N(R$_3$)—, —S(O)—, —S(O)$_2$—, —N(R$_3$)S(O)$_2$—, —S(O)$_2$N(R$_3$)—, —C(=NH)—, —C(=NH)N(R$_3$)—, or substituted or unsubstituted $C_1$-$C_4$alkylene;
Z is optionally present and when present is substituted or unsubstituted $C_1$-$C_3$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;
G is

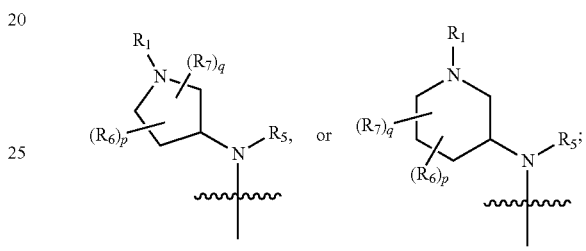

$R_1$ is —C(O)$R_9$, —C(O)O$R_4$, —C(O)N(R$_3$)(R$_4$), or —S(O)$_2$R$_9$;
each $R_3$ is independently is H, or substituted or unsubstituted $C_1$-$C_4$alkyl;
$R_4$ is substituted or unsubstituted $C_1$-$C_4$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;
$R_5$ is H, substituted or unsubstituted $C_1$-$C_4$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;
each $R_6$ and $R_7$ is independently halogen, —CN, —OH, —NH$_2$, substituted or unsubstituted $C_1$-$C_4$alkoxy, substituted or unsubstituted $C_1$-$C_4$alkyl, substituted or unsubstituted $C_3$-$C_6$cycloalkyl, substituted or unsubstituted $C_2$-$C_6$heterocycloalkyl, or —N(R$_3$)$_2$;
$R_9$ is substituted or unsubstituted $C_3$-$C_6$cycloalkyl, substituted or unsubstituted $C_2$-$C_7$heterocycloalkyl, substituted or unsubstituted $C_6$-$C_{12}$aryl, substituted or unsubstituted $C_1$-$C_{12}$heteroaryl, or

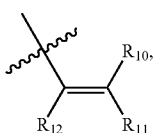

$R_{10}$ is H, halogen, —CN, or -$L_1$-$L_2$;
$R_{11}$ and $R_{12}$ are independently H, halogen, —CN, or -$L_1$-$L_2$; or $R_{11}$ and $R_{12}$ taken together form a bond;
each $L_1$ is optionally present and when present each $L_1$ is independently substituted or unsubstituted $C_1$-$C_6$alkyl, substituted or unsubstituted $C_3$-$C_6$cycloalkyl, substituted or unsubstituted $C_1$-$C_6$heteroalkyl, substituted or unsubstituted $C_2$-$C_7$heterocycloalkyl, substituted or unsubstituted $C_6$-$C_{12}$aryl, substituted or unsubstituted $C_1$-$C_{12}$heteroaryl, —C(=O)—, —O—, or —S—;

each $L_2$ is independently H, substituted or unsubstituted $C_1$-$C_6$alkyl, substituted or unsubstituted $C_3$-$C_6$cycloalkyl, substituted or unsubstituted $C_1$-$C_6$heteroalkyl, substituted or unsubstituted $C_2$-$C_7$heterocycloalkyl, substituted or unsubstituted $C_6$-$C_{12}$aryl, substituted or unsubstituted $C_1$-$C_{12}$heteroaryl or —N($R_{13}$)$_2$;

each $R_{13}$ is independently H, $C_1$-$C_6$alkyl, $C_3$-$C_6$cycloalkyl, $C_1$-$C_6$heteroalkyl, $C_2$-$C_7$ heterocycloalkyl, $C_6$-$C_{12}$aryl, or $C_1$-$C_{12}$heteroaryl;

p is 0-3; and q is 0-3;

or a pharmaceutically acceptable solvate, pharmaceutically acceptable salt, or pharmaceutically acceptable prodrug thereof.

In another embodiment is a compound of Formula (III) wherein ring A is substituted or unsubstituted $C_3$-$C_6$cycloalkyl. In another embodiment is a compound of Formula (III) wherein ring A is substituted or unsubstituted $C_2$-$C_7$heterocycloalkyl. In another embodiment is a compound of Formula (III) wherein ring A is substituted or unsubstituted $C_6$-$C_{12}$aryl. In another embodiment is a compound of Formula (III) wherein ring A is substituted or unsubstituted $C_1$-$C_{12}$heteroaryl.

In another embodiment is a compound of Formula (III) wherein ring A is substituted or unsubstituted phenyl. In another embodiment is a compound of Formula (III) wherein ring A is substituted or unsubstituted phenyl, Y is absent, and Z is substituted or unsubstituted $C_1$-$C_3$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl. In another embodiment is a compound of Formula (III) wherein ring A is substituted or unsubstituted phenyl, Y is absent, and Z is substituted or unsubstituted $C_1$-$C_3$alkyl. In another embodiment is a compound of Formula (III) wherein ring A is substituted or unsubstituted phenyl, Y is absent, and Z is substituted or unsubstituted $C_3$-$C_6$cycloalkyl. In another embodiment is a compound of Formula (III) wherein ring A is substituted or unsubstituted phenyl, Y is absent, and Z is substituted or unsubstituted $C_2$-$C_7$heterocycloalkyl. In another embodiment is a compound of Formula (III) wherein ring A is substituted or unsubstituted phenyl, Y is absent, and Z is substituted or unsubstituted $C_6$-$C_{12}$aryl. In another embodiment is a compound of Formula (III) wherein ring A is substituted or unsubstituted phenyl, Y is absent, and Z is substituted or unsubstituted $C_1$-$C_{12}$heteroaryl. In another embodiment is a compound of Formula (III) wherein ring A is substituted or unsubstituted phenyl, Y is absent, and Z is a substituted or unsubstituted pyrimidine. In another embodiment is a compound of Formula (III) wherein ring A is substituted or unsubstituted phenyl, Y is absent, and Z is a substituted or unsubstituted oxazole.

In another embodiment is a compound of Formula (III) wherein ring A is substituted or unsubstituted phenyl, Y is —C(O)—, and Z is substituted or unsubstituted $C_1$-$C_3$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl. In another embodiment is a compound of Formula (III) wherein ring A is substituted or unsubstituted phenyl, Y is —C(O)—, and Z is substituted or unsubstituted $C_1$-$C_3$alkyl. In another embodiment is a compound of Formula (III) wherein ring A is substituted or unsubstituted phenyl, Y is —C(O)—, and Z is substituted or unsubstituted $C_3$-$C_6$cycloalkyl. In another embodiment is a compound of Formula (III) wherein ring A is substituted or unsubstituted phenyl, Y is —C(O)—, and Z is substituted or unsubstituted $C_2$-$C_7$heterocycloalkyl. In another embodiment is a compound of Formula (III) wherein ring A is substituted or unsubstituted phenyl, Y is —C(O)—, and Z is substituted or unsubstituted morpholine. In another embodiment is a compound of Formula (III) wherein ring A is substituted or unsubstituted phenyl, Y is —C(O)—, and Z is substituted or unsubstituted $C_6$-$C_{12}$aryl. In another embodiment is a compound of Formula (III) wherein ring A is substituted or unsubstituted phenyl, Y is —C(O)—, and Z is substituted or unsubstituted $C_1$-$C_{12}$heteroaryl.

In another embodiment is a compound of Formula (III) wherein G is

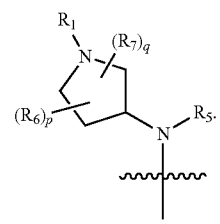

In another embodiment is a compound of Formula (III) wherein G is

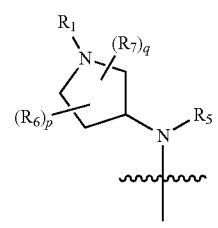

and $R_5$ is H. In another embodiment is a compound of Formula (III) wherein G is

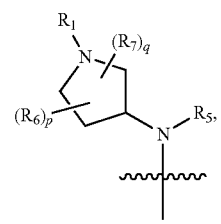

$R_5$ is H, and p and q are 0. In another embodiment is a compound of Formula (III) wherein G is

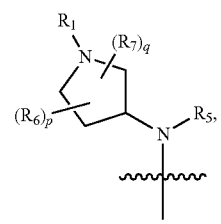

$R_5$ is H, p and q are 0, $R_1$ is —C(O)$R_9$, $R_9$ is substituted or unsubstituted $C_6$-$C_{12}$aryl. In another embodiment is a compound of Formula (III) wherein G is

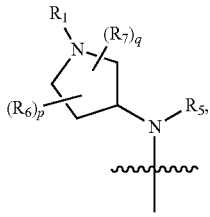

$R_5$ is H, p and q are 0, $R_1$ is —C(O)$R_9$, $R_9$ is substituted or unsubstituted phenyl. In another embodiment is a compound of Formula (III) wherein G is

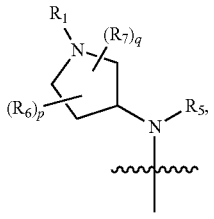

$R_5$ is H, p and q are 0, $R_1$ is —C(O)$R_9$, $R_9$ is substituted or unsubstituted $C_1$-$C_{12}$heteroaryl. In another embodiment is a compound of Formula (III) wherein G is

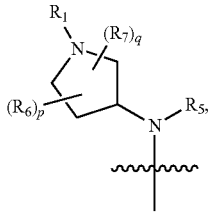

$R_5$ is H, p and q are 0, $R_1$ is —C(O)$R_9$, $R_9$ is substituted or unsubstituted $C_3$-$C_6$cycloalkyl. In another embodiment is a compound of Formula (III) wherein G is

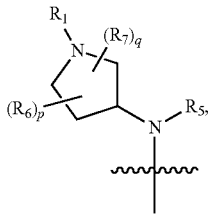

$R_5$ is H, p and q are 0, $R_1$ is —C(O)$R_9$, $R_9$ is substituted or unsubstituted $C_2$-$C_7$heterocycloalkyl. In another embodiment is a compound of Formula (III) wherein G is

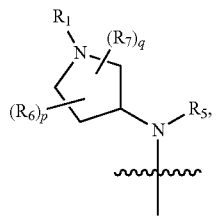

$R_5$ is H, p and q are 0, $R_1$ is —C(O)$R_9$, and $R_9$ is

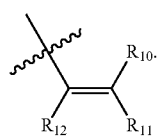

In another embodiment is a compound of Formula (III) wherein G is

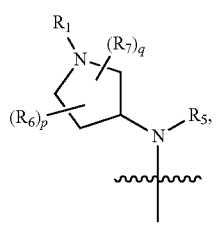

$R_5$ is H, p and q are 0, $R_1$ is —C(O)$R_9$, $R_9$ is

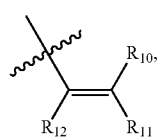

and $R_{10}$, $R_{11}$, and $R_{12}$ are each H. In another embodiment is a compound of Formula (III) wherein G is

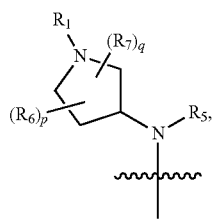

$R_5$ is H, p and q are 0, $R_1$ is —C(O)$R_9$, $R_9$ is

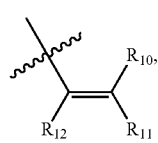

$R_{10}$ and $R_{12}$ are each H, $R_{11}$ is -$L_1$-$L_2$, $L_1$ is —$CH_2$—, and $L_2$ is —$N(CH_3)_2$. In another embodiment is a compound of Formula (III) wherein G is

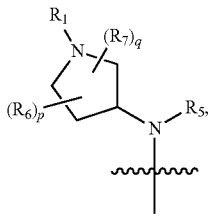

$R_5$ is H, p and q are 0, $R_1$ is —$C(O)R_9$, $R_9$ is

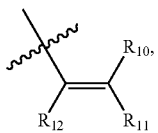

and $R_{11}$ and $R_{12}$ taken together form a bond.

In another embodiment is a compound of Formula (III) wherein G is

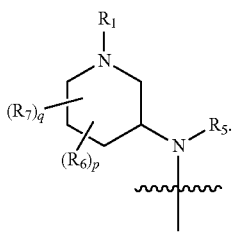

In another embodiment is a compound of Formula (III) wherein G is

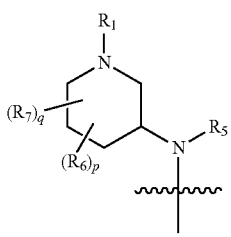

and $R_5$ is H. In another embodiment is a compound of Formula (III) wherein G is

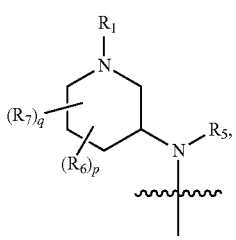

$R_5$ is H, and p and q are 0. In another embodiment is a compound of Formula (III) wherein G is

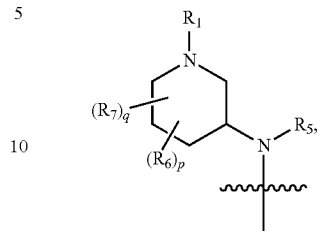

$R_5$ is H, p and q are 0, $R_1$ is —$C(O)R_9$, $R_9$ is substituted or unsubstituted $C_6$-$C_{12}$aryl. In another embodiment is a compound of Formula (III) wherein G is

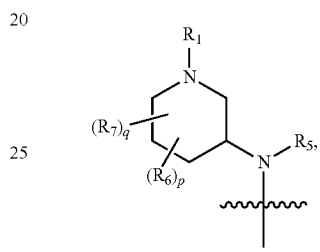

$R_5$ is H, p and q are 0, $R_1$ is —$C(O)R_9$, $R_9$ is substituted or unsubstituted phenyl. In another embodiment is a compound of Formula (III) wherein G is

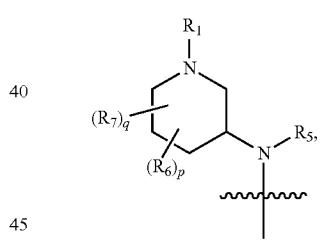

$R_5$ is H, p and q are 0, $R_1$ is —$C(O)R_9$, $R_9$ is substituted or unsubstituted $C_1$-$C_{12}$heteroaryl. In another embodiment is a compound of Formula (III) wherein G is

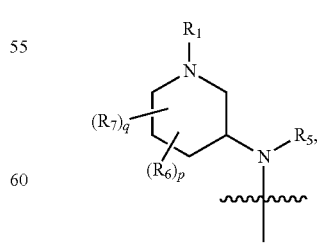

$R_5$ is H, p and q are 0, $R_1$ is —$C(O)R_9$, $R_9$ is substituted or unsubstituted $C_3$-$C_6$cycloalkyl. In another embodiment is a compound of Formula (III) wherein G is

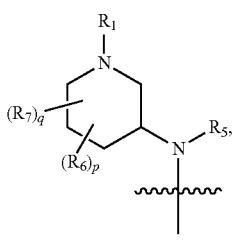

$R_5$ is H, p and q are 0, $R_1$ is —C(O)$R_9$, $R_9$ is substituted or unsubstituted $C_2$-$C_7$heterocycloalkyl. In another embodiment is a compound of Formula (III) wherein G is

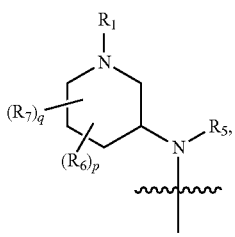

$R_5$ is H, p and q are 0, $R_1$ is —C(O)$R_9$, and $R_9$ is

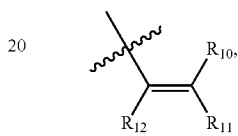

In another embodiment is a compound of Formula (III) wherein G is

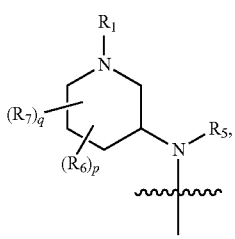

$R_5$ is H, p and q are 0, $R_1$ is —C(O)$R_9$, $R_9$ is

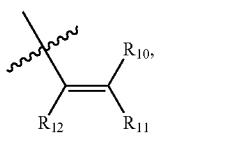

and $R_{10}$, $R_{11}$, and $R_{12}$ are each H. In another embodiment is a compound of Formula (III) wherein G is

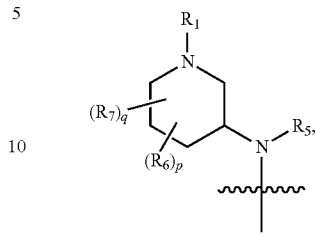

$R_5$ is H, p and q are 0, $R_1$ is —C(O)$R_9$, $R_9$ is

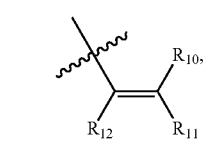

$R_{10}$ and $R_{12}$ are each H, $R_{11}$ is -$L_1$-$L_2$, $L_1$ is —$CH_2$—, and $L_2$ is —N($CH_3$)$_2$. In another embodiment is a compound of Formula (III) wherein G is

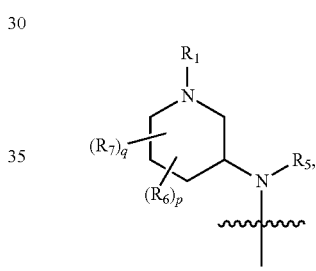

$R_5$ is H, p and q are 0, $R_1$ is —C(O)$R_9$, $R_9$ is

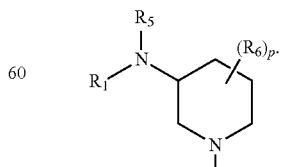

and $R_{11}$ and $R_{12}$ taken together form a bond.

In a particular embodiment, with respect to the compounds of Formula (IA), (I), (Ia), (II), (III), G is

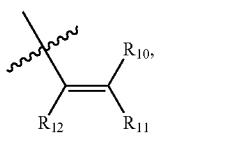

In one embodiment, p is 0. In another embodiment, p is 1.

In another embodiment, with respect to the compounds of Formula (IA), (I), (Ia), (II), (III), G is

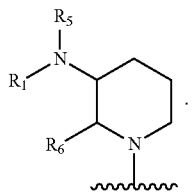

In one embodiment, $R_5$ is H or alkyl. In another embodiment, $R_5$ is H.

In another embodiment, with respect to the compounds of Formula (IA), (I), (Ia), (II), (III), G is

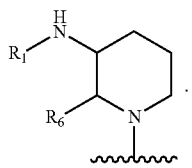

In a particular embodiment is a compound of Formula (IV) having the structure

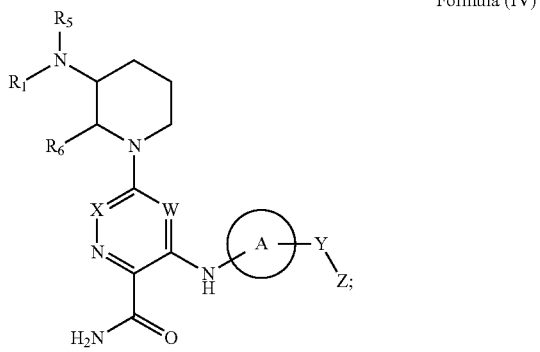

Formula (IV)

wherein A, W, X, Y, Z, $R_1$, $R_5$, and $R_6$ are as described for Formula (I); provided that when W is N, and $R_1$ is H, t-Boc, or C(O)—CH=CH$_2$; then X is other than C-Et or N.

In another embodiment is a compound of Formula (IV) wherein ring A is substituted or unsubstituted $C_3$-$C_6$cycloalkyl. In another embodiment is a compound of Formula (IV) wherein ring A is substituted or unsubstituted $C_2$-$C_7$heterocycloalkyl. In another embodiment is a compound of Formula (IV) wherein ring A is substituted or unsubstituted $C_6$-$C_{12}$aryl. In another embodiment is a compound of Formula (IV) wherein ring A is substituted or unsubstituted $C_1$-$C_{12}$heteroaryl.

In another embodiment is a compound of Formula (IV) wherein ring A is substituted or unsubstituted phenyl. In another embodiment is a compound of Formula (IV) wherein ring A is substituted or unsubstituted phenyl, Y is absent, and Z is substituted or unsubstituted $C_1$-$C_3$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl. In another embodiment is a compound of Formula (IV) wherein ring A is substituted or unsubstituted phenyl, Y is absent, and Z is substituted or unsubstituted $C_1$-$C_3$alkyl. In another embodiment is a compound of Formula (IV) wherein ring A is substituted or unsubstituted phenyl, Y is absent, and Z is substituted or unsubstituted $C_3$-$C_6$cycloalkyl. In another embodiment is a compound of Formula (IV) wherein ring A is substituted or unsubstituted phenyl, Y is absent, and Z is substituted or unsubstituted $C_2$-$C_7$heterocycloalkyl. In another embodiment is a compound of Formula (IV) wherein ring A is substituted or unsubstituted phenyl, Y is absent, and Z is substituted or unsubstituted $C_6$-$C_{12}$aryl. In another embodiment is a compound of Formula (IV) wherein ring A is substituted or unsubstituted phenyl, Y is absent, and Z is substituted or unsubstituted $C_1$-$C_{12}$heteroaryl. In another embodiment is a compound of Formula (IV) wherein ring A is substituted or unsubstituted phenyl, Y is absent, and Z is a substituted or unsubstituted pyrimidine. In another embodiment is a compound of Formula (IV) wherein ring A is substituted or unsubstituted phenyl, Y is absent, and Z is a substituted or unsubstituted oxazole.

In another embodiment is a compound of Formula (IV) wherein ring A is substituted or unsubstituted phenyl, Y is —C(O)—, and Z is substituted or unsubstituted $C_1$-$C_3$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl. In another embodiment is a compound of Formula (IV) wherein ring A is substituted or unsubstituted phenyl, Y is —C(O)—, and Z is substituted or unsubstituted $C_1$-$C_3$alkyl. In another embodiment is a compound of Formula (IV) wherein ring A is substituted or unsubstituted phenyl, Y is —C(O)—, and Z is substituted or unsubstituted $C_3$-$C_6$cycloalkyl. In another embodiment is a compound of Formula (IV) wherein ring A is substituted or unsubstituted phenyl, Y is —C(O)—, and Z is substituted or unsubstituted $C_2$-$C_7$heterocycloalkyl. In another embodiment is a compound of Formula (IV) wherein ring A is substituted or unsubstituted phenyl, Y is —C(O)—, and Z is substituted or unsubstituted morpholine. In another embodiment is a compound of Formula (IV) wherein ring A is substituted or unsubstituted phenyl, Y is —C(O)—, and Z is substituted or unsubstituted $C_6$-$C_{12}$aryl. In another embodiment is a compound of Formula (IV) wherein ring A is substituted or unsubstituted phenyl, Y is —C(O)—, and Z is substituted or unsubstituted $C_1$-$C_{12}$heteroaryl.

In one embodiment, $R_5$ is H or alkyl. In another embodiment, $R_5$ is H.

In one embodiment, $R_6$ is halogen, —CN, —OH, —NH$_2$, substituted or unsubstituted $C_1$-$C_4$alkoxy, substituted or unsubstituted $C_1$-$C_4$alkyl, substituted or unsubstituted $C_3$-$C_6$cycloalkyl, substituted or unsubstituted $C_2$-$C_6$heterocycloalkyl, or —N(R$_3$)$_2$. In another embodiment, $R_6$ is substituted or unsubstituted $C_1$-$C_4$alkyl. In a particular embodiment, $R_6$ is Me.

In one embodiment, $R_1$ is —CH$_2$R$_4$, —C(O)R$_9$, —C(O)C(O)R$_9$, —C(O)OR$_4$, —C(O)N(R$_3$)(R$_4$), or —S(O)$_2$R$_9$. In a particular embodiment, $R_1$ is —C(O)R$_9$.

In one embodiment, $R_9$ is —R$_4$, and $R_4$ is substituted or unsubstituted $C_6$-$C_{12}$aryl. In another embodiment, $R_9$ is —R$_4$, and $R_4$ is substituted or unsubstituted phenyl. In another embodiment, $R_9$ is —R$_4$, and $R_4$ is substituted or unsubstituted heteroaryl. In another embodiment, $R_9$ is —R$_4$, and $R_4$ is substituted or unsubstituted pyridine or pyrimidine. In another embodiment, $R_9$ is —R$_4$, and $R_4$ is substituted or unsubstituted $C_1$-$C_6$alkyl. In another embodiment, $R_9$ is —R$_4$, and $R_4$ is substituted or unsubstituted $C_3$-$C_6$cycloalkyl.

In another embodiment, $R_9$ is —$R_4$, and $R_4$ is substituted or unsubstituted $C_2$-$C_7$heterocycloalkyl.

In another embodiment, $R_9$ is

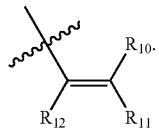

In another embodiment, $R_9$ is

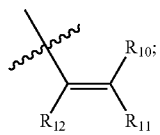

and $R_{10}$, $R_{11}$, and $R_{12}$ are each H. In another embodiment, $R_9$ is

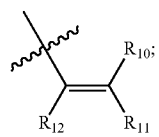

and $R_{11}$ and $R_{12}$ taken together form a bond.

In another embodiment, $R_9$ is

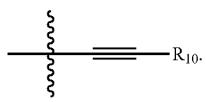

In one embodiment, X is C($R_2$). In another embodiment, X is C($R_2$); and $R_2$ is substituted or unsubstituted $C_1$-$C_4$alkyl. In another embodiment, $R_2$ is Me, Et, i-Pr, or $CF_3$. In another embodiment, $R_2$ is CN. In another embodiment, $R_2$ is halogen. In another embodiment, $R_2$ is F, Cl, or Br. In a particular embodiment, $R_2$ is H.

In one embodiment, $R_5$ is H, Me, Et, or i-Pr. In a particular embodiment, $R_5$ is H.

In another embodiment, X is N.

In one embodiment, W is C($R_2$). In another embodiment, W is C($R_2$); and $R_2$ is substituted or unsubstituted $C_1$-$C_4$alkyl. In another embodiment, $R_2$ is Me, Et, i-Pr, or $CF_3$. In another embodiment, $R_2$ is CN. In another embodiment, $R_2$ is halogen. In another embodiment, $R_2$ is F, Cl, or Br. In a particular embodiment, $R_2$ is H.

In another embodiment, W is N.

In another particular embodiment is a compound of Formula (Va), (Vb), (Vc), (Vd), (Ve), (Vf), (Vg), or (Vh) having the structure:

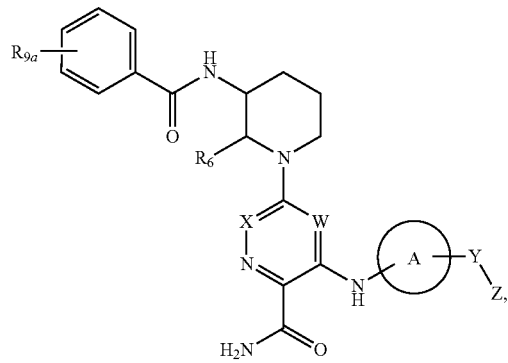

Formula (Va)

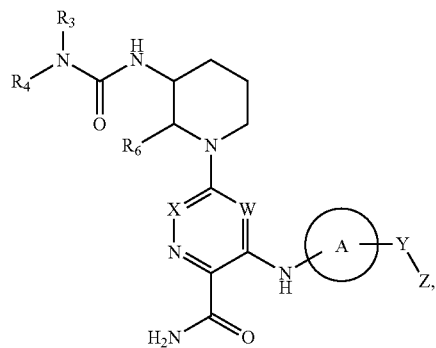

Formula (Vb)

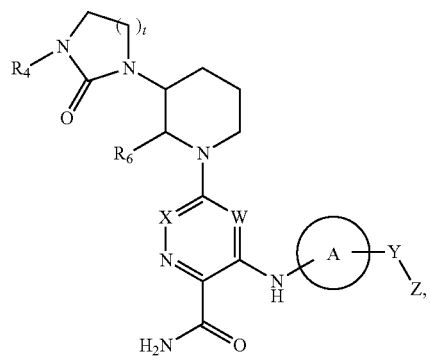

Formula (Vc)

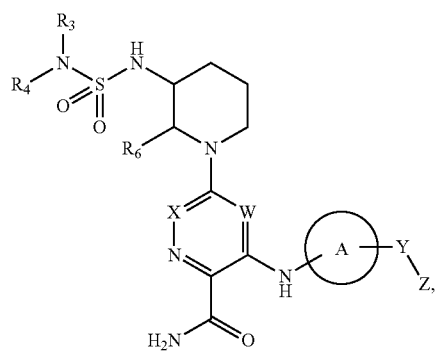

Formula (Vd)

-continued

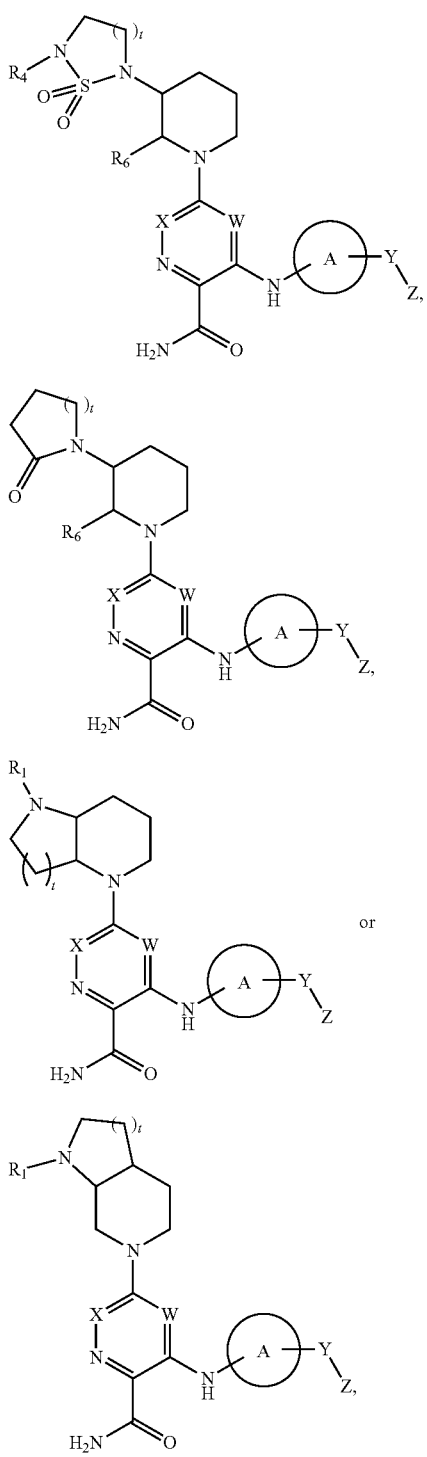

Formula (Ve)

Formula (Vf)

Formula (Vg)

Formula (Vh)

wherein A, W, X, Y, Z, $R_1$, $R_3$, $R_4$, and $R_6$ are as described for Formula (I);
$R_{9a}$ is substituted or unsubstituted $C_1$-$C_4$alkyl, substituted or unsubstituted $C_3$-$C_6$cycloalkyl, substituted or unsubstituted $C_3$-$C_6$heterocycloalkyl, substituted or unsubstituted $C_1$-$C_4$alkoxy, substituted or unsubstituted phenoxy, halo, or CN; and t is 1, 2, or 3.

In one embodiment, the compound is according to Formula (Va). In another embodiment, the compound is according to Formula (Vb). In another embodiment, the compound is according to Formula (Vc). In another embodiment, the compound is according to Formula (Vd). In another embodiment, the compound is according to Formula (Ve). In another embodiment, the compound is according to Formula (Vf). In another embodiment, the compound is according to Formula (Vg). In another embodiment, the compound is according to Formula (Vh).

In one embodiment, $R_{9a}$ is Me, Et, i-Pr, t-Bu, cyclopropyl, OMe, F, or Cl.

In one embodiment, each of $R_3$ and $R_4$ is independently H, or Me. In another embodiment, $R_4$ is substituted or unsubstituted phenyl. In a particular embodiment, $R_4$ is Me, Et, or 2-chlorophenyl.

In one embodiment, $R_1$ is Me, Et, —C(O)NMe$_2$, or C(O)-cyclopropyl.

In one embodiment, $R_6$ is H, Me, Et, or hydroxymethyl. In another embodiment, $R_6$ is Me or CH$_2$OH. In a particular embodiment, $R_6$ is (R)-Me.

In one embodiment, t is 1. In another embodiment, t is 2. In another embodiment, t is 3.

In one embodiment, each of W and X is N. In another embodiment, W is N; and X is CH.

In one embodiment, ring A is substituted or unsubstituted phenyl, substituted or unsubstituted pyridyl, substituted or unsubstituted quinolinyl, substituted or unsubstituted thiazolyl, substituted or unsubstituted isothiazolyl, substituted or unsubstituted oxazolyl, substituted or unsubstituted isoxazolyl, substituted or unsubstituted benzothiazolyl. In another embodiment, ring A is substituted or unsubstituted phenyl, or substituted or unsubstituted isothiazolyl.

In one embodiment, Y is absent. In another embodiment, Y is —O—, or —S(O)$_2$—.

In one embodiment, Z is as described for Formula (I). In another embodiment, Z is substituted or unsubstituted alkyl, or substituted or unsubstituted phenyl.

In another embodiment, Y is absent; and Z is halo, substituted or unsubstituted alkyl, substituted or unsubstituted cycloalkyl, or substituted or unsubstituted heterocycloalkyl.

In another embodiment, Y is absent; and Z is Cl, F, Me, Et, i-Pr, substituted or unsubstituted cyclopropyl, substituted or unsubstituted pyranyl, substituted or unsubstituted piperidinyl, substituted or unsubstituted piperizinyl, or substituted or unsubstituted morpholinyl.

In another embodiment, Y is absent; and Z is cyclopropyl unsubstituted or substituted with CN, or amido.

In another embodiment, Y is absent; and Z is piperidinyl unsubstituted or substituted with alkyl, cycloalkyl, phenyl, or pyridyl each of which is unsubstituted or substituted with one, two or three substituted or unsubstituted alkyl, or unsubstituted or substituted acyl.

In another embodiment, Y is absent; and Z is piperizinyl unsubstituted or substituted with alkyl, cycloalkyl, phenyl, or pyridyl each of which is unsubstituted or substituted with one, two or three substituted or unsubstituted alkyl, or unsubstituted or substituted acyl.

In a particular embodiment, the group -A-Y-Z is:

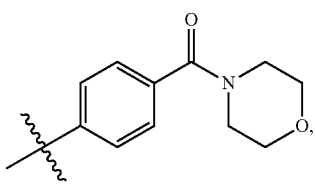

-continued

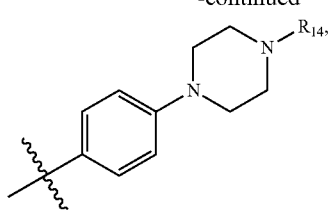

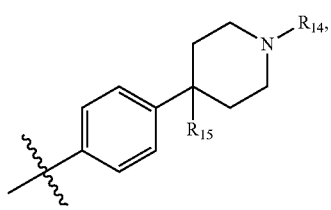

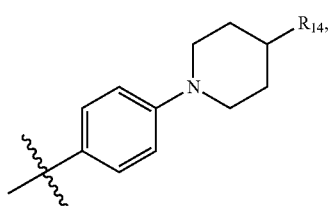

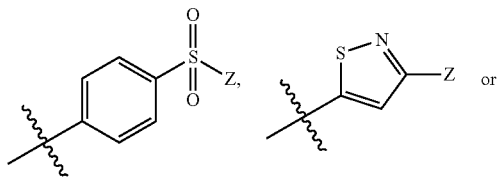

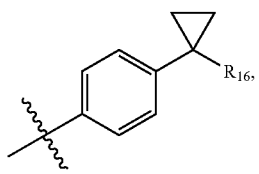

wherein Z is as described for Formula (I); $R_{14}$ is substituted or unsubstituted $C_1$-$C_4$alkyl, substituted or unsubstituted $C_1$-$C_4$acyl, substituted or unsubstituted $C_3$-$C_6$cycloalkyl, or —C(O)NR$_{14a}$R$_{14b}$; each of R$_{14a}$ and R$_{14b}$ is independently substituted or unsubstituted $C_1$-$C_4$alkyl or R$_{14a}$ and R$_{14b}$ together with the N they are attached to form a substituted or unsubstituted $C_2$-$C_9$heterocycloalkyl ring; each of R$_{15}$ and R$_{16}$ is independently H, substituted or unsubstituted $C_1$-$C_4$alkyl, CN, or —C(O)NR$_{14a}$R$_{14b}$.

In one embodiment, $R_{14}$ is Me, Et, i-Pr, cyclopropyl, cyclobutyl, cyclopentyl or cyclohexyl. In a particular embodiment, $R_{14}$ is cyclopropyl, cyclobutyl, or cyclopentyl. In another particular embodiment, $R_{14}$ is C(O)Me, or C(O)Et. In one embodiment, $R_{15}$ is H, Me, or CN. In one embodiment, $R_{16}$ is H, Me, CF$_3$, CN, CH2-NH$_2$, OH, NH$_2$, —C(O)NH$_2$, or —C(O)NMe$_2$. In one embodiment, Z is Me, Et, i-Pr, cyclopropyl, or Ph.

In a more particular embodiment, $R_{14}$ is C(O)Et, cyclopropyl, cyclobutyl, or cyclopentyl; and $R_{15}$ is H, CN, or Me.

In a more particular embodiment, the group -A-Y-Z is:

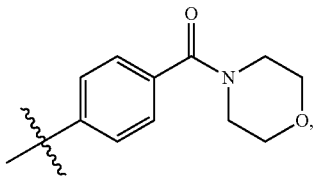

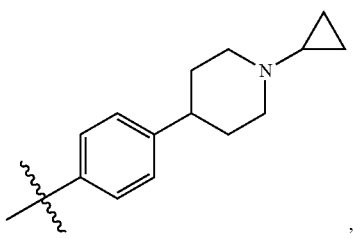

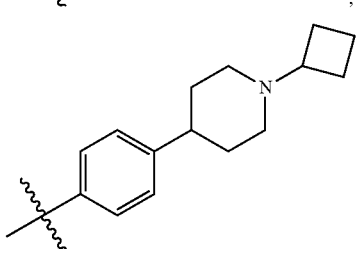

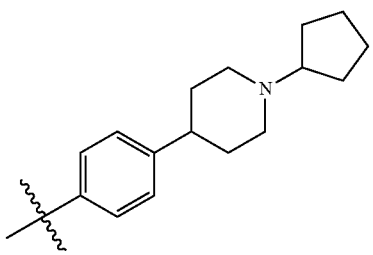

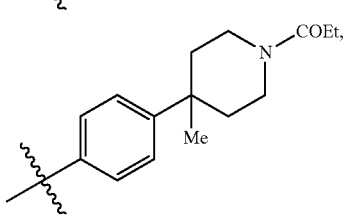

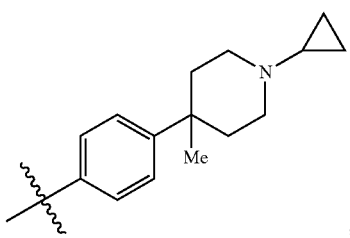

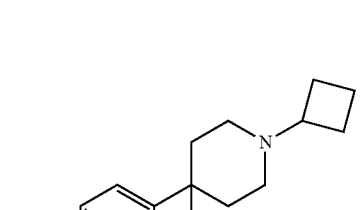

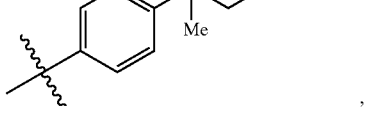

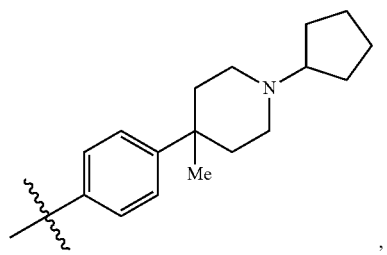
,
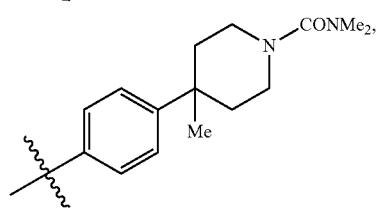
,
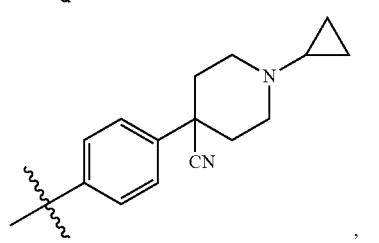
,
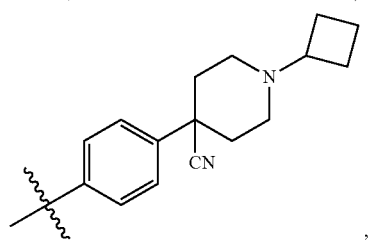
,
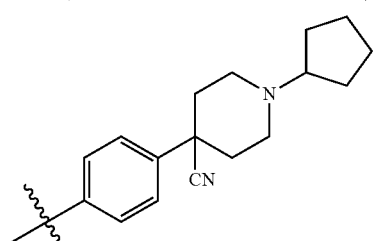
,
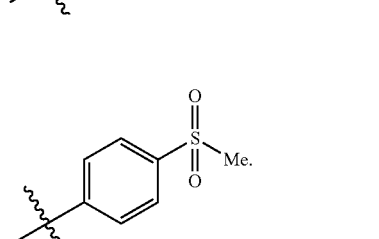
,
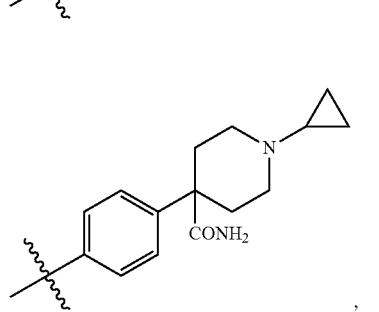
,
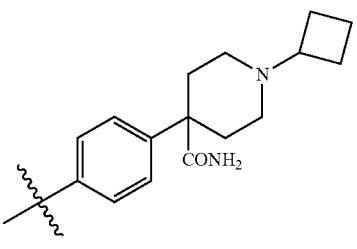
,
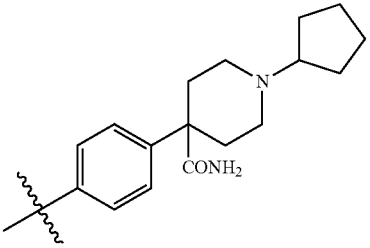
,
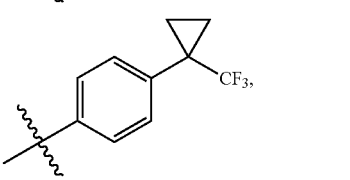
,
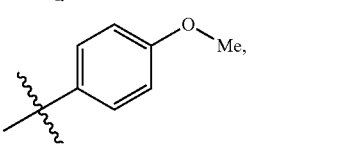
,
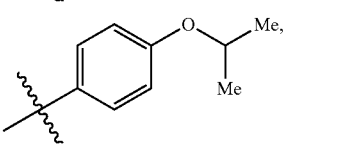
,
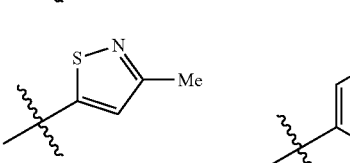
,
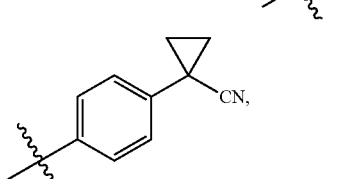
,
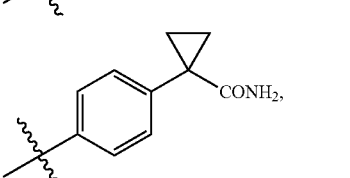
,
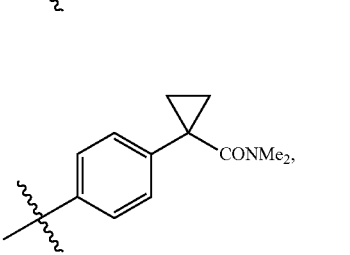
,

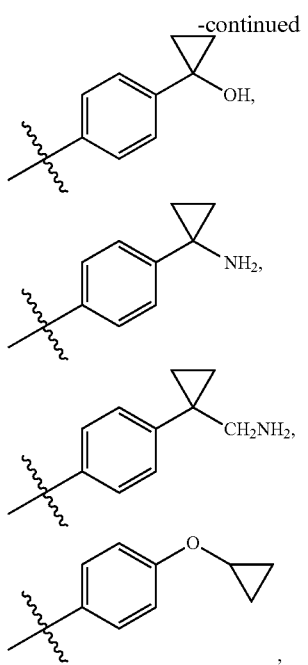

In another particular embodiment is a compound of Formula (VIa), or (VIb) having the structure:

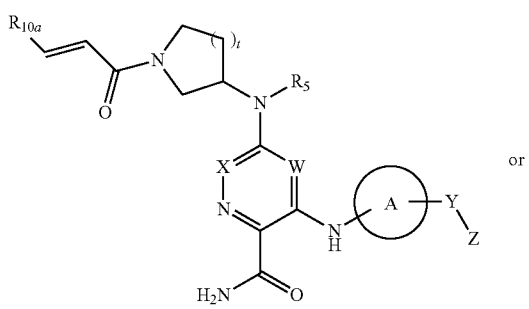

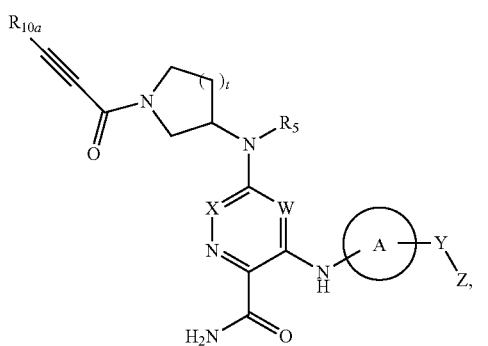

wherein A, W, X, Y, Z, and $R_5$ are as described for Formula (I); $R_{10a}$ is H, substituted or unsubstituted $C_1$-$C_4$alkyl; and t is 1, 2, or 3;

provided that when W is N; then X is CH or N.

In one embodiment, the compound is according to Formula (VIa). In another embodiment, the compound is according to Formula (VIb).

In one embodiment, $R_{10a}$ is H, Me, $CH_2$—$NMe_2$, or $CH_2$—N(Me)-cyclopropyl. In a particular embodiment, the compound is according to Formula (VIb), and $R_{10a}$ is Me. In one embodiment, t is 1. In another embodiment, t is 2. In another embodiment, t is 3.

In one embodiment, each of W and X is N. In another embodiment, W is N; and X is CH.

In one embodiment, ring A is substituted or unsubstituted phenyl, substituted or unsubstituted pyridyl, substituted or unsubstituted quinolinyl, substituted or unsubstituted thiazolyl, substituted or unsubstituted isothiazolyl, substituted or unsubstituted oxazolyl, substituted or unsubstituted isoxazolyl, substituted or unsubstituted benzothiazolyl. In another embodiment, ring A is substituted or unsubstituted phenyl, or substituted or unsubstituted isothiazolyl.

In one embodiment, Y is absent. In another embodiment, Y is —O—, or —$S(O)_2$—.

In one embodiment, Z is as described for Formula (I). In another embodiment, Z is substituted or unsubstituted alkyl, or substituted or unsubstituted phenyl.

In another embodiment, Y is absent; and Z is halo, substituted or unsubstituted alkyl, substituted or unsubstituted cycloalkyl, or substituted or unsubstituted heterocycloalkyl.

In another embodiment, Y is absent; and Z is Cl, F, Me, Et, i-Pr, substituted or unsubstituted cyclopropyl, substituted or unsubstituted pyranyl, substituted or unsubstituted piperidinyl, substituted or unsubstituted piperizinyl, or substituted or unsubstituted morpholinyl.

In another embodiment, Y is absent; and Z is cyclopropyl unsubstituted or substituted with CN, or amido.

In another embodiment, Y is absent; and Z is piperidinyl unsubstituted or substituted with alkyl, cycloalkyl, phenyl, or pyridyl each of which is unsubstituted or substituted with one, two or three substituted or unsubstituted alkyl, or unsubstituted or substituted acyl.

In another embodiment, Y is absent; and Z is piperizinyl unsubstituted or substituted with alkyl, cycloalkyl, phenyl, or pyridyl each of which is unsubstituted or substituted with one, two or three substituted or unsubstituted alkyl, or unsubstituted or substituted acyl.

In another embodiment is a compound of Formula (IA), (I), (Ia), (II), (III), (IV), (Va)-(Vh), or (VIa)-(VIb) wherein ring A is substituted or unsubstituted $C_1$-$C_{12}$heteroaryl. In a particular embodiment, ring A is pyridyl, pyrazolyl, thiazolyl, isothiazolyl, oxazolyl, or isoxazolyl.

In a particular embodiment, the group —A-Y-Z is:

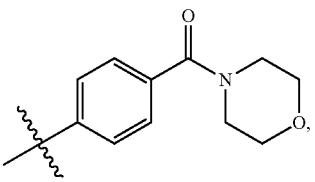

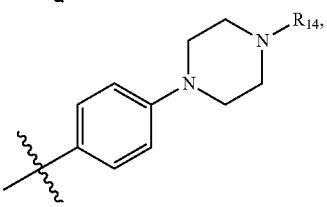

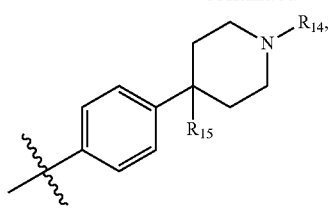

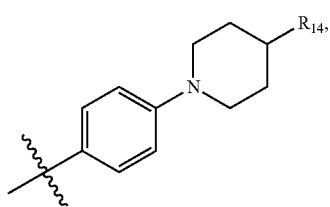

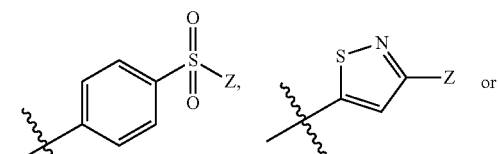

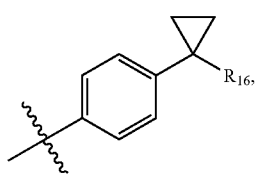

wherein Z is as described for Formula (I); $R_{14}$ is substituted or unsubstituted $C_1$-$C_4$alkyl, substituted or unsubstituted $C_1$-$C_4$acyl, substituted or unsubstituted $C_3$-$C_6$cycloalkyl, or —C(O)NR$_{14a}$R$_{14b}$; each of $R_{14a}$ and $R_{14b}$ is independently substituted or unsubstituted $C_1$-$C_4$alkyl or $R_{14a}$ and $R_{14b}$ together with the N they are attached to form a substituted or unsubstituted $C_2$-$C_9$heterocycloalkyl ring; each of $R_{15}$ and $R_{16}$ is independently H, substituted or unsubstituted $C_1$-$C_4$alkyl, CN, or —C(O)NR$_{14a}$R$_{14b}$.

In one embodiment, $R_{14}$ is Me, Et, i-Pr, cyclopropyl, cyclobutyl, cyclopentyl or cyclohexyl. In a particular embodiment, $R_{14}$ is cyclopropyl, cyclobutyl, or cyclopentyl. In another particular embodiment, $R_{14}$ is C(O)Me, or C(O)Et. In one embodiment, $R_{15}$ is H, Me, or CN. In one embodiment, $R_{16}$ is H, Me, CF$_3$, CN, CH2-NH$_2$, OH, NH$_2$, —C(O)NH$_2$, or —C(O)NMe$_2$. In one embodiment, Z is Me, Et, i-Pr, cyclopropyl, or Ph.

In a more particular embodiment, $R_{14}$ is —C(O)Et, cyclopropyl, cyclobutyl, or cyclopentyl; and $R_{15}$ is H, CN, or Me.

In a more particular embodiment, the group —A-Y-Z is:

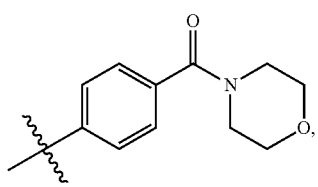

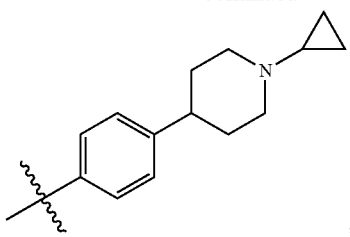

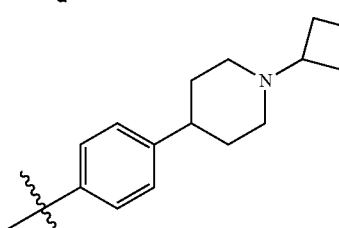

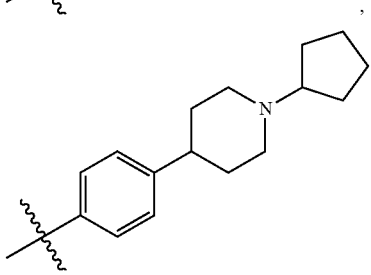

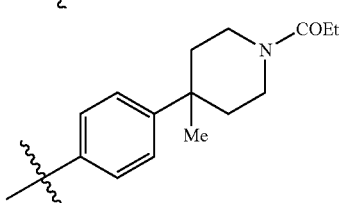

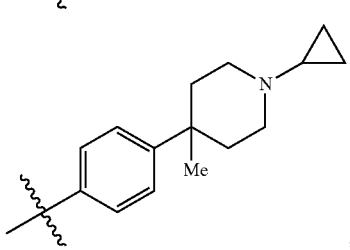

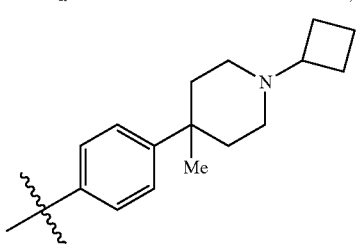

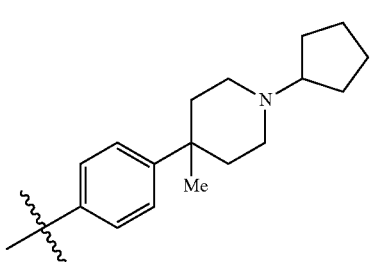

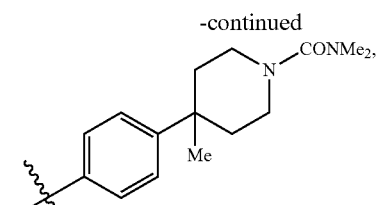
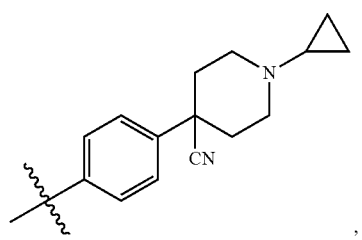
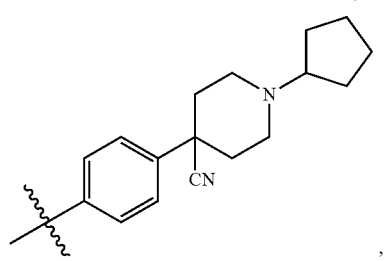
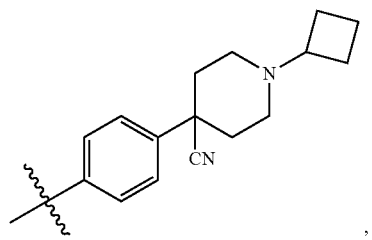
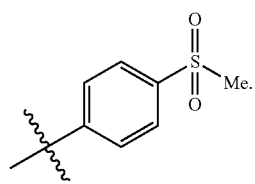
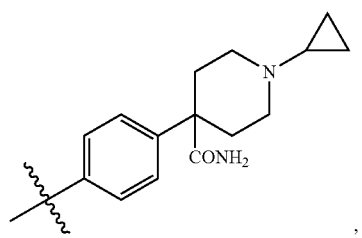
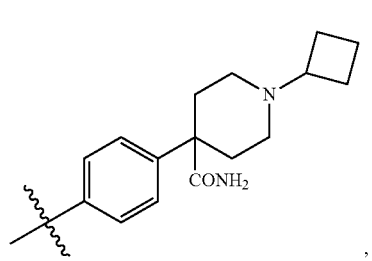
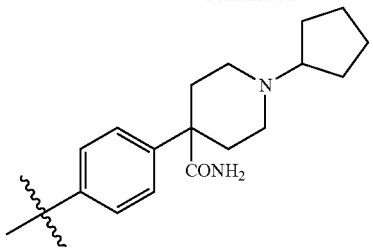
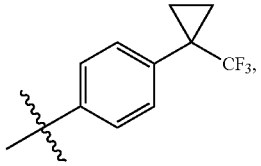
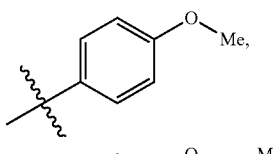
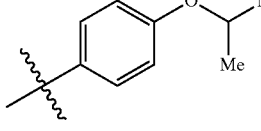
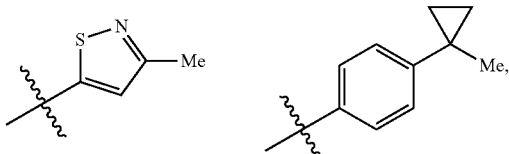
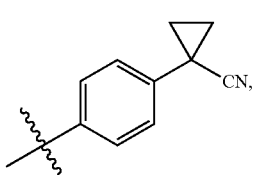
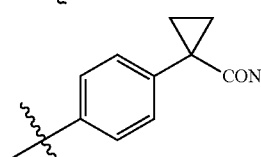
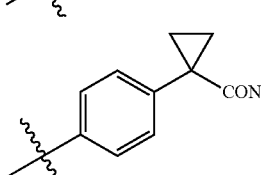
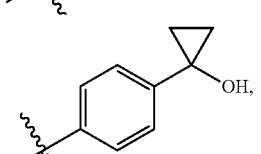
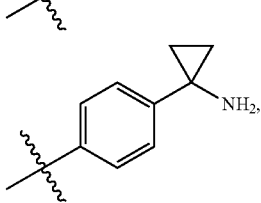

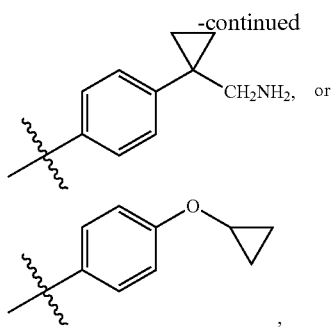

In a particular embodiment, the compound is any one of compounds selected from the group consisting of:

3-[(3R)-3-(4-tert-butylbenzamido)piperidin-1-yl]-5-{[4-(morpholine-4-carbonyl)phenyl]amino}-1,2,4-triazine-6-carboxamide;

3-[(3R)-3-(4-tert-butylbenzamido)pyrrolidin-1-yl]-5-{[4-(morpholine-4-carbonyl)phenyl]amino}-1,2,4-triazine-6-carboxamide;

5-{[4-(morpholine-4-carbonyl)phenyl]amino}-3-[(3R)-3-(trifluoroacetamido)pyrrolidin-1-yl]-1,2,4-triazine-6-carboxamide;

5-[(3R)-3-(4-tert-butylbenzamido)piperidin-1-yl]-3-{[4-(morpholine-4-carbonyl)phenyl]amino}pyrazine-2-carboxamide;

3-[(3R)-3-cyclopropaneamidopiperidin-1-yl]-5-{[4-(morpholine-4-carbonyl)phenyl]amino}-1,2,4-triazine-6-carboxamide;

3-{[(3R)-1-(4-tert-butylbenzoyl)piperidin-3-yl]amino}-5-{[4-(morpholine-4-carbonyl)phenyl]amino}-1,2,4-triazine-6-carboxamide;

3-{[(3R)-1-cyclopropanecarbonylpiperidin-3-yl]amino}-5-{[4-(morpholine-4-carbonyl)phenyl]amino}-1,2,4-triazine-6-carboxamide;

5-{[4-(morpholine-4-carbonyl)phenyl]amino}-3-{[(3R)-1-(prop-2-enoyl)piperidin-3-yl]amino}-1,2,4-triazine-6-carboxamide;

3-[(3R)-3-(4-methylbenzamido)piperidin-1-yl]-5-{[4-(morpholine-4-carbonyl)phenyl]amino}-1,2,4-triazine-6-carboxamide;

5-{[4-(morpholine-4-carbonyl)phenyl]amino}-3-[(3R)-3-[4-(trifluoromethyl)benzamido]piperidin-1-yl]-1,2,4-triazine-6-carboxamide;

3-[(3R)-3-(4-cyanobenzamido)piperidin-1-yl]-5-{[4-(morpholine-4-carbonyl)phenyl]amino}-1,2,4-triazine-6-carboxamide;

3-[(3R)-3-(4-chlorobenzamido)piperidin-1-yl]-5-{[4-(morpholine-4-carbonyl)phenyl]amino}-1,2,4-triazine-6-carboxamide;

3-[(3R)-3-(4-fluorobenzamido)piperidin-1-yl]-5-{[4-(morpholine-4-carbonyl)phenyl]amino}-1,2,4-triazine-6-carboxamide;

3-[(3R)-3-(4-methoxybenzamido)piperidin-1-yl]-5-{[4-(morpholine-4-carbonyl)phenyl]amino}-1,2,4-triazine-6-carboxamide;

3-[(3R)-3-cyclobutaneamidopiperidin-1-yl]-5-{[4-(morpholine-4-carbonyl)phenyl]amino}-1,2,4-triazine-6-carboxamide;

5-{[4-(morpholine-4-carbonyl)phenyl]amino}-3-[(3R)-3-[(pyrrolidine-1-carbonyl)amino]piperidin-1-yl]-1,2,4-triazine-6-carboxamide;

5-{[4-(morpholine-4-carbonyl)phenyl]amino}-3-[(3R)-3-propanamidopiperidin-1-yl]-1,2,4-triazine-6-carboxamide;

5-{[4-(morpholine-4-carbonyl)phenyl]amino}-3-[(3R)-3-(prop-2-enamido)piperidin-1-yl]-1,2,4-triazine-6-carboxamide;

3-[(3R)-3-(4-cyclopropylbenzamido)piperidin-1-yl]-5-{[4-(morpholine-4-carbonyl)phenyl]amino}-1,2,4-triazine-6-carboxamide;

3-[(3R)-3-(cyclopentylamino)piperidin-1-yl]-5-{[4-(morpholine-4-carbonyl)phenyl]amino}-1,2,4-triazine-6-carboxamide;

5-{[4-(morpholine-4-carbonyl)phenyl]amino}-3-[(3R)-3-[(propan-2-yl)amino]piperidin-1-yl]-1,2,4-triazine-6-carboxamide;

3-[(3R)-3-ethanesulfonamidopiperidin-1-yl]-5-{[4-(morpholine-4-carbonyl)phenyl]amino}-1,2,4-triazine-6-carboxamide;

3-[(3R)-3-aminopiperidin-1-yl]-5-{[4-(morpholine-4-carbonyl)phenyl]amino}-1,2,4-triazine-6-carboxamide;

3-[(3R)-3-[(morpholine-4-carbonyl)amino]piperidin-1-yl]-5-{[4-(morpholine-4-carbonyl)phenyl]amino}-1,2,4-triazine-6-carboxamide;

tert-butyl (3R)-3-[(6-carbamoyl-5-{[4-(morpholine-4-carbonyl)phenyl]amino}-1,2,4-triazin-3-yl)amino]pyrrolidine-1-carboxylate;

tert-butyl (3R)-3-[(6-carbamoyl-5-{[4-(morpholine-4-carbonyl)phenyl]amino}-1,2,4-triazin-3-yl)amino]piperidine-1-carboxylate;

3-[(3R)-3-(2-cyanoacetamido)piperidin-1-yl]-5-{[4-(morpholine-4-carbonyl)phenyl]amino}-1,2,4-triazine-6-carboxamide;

3-[(3R)-3-(1-cyanocyclopropaneamido)piperidin-1-yl]-5-{[4-(morpholine-4-carbonyl)phenyl]amino}-1,2,4-triazine-6-carboxamide;

3-[(3R)-3-(2-methylpropanamido)piperidin-1-yl]-5-{[4-(morpholine-4-carbonyl)phenyl]amino}-1,2,4-triazine-6-carboxamide;

5-{[4-(morpholine-4-carbonyl)phenyl]amino}-3-[(3R)-3-(pyridine-3-amido)piperidin-1-yl]-1,2,4-triazine-6-carboxamide;

3-[(3R)-3-benzamidopiperidin-1-yl]-5-{[4-(morpholine-4-carbonyl)phenyl]amino}-1,2,4-triazine-6-carboxamide;

5-{[4-(morpholine-4-carbonyl)phenyl]amino}-3-{[(3R)-pyrrolidin-3-yl]amino}-1,2,4-triazine-6-carboxamide;

5-{[4-(morpholine-4-carbonyl)phenyl]amino}-3-{[(3R)-piperidin-3-yl]amino}-1,2,4-triazine-6-carboxamide;

5-{[4-(morpholine-4-carbonyl)phenyl]amino}-3-{[(3R)-1-(prop-2-enoyl)pyrrolidin-3-yl]amino}-1,2,4-triazine-6-carboxamide;

3-{[(3R)-1-[(2E)-4-[cyclopropyl(methyl)amino]but-2-enoyl]pyrrolidin-3-yl]amino}-5-{[4-(morpholine-4-carbonyl)phenyl]amino}-1,2,4-triazine-6-carboxamide;

5-{[4-(morpholine-4-carbonyl)phenyl]amino}-3-{[(3R)-1-propanoylpiperidin-3-yl]amino}-1,2,4-triazine-6-carboxamide;

3-{[(3R)-1-[(2E)-4-[cyclopropyl(methyl)amino]but-2-enoyl]piperidin-3-yl]amino}-5-{[4-(morpholine-4-carbonyl)phenyl]amino}-1,2,4-triazine-6-carboxamide;

3-{[(3R)-1-[(2E)-4-(dimethylamino)but-2-enoyl]piperidin-3-yl]amino}-5-{[4-(morpholine-4-carbonyl)phenyl]amino}-1,2,4-triazine-6-carboxamide;

3-[(3R)-3-benzenesulfonamidopiperidin-1-yl]-5-{[4-(morpholine-4-carbonyl)phenyl]amino}-1,2,4-triazine-6-carboxamide;

5-{[4-(morpholine-4-carbonyl)phenyl]amino}-3-[(3R)-3-(pyridine-4-amido)piperidin-1-yl]-1,2,4-triazine-6-carboxamide;

5-{[4-(morpholine-4-carbonyl)phenyl]amino}-3-[(3R)-3-(pyridine-2-amido)piperidin-1-yl]-1,2,4-triazine-6-carboxamide;

3-[(3R)-3-benzamidopyrrolidin-1-yl]-5-{[4-(morpholine-4-carbonyl)phenyl]amino}-1,2,4-triazine-6-carboxamide;

5-{[4-(morpholine-4-carbonyl)phenyl]amino}-3-[(3R)-3-(oxane-4-amido)piperidin-1-yl]-1,2,4-triazine-6-carboxamide;

3-[(3R)-3-(1-methylpiperidine-4-amido)piperidin-1-yl]-5-{[4-(morpholine-4-carbonyl)phenyl]amino}-1,2,4-triazine-6-carboxamide;

3-[(3R)-3-(1-acetylpiperidine-4-amido)piperidin-1-yl]-5-{[4-(morpholine-4-carbonyl)phenyl]amino}-1,2,4-triazine-6-carboxamide;

3-[(3R)-3-cyclopentaneamidopiperidin-1-yl]-5-{[4-(morpholine-4-carbonyl)phenyl]amino}-1,2,4-triazine-6-carboxamide;

3-[(3R)-3-(5-chlorothiophene-2-amido)piperidin-1-yl]-5-{[4-(morpholine-4-carbonyl)phenyl]amino}-1,2,4-triazine-6-carboxamide;

N-[(3R)-1-(6-carbamoyl-5-{[4-(morpholine-4-carbonyl)phenyl]amino}-1,2,4-triazin-3-yl)piperidin-3-yl]quinoline-3-carboxamide;

3-[(3R)-3-(N-methyl4-tert-butylbenzamido)piperidin-1-yl]-5-{[4-(morpholine-4-carbonyl)phenyl]amino}-1,2,4-triazine-6-carboxamide;

3-[(3R)-3-(4-tert-butylbenzamido)piperidin-1-yl]-5-[(5-fluoropyridin-3-yl)amino]-1,2,4-triazine-6-carboxamide;

3-[(3R)-3-(4-tert-butylbenzamido)piperidin-1-yl]-5-[(4-methylphenyl)amino]-1,2,4-triazine-6-carboxamide;

3-[(3R)-3-(4-tert-butylbenzamido)piperidin-1-yl]-5-[(3-methylphenyl)amino]-1,2,4-triazine-6-carboxamide;

3-[(3R)-3-(4-tert-butylbenzamido)piperidin-1-yl]-5-{[4-(pyrimidin-2-yl)phenyl]amino}-1,2,4-triazine-6-carboxamide;

3-[(3R)-3-(4-tert-butylbenzamido)piperidin-1-yl]-5-{[3-(pyrimidin-2-yl)phenyl]amino}-1,2,4-triazine-6-carboxamide;

5-{[4-(morpholine-4-carbonyl)phenyl]amino}-3-[(3R)-3-(2-oxopyrrolidin-1-yl)piperidin-1-yl]-1,2,4-triazine-6-carboxamide;

3-{methyl[(3R)-1-(prop-2-enoyl)pyrrolidin-3-yl]amino}-5-{[4-(morpholine-4-carbonyl)phenyl]amino}-1,2,4-triazine-6-carboxamide;

3-[(3R)-3-(isoquinolin-1-yloxy)piperidin-1-yl]-5-{[4-(morpholine-4-carbonyl)phenyl]amino}-1,2,4-triazine-6-carboxamide;

5-{[4-(morpholine-4-carbonyl)phenyl]amino}-3-[(3R)-3-(pyrimidine-2-amido)piperidin-1-yl]-1,2,4-triazine-6-carboxamide;

5-{[4-(morpholine-4-carbonyl)phenyl]amino}-3-[(3R)-3-(1,3-thiazole-2-amido)piperidin-1-yl]-1,2,4-triazine-6-carboxamide;

3-[(3R)-3-(1-cyclopropylpiperidine-4-amido)piperidin-1-yl]-5-{[4-(morpholine-4-carbonyl)phenyl]amino}-1,2,4-triazine-6-carboxamide;

3-[(3R)-3-(1-cyclopentylpiperidine-4-amido)piperidin-1-yl]-5-{[4-(morpholine-4-carbonyl)phenyl]amino}-1,2,4-triazine-6-carboxamide;

3-[(3R)-3-(but-2-ynamido)piperidin-1-yl]-5-{[4-(morpholine-4-carbonyl)phenyl]amino}-1,2,4-triazine-6-carboxamide;

3-[(3R)-3-{imidazo[1,2-a]pyridine-6-amido}piperidin-1-yl]-5-{[4-(morpholine-4-carbonyl)phenyl]amino}-1,2,4-triazine-6-carboxamide;

3-[(3R)-3-{imidazo[1,2-a]pyridine-7-amido}piperidin-1-yl]-5-{[4-(morpholine-4-carbonyl)phenyl]amino}-1,2,4-triazine-6-carboxamide;

3-[(3R)-3-(4-tert-butylbenzamido)piperidin-1-yl]-5-{[4-(1,3-oxazol-2-yl)phenyl]amino}-1,2,4-triazine-6-carboxamide;

3-[(3R)-3-[(morpholine-4-carbonyl)amino]piperidin-1-yl]-5-{[4-(1,3-oxazol-2-yl)phenyl]amino}-1,2,4-triazine-6-carboxamide;

3-[(3R)-3-{methyl(phenyl)carbamoyl]amino}piperidin-1-yl]-5-{[4-(morpholine-4-carbonyl)phenyl]amino}-1,2,4-triazine-6-carboxamide;

5-{[4-(morpholine-4-carbonyl)phenyl]amino}-3-[(3R)-3-[(piperidine-1-carbonyl)amino]piperidin-1-yl]-1,2,4-triazine-6-carboxamide;

5-{[4-(morpholine-4-carbonyl)phenyl]amino}-3-[(3R)-3-{[4-(piperidin-1-yl)piperidine-1-carbonyl]amino}piperidin-1-yl]-1,2,4-triazine-6-carboxamide;

3-[(3R)-3-(4-tert-butylbenzamido)piperidin-1-yl]-5-[(4-methanesulfonylphenyl)amino]-1,2,4-triazine-6-carboxamide;

5-{methyl[(3R)-1-(prop-2-enoyl)piperidin-3-yl]amino}-3-{[4-(morpholine-4-carbonyl)phenyl]amino}pyrazine-2-carboxamide;

5-{[(3R)-1-[(2E)-4-(dimethylamino)but-2-enoyl]piperidin-3-yl](methyl)amino}-3-{[4-(morpholine-4-carbonyl)phenyl]amino}pyrazine-2-carboxamide;

5-{[4-(morpholine-4-carbonyl)phenyl]amino}-3-[(3R)-3-{[(propan-2-yloxy)carbonyl]({[(propan-2-yloxy)carbonyl]amino})amino}piperidin-1-yl]-1,2,4-triazine-6-carboxamide;

3-[(3R)-3-(6-cyclopropyl-8-fluoro-1-oxo-1,2-dihydroisoquinolin-2-yl)piperidin-1-yl]-5-{[4-(morpholine-4-carbonyl)phenyl]amino}-1,2,4-triazine-6-carboxamide;

3-[(3R)-3-[(6-cyclopropyl-8-fluoroisoquinolin-1-yl)oxy]piperidin-1-yl]-5-{[4-(morpholine-4-carbonyl)phenyl]amino}-1,2,4-triazine-6-carboxamide;

5-{[4-(morpholine-4-carbonyl)phenyl]amino}-3-[(3R)-3-[(phenylcarbamoyl)amino]piperidin-1-yl]-1,2,4-triazine-6-carboxamide;

N-[(3R)-1-(6-carbamoyl-5-{[4-(morpholine-4-carbonyl)phenyl]amino}-1,2,4-triazin-3-yl)piperidin-3-yl]quinoline-2-carboxamide;

N-[(3R)-1-(6-carbamoyl-5-{[4-(morpholine-4-carbonyl)phenyl]amino}-1,2,4-triazin-3-yl)piperidin-3-yl]quinoline-6-carboxamide;

5-{[4-(morpholine-4-carbonyl)phenyl]amino}-3-[(3R)-3-(1-oxo-2,3-dihydro-1H-isoindol-2-yl)piperidin-1-yl]-1,2,4-triazine-6-carboxamide;

5-{[4-(morpholine-4-carbonyl)phenyl]amino}-3-[(3R)-3-[4-(2,2,2-trifluoroethoxy)benzamido]piperidin-1-yl]-1,2,4-triazine-6-carboxamide;

3-[(3R)-3-(5-methylthiophene-2-amido)piperidin-1-yl]-5-{[4-(morpholine-4-carbonyl)phenyl]amino}-1,2,4-triazine-6-carboxamide;

5-[(3R)-3-(4-tert-butylbenzamido)piperidin-1-yl]-3-{[4-(1-methylpiperidin-4-yl)phenyl]amino}pyrazine-2-carboxamide;

5-[(3R)-3-(4-tert-butylbenzamido)piperidin-1-yl]-3-{[4-(4-methylpiperazin-1-yl)phenyl]amino}pyrazine-2-carboxamide;

5-{[(3R)-1-(but-2-ynoyl)piperidin-3-yl](methyl)amino}-3-{[4-(morpholine-4-carbonyl)phenyl]amino}pyrazine-2-carboxamide;

5-{[(3R)-1-[(2E)-4-[cyclopropyl(methyl)amino]but-2-enoyl]piperidin-3-yl](methyl)amino}-3-{[4-(morpholine-4-carbonyl)phenyl]amino}pyrazine-2-carboxamide;

3-{[(3R)-1-(but-2-ynoyl)piperidin-3-yl]amino}-5-[(4-methanesulfonylphenyl)amino]-1,2,4-triazine-6-carboxamide;

3-{[(3R)-1-[(2E)-4-(dimethylamino)but-2-enoyl]piperidin-3-yl]amino}-5-[(4-methanesulfonylphenyl)amino]-1,2,4-triazine-6-carboxamide;

3-{[(3R)-1-[(2E)-4-[cyclopropyl(methyl)amino]but-2-enoyl]piperidin-3-yl]amino}-5-[(4-methanesulfonylphenyl)amino]-1,2,4-triazine-6-carboxamide;

3-{[4-(1-methylpiperidin-4-yl)phenyl]amino}-5-[(3R)-3-[(piperidine-1-carbonyl)amino]piperidin-1-yl]pyrazine-2-carboxamide;

3-{[4-(4-methylpiperazin-1-yl)phenyl]amino}-5-[(3R)-3-[(piperidine-1-carbonyl)amino]piperidin-1-yl]pyrazine-2-carboxamide;

3-[(3R)-3-{[(4-tert-butylphenyl)carbamoyl]amino}piperidin-1-yl]-5-{[4-(morpholine-4-carbonyl)phenyl]amino}-1,2,4-triazine-6-carboxamide;

3-[(3R)-3-{[(4-methoxyphenyl)carbamoyl]amino}piperidin-1-yl]-5-{[4-(morpholine-4-carbonyl)phenyl]amino}-1,2,4-triazine-6-carboxamide;

3-[(3R)-3-(4-ethoxybenzamido)piperidin-1-yl]-5-{[4-(morpholine-4-carbonyl)phenyl]amino}-1,2,4-triazine-6-carboxamide;

5-{[4-(morpholine-4-carbonyl)phenyl]amino}-3-[(3R)-3-(4-propoxybenzamido)piperidin-1-yl]-1,2,4-triazine-6-carboxamide;

5-{[4-(morpholine-4-carbonyl)phenyl]amino}-3-[(3R)-3-[4-(propan-2-yloxy)benzamido]piperidin-1-yl]-1,2,4-triazine-6-carboxamide;

3-[(3R)-3-(5-methyl-1,2-oxazole-3-amido)piperidin-1-yl]-5-{[4-(morpholine-4-carbonyl)phenyl]amino}-1,2,4-triazine-6-carboxamide;

N-[(3R)-1-(6-carbamoyl-5-{[4-(morpholine-4-carbonyl)phenyl]amino}-1,2,4-triazin-3-yl)piperidin-3-yl]-1-(propan-2-yl)-1H-1,2,3-benzotriazole-5-carboxamide;

3-[(3R)-3-(5-methyl-1,3-thiazole-2-amido)piperidin-1-yl]-5-{[4-(morpholine-4-carbonyl)phenyl]amino}-1,2,4-triazine-6-carboxamide;

3-[(3R)-3-(2-methyl-1,3-thiazole-5-amido)piperidin-1-yl]-5-{[4-(morpholine-4-carbonyl)phenyl]amino}-1,2,4-triazine-6-carboxamide;

N-[(3R)-1-(6-carbamoyl-5-{[4-(morpholine-4-carbonyl)phenyl]amino}-1,2,4-triazin-3-yl)piperidin-3-yl]-1,3-benzothiazole-2-carboxamide;

5-[(3R)-3-(4-methoxybenzamido)piperidin-1-yl]-3-{[4-(1-propanoylpiperidin-4-yl)phenyl]amino}pyrazine-2-carboxamide;

3-({4-[1-(cyanomethyl)piperidin-4-yl]phenyl}amino)-5-[(3R)-3-(4-methoxybenzamido)piperidin-1-yl]pyrazine-2-carboxamide;

5-[(3R)-3-(4-methoxybenzamido)piperidin-1-yl]-3-({4-[1-(2,2,2-trifluoroethyl)piperidin-4-yl]phenyl}amino)pyrazine-2-carboxamide;

3-[(3R)-3-(5-cyclopropyl-1,2-oxazole-3-amido)piperidin-1-yl]-5-{[4-(morpholine-4-carbonyl)phenyl]amino}-1,2,4-triazine-6-carboxamide;

5-{[4-(morpholine-4-carbonyl)phenyl]amino}-3-[(3R)-3-(4-phenoxybenzamido)piperidin-1-yl]-1,2,4-triazine-6-carboxamide;

3-{[3-fluoro-4-(morpholin-4-yl)phenyl]amino}-5-[(3R)-3-(4-methoxybenzamido)piperidin-1-yl]pyrazine-2-carboxamide;

5-[(3R)-3-(4-methoxybenzamido)piperidin-1-yl]-3-{[4-(3-oxomorpholin-4-yl)phenyl]amino}pyrazine-2-carboxamide;

N-[(3R)-1-(6-carbamoyl-5-{[4-(morpholine-4-carbonyl)phenyl]amino}-1,2,4-triazin-3-yl)piperidin-3-yl]-1,3-benzoxazole-2-carboxamide;

5-{[(3R)-1-[(2E)-4-(dimethylamino)but-2-enoyl]piperidin-3-yl](methyl)amino}-3-[(4-phenoxyphenyl)amino]pyrazine-2-carboxamide;

5-[(3R)-3-(4-methoxybenzamido)piperidin-1-yl]-3-[(3-methyl-1,2-thiazol-5-yl)amino]pyrazine-2-carboxamide;

3-[(3R)-3-(4-methyl-1,3-thiazole-2-amido)piperidin-1-yl]-5-{[4-(morpholine-4-carbonyl)phenyl]amino}-1,2,4-triazine-6-carboxamide;

3-({4-[2-(dimethylamino)ethoxy]phenyl}amino)-5-[(3R)-3-(4-methoxybenzamido)piperidin-1-yl]pyrazine-2-carboxamide;

3-({4-[2-(dimethyl-oxo-$1^{5}$-azanyl)ethoxy]phenyl}amino)-5-[(3R)-3-(4-methoxybenzamido)piperidin-1-yl]pyrazine-2-carboxamide;

3-{[4-(dimethylcarbamoyl)phenyl]amino}-5-[(3R)-3-(4-methoxybenzamido)piperidin-1-yl]pyrazine-2-carboxamide;

3-({4-[4-(dimethylcarbamoyl)piperidin-1-yl]phenyl}amino)-5-[(3R)-3-(4-methoxybenzamido)piperidin-1-yl]pyrazine-2-carboxamide;

N-[(3R)-1-(6-carbamoyl-5-{[4-(morpholine-4-carbonyl)phenyl]amino}-1,2,4-triazin-3-yl)piperidin-3-yl]-1-ethyl-1H-1,2,3-benzotriazole-5-carboxamide;

N-[(3R)-1-(6-carbamoyl-5-{[4-(morpholine-4-carbonyl)phenyl]amino}-1,2,4-triazin-3-yl)piperidin-3-yl]-1-cyclopropyl-1H-1,2,3-benzotriazole-5-carboxamide;

N-[(3R)-1-(6-carbamoyl-5-{[4-(morpholine-4-carbonyl)phenyl]amino}-1,2,4-triazin-3-yl)piperidin-3-yl]-1-propyl-1H-1,2,3-benzotriazole-5-carboxamide;

5-{[4-(morpholine-4-carbonyl)phenyl]amino}-3-[(3R)-3-{[4-(propan-2-yl)piperidine-1-carbonyl]amino}piperidin-1-yl]-1,2,4-triazine-6-carboxamide;

5-[(3R)-3-(4-methoxybenzamido)piperidin-1-yl]-3-({4-[1-(propan-2-yl)piperidin-4-yl]phenyl}amino)pyrazine-2-carboxamide;

3-{[4-(1-cyclopentylpiperidin-4-yl)phenyl]amino}-5-[(3R)-3-(4-methoxybenzamido)piperidin-1-yl]pyrazine-2-carboxamide;

3-{[4-(1-formylpiperidin-4-yl)phenyl]amino}-5-[(3R)-3-(4-methoxybenzamido)piperidin-1-yl]pyrazine-2-carboxamide;

5-{[4-(morpholine-4-carbonyl)phenyl]amino}-3-[(3R)-3-[2-oxo-2-(piperidin-1-yl)acetamido]piperidin-1-yl]-1,2,4-triazine-6-carboxamide;

5-[(3R)-3-(4-methoxybenzamido)piperidin-1-yl]-3-{[4-(morpholin-4-yl)phenyl]amino}pyrazine-2-carboxamide;

3-[(6-ethoxypyridin-3-yl)amino]-5-[(3R)-3-(4-methoxybenzamido)piperidin-1-yl]pyrazine-2-carboxamide;

3-[(4-methanesulfonylphenyl)amino]-5-[(3R)-3-(4-methoxybenzamido)piperidin-1-yl]pyrazine-2-carboxamide;

5-[(3R)-3-(4-methoxybenzamido)piperidin-1-yl]-3-{[4-(2-oxo-1,2-dihydropyridin-1-yl)phenyl]amino}pyrazine-2-carboxamide;

3-{[4-(1-methanesulfonylpiperidin-4-yl)phenyl]amino}-5-[(3R)-3-(4-methoxybenzamido)piperidin-1-yl]pyrazine-2-carboxamide;

3-({4-[1-(2-cyanoacetyl)piperidin-4-yl]phenyl}amino)-5-[(3R)-3-(4-methoxybenzamido)piperidin-1-yl]pyrazine-2-carboxamide;

3-[(4-methanesulfonylphenyl)amino]-5-[(3R)-3-[(piperidine-1-carbonyl)amino]piperidin-1-yl]pyrazine-2-carboxamide;

3-{[4-(2-ethoxyethoxy)phenyl]amino}-5-[(3R)-3-(4-methoxybenzamido)piperidin-1-yl]pyrazine-2-carboxamide;

3-[(4-ethoxyphenyl)amino]-5-[(3R)-3-(4-methoxybenzamido)piperidin-1-yl]pyrazine-2-carboxamide;

5-[(3R)-3-(4-methoxybenzamido)piperidin-1-yl]-3-{[4-(oxan-4-yl)phenyl]amino}pyrazine-2-carboxamide;

5-[(3R)-3-(4-methoxybenzamido)piperidin-1-yl]-3-{[4-(2-oxopiperidin-1-yl)phenyl]amino}pyrazine-2-carboxamide;

3-[(3R)-3-[(piperidine-1-carbonyl)amino]piperidin-1-yl]-5-[(quinolin-3-yl)amino]-1,2,4-triazine-6-carboxamide;

3-[(3R)-3-[(piperidine-1-carbonyl)amino]piperidin-1-yl]-5-[(quinolin-7-yl)amino]-1,2,4-triazine-6-carboxamide;

3-[(3R)-3-[(dimethylcarbamoyl)amino]piperidin-1-yl]-5-{[4-(morpholine-4-carbonyl)phenyl]amino}-1,2,4-triazine-6-carboxamide;

3-({4-[1-(dimethylcarbamoyl)piperidin-4-yl]phenyl}amino)-5-[(3R)-3-(4-methoxybenzamido)piperidin-1-yl]pyrazine-2-carboxamide;

5-[(3R)-3-[(piperidine-1-carbonyl)amino]piperidin-1-yl]-3-{[4-(1-propanoylpiperidin-4-yl)phenyl]amino}pyrazine-2-carboxamide;

3-{[4-(1-acetylpiperidin-4-yl)phenyl]amino}-5-[(3R)-3-(4-methoxybenzamido)piperidin-1-yl]pyrazine-2-carboxamide;

3-{[4-(1-formylpiperidin-4-yl)phenyl]amino}-5-[(3R)-3-[(piperidine-1-carbonyl)amino]piperidin-1-yl]pyrazine-2-carboxamide;

5-[(3R)-3-(4-methoxybenzamido)piperidin-1-yl]-3-{[4-(1-methylpiperidin-4-yl)phenyl]amino}pyrazine-2-carboxamide;

5-[(3R)-3-(4-methoxybenzamido)piperidin-1-yl]-3-{[6-(morpholin-4-yl)pyridin-3-yl]amino}pyrazine-2-carboxamide;

5-[(3R)-3-(4-methoxybenzamido)piperidin-1-yl]-3-[(quinolin-6-yl)amino]pyrazine-2-carboxamide;

3-[(1,3-benzothiazol-6-yl)amino]-5-[(3R)-3-(4-methoxybenzamido)piperidin-1-yl]pyrazine-2-carboxamide;

5-[(3R)-3-(4-methoxybenzamido)piperidin-1-yl]-3-[(4-methoxyphenyl)amino]pyrazine-2-carboxamide;

5-[(3R)-3-(4-methoxybenzamido)piperidin-1-yl]-3-{[4-(2-methoxyethoxy)phenyl]amino}pyrazine-2-carboxamide;

3-({4-[1-(2-cyanoacetyl)piperidin-4-yl]phenyl}amino)-5-[(3R)-3-[(piperidine-1-carbonyl)amino]piperidin-1-yl]pyrazine-2-carboxamide;

5-[(3R)-3-[(dimethylcarbamoyl)amino]piperidin-1-yl]-3-[(4-methanesulfonylphenyl)amino]pyrazine-2-carboxamide;

3-[(3R)-3-[(diethylcarbamoyl)amino]piperidin-1-yl]-5-{[4-(morpholine-4-carbonyl)phenyl]amino}-1,2,4-triazine-6-carboxamide;

3-({4-[1-(2-cyanoacetyl)piperidin-4-yl]phenyl}amino)-5-[(3R)-3-[(dimethylcarbamoyl)amino]piperidin-1-yl]pyrazine-2-carboxamide;

3-{[4-(1-cyclopentylpiperidin-4-yl)phenyl]amino}-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-{[4-(piperidin-4-yl)phenyl]amino}pyrazine-2-carboxamide;

5-[(3R)-3-[(dimethylcarbamoyl)amino]piperidin-1-yl]-3-{[4-(1-propanoylpiperidin-4-yl)phenyl]amino}pyrazine-2-carboxamide;

5-[(4-cyanophenyl)amino]-3-[(3R)-3-(4-ethoxybenzamido)piperidin-1-yl]-1,2,4-triazine-6-carboxamide;

3-{[4-(1-ethylpiperidin-4-yl)phenyl]amino}-5-[(3R)-3-(4-methoxybenzamido)piperidin-1-yl]pyrazine-2-carboxamide;

3-{[4-(1-cyclopropylpiperidin-4-yl)phenyl]amino}-5-[(3R)-3-(4-methoxybenzamido)piperidin-1-yl]pyrazine-2-carboxamide;

3-[(3R)-3-[(piperidine-1-carbonyl)amino]piperidin-1-yl]-5-{[4-(1-propanoylpiperidin-4-yl)phenyl]amino}-1,2,4-triazine-6-carboxamide;

5-{[4-(1-acetylpiperidin-4-yl)phenyl]amino}-3-[(3R)-3-[(piperidine-1-carbonyl)amino]piperidin-1-yl]-1,2,4-triazine-6-carboxamide;

5-{[4-(1-formylpiperidin-4-yl)phenyl]amino}-3-[(3R)-3-[(piperidine-1-carbonyl)amino]piperidin-1-yl]-1,2,4-triazine-6-carboxamide;

3-[(3R)-3-(4-ethoxybenzamido)piperidin-1-yl]-5-{[4-(1-methyl-4,5-dihydro-1H-imidazol-2-yl)phenyl]amino}-1,2,4-triazine-6-carboxamide;

5-{[4-(N,N-dimethylcarbamimidoyl)phenyl]amino}-3-[(3R)-3-(4-ethoxybenzamido)piperidin-1-yl]-1,2,4-triazine-6-carboxamide;

3-[(3R)-3-(4-ethoxybenzamido)piperidin-1-yl]-5-{[4-(pyrrolidine-1-carboximidoyl)phenyl]amino}-1,2,4-triazine-6-carboxamide;

5-{[4-(1-cyclopentylpiperidin-4-yl)phenyl]amino}-3-[(3R)-3-[(piperidine-1-carbonyl)amino]piperidin-1-yl]-1,2,4-triazine-6-carboxamide;

5-({4-[1-(2-cyanoacetyl)piperidin-4-yl]phenyl}amino)-3-[(3R)-3-[(piperidine-1-carbonyl)amino]piperidin-1-yl]-1,2,4-triazine-6-carboxamide;

3-[(3R)-3-[(piperidine-1-carbonyl)amino]piperidin-1-yl]-54{4-[1-(prop-2-enoyl)piperidin-4-yl]phenyl}amino)-1,2,4-triazine-6-carboxamide;

5-[(3R)-3-[(dimethylcarbamoyl)amino]piperidin-1-yl]-3-{[4-(1-methylpiperidin-4-yl)phenyl]amino}pyrazine-2-carboxamide;

5-[(3R)-3-{[ethyl(methyl)carbamoyl]amino}piperidin-1-yl]-3-{[4-(1-methylpiperidin-4-yl)phenyl]amino}pyrazine-2-carboxamide;

5-[(3R)-3-[(diethylcarbamoyl)amino]piperidin-1-yl]-3-{[4-(1-methylpiperidin-4-yl)phenyl]amino}pyrazine-2-carboxamide;

5-[(3R)-3-(4-fluorobenzamido)piperidin-1-yl]-3-{[4-(1-methylpiperidin-4-yl)phenyl]amino}pyrazine-2-carboxamide;

5-[(3R)-3-(4-ethoxybenzamido)piperidin-1-yl]-3-{[4-(1-methylpiperidin-4-yl)phenyl]amino}pyrazine-2-carboxamide;

5-[(3R)-3-(4-methoxybenzamido)piperidin-1-yl]-3-{[4-(propan-2-yl)phenyl]amino}pyrazine-2-carboxamide;

3-{[4-(1,1-dioxo-1λ$^6$-thiomorpholin-4-yl)phenyl]amino}-5-[(3R)-3-(4-methoxybenzamido)piperidin-1-yl]pyrazine-2-carboxamide;

5-{[4-(piperidin-4-yl)phenyl]amino}-3-[(3R)-3-[(piperidine-1-carbonyl)amino]piperidin-1-yl]-1,2,4-triazine-6-carboxamide;

3-[(3R)-3-(4-methoxybenzamido)piperidin-1-yl]-5-{[4-(piperidin-4-yl)phenyl]amino}-1,2,4-triazine-6-carboxamide;

5-{[4-(1-cyclopentylpiperidin-4-yl)phenyl]amino}-3-[(3R)-3-(4-methoxybenzamido)piperidin-1-yl]-1,2,4-triazine-6-carboxamide;

5-{[4-(4-cyclopentylpiperazin-1-yl)phenyl]amino}-3-[(3R)-3-(4-methoxybenzamido)piperidin-1-yl]-1,2,4-triazine-6-carboxamide;

5-({4-[4-(dimethylcarbamoyl)piperidin-1-yl]phenyl}amino)-3-[(3R)-3-(4-methoxybenzamido)piperidin-1-yl]-1,2,4-triazine-6-carboxamide;

5-[(3R)-3-[(dimethylcarbamoyl)(methyl)amino]piperidin-1-yl]-3-{[4-(1,1-dioxo-1λ⁶-thiomorpholin-4-yl)phenyl]amino}pyrazine-2-carboxamide;

3-{[2-fluoro-4-(piperidin-4-yl)phenyl]amino}-5-[(3R)-3-(4-methoxybenzamido)piperidin-1-yl]pyrazine-2-carboxamide;

3-{[3-fluoro-4-(piperidin-4-yl)phenyl]amino}-5-[(3R)-3-(4-methoxybenzamido)piperidin-1-yl]pyrazine-2-carboxamide;

5-[(3R)-3-[(dimethylcarbamoyl)(methyl)amino]piperidin-1-yl]-3-{[4-(1-propanoylpiperidin-4-yl)phenyl]amino}pyrazine-2-carboxamide;

5-[(3R)-3-[(dimethylcarbamoyl)(methyl)amino]piperidin-1-yl]-3-({4-[1-(dimethylcarbamoyl)piperidin-4-yl]phenyl}amino)pyrazine-2-carboxamide;

5-[(3R)-3-[(dimethylcarbamoyl)(methyl)amino]piperidin-1-yl]-3-{[4-(1-methanesulfonylpiperidin-4-yl)phenyl]amino}pyrazine-2-carboxamide;

3-{[4-(1-cyclopentylpiperidin-4-yl)phenyl]amino}-5-[(3R)-3-[(dimethylcarbamoyl)(methyl)amino]piperidin-1-yl]pyrazine-2-carboxamide;

3-{[4-(1,1-dioxo-1λ⁶-thiomorpholin-4-yl)phenyl]amino}-5-[(3R)-3-(3-methyl-2-oxoimidazolidin-1-yl)piperidin-1-yl]pyrazine-2-carboxamide;

5-[(3R)-3-{imidazo[1,2-a]pyridine-6-amido}piperidin-1-yl]-3-{[4-(oxan-4-yl)phenyl]amino}pyrazine-2-carboxamide;

5-[(3R)-3-{5-hydroxyimidazo[1,2-a]pyridine-6-amido}piperidin-1-yl]-3-{[4-(oxan-4-yl)phenyl]amino}pyrazine-2-carboxamide;

5-[(3R)-3-(4-methoxybenzamido)piperidin-1-yl]-3-{[4-(piperidin-1-yl)phenyl]amino}pyrazine-2-carboxamide;

3-{[4-(1-cyclopropylpiperidin-4-yl)phenyl]amino}-5-[(3R)-3-(3-methyl-2-oxoimidazolidin-1-yl)piperidin-1-yl]pyrazine-2-carboxamide;

5-[(3R)-3-[(dimethylcarbamoyl)amino]piperidin-1-yl]-3-{[4-(1,1-dioxo-1λ⁶-thiomorpholin-4-yl)phenyl]amino}pyrazine-2-carboxamide;

3-{[4-(1-cyclopentylpiperidin-4-yl)phenyl]amino}-5-[(3R)-3-(3-methyl-2-oxoimidazolidin-1-yl)piperidin-1-yl]pyrazine-2-carboxamide;

3-{[4-(1-ethylpiperidin-4-yl)phenyl]amino}-5-[(3R)-3-(3-methyl-2-oxoimidazolidin-1-yl)piperidin-1-yl]pyrazine-2-carboxamide;

3-{[4-(1-cyclopentylpiperidin-4-yl)phenyl]amino}-5-[(3R)-3-{[ethyl(methyl)carbamoyl]amino}piperidin-1-yl]pyrazine-2-carboxamide;

3-{[4-(1-cyclopentylpiperidin-4-yl)phenyl]amino}-5-[(3R)-3-propanamidopiperidin-1-yl]pyrazine-2-carboxamide;

5-{[4-(1-cyclopentylpiperidin-4-yl)phenyl]amino}-3-[(3R)-3-[(dimethylcarbamoyl)amino]piperidin-1-yl]-1,2,4-triazine-6-carboxamide;

5-{[4-(1-cyclopentylpiperidin-4-yl)phenyl]amino}-3-[(3R)-3-propanamidopiperidin-1-yl]-1,2,4-triazine-6-carboxamide;

3-{[4-(1-cyclopentylpiperidin-4-yl)phenyl]amino}-5-[(3R)-3-(4-fluorobenzamido)piperidin-1-yl]pyrazine-2-carboxamide;

5-[(3R)-3-[(dimethylcarbamoyl)amino]piperidin-1-yl]-3-(phenylamino)pyrazine-2-carboxamide;

5-[(3R)-3-[(dimethylcarbamoyl)amino]piperidin-1-yl]-3-{[4-(4-methylpiperidin-4-yl)phenyl]amino}pyrazine-2-carboxamide;

5-[(3R)-3-[(dimethylcarbamoyl)amino]piperidin-1-yl]-3-{[4-(1-ethylpiperidin-4-yl)phenyl]amino}pyrazine-2-carboxamide;

3-{[4-(1-cyclopropylpiperidin-4-yl)phenyl]amino}-5-[(3R)-3-[(dimethylcarbamoyl)amino]piperidin-1-yl]pyrazine-2-carboxamide;

3-[(4-chlorophenyl)amino]-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-({4-[1-(propan-2-yl)piperidin-4-yl]phenyl}amino)pyrazine-2-carboxamide;

4-[4-({3-carbamoyl-6-[(3R)-3-[(dimethylcarbamoyl)amino]piperidin-1-yl]pyrazin-2-yl}amino)phenyl]-1-(propan-2-yl)piperidin-1-ium-1-olate;

3-[(4-chloro-3-methoxyphenyl)amino]-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-[(3-methoxy-4-methylphenyl)amino]pyrazine-2-carboxamide;

5-[(3R)-3-[(dimethylcarbamoyl)amino]piperidin-1-yl]-3-{[4-(4-methyl-1-propanoylpiperidin-4-yl)phenyl]amino}pyrazine-2-carboxamide;

3-({4-[1-(dimethylcarbamoyl)-4-methylpiperidin-4-yl]phenyl}amino)-5-[(3R)-3-[(dimethylcarbamoyl)amino]piperidin-1-yl]pyrazine-2-carboxamide;

3-{[4-(1-cyclopentyl-4-methylpiperidin-4-yl)phenyl]amino}-5-[(3R)-3-[(dimethylcarbamoyl)amino]piperidin-1-yl]pyrazine-2-carboxamide;

3-{[4-(4-cyclopropylpiperazin-1-yl)phenyl]amino}-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-[(4-fluorophenyl)amino]pyrazine-2-carboxamide;

3-{[4-(4-cyclopentylpiperazin-1-yl)phenyl]amino}-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-({4-[(pyridin-2-yl)carbamoyl]phenyl}amino)pyrazine-2-carboxamide;

5-[(3R)-3-{[methyl(phenyl)carbamoyl]amino}piperidin-1-yl]-3-(phenylamino)pyrazine-2-carboxamide;

3-{[2-chloro-4-(piperidin-4-yl)phenyl]amino}-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-({4-[1-(dimethylcarbamoyl)piperidin-4-yl]phenyl}amino)pyrazine-2-carboxamide;

3-{[4-(1-cyclobutylpiperidin-4-yl)phenyl]amino}-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-({4-[1-(oxan-4-yl)piperidin-4-yl]phenyl}amino)pyrazine-2-carboxamide;

5-[(3R)-3-[(dimethylcarbamoyl)amino]piperidin-1-yl]-3-[(4-{1-[2-(2-hydroxyethoxy)ethyl]piperidin-4-yl}phenyl)amino]pyrazine-2-carboxamide;

3-{[4-(1-cyclopropanecarbonylpiperidin-4-yl)phenyl]amino}-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-{[4-(1-methanesulfonylpiperidin-4-yl)phenyl]amino}pyrazine-2-carboxamide;

ethyl N-[(3R)-1-(5-carbamoyl-6-{[4-(1-cyclopentylpiperidin-4-yl)phenyl]amino}pyrazin-2-yl)piperidin-3-yl]carbamate;

5-[(3R)-3-[(dimethylcarbamoyl)amino]piperidin-1-yl]-3-[(5-fluoro-6-methylpyridin-2-yl)amino]pyrazine-2-carboxamide;

5-[(3R)-3-[(dimethylcarbamoyl)amino]piperidin-1-yl]-3-({4-[1-(pyridin-2-yl)piperidin-4-yl]phenyl}amino)pyrazine-2-carboxamide;

5-[(3R)-3-[(dimethylcarbamoyl)amino]piperidin-1-yl]-3-{[4-(dimethylcarbamoyl)phenyl]amino}pyrazine-2-carboxamide;

5-[(3R)-3-[(dimethylcarbamoyl)amino]piperidin-1-yl]-3-{[4-(pyrrolidine-1-carbonyl)phenyl]amino}pyrazine-2-carboxamide;

5-[(3R)-3-[(dimethylcarbamoyl)amino]piperidin-1-yl]-3-{[4-(1-phenylpiperidin-4-yl)phenyl]amino}pyrazine-2-carboxamide;

3-{[4-(1-cyclohexylpiperidin-4-yl)phenyl]amino}-5-[(3R)-3-[(dimethylcarbamoyl)amino]piperidin-1-yl]pyrazine-2-carboxamide;

5-[(3R)-3-aminopiperidin-1-yl]-3-{[4-(1-cyclopentylpiperidin-4-yl)phenyl]amino}pyrazine-2-carboxamide;

3-{[4-(1-cyclopentylpiperidin-4-yl)phenyl]amino}-5-[(3R)-3-formamidopiperidin-1-yl]pyrazine-2-carboxamide;

3-{[4-(1-cyclopentylpiperidin-4-yl)phenyl]amino}-5-[(3R)-3-methanesulfonamidopiperidin-1-yl]pyrazine-2-carboxamide;

3-{[4-(1-cyclopentylpiperidin-4-yl)phenyl]amino}-5-[(3R)-3-ethanesulfonamidopiperidin-1-yl]pyrazine-2-carboxamide;

5-[(3R)-3-benzamidopiperidin-1-yl]-3-{[4-(1-cyclopentylpiperidin-4-yl)phenyl]amino}pyrazine-2-carboxamide;

3-{[4-(1-cyclopentylpiperidin-4-yl)phenyl]amino}-5-[(3R)-3-(pyridine-3-amido)piperidin-1-yl]pyrazine-2-carboxamide;

3-{[4-(1-cyclopentylpiperidin-4-yl)phenyl]amino}-5-[(3R)-3-(5-fluoropyridine-3-amido)piperidin-1-yl]pyrazine-2-carboxamide;

3-{[4-(1-cyclopentylpiperidin-4-yl)phenyl]amino}-5-[(3R)-3-(1-oxo-2,3-dihydro-1H-isoindol-2-yl)piperidin-1-yl]pyrazine-2-carboxamide;

3-{[4-(1-cyclopentylpiperidin-4-yl)phenyl]amino}-5-[(3R)-3-(2-oxopyrrolidin-1-yl)piperidin-1-yl]pyrazine-2-carboxamide;

3-{[4-(1-cyclopentylpiperidin-4-yl)phenyl]amino}-5-[(3R)-3-cyclopropaneamidopiperidin-1-yl]pyrazine-2-carboxamide;

5-[(3R)-3-[(dimethylcarbamoyl)amino]piperidin-1-yl]-3-({4-[1-(oxetan-3-yl)piperidin-4-yl]phenyl}amino)pyrazine-2-carboxamide;

3-{[4-(1-cyclopentylpiperidin-4-yl)phenyl]amino}-5-[(3R)-3-(3-ethyl-2-oxoimidazolidin-1-yl)piperidin-1-yl]pyrazine-2-carboxamide;

3-{[4-(1-cyclopentylpiperidin-4-yl)phenyl]amino}-5-[(2R,3R)-3-[(dimethylcarbamoyl)amino]-2-methylpiperidin-1-yl]pyrazine-2-carboxamide;

3-{[4-(1-cyclopentylpiperidin-4-yl)phenyl]amino}-5-[(2S,3R)-3-[(dimethylcarbamoyl)amino]-2-methylpiperidin-1-yl]pyrazine-2-carboxamide;

3-({4-[4-methyl-1-(propan-2-yl)piperidin-4-yl]phenyl}amino)-5-[(3R)-3-(3-methyl-2-oxoimidazolidin-1-yl)piperidin-1-yl]pyrazine-2-carboxamide;

3-{[4-(1-cyclopropyl-4-methylpiperidin-4-yl)phenyl]amino}-5-[(3R)-3-(3-methyl-2-oxoimidazolidin-1-yl)piperidin-1-yl]pyrazine-2-carboxamide;

3-({4-[4-methyl-1-(oxetan-3-yl)piperidin-4-yl]phenyl}amino)-5-[(3R)-3-(3-methyl-2-oxoimidazolidin-1-yl)piperidin-1-yl]pyrazine-2-carboxamide;

3-{[4-(1-cyclobutyl-4-methylpiperidin-4-yl)phenyl]amino}-5-[(3R)-3-(3-methyl-2-oxoimidazolidin-1-yl)piperidin-1-yl]pyrazine-2-carboxamide;

3-{[4-(1-cyclopentyl-4-methylpiperidin-4-yl)phenyl]amino}-5-[(3R)-3-(3-methyl-2-oxoimidazolidin-1-yl)piperidin-1-yl]pyrazine-2-carboxamide;

3-{[4-(1-formyl-4-methylpiperidin-4-yl)phenyl]amino}-5-[(3R)-3-(3-methyl-2-oxoimidazolidin-1-yl)piperidin-1-yl]pyrazine-2-carboxamide;

3-{[4-(4-methyl-1-propanoylpiperidin-4-yl)phenyl]amino}-5-[(3R)-3-(3-methyl-2-oxoimidazolidin-1-yl)piperidin-1-yl]pyrazine-2-carboxamide;

3-{[4-(1-cyclopropanecarbonyl-4-methylpiperidin-4-yl)phenyl]amino}-5-[(3R)-3-(3-methyl-2-oxoimidazolidin-1-yl)piperidin-1-yl]pyrazine-2-carboxamide;

3-{[4-(1-cyclopentylpiperidin-4-yl)phenyl]amino}-5-[(3R)-3-[(dimethylsulfamoyl)amino]piperidin-1-yl]pyrazine-2-carboxamide;

5-[(3R)-3-[(dimethylcarbamoyl)amino]piperidin-1-yl]-3-({4-[1-(dimethylsulfamoyl)piperidin-4-yl]phenyl}amino)pyrazine-2-carboxamide;

5-[(2R,3R)-3-amino-2-methylpiperidin-1-yl]-3-{[4-(1-cyclopentylpiperidin-4-yl)phenyl]amino}pyrazine-2-carboxamide;

5-[(2S,3R)-3-amino-2-methylpiperidin-1-yl]-3-{[4-(1-cyclopentylpiperidin-4-yl)phenyl]amino}pyrazine-2-carboxamide;

5-[(3R)-3-aminopiperidin-1-yl]-3-{[4-(1-cyclopropylpiperidin-4-yl)phenyl]amino}pyrazine-2-carboxamide;

3-[(4-cyclohexylphenyl)amino]-5-[(3R)-3-[(dimethylcarbamoyl)amino]piperidin-1-yl]pyrazine-2-carboxamide;

3-{[4-(1-cyanocyclopentyl)phenyl]amino}-5-[(3R)-3-[(dimethylcarbamoyl)amino]piperidin-1-yl]pyrazine-2-carboxamide;

3-{[4-(1-cyclopropylpiperidin-4-yl)phenyl]amino}-5-[(3R)-3-{spiro[3.3]heptane-2-amido}piperidin-1-yl]pyrazine-2-carboxamide;

3-{[4-(1-cyclopropylpiperidin-4-yl)phenyl]amino}-5-[(3R)-3-(4-phenylbenzamido)piperidin-1-yl]pyrazine-2-carboxamide;

3-{[4-(1-cyclopropylpiperidin-4-yl)phenyl]amino}-5-[(3R)-3-(6-phenylpyridine-3-amido)piperidin-1-yl]pyrazine-2-carboxamide;

5-[(2R,3R)-3-benzamido-2-methylpiperidin-1-yl]-3-{[4-(1-cyclopentylpiperidin-4-yl)phenyl]amino}pyrazine-2-carboxamide;

5-[(2S,3R)-3-benzamido-2-methylpiperidin-1-yl]-3-{[4-(1-cyclopentylpiperidin-4-yl)phenyl]amino}pyrazine-2-carboxamide;

5-[(3R)-3-(1-benzothiophene-2-amido)piperidin-1-yl]-3-{[4-(1-cyclopropylpiperidin-4-yl)phenyl]amino}pyrazine-2-carboxamide;

5-[(3R)-3-(3-chlorobenzamido)piperidin-1-yl]-3-{[4-(1-cyclopropylpiperidin-4-yl)phenyl]amino}pyrazine-2-carboxamide;

5-[(3R)-3-(4-chlorobenzamido)piperidin-1-yl]-3-{[4-(1-cyclopropylpiperidin-4-yl)phenyl]amino}pyrazine-2-carboxamide;

5-[(3R)-3-(5-chlorothiophene-2-amido)piperidin-1-yl]-3-{[4-(1-cyclopropylpiperidin-4-yl)phenyl]amino}pyrazine-2-carboxamide;

5-[(3R)-3-cyclopentaneamidopiperidin-1-yl]-3-{[4-(1-cyclopropylpiperidin-4-yl)phenyl]amino}pyrazine-2-carboxamide;

3-{[4-(1-cyclopropylpiperidin-4-yl)phenyl]amino}-5-[(3R)-3-(4,5,6,7-tetrahydro-1-benzothiophene-2-amido)piperidin-1-yl]pyrazine-2-carboxamide;

5-[(3R)-3-(5-chloropyridine-3-amido)piperidin-1-yl]-3-{[4-(1-cyclopropylpiperidin-4-yl)phenyl]amino}pyrazine-2-carboxamide;

3-{[4-(1-cyclopropylpiperidin-4-yl)phenyl]amino}-5-[(3R)-3-(naphthalene-2-amido)piperidin-1-yl]pyrazine-2-carboxamide;

3-{[4-(1-cyclopropylpiperidin-4-yl)phenyl]amino}-5-[(2R,3R)-3-[(dimethylcarbamoyl)amino]-2-methylpiperidin-1-yl]pyrazine-2-carboxamide;

3-{[4-(1-cyclobutyl-4-methylpiperidin-4-yl)phenyl]amino}-5-[(2R,3R)-3-[(dimethylcarbamoyl)amino]-2-methylpiperidin-1-yl]pyrazine-2-carboxamide;

3-{[4-(1-cyclopentyl-4-methylpiperidin-4-yl)phenyl]amino}-5-[(2R,3R)-3-[(dimethylcarbamoyl)amino]-2-methylpiperidin-1-yl]pyrazine-2-carboxamide;

3-{[4-(1-cyano-1-methylethyl)phenyl]amino}-5-[(3R)-3-[(dimethylcarbamoyl)amino]piperidin-1-yl]pyrazine-2-carboxamide;

3-{[4-(1-carbamoyl-1-methylethyl)phenyl]amino}-5-[(3R)-3-[(dimethylcarbamoyl)amino]piperidin-1-yl]pyrazine-2-carboxamide;

3-{[4-(1-cyanocyclopentyl)phenyl]amino}-5-[(2R,3R)-3-[(dimethylcarbamoyl)amino]-2-methylpiperidin-1-yl]pyrazine-2-carboxamide;

3-{[4-(1-carbamoylcyclopentyl)phenyl]amino}-5-[(2R,3R)-3-[(dimethylcarbamoyl)amino]-2-methylpiperidin-1-yl]pyrazine-2-carboxamide;

3-{[4-(4-cyano-1-cyclopentylpiperidin-4-yl)phenyl]amino}-5-[(3R)-3-(3-methyl-2-oxoimidazolidin-1-yl)piperidin-1-yl]pyrazine-2-carboxamide;

3-{[4-(4-carbamoyl-1-cyclopentylpiperidin-4-yl)phenyl]amino}-5-[(3R)-3-(3-methyl-2-oxoimidazolidin-1-yl)piperidin-1-yl]pyrazine-2-carboxamide;

5-[(3aR,7aR)-1-(dimethylcarbamoyl)-octahydro-1H-pyrrolo[3,2-b]pyridin-4-yl]-3-{[4-(1-cyclopentylpiperidin-4-yl)phenyl]amino}pyrazine-2-carboxamide;

5-[(3aR,7aR)-1-cyclopropanecarbonyl-octahydro-1H-pyrrolo[3,2-b]pyridin-4-yl]-3-{[4-(1-cyclopentylpiperidin-4-yl)phenyl]amino}pyrazine-2-carboxamide;

3-{[4-(1-cyanocyclopropyl)phenyl]amino}-5-[(3R)-3-[(dimethylcarbamoyl)amino]piperidin-1-yl]pyrazine-2-carboxamide;

3-{[4-(1-carbamoylcyclopropyl)phenyl]amino}-5-[(3R)-3-[(dimethylcarbamoyl)amino]piperidin-1-yl]pyrazine-2-carboxamide;

3-{[4-(4-cyano-1-cyclobutylpiperidin-4-yl)phenyl]amino}-5-[(3R)-3-(3-methyl-2-oxoimidazolidin-1-yl)piperidin-1-yl]pyrazine-2-carboxamide;

5-[(3aR,7aR)-octahydro-1H-pyrrolo[3,2-b]pyridin-4-yl]-3-{[4-(1-cyclopentylpiperidin-4-yl)phenyl]amino}pyrazine-2-carboxamide;

3-{[4-(1-cyclobutylpiperidin-4-yl)phenyl]amino}-5-[(3R)-3-(3-methyl-2-oxoimidazolidin-1-yl)piperidin-1-yl]pyrazine-2-carboxamide;

5-[(3R)-3-[3-(3-chlorophenyl)-2-oxoimidazolidin-1-yl]piperidin-1-yl]-3-{[4-(1-cyclopentylpiperidin-4-yl)phenyl]amino}pyrazine-2-carboxamide;

5-[(2R,3R)-2-methyl-3-(3-methyl-2-oxoimidazolidin-1-yl)piperidin-1-yl]-3-{[4-(4-methylpiperidin-4-yl)phenyl]amino}pyrazine-2-carboxamide;

3-{[4-(1-cyclobutyl-4-methylpiperidin-4-yl)phenyl]amino}-5-[(2R,3R)-2-methyl-3-(3-methyl-2-oxoimidazolidin-1-yl)piperidin-1-yl]pyrazine-2-carboxamide;

3-{[4-(1-cyclopentyl-4-methylpiperidin-4-yl)phenyl]amino}-5-[(2R,3R)-2-methyl-3-(3-methyl-2-oxoimidazolidin-1-yl)piperidin-1-yl]pyrazine-2-carboxamide;

5-[(3R)-3-(3-methyl-2-oxoimidazolidin-1-yl)piperidin-1-yl]-3-(phenylamino)pyrazine-2-carboxamide;

5-[(3R)-3-(3-methyl-2-oxoimidazolidin-1-yl)piperidin-1-yl]-3-({4-[1-(trifluoromethyl)cyclopropyl]phenyl}amino)pyrazine-2-carboxamide;

5-[(3aR,7aR)-octahydro-1H-pyrrolo[2,3-c]pyridin-6-yl]-3-{[4-(1-cyclopentylpiperidin-4-yl)phenyl]amino}pyrazine-2-carboxamide;

3-{[4-(1-cyclopentylpiperidin-4-yl)phenyl]amino}-5-[(3R)-3-(3-methyl-2-oxo-1,3-diazinan-1-yl)piperidin-1-yl]pyrazine-2-carboxamide;

3-{[4-(1-cyclopropyl-4-methylpiperidin-4-yl)phenyl]amino}-5-[(2R,3R)-3-[(dimethylcarbamoyl)amino]-2-methylpiperidin-1-yl]pyrazine-2-carboxamide;

3-{[4-(1-cyclopentylpiperidin-4-yl)phenyl]amino}-5-[(3R,4R)-3-[(dimethylcarbamoyl)amino]-4-methylpiperidin-1-yl]pyrazine-2-carboxamide;

5-[(3aS,7aR)-1-(dimethylcarbamoyl)-octahydro-1H-pyrrolo[2,3-c]pyridin-6-yl]-3-{[4-(1-cyclopentylpiperidin-4-yl)phenyl]amino}pyrazine-2-carboxamide;

5-[(3aS,7aR)-1-cyclopropanecarbonyl-octahydro-1H-pyrrolo[2,3-c]pyridin-6-yl]-3-{[4-(1-cyclopentylpiperidin-4-yl)phenyl]amino}pyrazine-2-carboxamide;

3-{[4-(1-cyclobutylpiperidin-4-yl)phenyl]amino}-5-[(2R,3R)-3-[(dimethylcarbamoyl)amino]-2-methylpiperidin-1-yl]pyrazine-2-carboxamide;

3-{[4-(4-methyl-1-propanoylpiperidin-4-yl)phenyl]amino}-5-[(2R,3R)-2-methyl-3-(3-methyl-2-oxoimidazolidin-1-yl)piperidin-1-yl]pyrazine-2-carboxamide;

3-{[4-(1-cyclopentylpiperidin-4-yl)phenyl]amino}-5-[(3R)-3-(2-oxoimidazolidin-1-yl)piperidin-1-yl]pyrazine-2-carboxamide;

3-{[4-(1-cyclopentylpiperidin-4-yl)phenyl]amino}-5-[(3R)-3-(3-cyclopropyl-2-oxoimidazolidin-1-yl)piperidin-1-yl]pyrazine-2-carboxamide;

5-[(3R)-3-(3-cyclopropyl-2-oxoimidazolidin-1-yl)piperidin-1-yl]-3-{[4-(1-cyclopropyl-4-methylpiperidin-4-yl)phenyl]amino}pyrazine-2-carboxamide;

3-{[4-(1-cyclobutylpiperidin-4-yl)phenyl]amino}-5-[(3R)-3-(3-cyclopropyl-2-oxoimidazolidin-1-yl)piperidin-1-yl]pyrazine-2-carboxamide;

3-{[4-(4-cyano-1-cyclopentylpiperidin-4-yl)phenyl]amino}-5-[(2R,3R)-3-[(dimethylcarbamoyl)amino]-2-methylpiperidin-1-yl]pyrazine-2-carboxamide;

3-{[4-(4-carbamoyl-1-cyclopentylpiperidin-4-yl)phenyl]amino}-5-[(2R,3R)-3-[(dimethylcarbamoyl)amino]-2-methylpiperidin-1-yl]pyrazine-2-carboxamide;

5-[(2R,3R)-3-[(dimethylcarbamoyl)amino]-2-methylpiperidin-1-yl]-3-({4-[1-(trifluoromethyl)cyclopropyl]phenyl}amino)pyrazine-2-carboxamide;

3-{[4-(1-cyanocyclopropyl)phenyl]amino}-5-[(2R,3R)-3-[(dimethylcarbamoyl)amino]-2-methylpiperidin-1-yl]pyrazine-2-carboxamide;

3-{[4-(1-carbamoylcyclopropyl)phenyl]amino}-5-[(2R,3R)-3-[(dimethylcarbamoyl)amino]-2-methylpiperidin-1-yl]pyrazine-2-carboxamide;

3-({4-[1-(aminomethyl)cyclopentyl]phenyl}amino)-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-({4-[1-(dimethylcarbamoyl)cyclopropyl]phenyl}amino)pyrazine-2-carboxamide;

5-[(3R)-3-({[3-chloro-5-(trifluoromethyl)phenyl](methyl)carbamoyl}amino)piperidin-1-yl]-3-[(4-fluorophenyl)amino]pyrazine-2-carboxamide;

5-[(3R)-3-({[3-chloro-5-(trifluoromethyl)phenyl](methyl)carbamoyl}amino)piperidin-1-yl]-3-{[4-(1-cyanocyclopropyl)phenyl]amino}pyrazine-2-carboxamide;

3-{[4-(1-carbamoylcyclopropyl)phenyl]amino}-5-[(3R)-3-({[3-chloro-5-(trifluoromethyl)phenyl](methyl)carbamoyl}amino)piperidin-1-yl]pyrazine-2-carboxamide;

3-{[4-(1-cyclopropylpiperidin-4-yl)phenyl]amino}-5-[(3R)-3-(3-methyl-2-oxo-1,3-diazinan-1-yl)piperidin-1-yl]pyrazine-2-carboxamide;

3-{[4-(1-cyclopropyl-4-methylpiperidin-4-yl)phenyl]amino}-5-[(3R)-3-(3-methyl-2-oxo-1,3-diazinan-1-yl)piperidin-1-yl]pyrazine-2-carboxamide;

3-[(1-cyclopropyl-1H-pyrazol-4-yl)amino]-5-[(3R)-3-[(dimethylcarbamoyl)amino]piperidin-1-yl]pyrazine-2-carboxamide;

3-[(1-cyclopentyl-1H-pyrazol-4-yl)amino]-5-[(3R)-3-[(dimethylcarbamoyl)amino]piperidin-1-yl]pyrazine-2-carboxamide;

3-{[4-(1-cyclopentyl-4-methylpiperidin-4-yl)phenyl]amino}-5-[(3R)-3-(3-methyl-2-oxo-1,3-diazinan-1-yl)piperidin-1-yl]pyrazine-2-carboxamide;

3-{[4-(1-cyclopropyl-4-methylpiperidin-4-yl)phenyl]amino}-5-[(3R)-3-(3-ethyl-2-oxoimidazolidin-1-yl)piperidin-1-yl]pyrazine-2-carboxamide;

3-{[4-(1-cyclopentylpiperidin-4-yl)phenyl]amino}-5-[(2R,3R)-2-methyl-3-(3-methyl-2-oxo-1,3-diazinan-1-yl)piperidin-1-yl]pyrazine-2-carboxamide;

3-({4-[1-(aminomethyl)cyclopropyl]phenyl}amino)-5-[(3R)-3-[(dimethylcarbamoyl)amino]piperidin-1-yl]pyrazine-2-carboxamide;

3-({4-[(dimethylamino)methyl]phenyl}amino)-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-[(1-methyl-2-oxo-1,2-dihydropyridin-4-yl)amino]pyrazine-2-carboxamide;

3-{[4-(1-cyclopentylpiperidin-4-yl)phenyl]amino}-5-[(3R)-3-[(dimethylcarbamoyl)amino]azepan-1-yl]pyrazine-2-carboxamide;

3-{[4-(1-cyclopentylpiperidin-4-yl)phenyl]amino}-5-[(3R)-3-cyclopropaneamidoazepan-1-yl]pyrazine-2-carboxamide;

3-{[1-(1-cyclopentylazetidin-3-yl)-1H-pyrazol-4-yl]amino}-5-[(3R)-3-[(dimethylcarbamoyl)amino]piperidin-1-yl]pyrazine-2-carboxamide;

3-{[1-(1-cyclopentylpiperidin-4-yl)-1H-pyrazol-4-yl]amino}-5-[(3R)-3-[(dimethylcarbamoyl)amino]piperidin-1-yl]pyrazine-2-carboxamide;

3-{[1-(1-cyclopropanecarbonylpiperidin-4-yl)-1H-pyrazol-4-yl]amino}-5-[(3R)-3-[(dimethylcarbamoyl)amino]piperidin-1-yl]pyrazine-2-carboxamide;

(4aR,8aR)-5-(5-carbamoyl-6-{[4-(1-cyclopentylpiperidin-4-yl)phenyl]amino}pyrazin-2-yl)-N,N-dimethyl-decahydro-1,5-naphthyridine-1-carboxamide;

5-[(3R)-3-[(dimethylcarbamoyl)amino]piperidin-1-yl]-3-[(3-methyl-1,2-thiazol-5-yl)amino]pyrazine-2-carboxamide;

5-[(3R)-3-[(dimethylcarbamoyl)amino]piperidin-1-yl]-3-[(1-methyl-6-oxo-1,6-dihydropyridin-3-yl)amino]pyrazine-2-carboxamide;

5-[(3R)-3-[(dimethylcarbamoyl)amino]piperidin-1-yl]-3-{[4-(propan-2-yloxy)phenyl]amino}pyrazine-2-carboxamide;

5-[(3R)-3-[(dimethylcarbamoyl)amino]piperidin-1-yl]-3-{[4-(2-methoxyethoxyl)phenyl]amino}pyrazine-2-carboxamide;

3-({4-[2-(dimethylamino)ethoxy]phenyl}amino)-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-[(4-nitrophenyl)amino]pyrazine-2-carboxamide;

3-{[4-(1-cyclobutylpiperidin-4-yl)phenyl]amino}-5-[(2R,3R)-3-[(dimethylcarbamoyl)amino]-2-ethylpiperidin-1-yl]pyrazine-2-carboxamide;

3-{[(3R)-1-(but-2-ynoyl)pyrrolidin-3-yl]amino}-5-{[4-(morpholine-4-carbonyl)phenyl]amino}-1,2,4-triazine-6-carboxamide;

3-{[4-(cyclopentyloxy)phenyl]amino}-5-[(3R)-3-[(dimethylcarbamoyl)amino]piperidin-1-yl]pyrazine-2-carboxamide;

5-[(2R,3R)-3-[(dimethylcarbamoyl)amino]-2-methylpiperidin-1-yl]-3-[(3-methyl-1,2-thiazol-5-yl)amino]pyrazine-2-carboxamide;

5-[(2R,3R)-3-[(dimethylcarbamoyl)amino]-2-methylpiperidin-1-yl]-3-{[4-(propan-2-yloxy)phenyl]amino}pyrazine-2-carboxamide; and 5-[(2R,3R)-3-[(dimethylcarbamoyl)amino]-2-methylpiperidin-1-yl]-3-[(4-methanesulfonylphenyl)amino]pyrazine-2-carboxamide;

or a pharmaceutically acceptable solvate, pharmaceutically acceptable salt, or pharmaceutically acceptable prodrug thereof.

At least some of the chemical names of compounds of the invention as given and set forth in this application, may have been generated on an automated basis by use of a commercially available chemical naming software program, and have not been independently verified. Representative programs performing this function include the Chemdraw naming tool sold by Cambridge Software, Inc. and the Instant JChem Software tool sold by ChemAxon, Inc. In the instance where the indicated chemical name and the depicted structure differ, the depicted structure will control.

In another aspect is a pharmaceutical composition comprising a therapeutically effective amount of a compound of Formula (IA), (I), (Ia), (II), (III), (IV), (Va)-(Vh), or (VIa)-(VIb), or a pharmaceutically acceptable salt, pharmaceutically acceptable solvate, or pharmaceutically acceptable prodrug thereof, and a pharmaceutically acceptable excipient. In one embodiment, the pharmaceutical composition comprising the compound of Formula (IA), (I), (Ia), (II), (III), (IV), (Va)-(Vh), or (VIa)-(VIb), or a pharmaceutically acceptable salt, pharmaceutically acceptable solvate, or pharmaceutically acceptable prodrug thereof, is formulated for a route of administration selected from oral administration, parenteral administration, buccal administration, nasal administration, topical administration, or rectal administration.

In another aspect is a method for treating an autoimmune disease or condition comprising administering to a patient in need a therapeutically effective amount of a compound of Formula (IA), (I), (Ia), (II), (III), (IV), (Va)-(Vh), or (VIa)-(VIb), or a pharmaceutically acceptable salt, pharmaceutically acceptable solvate, or pharmaceutically acceptable prodrug thereof. In one embodiment the autoimmune disease is selected from rheumatoid arthritis or lupus. In a further aspect is a method for treating a heteroimmune disease or condition comprising administering to a patient in need a therapeutically effective amount of a compound of Formula (IA), (I), (Ia), (II), (III), (IV), (Va)-(Vh), or (VIa)-(VIb), or a pharmaceutically acceptable salt, pharmaceutically acceptable solvate, or pharmaceutically acceptable prodrug thereof. In yet another embodiment is a method for treating a cancer comprising administering to a patient in need a therapeutically effective amount of a compound of Formula (IA), (I), (Ia), (II), (III), (IV), (Va)-(Vh), or (VIa)-(VIb), or a pharmaceutically acceptable salt, pharmaceutically acceptable solvate, or pharmaceutically acceptable prodrug thereof. In one embodiment the cancer is a B-cell proliferative disorder. In another embodiment the B-cell proliferative disorder is diffuse large B cell lymphoma, follicular lymphoma, mantel cell lymphoma, or chronic lymphocytic leukemia.

In yet a further aspect is a method for treating mastocytosis comprising administering to a patient in need a therapeutically effective amount of a compound of Formula (IA), (I), (Ia), (II), (III), (IV), (Va)-(Vh), or (VIa)-(VIb), or a pharmaceutically acceptable salt, pharmaceutically acceptable solvate, or pharmaceutically acceptable prodrug thereof.

In another aspect is a method for treating osteoporosis or bone resorption disorders comprising administering to a patient in need a therapeutically effective amount of a compound of Formula (IA), (I), (Ia), (II), (III), (IV), (Va)-(Vh), or (VIa)-(VIb), or a pharmaceutically acceptable salt, pharmaceutically acceptable solvate, or pharmaceutically acceptable prodrug thereof.

In a further aspect is a method for treating an inflammatory disease or condition comprising administering to a patient in need a therapeutically effective amount of a compound of Formula (IA), (I), (Ia), (II), (III), (IV), (Va)-(Vh), or (VIa)-(VIb), or a pharmaceutically acceptable salt, pharmaceutically acceptable solvate, or pharmaceutically acceptable prodrug thereof.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Throughout the specification, groups and substituents thereof can be chosen by one skilled in the field to provide stable moieties and compounds.

In some embodiments, the compounds of Formula (IA), (I), (Ia), (II), (III), (IV), (Va)-(Vh), or (VIa)-(VIb) reversibly inhibit Btk and in other embodiments are used to treat patients suffering from Bruton's tyrosine kinase-dependent or Bruton's tyrosine kinase mediated conditions or diseases, including, but not limited to, cancer, autoimmune and other inflammatory diseases.

In some embodiments, the compounds of Formula (IA), (I), (Ia), (II), (III), (IV), (Va)-(Vh), or (VIa)-(VIb) irreversibly inhibit Btk and in other embodiments are used to treat patients suffering from Bruton's tyrosine kinase-dependent or Bruton's tyrosine kinase mediated conditions or diseases, including, but not limited to, cancer, autoimmune and other inflammatory diseases.

Preparation of Compounds

Compounds of any of Formula (IA), (I), (Ia), (II), (III), (IV), (Va)-(Vh), or (VIa)-(VIb) may be synthesized using standard synthetic reactions known to those of skill in the art or using methods known in the art. The reactions can be employed in a linear sequence to provide the compounds or they may be used to synthesize fragments which are subsequently joined by the methods known in the art.

Described herein are compounds that inhibit the activity of tyrosine kinase(s), such as Btk, and processes for their preparation. Also described herein are pharmaceutically acceptable salts, pharmaceutically acceptable solvates, pharmaceutically active metabolites and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY $4^{th}$ Ed., (Wiley 1992); Carey and Sundberg, ADVANCED ORGANIC CHEMISTRY $4^{th}$ Ed., Vols. A and B (Plenum 2000, 2001); Green and Wuts, PROTECTIVE GROUPS IN ORGANIC SYNTHESIS $3^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). Other methods for the synthesis of compounds described herein may be found in International Patent Publication No. WO 01/01982901, Arnold et al. *Bioorganic & Medicinal Chemistry Letters* 10 (2000) 2167-2170; Burchat et al. *Bioorganic & Medicinal Chemistry Letters* 12 (2002) 1687-1690. General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared as a single isomer or a mixture of isomers.

Further Forms of Compounds

Compounds disclosed herein have a structure of Formula (IA), (I), (Ia), (II), (III), (IV), (Va)-(Vh), or (VIa)-(VIb). It is understood that when reference is made to compounds described herein, it is meant to include compounds of any of Formula (IA), (I), (Ia), (II), (III), (IV), (Va)-(Vh), or (VIa)-(VIb), as well as to all of the specific compounds that fall within the scope of these generic formulae, unless otherwise indicated.

The compounds described herein may possess one or more stereocenters and each center may exist in the R or S configuration. The compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

Diasteromeric mixtures can be separated into their individual diastereomers on the basis of their physical chemical differences by methods known, for example, by chromatography and/or fractional crystallization. In one embodiment, enantiomers can be separated by chiral chromatographic columns. In other embodiments, enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

The methods and formulations described herein include the use of N-oxides, crystalline forms (also known as polymorphs), or pharmaceutically acceptable salts of compounds described herein, as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Compounds of any of Formula (IA), (I), (Ia), (II), (III), (IV), (Va)-(Vh), or (VIa)-(VIb) in unoxidized form can be prepared from N-oxides of compounds of any of Formula (IA), (I), (Ia), (II), (III), (IV), (Va)-(Vh), or (VIa)-(VIb) by treating with a reducing agent, such as, but not limited to, sulfur, sulfur dioxide, triphenyl phosphine, lithium borohydride, sodium borohydride, phosphorus trichloride, tribromide, or the like in a suitable inert organic solvent, such as, but not limited to, acetonitrile, ethanol, aqueous dioxane, or the like at 0 to 80° C.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. (see, for example, Nogrady (1985) *Medicinal Chemistry A Biochemical Approach*, Oxford University Press, New York, pages 388-392; Silverman (1992), *The Organic Chemistry of Drug Design and Drug Action*, Academic Press, Inc., San Diego, pages 352-401, Saulnier et al., (1994), *Bioorganic and Medicinal Chemistry Letters*, Vol. 4, p. 1985).

Prodrug forms of the herein described compounds, wherein the prodrug is metabolized in vivo to produce a derivative as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., *Am. J. Physiol.*, 269:G210-218 (1995); McLoed et al., *Gastroenterol*, 106:405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein in their entirety.

Sites on the aromatic ring portion of compounds of any of Formula (IA), (I), (Ia), (II), (III), (IV), (Va)-(Vh), or (VIa)-(VIb) can be susceptible to various metabolic reactions, therefore incorporation of appropriate substituents on the aromatic ring structures, such as, by way of example only, halogens can reduce, minimize or eliminate this metabolic pathway.

Compounds described herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as $^{2}H$, $^{3}H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^{3}H$ and $^{14}C$ are incorporated, are useful in drug and/or substrate tissue distribution assays. Further, substitution with isotopes such as deuterium, i.e., $^{2}H$, can afford certain therapeutic advantages resulting from greater metabolic stability, for example increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed) by reacting the free base form of the compound with a pharmaceutically acceptable: inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-

[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds described herein may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen by one skilled in the field to provide stable moieties and compounds.

Pharmaceutical Composition/Formulation

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

A pharmaceutical composition, as used herein, refers to a mixture of a compound described herein, such as, for example, compounds of any of Formula (IA), (I), (Ia), (II), (III), (IV), (Va)-(Vh), or (VIa)-(VIb), with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound described herein, such as, for example, a compound of any of Formula (IA), (I), (Ia), (II), (III), (IV), (Va)-(Vh), or (VIa)-(VIb), as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as *acacia*, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of any of Formula (IA), (I), (Ia), (II), (III), (IV), (Va)-(Vh), or (VIa)-(VIb), and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, *acacia*, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: *The Science*

*and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum *acacia*, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizcers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., *acacia* syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, *stevia*, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-*eucalyptus*, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, µg, or ng of therapeutic agent per ml, dl, or l of blood serum, absorbed into the bloodstream after administration. As used herein, measurable plasma concentrations are typically measured in ng/ml or µg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Steady state," as used herein, is when the amount of drug administered is equal to the amount of drug eliminated within one dosing interval resulting in a plateau or constant plasma drug exposure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum *acacia*, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, *acacia*, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Dosage Forms

The compositions described herein can be formulated for administration to a subject via any conventional means including, but not limited to, oral, parenteral (e.g., intravenous, subcutaneous, or intramuscular), buccal, intranasal, rectal or transdermal administration routes. As used herein, the term "subject" is used to mean an animal, preferably a mammal, including a human or non-human. The terms patient and subject may be used interchangeably.

Moreover, the pharmaceutical compositions described herein, which include a compound of any of Formula (IA), (I), (Ia), (II), (III), (IV), (Va)-(Vh), or (VIa)-(VIb) can be formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound of any of Formula (IA), (I), (Ia), (II), (III), (IV), (Va)-(Vh), or (VIa)-(VIb), with one or more pharmaceutical excipients to form a bulk blend composition. When referring to these bulk blend compositions as homogeneous, it is meant that the particles of the compound of any of Formula (IA), (I), (Ia), (II), (III), (IV), (Va)-(Vh), or (VIa)-(VIb), are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of the compound of any of Formula (IA), (I), (Ia), (II), (III), (IV), (Va)-(Vh), or (VIa)-(VIb). In one embodiment, some or all of the particles of the compound of any of Formula (IA), (I), (Ia), (II), (III), (IV), (Va)-(Vh), or (VIa)-(VIb), are coated. In another embodiment, some or all of the particles of the compound of any of Formula (IA), (I), (Ia), (II), (III), (IV), (Va)-(Vh), or (VIa)-(VIb), are microencapsulated. In still another embodiment, the particles of the compound of any of Formula (IA), (I), (Ia), (II), (III), (IV), (Va)-(Vh), or (VIa)-(VIb), are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of any of Formula (IA), (I), (Ia), (II), (III), (IV), (Va)-(Vh), or (VIa)-(VIb), from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as *acacia*, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxypropylmethylcellulose, polysorbate-80, hydroxyethylcellulose, sodium alginate, gums, such as, e.g., gum tragacanth and gum *acacia*, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of the compound of of any of Formula (IA), (I), (Ia), (II), (III), (IV), (Va)-(Vh), or (VIa)-(VIb), from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound of any of Formula (IA), (I), (Ia), (II), (III), (IV), (Va)-(Vh), or (VIa)-(VIb), described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound of any of Formula (IA), (I), (Ia), (II), (III), (IV), (Va)-(Vh), or (VIa)-(VIb), and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds of any of Formula (IA), (I), (Ia), (II), (III), (IV), (Va)-(Vh), or (VIa)-(VIb), which sufficiently isolate the compound of any of Formula (IA), (I), (Ia), (II), (III), (IV), (Va)-(Vh), or (VIa)-(VIb), from other non-compatible excipients. Materials compatible with compounds of any of Formula (IA), (I), (Ia), (II), (III), (IV), (Va)-(Vh), or (VIa)-(VIb), are those that delay the release of the compounds of any of Formula (IA), (I), (Ia), (II), (III), (IV), (Va)-(Vh), or (VIa)-(VIb), in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, OpadryYS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds of any of Formula (IA), (I), (Ia), (II), (III), (IV), (Va)-(Vh), or (VIa)-(VIb), may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, inliquid drying, and desolvation in liquid media could also be used. Furthermore, other methods such as roller compaction, extrusion/spheronization, coacervation, or nanoparticle coating may also be used.

In one embodiment, the particles of compounds of any of Formula (IA), (I), (Ia), (II), (III), (IV), (Va)-(Vh), or (VIa)-(VIb), are microencapsulated prior to being formulated into one of the above forms. In still another embodiment, some or most of the particles are coated prior to being further formulated by using standard coating procedures, such as those described in *Remington's Pharmaceutical Sciences*, 20th Edition (2000).

In other embodiments, the solid dosage formulations of the compounds of any of Formula (IA), (I), (Ia), (II), (III), (IV), (Va)-(Vh), or (VIa)-(VIb), are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with a compound of any of Formula (IA), (I), (Ia), (II), (III), (IV), (Va)-(Vh), or (VIa)-(VIb), described herein, may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, the formulations described herein, which include a compound of Formula (IA), (I), (Ia), (II), (III), (IV), (Va)-(Vh), or (VIa)-(VIb), are solid dispersions. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl 2004/0013734, each of which is specifically incorporated by reference. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518, each of which is specifically incorporated by reference.

The pharmaceutical solid oral dosage forms including formulations described herein, which include a compound of any of Formula (IA), (I), (Ia), (II), (III), (IV), (Va)-(Vh), or (VIa)-(VIb), can be further formulated to provide a controlled release of the compound of Formula (IA), (I), (Ia), (II), (III), (IV), (Va)-(Vh), or (VIa)-(VIb). Controlled release refers to the release of the compound of any of Formula (IA), (I), (Ia), (II), (III), (IV), (Va)-(Vh), or (VIa)-(VIb), from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

Shellac, also called purified lac, a refined product obtained from the resinous secretion of an insect. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles <1 µm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions;

Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include a compound of Formula (IA), (I), (Ia), (II), (III), (IV), (Va)-(Vh), or (VIa)-(VIb), are delivered using a pulsatile dosage form. A pulsatile dosage form is capable of providing one or more immediate release pulses at predetermined time points after a controlled lag time or at specific sites. Pulsatile dosage forms including the formulations described herein, which include a compound of any of Formula (IA), (I), (Ia), (II), (III), (IV), (Va)-(Vh), or (VIa)-(VIb), may be administered using a variety of pulsatile formulations known in the art. For example, such formulations include, but are not limited to, those described in U.S. Pat. Nos. 5,011,692, 5,017,381, 5,229,135, and 5,840,329, each of which is specifically incorporated by reference. Other pulsatile release dosage forms suitable for use with the present formulations include, but are not limited to, for example, U.S. Pat. Nos. 4,871,549, 5,260,068, 5,260,069, 5,508,040, 5,567,441 and 5,837,284, all of which are specifically incorporated by reference. In one embodiment, the controlled release dosage form is pulsatile release solid oral dosage form including at least two groups of particles, (i.e. multiparticulate) each containing the formulation described herein. The first group of particles provides a substantially immediate dose of the compound of any of Formula (IA), (I), (Ia), (II), (III), (IV), (Va)-(Vh), or (VIa)-(VIb), upon ingestion by a mammal. The first group of particles can be either uncoated or include a coating and/or sealant. The second group of particles includes coated particles, which includes from about 2% to about 75%, from about 2.5% to about 70%, or from about 40% to about 70%, by weight of the total dose of the compound of any of Formula (IA), (I), (Ia), (II), (III), (IV), (Va)-(Vh), or (VIa)-(VIb), in said formulation, in admixture with one or more binders. The coating includes a pharmaceutically acceptable ingredient in an amount sufficient to provide a delay of from about 2 hours to about 7 hours following ingestion before release of the second dose. Suitable coatings include one or more differentially degradable coatings such as, by way of example only, pH sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, and Eudragit® NE30D, Eudragit® NE 40D®) either alone or blended with cellulose derivatives, e.g., ethylcellulose, or non-enteric coatings having variable thickness to provide differential release of the formulation that includes a compound of any of Formula (IA), (I), (Ia), (II), (III), (IV), (Va)-(Vh), or (VIa)-(VIb).

Many other types of controlled release systems known to those of ordinary skill in the art and are suitable for use with the formulations described herein. Examples of such delivery systems include, e.g., polymer-based systems, such as polylactic and polyglycolic acid, polyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms*, 2 Ed., Vol. 1, pp. 209-214 (1990); Singh et al., *Encyclopedia of Pharmaceutical Technology*, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference.

In some embodiments, pharmaceutical formulations are provided that include particles of the compounds of any of Formula (IA), (I), (Ia), (II), (III), (IV), (Va)-(Vh), or (VIa)-(VIb), described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., *Encyclopedia of Pharmaceutical Technology*, $2^{nd}$ Ed., pp. 754-757 (2002). In addition to the particles of compound of Formula (IA), (I), (Ia), (II), (III), (IV), (Va)-(Vh), or (VIa)-(VIb), the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose)(Ac-Di-Sol®, cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, *acacia*, chitosans and combinations thereof. The concentration of the viscosity enhancing agent will depend upon the agent selected and the viscosity desired.

Examples of sweetening agents suitable for the aqueous suspensions or dispersions described herein include, for example, *acacia* syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, monoammonium glyrrhizinate) (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, *stevia*, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-*eucalyptus*, orange-cream, vanilla-mint, and mixtures thereof. In one embodiment, the aqueous liquid dispersion can comprise a sweetening agent or flavoring agent in a concentration ranging from about 0.001% to about 1.0% the volume of the aqueous dispersion. In another embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563, each of which is specifically incorporated by reference.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Intranasal Formulations

Intranasal formulations are known in the art and are described in, for example, U.S. Pat. Nos. 4,476,116, 5,116,817 and 6,391,452, each of which is specifically incorporated by reference. Formulations that include a compound of any of Formula (IA), (I), (Ia), (II), (III), (IV), (Va)-(Vh), or (VIa)-(VIb), which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. The nasal dosage form should be isotonic with nasal secretions.

For administration by inhalation, the compounds of any of Formula (IA), (I), (Ia), (II), (III), (IV), (Va)-(Vh), or (VIa)-(VIb), described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal Formulations

Buccal formulations that include compounds of any of Formula (IA), (I), (Ia), (II), (III), (IV), (Va)-(Vh), or (VIa)-(VIb), may be administered using a variety of formulations known in the art. For example, such formulations include, but are not limited to, U.S. Pat. Nos. 4,229,447, 4,596,795, 4,755,386, and 5,739,136, each of which is specifically incorporated by reference. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound of any of Formula (IA), (I), (Ia), (II), (III), (IV), (Va)-(Vh), or (VIa)-(VIb), is provided essentially throughout. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with the compound of any of Formula (IA), (I), (Ia), (II), (III), (IV), (Va)-(Vh), or (VIa)-(VIb), and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal Formulations

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety.

The transdermal dosage forms described herein may incorporate certain pharmaceutically acceptable excipients which are conventional in the art. In one embodiments, the transdermal formulations described herein include at least three components: (1) a formulation of a compound of any of Formula (IA), (I), (Ia), (II), (III), (IV), (Va)-(Vh), or (VIa)-(VIb); (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds of any of Formula (IA), (I), (Ia), (II), (III), (IV), (Va)-(Vh), or (VIa)-(VIb). The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Injectable Formulations

Formulations that include a compound of any of Formula (IA), (I), (Ia), (II), (III), (IV), (Va)-(Vh), or (VIa)-(VIb), suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Other Formulations

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly (methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Examples of Methods of Dosing and Treatment Regimens

The compounds described herein can be used in the preparation of medicaments for the inhibition of Btk or a homolog thereof, or for the treatment of diseases or conditions that would benefit, at least in part, from inhibition of Btk or a homolog thereof. In addition, a method for treating any of the diseases or conditions described herein in a subject in need of such treatment, involves administration of pharmaceutical compositions containing at least one compound of any of Formula (IA), (I), (Ia), (II), (III), (IV), (Va)-(Vh), or (VIa)-(VIb), described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, or from about 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The foregoing ranges are merely suggestive, as the number of variables in regard to an individual treatment regime is large, and considerable excursions from these recommended values are not uncommon Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

The reversible or irreversible Btk inhibitor compositions described herein can also be used in combination with other well known therapeutic reagents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

In certain instances, it may be appropriate to administer at least one reversible or irreversible Btk inhibitor compound described herein in combination with another therapeutic agent. By way of example only, if one of the side effects experienced by a patient upon receiving one of the reversible or irreversible Btk inhibitor compounds described herein is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the skilled physician after evaluation of the disease being treated and the condition of the patient.

It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formula (IA), (I), (Ia), (II), (III), (IV), (Va)-(Vh), or (VIa)-(VIb) described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/ or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, within the first 6 hours of the onset of the symptoms, or within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound should be administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, between about 1 month to about 5 years, or from about 1 month to about 3 years.

Exemplary Therapeutic Agents for Use in Combination with a Reversible or Irreversible Btk Inhibitor Compound Where the subject is suffering from or at risk of suffering from an autoimmune disease, an inflammatory disease, or an allergy disease, a reversible or irreversible Btk inhibitor compound can be used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, or anticholinergics.

Where the subject is suffering from or at risk of suffering from a B-cell proliferative disorder (e.g., plasma cell myeloma), the subjected can be treated with a reversible or irreversible Btk inhibitor compound in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a reversible or irreversible Btk inhibitor compound include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a reversible or irreversible Btk inhibitor compound include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a reversible or irreversible Btk inhibitor compound include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a reversible or irreversible Btk inhibitor compound include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a reversible or irreversible Btk inhibitor compound include but are not limited to *vinca* alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a reversible or irreversible Btk inhibitor compound include, but are not limited to, nitrogen mustards (e.g., mechloroethamine, cyclophosphamide, chlorambucil, meiphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists useful in combination with a reversible or irreversible Btk inhibitor compound include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with a reversible or irreversible Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (*Asta medica*), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, lnanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (*Asta medica*), D-68144 (*Asta medica*), Diazonamide A, A-293620 (Abbott), NPI-2350 (Nereus), Taccalonolide A, TUB-245 (Aventis), A-259754 (Abbott), Diozostatin, (–)-Phenylahistin (also known as NSCL-96F037), D-68838 (*Asta medica*), D-68836 (*Asta medica*), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Where the subject is suffering from or at risk of suffering from a thromboembolic disorder (e.g., stroke), the subject can be treated with a reversible or irreversible Btk inhibitor compound in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of Btk, or in which Btk is a mediator or contributor to the symptoms or cause.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

Example 1

Synthesis of (E)-4-(6-amino-9-(3-(4-(dimethylamino)-N-methylbut-2-enamido)phenyl)-8-oxo-8,9-dihydro-7H-purin-7-yl)-N-(pyridin-2-yl)benzamide (6)

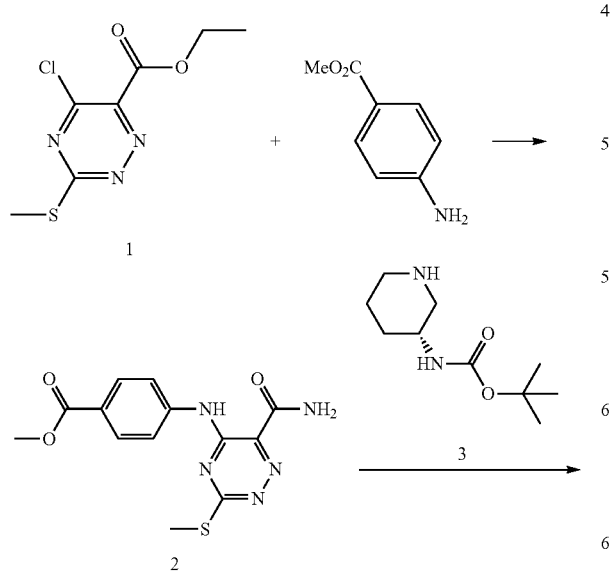

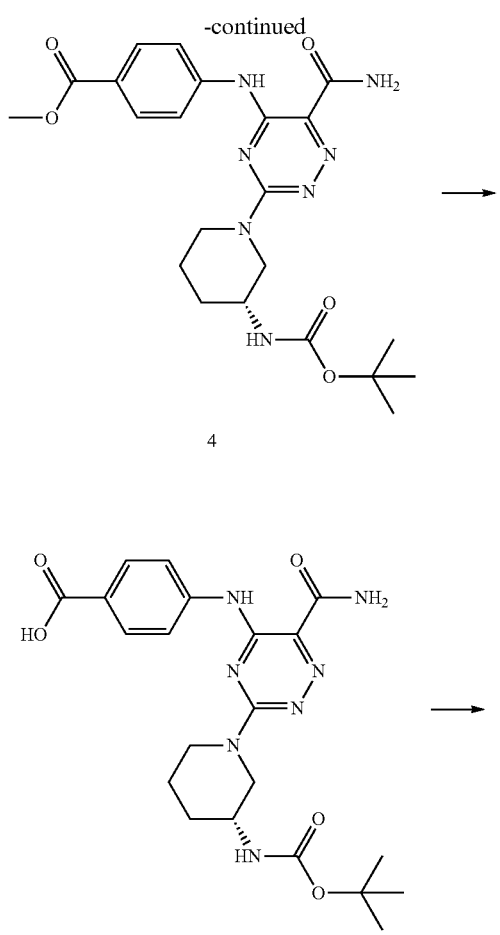

To ethyl 5-chloro-3-(methylthio)-1,2,4-triazine-6-carboxylate (1) (350 mg, 1.50 mmol) in acetonitrile (10 mL) was added methyl 4-aminobenzoate (340 mg, 2.25 mmol) and then diisopropylethylamine (DIEA, 0.39 mL, 2.25 mmol). The mixture was stirred at RT for 3 h. To the mixture was then added ammonia (7.0 N solution in methanol, 30 mL). The mixture was stirred overnight. The solid was isolated by filtration, washed with a minimum amount of cold acetonitrile and then washed with hexane. The solid was dried in a vacuum oven to afford methyl 4-(6-carbamoyl-3-(methylthio)-1,2,4-triazin-5-ylamino)benzoate (2) (348 mg, 73% yield) in high purity.

To a solution of 2 (200 mg, 0.62 mmol) in NMP (10 mL) was added mCPBA (77% strength, 420 mg, 1.86 mmol). The mixture was stirred at RT for 1 h. To the mixture was added DIEA (0.52 mL, 3.00 mmol) and (R)-(3-BOC-amino)piperidine (3) (240 mg, 1.20 mmol). The mixture was stirred at 90° C. for 90 min. The mixture was cooled, diluted with 200 mL EtOAc, washed with 1N NaOH and brine, dried, and concentrated in vacuo. The residue was subjected to flash column chromatography with 0 to 30% EtOAc in DCM to yield (R)-methyl 4-(3-(3-(tert-butoxycarbonylamino)piperidin-1-yl)-6-carbamoyl-1,2,4-triazin-5-ylamino)benzoate (4) in quantitative yield.

To a solution of 4 in MeOH (10 mL), water (10 mL) and THF (40 mL) at RT was added LiOH hydrate (126 mg, 3.0 mmol). The mixture was stirred overnight. The mixture was concentrated in vacuo, acidified with HCl (until pH ~2), and extracted with EtOAc (×3). The organic extracts were combined, dried and concentrated in vacuo to dryness to yield (R)-4-(3-(3-(tert-butoxycarbonylamino)piperidin-1-yl)-6-carbamoyl-1,2,4-triazin-5-ylamino)benzoic acid (5) in quantitative yield.

Compound 5 (90 mg, 0.20 mmol) was mixed with morpholine (53 µL, 0.60 mmol) in DMF (5 mL). To the mixture were added DIEA (105 µL, 0.60 mmol) and PyBOP (312 mg, 0.60 mmol). The mixture was stirred for 5 min, diluted with 100 mL EtOAc, washed with brine ×2, dried, and concentrated in vacuo. The residue was subjected to flash column chromatography with 50 to 100% EtOAc in hexane to isolate (R)-tert-butyl 1-(6-carbamoyl-5-(4-(morpholine-4-carbonyl)phenylamino)-1,2,4-triazin-3-yl)piperidin-3-ylcarbamate in quantitative yield. (R)-tert-butyl 1-(6-carbamoyl-5-(4-(morpholine-4-carbonyl)phenylamino)-1,2,4-triazin-3-yl)piperidin-3-ylcarbamate was treated with DCM (10 mL) and TFA (3 mL) for 1 h at RT. The mixture was concentrated in vacuo to dryness. The residue was subjected to reverse phase prep HPLC to isolate the (R)-3-(3-aminopiperidin-1-yl)-5-(4-(morpholine-4-carbonyl)phenylamino)-1,2,4-triazine-6-carboxamide (6) as HCl salt. MS found for $C_{20}H_{26}N_8O_3$ as $(M+H)^+$ 427.1, $(M-H)^-$ 425.2. UV: $\lambda$=270 nm.

Example 2

Synthesis of (R)-3-(3-(4-tert-butylbenzamido)piperidin-1-yl)-5-(4-(morpholine-4-carbonyl)phenylamino)-1,2,4-triazine-6-carboxamide (7)

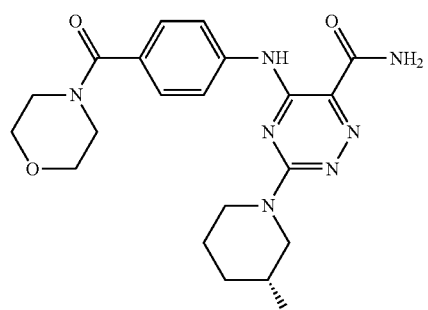

6

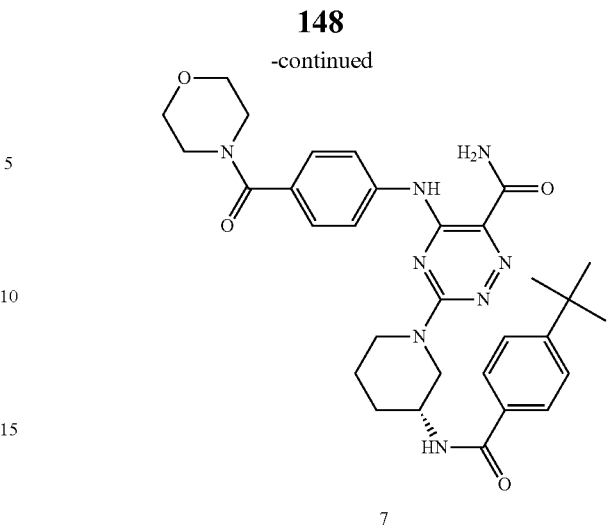

7

To a solution of 6 HCl salt (46 mg, 0.10 mmol) in NMP (2 mL) was added DIEA (70 µL, 0.40 mmol) and then 4-tert-butylbenzoyl chloride (39 mg, 0.20 mmol). The mixture was stirred at RT for 45 min, quenched with TFA (0.1 mL), diluted with water (2 mL), and subjected to reverse phase prep HPLC to afford (R)-3-(3-(4-tert-butylbenzamido)piperidin-1-yl)-5-(4-(morpholine-4-carbonyl)phenylamino)-1,2,4-triazine-6-carboxamide (7) (27 mg) as HCl salt. MS found for $C_{31}H_{38}N_8O_4$ as $(M+H)^+$ 587.2, $(M-H)^-$ 585.4. UV: $\lambda$=273 nm.

Example 3

Synthesis of (R)-3-(3-(4-tert-butyl-N-methylbenzamido)piperidin-1-yl)-5-(4-(morpholine-4-carbonyl)phenylamino)-1,2,4-triazine-6-carboxamide (11)

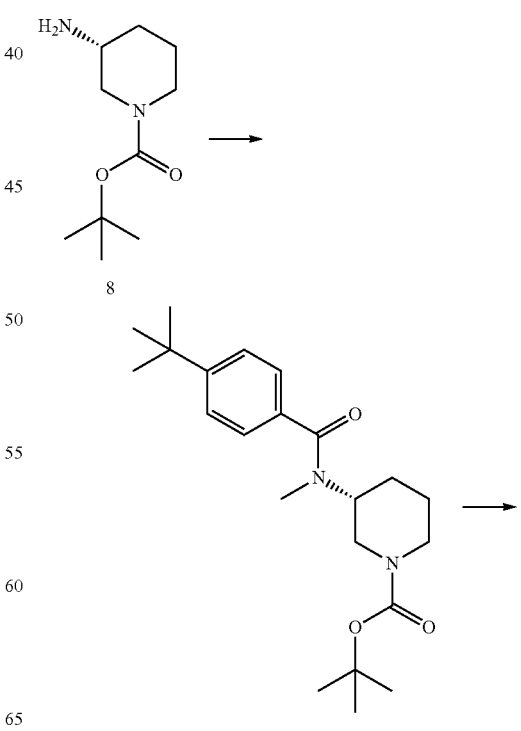

8

9

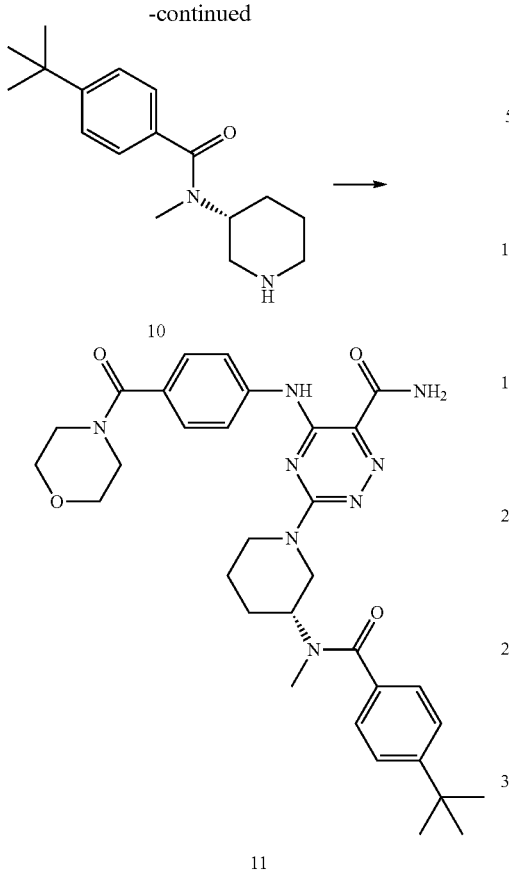

To a solution of (R)-tert-butyl 3-aminopiperidine-1-carboxylate (8) (6.27 g, 33.5 mmol) in DCM (100 mL) was added DIEA (8.75 mL, 50.3 mmol) and then 4-tert-butylbenzoyl chloride (8.0 mL, 43.6 mmol) in drop-wise manner. The mixture was stirred for 3 h at RT, diluted with DCM, washed with 1N NaOH, dried, and concentrated. The residue was subjected to flash column chromatography with 0 to 10% EtOAc in DCM to give (R)-tert-butyl 3-(4-tert-butylbenzamido)piperidine-1-carboxylate (11.0 g, 91%). To a solution of (R)-tert-butyl 3-(4-tert-butylbenzamido)piperidine-1-carboxylate (850 mg, 2.36 mmol) in DMF (10 mL) was added NaH (60% in mineral oil, 190 mg, 4.72 mmol). The mixture was stirred at RT for 10 min and then iodomethane (0.44 mL, 7.08 mmol) was added. The mixture was stirred at RT for 1 h, and diluted with 150 mL EtOAc. The mixture was washed with water ×2, dried, and concentrated. The residue was subjected to flash column with 0 to 3% MeOH in DCM to afford (R)-tert-butyl 3-(4-tert-butyl-N-methylbenzamido)piperidine-1-carboxylate (9) in quantitative yield. It was treated with 15 mL 4N HCl in dioxane at RT for 1 h. The mixture was concentrated in vacuo to dryness to afford (R)-4-tert-butyl-N-methyl-N-(piperidin-3-yl)benzamide (10) HCl salt in quantitative yield.

To a solution of 3-(methylthio)-5-(4-(morpholine-4-carbonyl)phenylamino)-1,2,4-triazine-6-carboxamide (75 mg, 0.20 mmol) in NMP (5 mL) was added mCPBA (77% strength, 150 mg, 0.60 mmol). The mixture was stirred at RT for 1 h to yield a mixture of corresponding sulfone and sulfoxide. To the mixture was added DIEA (0.35 mL, 2.00 mmol) and 10 (125 mg, 0.40 mmol). The mixture was stirred at 90° C. for 90 min. The mixture was cooled, diluted with 100 mL EtOAc, washed with 1N NaOH and brine, dried, and concentrated in vacuo. The residue was subjected to flash column chromatography with 0 to 5% MeOH in DCM and further purified using reverse phase preparative HPLC to yield the title compound (11) as HCl salt (100 mg). MS found for $C_{32}H_{40}N_8O_4$ as $(M+H)^+$ 601.3, $(M-H)^-$ 599.3. UV: $\lambda=277$ nm.

Example 4

Synthesis of (R)-3-(3-(4-methylbenzamido)piperidin-1-yl)-5-(4-(morpholine-4-carbonyl)phenylamino)-1,2,4-triazine-6-carboxamide (12)

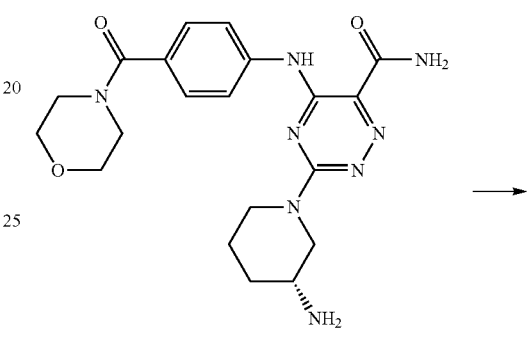

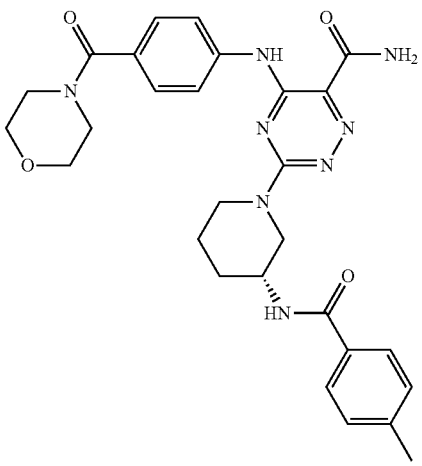

To a solution of 6 HCl salt (90 mg, 0.19 mmol) in DMF (3 mL) was added DIEA (135 µL, 0.76 mmol) and then p-toluoyl chloride (50 µL, 0.38 mmol). The mixture was stirred at RT for 30 min, diluted with 100 mL EtOAc, washed with water, dried, and concentrated. The residue was subjected to flash column chromatography with 0 to 7% MeOH in DCM to isolate the title compound (12) (61 mg). MS found for $C_{28}H_{32}N_8O_4$ as $(M+H)^+$ 545.2, $(M-H)^-$ 543.2. UV: $\lambda=272$ nm.

Example 5

Synthesis of (R)-3-(3-benzamidopiperidin-1-yl)-5-(4-(morpholine-4-carbonyl)phenylamino)-1,2,4-triazine-6-carboxamide (13)

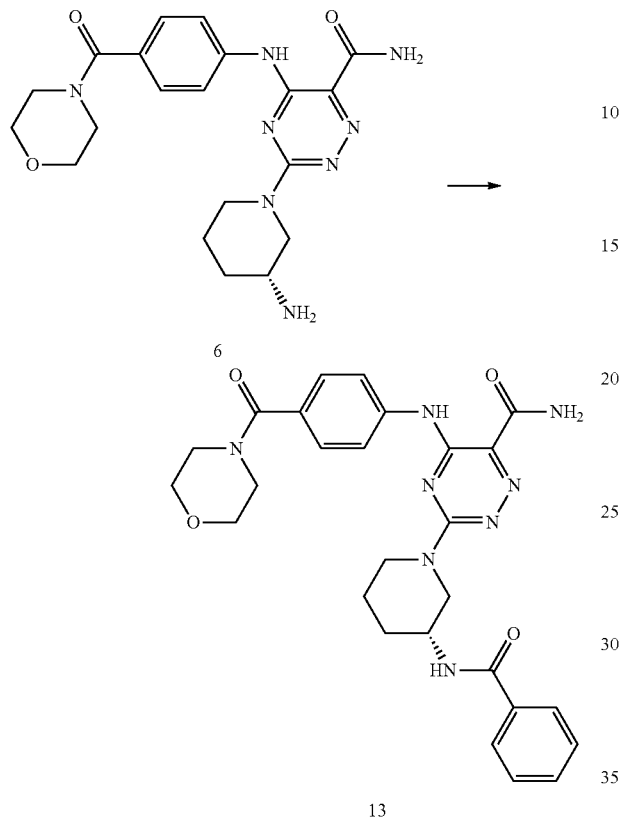

In a similar manner as described in Example 4, (R)-3-(3-benzamidopiperidin-1-yl)-5-(4-(morpholine-4-carbonyl)phenylamino)-1,2,4-triazine-6-carboxamide (13) was prepared using benzoyl chloride. MS found for $C_{27}H_{30}N_8O_4$ as $(M+H)^+$ 531.1, $(M-H)^-$ 529.3. UV: $\lambda$=274 nm.

Example 6

Synthesis of (R)-5-(4-(morpholine-4-carbonyl)phenylamino)-3-(3-(4-(trifluoromethyl)benzamido)piperidin-1-yl)-1,2,4-triazine-6-carboxamide (14)

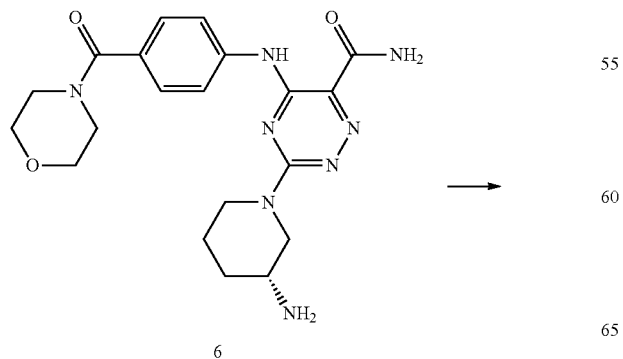

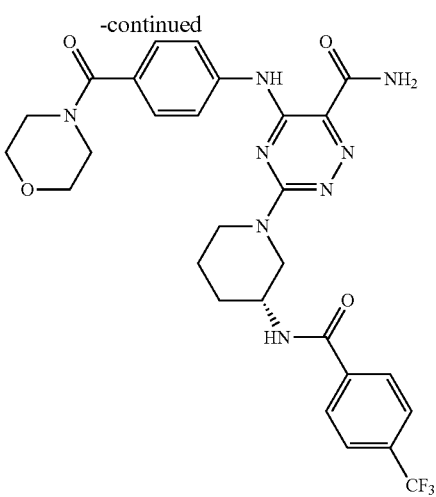

In a similar manner as described in Example 4, (R)-5-(4-(morpholine-4-carbonyl)phenylamino)-3-(3-(4-(trifluoromethyl)benzamido)piperidin-1-yl)-1,2,4-triazine-6-carboxamide (14) was prepared using 3-trifluoromethylbenzoyl chloride. MS found for $C_{28}H_{29}F_3N_8O_4$ as $(M+H)^+$ 599.1, $(M-H)^-$ 597.2. UV: $\lambda$=275 nm.

Example 7

Synthesis of (R)-3-(3-(4-cyanobenzamido)piperidin-1-yl)-5-(4-(morpholine-4-carbonyl)phenylamino)-1,2,4-triazine-6-carboxamide (15)

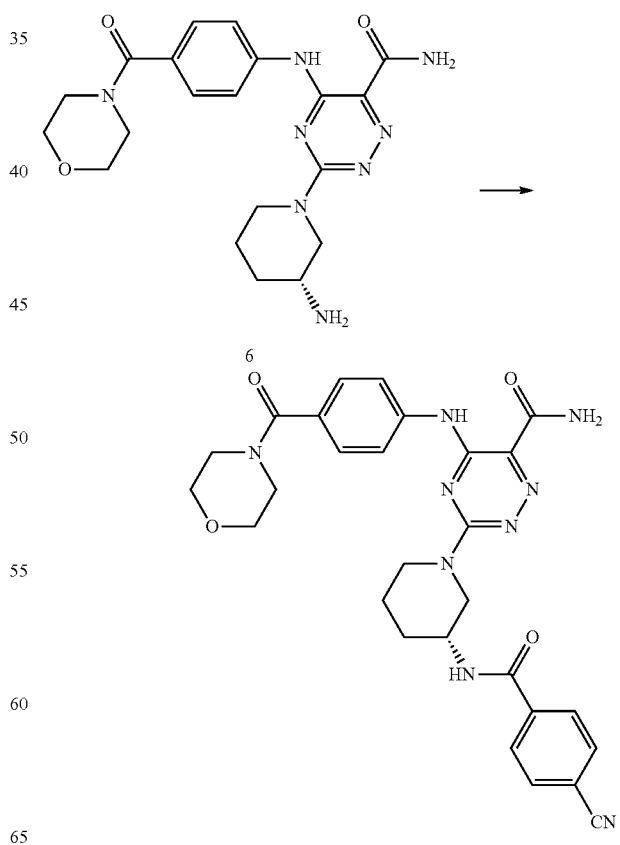

In a similar manner as described in Example 4, (R)-3-(3-(4-cyanobenzamido)piperidin-1-yl)-5-(4-(morpholine-4-carbonyl)phenylamino)-1,2,4-triazine-6-carboxamide (15) was prepared using 4-cyanobenzoyl chloride. MS found for $C_{28}H_{29}N_9O_4$ as (M+H)$^+$ 556.2, (M−H)$^−$ 554.3. UV: λ=272 nm.

Example 8

Synthesis of (R)-3-(3-(4-chlorobenzamido)piperidin-1-yl)-5-(4-(morpholine-4-carbonyl)phenylamino)-1,2,4-triazine-6-carboxamide (16)

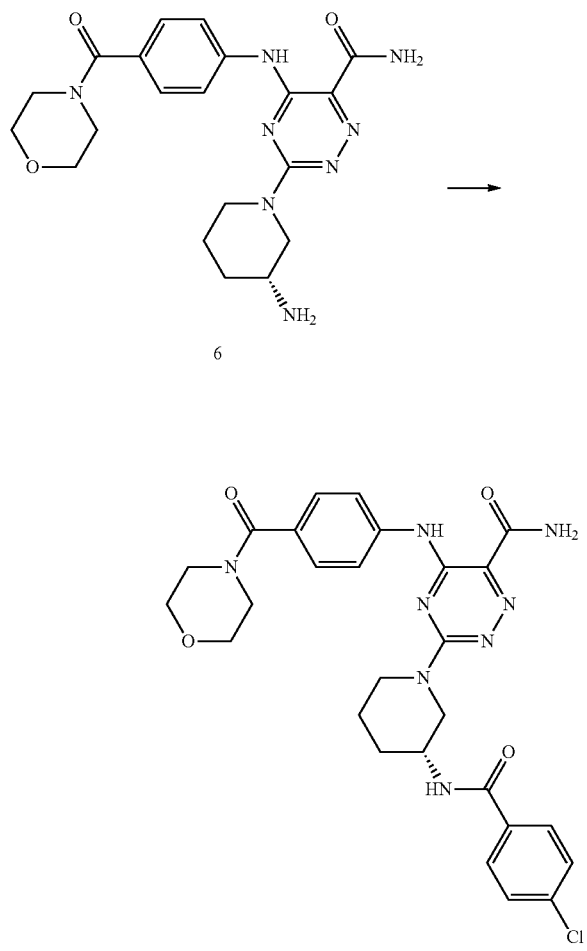

In a similar manner as described in Example 4, (R)-3-(3-(4-chlorobenzamido)piperidin-1-yl)-5-(4-(morpholine-4-carbonyl)phenylamino)-1,2,4-triazine-6-carboxamide (16) was prepared using 4-chlorobenzoyl chloride. MS found for $C_{27}H_{29}ClN_8O_4$ as (M+H)$^+$ 565.1 (chloro pattern), (M−H)$^−$ 563.2 (chloro pattern). UV: λ=272 nm.

Example 9

Synthesis of (R)-3-(3-(4-fluorobenzamido)piperidin-1-yl)-5-(4-(morpholine-4-carbonyl)phenylamino)-1,2,4-triazine-6-carboxamide (17)

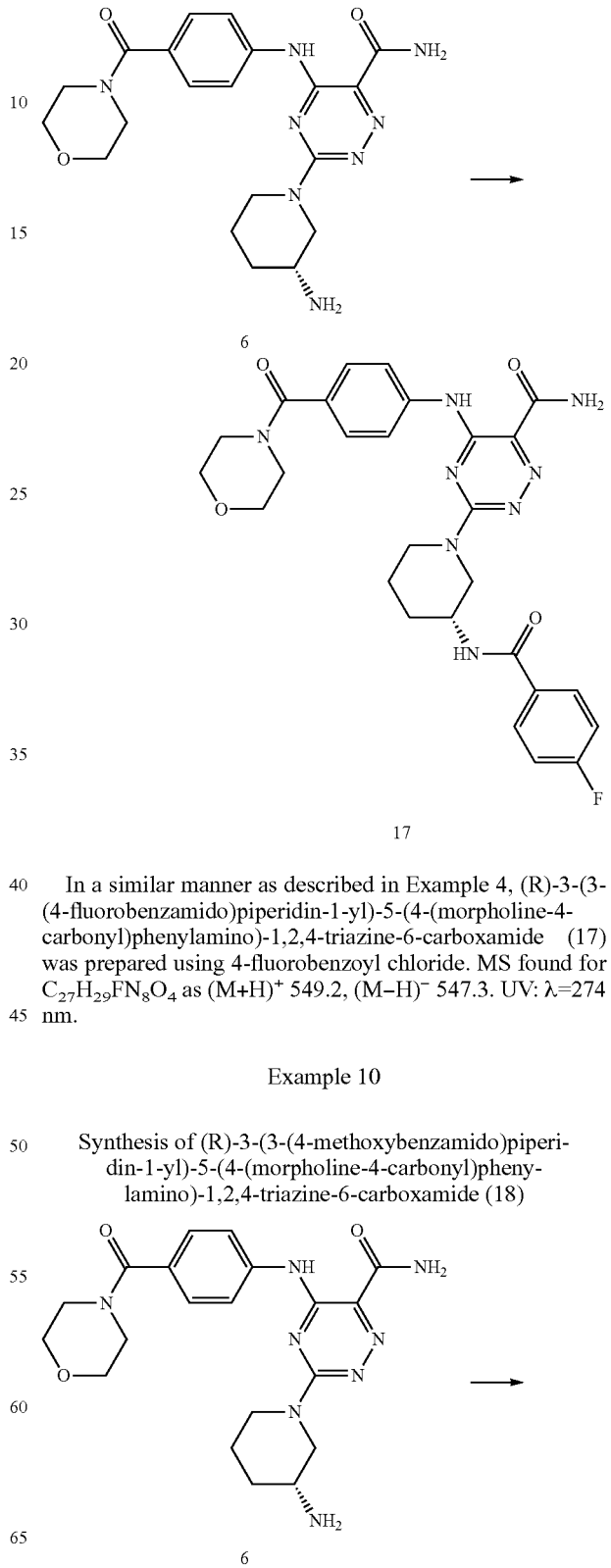

In a similar manner as described in Example 4, (R)-3-(3-(4-fluorobenzamido)piperidin-1-yl)-5-(4-(morpholine-4-carbonyl)phenylamino)-1,2,4-triazine-6-carboxamide (17) was prepared using 4-fluorobenzoyl chloride. MS found for $C_{27}H_{29}FN_8O_4$ as (M+H)$^+$ 549.2, (M−H)$^−$ 547.3. UV: λ=274 nm.

Example 10

Synthesis of (R)-3-(3-(4-methoxybenzamido)piperidin-1-yl)-5-(4-(morpholine-4-carbonyl)phenylamino)-1,2,4-triazine-6-carboxamide (18)

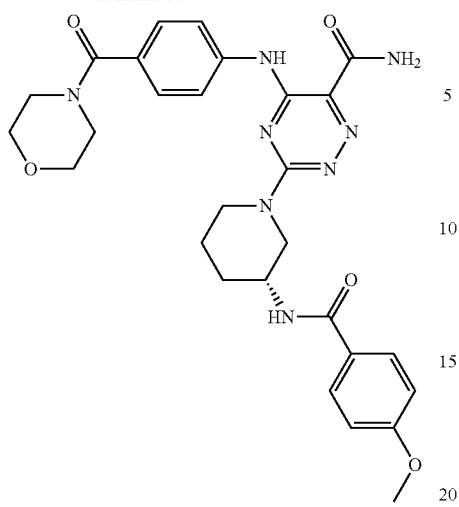

18

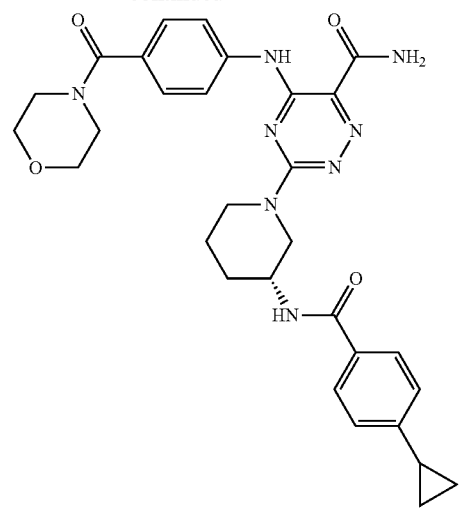

19

To a solution of 6 (65 mg, 0.14 mmol) in DMF (3 mL) was added p-anisic acid (43 mg, 0.28 mmol), DIEA (200 μL, 1.12 mmol) and then PyBOP (150 mg, 0.28 mmol). The mixture was stirred at RT for 1 h, acidified with TFA (0.3 mL), diluted with water (2 mL), and subjected to reverse phase preparative HPLC to isolate the title compound (18) (55 mg) as HCl salt. MS found for $C_{28}H_{32}N_8O_5$ as $(M+H)^+$ 561.2, $(M-H)^-$ 559.3. UV: $\lambda$=261 nm.

Example 11

Synthesis of (R)-3-(3-(4-cyclopropylbenzamido)piperidin-1-yl)-5-(4-(morpholine-4-carbonyl)phenylamino)-1,2,4-triazine-6-carboxamide (19)

In a similar manner as described in Example 10, (R)-3-(3-(4-cyclopropylbenzamido)piperidin-1-yl)-5-(4-(morpholine-4-carbonyl)phenylamino)-1,2,4-triazine-6-carboxamide (19) was prepared using 4-cyclopropylbenzoic acid. MS found for $C_{30}H_{34}N_8O_4$ as $(M+H)^+$ 571.2, $(M-H)^-$ 569.3. UV: $\lambda$=260 nm.

Example 12

Synthesis of (R)-5-(4-(morpholine-4-carbonyl)phenylamino)-3-(3-(picolinamido)piperidin-1-yl)-1,2,4-triazine-6-carboxamide (20)

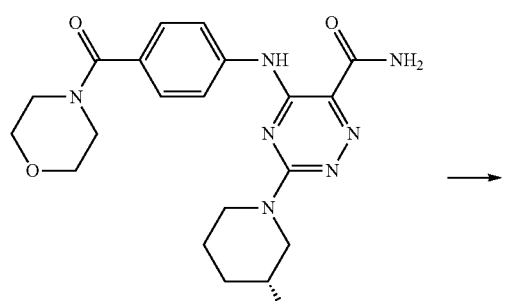

6

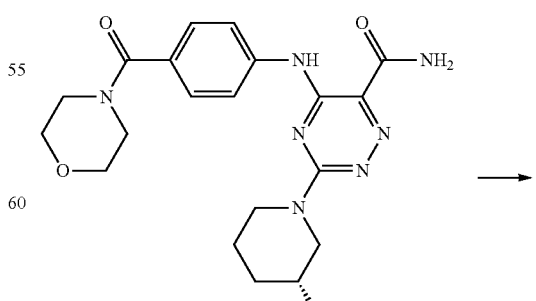

6

-continued

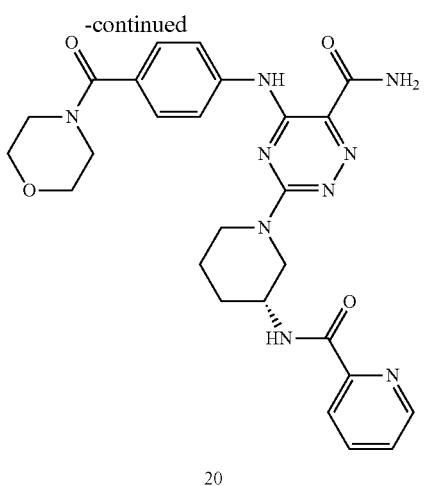

20

In a similar manner as described in Example 10, (R)-5-(4-(morpholine-4-carbonyl)phenylamino)-3-(3-(picolinamido)piperidin-1-yl)-1,2,4-triazine-6-carboxamide (20) was prepared using picolinic acid. MS found $C_{26}H_{29}N_9O_4$ as $(M+H)^+$ 532.2, $(M-H)^-$ 530.3. UV: $\lambda=269$ nm.

Example 13

Synthesis of (R)-5-(4-(morpholine-4-carbonyl)phenylamino)-3-(3-(nicotinamido)piperidin-1-yl)-1,2,4-triazine-6-carboxamide (21)

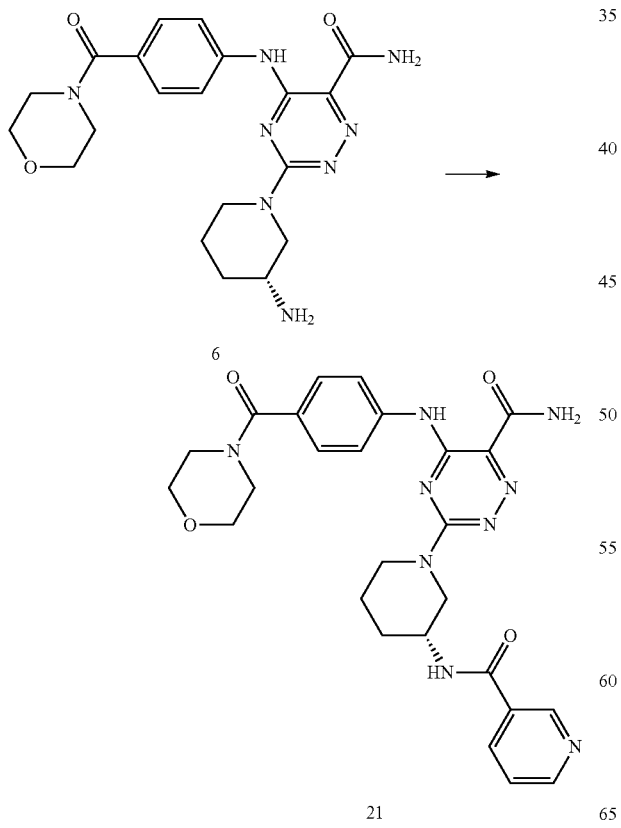

In a similar manner as described in Example 10, (R)-5-(4-(morpholine-4-carbonyl)phenylamino)-3-(3-(nicotinamido)piperidin-1-yl)-1,2,4-triazine-6-carboxamide (21) was prepared using nicotinic acid. MS found $C_{26}H_{29}N_9O_4$ as $(M+H)^+$ 532.1, $(M-H)^-$ 530.3. UV: $\lambda=269$ nm.

Example 14

Synthesis of (R)-3-(3-(isonicotinamido)piperidin-1-yl)-5-(4-(morpholine-4-carbonyl)phenylamino)-1,2,4-triazine-6-carboxamide (22)

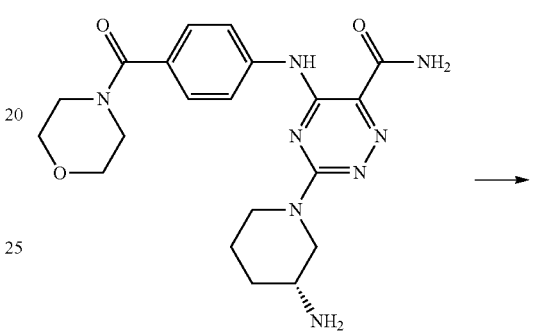

In a similar manner as described in Example 10, (R)-3-(3-(isonicotinamido)piperidin-1-yl)-5-(4-(morpholine-4-carbonyl)phenylamino)-1,2,4-triazine-6-carboxamide (22) was prepared using isonicotinic acid. MS found $C_{26}H_{29}N_9O_4$ as $(M+H)^+$ 532.2, $(M-H)^-$ 530.3. UV: $\lambda=270$ nm.

Example 15

Synthesis of (R)-5-(4-(morpholine-4-carbonyl)phenylamino)-3-(3-(pyrimidine-2-carboxamido)piperidin-1-yl)-1,2,4-triazine-6-carboxamide (23)

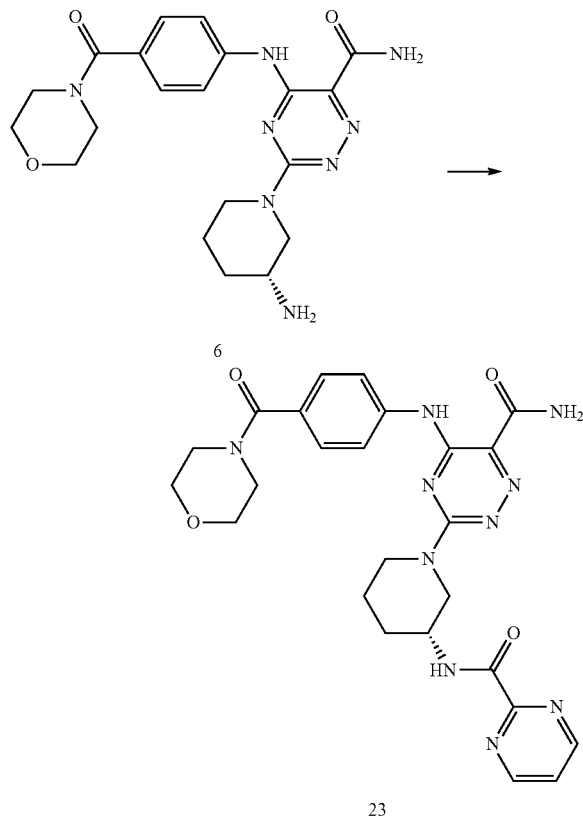

In a similar manner as described in Example 10, (R)-5-(4-(morpholine-4-carbonyl)phenylamino)-3-(3-(pyrimidine-2-carboxamido)piperidin-1-yl)-1,2,4-triazine-6-carboxamide (23) was prepared using pyrimidine-2-carboxylic acid. MS found $C_{25}H_{28}N_{10}O_4$ as $(M+H)^+$ 533.2, $(M-H)^-$ 531.2. UV: $\lambda=271$ nm.

Example 16

Synthesis of (R)—N-(1-(6-carbamoyl-5-(4-(morpholine-4-carbonyl)phenylamino)-1,2,4-triazin-3-yl)piperidin-3-yl)thiazole-2-carboxamide (24)

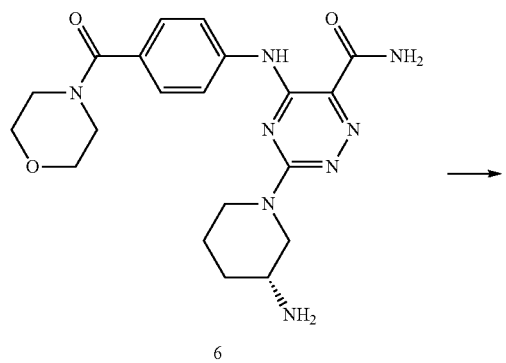

In a similar manner as described in Example 10, (R)—N-(1-(6-carbamoyl-5-(4-(morpholine-4-carbonyl)phenylamino)-1,2,4-triazin-3-yl)piperidin-3-yl)thiazole-2-carboxamide (24) was prepared using thiazole-2-carboxylic acid. MS found $C_{24}H_{27}N_9O_4S$ as $(M+H)^+$ 538.2, $(M-H)^-$ 536.2. UV: $\lambda=275$ nm.

Example 17

Synthesis of (R)-3-(3-(5-chlorothiophene-2-carboxamido)piperidin-1-yl)-5-(4-(morpholine-4-carbonyl)phenylamino)-1,2,4-triazine-6-carboxamide (25)

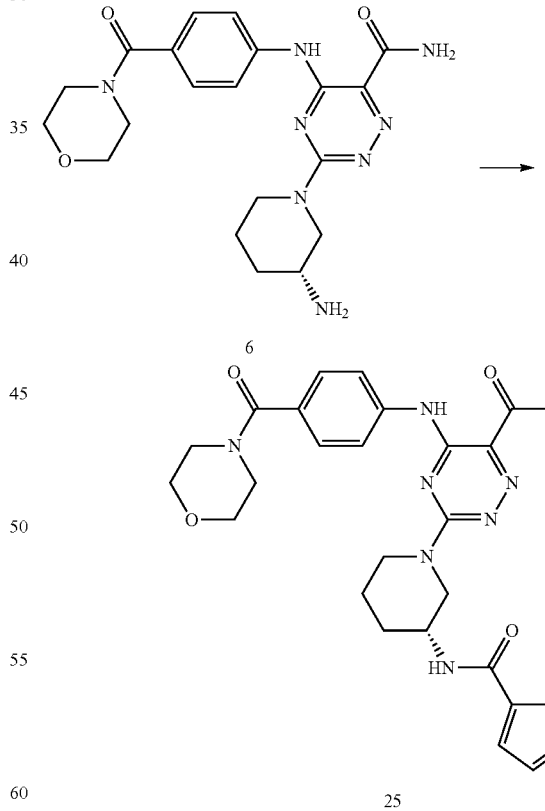

In a similar manner as described in Example 10, (R)-3-(3-(5-chlorothiophene-2-carboxamido)piperidin-1-yl)-5-(4-(morpholine-4-carbonyl)phenylamino)-1,2,4-triazine-6-carboxamide (25) was prepared using 5-chlorothiophene-2-carboxylic acid. MS found $C_{25}H_{27}ClN_8O_4S$ as $(M+H)^+$ 570.1, $(M-H)^-$ 569.2. UV: $\lambda=278$ nm.

Example 18

Synthesis of (R)—N-(1-(6-carbamoyl-5-(4-(morpholine-4-carbonyl)phenylamino)-1,2,4-triazin-3-yl)piperidin-3-yl)quinoline-3-carboxamide (26)

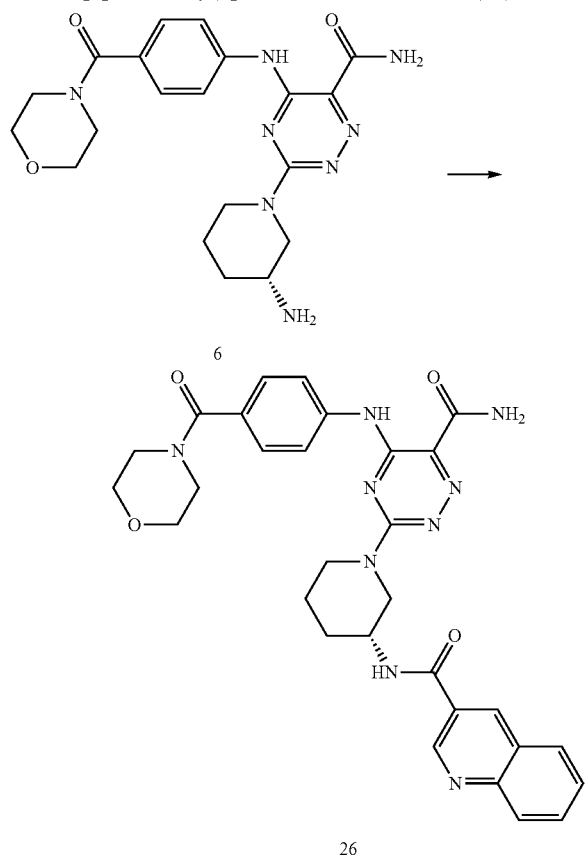

In a similar manner as described in Example 10, (R)—N-(1-(6-carbamoyl-5-(4-(morpholine-4-carbonyl)phenylamino)-1,2,4-triazin-3-yl)piperidin-3-yl)quinoline-3-carboxamide (26) was prepared using quinoline-3-carboxylic acid. MS found $C_{30}H_{31}N_9O_4$ as $(M+H)^+$ 582.2, $(M-H)^-$ 580.3. UV: $\lambda$=277 nm.

Example 19

Synthesis of (R)—N-(1-(6-carbamoyl-5-(4-(morpholine-4-carbonyl)phenylamino)-1,2,4-triazin-3-yl)piperidin-3-yl)imidazo[1,2-a]pyridine-6-carboxamide (27)

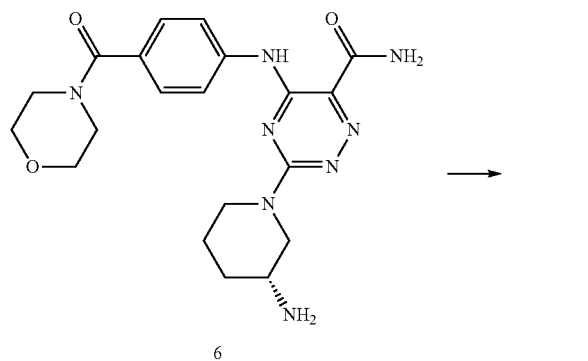

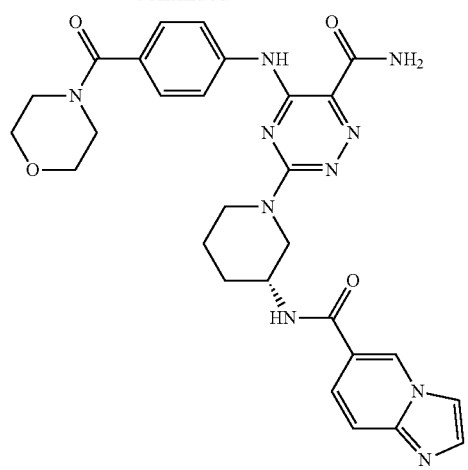

In a similar manner as described in Example 10, (R)—N-(1-(6-carbamoyl-5-(4-(morpholine-4-carbonyl)phenylamino)-1,2,4-triazin-3-yl)piperidin-3-yl)imidazo[1,2-a]pyridine-6-carboxamide (27) was prepared using imidazo[1,2-a]pyridine-6-carboxylic acid. MS found $C_{28}H_{30}N_{10}O_4$ as $(M+H)^+$ 571.2, $(M-H)^-$ 569.3. UV: $\lambda$=276 nm.

Example 20

Synthesis of (R)—N-(1-(6-carbamoyl-5-(4-(morpholine-4-carbonyl)phenylamino)-1,2,4-triazin-3-yl)piperidin-3-yl)imidazo[1,2-a]pyridine-7-carboxamide (28)

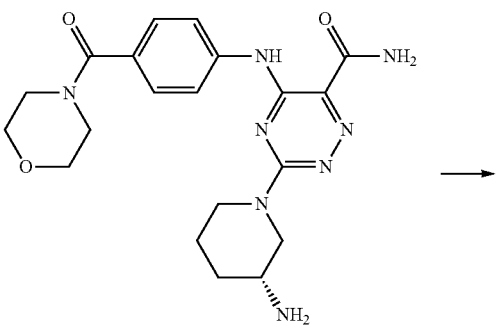

-continued

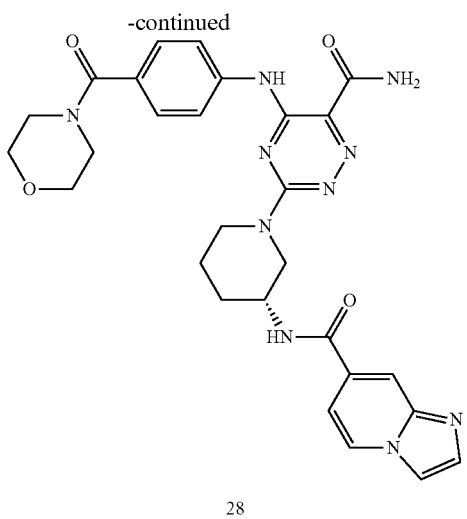

28

In a similar manner as described in Example 10, (R)—N-(1-(6-carbamoyl-5-(4-(morpholine-4-carbonyl)phenylamino)-1,2,4-triazin-3-yl)piperidin-3-yl)imidazo[1,2-a]pyridine-7-carboxamide (28) was prepared using imidazo[1,2-a]pyridine-7-carboxylic acid. MS found $C_{28}H_{30}N_{10}O_4$ as $(M+H)^+$ 571.2, $(M-H)^-$ 569.3. UV: $\lambda=281$ nm.

Example 21

Synthesis of (R)-5-(4-(morpholine-4-carbonyl)phenylamino)-3-(3-propionamidopiperidin-1-yl)-1,2,4-triazine-6-carboxamide (29)

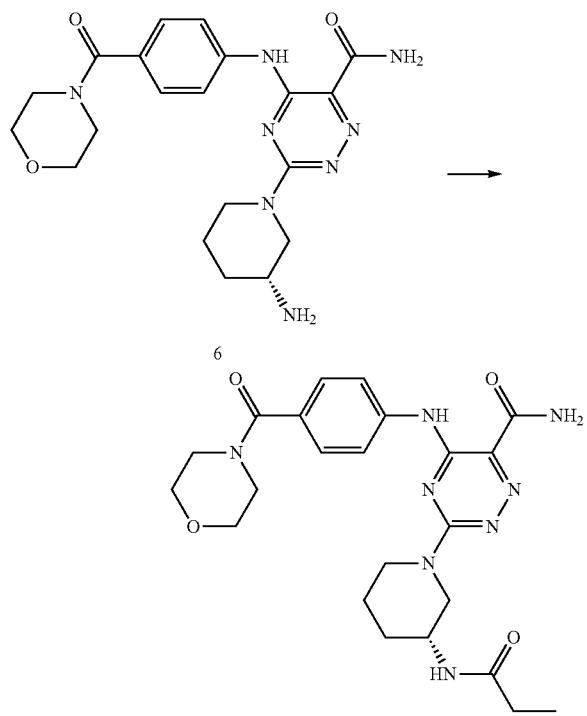

In a similar manner as described in Example 4, (R)-5-(4-(morpholine-4-carbonyl)phenylamino)-3-(3-propionamidopiperidin-1-yl)-1,2,4-triazine-6-carboxamide (29) was prepared using propionyl chloride. MS found for $C_{23}H_{30}N_8O_4$ as $(M+H)^+$ 483.1, $(M-H)^-$ 481.2. UV: $\lambda=275$ nm.

Example 22

Synthesis of (R)-3-(3-acrylamidopiperidin-1-yl)-5-(4-(morpholine-4-carbonyl)phenylamino)-1,2,4-triazine-6-carboxamide (30)

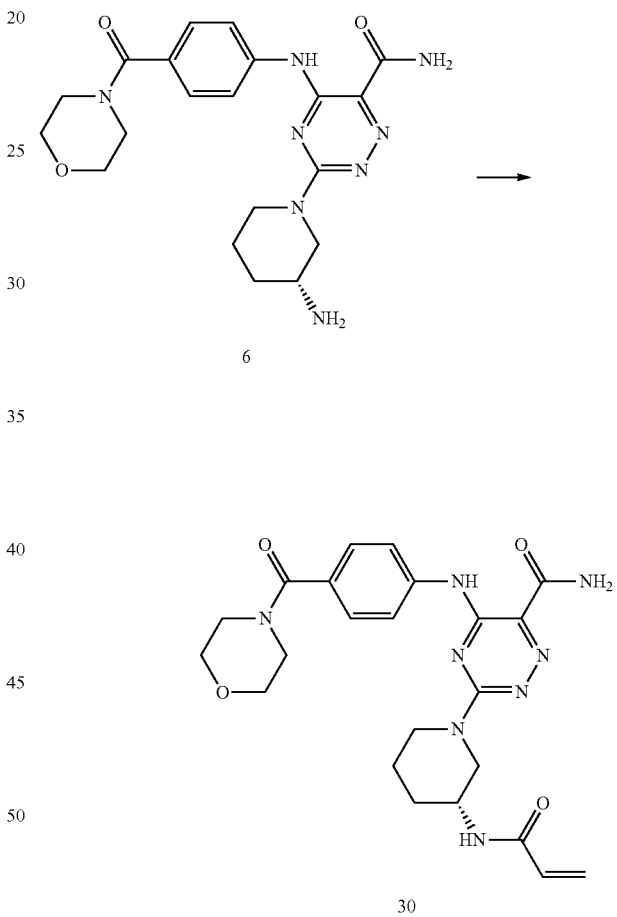

In a similar manner as described in Example 4, (R)-3-(3-acrylamidopiperidin-1-yl)-5-(4-(morpholine-4-carbonyl)phenylamino)-1,2,4-triazine-6-carboxamide (30) was prepared using acryloyl chloride. MS found for $C_{23}H_{28}N_8O_4$ as $(M+H)^+$ 481.1, $(M-H)^-$ 479.3. UV: $\lambda=274$ nm.

Example 23

Synthesis of (R)-3-(3-but-2-ynamidopiperidin-1-yl)-5-(4-(morpholine-4-carbonyl)phenylamino)-1,2,4-triazine-6-carboxamide (31)

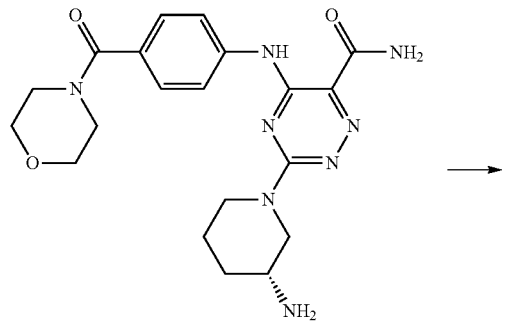

6

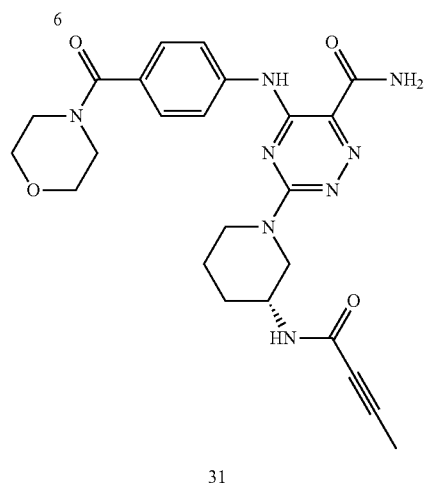

31

In a similar manner as described in Example 10, (R)-3-(3-but-2-ynamidopiperidin-1-yl)-5-(4-(morpholine-4-carbonyl)phenylamino)-1,2,4-triazine-6-carboxamide (31) was prepared using but-2-ynoic acid. MS found $C_{24}H_{28}N_8O_4$ as $(M+H)^+$ 493.1, $(M-H)^-$ 491.2. UV: $\lambda=274$ nm.

Example 24

Synthesis of (R)-3-(3-isobutyramidopiperidin-1-yl)-5-(4-(morpholine-4-carbonyl)phenylamino)-1,2,4-triazine-6-carboxamide (32)

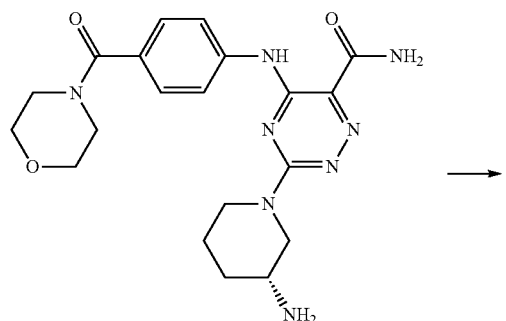

6

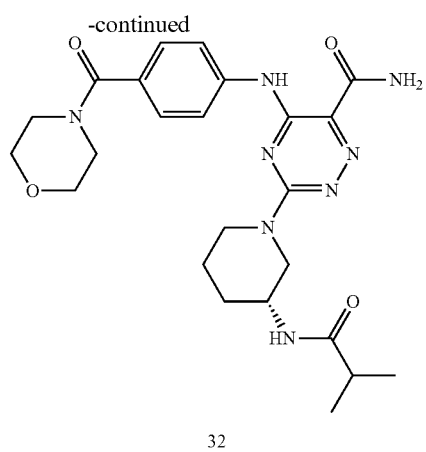

32

In a similar manner as described in Example 4, (R)-3-(3-isobutyramidopiperidin-1-yl)-5-(4-(morpholine-4-carbonyl)phenylamino)-1,2,4-triazine-6-carboxamide (32) was prepared using isobutyryl chloride. MS found for $C_{24}H_{32}N_8O_4$ as $(M+H)^+$ 497.2, $(M-H)^-$ 495.3. UV: $\lambda=275$ nm.

Example 25

Synthesis of (R)-3-(3-(cyclopropanecarboxamido)piperidin-1-yl)-5-(4-(morpholine-4-carbonyl)phenylamino)-1,2,4-triazine-6-carboxamide (33)

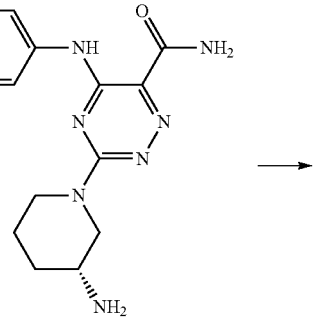

6

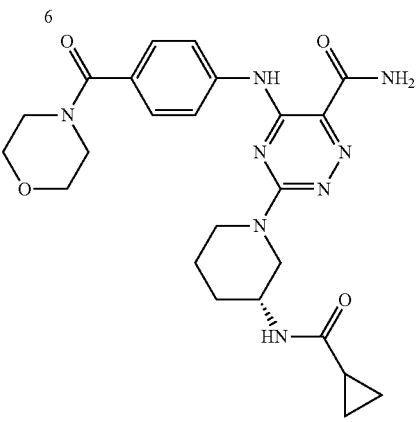

33

In a similar manner as described in Example 4, (R)-3-(3-(cyclopropanecarboxamido)piperidin-1-yl)-5-(4-(morpholine-4-carbonyl)phenylamino)-1,2,4-triazine-6-carboxamide (33) was prepared using cyclopropanecarbonyl chloride. MS found for $C_{24}H_{30}N_8O_4$ as $(M+H)^+$ 495.1, $(M-H)^-$ 493.3. UV: $\lambda=275$ nm.

Example 26

Synthesis of (R)-3-(3-(cyclobutanecarboxamido) piperidin-1-yl)-5-(4-(morpholine-4-carbonyl)phenylamino)-1,2,4-triazine-6-carboxamide (34)

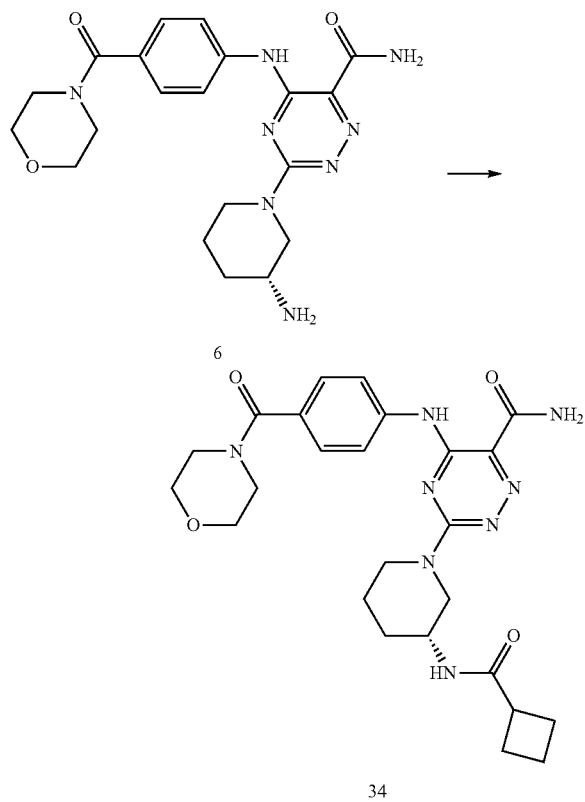

In a similar manner as described in Example 10, (R)-3-(3-(cyclobutanecarboxamido)piperidin-1-yl)-5-(4-(morpholine-4-carbonyl)phenylamino)-1,2,4-triazine-6-carboxamide (34) was prepared using cyclobutanecarboxylic acid. MS found for $C_{25}H_{32}N_8O_4$ as $(M+H)^+$ 509.1, $(M-H)^-$ 507.3. UV: $\lambda=276$ nm.

Example 27

Synthesis of (R)-3-(3-(2-cyanoacetamido)piperidin-1-yl)-5-(4-(morpholine-4-carbonyl)phenylamino)-1,2,4-triazine-6-carboxamide (35)

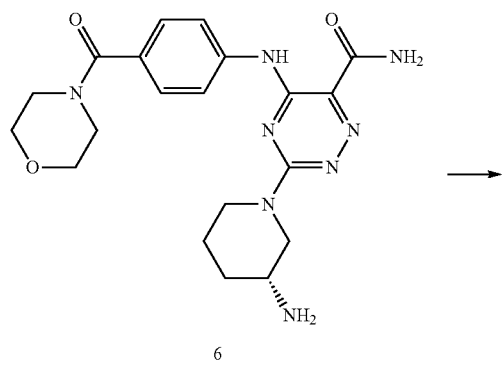

In a similar manner as described in Example 10, (R)-3-(3-(2-cyanoacetamido)piperidin-1-yl)-5-(4-(morpholine-4-carbonyl)phenylamino)-1,2,4-triazine-6-carboxamide (35) was prepared using 2-cyanoacetic acid. MS found for $C_{23}H_{27}N_9O_4$ as $(M+H)^+$ 494.1, $(M-H)^-$ 492.2. UV: $\lambda=275$ nm.

Example 28

Synthesis of (R)-3-(3-(1-cyanocyclopropanecarboxamido)piperidin-1-yl)-5-(4-(morpholine-4-carbonyl)phenylamino)-1,2,4-triazine-6-carboxamide (36)

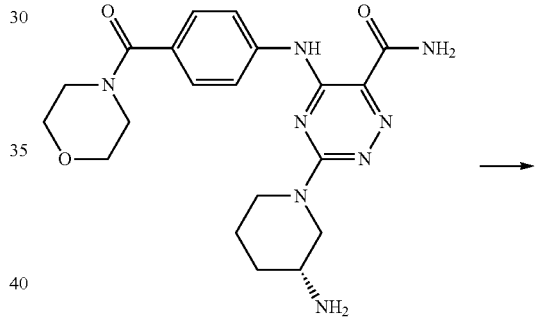

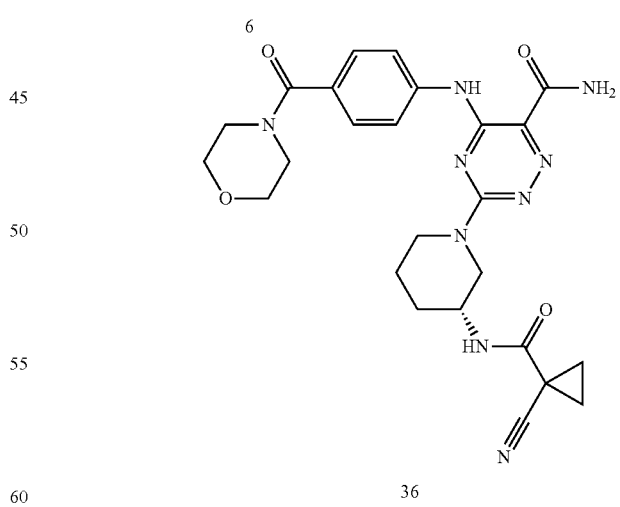

In a similar manner as described in Example 10, (R)-3-(3-(1-cyanocyclopropanecarboxamido)piperidin-1-yl)-5-(4-(morpholine-4-carbonyl)phenylamino)-1,2,4-triazine-6-carboxamide (36) was prepared using 1-cyanocyclopropanecarboxylic acid. MS found for $C_{25}H_{29}N_9O_4$ as $(M+H)^+$ 520.2, $(M-H)^-$ 518.2. UV: $\lambda=276$ nm.

Example 29

Synthesis of (R)-3-(3-(cyclopentanecarboxamido)piperidin-1-yl)-5-(4-(morpholine-4-carbonyl)phenylamino)-1,2,4-triazine-6-carboxamide (37)

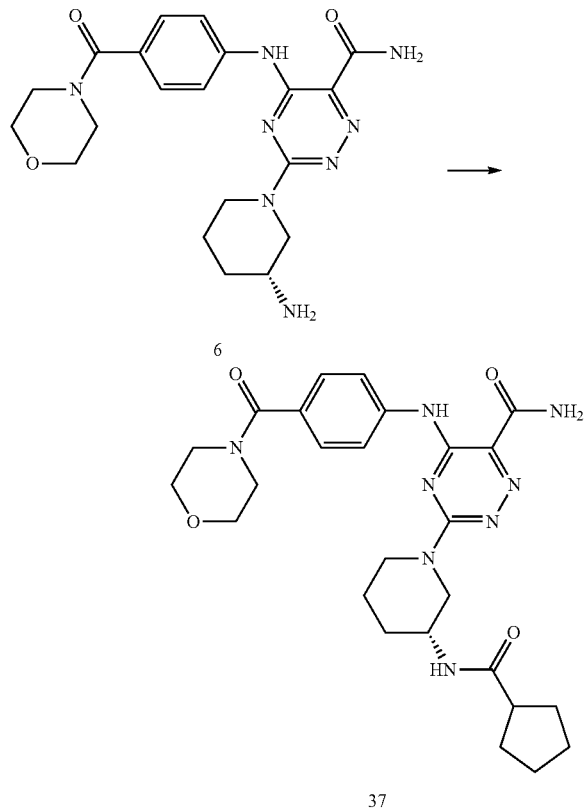

In a similar manner as described in Example 4, (R)-3-(3-(cyclopentanecarboxamido)piperidin-1-yl)-5-(4-(morpholine-4-carbonyl)phenylamino)-1,2,4-triazine-6-carboxamide (37) was prepared using cyclopentanecarbonyl chloride. MS found for $C_{26}H_{34}N_8O_4$ as $(M+H)^+$ 523.2, $(M-H)^-$ 521.3. UV: λ=276 nm.

Example 30

Synthesis of (R)-5-(4-(morpholine-4-carbonyl)phenylamino)-3-(3-(tetrahydro-2H-pyran-4-carboxamido)piperidin-1-yl)-1,2,4-triazine-6-carboxamide (38)

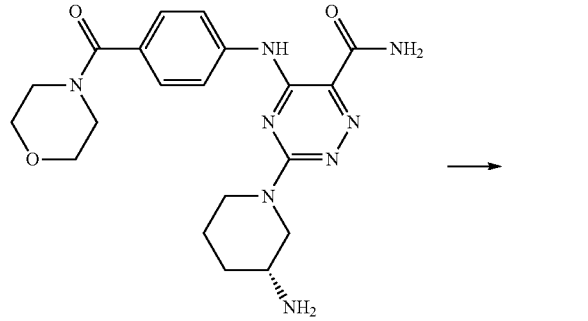

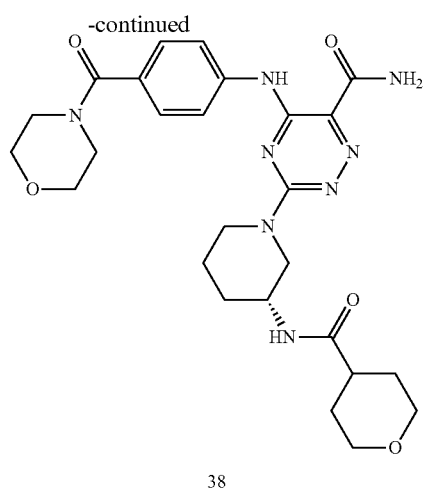

In a similar manner as described in Example 10, (R)-5-(4-(morpholine-4-carbonyl)phenylamino)-3-(3-(tetrahydro-2H-pyran-4-carboxamido)piperidin-1-yl)-1,2,4-triazine-6-carboxamide (38) was prepared using tetrahydro-2H-pyran-4-carboxylic acid. MS found for $C_{26}H_{34}N_8O_5$ as $(M+H)^+$ 539.2, $(M-H)^-$ 537.3. UV: λ=275 nm.

Example 31

Synthesis of (R)-3-(3-(1-methylpiperidine-4-carboxamido)piperidin-1-yl)-5-(4-(morpholine-4-carbonyl)phenylamino)-1,2,4-triazine-6-carboxamide (39)

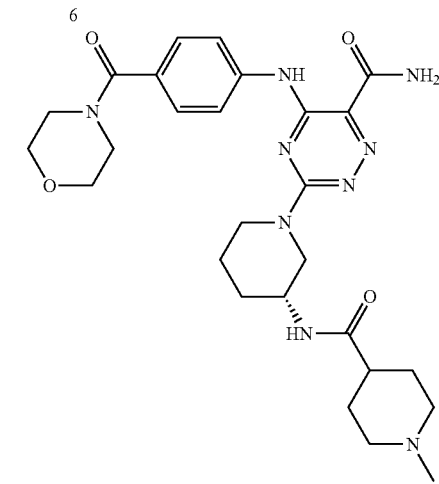

In a similar manner as described in Example 10, (R)-5-(4-(morpholine-4-carbonyl)phenylamino)-3-(3-(tetrahydro-2H-pyran-4-carboxamido)piperidin-1-yl)-1,2,4-triazine-6-carboxamide (39) was prepared using 1-methylpiperidine-4-carboxylic acid. MS found for $C_{27}H_{37}N_9O_4$ as $(M+H)^+$ 552.2, $(M-H)^-$ 550.3. UV: λ=276 nm.

Example 32

Synthesis of (R)-3-(3-(1-cyclopropylpiperidine-4-carboxamido)piperidin-1-yl)-5-(4-(morpholine-4-carbonyl)phenylamino)-1,2,4-triazine-6-carboxamide (40)

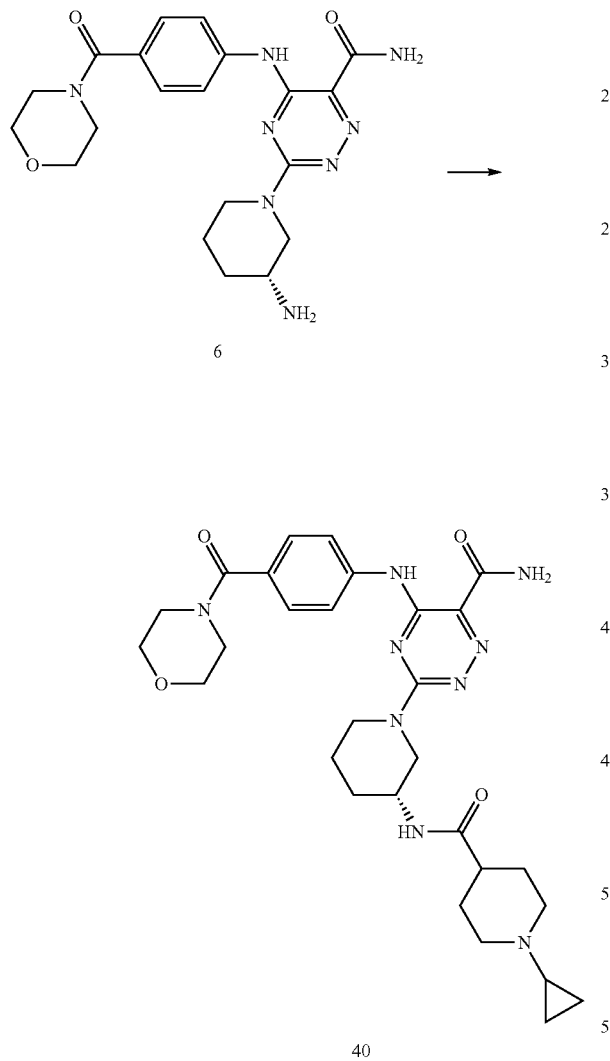

In a similar manner as described in Example 10, (R)-3-(3-(1-cyclopropylpiperidine-4-carboxamido)piperidin-1-yl)-5-(4-(morpholine-4-carbonyl)phenylamino)-1,2,4-triazine-6-carboxamide (40) was prepared using 1-cyclopropylpiperidine-4-carboxylic acid. MS found for $C_{29}H_{39}N_9O_4$ as $(M+H)^+$ 578.2, $(M-H)^-$ 576.3. UV: λ=276 nm.

Example 33

Synthesis of (R)-3-(3-(1-cyclopentylpiperidine-4-carboxamido)piperidin-1-yl)-5-(4-(morpholine-4-carbonyl)phenylamino)-1,2,4-triazine-6-carboxamide (41)

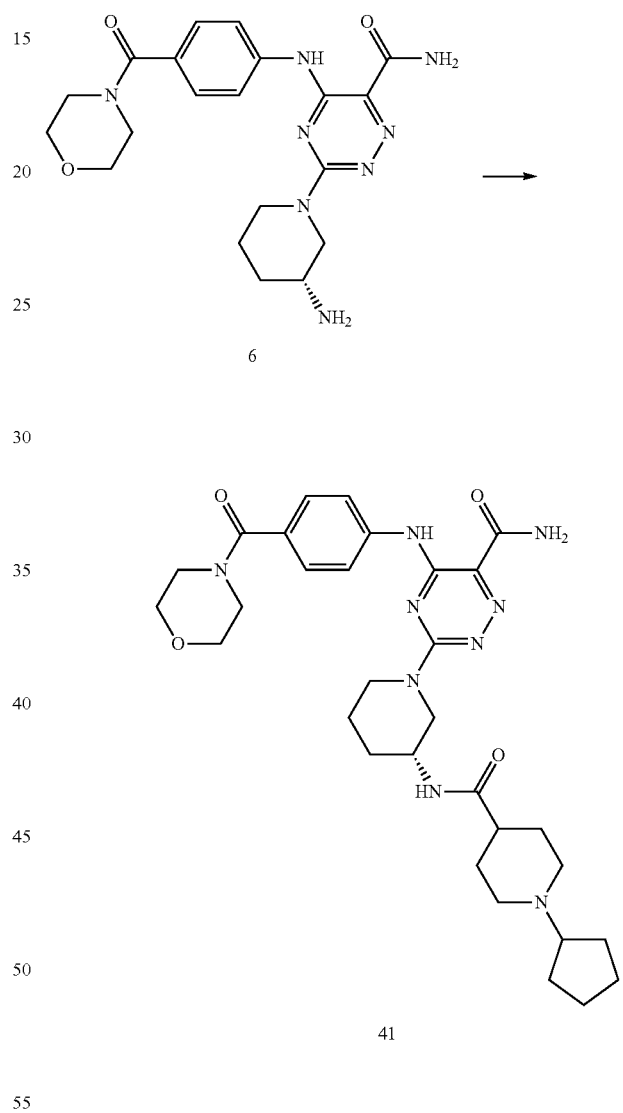

In a similar manner as described in Example 10, (R)-3-(3-(1-cyclopentylpiperidine-4-carboxamido)piperidin-1-yl)-5-(4-(morpholine-4-carbonyl)phenylamino)-1,2,4-triazine-6-carboxamide (41) was prepared using 1-cyclopentylpiperidine-4-carboxylic acid. MS found for $C_{31}H_{43}N_9O_4$ as $(M+H)^+$ 606.3, $(M-H)^-$ 604.4. UV: λ=276 nm.

Example 34

Synthesis of (R)-3-(3-(1-acetylpiperidine-4-carboxamido)piperidin-1-yl)-5-(4-(morpholine-4-carbonyl)phenylamino)-1,2,4-triazine-6-carboxamide (42)

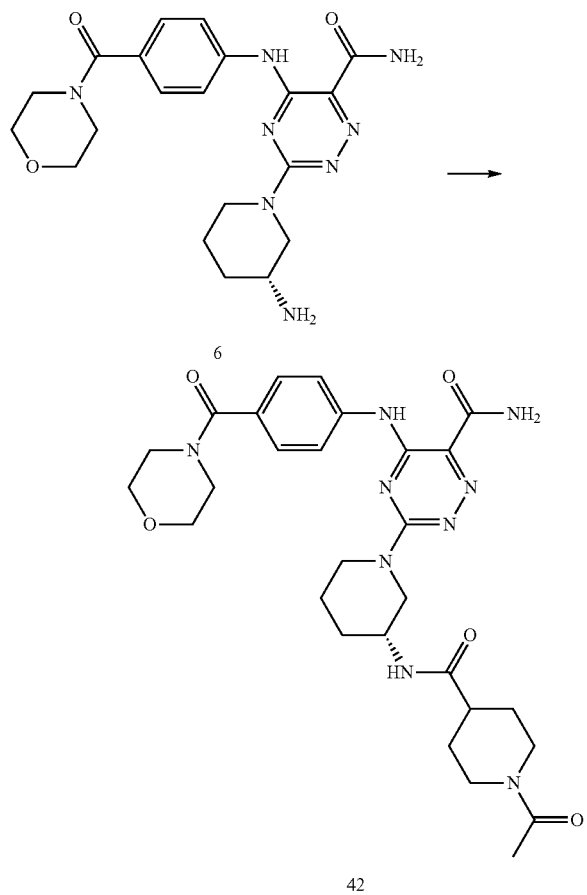

In a similar manner as described in Example 10, (R)-3-(3-(1-acetylpiperidine-4-carboxamido)piperidin-1-yl)-5-(4-(morpholine-4-carbonyl)phenylamino)-1,2,4-triazine-6-carboxamide (42) was prepared using 1-acetylpiperidine-4-carboxylic acid. MS found for $C_{28}H_{37}N_9O_5$ as $(M+H)^+$ 580.2, $(M-H)^-$ 578.3. UV: $\lambda=275$ nm.

Example 35

Synthesis of (R)-5-(4-(morpholine-4-carbonyl)phenylamino)-3-(3-(pyrrolidine-1-carboxamido)piperidin-1-yl)-1,2,4-triazine-6-carboxamide (43)

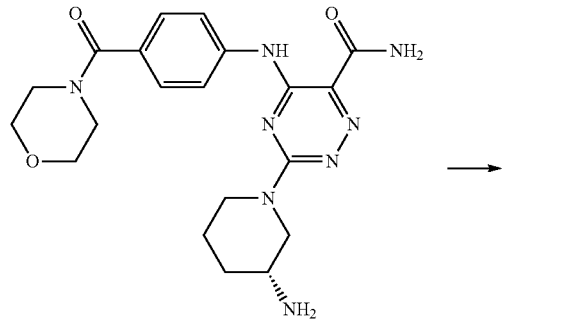

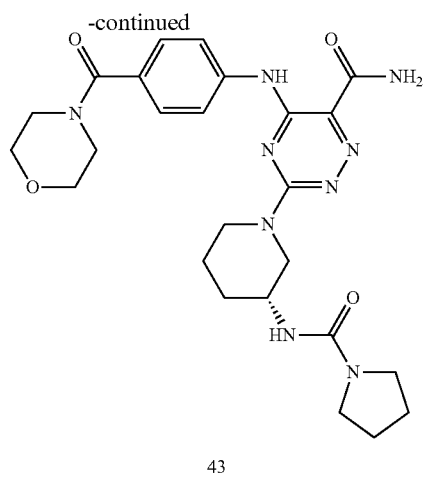

In a similar manner as described in Example 4, (R)-5-(4-(morpholine-4-carbonyl)phenylamino)-3-(3-(pyrrolidine-1-carboxamido)piperidin-1-yl)-1,2,4-triazine-6-carboxamide (43) was prepared using 1-pyrrolidinecarbonyl chloride. MS found for $C_{25}H_{33}N_9O_4$ as $(M+H)^+$ 524.2, $(M-H)^-$ 522.3. UV: $\lambda=275$ nm.

Example 36

Synthesis of (R)-3-(3-(1-acetylpiperidine-4-carboxamido)piperidin-1-yl)-5-(4-(morpholine-4-carbonyl)phenylamino)-1,2,4-triazine-6-carboxamide (44)

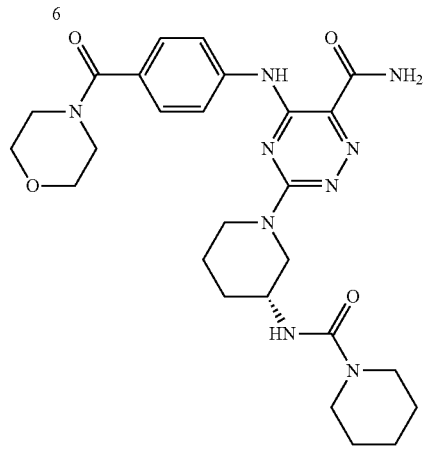

In a similar manner as described in Example 4, (R)-3-(3-(1-acetylpiperidine-4-carboxamido)piperidin-1-yl)-5-(4-(morpholine-4-carbonyl)phenylamino)-1,2,4-triazine-6-carboxamide (44) was prepared using 1-piperidinecarbonyl chloride. MS found for $C_{26}H_{35}N_9O_4$ as $(M+H)^+$ 538.2, $(M-H)^-$ 536.3. UV: $\lambda=276$ nm.

Example 37

Synthesis of (R)—N-(1-(6-carbamoyl-5-(4-(morpholine-4-carbonyl)phenylamino)-1,2,4-triazin-3-yl)piperidin-3-yl)-1,4'-bipiperidine-1'-carboxamide (45)

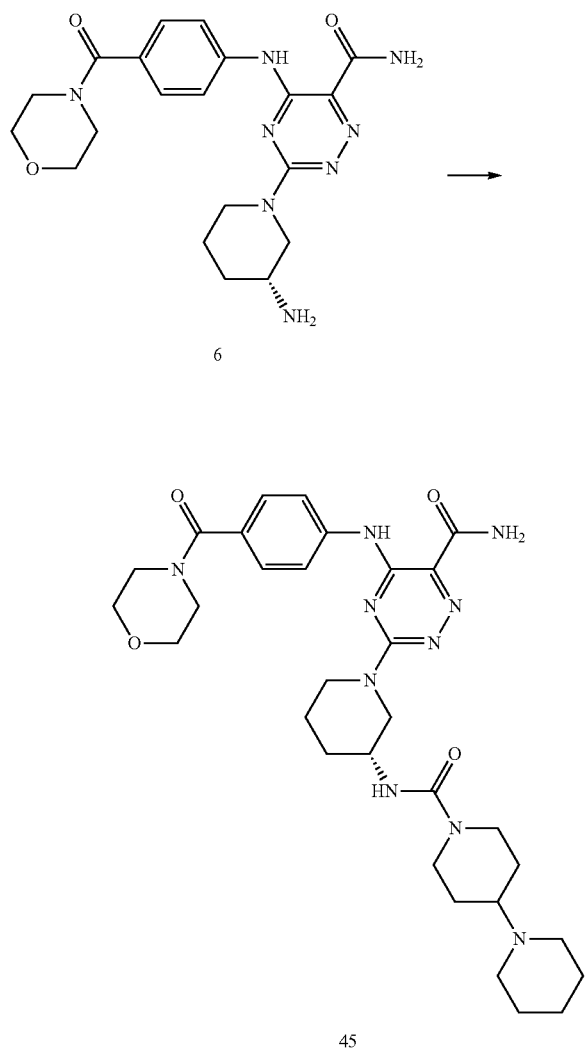

45

In a similar manner as described in Example 4, (R)—N-(1-(6-carbamoyl-5-(4-(morpholine-4-carbonyl)phenylamino)-1,2,4-triazin-3-yl)piperidin-3-yl)-1,4'-bipiperidine-1'-carboxamide (45) was prepared using 4-piperidinopiperidine-1-carbonyl chloride. MS found for $C_{31}H_{44}N_{10}O_4$ as $(M+H)^+$ 621.2, $(M-H)^-$ 619.4. UV: $\lambda=277$ nm.

Example 38

Synthesis of (R)—N-(1-(6-carbamoyl-5-(4-(morpholine-4-carbonyl)phenylamino)-1,2,4-triazin-3-yl)piperidin-3-yl)morpholine-4-carboxamide (46)

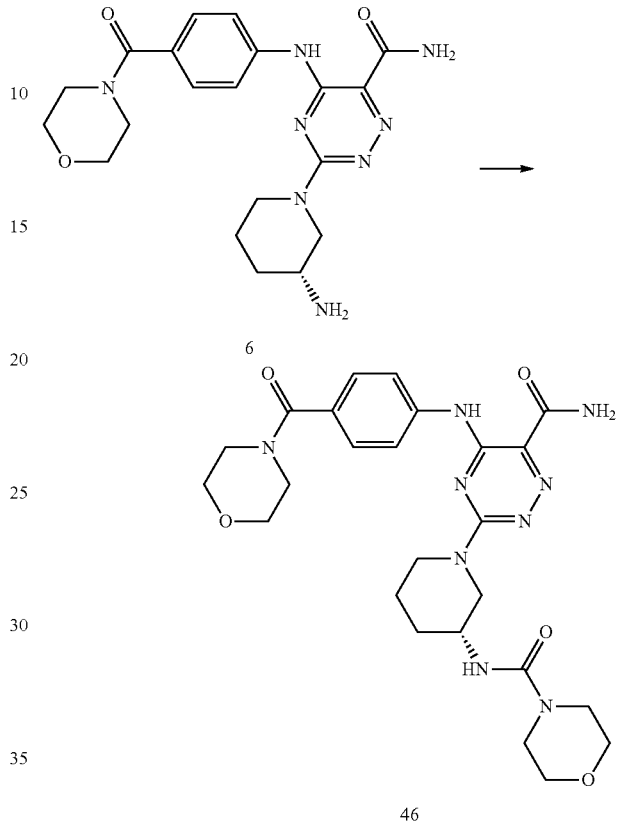

46

In a similar manner as described in Example 4, (R)—N-(1-(6-carbamoyl-5-(4-(morpholine-4-carbonyl)phenylamino)-1,2,4-triazin-3-yl)piperidin-3-yl)morpholine-4-carboxamide (46) was prepared using morpholine-4-carbonyl chloride. MS found for $C_{25}H_{33}N_9O_5$ as $(M+H)^+$ 540.2, $(M-H)^-$ 538.3. UV: $\lambda=275$ nm.

Example 39

Synthesis of (R)-3-(3-(3-methyl-3-phenylureido)piperidin-1-yl)-5-(4-(morpholine-4-carbonyl)phenylamino)-1,2,4-triazine-6-carboxamide (47)

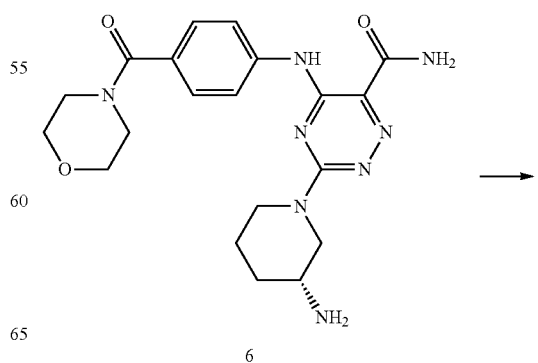

6

-continued

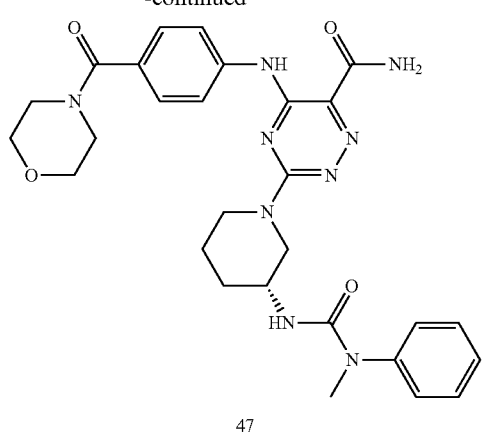

47

In a similar manner as described in Example 4, (R)-3-(3-(3-methyl-3-phenylureido)piperidin-1-yl)-5-(4-(morpholine-4-carbonyl)phenylamino)-1,2,4-triazine-6-carboxamide (47) was prepared using N-methyl-N-phenylcarbamoyl chloride. MS found for $C_{28}H_{33}N_9O_4$ as $(M+H)^+$ 560.2, $(M-H)^-$ 558.3. UV: $\lambda$=279 nm.

Example 40

Synthesis of (R)-3-(3-(cyclopropanesulfonamido)piperidin-1-yl)-5-(4-(morpholine-4-carbonyl)phenylamino)-1,2,4-triazine-6-carboxamide (48)

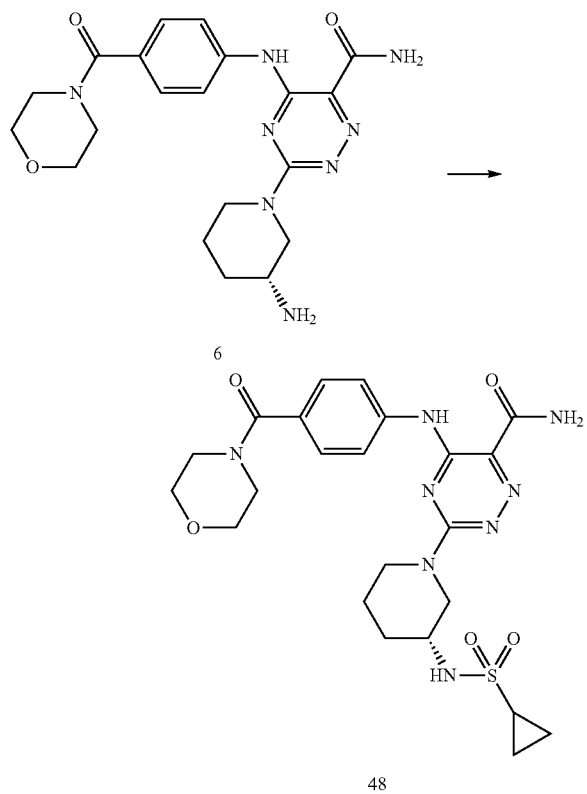

In a similar manner as described in Example 4, (R)-3-(3-(cyclopropanesulfonamido)piperidin-1-yl)-5-(4-(morpholine-4-carbonyl)phenylamino)-1,2,4- triazine-6-carboxamide (48) was prepared using cyclopropanesulfonyl chloride. MS found for $C_{23}H_{30}N_8O_5S$ as $(M+H)^+$ 519.1, $(M-H)^-$ 517.2. UV: $\lambda$=275 nm.

Example 41

Synthesis of (R)-5-(4-(morpholine-4-carbonyl)phenylamino)-3-(3-(phenylsulfonamido)piperidin-1-yl)-1,2,4-triazine-6-carboxamide (49)

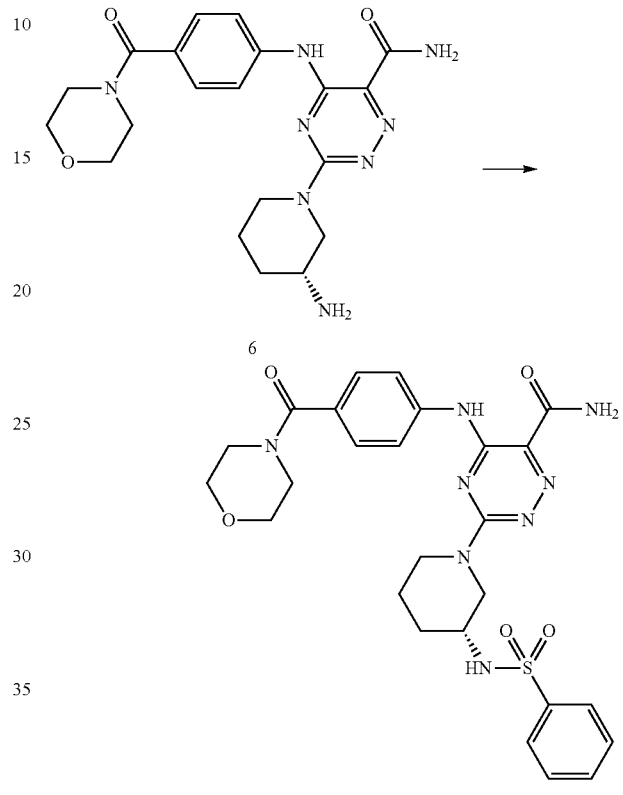

In a similar manner as described in Example 4, (R)-5-(4-(morpholine-4-carbonyl)phenylamino)-3-(3-(phenylsulfonamido)piperidin-1-yl)-1,2,4-triazine-6-carboxamide (49) was prepared using benzenesulfonyl chloride. MS found for $C_{26}H_{30}N_8O_5S$ as $(M+H)^+$567.1, $(M-H)^-$ 565.2. UV: $\lambda$=273 nm.

Example 42

Synthesis of (R)-3-(3-(isopropylamino)piperidin-1-yl)-5-(4-(morpholine-4-carbonyl)phenylamino)-1,2,4-triazine-6-carboxamide (50)

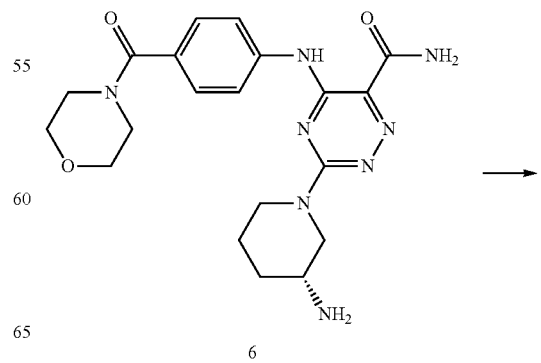

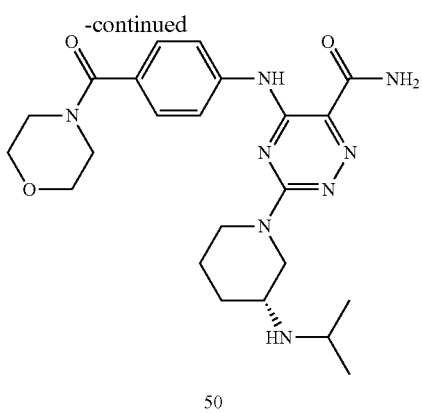

50

To a solution of (R)-3-(3-aminopiperidin-1-yl)-5-(4-(morpholine-4-carbonyl)phenylamino)-1,2,4-triazine-6-carboxamide HCl salt (100 mg, 0.21 mmol) in 1,2-dichloroethane (10 mL) and dioxane (10 mL) was added DIEA (0.18 mL, 1.05 mmol) and then acetone (0.31 mL, 4.2 mmol). The mixture was stirred for 3 h at RT. To the mixture was added HOAc (0.12 mL, 2.1 mmol) and then NaBH(OAc)$_3$ (223 mg, 1.05 mmol). The mixture was stirred at RT overnight and then water (2 mL) was added. The mixture was concentrated in vacuo and subjected to reverse phase preparative HPLC to afford the title compound as HCl salt (50) (17 mg). MS found for $C_{23}H_{32}N_8O_3$ as (M+H)$^+$ 469.2, (M−H)$^−$ 467.3. UV: λ=268 nm.

Example 43

Synthesis of (R)-3-(3-(cyclopentylamino)piperidin-1-yl)-5-(4-(morpholine-4-carbonyl)phenylamino)-1,2,4-triazine-6-carboxamide (51)

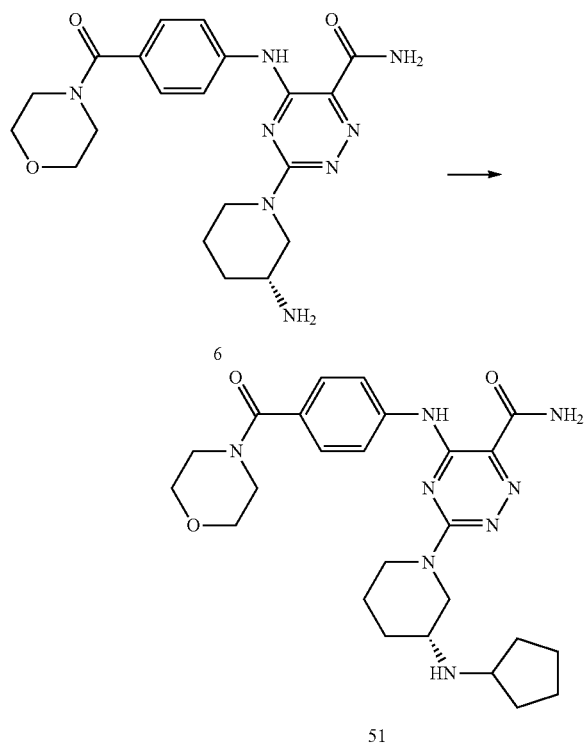

In a similar manner as described in Example 42, (R)-3-(3-(cyclopentylamino)piperidin-1-yl)-5-(4-(morpholine-4-carbonyl)phenylamino)-1,2,4-triazine-6-carboxamide (51) was prepared using cyclopentanone. MS found for $C_{25}H_{34}N_8O_3$ as (M+H)$^+$ 495.2, (M−H)$^−$ 493.3. UV: λ=270 nm.

Example 44

Synthesis of (R)-5-(4-(morpholine-4-carbonyl)phenylamino)-3-(3-(2-oxopyrrolidin-1-yl)piperidin-1-yl)-1,2,4-triazine-6-carboxamide (52)

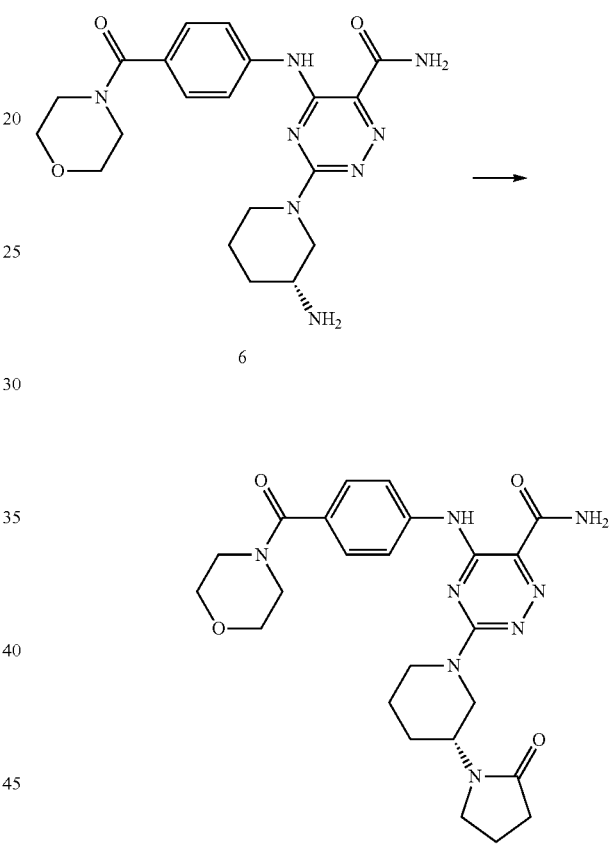

To a solution of (R)-3-(3-aminopiperidin-1-yl)-5-(4-(morpholine-4-carbonyl)phenylamino)-1,2,4-triazine-6-carboxamide HCl salt (6) (90 mg, 0.19 mmol) in NMP (3 mL) was added DIEA (0.27 mL, 1.52 mmol) and then 3-bromopropanoyl chloride (108 mg, 0.58 mmol). The mixture was stirred at RT for 1 h and then at 60° C. for 1 h. The mixture was cooled to RT, diluted with EtOAc, washed with water and concentrated in vacuo to afford crude (R)-3-(3-(4-chlorobutanamido)piperidin-1-yl)-5-(4-(morpholine-4-carbonyl)phenylamino)-1,2,4-triazine-6-carboxamide. To a solution of (R)-3-(3-(4-chlorobutanamido)piperidin-1-yl)-5-(4-(morpholine-4-carbonyl)phenylamino)-1,2,4-triazine-6-carboxamide in DMF (3 mL) was added NaH (60% in mineral oil, 30 mg, 0.75 mmol). The mixture was stirred at RT for 1 h. The mixture was diluted with water, acidified with TFA, and subjected to reverse phase preparative HPLC to isolate the title compound (52) as HCl salt (31 mg). MS found for $C_{24}H_{30}N_8O_4$ as (M+H)$^+$ 495.1, (M−H)$^−$ 493.2. UV: λ=275 nm.

Example 45

Synthesis of (R)-3-(3-(isoquinolin-1-yloxy)piperidin-1-yl)-5-(4-(morpholine-4-carbonyl)phenylamino)-1,2,4-triazine-6-carboxamide (55)

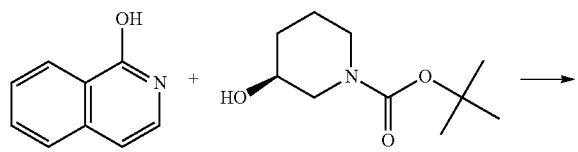

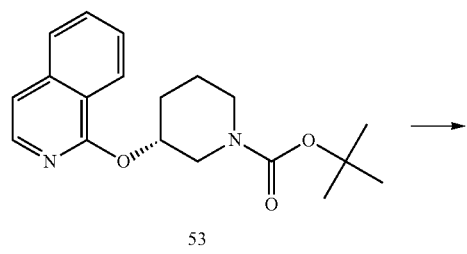

53

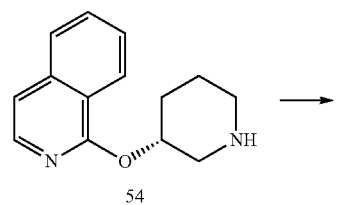

54

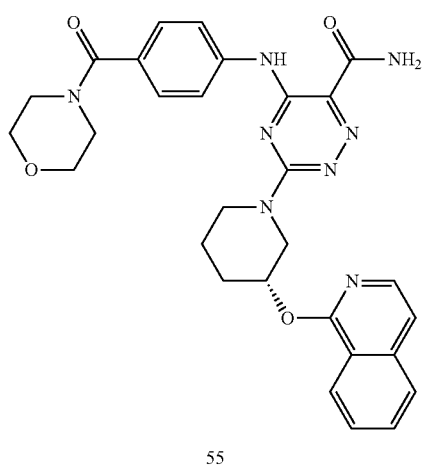

55

A mixture of 1-hydroxyisoquinoline (1.00 g, 6.9 mmol), (S)-1-BOC-3-hydroxypiperidine (4.17 g, 20.7 mmol), Ph$_3$P (7.23 g, 27.6 mmol) in THF (40 mL) was stirred at RT into a clear solution. DIAD (5.43 mL, 27.6 mmol) was added dropwise. The mixture was stirred at RT for 1 h and then at 50° C. for overnight. The mixture was diluted with EtOAc, washed with water ×3, dried, and concentrated in vacuo. The residue was subjected to flash column chromatography with 0% to 15% EtOAc in DCM to afford (R)-tert-butyl 3-(isoquinolin-1-yloxy)piperidine-1-carboxylate (53).

Compound 53 was treated with 4N HCl in dioxane (40 mL) at RT for 3 h. The mixture was concentrated in vacuo to give a viscous oil which was dissolved in MeCN (200 mL). To the solution was added NaHCO$_3$ powder (2.0 g). The mixture was stirred at RT overnight. The mixture was filtered and the filtrate was concentrated. The residue was subjected to flash column chromatography with 0%-100% EtOAc in DCM and then 0%-9% MeOH in DCM to isolate (R)-1-(piperidin-3-yloxy)isoquinoline (54).

To a solution of 3-(methylthio)-5-(4-(morpholine-4-carbonyl)phenylamino)-1,2,4-triazine-6-carboxamide (75 mg, 0.20 mmol) in NMP (4 mL) was added mCPBA (77% strength, 140 mg, 0.60 mmol). The mixture was stirred at RT for 30 m to yield a mixture of corresponding sulfone and sulfoxide. To the mixture was then added DIEA (0.28 mL, 1.60 mmol) and Compound 54 (100 mg, 0.40 mmol). The mixture was heated at 90° C. for 90 min. The mixture was cooled, diluted with EtOAc (100 mL), washed with 1N NaOH and brine, dried, and concentrated in vacuo. The residue was subjected to flash column chromatography with 50 to 100% EtOAc in DCM and further subjected to reverse phase preparative HPLC to afford the title compound (55) as an HCl salt (45 mg). MS found for $C_{29}H_{30}N_8O_4$ as (M+H)$^+$ 555.2, (M−H)$^−$ 553.3. UV: λ=275 nm.

Example 46

Synthesis of (R)-diisopropyl 1-(1-(6-carbamoyl-5-(4-(morpholine-4-carbonyl)phenylamino)-1,2,4-triazin-3-yl)piperidin-3-yl)hydrazine-1,2-dicarboxylate (56)

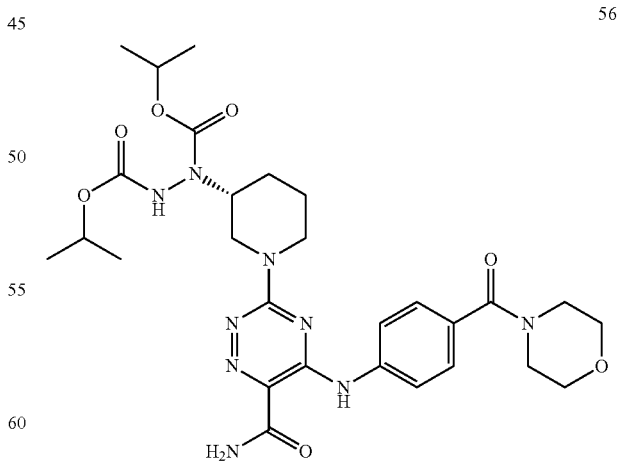

56

The title compound (56) was isolated as a by-product from the final-step reaction mixture during synthetic preparation of (R)-3-(3-(isoquinolin-1-yloxy)piperidin-1-yl)-5-(4-(morpholine-4-carbonyl)phenylamino)-1,2,4-triazine-6-carboxamide (55) as an HCl salt using reverse phase preparative HPLC. MS found for $C_{28}H_{39}N_9O_7$ as $(M+H)^+$ 614.2, $(M-H)^-$ 612.3. UV: $\lambda$=277 nm.

Example 47

Synthesis of (R)-3-(3-(6-cyclopropyl-8-fluoro-1-oxoisoquinolin-2(1H)-yl)piperidin-1-yl)-5-(4-(morpholine-4-carbonyl)phenylamino)-1,2,4-triazine-6-carboxamide (60)

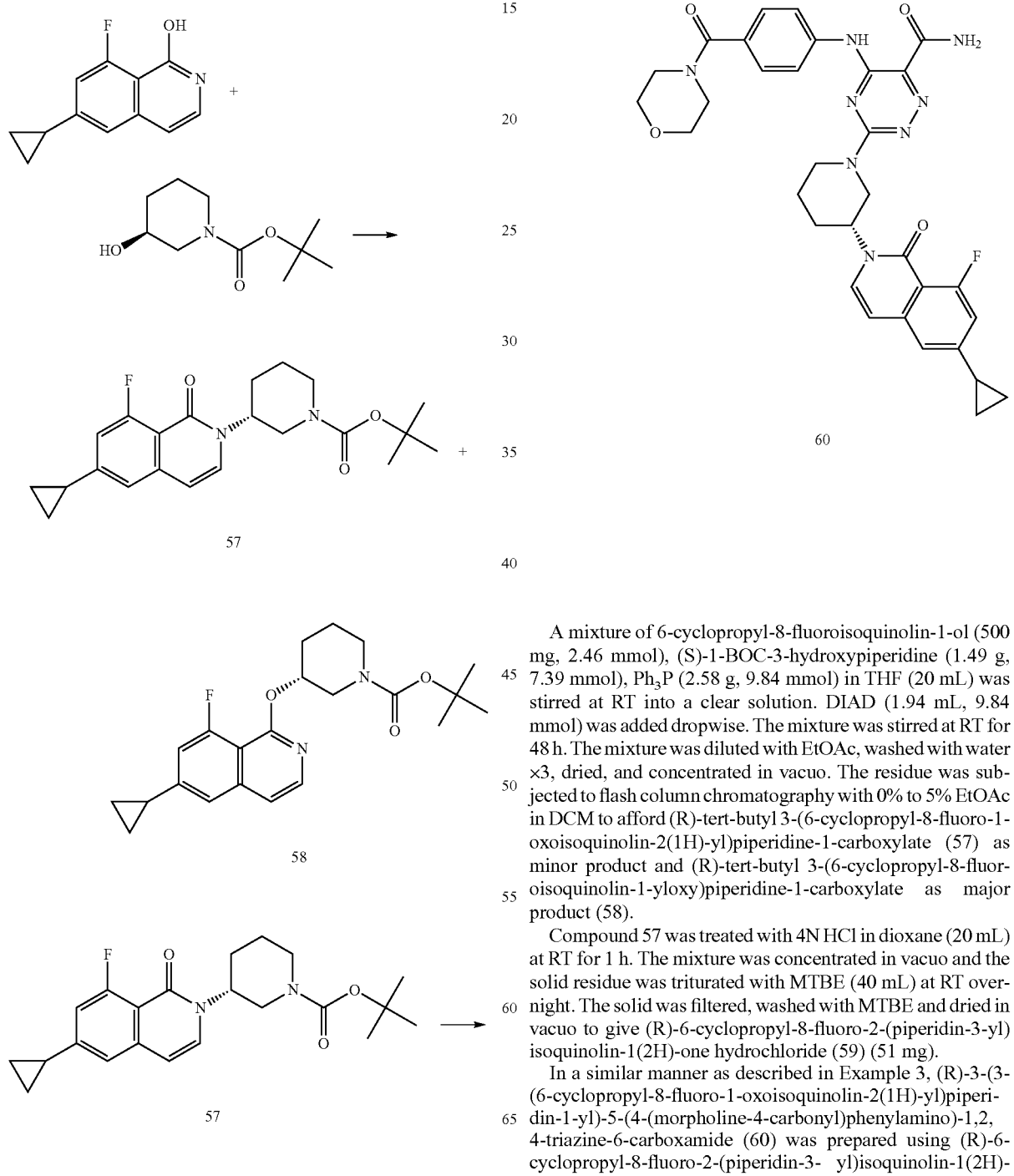

A mixture of 6-cyclopropyl-8-fluoroisoquinolin-1-ol (500 mg, 2.46 mmol), (S)-1-BOC-3-hydroxypiperidine (1.49 g, 7.39 mmol), Ph₃P (2.58 g, 9.84 mmol) in THF (20 mL) was stirred at RT into a clear solution. DIAD (1.94 mL, 9.84 mmol) was added dropwise. The mixture was stirred at RT for 48 h. The mixture was diluted with EtOAc, washed with water ×3, dried, and concentrated in vacuo. The residue was subjected to flash column chromatography with 0% to 5% EtOAc in DCM to afford (R)-tert-butyl 3-(6-cyclopropyl-8-fluoro-1-oxoisoquinolin-2(1H)-yl)piperidine-1-carboxylate (57) as minor product and (R)-tert-butyl 3-(6-cyclopropyl-8-fluoroisoquinolin-1-yloxy)piperidine-1-carboxylate as major product (58).

Compound 57 was treated with 4N HCl in dioxane (20 mL) at RT for 1 h. The mixture was concentrated in vacuo and the solid residue was triturated with MTBE (40 mL) at RT overnight. The solid was filtered, washed with MTBE and dried in vacuo to give (R)-6-cyclopropyl-8-fluoro-2-(piperidin-3-yl)isoquinolin-1(2H)-one hydrochloride (59) (51 mg).

In a similar manner as described in Example 3, (R)-3-(3-(6-cyclopropyl-8-fluoro-1-oxoisoquinolin-2(1H)-yl)piperidin-1-yl)-5-(4-(morpholine-4-carbonyl)phenylamino)-1,2,4-triazine-6-carboxamide (60) was prepared using (R)-6-cyclopropyl-8-fluoro-2-(piperidin-3- yl)isoquinolin-1(2H)- one hydrochloride (59). MS found for $C_{32}H_{33}FN_8O_4$ as $(M+H)^+$ 613.1, $(M-H)^-$ 611.3. UV: $\lambda$=246, 267, 274, 323, 328 nm.

Example 48

Synthesis of (R)-3-(3-(6-cyclopropyl-8-fluoroisoquinolin-1-yloxy)piperidin-1-yl)-5-(4-(morpholine-4-carbonyl)phenylamino)-1,2,4-triazine-6-carboxamide (62)

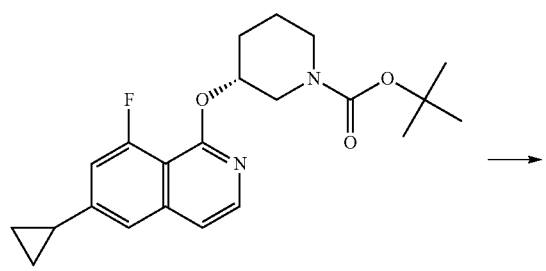

58

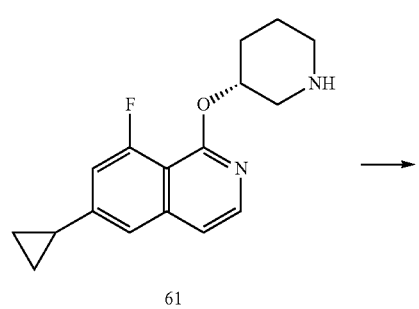

61

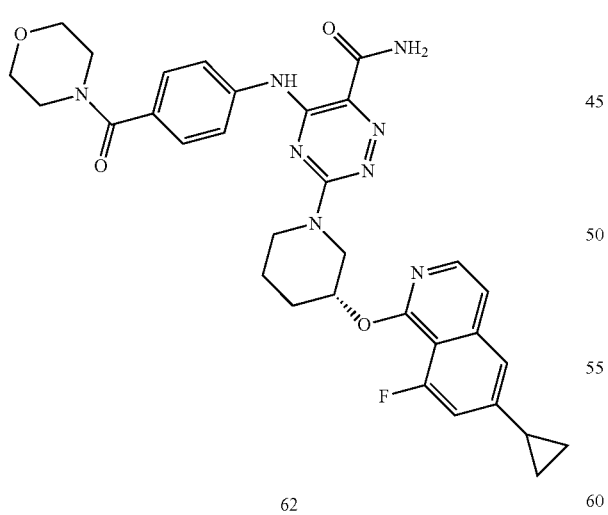

62

In a similar manner as described in Example 47, (R)-3-(3-(6-cyclopropyl-8-fluoroisoquinolin-1-yloxy)piperidin-1-yl)-5-(4-(morpholine-4-carbonyl)phenylamino)-1,2,4-triazine-6-carboxamide (62) was prepared using (R)-tert-butyl 3-(6-cyclopropyl-8-fluoroisoquinolin-1-yloxy)piperidine-1-carboxylate (58). MS found for $C_{32}H_{33}FN_8O_4$ as $(M+H)^+$ 613.2, $(M-H)^-$ 611.3. UV: $\lambda$=282 nm.

Example 49

Synthesis of (R)-3-(3-(4-tert-butylbenzamido)pyrrolidin-1-yl)-5-(4-(morpholine-4-carbonyl)phenylamino)-1,2,4-triazine-6-carboxamide (63)

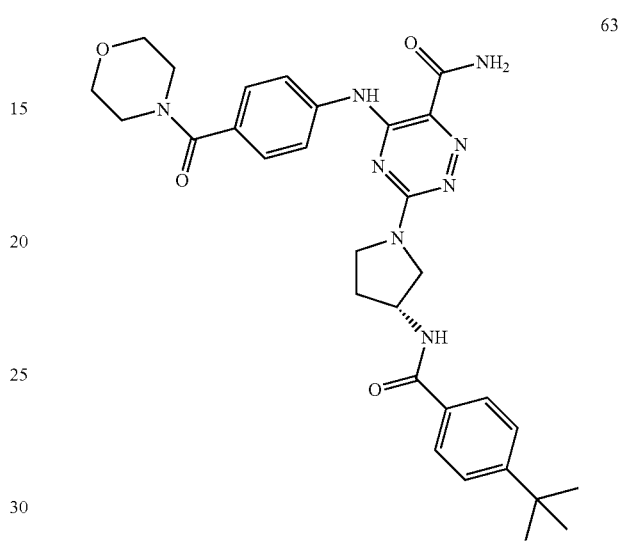

63

In a similar manner as described in Example 4, (R)-3-(3-(4-tert-butylbenzamido)pyrrolidin-1-yl)-5-(4-(morpholine-4-carbonyl)phenylamino)-1,2,4-triazine-6-carboxamide (63) was prepared using (R)-3-BOC-aminopyrrolidine and 4-tert-butylbenzoyl chloride. MS found for $C_{30}H_{36}N_8O_4$ as $(M+H)^+$ 573.2, $(M-H)^-$ 571.4. UV: $\lambda$=244 nm.

Example 50

Synthesis of (R)-3-(3-benzamidopyrrolidin-1-yl)-5-(4-(morpholine-4-carbonyl)phenylamino)-1,2,4-triazine-6-carboxamide (64)

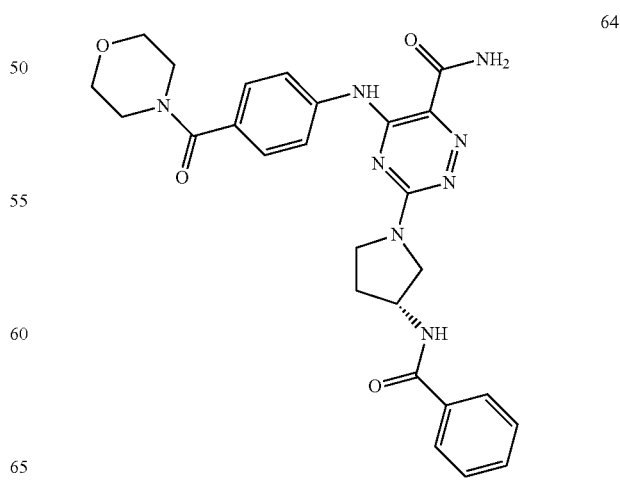

64

In a similar manner as described in Example 5, (R)-3-(3-benzamidopyrrolidin-1-yl)-5-(4-(morpholine-4-carbonyl)phenylamino)-1,2,4-triazine-6-carboxamide (64) was prepared using (R)-3-BOC-aminopyrrolidine. MS found for $C_{26}H_{28}N_8O_4$ as (M+H)$^+$ 517.1, (M−H)$^−$ 515.2. UV: λ=238, 247, 268, 270 nm.

Example 51

Synthesis of (R)-5-(4-(morpholine-4-carbonyl)phenylamino)-3-(3-(2,2,2-trifluoroacetamido)pyrrolidin-1-yl)-1,2,4-triazine-6-carboxamide (65)

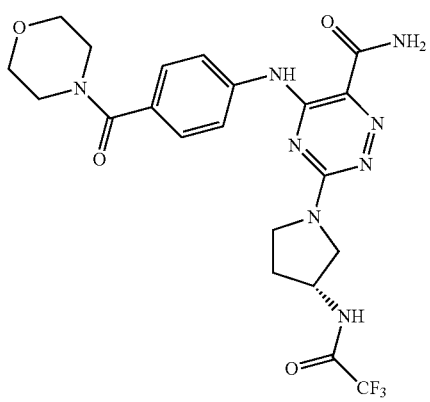

65

In a similar manner as described in Example 4, (R)-5-(4-(morpholine-4-carbonyl)phenylamino)-3-(3-(2,2,2-trifluoroacetamido)pyrrolidin-1-yl)-1,2,4-triazine-6-carboxamide (65) was prepared using (R)-3-BOC-aminopyrrolidine and trifluoroacetyl chloride. MS found for $C_{21}H_{23}F_3N_8O_4$ as (M+H)$^+$ 509.1, (M−H)$^−$ 507.2. UV: λ=239, 275 nm.

Example 52

Synthesis of (R)-3-(3-(4-tert-butylbenzamido)piperidin-1-yl)-5-(5-fluoropyridin-3-ylamino)-1,2,4-triazine-6-carboxamide (66)

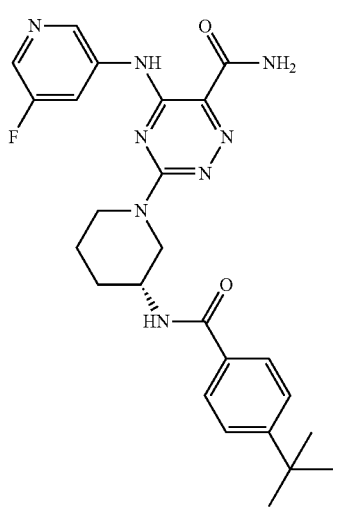

66

In a similar manner as described in Example 4, (R)-3-(3-(4-tert-butylbenzamido)piperidin-1-yl)-5-(5-fluoropyridin-3-ylamino)-1,2,4-triazine-6-carboxamide (66) was prepared using 3-amino-5-fluoropyridine and 4-tert-butylbenzoyl chloride. MS found for C25H29FN8O2 as (M+H)$^+$ 493.2, (M−H)$^−$ 491.3. UV: λ=259, 323, 343 nm.

Example 53

Synthesis of (R)-3-(3-(4-tert-butylbenzamido)piperidin-1-yl)-5-(p-tolylamino)-1,2,4-triazine-6-carboxamide (67)

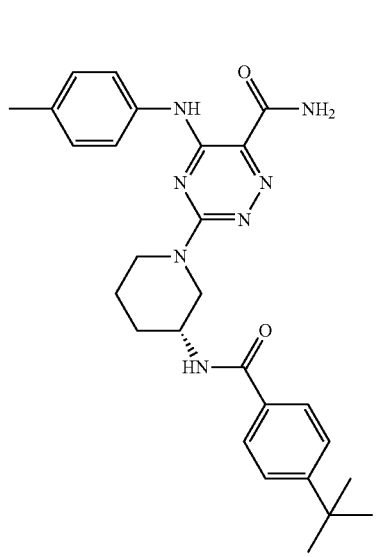

67

In a similar manner as described in Example 4, (R)-3-(3-(4-tert-butylbenzamido)piperidin-1-yl)-5-(p-tolylamino)-1,2,4-triazine-6-carboxamide (67) was prepared using p-toluidine and 4-tert-butylbenzoyl chloride. MS found for $C_{27}H_{33}N_7O_2$ as (M+H)$^+$ 488.2, (M−H)$^−$ 486.3. UV: λ=240, 248, 256, 322, 347 nm.

Example 54

Synthesis of (R)-3-(3-(4-tert-butylbenzamido)piperidin-1-yl)-5-(m-tolylamino)-1,2,4-triazine-6-carboxamide (68)

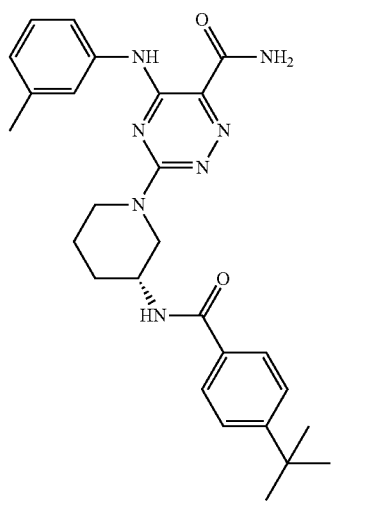

68

In a similar manner as described in Example 4, (R)-3-(3-(4-tert-butylbenzamido)piperidin-1-yl)-5-(m-tolylamino)-1,2,4-triazine-6-carboxamide (68) was prepared using m-toluidine and 4-tert-butylbenzoyl chloride. MS found for $C_{27}H_{33}N_7O_2$ as $(M+H)^+$ 488.2, $(M-H)^-$ 486.3. UV: $\lambda$=258, 319, 347 nm.

Example 55

Synthesis of (R)-3-(3-(4-tert-butylbenzamido)piperidin-1-yl)-5-(4-(methylsulfonyl)phenylamino)-1,2,4-triazine-6-carboxamide (69)

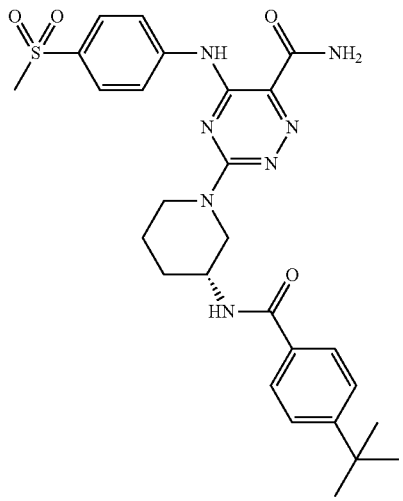

69

In a similar manner as described in Example 4, (R)-3-(3-(4-tert-butylbenzamido)piperidin-1-yl)-5-(4-(methylsulfonyl)phenylamino)-1,2,4-triazine-6-carboxamide (69) was prepared using 4-methylsulfonylaniline and 4-tert-butylbenzoyl chloride. MS found for $C_{27}H_{33}N_7O_4S$ as $(M+H)^+$ 552.2, $(M-H)^-$ 550.3. UV: $\lambda$=283 nm.

Example 56

Synthesis of (R)-3-(3-(4-tert-butylbenzamido)piperidin-1-yl)-5-(4-(pyrimidin-2-yl)phenylamino)-1,2,4-triazine-6-carboxamide (70)

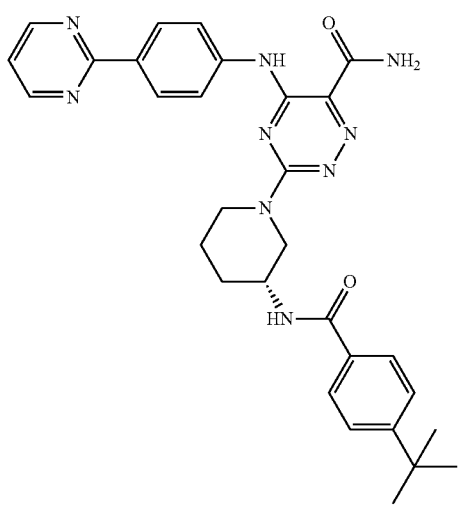

70

In a similar manner as described in Example 4, (R)-3-(3-(4-tert-butylbenzamido)piperidin-1-yl)-5-(4-(pyrimidin-2-yl)phenylamino)-1,2,4-triazine-6-carboxamide (70) was prepared using 4-(pyrimidin-2-yl)aniline and 4-tert-butylbenzoyl chloride. MS found for $C_{30}H_{33}N_9O_2$ as $(M+H)^+$ 522.2, $(M-H)^-$ 550.3. UV: $\lambda$=260, 313 nm.

Example 57

Synthesis of (R)-3-(3-(4-tert-butylbenzamido)piperidin-1-yl)-5-(3-(pyrimidin-2-yl)phenylamino)-1,2,4-triazine-6-carboxamide (71)

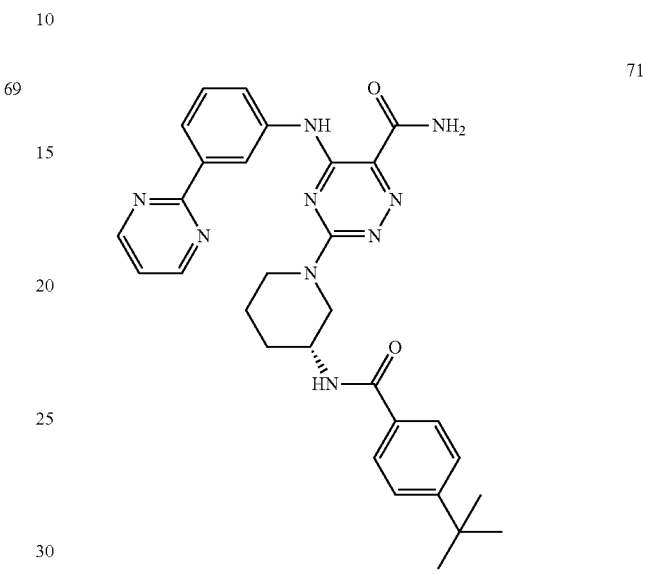

71

In a similar manner as described in Example 4, (R)-3-(3-(4-tert-butylbenzamido)piperidin-1-yl)-5-(3-(pyrimidin-2-yl)phenylamino)-1,2,4-triazine-6-carboxamide (71) was prepared using 3-(pyrimidin-2-yl)aniline and 4-tert-butylbenzoyl chloride. MS found for $C_{30}H_{33}N_9O_2$ as $(M+H)^+$ 522.2, $(M-H)^-$ 550.3. UV: $\lambda$=259, 331, 334 nm.

Example 58

Synthesis of (R)-3-(3-(4-tert-butylbenzamido)piperidin-1-yl)-5-(4-(oxazol-2-yl)phenylamino)-1,2,4-triazine-6-carboxamide (72)

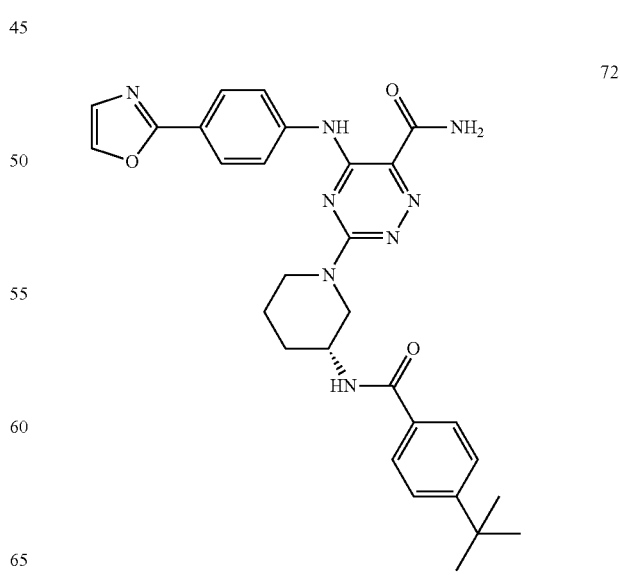

72

In a similar manner as described in Example 4, (R)-3-(3-(4-tert-butylbenzamido)piperidin-1-yl)-5-(4-(oxazol-2-yl)phenylamino)-1,2,4-triazine-6-carboxamide (72) was prepared using 4-(oxazol-2-yl)aniline and 4-tert-butylbenzoyl chloride. MS found for $C_{29}H_{32}N_8O_3$ as $(M+H)^+$ 541.2, $(M-H)^-$ 539.3. UV: $\lambda$=311 nm.

Example 59

Synthesis of (R)—N-(1-(6-carbamoyl-5-(4-(oxazol-2-yl)phenylamino)-1,2,4-triazin-3-yl)piperidin-3-yl)morpholine-4-carboxamide (73)

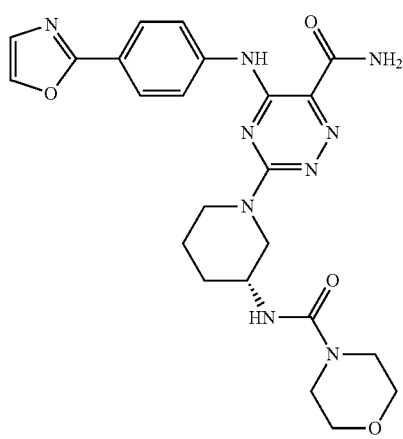

73

In a similar manner as described in Example 4, (R)—N-(1-(6-carbamoyl-5-(4-(oxazol-2-yl)phenylamino)-1,2,4-triazin-3-yl)piperidin-3-yl)morpholine-4-carboxamide (73) was prepared using 4-(oxazol-2-yl)aniline and morpholine-4-carbonyl chloride. MS found for $C_{23}H_{27}N_9O_4$ as $(M+H)^+$ 494.2, $(M-H)^-$ 492.2. UV: $\lambda$=310 nm.

Example 60

Synthesis of (R)-tert-butyl 3-(6-carbamoyl-5-(4-(morpholine-4-carbonyl)phenylamino)-1,2,4-triazin-3-ylamino)piperidine-1-carboxylate (74)

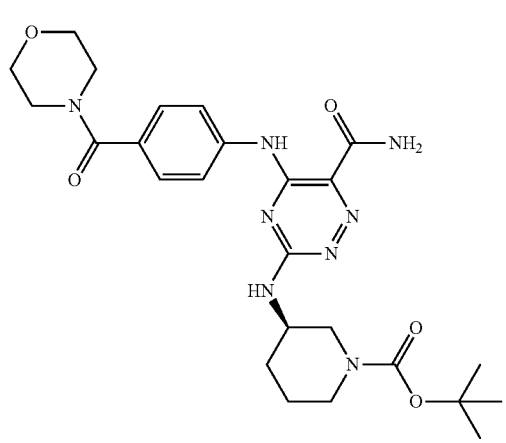

74

To a solution of 3-(methylthio)-5-(4-(morpholine-4-carbonyl)phenylamino)-1,2,4-triazine-6-carboxamide (170 mg, 0.46 mmol) in NMP (20 mL) was added mCPBA (77% strength, 310 mg, 1.38 mmol). The mixture was stirred at RT for 1 h to yield a mixture of corresponding sulfone and sulfoxide. To the mixture was then added DIEA (0.40 mL, 2.30 mmol) and (R)-tert-butyl 3-aminopiperidine-1-carboxylate (184 mg, 0.92 mmol). The mixture was heated at 90° C. for 90 m. The mixture was cooled, diluted with 300 mL EtOAc, washed with 1N NaOH and brine, dried, and concentrated in vacuo. The residue was subjected to flash column chromatography with 0 to 6% MeOH in DCM to yield the title compound (74) (210 mg, 87% yield). MS found $C_{25}H_{34}N_8O_5$ as $(M+H)^+$ 527.2, $(M-H)^-$ 525.3. UV: $\lambda$=252, 267, 283 nm.

Example 61

Synthesis of (R)-5-(4-(morpholine-4-carbonyl)phenylamino)-3-(piperidin-3-ylamino)-1,2,4-triazine-6-carboxamide (75)

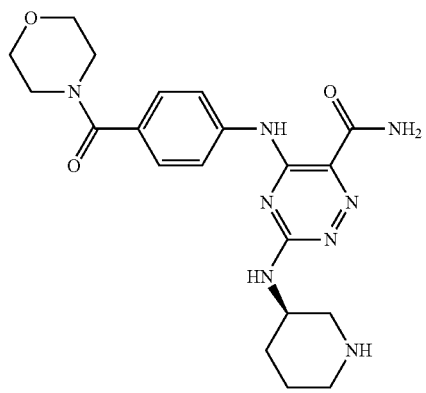

75

(R)-tert-butyl 3-(6-carbamoyl-5-(4-(morpholine-4-carbonyl)phenylamino)-1,2,4-triazin-3-ylamino)piperidine-1-carboxylate (74) (180 mg) was treated with 4N HCl in dioxane (30 mL) at RT for 3 h. The mixture was concentrated in vacuo to yield the title compound (75) as HCl salt in quantitative yield. MS found $C_{20}H_{26}N_8O_3$ as $(M+H)^+$ 427.1, $(M-H)^-$ 425.2. UV: $\lambda$=264, 283 nm.

Example 62

Synthesis of (R)-3-(1-(4-tert-butylbenzoyl)piperidin-3-ylamino)-5-(4-(morpholine-4-carbonyl)phenylamino)-1,2,4-triazine-6-carboxamide (76)

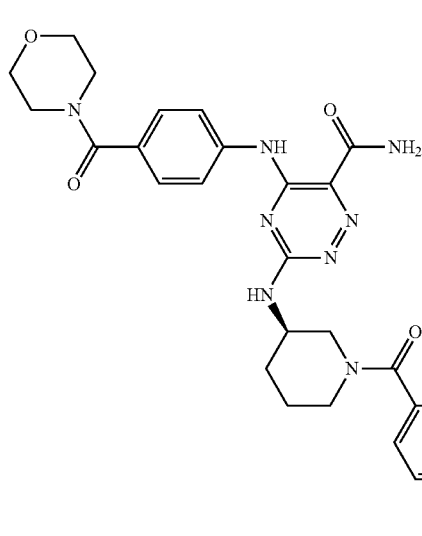

76

To a solution of (R)-5-(4-(morpholine-4-carbonyl)phenylamino)-3-(piperidin-3-ylamino)-1,2,4-triazine-6-carboxamide (75) HCl salt (60 mg, 0.13 mmol) in NMP (3 mL) was added DIEA (90 μL, 0.76 mmol) and then 4-tert-butylbenzoyl chloride (39 mg, 0.20 mmol). The mixture was stirred at RT for 20 min, quenched with TFA (0.1 mL), diluted with 2 mL water, and subjected to reverse phase preparative HPLC to afford the title compound (76) as an HCl salt. MS found for $C_{31}H_{38}N_8O_4$ as $(M+H)^+$ 587.2, $(M-H)^-$ 585.2. UV: λ=268, 287 nm.

Example 63

Synthesis of (R)-5-(4-(morpholine-4-carbonyl)phenylamino)-3-(1-propionylpiperidin-3-ylamino)-1,2,4-triazine-6-carboxamide (77)

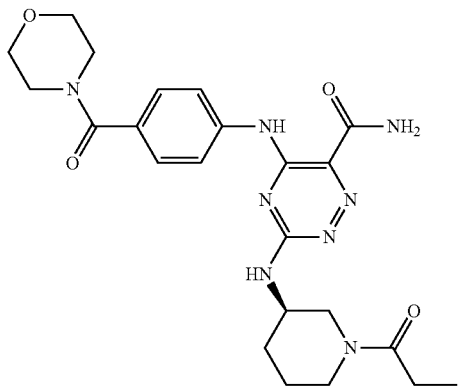

In a similar manner as described in Example 62, (R)-5-(4-(morpholine-4-carbonyl)phenylamino)-3-(1-propionylpiperidin-3-ylamino)-1,2,4-triazine-6-carboxamide (77) was prepared using propionyl chloride. MS found for $C_{23}H_{30}N_8O_4$ as $(M+H)^+$ 483.2, $(M-H)^-$ 481.3. UV: λ=243, 268, 279 nm.

Example 64

Synthesis of (R)-3-(1-(cyclopropanecarbonyl)piperidin-3-ylamino)-5-(4-(morpholine-4-carbonyl)phenylamino)-1,2,4-triazine-6-carboxamide (78)

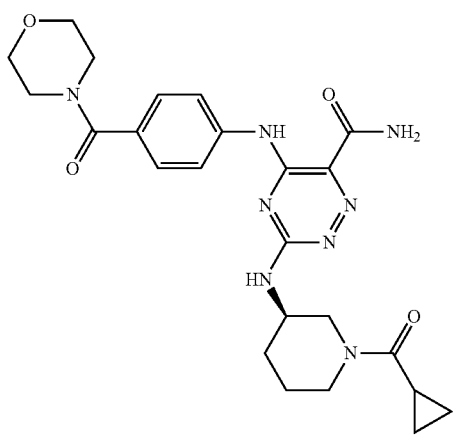

In a similar manner as described in Example 62, (R)-3-(1-(cyclopropanecarbonyl)piperidin-3-ylamino)-5-(4-(morpholine-4-carbonyl)phenylamino)-1,2,4-triazine-6-carboxamide (78) was prepared using cyclopropanecarbonyl chloride. MS found for $C_{24}H_{30}N_8O_4$ as $(M+H)^+$ 495.1, $(M-H)^-$ 493.2. UV: λ=269, 280 nm.

Example 65

Synthesis of (R)-3-(1-acryloylpiperidin-3-ylamino)-5-(4-(morpholine-4-carbonyl)phenylamino)-1,2,4-triazine-6-carboxamide (79)

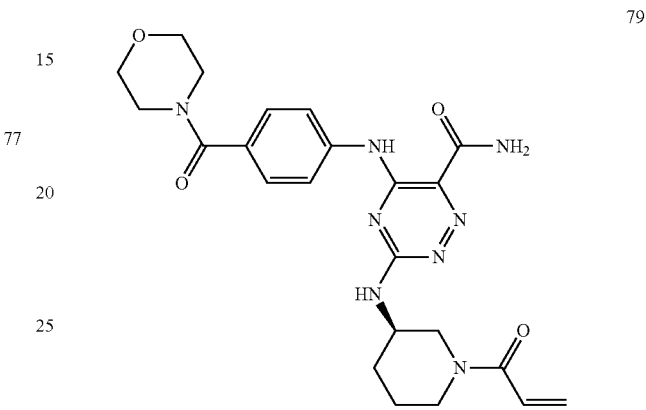

In a similar manner as described in Example 62, (R)-3-(1-acryloylpiperidin-3-ylamino)-5-(4-(morpholine-4-carbonyl)phenylamino)-1,2,4-triazine-6-carboxamide (79) was prepared using acryloyl chloride. MS found for $C_{23}H_{28}N_8O_4$ as $(M+H)^+$ 481.1, $(M-H)^-$ 479.2. UV: slope like, no obvious peak.

Example 66

Synthesis of (R,E)-3-(1-(4-(dimethylamino)but-2-enoyl)piperidin-3-ylamino)-5-(4-(morpholine-4-carbonyl)phenylamino)-1,2,4-triazine-6-carboxamide (80)

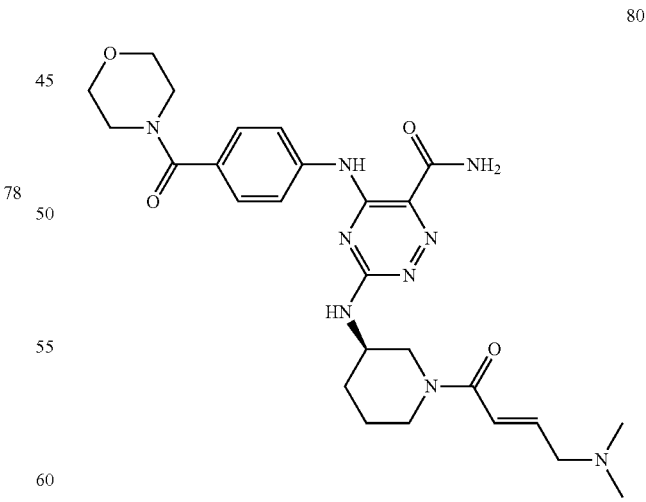

To a solution of (R)-5-(4-(morpholine-4-carbonyl)phenylamino)-3-(piperidin-3-ylamino)-1,2,4-triazine-6-carboxamide HCl salt (47 mg, 0.10 mmol) in NMP (4 mL) was added (E)-4-(dimethylamino)but-2-enoic acid (50 mg, 0.30 mmol), DIEA (180 μL, 1.0 mmol) and then PyBOP (104 mg, 0.20 mmol). The mixture was stirred at RT for 2 h, quenched with TFA (0.2 mL), diluted with 2 mL water, and subjected to reverse phase preparative HPLC to isolate the title compound (80) as an HCl salt (32 mg). MS found for $C_{26}H_{35}N_9O_4$ as $(M+H)^+$ 538.2, $(M-H)^-$ 536.3. UV: $\lambda=246$ nm.

Example 67

Synthesis of (R,E)-3-(1-(4-(cyclopropyl(methyl)amino)but-2-enoyl)piperidin-3-ylamino)-5-(4-(morpholine-4-carbonyl)phenylamino)-1,2,4-triazine-6-carboxamide (81)

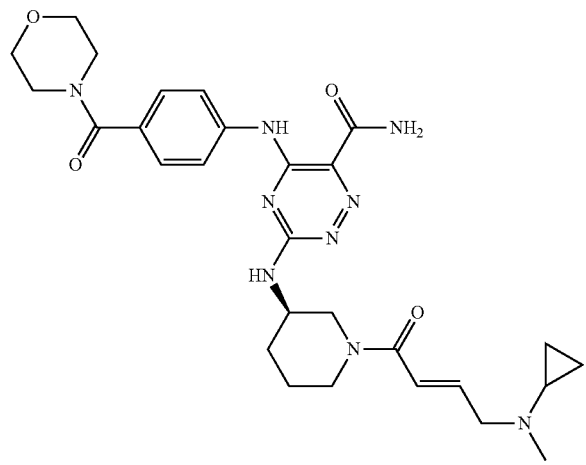

In a similar manner as described in Example 66, (R,E)-3-(1-(4-(cyclopropyl(methyl)amino)but-2-enoyl)piperidin-3-ylamino)-5-(4-(morpholine-4-carbonyl)phenylamino)-1,2,4-triazine-6-carboxamide (81) was prepared using (E)-4-(cyclopropyl(methyl)amino)but-2-enoic acid. MS found for $C_{28}H_{37}N_9O_4$ as $(M+H)^+$ 564.2, $(M-H)^-$ 562.3. UV: $\lambda=247$ nm.

Example 68

Synthesis of (R)-tert-butyl 3-(6-carbamoyl-5-(4-(morpholine-4-carbonyl)phenylamino)-1,2,4-triazin-3-ylamino)pyrrolidine-1-carboxylate (82)

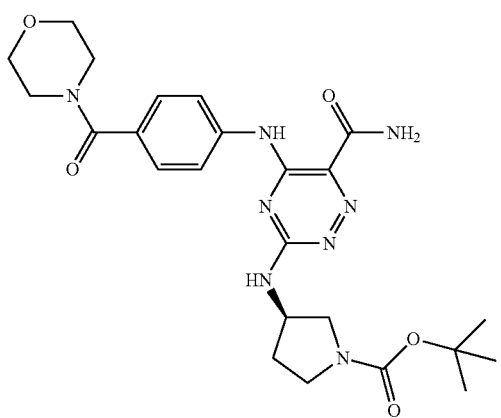

In a similar manner as described in Example 60, (R)-tert-butyl 3-(6-carbamoyl-5-(4-(morpholine-4-carbonyl)phenylamino)-1,2,4-triazin-3-ylamino)pyrrolidine-1-carboxylate (82) was prepared using (R)-tert-butyl 3-aminopyrrolidine-1-carboxylate. MS found for $C_{24}H_{32}N_8O_5$ as $(M+H)^+$ 513.2, $(M-H)^-$ 511.3. UV: $\lambda=247, 265, 283$ nm.

Example 69

Synthesis of (R)-5-(4-(morpholine-4-carbonyl)phenylamino)-3-(pyrrolidin-3-ylamino)-1,2,4-triazine-6-carboxamide (83)

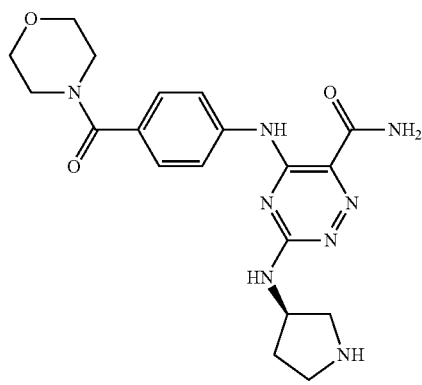

(R)-tert-butyl 3-(6-carbamoyl-5-(4-(morpholine-4-carbonyl)phenylamino)-1,2,4-triazin-3-ylamino)pyrrolidine-1-carboxylate (82) (160 mg) was treated with 4N HCl in dioxane (30 mL) at RT for 3 h. The mixture was concentrated in vacuo to yield the title compound (83) as an HCl salt in quantitative yield. MS found $C_{19}H_{24}N_8O_3$ as $(M+H)^+$ 413.1, $(M-H)^-$ 411.3. UV: $\lambda=264, 283$ nm.

Example 70

Synthesis of (R)-3-(1-acryloylpyrrolidin-3-ylamino)-5-(4-(morpholine-4-carbonyl)phenylamino)-1,2,4-triazine-6-carboxamide (84)

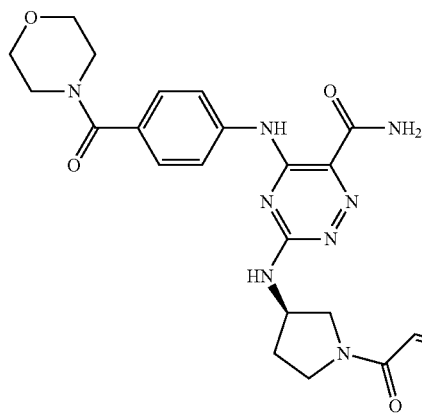

To a solution of (R)-5-(4-(morpholine-4-carbonyl)phenylamino)-3-(pyrrolidin-3-ylamino)-1,2,4-triazine-6-carboxamide (83) HCl salt (60 mg, 0.13 mmol) in NMP (4 mL) was added DIEA (160 µL, 0.90 mmol) and then acryloyl chloride (25 µL, 0.30 mmol). The mixture was stirred at RT for 30 min, quenched with TFA (0.2 mL), diluted with 2 mL water, and subjected to reverse phase preparative HPLC to afford the title compound (84) as an HCl salt. MS found for $C_{22}H_{26}N_8O_4$ as $(M+H)^+$ 467.1, $(M-H)^-$ 465.2. UV: $\lambda=242$ nm.

Example 71

Synthesis of (R,E)-3-(1-(4-(cyclopropyl(methyl)amino)but-2-enoyl)pyrrolidin-3-ylamino)-5-(4-(morpholine-4-carbonyl)phenylamino)-1,2,4-triazine-6-carboxamide (85)

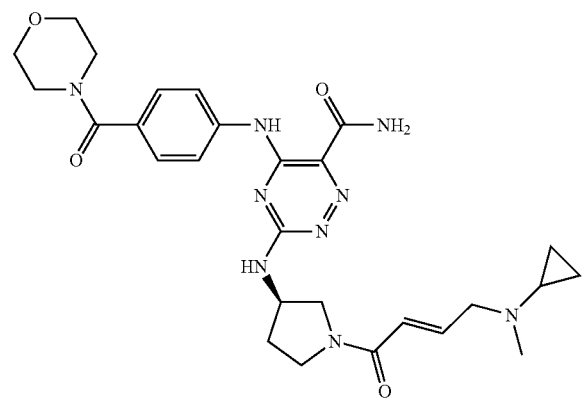

85

To a solution of (E)-4-(cyclopropyl(methyl)amino)but-2-enoic acid (2.00 g, 12.9 mmol) in DCM (60 mL) was added DMF (0.2 mL) and oxalyl chloride (4.42 mL, 51.6 mmol). The mixture was stirred at RT for 4 h and concentrated in vacuo to dryness to afford (E)-4-(cyclopropyl(methyl)amino)but-2-enoyl chloride. In a similar manner as described in Example 70, (R,E)-3-(1-(4-(cyclopropyl(methyl)amino)but-2-enoyl)pyrrolidin-3-ylamino)-5-(4-(morpholine-4-carbonyl)phenylamino)-1,2,4-triazine-6-carboxamide (85) was prepared using (E)-4-(cyclopropyl(methyl)amino)but-2-enoyl chloride. MS found for $C_{27}H_{35}N_9O_4$ as $(M+H)^+$ 550.2, $(M-H)^-$ 548.3. UV: $\lambda=248$ nm.

Example 72

Synthesis of (R)-3-(1-acryloylpyrrolidin-3-ylamino)-5-(4-(morpholine-4-carbonyl)phenylamino)-1,2,4-triazine-6-carboxamide (86)

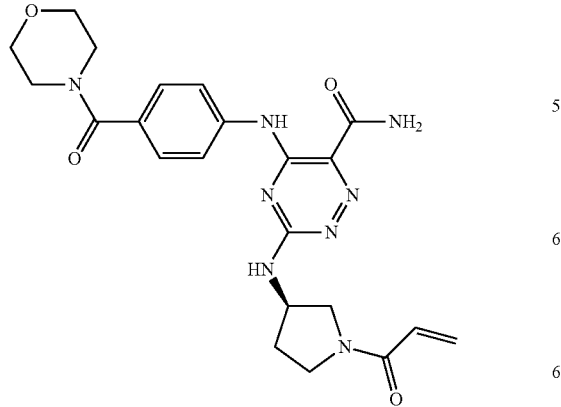

86

In a similar manner as described in Example 70, (R)-3-(1-acryloylpyrrolidin-3-ylamino)-5-(4-(morpholine-4-carbonyl)phenylamino)-1,2,4-triazine-6-carboxamide (86) was prepared using (R)-tert-butyl 3-(methylamino)pyrrolidine-1-carboxylate. MS found for $C_{23}H_{28}N_8O_4$ as $(M+H)^+$ 481.1, $(M-H)^-$ 479.2. UV: $\lambda=265$ nm.

Example 73

Synthesis of (R)-5-(3-(4-tert-butylbenzamido)piperidin-1-yl)-3-(4-(morpholine-4-carbonyl)phenylamino)pyrazine-2-carboxamide (91)

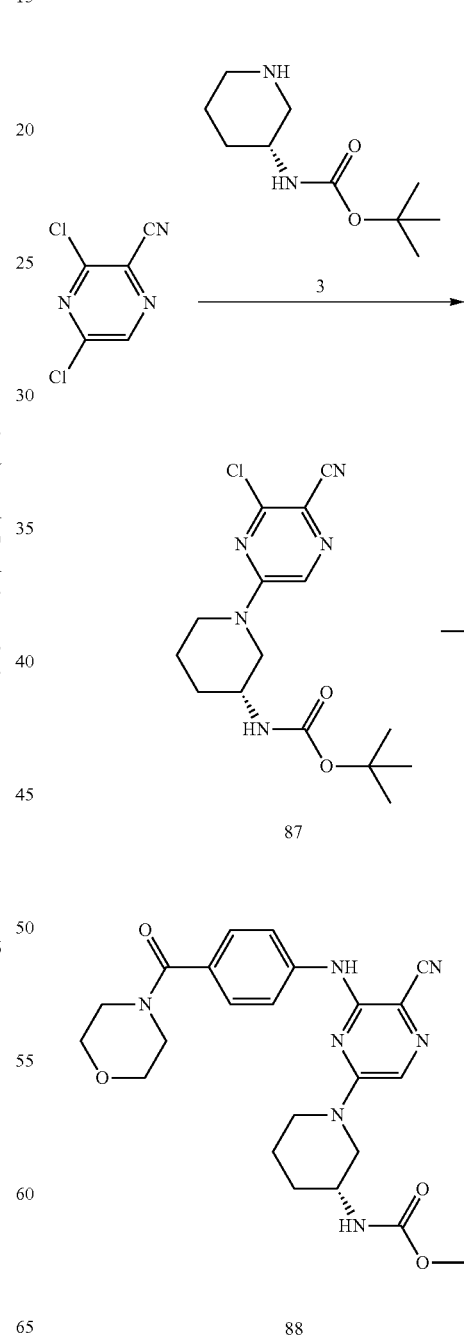

-continued

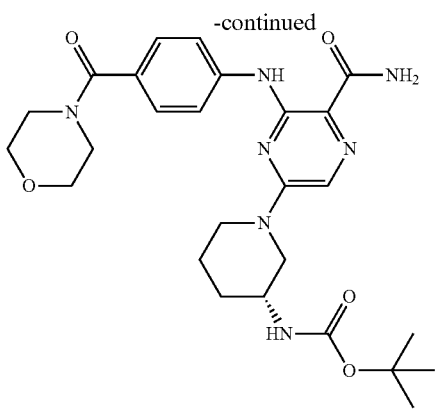

89

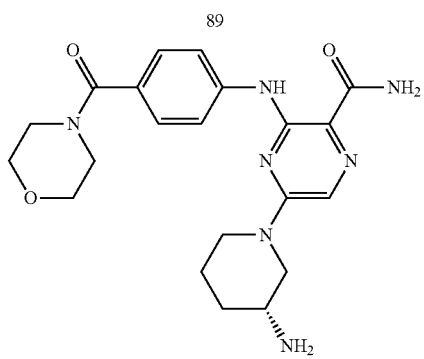

90

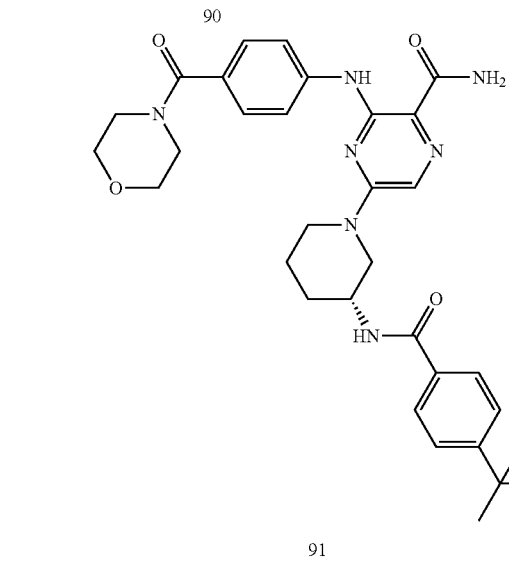

91

To a solution of 3,5-dichloropyrazine-2-carbonitrile (500 mg, 2.87 mmol) in DMF (10 mL) was added (R)-(3-BOC-amino)piperidine (690 mg, 3.45 mmol) and then DIEA (1.0 mL, 5.74 mmol) in a dropwise manner. The mixture was stirred at RT for 90 min. The mixture was diluted with EtOAc (200 mL), washed with water ×2, dried, and concentrated in vacuo. The residue was subjected to flash column chromatography with 0 to 25% EtOAc in DCM to isolate (R)-tert-butyl 1-(6-chloro-5-cyanopyrazin-2-yl)piperidin-3-ylcarbamate (87) (940 mg, 97% yield).

A mixture of (R)-tert-butyl 1-(6-chloro-5-cyanopyrazin-2-yl)piperidin-3-ylcarbamate (400 mg, 1.19 mmol), (4-aminophenyl)(morpholino)methanone (490 mg, 2.38 mmol), Pd(OAc)$_2$ (54 mg, 0.24 mmol), BINAP (150 mg, 0.24 mmol), fine powder Cs$_2$CO$_3$ (1.55 g, 4.76 mmol) in dioxane (40 mL) was degassed with nitrogen stream for 3 min. The mixture was stirred in a nitrogen atmosphere at 115° C. for 2.5 h. The mixture was cooled, diluted with 100 mL EtOAc, filtered through celite, and concentrated in vacuo. The residue was subjected to flash column chromatography with 0 to 65% EtOAc in DCM to give (R)-tert-butyl 1-(5-cyano-6-(4-(morpholine-4-carbonyl)phenylamino)pyrazin-2-yl)piperidin-3-ylcarbamate (88) (yield >85%).

To a solution of (R)-tert-butyl 1-(5-cyano-6-(4-(morpholine-4-carbonyl)phenylamino)pyrazin-2-yl)piperidin-3-ylcarbamate (88) in MeOH (15 mL) and DMSO (1.5 mL) was added solid NaOH (200 mg) and 30% H$_2$O$_2$ (1.5 mL). The mixture was stirred at RT for 20 min, diluted with acetonitrile (10 mL), and EtOAc (200 mL) 10 min later. The organic phase was washed with water ×2, dried, and concentrated in vacuo. The residue was subjected to flash column chromatography with 0 to 7% MeOH in DCM to isolate (R)-tert-butyl 1-(5-carbamoyl-6-(4-(morpholine-4-carbonyl)phenylamino)pyrazin-2-yl)piperidin-3-ylcarbamate (89) (yield >95%). (R)-tert-butyl 1-(5-carbamoyl-6-(4-(morpholine-4-carbonyl)phenylamino)pyrazin-2-yl)piperidin-3-ylcarbamate (89) was treated with 4N HCl in dioxane (30 mL) for 40 min. The mixture was concentrated in vacuo to dryness to afford (R)-5-(3-aminopiperidin-1-yl)-3-(4-(morpholine-4-carbonyl)phenylamino)pyrazine-2-carboxamide hydrochloride (90).

To a solution of (R)-5-(3-aminopiperidin-1-yl)-3-(4-(morpholine-4-carbonyl)phenylamino)pyrazine-2-carboxamide hydrochloride (90) (120 mg, 0.27 mmol) in NMP (3 mL) was added DIEA (190 µL, 1.08 mmol) and then 4-tert-butylbenzoyl chloride (106 mg, 0.54 mmol). The mixture was stirred at RT for 1 h, diluted with 100 mL EtOAc, washed with water ×2, dried, and concentrated in vacuo. The residue was subjected to flash column chromatography with 0 to 5% MeOH in DCM to isolate the title compound (91) (yield 114 mg). MS found for C$_{32}$H$_{39}$N$_7$O$_4$ as (M+H)$^+$ 586.2, (M−H)$^-$ 584.3. UV: λ=259, 276, 286, 314, 344, 369 nm.

Example 74

Synthesis of (R)-5-((1-acryloylpiperidin-3-yl)(methyl)amino)-3-(4-(morpholine-4-carbonyl)phenylamino)pyrazine-2-carboxamide (93)

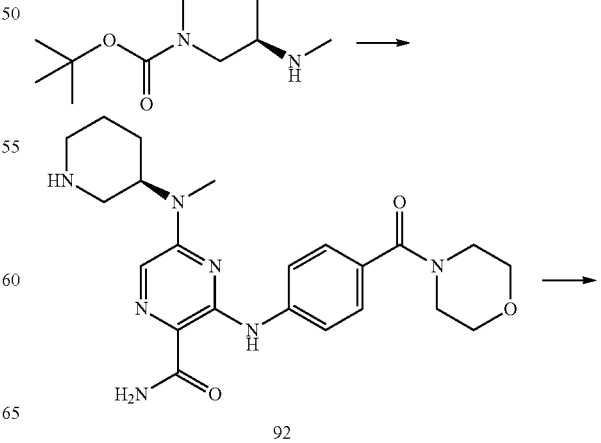

92

-continued

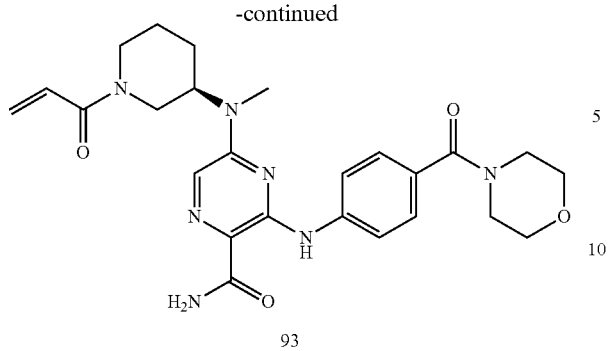

93

In a similar manner as described in Example 73, (R)-5-(methyl(piperidin-3-yl)amino)-3-(4-(morpholine-4-carbonyl)phenylamino)pyrazine-2-carboxamide hydrochloride (92) was prepared using (R)-tert-butyl 3-(methylamino)piperidine-1-carboxylate.

To a solution of (R)-5-(methyl(piperidin-3-yl)amino)-3-(4-(morpholine-4-carbonyl)phenylamino)pyrazine-2-carboxamide hydrochloride (92) (40 mg, 0.084 mmol) in NMP (3 mL) was added DIEA (150 µL, 0.84 mmol) and then acryloyl chloride (23 mg, 0.25 mmol). The mixture was stirred at RT for 1.5 h, quenched with TFA (0.2 mL), diluted with 2 mL water, and subjected to reverse phase preparative HPLC to isolate the title compound (93) as an HCl salt (25 mg). MS found for $C_{25}H_{31}N_7O_4$ as $(M+H)^+$ 494.1, $(M-H)^-$ 492.3. UV: $\lambda$=275, 280, 313, 343, 369 nm.

Example 75

Synthesis of (R,E)-5-((1-(4-(dimethylamino)but-2-enoyl)piperidin-3-yl)(methyl)amino)-3-(4-(morpholine-4-carbonyl)phenylamino)pyrazine-2-carboxamide (94)

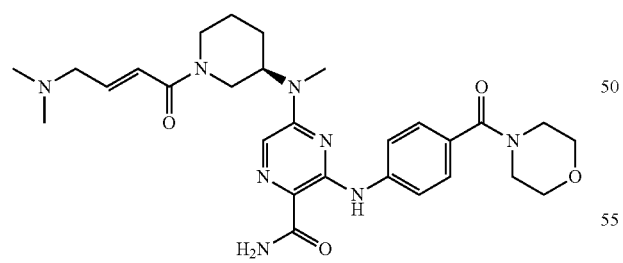

94

To a solution of (R)-5-(methyl(piperidin-3-yl)amino)-3-(4-(morpholine-4-carbonyl)phenylamino)pyrazine-2-carboxamide hydrochloride (92) (40 mg, 0.084 mmol) in NMP (3 mL) was added (E)-4-(dimethylamino)but-2-enoic acid (42 mg, 0.25 mmol), DIEA (150 µL, 0.84 mmol) and then PyBOP (88 mg, 0.17 mmol). The mixture was stirred at RT for 1.5 h, quenched with TFA (0.2 mL), diluted with 2 mL water, and subjected to reverse phase preparative HPLC to isolate the title compound (94) as an HCl salt (29 mg). MS found for $C_{28}H_{38}N_8O_4$ as $(M+H)^+$ 551.3, $(M-H)^-$ 549.3. UV: $\lambda$=274, 281, 313, 344, 369 nm.

Example 76

Synthesis of (R)-5-(3-(4-tert-butylbenzamido)piperidin-1-yl)-3-(4-(morpholine-4-carbonyl)phenylamino)picolinamide (99)

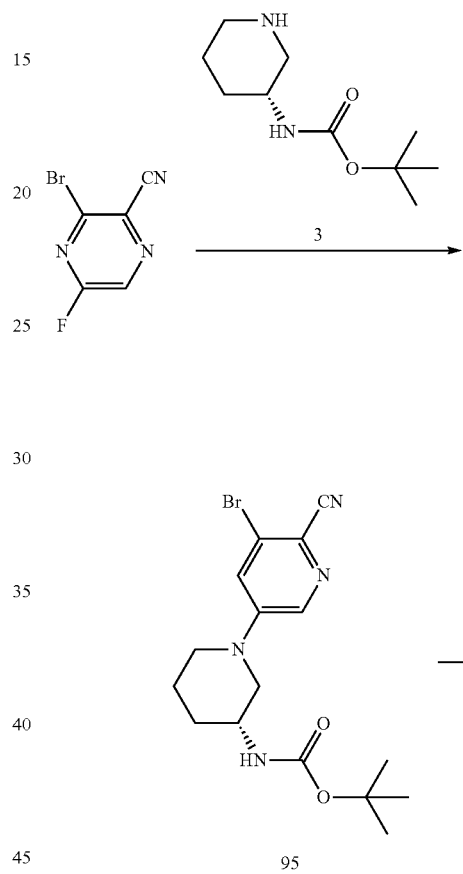

95

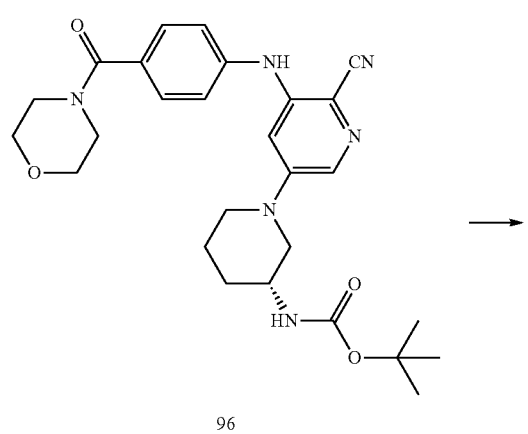

96

-continued

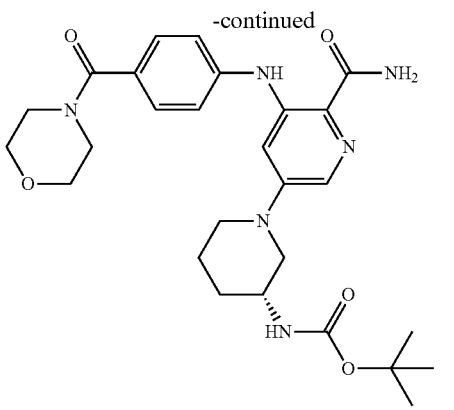

97

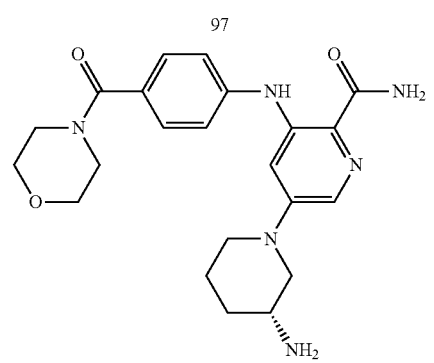

98

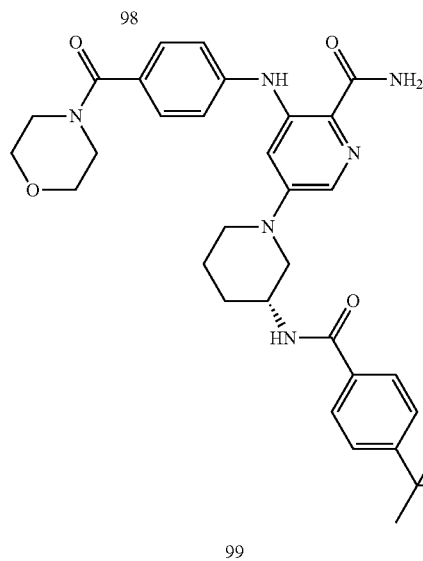

99

To a solution of 3-bromo-5-fluoropicolinonitrile (660 mg, 3.28 mmol) in NMP (20 mL) was added (R)-(3-BOC-amino) piperidine (1.31 g, 6.56 mmol) and then DIEA (2.28 mL, 13.12 mmol) in a dropwise manner. The mixture was stirred at 100° C. for 90 min. The mixture was diluted with EtOAc (300 mL), washed with water ×2, dried, and concentrated in vacuo. The residue was subjected to flash column chromatography with 10 to 50% EtOAc in hexane to isolate (R)-tert-butyl 1-(5-bromo-6-cyanopyridin-3-yl)piperidin-3-ylcarbamate (95) (1.30 g, quantitative yield).

A mixture of (R)-tert-butyl 1-(5-bromo-6-cyanopyridin-3-yl)piperidin-3-ylcarbamate (95) (300 mg, 0.78 mmol), (4-aminophenyl)(morpholino)methanone (322 mg, 1.56 mmol), Pd$_2$(dba)$_3$ (73 mg, 0.08 mmol), XantPhos (93 mg, 0.16 mmol), fine powder Cs$_2$CO$_3$ (765 mg, 2.34 mmol) in dioxane (50 mL) was degassed with nitrogen stream for 3 min. The mixture was stirred in a nitrogen atmosphere at 115° C. for 2 h. The mixture was cooled, diluted with 200 mL EtOAc, filtered through celite, and concentrated in vacuo. The residue was subjected to flash column chromatography with 20 to 100% EtOAc in DCM to isolate (R)-tert-butyl 1-(6-cyano-5-(4-(morpholine-4-carbonyl)phenylamino)pyridin-3-yl)piperidin-3-ylcarbamate (96) (yield >80%).

To a solution of (R)-tert-butyl 1-(6-cyano-5-(4-(morpholine-4-carbonyl)phenylamino)pyridin-3-yl)piperidin-3-ylcarbamate (96) in MeOH (15 mL) and DMSO (1.5 mL) was added solid NaOH (100 mg) and 30% H$_2$O$_2$ (1.5 mL). The mixture was stirred at RT for 20 min, diluted with acetonitrile (5 mL), and EtOAc (200 mL) 10 min later. The organic phase was washed with water ×2, dried, and concentrated in vacuo. The residue was subjected to flash column chromatography with 0 to 5% MeOH in DCM to give (R)-tert-butyl 1-(6-carbamoyl-5-(4-(morpholine-4-carbonyl)phenylamino)pyridin-3-yl)piperidin-3-ylcarbamate (97) (yield >90%). (R)-tert-butyl 1-(6-carbamoyl-5-(4-(morpholine-4-carbonyl)phenylamino)pyridin-3-yl)piperidin-3-ylcarbamate (97) was treated with 4N HCl in dioxane (30 mL) for 30 min. The mixture was concentrated in vacuo to dryness to afford (R)-5-(3-aminopiperidin-1-yl)-3-(4-(morpholine-4-carbonyl) phenylamino)picolinamide, HCl salt (98).

To a solution of (R)-5-(3-aminopiperidin-1-yl)-3-(4-(morpholine-4-carbonyl)phenylamino)picolinamide, HCl salt (98) (99 mg, 0.50 mmol) in DMF (4 mL) was added DIEA (230 μL, 1.32 mmol) and then 4-tert-butylbenzoyl chloride (106 mg, 0.54 mmol). The mixture was stirred at RT for 10 min, diluted with 100 mL EtOAc, washed with water ×2, dried, and concentrated in vacuo. The residue was subjected to flash column chromatography with 0 to 5% MeOH in DCM to isolate the title compound (99). MS found for C$_{33}$H$_{40}$N$_6$O$_4$ as (M+H)$^+$ 585.2, (M−H)$^-$ 583.3. UV: λ=263, 310 nm.

Example 77

Synthesis of (R)-5-(3-(4-tert-butylbenzamido)piperidin-1-yl)-3-(3-methylisothiazol-5-ylamino)picolinamide (100)

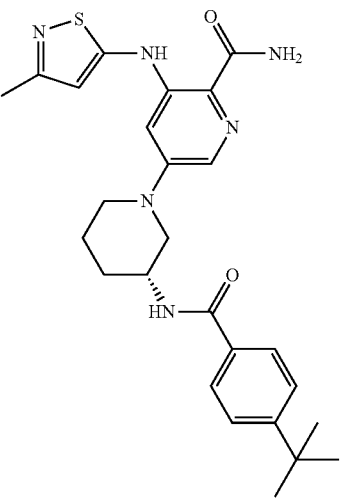

100

In a similar manner as described in Example 76, (R)-5-(3-(4-tert-butylbenzamido)piperidin-1-yl)-3-(3-methylisothiazol-5-ylamino)picolinamide (100) was prepared using 3-methylisothiazol-5-amine. MS found for C$_{26}$H$_{32}$N$_6$O$_2$S as (M+H)$^+$ 493.1, (M−H)$^-$ 491.3. UV: λ=307 nm.

Example 78

Synthesis of ((R)-5-(4-(morpholine-4-carbonyl)phenylamino)-3-(3-(3-phenylureido)piperidin-1-yl)-1,2,4-triazine-6-carboxamide (101)

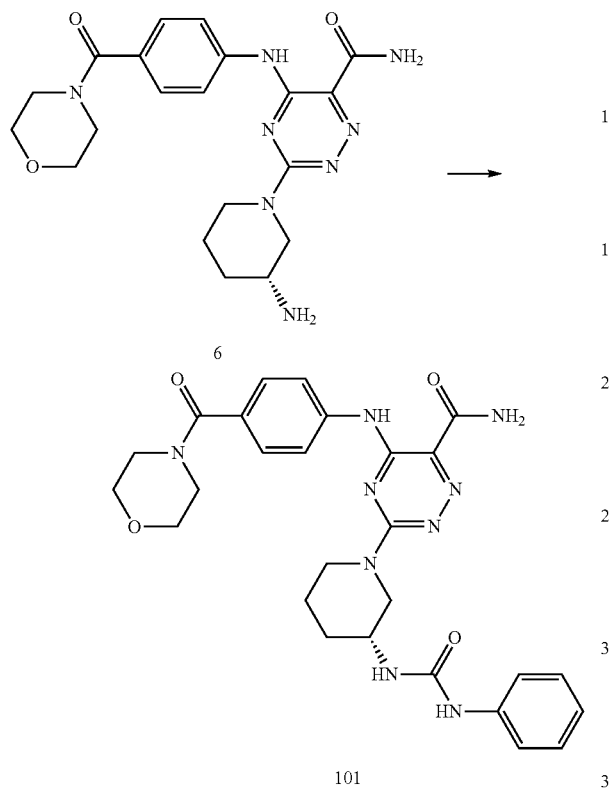

To a solution of 6 (50 mg, 0.11 mmol) in NMP (3 mL) were added DIEA (96 µL, 0.55 mmol) and then phenyl isocyanate (26 mg, 0.22 mmol), The mixture was stirred at RT for 50 m and treated with TFA (0.2 mL). The mixture was subjected to reverse phase preparative HPLC to isolate the title compound (101) (36 mg) as HCl salt. MS found for $C_{27}H_{31}N_9O_4$ as (M+H)$^+$ 546.2, (M−H)$^−$ 544.3. UV: λ=240, 257, 276 nm.

Example 79

Synthesis of (R)-3-(3-(3-(4-tert-butylphenyl)ureido)piperidin-1-yl)-5-(4-(morpholine-4-carbonyl)phenylamino)-1,2,4-triazine-6-carboxamide (102)

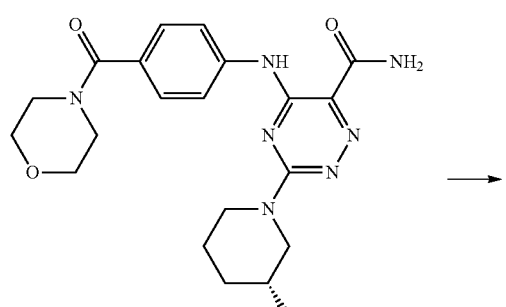

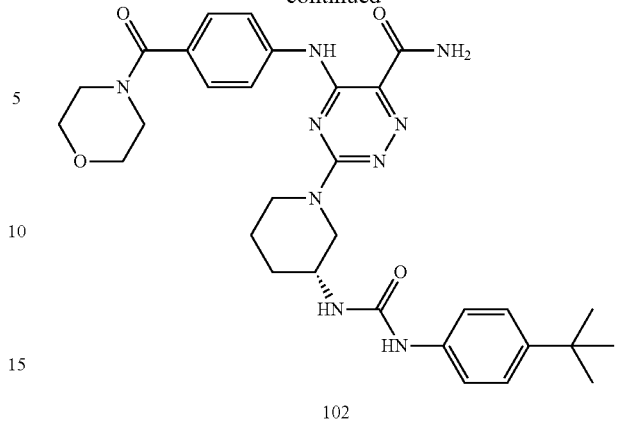

To a solution of 6 (50 mg, 0.11 mmol) in NMP (3 mL) were added DIEA (96 µL, 0.55 mmol) and then 4-tert-butylphenyl isocyanate (39 mg, 0.22 mmol), The mixture was stirred at RT for 1 h and treated with TFA (0.2 mL). The mixture was subjected to reverse phase preparative HPLC to isolate the title compound (102) (73 mg) as HCl salt. MS found for $C_{31}H_{39}N_9O_4$ as (M+H)$^+$ 602.2, (M−H)$^−$ 600.4. UV: λ=243, 260, 278 nm.

Example 80

Synthesis of (R)-3-(3-(3-(4-methoxyphenyl)ureido)piperidin-1-yl)-5-(4-(morpholine-4-carbonyl)phenylamino)-1,2,4-triazine-6-carboxamide (103)

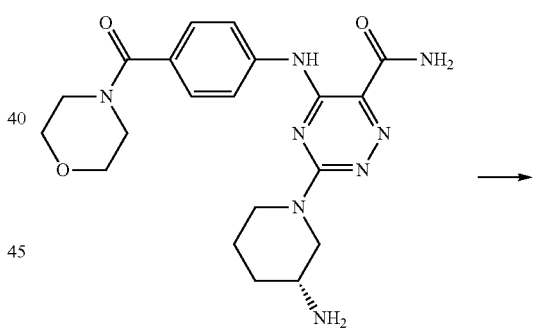

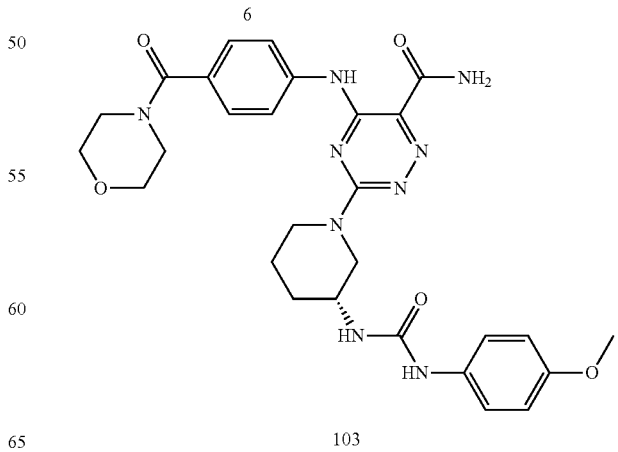

To a solution of 6 (50 mg, 0.11 mmol) in NMP (3 mL) were added DIEA (96 μL, 0.55 mmol) and then 4-methoxyphenyl isocyanate (33 mg, 0.22 mmol), The mixture was stirred at RT for 1 h and treated with TFA (0.2 mL). The mixture was subjected to reverse phase preparative HPLC to isolate the title compound (103) (75 mg) as HCl salt. MS found for $C_{28}H_{33}N_9O_5$ as $(M+H)^+$ 576.2, $(M-H)^-$ 574.2. UV: $\lambda$=244, 262, 279 nm.

Example 81

Synthesis of (R)-3-(3-(3,3-dimethylureido)piperidin-1-yl)-5-(4-(morpholine-4-carbonyl)phenylamino)-1,2,4-triazine-6-carboxamide (104)

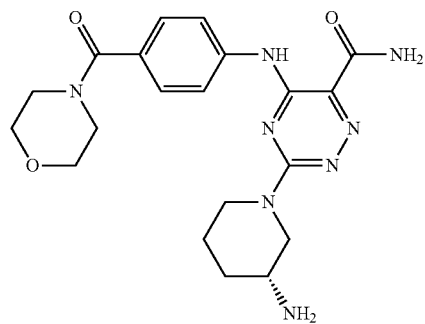

In a similar manner as described in Example 4, (R)-3-(3-(3,3-dimethylureido)piperidin-1-yl)-5-(4-(morpholine-4-carbonyl)phenylamino)-1,2,4-triazine-6-carboxamide (104) was prepared using dimethylcarbamic chloride. MS found for $C_{23}H_{31}N_9O_4$ as $(M+H)^+$ 498.2, $(M-H)^-$ 496.3. UV: $\lambda$=273 nm.

Example 82

Synthesis of (R)-3-(3-(4-isopropylpiperidine-1-carboxamido)piperidin-1-yl)-5-(4-(morpholine-4-carbonyl)phenylamino)-1,2,4-triazine-6-carboxamide (105)

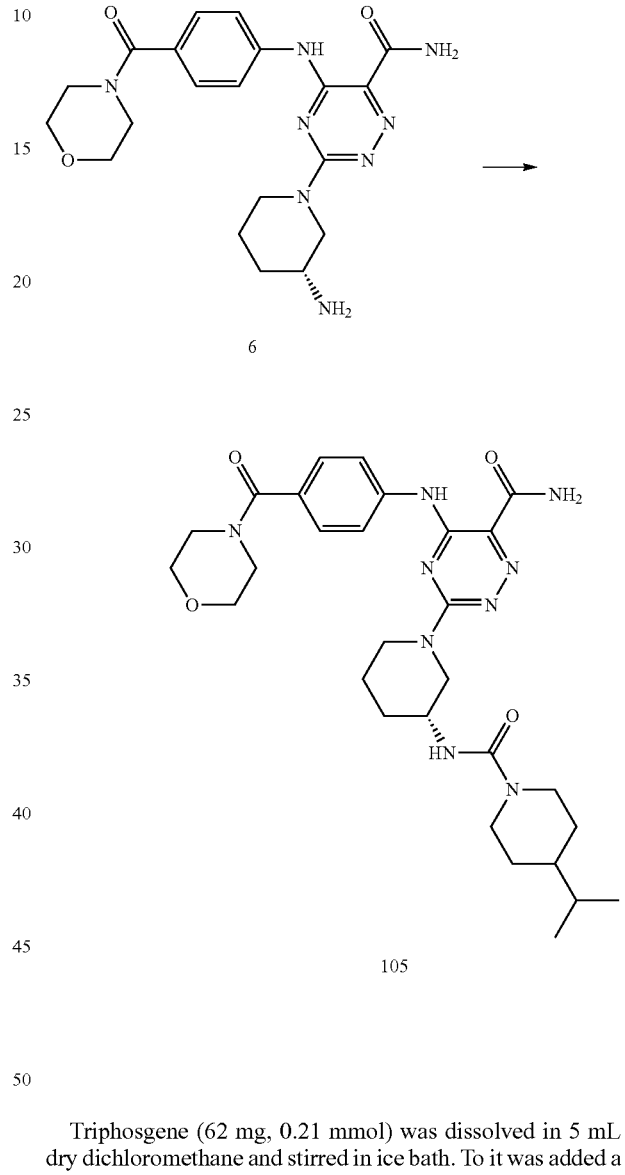

Triphosgene (62 mg, 0.21 mmol) was dissolved in 5 mL dry dichloromethane and stirred in ice bath. To it was added a solution of 4-isopropylpiperidine (81 μL, 0.55 mmol) in 5 mL dichloromethane with DIEA (190 μL, 1.1 mmol) in dropwise manner. The mixture was stirred for overnight. It was diluted with 50 mL EtOAc, filtered through a short silica plug. The plug was rinsed with EtOAc three times. The filtrate was concentrated in vacuo to dryness.

To a solution of 6 HCl salt (50 mg, 0.11 mmol) in NMP (4 mL) was added DIEA (191 μL, 1.1 mmol) and then the crude 4-isopropylpiperidinecarbonyl chloride as prepared above. The mixture was stirred at RT for 2.5 h, quenched with TFA (0.3 mL) and subjected to reverse phase prep HPLC to isolate the title compound (105) (33 mg) as HCl salt. MS found for $C_{29}H_{41}N_9O_4$ as $(M+H)^+$ 580.3, $(M-H)^-$ 578.3. UV: $\lambda$=278 nm.

Example 83

Synthesis of (R)-5-(4-(morpholine-4-carbonyl)phenylamino)-3-(3-(2-oxo-2-(piperidin-1-yl)acetamido)piperidin-1-yl)-1,2,4-triazine-6-carboxamide (106)

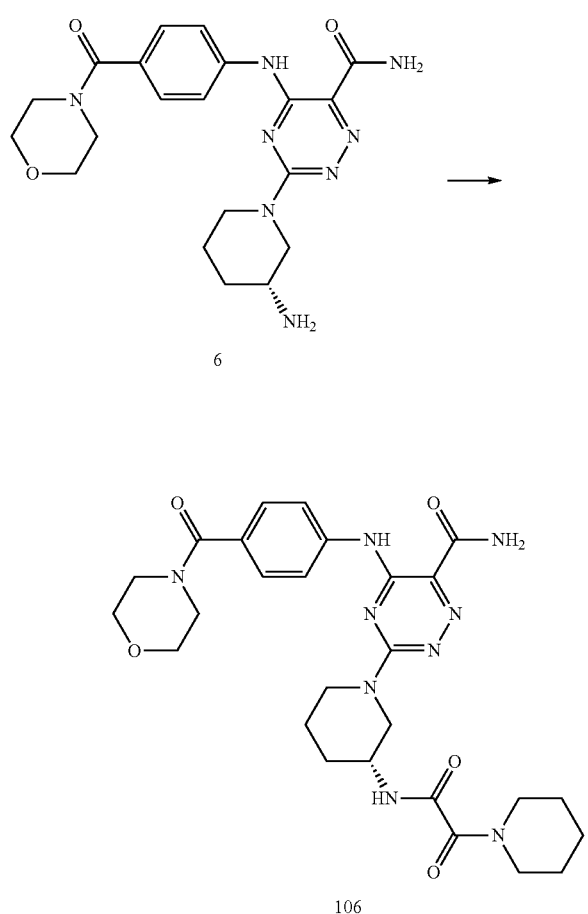

To a solution of 6 HCl salt (60 mg, 0.13 mmol) in NMP (3 mL) was added DIEA (180 μL, 1.04 mmol) and then ethyl chloroglyoxylate (43 μL, 0.39 mmol). The mixture was stirred at RT for 30 m, diluted with EtOAc, washed with sat ammonium chloride aq solution and water, concentrated in vacuo to dryness. It was dissolved in 20 mL THF, To it were added 2 mL water and lithium hydroxide hydrate (100 mg, 2.38 mmol). The mixture was stirred for 2 h, acidified, concentrated in vacuo and subjected to reverse phase prep HPLC to isolate (R)-2-(1-(6-carbamoyl-5-(4-(morpholine-4-carbonyl)phenylamino)-1,2,4-triazin-3-yl)piperidin-3-ylamino)-2-oxoacetic acid as HCl salt. It was dissolved in 3 mL DMF. To it were added piperidine (130 μL, 1.30 mmol) and then PyBOP (200 mg, 0.39 mmol). The mixture was stirred at RT for 3.5 h, quenched with TFA (0.3 mL) and subjected to reverse phase prep HPLC to isolate the title compound (106) (16 mg) as HCl salt. MS found for $C_{27}H_{35}N_9O_5$ as $(M+H)^+$ 566.3, $(M-H)^-$ 564.3. UV: λ=276 nm.

Example 84

Synthesis of (R)—N-(1-(6-carbamoyl-5-(4-(morpholine-4-carbonyl)phenylamino)-1,2,4-triazin-3-yl)piperidin-3-yl)quinoline-2-carboxamide (107)

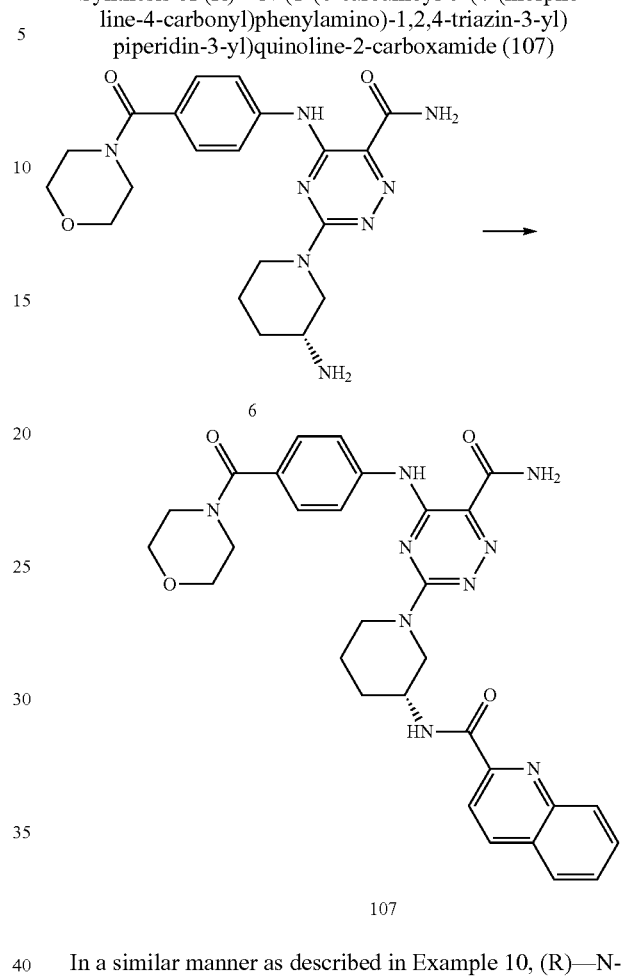

In a similar manner as described in Example 10, (R)—N-(1-(6-carbamoyl-5-(4-(morpholine-4-carbonyl)phenylamino)-1,2,4-triazin-3-yl)piperidin-3-yl)quinoline-2-carboxamide (107) was prepared using quinaldic acid. MS found $C_{30}H_{31}N_9O_4$ as $(M+H)^+$ 582.2, $(M-H)^-$ 580.3. UV: λ=238, 255, 279 nm.

Example 85

Synthesis of (R)—N-(1-(6-carbamoyl-5-(4-(morpholine-4-carbonyl)phenylamino)-1,2,4-triazin-3-yl)piperidin-3-yl)quinoline-6-carboxamide (108)

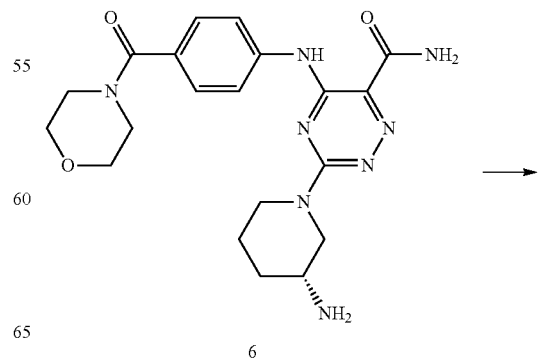

-continued

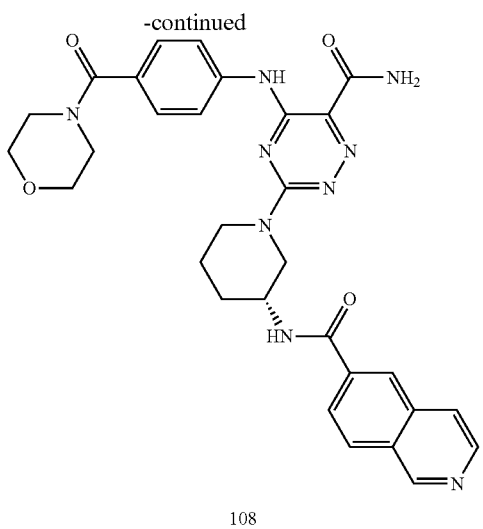

108

In a similar manner as described in Example 10, (R)—N-(1-(6-carbamoyl-5-(4-(morpholine-4-carbonyl)phenylamino)-1,2,4-triazin-3-yl)piperidin-3-yl)quinoline-6-carboxamide (108) was prepared using quinolin-6-carboxylic acid. MS found $C_{30}H_{31}N_9O_4$ as $(M+H)^+$ 582.2, $(M-H)^-$ 580.3. UV: $\lambda$=237, 255, 275 nm.

Example 86

Synthesis of (R)-5-(4-(morpholine-4-carbonyl)phenylamino)-3-(3-(4-(2,2,2-trifluoroethoxy)benzamido)piperidin-1-yl)-1,2,4-triazine-6-carboxamide (109)

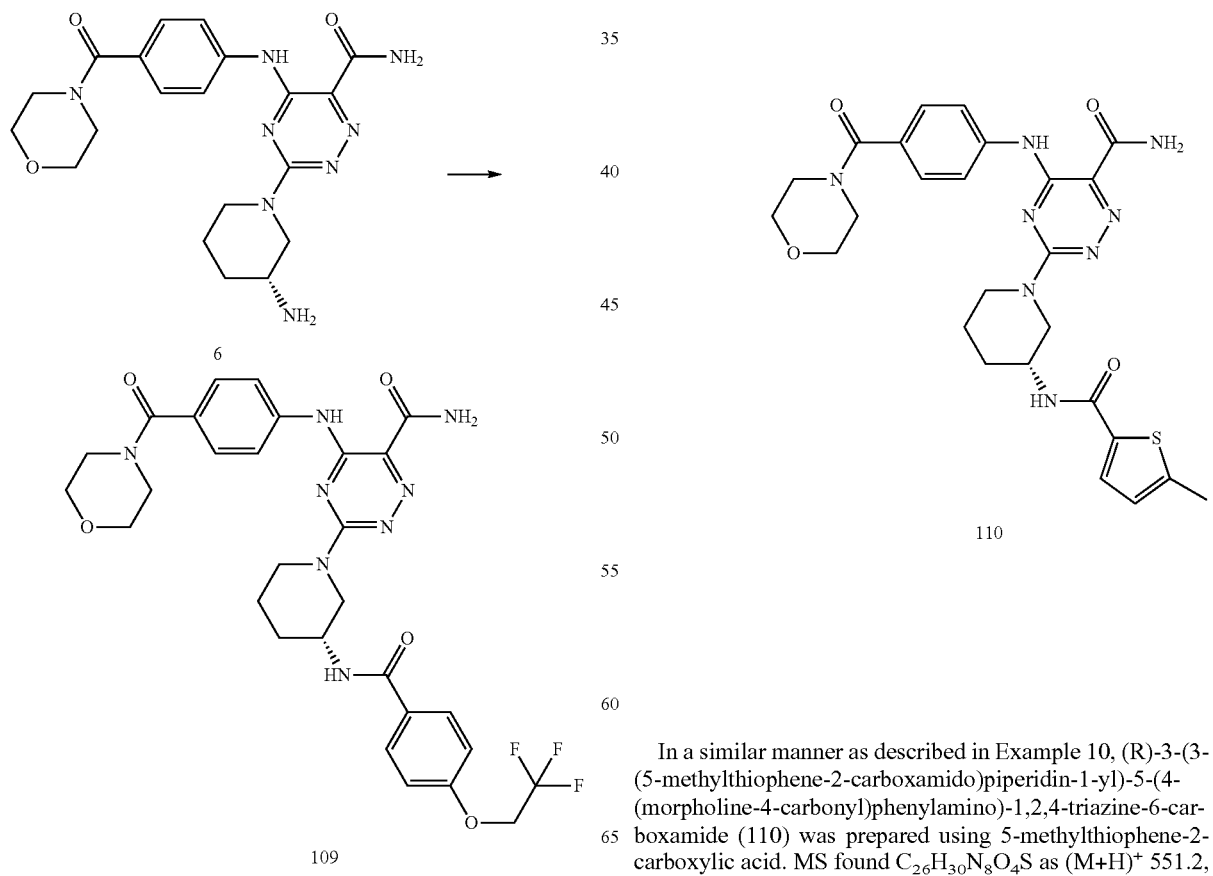

In a similar manner as described in Example 10, (R)-5-(4-(morpholine-4-carbonyl)phenylamino)-3-(3-(4-(2,2,2-trifluoroethoxy)benzamido)piperidin-1-yl)-1,2,4-triazine-6-carboxamide (109) was prepared using 4-(2,2,2-trifluoroethoxy)benzoic acid. MS found $C_{29}H_{31}F_3N_8O_5$ as $(M+H)^+$ 629.2, $(M-H)^-$ 627.3. UV: $\lambda$=270 nm.

Example 87

Synthesis of (R)-3-(3-(5-methylthiophene-2-carboxamido)piperidin-1-yl)-5-(4-(morpholine-4-carbonyl)phenylamino)-1,2,4-triazine-6-carboxamide (110)

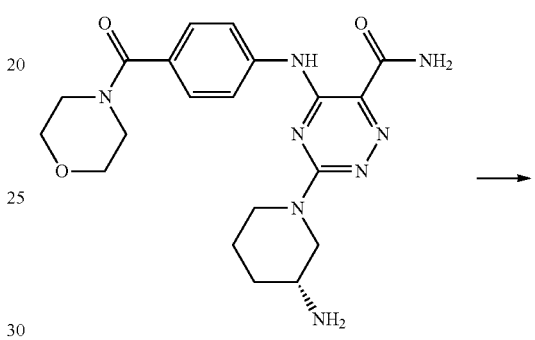

In a similar manner as described in Example 10, (R)-3-(3-(5-methylthiophene-2-carboxamido)piperidin-1-yl)-5-(4-(morpholine-4-carbonyl)phenylamino)-1,2,4-triazine-6-carboxamide (110) was prepared using 5-methylthiophene-2-carboxylic acid. MS found $C_{26}H_{30}N_8O_4S$ as $(M+H)^+$ 551.2, $(M-H)^-$ 549.2. UV: $\lambda$=278 nm.

Example 88

Synthesis of (R)-3-(3-(4-ethoxybenzamido)piperidin-1-yl)-5-(4-(morpholine-4-carbonyl)phenylamino)-1,2,4-triazine-6-carboxamide (111)

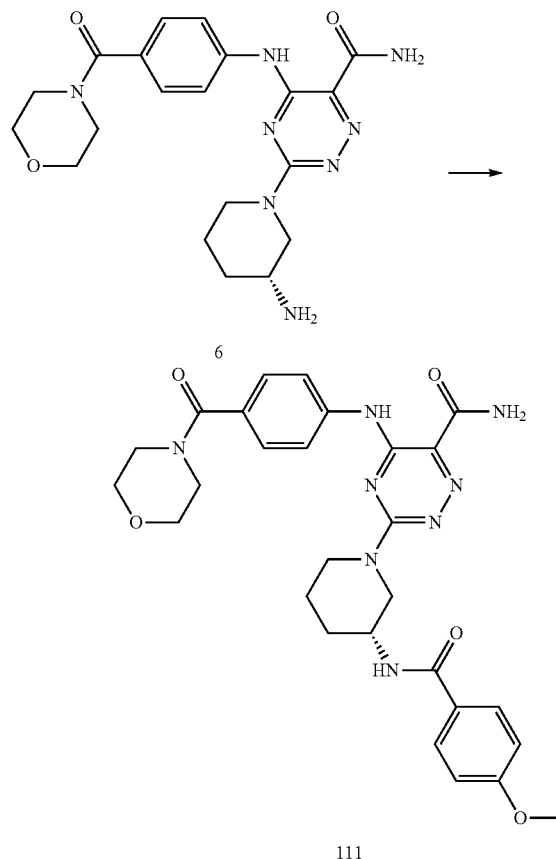

111

In a similar manner as described in Example 10, (R)-3-(3-(4-ethoxybenzamido)piperidin-1-yl)-5-(4-(morpholine-4-carbonyl)phenylamino)-1,2,4-triazine-6-carboxamide (111) was prepared using 4-ethoxybenzoic acid. MS found $C_{29}H_{34}N_8O_5$ as $(M+H)^+$ 575.2, $(M-H)^-$ 573.3. UV: $\lambda$=262 nm.

Example 89

Synthesis of (R)-5-(4-(morpholine-4-carbonyl)phenylamino)-3-(3-(4-propoxybenzamido)piperidin-1-yl)-1,2,4-triazine-6-carboxamide (112)

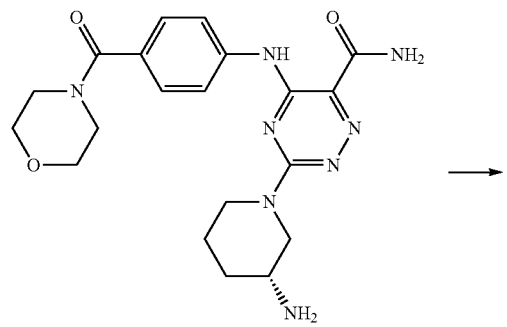

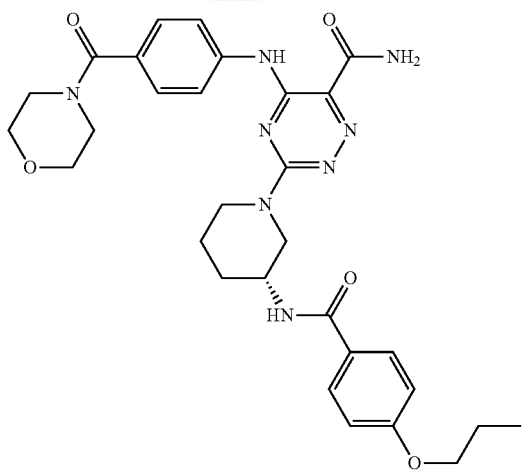

112

In a similar manner as described in Example 10, (R)-5-(4-(morpholine-4-carbonyl)phenylamino)-3-(3-(4-propoxybenzamido)piperidin-1-yl)-1,2,4-triazine-6-carboxamide (112) was prepared using 4-propoxybenzoic acid. MS found $C_{30}H_{36}N_8O_5$ as $(M+H)^+$ 589.2, $(M-H)^-$ 587.3. UV: $\lambda$=263 nm.

Example 90

Synthesis of (R)-5-(4-(morpholine-4-carbonyl)phenylamino)-3-(3-(4-isopropoxybenzamido)piperidin-1-yl)-1,2,4-triazine-6-carboxamide (113)

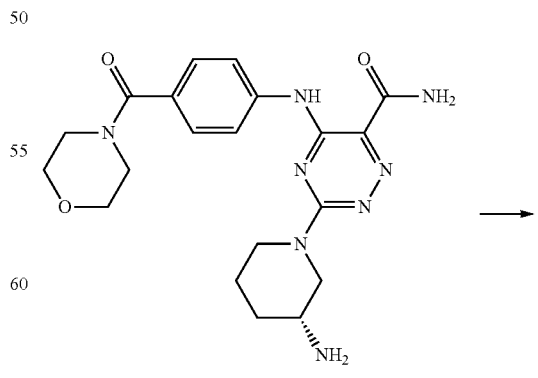

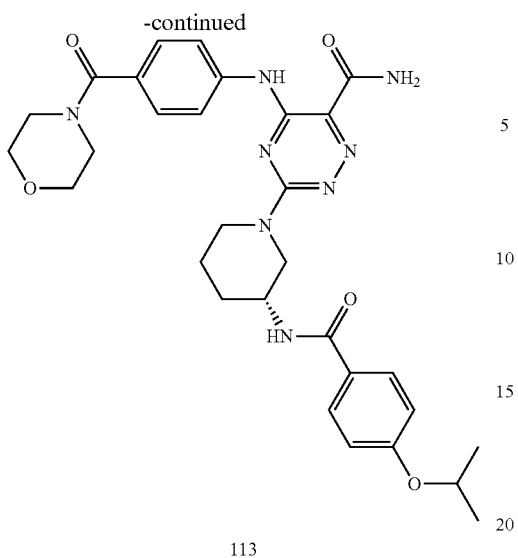

113

In a similar manner as described in Example 10, (R)-3-(3-(4-isopropoxybenzamido)piperidin-1-yl)-5-(4-(morpholine-4-carbonyl)phenylamino)-1,2,4-triazine-6-carboxamide (113) was prepared using 4-isopropoxybenzoic acid. MS found $C_{30}H_{36}N_8O_5$ as $(M+H)^+$ 589.2, $(M-H)^-$ 587.3. UV: $\lambda=263$ nm.

Example 91

Synthesis of (R)—N-(1-(6-carbamoyl-5-(4-(morpholine-4-carbonyl)phenylamino)-1,2,4-triazin-3-yl)piperidin-3-yl)-5-methylisoxazole-3-carboxamide (114)

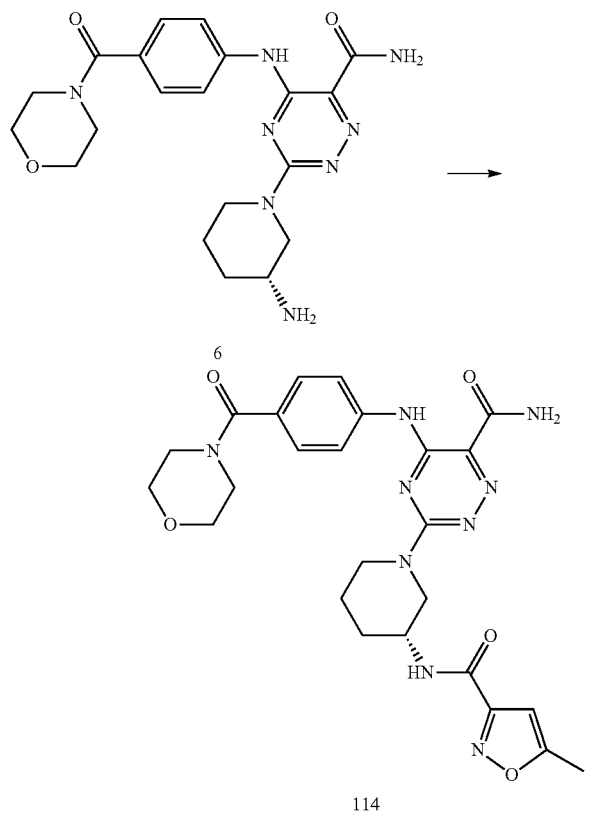

114

In a similar manner as described in Example 10, (R)—N-(1-(6-carbamoyl-5-(4-(morpholine-4-carbonyl)phenylamino)-1,2,4-triazin-3-yl)piperidin-3-yl)-5-methylisoxazole-3-carboxamide (114) was prepared using 5-methylisoxazole-3-carboxylic acid. MS found $C_{25}H_{29}N_9O_5$ as $(M+H)^+$ 536.1, $(M-H)^-$ 534.3. UV: $\lambda=275$ nm.

Example 92

Synthesis of (R)—N-(1-(6-carbamoyl-5-(4-(morpholine-4-carbonyl)phenylamino)-1,2,4-triazin-3-yl)piperidin-3-yl)-5-methylthiazole-2-carboxamide (115)

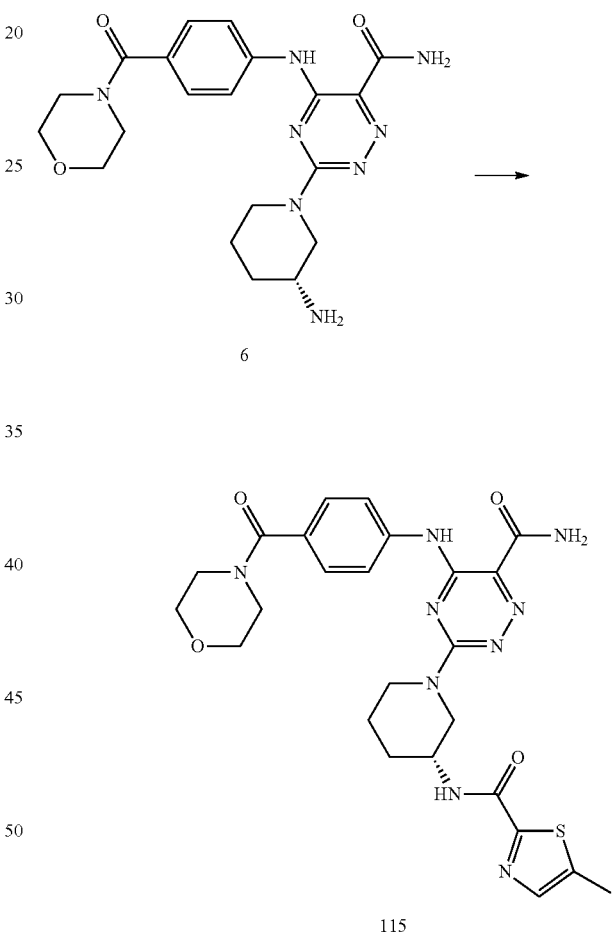

115

In a similar manner as described in Example 10, (R)—N-(1-(6-carbamoyl-5-(4-(morpholine-4-carbonyl)phenylamino)-1,2,4-triazin-3-yl)piperidin-3-yl)-5-methylthiazole-2-carboxamide (115) was prepared using 5-methylthiazole-2-carboxylic acid. MS found $C_{25}H_{29}N_9O_4S$ as $(M+H)^+$ 552.1, $(M-H)^-$ 550.2. UV: $\lambda=282$ nm.

Example 93

Synthesis of (R)—N-(1-(6-carbamoyl-5-(4-(morpholine-4-carbonyl)phenylamino)-1,2,4-triazin-3-yl)piperidin-3-yl)-2-methylthiazole-5-carboxamide (116)

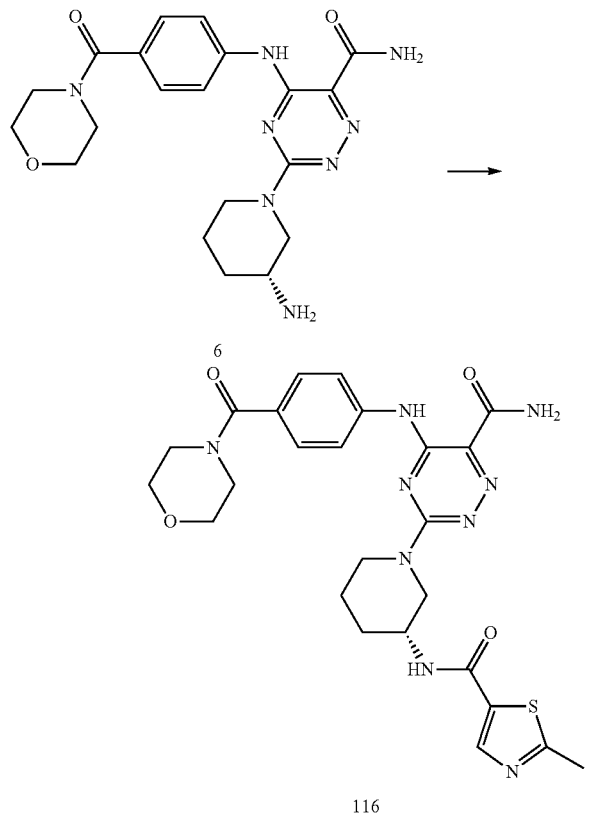

In a similar manner as described in Example 10, (R)—N-(1-(6-carbamoyl-5-(4-(morpholine-4-carbonyl)phenylamino)-1,2,4-triazin-3-yl)piperidin-3-yl)-2-methylthiazole-5-carboxamide (116) was prepared using 2-methylthiazole-5-carboxylic acid. MS found $C_{25}H_{29}N_9O_4S$ as $(M+H)^+$ 552.1, $(M-H)^-$ 550.2. UV: λ=265 nm.

Example 94

Synthesis of (R)—N-(1-(6-carbamoyl-5-(4-(morpholine-4-carbonyl)phenylamino)-1,2,4-triazin-3-yl)piperidin-3-yl)benzo[d]thiazole-2-carboxamide (117)

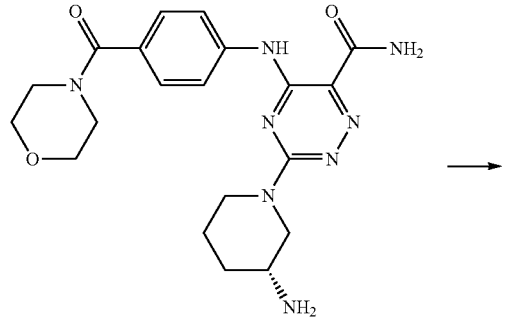

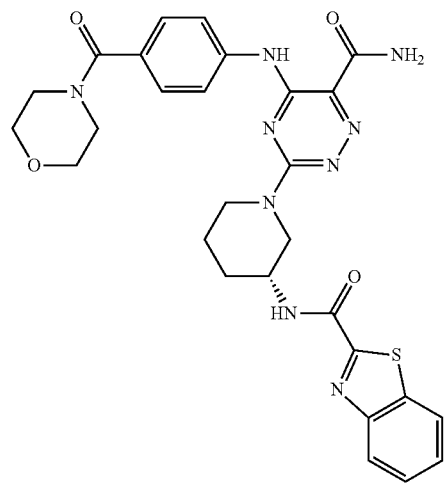

In a similar manner as described in Example 10, (R)—N-(1-(6-carbamoyl-5-(4-(morpholine-4-carbonyl)phenylamino)-1,2,4-triazin-3-yl)piperidin-3-yl)benzo[d]thiazole-2-carboxamide (117) was prepared using benzo[d]thiazole-2-carboxylic acid. MS found $C_{28}H_{29}N_9O_4S$ as $(M+H)^+$ 588.1, $(M-H)^-$ 586.2. UV: λ=243, 251, 282 nm.

Example 95

Synthesis of (R)—N-(1-(6-carbamoyl-5-(4-(morpholine-4-carbonyl)phenylamino)-1,2,4-triazin-3-yl)piperidin-3-yl)-5-cyclopropylisoxazole-3-carboxamide (118)

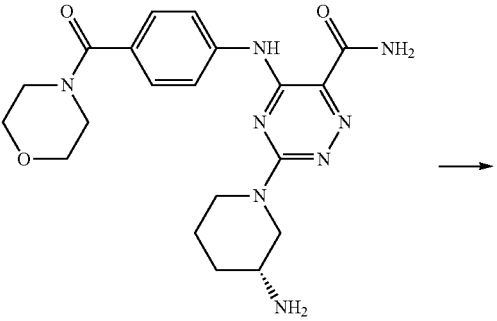

-continued

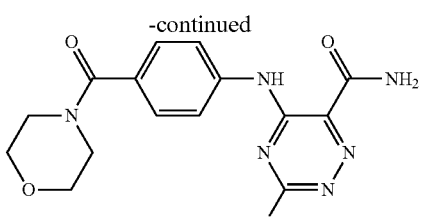

118

In a similar manner as described in Example 10, (R)—N-(1-(6-carbamoyl-5-(4-(morpholine-4-carbonyl)phenylamino)-1,2,4-triazin-3-yl)piperidin-3-yl)-5-cyclopropylisoxazole-3-carboxamide (118) was prepared using 5-cyclopropylisoxazole-3-carboxylic acid. MS found $C_{27}H_{31}N_9O_5$ as $(M+H)^+$ 562.2, $(M-H)^-$ 560.3. UV: λ=273 nm.

Example 96

Synthesis of (R)-5-(4-(morpholine-4-carbonyl)phenylamino)-3-(3-(4-phenoxybenzamido)piperidin-1-yl)-1,2,4-triazine-6-carboxamide (119)

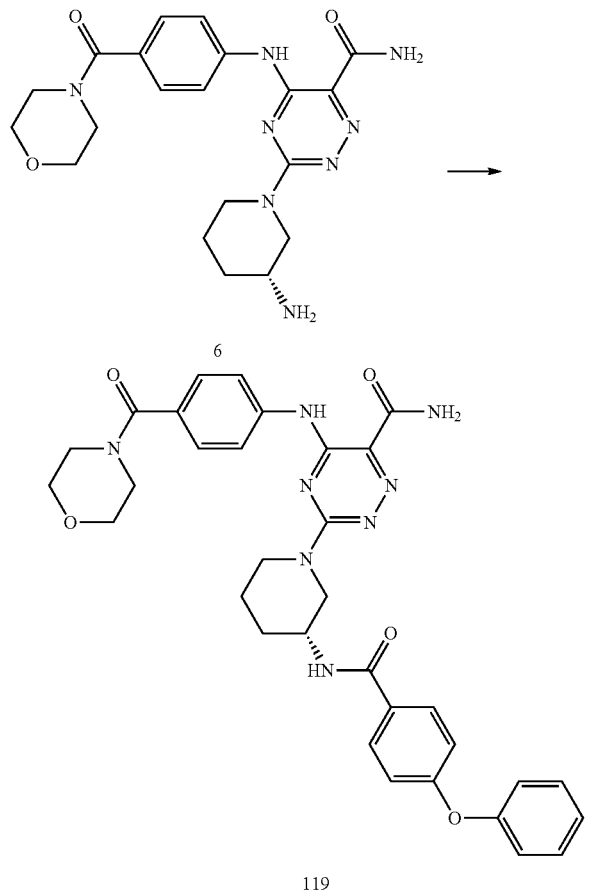

119

In a similar manner as described in Example 10, (R)-5-(4-(morpholine-4-carbonyl)phenylamino)-3-(3-(4-phenoxybenzamido)piperidin-1-yl)-1,2,4-triazine-6-carboxamide (119) was prepared using 4-phenoxybenzoic acid. MS found $C_{33}H_{34}N_8O_5$ as $(M+H)^+$ 623.2, $(M-H)^-$ 621.3. UV: λ=265 nm.

Example 97

Synthesis of (R)—N-(1-(6-carbamoyl-5-(4-(morpholine-4-carbonyl)phenylamino)-1,2,4-triazin-3-yl)piperidin-3-yl)benzo[d]oxazole-2-carboxamide (120)

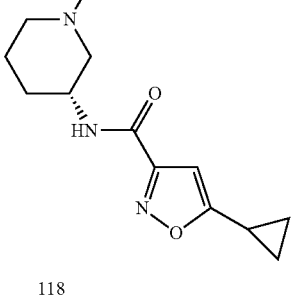

6

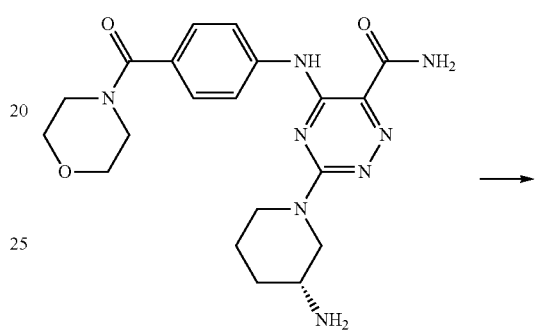

120

In a similar manner as described in Example 10, (R)—N-(1-(6-carbamoyl-5-(4-(morpholine-4-carbonyl)phenylamino)-1,2,4-triazin-3-yl)piperidin-3-yl)benzo[d]oxazole-2-carboxamide (120) was prepared using benzo[d]oxazole-2-carboxylic acid. MS found $C_{28}H_{29}N_9O_5$ as $(M+H)^+$ 572.1, $(M-H)^-$ 570.3. UV: λ=279 nm.

Example 98

Synthesis of (R)—N-(1-(6-carbamoyl-5-(4-(morpholine-4-carbonyl)phenylamino)-1,2,4-triazin-3-yl)piperidin-3-yl)-4-methylthiazole-2-carboxamide (121)

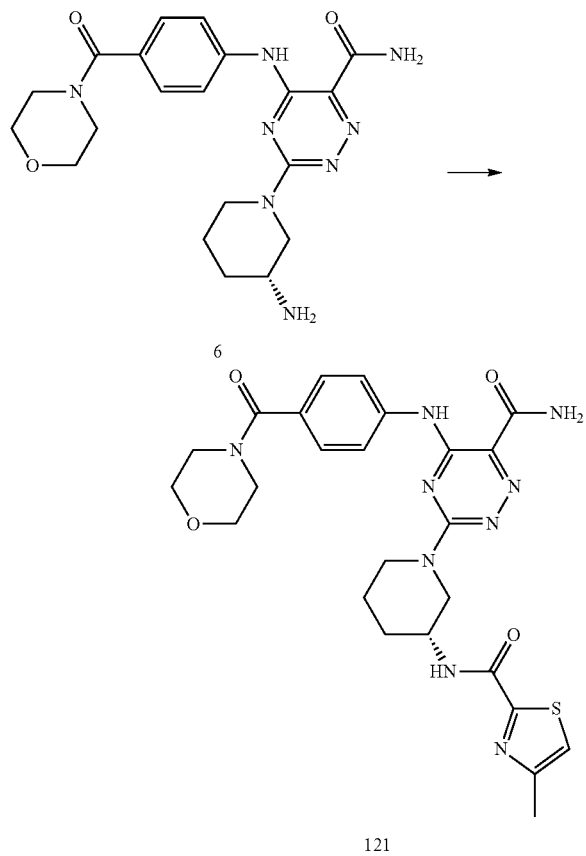

In a similar manner as described in Example 10, (R)—N-(1-(6-carbamoyl-5-(4-(morpholine-4-carbonyl)phenylamino)-1,2,4-triazin-3-yl)piperidin-3-yl)-4-methylthiazole-2-carboxamide (121) was prepared using 4-methylthiazole-2-carboxylic acid. MS found $C_{25}H_{29}N_9O_4S$ as $(M+H)^+$ 552.1, $(M-H)^-$ 550.2. UV: $\lambda$=281 nm.

Example 99

Synthesis of (R)-3-(3-(3,3-diethylureido)piperidin-1-yl)-5-(4-(morpholine-4-carbonyl)phenylamino)-1,2,4-triazine-6-carboxamide (122)

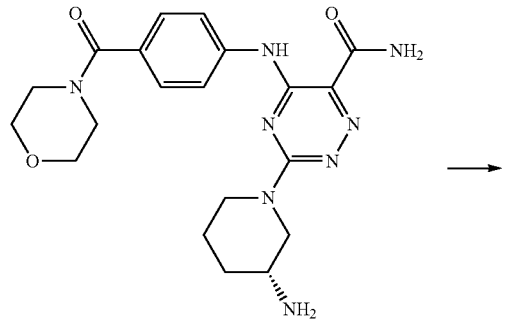

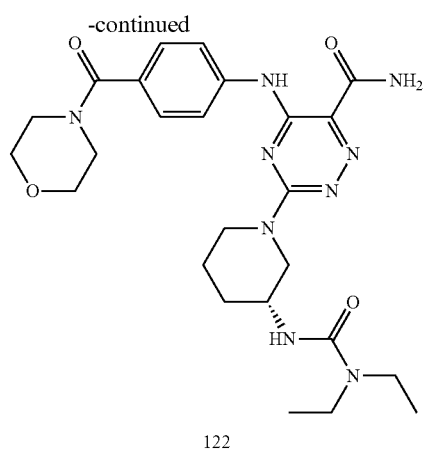

In a similar manner as described in Example 4, (R)-3-(3-(3,3-diethylureido)piperidin-1-yl)-5-(4-(morpholine-4-carbonyl)phenylamino)-1,2,4-triazine-6-carboxamide (122) was prepared using diethylcarbamic chloride. MS found for $C_{25}H_{35}N_9O_4$ as $(M+H)^+$ 526.2, $(M-H)^-$ 524.3. UV: $\lambda$=276 nm.

Example 100

Synthesis of (R)—N-(1-(6-carbamoyl-5-(4-(morpholine-4-carbonyl)phenylamino)-1,2,4-triazin-3-yl)piperidin-3-yl)-1-ethyl-1H-benzo[d][1,2,3]triazole-5-carboxamide (123)

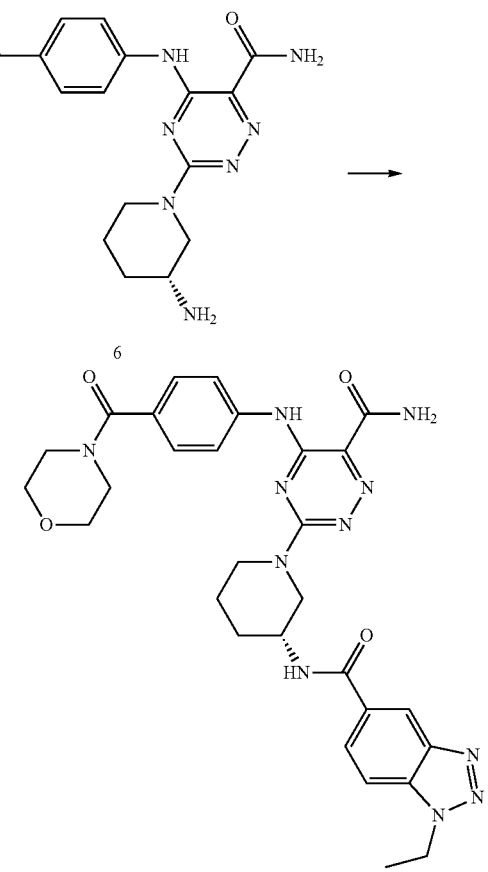

In a similar manner as described in Example 10, (R)—N-(1-(6-carbamoyl-5-(4-(morpholine-4-carbonyl)phenylamino)-1,2,4-triazin-3-yl)piperidin-3-yl)-1-ethyl-1H-benzo[d][1,2,3]triazole-5-carboxamide (123) was prepared using 1-ethyl-1H-benzo[d][1,2,3]triazole-5-carboxylic acid. MS found $C_{29}H_{33}N_{11}O_4$ as $(M+H)^+$ 600.2, $(M-H)^-$ 598.3. UV: $\lambda=276$ nm.

Example 101

Synthesis of (R)—N-(1-(6-carbamoyl-5-(4-(morpholine-4-carbonyl)phenylamino)-1,2,4-triazin-3-yl)piperidin-3-yl)-1-isopropyl-1H-benzo[d][1,2,3]triazole-5-carboxamide (124)

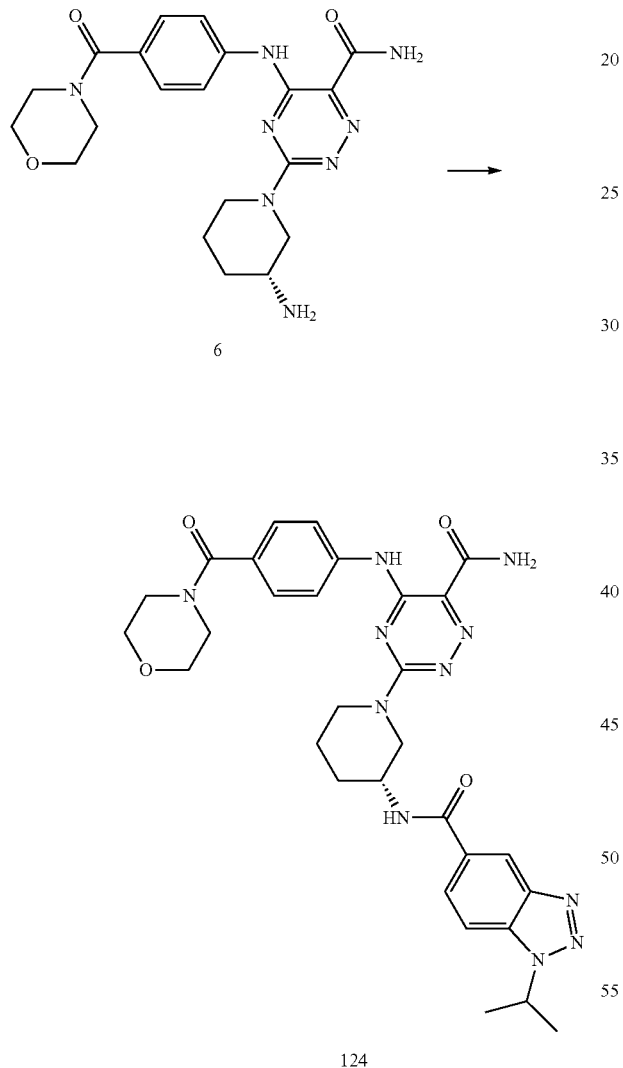

124

In a similar manner as described in Example 10, (R)—N-(1-(6-carbamoyl-5-(4-(morpholine-4-carbonyl)phenylamino)-1,2,4-triazin-3-yl)piperidin-3-yl)-1-isopropyl-1H-benzo[d][1,2,3]triazole-5-carboxamide (124) was prepared using 1-isopropyl-1H-benzo[d][1,2,3]triazole-5-carboxylic acid. MS found $C_{30}H_{35}N_{11}O_4$ as $(M+H)^+$ 614.2, $(M-H)^-$ 612.3. UV: $\lambda=276$ nm.

Example 102

Synthesis of (R)—N-(1-(6-carbamoyl-5-(4-(morpholine-4-carbonyl)phenylamino)-1,2,4-triazin-3-yl)piperidin-3-yl)-1-cyclopropyl-1H-benzo[d][1,2,3]triazole-5-carboxamide (125)

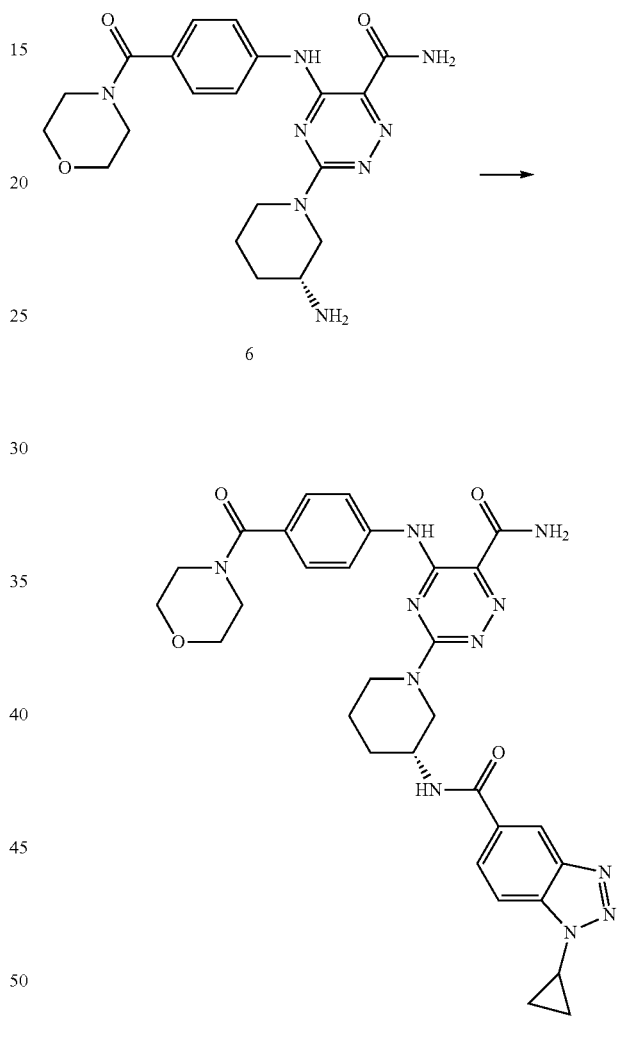

125

In a similar manner as described in Example 10, (R)—N-(1-(6-carbamoyl-5-(4-(morpholine-4-carbonyl)phenylamino)-1,2,4-triazin-3-yl)piperidin-3-yl)-1-cyclopropyl-1H-benzo[d][1,2,3]triazole-5-carboxamide (125) was prepared using 1-cyclopropyl-1H-benzo[d][1,2,3]triazole-5-carboxylic acid. MS found $C_{30}H_{33}N_{11}O_4$ as $(M+H)^+$ 612.2, $(M-H)^-$ 610.3. UV: $\lambda=276$ nm.

Example 103

Synthesis of (R)—N-(1-(6-carbamoyl-5-(4-(morpholine-4-carbonyl)phenylamino)-1,2,4-triazin-3-yl)piperidin-3-yl)-1-propyl-1H-benzo[d][1,2,3]triazole-5-carboxamide (126)

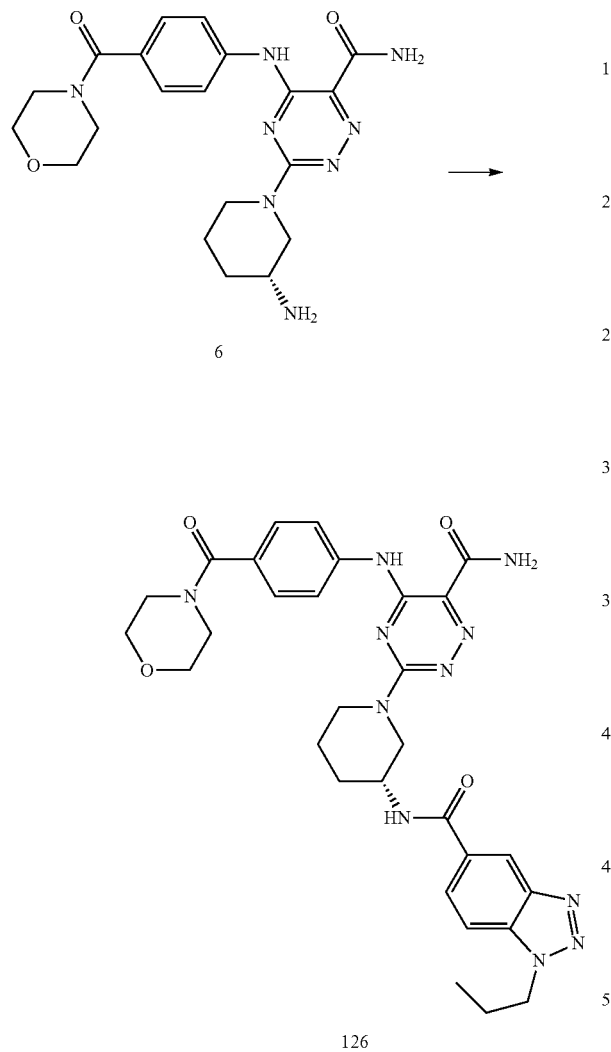

In a similar manner as described in Example 10, (R)—N-(1-(6-carbamoyl-5-(4-(morpholine-4-carbonyl)phenylamino)-1,2,4-triazin-3-yl)piperidin-3-yl)-1-propyl-1H-benzo[d][1,2,3]triazole-5-carboxamide (126) was prepared using 1-propyl-1H-benzo[d][1,2,3]triazole-5-carboxylic acid. MS found $C_{30}H_{35}N_{11}O_4$ as $(M+H)^+$ 614.2, $(M-H)^-$ 612.3. UV: λ=277 nm.

Example 104

Synthesis of (R)-5-(4-(morpholine-4-carbonyl)phenylamino)-3-(3-(1-oxoisoindolin-2-yl)piperidin-1-yl)-1,2,4-triazine-6-carboxamide (128)

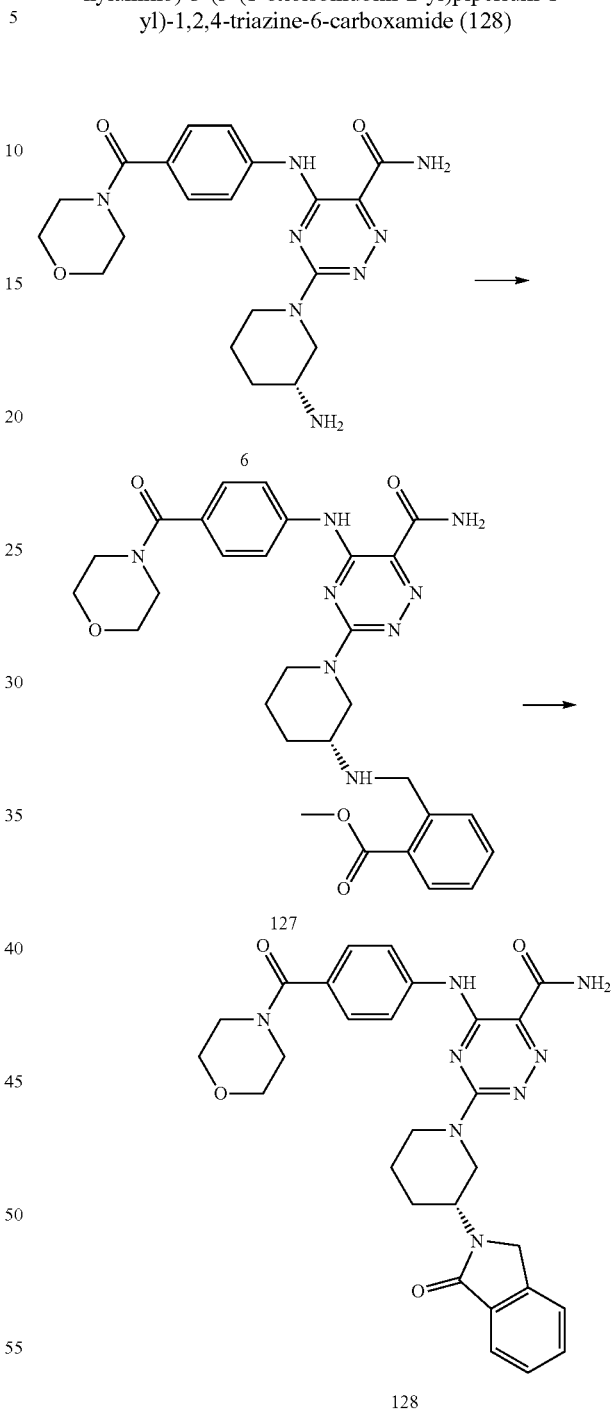

To a solution of 6 HCl salt (70 mg, 0.15 mmol) in NMP (3 mL) was added DIEA (210 μL, 1.2 mmol) and then methyl 2-bromomethylbenzoate (103 mg, 0.45 mmol). The mixture was stirred at RT for 3 h, diluted with EtOAc, washed with brine twice, dried, concentrated in vacuo and subjected to flash column with 0-15% MeOH in dichloromethane to isolate compound 127. It was dissolved in 3 mL NMP. To it was added DIEA (0.2 mL). The mixture was stirred at 80° C. for 2 h. It was acidified with TFA (0.3 mL) and directly subjected to reverse phase prep HPLC to isolate the title compound, (R)-5-(4-(morpholine-4-carbonyl)phenylamino)-3-(3-(1-oxoisoindolin-2-yl)piperidin-1-yl)-1,2,4-triazine-6-carboxamid (128) as HCl salt. MS found for $C_{28}H_{30}N_8O_4$ as $(M+H)^+$ 543.2, $(M-H)^-$ 541.3. UV: $\lambda$=272 nm.

Example 105

Synthesis of (R)-3-(1-but-2-ynoylpiperidin-3-ylamino)-5-(4-(methylsulfonyl)phenylamino)-1,2,4-triazine-6-carboxamide (129)

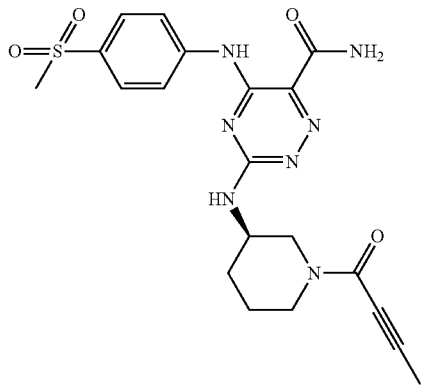

129

In a similar manner as described in Example 66, (R)-3-(1-but-2-ynoylpiperidin-3-ylamino)-5-(4-(methylsulfonyl)phenylamino)-1,2,4-triazine-6-carboxamide (129) was prepared using 4-methylsulfonylaniline and 2-butynoic acid. MS found for $C_{20}H_{23}N_7O_4S$ as $(M+H)^+$ 458.1, $(M-H)^-$ 456.1. UV: $\lambda$=256, 269, 293 nm.

Example 106

Synthesis of (R,E)-3-(1-(4-(dimethylamino)but-2-enoyl)piperidin-3-ylamino)-5-(4-(methylsulfonyl)phenylamino)-1,2,4-triazine-6-carboxamide (130)

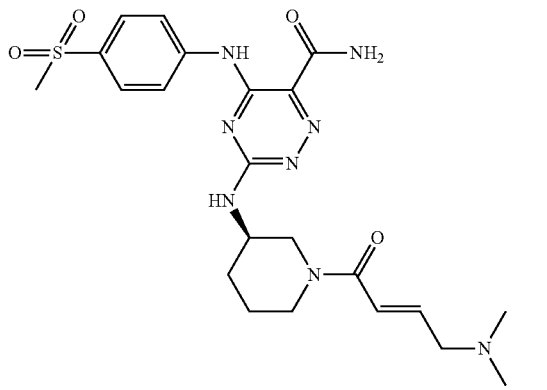

130

In a similar manner as described in Example 66, (R,E)-3-(1-(4-(dimethylamino)but-2-enoyl)piperidin-3-ylamino)-5-(4-(methylsulfonyl)phenylamino)-1,2,4-triazine-6-carboxamide (130) was prepared using 4-methylsulfonylaniline and (E)-4-(dimethylamino)but-2-enoic acid. MS found for $C_{22}H_{30}N_8O_4S$ as $(M+H)^+$ 503.1, $(M-H)^-$ 501.2. UV: $\lambda$=258, 272, 286 nm.

Example 107

Synthesis of (R,E)-3-(1-(4-(cyclopropyl(methyl)amino)but-2-enoyl)piperidin-3-ylamino)-5-(4-(methylsulfonyl)phenylamino)-1,2,4-triazine-6-carboxamide (131)

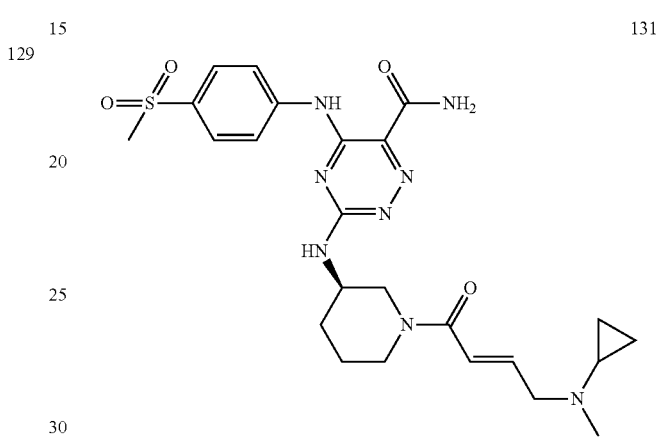

131

In a similar manner as described in Example 66, (R,E)-3-(1-(4-(cyclopropyl(methyl)amino)but-2-enoyl)piperidin-3-ylamino)-5-(4-(methylsulfonyl)phenylamino)-1,2,4-triazine-6-carboxamide (131) was prepared using 4-methylsulfonylaniline and (E)-4-(cyclopropyl(methyl)amino)but-2-enoic acid. MS found for $C_{24}H_{32}N_8O_4S$ as $(M+H)^+$ 529.1, $(M-H)^-$ 527.3. UV: $\lambda$=259, 270, 287 nm.

Example 108

Synthesis of (R)-3-(3-(piperidine-1-carboxamido)piperidin-1-yl)-5-(quinolin-3-ylamino)-1,2,4-triazine-6-carboxamide (132)

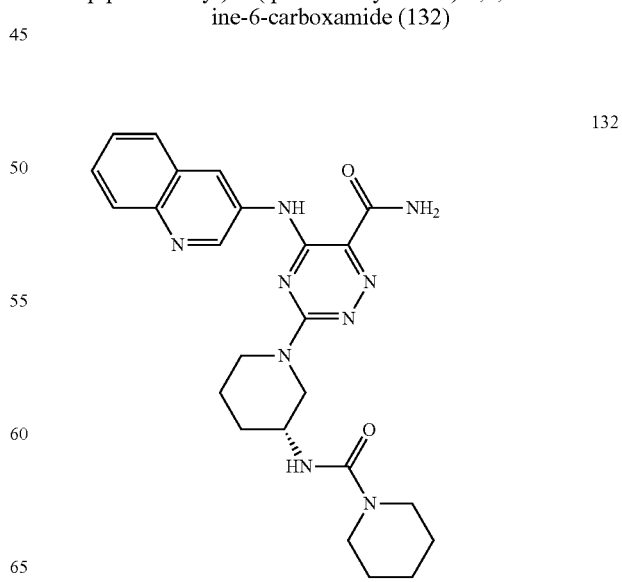

132

In a similar manner as described in Example 36, (R)-3-(3-(piperidine-1-carboxamido)piperidin-1-yl)-5-(quinolin-3-ylamino)-1,2,4-triazine-6-carboxamide (132) was prepared using 3-aminoquinoline. MS found for $C_{24}H_{29}N_9O_2$ as $(M+H)^+$ 476.1, $(M-H)^-$ 474.2. UV: $\lambda$=268, 316, 333 nm.

Example 109

Synthesis of (R)-3-(3-(piperidine-1-carboxamido)piperidin-1-yl)-5-(quinolin-7-ylamino)-1,2,4-triazine-6-carboxamide (133)

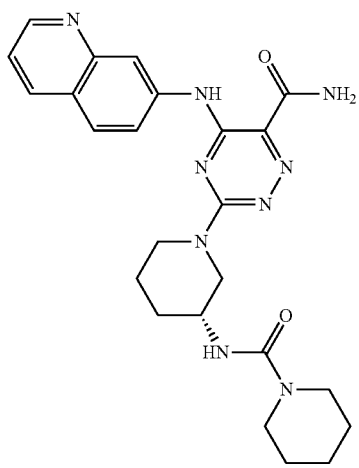

133

In a similar manner as described in Example 36, (R)-3-(3-(piperidine-1-carboxamido)piperidin-1-yl)-5-(quinolin-7-ylamino)-1,2,4-triazine-6-carboxamide (133) was prepared using 7-aminoquinoline. MS found for $C_{24}H_{29}N_9O_2$ as $(M+H)^+$ 476.2, $(M-H)^-$ 474.3. UV: $\lambda$=273, 330, 372 nm.

Example 110

Synthesis of (R)-5-(3-(4-methoxybenzamido)piperidin-1-yl)-3-(4-methoxyphenylamino)pyrazine-2-carboxamide (137)

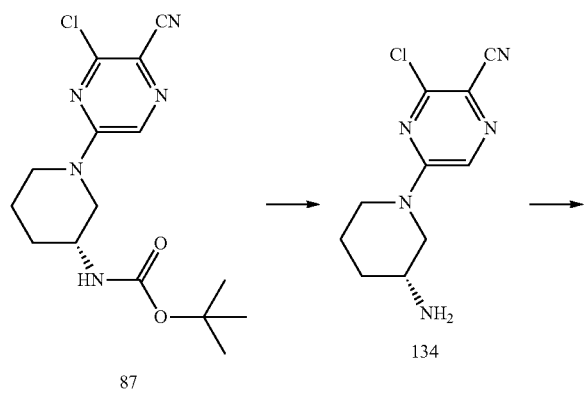

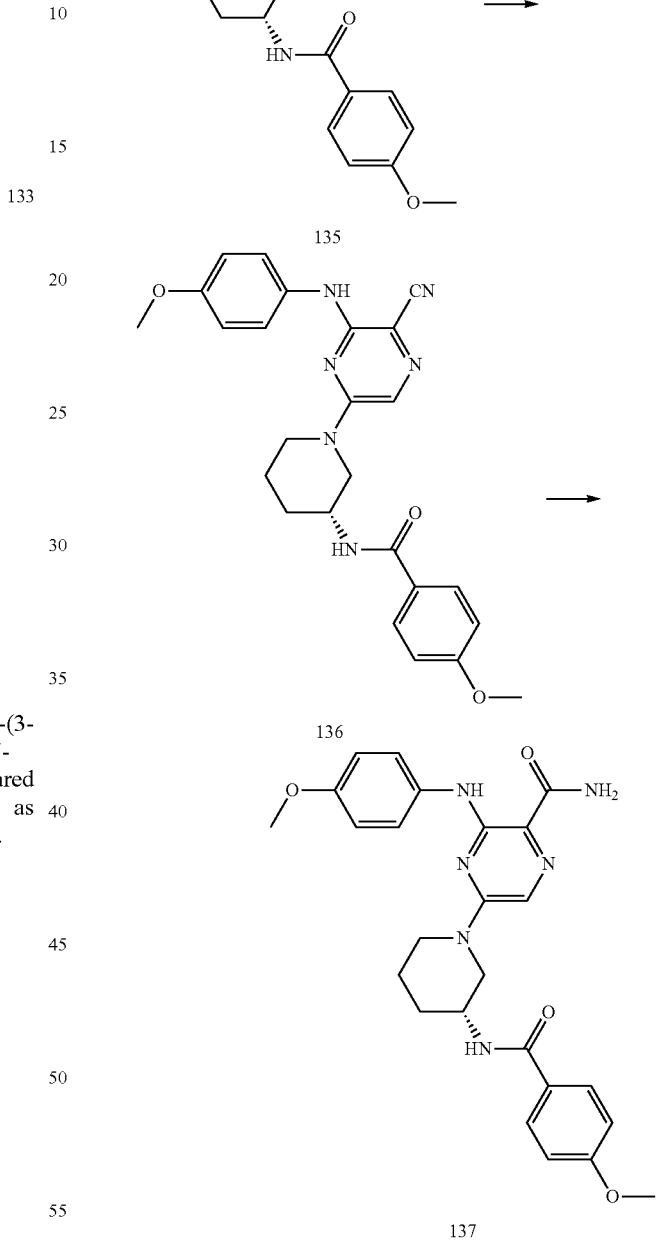

(R)-tert-butyl 1-(6-chloro-5-cyanopyrazin-2-yl)piperidin-3-ylcarbamate (87) (1.5 g) was treated with 30 mL "4N HCl in dioxane" at RT for 1 h. The mixture was concentrated in vacuo to dryness to afford (R)-5-(3-aminopiperidin-1-yl)-3-chloropyrazine-2-carbonitrile hydrochloride (134) in quantitative yield. Compound 134 (1.20 g, 4.4 mmol) and p-anisic acid (1.34 g, 8.8 mmol) were dissolved in 20 mL DMF with DIEA (3.82 mL, 22.0 mmol). To it was added PyBOP (4.58 g, 8.8 mmol). The mixture was stirred at RT for 30 m. It was diluted with EtOAc (200 mL), washed with 1N NaOH and water. The organic phase was dried, concentrated and subjected to flash column with 0 to 50% EtOAc in DCM to isolate (R)—N-(1-(6-chloro-5-cyanopyrazin-2-yl)piperidin-3-yl)-4-methoxybenzamide, compound 135 (yield >90%).

The mixture of compound 135 (70 mg, 0.19 mmol), p-anisidine (70 mg, 0.57 mmol), Pd(OAc)$_2$ (22 mg, 0.10 mmol), BINAP (62 mg, 0.10 mmol), fine powder Cs$_2$CO$_3$ (326 mg, 1.00 mmol) in 15 mL dioxane was degassed with nitrogen stream for 3 m. It was stirred at 115° C. under nitrogen atmosphere for 3 h. It was cooled to RT, diluted with 100 mL EtOAc, vigorously stirred, and filtered through celite. The filtrate was concentrated in vacuo and subjected to flash column with 0 to 3% MeOH in dichloromethane to afford (R)—N-(1-(5-cyano-6-(4-methoxyphenylamino)pyrazin-2-yl)piperidin-3-yl)-4-methoxybenzamide, compound 136.

Compound 136 was dissolved in the mixture of 3 mL DMSO and 6 mL MeOH and stirred at RT. To it were added one crystal chip of NaOH (about 50 to 100 mg) and the 1 mL 30% H$_2$O$_2$. The mixture was stirred at RT for 2.5 h, diluted with 3 mL acetonitrile, and concentrated in vacuo. The mixture was diluted with water, acidified with HCl till pH about 2. The solid was isolated by filtration, washed with water and MTBE. It was dried in vacuum to afford (R)-5-(3-(4-methoxybenzamido)piperidin-1-yl)-3-(4-methoxyphenylamino)pyrazine-2-carboxamide (137) as HCl salt (25 mg). MS found C$_{25}$H$_{28}$N$_6$O$_4$ as (M+H)$^+$ 477.1, (M−H)$^-$ 475.3. UV: λ=258, 279, 303, 338, 373 nm.

Example 111

Synthesis of (R)-3-(4-ethoxyphenylamino)-5-(3-(4-methoxybenzamido)piperidin-1-yl)pyrazine-2-carboxamide (138)

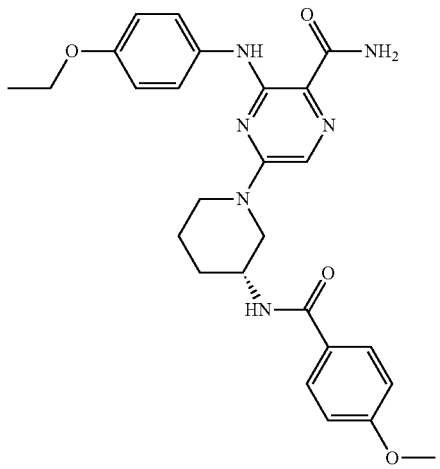

138

In a similar manner as described in Example 110, (R)-3-(4-ethoxyphenylamino)-5-(3-(4-methoxybenzamido)piperidin-1-yl)pyrazine-2-carboxamide (138) was prepared using 4-ethoxyaniline. MS found for C$_{26}$H$_{30}$N$_6$O$_4$ as (M+H)$^+$ 491.1, (M−H)$^-$ 489.2. UV: λ=258, 279, 303, 339, 373 nm.

Example 112

Synthesis of (R)-5-(3-(4-methoxybenzamido)piperidin-1-yl)-3-(4-(2-methoxyethoxyl)phenylamino)pyrazine-2-carboxamide (139)

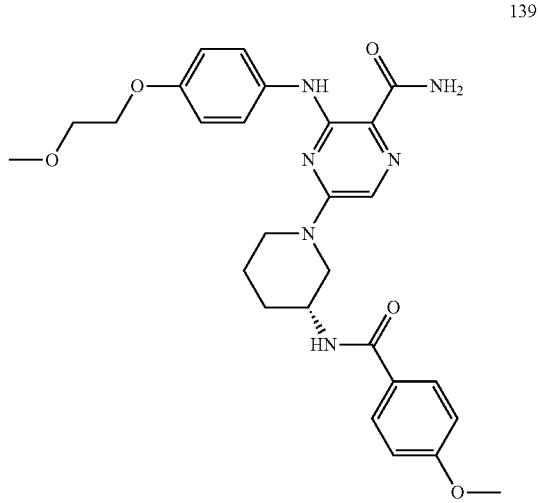

139

In a similar manner as described in Example 110, (R)-5-(3-(4-methoxybenzamido)piperidin-1-yl)-3-(4-(2-methoxyethoxyl)phenylamino)pyrazine-2-carboxamide (139) was prepared using 4-(2-methoxyethoxy)aniline. MS found for C$_{27}$H$_{32}$N$_6$O$_5$ as (M+H)$^+$ 521.2, (M−H)$^-$ 519.3. UV: λ=257, 279, 303, 338, 373 nm.

Example 113

Synthesis of (R)-3-(4-(2-ethoxyethoxyl)phenylamino)-5-(3-(4-methoxybenzamido)piperidin-1-yl)pyrazine-2-carboxamide (140)

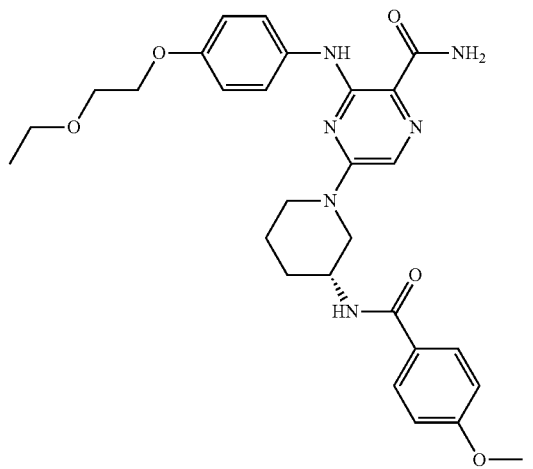

140

In a similar manner as described in Example 110, (R)-3-(4-(2-ethoxyethoxyl)phenylamino)-5-(3-(4-methoxybenzamido)piperidin-1-yl)pyrazine-2-carboxamide (140) was prepared using 4-(2-ethoxyethoxy)aniline. MS found for $C_{28}H_{34}N_6O_5$ as $(M+H)^+$ 535.2, $(M-H)^-$ 533.3. UV: $\lambda=257$, 279, 303, 338, 373 nm.

Example 114

Synthesis of (R)-3-(6-ethoxypyridin-3-ylamino)-5-(3-(4-methoxybenzamido)piperidin-1-yl)pyrazine-2-carboxamide (141)

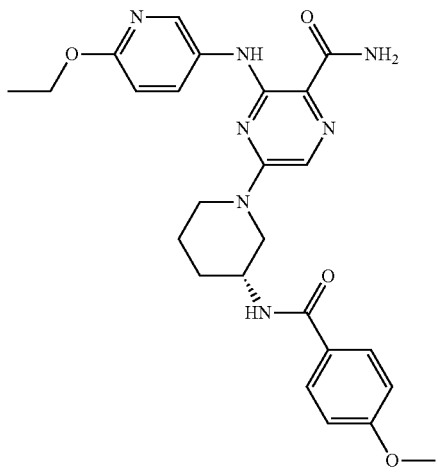

141

The mixture of compound 135 (65 mg, 0.17 mmol), 6-ethoxypyridin-3-amine (71 mg, 0.51 mmol), Pd(OAc)$_2$ (19 mg, 0.085 mmol), BINAP (53 mg, 0.085 mmol), fine powder Cs$_2$CO$_3$ (280 mg, 0.85 mmol) in 10 mL dioxane was degassed with nitrogen stream for 3 m. It was stirred at 115° C. under nitrogen atmosphere for 3 h. It was cooled to RT, diluted with 100 mL EtOAc, vigorously stirred, and filtered through celite. The filtrate was concentrated in vacuo and subjected to flash column with 0 to 4% MeOH in dichloromethane to afford (R)—N-(1-(5-cyano-6-(6-ethoxypyridin-3-ylamino)pyrazin-2-yl)piperidin-3-yl)-4-methoxybenzamide. It was dissolved in the mixture of 3 mL DMSO and 6 mL MeOH and stirred at RT. To it were added one crystal chip of NaOH (about 50 to 100 mg) and the 1 mL 30% H$_2$O$_2$. The mixture was stirred at RT for 1 h, diluted with 3 mL acetonitrile, and concentrated in vacuo. The mixture was acidified with TFA (1 mL) and directly subjected to reverse phase prep HPLC to isolate (R)-3-(6-ethoxypyridin-3-ylamino)-5-(3-(4-methoxybenzamido)piperidin-1-yl)pyrazine-2-carboxamide (141) as HCl salt (58 mg). MS found $C_{25}H_{29}N_7O_4$ as $(M+H)^+$ 492.2, $(M-H)^-$ 490.3. UV: $\lambda=257$, 278, 300, 336, 369 nm.

Example 115

Synthesis of (R)-3-(4-(2-(dimethylamino)ethoxy)phenylamino)-5-(3-(4-methoxybenzamido)piperidin-1-yl)pyrazine-2-carboxamide (142)

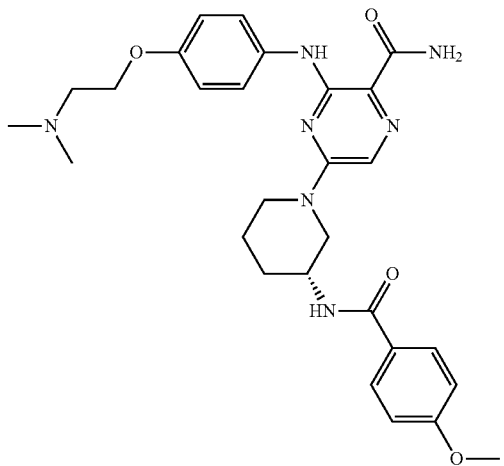

142

In a similar manner as described in Example 114, (R)-3-(4-(2-(dimethylamino)ethoxy)phenylamino)-5-(3-(4-methoxybenzamido)piperidin-1-yl)pyrazine-2-carboxamide (142) was prepared using 4-(2-(dimethylamino)ethoxy)aniline. MS found for $C_{28}H_{35}N_7O_4$ as $(M+H)^+$ 534.2, $(M-H)^-$ 532.3. UV: $\lambda=258$, 279, 303, 337, 373 nm.

Example 116

Synthesis of (R)-2-(4-(3-carbamoyl-6-(3-(4-methoxybenzamido)piperidin-1-yl)pyrazin-2-ylamino)phenoxy)-N,N-dimethylethanamine oxide (143)

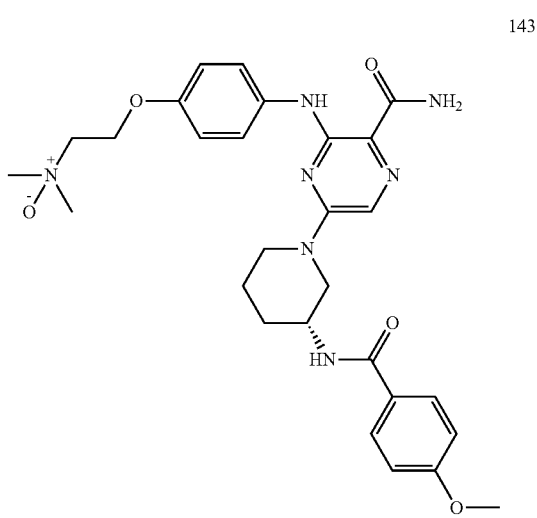

143

(R)-2-(4-(3-carbamoyl-6-(3-(4-methoxybenzamido)piperidin-1-yl)pyrazin-2-ylamino)phenoxy)-N,N-dimethylethanamine oxide (143) was isolated as a byproduct during the synthesis of (R)-3-(4-(2-(dimethylamino)ethoxy)phenylamino)-5-(3-(4-methoxybenzamido)piperidin-1-yl)pyrazine-2-carboxamide (142) in Example 115. MS found for $C_{28}H_{35}N_7O_5$ as (M+H)$^+$ 550.2, (M−H)$^-$ 548.4. UV: λ=258, 279, 303, 337, 373 nm.

Example 117

Synthesis of (R)-5-(3-(4-methoxybenzamido)piperidin-1-yl)-3-(4-(methylsulfonyl)phenylamino)pyrazine-2-carboxamide (144)

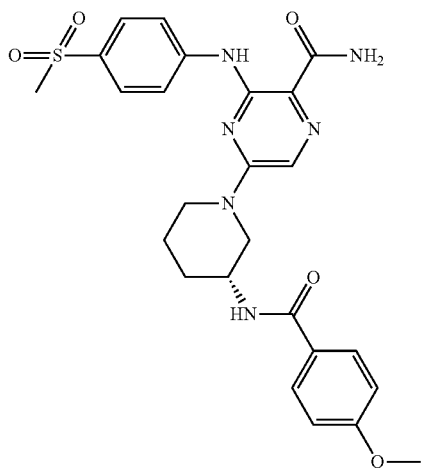

144

In a similar manner as described in Example 114, (R)-5-(3-(4-methoxybenzamido)piperidin-1-yl)-3-(4-(methylsulfonyl)phenylamino)pyrazine-2-carboxamide (144) was prepared using 4-methylsulfonylaniline. MS found for $C_{25}H_{28}N_6O_5S$ as (M+H)$^+$ 525.1, (M−H)$^-$ 523.3. UV: λ=256, 262, 274, 293, 318, 346, 367 nm.

Example 118

Synthesis of (R)-3-(4-(dimethylcarbamoyl)phenylamino)-5-(3-(4-methoxybenzamido)piperidin-1-yl)pyrazine-2-carboxamide (145)

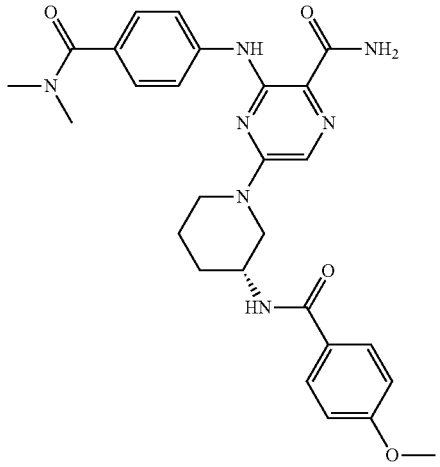

145

In a similar manner as described in Example 114, (R)-3-(4-(dimethylcarbamoyl)phenylamino)-5-(3-(4-methoxybenzamido)piperidin-1-yl)pyrazine-2-carboxamide (145) was prepared using 4-amino-N,N-dimethylbenzamide. MS found for $C_{27}H_{31}N_7O_4$ as (M+H)$^+$ 518.2, (M−H)$^-$ 516.3. UV: λ=256, 262, 272, 288, 313, 342, 370 nm.

Example 119

Synthesis of (R)-5-(3-(4-methoxybenzamido)piperidin-1-yl)-3-(3-methylisothiazol-5-ylamino)pyrazine-2-carboxamide (146)

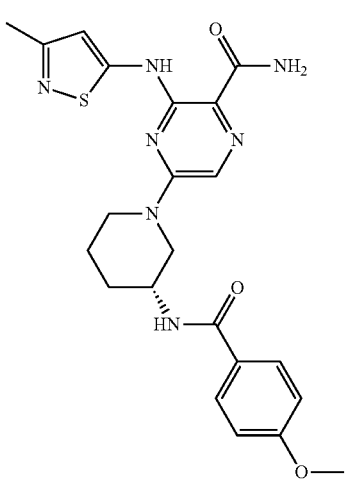

146

In a similar manner as described in Example 114, (R)-5-(3-(4-methoxybenzamido)piperidin-1-yl)-3-(3-methylisothiazol-5-ylamino)pyrazine-2-carboxamide (146) was prepared using 3-methylisothiazol-5-amine. MS found for $C_{22}H_{25}N_7O_3S$ as (M+H)$^+$468.1, (M−H)$^-$ 466.2. UV: λ=257, 262, 271, 289, 314, 341, 368 nm.

Example 120

Synthesis of (R)-5-(3-(4-methoxybenzamido)piperidin-1-yl)-3-(quinolin-6-ylamino)pyrazine-2-carboxamide (147)

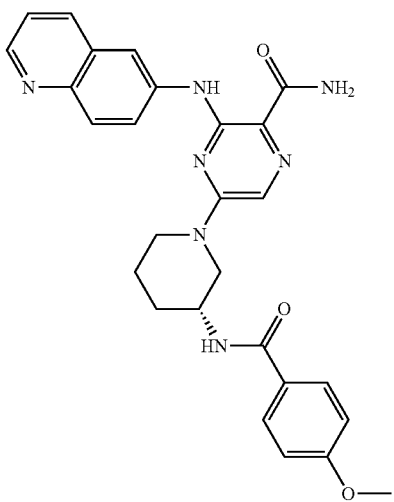

147

In a similar manner as described in Example 110, (R)-5-(3-(4-methoxybenzamido)piperidin-1-yl)-3-(quinolin-6-ylamino)pyrazine-2-carboxamide (147) was prepared using 6-aminoquinoline. MS found for $C_{27}H_{27}N_7O_3$ as $(M+H)^+$ 498.2, $(M-H)^-$ 496.3. UV: $\lambda=264, 273, 284, 300, 338, 369$ nm.

Example 121

Synthesis of (R)-3-(benzo[d]thiazol-6-ylamino)-5-(3-(4-methoxybenzamido)piperidin-1-yl)pyrazine-2-carboxamide (148)

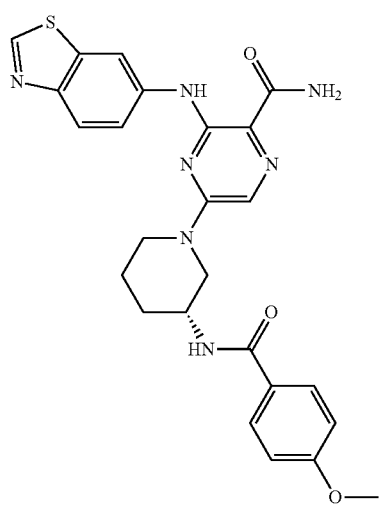

148

In a similar manner as described in Example 110, (R)-3-(benzo[d]thiazol-6-ylamino)-5-(3-(4-methoxybenzamido)piperidin-1-yl)pyrazine-2-carboxamide (148) was prepared using 6-aminobenzothiazole. MS found for $C_{25}H_{25}N_7O_3S$ as $(M+H)^+$ 504.1, $(M-H)^-$ 502.3. UV: $\lambda=317, 348, 370$ nm.

Example 122

Synthesis of (R)-5-(3-(4-methoxybenzamido)piperidin-1-yl)-3-(4-(tetrahydro-2H-pyran-4-yl)phenylamino)pyrazine-2-carboxamide (149)

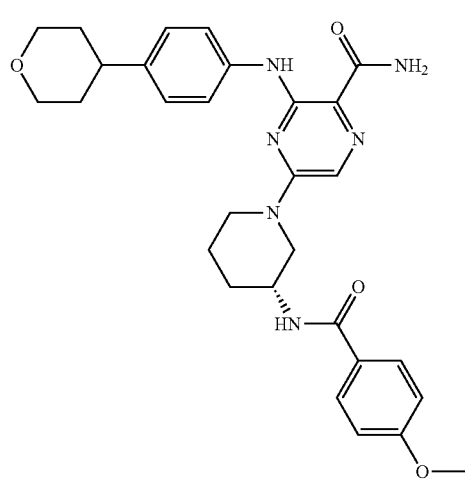

149

In a similar manner as described in Example 110, (R)-5-(3-(4-methoxybenzamido)piperidin-1-yl)-3-(4-(tetrahydro-2H-pyran-4-yl)phenylamino)pyrazine-2-carboxamide (149) was prepared using 4-(tetrahydro-2H-pyran-4-yl)aniline. MS found for $C_{29}H_{34}N_6O_4$ as $(M+H)^+$ 531.2, $(M-H)^-$ 529.3. UV: $\lambda=257, 279, 304, 335, 372$ nm.

Example 123

Synthesis of (R)-5-(3-(4-methoxybenzamido)piperidin-1-yl)-3-(4-morpholinophenylamino)pyrazine-2-carboxamide (150)

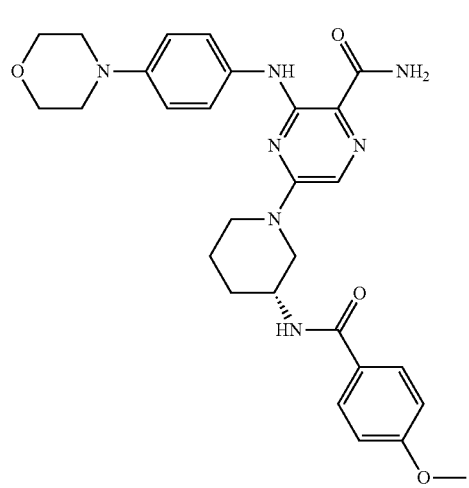

150

In a similar manner as described in Example 114, (R)-5-(3-(4-methoxybenzamido)piperidin-1-yl)-3-(4-morpholinophenylamino)pyrazine-2-carboxamide (150) was prepared using 4-morpholinoaniline. MS found for $C_{28}H_{33}N_7O_4$ as $(M+H)^+$ 532.2, $(M-H)^-$ 530.3. UV: $\lambda=259, 285, 309, 345, 372$ nm.

Example 124

Synthesis of (R)-5-(3-(4-methoxybenzamido)piperidin-1-yl)-3-(6-morpholinopyridin-3-ylamino)pyrazine-2-carboxamide (151)

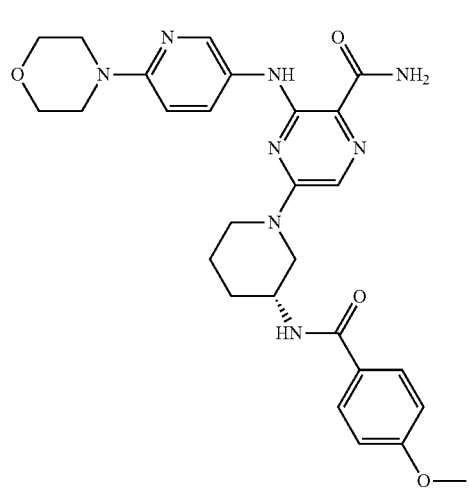

151

In a similar manner as described in Example 114, (R)-5-(3-(4-methoxybenzamido)piperidin-1-yl)-3-(6-morpholinopyridin-3-ylamino)pyrazine-2-carboxamide (151) was prepared using 6-morpholinopyridin-3-amine. MS found for $C_{27}H_{32}N_8O_4$ as $(M+H)^+$ 533.2, $(M-H)^-$ 531.3. UV: λ=257, 285, 308, 337, 367 nm.

Example 125

Synthesis of (R)-3-(3-fluoro-4-morpholinophenylamino)-5-(3-(4-methoxybenzamido)piperidin-1-yl)pyrazine-2-carboxamide (152)

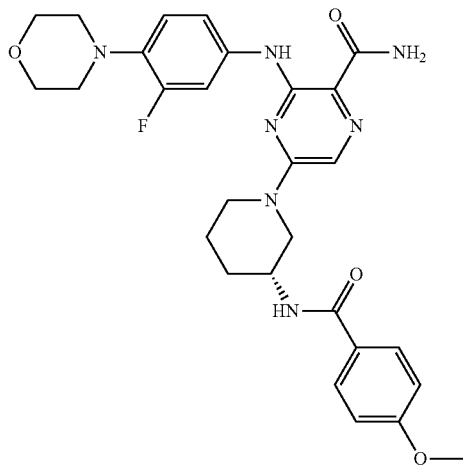

152

In a similar manner as described in Example 114, (R)-3-(3-fluoro-4-morpholinophenylamino)-5-(3-(4-methoxybenzamido)piperidin-1-yl)pyrazine-2-carboxamide (152) was prepared using 3-fluoro-4-morpholinoaniline. MS found for $C_{28}H_{32}FN_7O_4$ as $(M+H)^+$ 550.2, $(M-H)^-$ 548.3. UV: λ=310, 343, 372 nm.

Example 126

Synthesis of (R)-5-(3-(4-methoxybenzamido)piperidin-1-yl)-3-(4-(3-oxomorpholino)phenylamino)pyrazine-2-carboxamide (153)

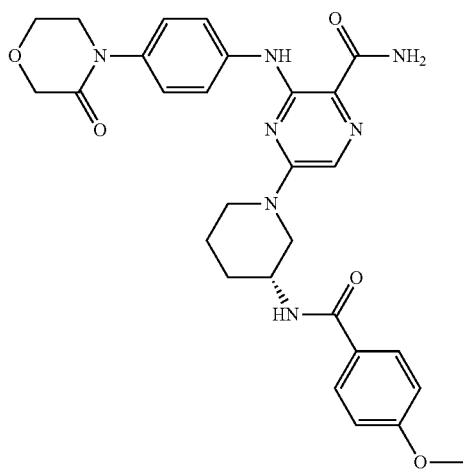

153

In a similar manner as described in Example 114, (R)-5-(3-(4-methoxybenzamido)piperidin-1-yl)-3-(4-(3-oxomorpholino)phenylamino)pyrazine-2-carboxamide (153) was prepared using 4-(4-aminophenyl)morpholin-3-one. MS found for $C_{28}H_{31}N_7O_5$ as $(M+H)^+$ 546.2, $(M-H)^-$ 544.3. UV: λ=261, 285, 308, 338, 372 nm.

Example 127

Synthesis of (R)-5-(3-(4-methoxybenzamido)piperidin-1-yl)-3-(4-(2-oxopyridin-1(2H)-yl)phenylamino)pyrazine-2-carboxamide (154)

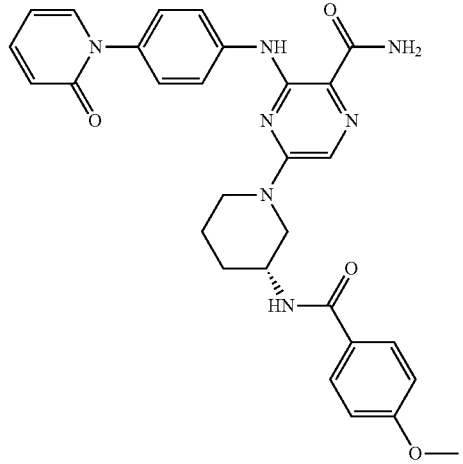

154

In a similar manner as described in Example 114, (R)-5-(3-(4-methoxybenzamido)piperidin-1-yl)-3-(4-(2-oxopyridin-1(2H)-yl)phenylamino)pyrazine-2-carboxamide (154) was prepared using 1-(4-aminophenyl)pyridin-2(1H)-one. MS found for $C_{29}H_{29}N_7O_4$ as $(M+H)^+$ 540.1, $(M-H)^-$ 538.3. UV: λ=260, 285, 308, 346, 369 nm Synthesis of 1-(4-aminophenyl)pyridin-2(1H)-one: The mixture of 4-iodoaniline (1.00 g, 4.56 mmol), 2-hydroxypyridine (650 mg, 6.84 mmol), fine powder $Cs_2CO_3$ (2.97 g, 9.12 mmol), fine powder CuI (180 mg, 0.92 mmol), 8-hydroxyquinoline (140 mg, 0.92 mmol) in 6 mL DMSO and 10 mL dioxane was stirred in a sealed tube at 120° C. for 15 h. The mixture was diluted with 300 mL EtOAc, filtered through celite, washed with brine, dried, concentrated and subjected to flash column with 0 to 7% MeOH in dichloromethane to isolate this compound (590 mg, yield 70%).

Example 128

Synthesis of (R)-5-(3-(4-methoxybenzamido)piperidin-1-yl)-3-(4-(2-oxopiperidin-1-yl)phenylamino)pyrazine-2-carboxamide (155)

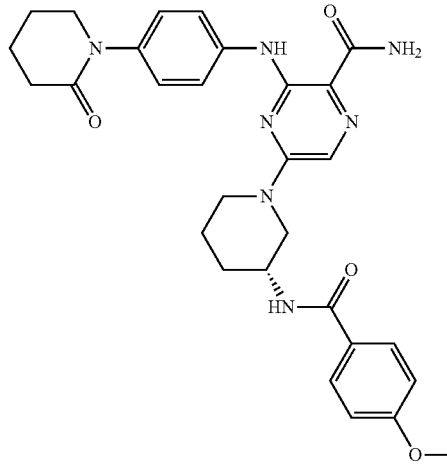

155

Compound (R)-5-(3-(4-methoxybenzamido)piperidin-1-yl)-3-(4-(2-oxopyridin-1(2H)-yl)phenylamino)pyrazine-2-carboxamide (154) (20 mg) was dissolved in 20 mL MeOH.

To it was added 10% Pd/C (20 mg). The mixture was stirred at RT for overnight under a hydrogen balloon. It was filtered through celite, concentrated in vacuo and subjected to reverse preparative HPLC to isolate (R)-5-(3-(4-methoxybenzamido)piperidin-1-yl)-3-(4-(2-oxopiperidin-1-yl)phenylamino)pyrazine-2-carboxamide (155) as HCl salt. MS found for $C_{29}H_{33}N_7O_4$ as $(M+H)^+$ 544.2, $(M-H)^-$ 542.3. UV: $\lambda$=259, 282, 307, 337, 372 nm.

Example 129

Synthesis of (R)-5-(3-(4-tert-butylbenzamido)piperidin-1-yl)-3-(4-(4-methylpiperazin-1-yl)phenylamino)pyrazine-2-carboxamide (156)

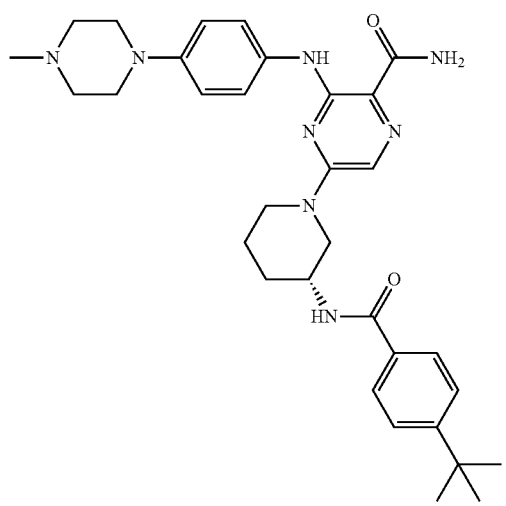

156

In a similar manner as described in Example 114, (R)-5-(3-(4-tert-butylbenzamido)piperidin-1-yl)-3-(4-(4-methylpiperazin-1-yl)phenylamino)pyrazine-2-carboxamide (156) was prepared using 4-(4-methylpiperazin-1-yl)aniline and 4-tert-butylbenzoyl chloride. MS found for $C_{32}H_{42}N_8O_2$ as $(M+H)^+$ 571.3, $(M-H)^-$ 569.4. UV: $\lambda$=309, 346, 372 nm.

Example 130

Synthesis of (R)-5-(3-(4-tert-butylbenzamido)piperidin-1-yl)-3-(4-(1-methylpiperidin-4-yl)phenylamino)pyrazine-2-carboxamide (157)

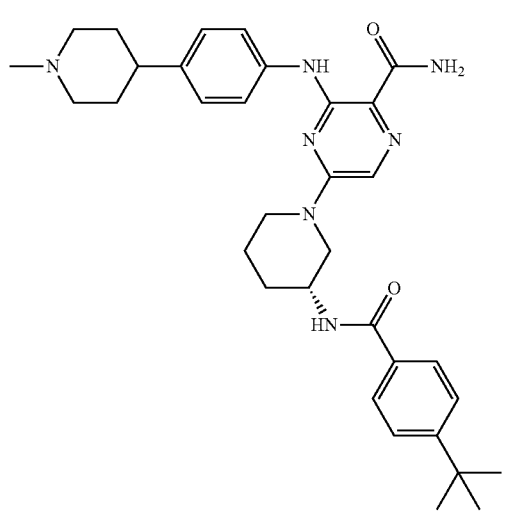

157

In a similar manner as described in Example 114, (R)-5-(3-(4-tert-butylbenzamido)piperidin-1-yl)-3-(4-(1-methylpiperidin-4-yl)phenylamino)pyrazine-2-carboxamide (157) was prepared using 4-(1-methylpiperidin-4-yl)aniline and 4-tert-butylbenzoyl chloride. MS found for $C_{33}H_{43}N_7O_2$ as $(M+H)^+$ 570.3, $(M-H)^-$ 568.4. UV: $\lambda$=264, 277, 305, 335, 372 nm.

Example 131

Synthesis of (R)-5-(3-(4-methoxybenzamido)piperidin-1-yl)-3-(4-(1-methylpiperidin-4-yl)phenylamino)pyrazine-2-carboxamide (158)

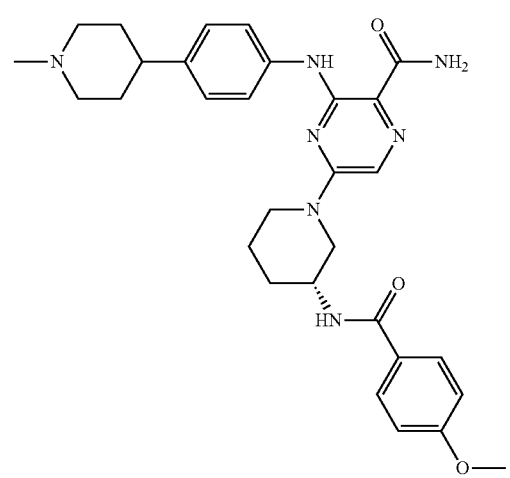

158

In a similar manner as described in Example 114, (R)-5-(3-(4-methoxybenzamido)piperidin-1-yl)-3-(4-(1-methylpiperidin-4-yl)phenylamino)pyrazine-2-carboxamide (158) was prepared using 4-(1-methylpiperidin-4-yl)aniline. MS found for $C_{30}H_{37}N_7O_3$ as $(M+H)^+$ 544.2, $(M-H)^-$ 542.3. UV: $\lambda$=258, 280, 305, 336, 372 nm.

Example 132

Synthesis of (R)-3-(4-(1-ethylpiperidin-4-yl)phenylamino)-5-(3-(4-methoxybenzamido)piperidin-1-yl)pyrazine-2-carboxamide (159)

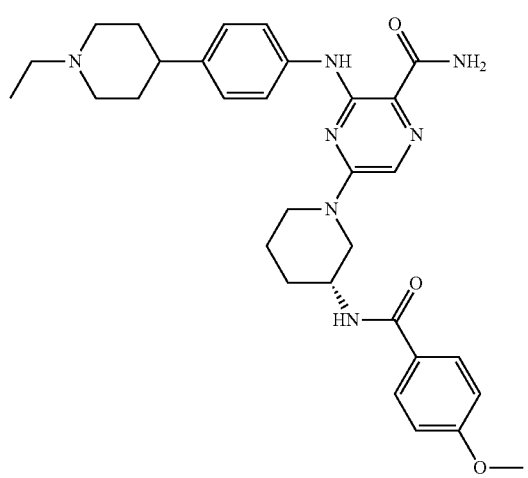

159

In a similar manner as described in Example 114, (R)-3-(4-(1-ethylpiperidin-4-yl)phenylamino)-5-(3-(4-methoxybenzamido)piperidin-1-yl)pyrazine-2-carboxamide (159) was prepared using 4-(1-ethylpiperidin-4-yl)aniline. MS found for $C_{31}H_{39}N_7O_3$ as $(M+H)^+$ 558.2, $(M-H)^-$ 556.3. UV: $\lambda$=258, 280, 305, 336, 372 nm.

Example 133

Synthesis of (R)-3-(4-(1-cyclopropylpiperidin-4-yl)phenylamino)-5-(3-(4-methoxybenzamido)piperidin-1-yl)pyrazine-2-carboxamide (160)

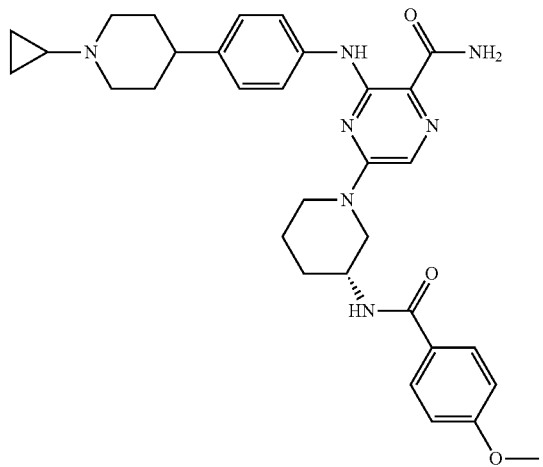

160

In a similar manner as described in Example 114, (R)-3-(4-(1-cyclopropylpiperidin-4-yl)phenylamino)-5-(3-(4-methoxybenzamido)piperidin-1-yl)pyrazine-2-carboxamide (160) was prepared using 4-(1-cyclopropylpiperidin-4-yl)aniline. MS found for $C_{32}H_{39}N_7O_3$ as $(M+H)^+$ 570.2, $(M-H)^-$ 568.3. UV: $\lambda$=258, 280, 305, 336, 372 nm.

Example 134

Synthesis of (R)-3-(4-(1-isopropylpiperidin-4-yl)phenylamino)-5-(3-(4-methoxybenzamido)piperidin-1-yl)pyrazine-2-carboxamide (164)

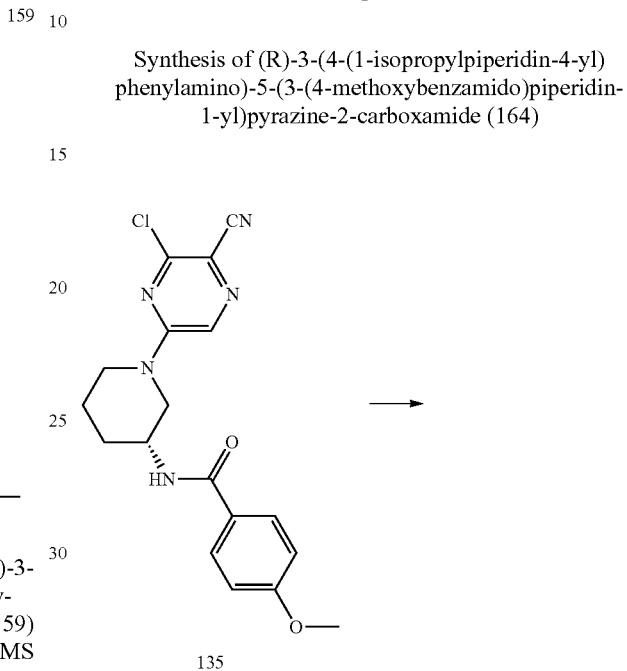

135

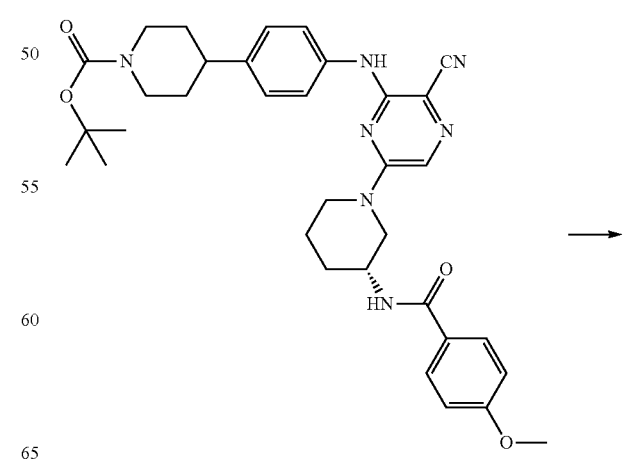

161

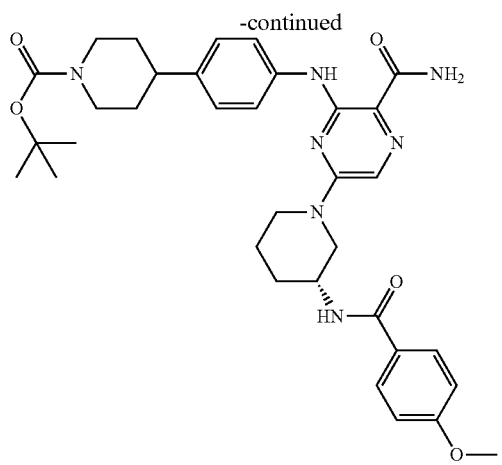

162

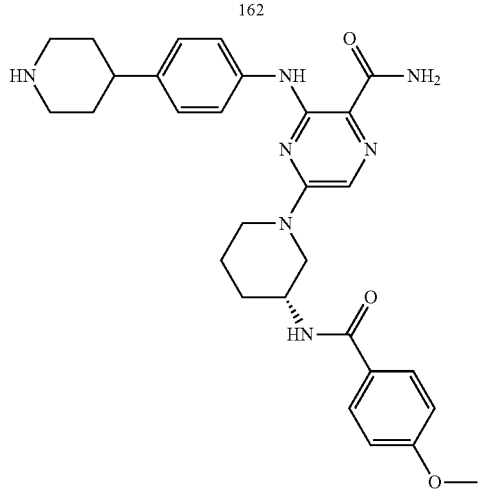

163

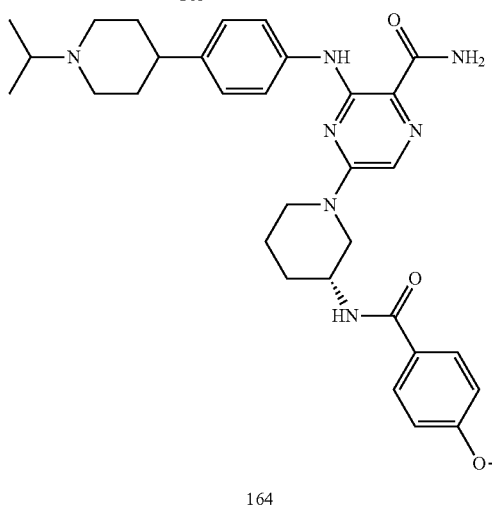

164

The mixture of compound 135 (580 mg, 1.56 mmol), tert-butyl 4-(4-aminophenyl)piperidine-1-carboxylate (870 mg, 3.12 mmol), Pd(OAc)$_2$ (70 mg, 0.31 mmol), BINAP (200 mg, 0.31 mmol), fine powder Cs$_2$CO$_3$ (2.04 g, 6.24 mmol) in 80 mL dioxane was degassed with nitrogen stream for 3 m. It was stirred at 115° C. under nitrogen atmosphere for 3 h. It was cooled to RT, diluted with 300 mL EtOAc, vigorously stirred, and filtered through celite. The filtrate was concentrated in vacuo and subjected to flash column with 0 to 5% MeOH in dichloromethane to afford compound 161.

Compound 161 was dissolved in the mixture of 10 mL DMSO and 40 mL MeOH and stirred at RT. To it were added three crystal chip of NaOH (about 150 to 300 mg) and the 10 mL 30% H$_2$O$_2$. The mixture was stirred at RT for 1 h, diluted with 10 mL acetonitrile. To the mixture then was poured 200 mL water. The mixture was vigorously stirred. The solid precipitates were isolated by filtration, washed with water thoroughly and dried in vacuo to afford compound 162 in good purity (1.00 g).

Compound 162 was treated with 50 mL "4N HCl in dioxane" at RT for overnight. The mixture was concentrated in vacuo and pumped to dryness to afford (R)-5-(3-(4-methoxybenzamido)piperidin-1-yl)-3-(4-(piperidin-4-yl)phenylamino)pyrazine-2-carboxamide (163) as HCl salt.

Compound 163 (70 mg, 0.12 mmol) was dissolved in 8 mL 1,2-dichloroethane and 8 mL dioxane with DIEA (105 µL, 0.60 mmol). To it was added acetone (180 µL, 2.4 mmol). The mixture was stirred at RT for 2 h. To it were added acetic acid (68 µL, 1.2 mmol) and then NaBH(OAc)$_3$ (127 mg, 0.60 mmol). The mixture was stirred for overnight. It was diluted with 2 mL water, concentrated in vacuo, treated with TFA (0.2 mL) and subjected to reverse phase preparative HPLC to isolate (R)-3-(4-(1-isopropylpiperidin-4-yl)phenylamino)-5-(3-(4-methoxybenzamido)piperidin-1-yl)pyrazine-2-carboxamide (164) as HCl salt (34 mg). MS found for C$_{32}$H$_{41}$N$_7$O$_3$ as (M+H)$^+$ 572.3, (M−H)$^-$ 570.4. UV: λ=258, 279, 305, 335, 372 nm.

Example 135

Synthesis of (R)-3-(4-(1-cyclopentylpiperidin-4-yl)phenylamino)-5-(3-(4-methoxybenzamido)piperidin-1-yl)pyrazine-2-carboxamide (165)

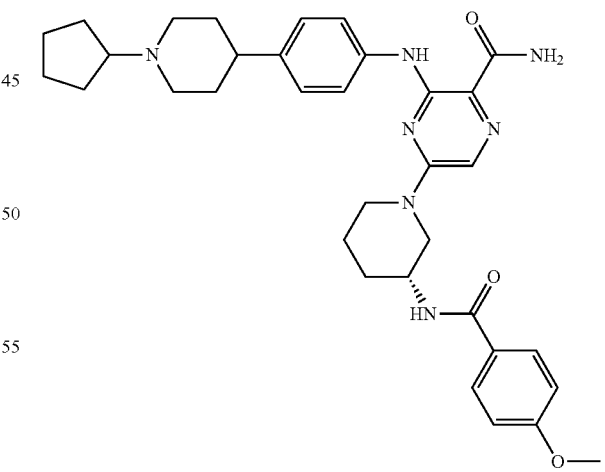

165

In a similar manner as described in Example 134, (R)-3-(4-(1-cyclopentylpiperidin-4-yl)phenylamino)-5-(3-(4-methoxybenzamido)piperidin-1-yl)pyrazine-2-carboxamide (165) was prepared using cyclopentanone. MS found for C$_{34}$H$_{43}$N$_7$O$_3$ as (M+H)$^+$ 598.3, (M−H)$^-$ 596.4. UV: λ=258, 279, 305, 335, 372 nm.

Example 136

Synthesis of (R)-3-(4-(1-(cyanomethyl)piperidin-4-yl)phenylamino)-5-(3-(4-methoxybenzamido)piperidin-1-yl)pyrazine-2-carboxamide (166)

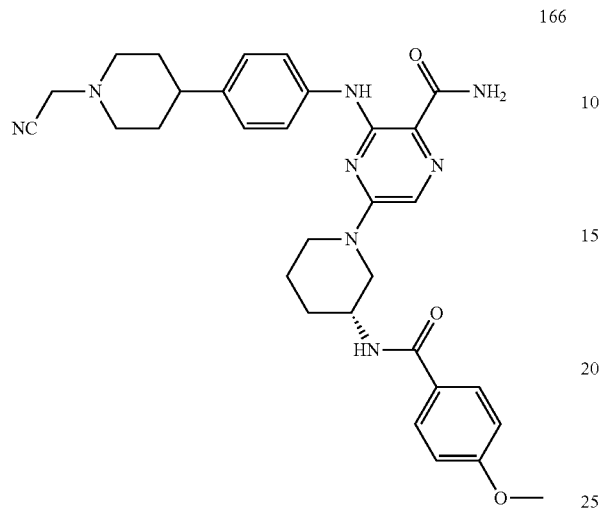

166

Compound 163 (50 mg, 0.085 mmol) was dissolved in 3 mL NMP. To it were added DIEA (74 μL, 0.43 mmol) and then bromoacetonitrile (31 mg, 0.26 mmol). The mixture was stirred at RT for 4 h. It was acidified with TFA (0.2 mL) and directly subjected to reverse phase preparative HPLC to isolate (R)-3-(4-(1-(cyanomethyl)piperidin-4-yl)phenylamino)-5-(3-(4-methoxybenzamido)piperidin-1-yl)pyrazine-2-carboxamide (166) as HCl salt (37 mg). MS found for $C_{31}H_{36}N_8O_3$ as $(M+H)^+$ 569.2, $(M-H)^-$ 567.3. UV: λ=256, 280, 305, 335, 372 nm.

Example 137

Synthesis of (R)-5-(3-(4-methoxybenzamido)piperidin-1-yl)-3-(4-(1-(2,2,2-trifluoroethyl)piperidin-4-yl)phenylamino)pyrazine-2-carboxamide (167)

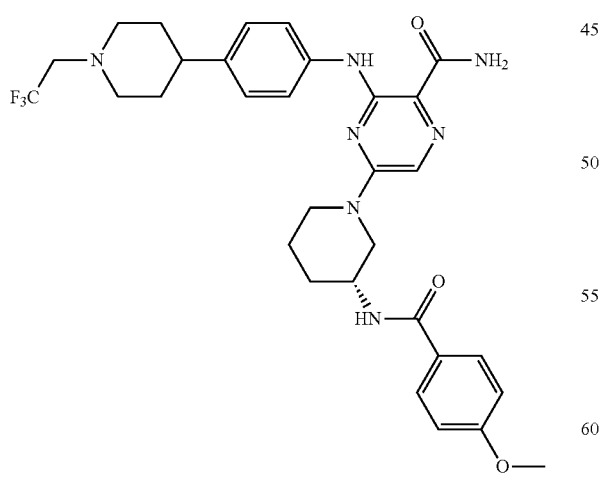

167

Compound 163 (50 mg, 0.085 mmol) was dissolved in 3 mL NMP. To it were added DIEA (74 μL, 0.43 mmol) and then 2,2,2-trifluoroethyl trifluoromethanesulfonate (60 mg, 0.26 mmol). The mixture was stirred at RT for 4 h. It was acidified with TFA (0.2 mL) and directly subjected to reverse phase preparative HPLC to isolate (R)-5-(3-(4-methoxybenzamido)piperidin-1-yl)-3-(4-(1-(2,2,2-trifluoroethyl)piperidin-4-yl)phenylamino)pyrazine-2-carboxamide (167) as HCl salt (8 mg). MS found for $C_{31}H_{36}F_3N_7O_3$ as $(M+H)^+$ 612.2, $(M-H)^-$ 610.3. UV: λ=305, 335, 372 nm.

Example 138

Synthesis of (R)-3-(4-(1-formylpiperidin-4-yl)phenylamino)-5-(3-(4-methoxybenzamido)piperidin-1-yl)pyrazine-2-carboxamide (168)

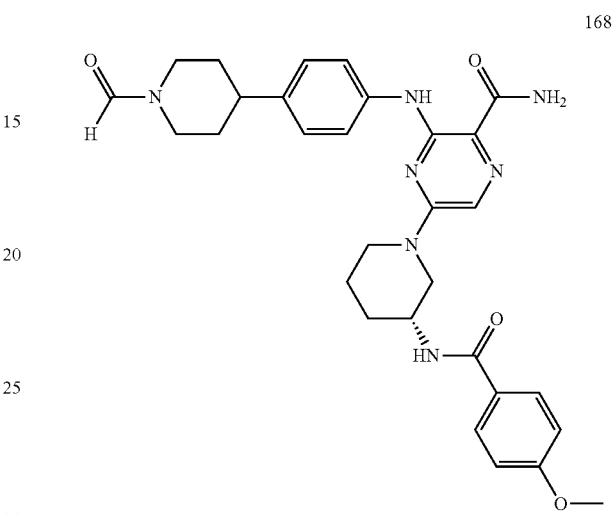

168

Compound 163 (36 mg, 0.06 mmol) was dissolved in 3 mL DMF with 0.5 mL DIEA in a sealed tube. The mixture was stirred at 130° C. for 2 days. It was cooled to RT, acidified with 1 mL TFA, and directly subjected to reverse phase preparative HPLC to isolate (R)-3-(4-(1-formylpiperidin-4-yl)phenylamino)-5-(3-(4-methoxybenzamido)piperidin-1-yl)pyrazine-2-carboxamide (168) as HCl salt (9 mg). MS found for $C_{30}H_{35}N_7O_4$ as $(M+H)^+$ 558.2, $(M-H)^-$ 556.3. UV: λ=257, 279, 304, 335, 372 nm.

Example 139

Synthesis of (R)-3-(4-(1-acetylpiperidin-4-yl)phenylamino)-5-(3-(4-methoxybenzamido)piperidin-1-yl)pyrazine-2-carboxamide (169)

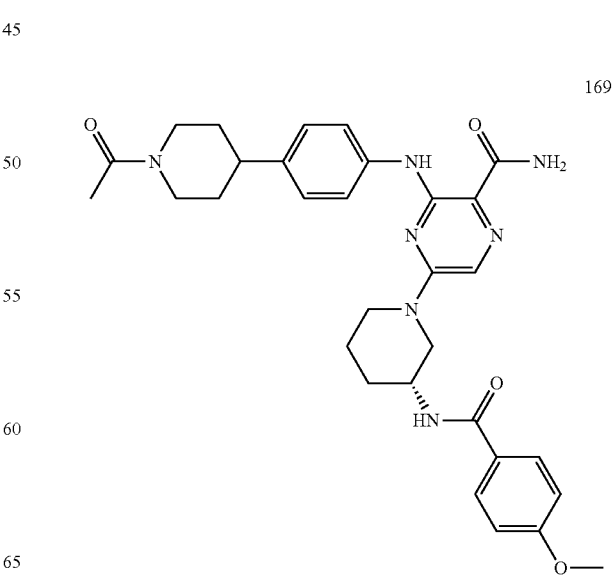

169

Compound 163 (42 mg, 0.07 mmol) was dissolved in 2 mL DMSO with 1 mL acetic acid and 1 mL Et$_3$N. To the mixture was added PyBOP (200 mg, 0.38 mmol). The mixture was stirred for overnight, concentrated in vacuo, acidified with TFA (1 mL), and directly subjected to reverse phase preparative HPLC to isolate (R)-3-(4-(1-acetylpiperidin-4-yl)phenylamino)-5-(3-(4-methoxybenzamido)piperidin-1-yl)pyrazine-2-carboxamide (169) as HCl salt (12 mg). MS found for C$_{31}$H$_{37}$N$_7$O$_4$ as (M+H)$^+$ 572.2, (M−H)$^−$ 570.4. UV: λ=257, 279, 304, 335, 372 nm.

Example 140

Synthesis of (R)-5-(3-(4-methoxybenzamido)piperidin-1-yl)-3-(4-(1-propionylpiperidin-4-yl)phenylamino)pyrazine-2-carboxamide (170)

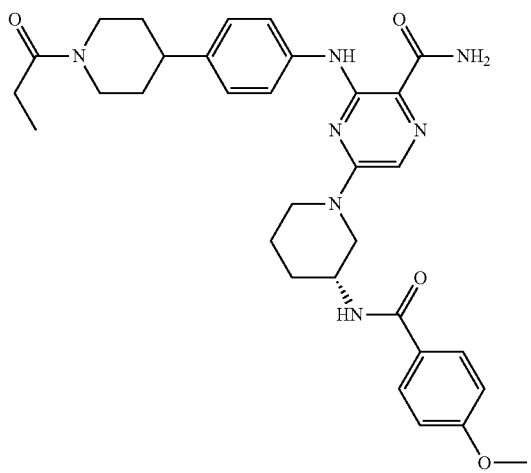

170

Example 141

Synthesis of (R)-3-(4-(1-(2-cyanoacetyl)piperidin-4-yl)phenylamino)-5-(3-(4-methoxybenzamido)piperidin-1-yl)pyrazine-2-carboxamide (171)

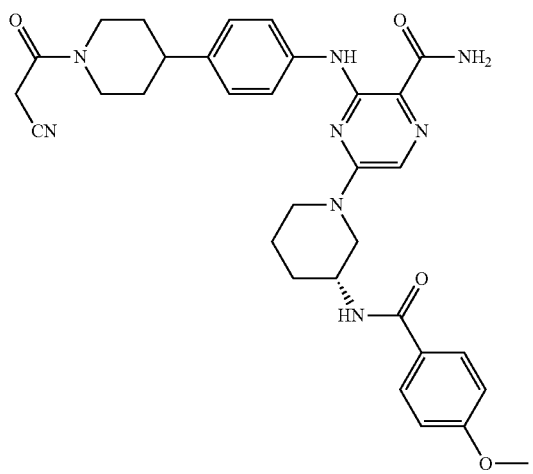

171

Compound 163 (50 mg, 0.085 mmol) was dissolved in 3 mL NMP. To it were added cyanoacetic acid (22 mg, 0.255 mmol), DIEA 150 μL, 0.85 mmol) and then PyBOP (88 mg, 0.17 mmol). The reaction was quenched in 1.5 h using TFA (0.2 mL). The mixture was directly subjected to reverse phase preparative HPLC to isolate (R)-3-(4-(1-(2-cyanoacetyl)piperidin-4-yl)phenylamino)-5-(3-(4-methoxybenzamido)piperidin-1-yl)pyrazine-2-carboxamide (171) as HCl salt. MS found for C$_{32}$H$_{36}$N$_8$O$_4$ as (M+H)$^+$ 597.2, (M−H)$^−$ 595.3. UV: λ=305, 336, 372 nm.

Example 142

Synthesis of (R)-3-(4-(1-(dimethylcarbamoyl)piperidin-4-yl)phenylamino)-5-(3-(4-methoxybenzamido)piperidin-1-yl)pyrazine-2-carboxamide (172)

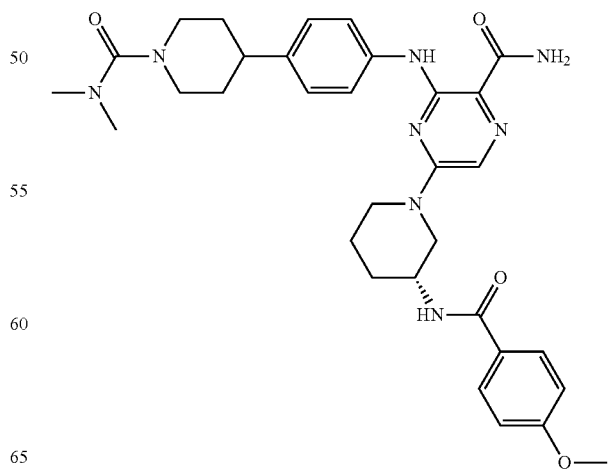

172

Compound 163 (50 mg, 0.085 mmol) was dissolved in 3 mL NMP. To it were added DIEA (74 μL, 0.425 mmol) and then propionyl chloride (23 mg, 0.255 mmol). The reaction was quenched in 10 m using TFA (0.2 mL). The mixture was directly subjected to reverse phase preparative HPLC to isolate (R)-5-(3-(4-methoxybenzamido)piperidin-1-yl)-3-(4-(1-propionylpiperidin-4-yl)phenylamino)pyrazine-2-carboxamide (170) as HCl salt. MS found for C$_{32}$H$_{39}$N$_7$O$_4$ as (M+H)$^+$ 586.2, (M−H)$^−$ 584.4. UV: λ=257, 279, 304, 335, 372 nm.

Compound 163 (40 mg, 0.07 mmol) was dissolved in 3 mL NMP. To it were added DIEA (125 μL, 0.71 mmol) and then dimethylcarbamic chloride (20 μL, 0.21 mmol). The reaction was quenched in 1 h using TFA (0.2 mL). The mixture was directly subjected to reverse phase preparative HPLC to isolate (R)-3-(4-(1-(dimethylcarbamoyl)piperidin-4-yl)phenylamino)-5-(3-(4-methoxybenzamido)piperidin-1-yl)pyrazine-2-carboxamide (172) as HCl salt (13 mg). MS found for $C_{32}H_{40}N_8O_4$ as $(M+H)^+$ 601.3, $(M-H)^-$ 599.3. UV: λ=257, 279, 304, 336, 372 nm.

Example 143

Synthesis of (R)-5-(3-(4-methoxybenzamido)piperidin-1-yl)-3-(4-(1-(methylsulfonyl)piperidin-4-yl)phenylamino)pyrazine-2-carboxamide (173)

Example 144

Synthesis of (R)-3-(4-(4-(dimethylcarbamoyl)piperidin-1-yl)phenylamino)-5-(3-(4-methoxybenzamido)piperidin-1-yl)pyrazine-2-carboxamide (177)

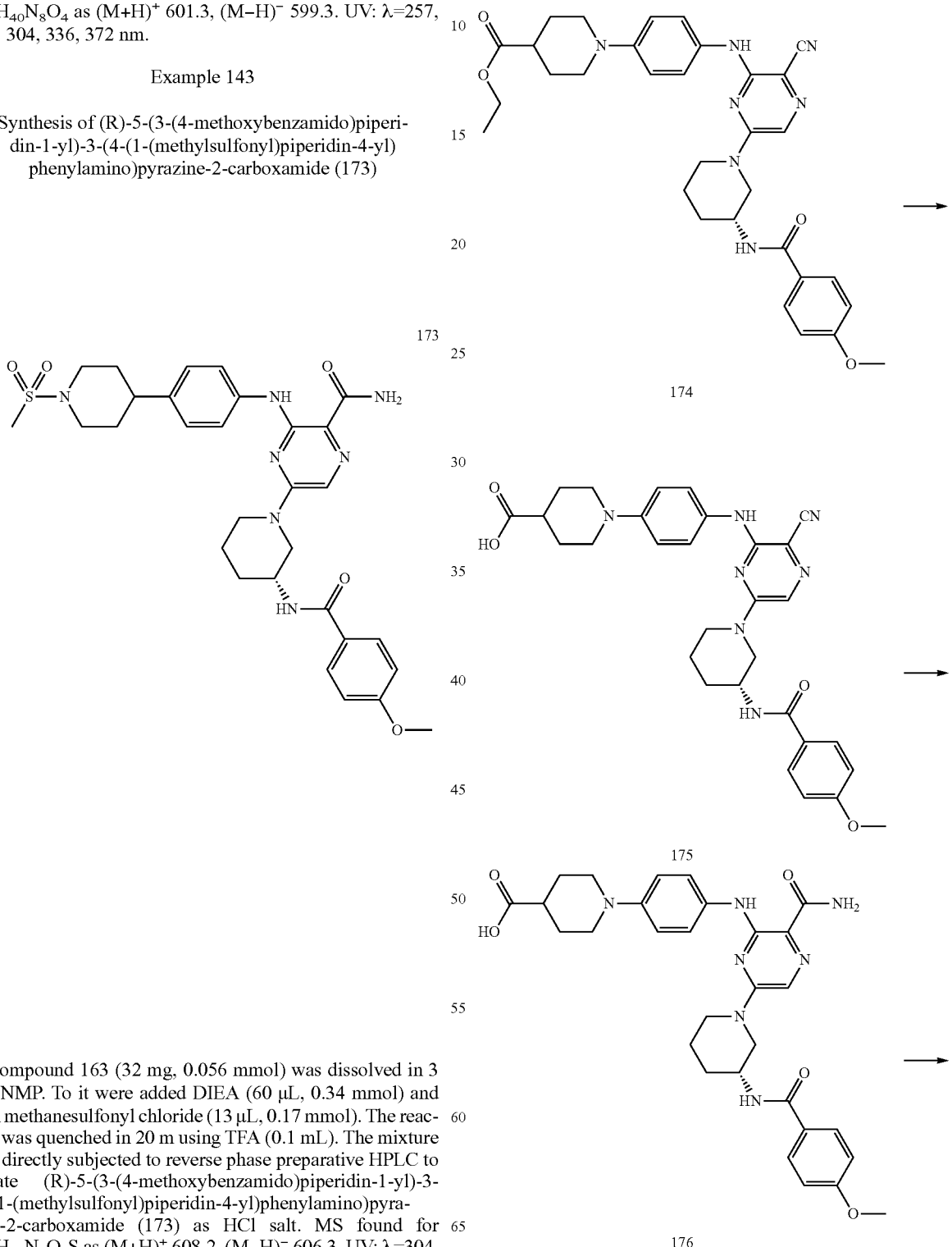

Compound 163 (32 mg, 0.056 mmol) was dissolved in 3 mL NMP. To it were added DIEA (60 μL, 0.34 mmol) and then methanesulfonyl chloride (13 μL, 0.17 mmol). The reaction was quenched in 20 m using TFA (0.1 mL). The mixture was directly subjected to reverse phase preparative HPLC to isolate (R)-5-(3-(4-methoxybenzamido)piperidin-1-yl)-3-(4-(1-(methylsulfonyl)piperidin-4-yl)phenylamino)pyrazine-2-carboxamide (173) as HCl salt. MS found for $C_{30}H_{37}N_7O_5S$ as $(M+H)^+$ 608.2, $(M-H)^-$ 606.3. UV: λ=304, 335, 372 nm.

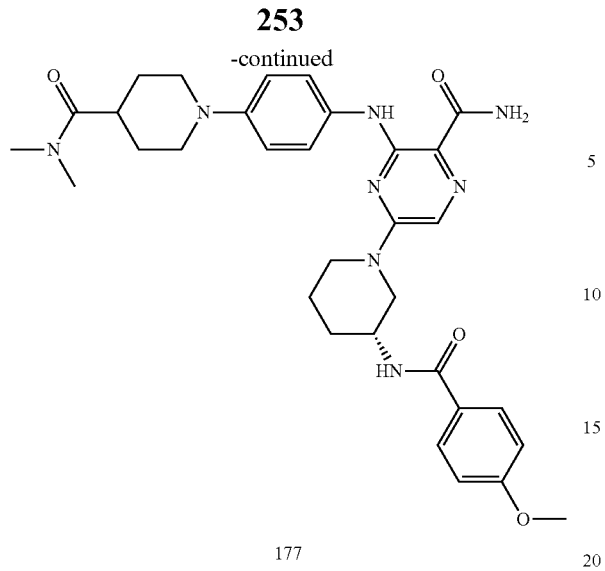

177

In a similar manner as described in Example 110, (R)-ethyl 1-(4-(3-cyano-6-(3-(4-methoxybenzamido)piperidin-1-yl)pyrazin-2-ylamino)phenyl)piperidine-4-carboxylate (174) was prepared using ethyl 1-(4-aminophenyl)piperidine-4-carboxylate. Compound 174 (155 mg, 0.27 mmol) was dissolved in 20 mL THF. To it was added lithium hydroxide hydrate (61 mg, 1.5 mmol) and 5 mL water. The mixture was stirred at RT for overnight and concentrated in vacuo to dryness to afford crude compound 175. It was dissolved in 15 mL MeOH and 3 mL DMSO. To it was added NaOH (100 mg) and then 2 mL 30% $H_2O_2$. The mixture was stirred at RT for 1 h and diluted with acetonitrile (3 mL). The mixture was concentrated in vacuo, acidified and subjected to reverse phase preparative HPLC to isolate compound 176 as HCl salt.

Compound 176 (70 mg, 0.12 mmol) was dissolved in 3 mL NMP. To it were added dimethylamine (2.0M solution in THF, 0.6 mL, 1.2 mmol) and then PyBOP (125 mg, 0.24 mmol). The mixture was stirred for overnight. It was quenched with TFA (1 mL) and then directly subjected to reverse phase preparative HPLC to isolate (R)-3-(4-(4-(dimethylcarbamoyl)piperidin-1-yl)phenylamino)-5-(3-(4-methoxybenzamido)piperidin-1-yl)pyrazine-2-carboxamide (177) as HCl salt (36 mg). MS found for $C_{32}H_{40}N_8O_4$ as $(M+H)^+$ 601.2, $(M-H)^-$ 599.4. UV: λ=262, 285, 308, 335, 369 nm.

Example 145

Synthesis of (R)-3-(4-(methylsulfonyl)phenylamino)-5-(3-(piperidine-1-carboxamido)piperidin-1-yl)pyrazine-2-carboxamide (180)

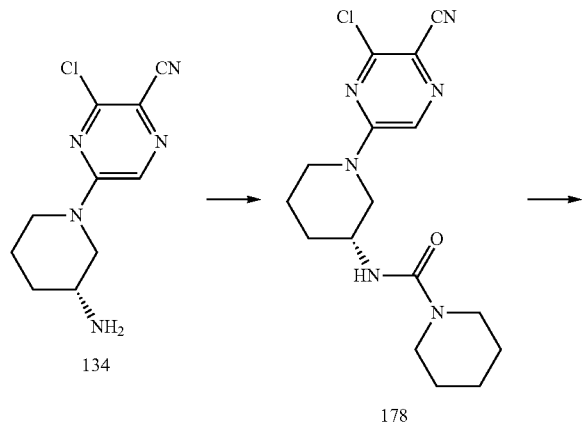

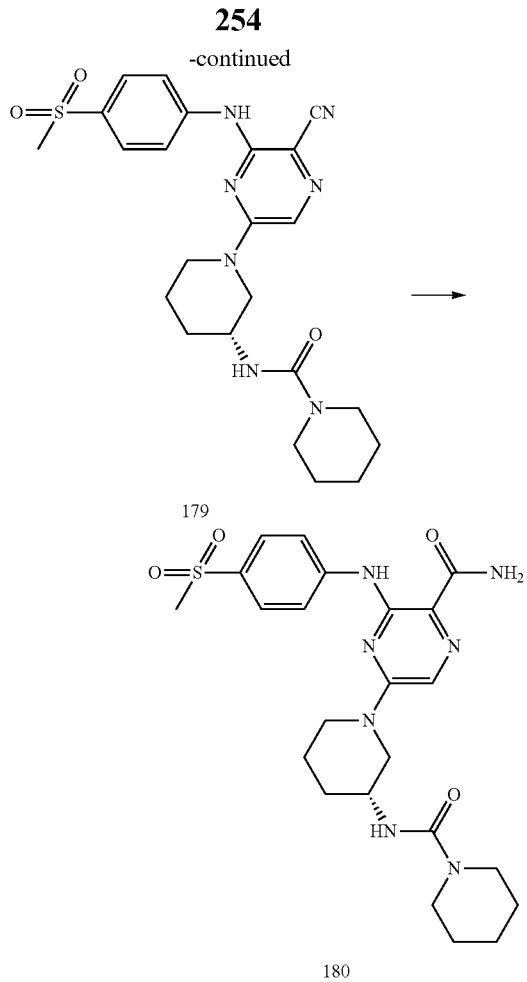

Compound 134 (600 mg, 2.2 mmol) was dissolved in 10 mL DMF and 10 mL dioxane. To the stirred solution were added DIEA (1.9 mL, 11 mmol) and then dropwise 1-piperidinecarbonyl chloride (550 μL, 4.4 mmol). The mixture was stirred for overnight, concentrated in vacuo, taken into 200 mL EtOAc, washed with brine, dried, concentrated and subjected to flash column with 0 to 4% MeOH in dichloromethane to afford compound 178 (730 mg, 95%). The mixture of compound 178 (90 mg, 0.26 mmol), 4-methylsulfonylaniline (133 mg, 0.78 mmol), Pd(OAc)$_2$ (30 mg, 0.13 mmol), BINAP (81 mg, 0.13 mmol), fine powder Cs$_2$CO$_3$ (430 mg, 1.30 mmol) in 15 mL dioxane was degassed with nitrogen stream for 3 m. It was stirred at 115° C. under nitrogen atmosphere for 3 h. It was cooled to RT, diluted with 100 mL EtOAc, vigorously stirred, and filtered through celite. The filtrate was concentrated in vacuo and subjected to flash column with 0 to 5% MeOH in dichloromethane to afford compound 179. Compound 179 was dissolved in the mixture of 3 mL DMSO and 6 mL MeOH and stirred at RT. To it were added one crystal chip of NaOH (about 50 to 100 mg) and the 1 mL 30% H$_2$O$_2$. The mixture was stirred at RT for 1 h, diluted with 3 mL acetonitrile, and concentrated in vacuo. It was acidified with TFAS (0.2 mL) and directly subjected to reverse phase preparative HPLC to afford (R)-3-(4-(methylsulfonyl)phenylamino)-5-(3-(piperidine-1-carboxamido)piperidin-1-yl)pyrazine-2-carboxamide (180) as HCl salt (61 mg). MS found $C_{23}H_{31}N_7O_4S$ as $(M+H)^+$ 502.1, $(M-H)^-$ 500.2. UV: $\lambda$=280, 293, 319, 346, 367 nm.

Example 146

Synthesis of (R)-3-(4-(4-methylpiperazin-1-yl)phenylamino)-5-(3-(piperidine-1-carboxamido)piperidin-1-yl)pyrazine-2-carboxamide (181)

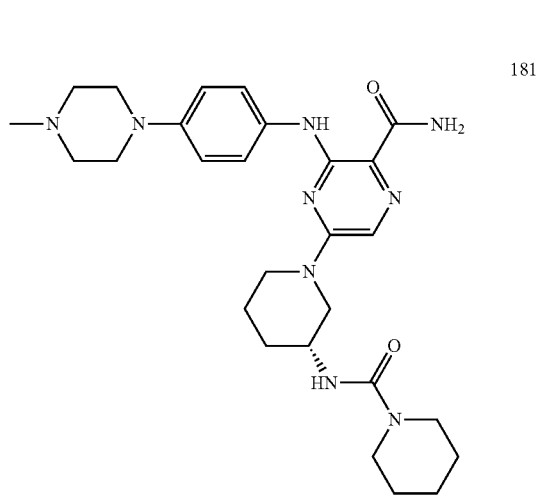 [SMILES: CN1CCN(c2ccc(Nc3nc(N4CCC[C@@H](NC(=O)N5CCCCC5)C4)cnc3C(N)=O)cc2)CC1]

In a similar manner as described in Example 145, (R)-3-(4-(4-methylpiperazin-1-yl)phenylamino)-5-(3-(piperidine-1-carboxamido)piperidin-1-yl)pyrazine-2-carboxamide (181) was prepared using 4-(4-methylpiperazin-1-yl)aniline. MS found for $C_{27}H_{39}N_9O_2$ as $(M+H)^+$ 522.3, $(M-H)^-$ 520.4. UV: $\lambda$=310, 346, 373 nm.

Example 147

Synthesis of (R)-3-(4-(1-methylpiperidin-4-yl)phenylamino)-5-(3-(piperidine-1-carboxamido)piperidin-1-yl)pyrazine-2-carboxamide (182)

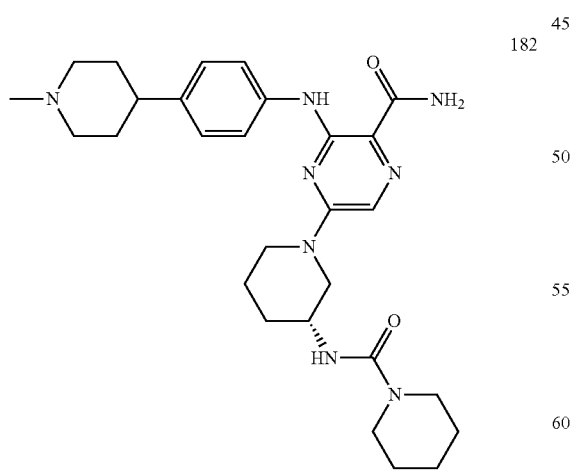

In a similar manner as described in Example 145, (R)-3-(4-(1-methylpiperidin-4-yl)phenylamino)-5-(3-(piperidine-1-carboxamido)piperidin-1-yl)pyrazine-2-carboxamide (182) was prepared using 4-(1-methylpiperidin-4-yl)aniline.

MS found for $C_{28}H_{40}N_8O_2$ as $(M+H)^+$ 521.3, $(M-H)^-$ 519.4. UV: $\lambda$=268, 278, 306, 336, 372 nm.

Example 148

Synthesis of (R)-3-(4-(1-formylpiperidin-4-yl)phenylamino)-5-(3-(piperidine-1-carboxamido)piperidin-1-yl)pyrazine-2-carboxamide (183)

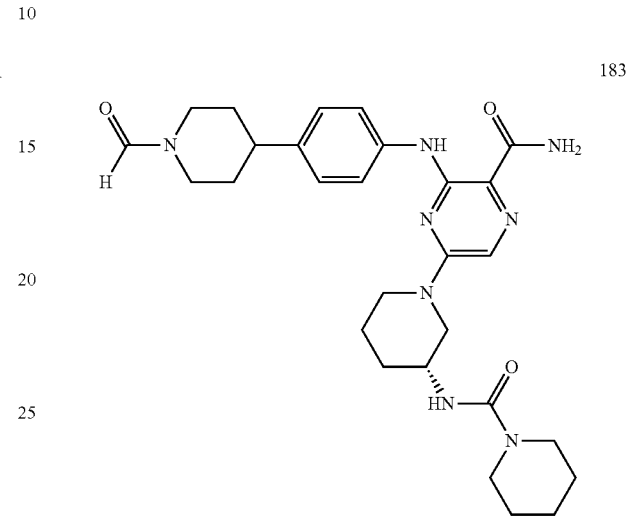

In a similar manner as described in Example 138 and Example 145, (R)-3-(4-(1-formylpiperidin-4-yl)phenylamino)-5-(3-(piperidine-1-carboxamido)piperidin-1-yl)pyrazine-2-carboxamide (183) was prepared. MS found for $C_{28}H_{38}N_8O_3$ as $(M+H)^+$ 535.2, $(M-H)^-$ 533.3. UV: $\lambda$=268, 277, 306, 336, 373 nm.

Example 149

Synthesis of (R)-5-(3-(piperidine-1-carboxamido)piperidin-1-yl)-3-(4-(1-propionylpiperidin-4-yl)phenylamino)pyrazine-2-carboxamide (184)

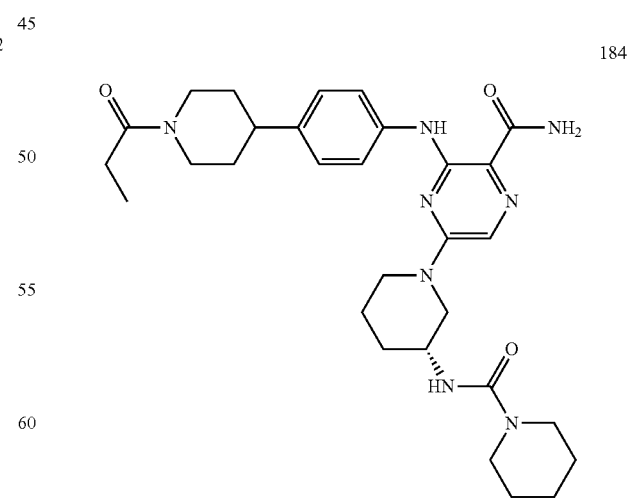

In a similar manner as described in Example 140 and Example 145, (R)-5-(3-(piperidine-1-carboxamido)piperidin-1-yl)-3-(4-(1-propionylpiperidin-4-yl)phenylamino)

pyrazine-2-carboxamide (184) was prepared. MS found for C$_{30}$H$_{42}$N$_8$O$_3$ as (M+H)$^+$ 563.2, (M−H)$^-$ 561.4. UV: λ=268, 277, 305, 336, 372 nm.

Example 150

Synthesis of (R)-3-(4-(1-(2-cyanoacetyl)piperidin-4-yl)phenylamino)-5-(3-(piperidine-1-carboxamido)piperidin-1-yl)pyrazine-2-carboxamide (185)

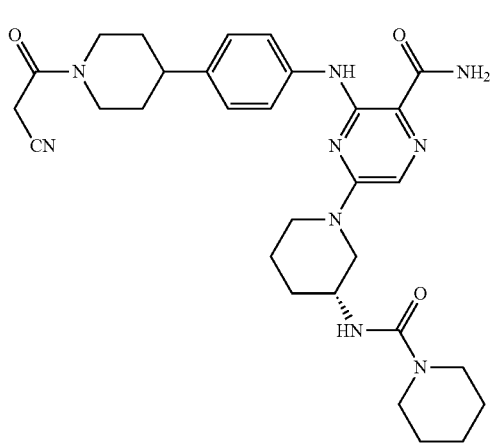

185

In a similar manner as described in Example 141 and Example 145, (R)-3-(4-(1-(2-cyanoacetyl)piperidin-4-yl)phenylamino)-5-(3-(piperidine-1-carboxamido)piperidin-1-yl)pyrazine-2-carboxamide (185) was prepared. MS found for C$_{30}$H$_{39}$N$_9$O$_3$ as (M+H)$^+$ 574.2, (M−H)$^-$ 572.4. UV: λ=268, 277, 306, 336, 372 nm.

Example 151

Synthesis of (R)-5-(3-(3,3-dimethylureido)piperidin-1-yl)-3-(4-(methylsulfonyl)phenylamino)pyrazine-2-carboxamide (186)

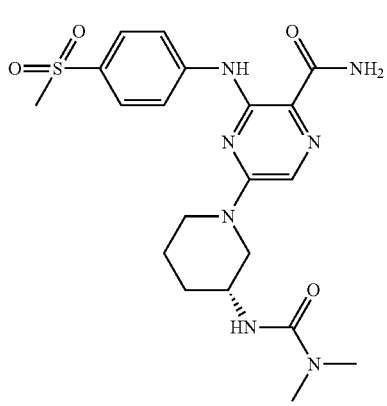

186

In a similar manner as described in Example 145, (R)-5-(3-(3,3-dimethylureido)piperidin-1-yl)-3-(4-(methylsulfonyl)phenylamino)pyrazine-2-carboxamide (186) was prepared using dimethylcarbamic chloride. MS found for C$_{20}$H$_{27}$N$_7$O$_4$S as (M+H)$^+$ 462.1, (M−H)$^-$ 460.2. UV: λ=280, 293, 319, 346, 367 nm.

Example 152

Synthesis of (R)-5-(3-(3,3-dimethylureido)piperidin-1-yl)-3-(4-(1-propionylpiperidin-4-yl)phenylamino)pyrazine-2-carboxamide (187)

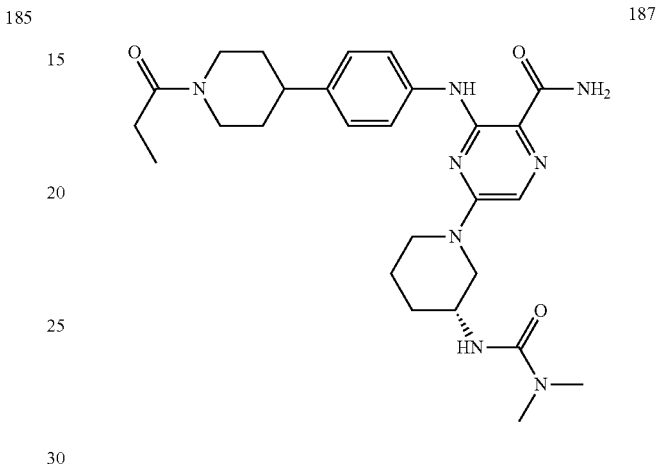

187

In a similar manner as described in Example 149, (R)-5-(3-(3,3-dimethylureido)piperidin-1-yl)-3-(4-(1-propionylpiperidin-4-yl)phenylamino)pyrazine-2-carboxamide (187) was prepared using dimethylcarbamic chloride. MS found for C$_{27}$H$_{38}$N$_8$O$_3$ as (M+H)$^+$ 523.2, (M−H)$^-$ 521.4. UV: λ=268, 276, 305, 336, 372 nm.

Example 153

Synthesis of (R)-3-(4-(1-(2-cyanoacetyl)piperidin-4-yl)phenylamino)-5-(3-(3,3-dimethylureido)piperidin-1-yl)pyrazine-2-carboxamide (188)

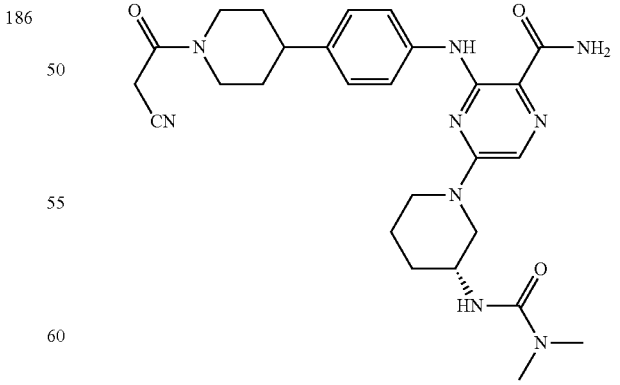

188

In a similar manner as described in Example 149, (R)-3-(4-(1-(2-cyanoacetyl)piperidin-4-yl)phenylamino)-5-(3-(3,3-dimethylureido)piperidin-1-yl)pyrazine-2-carboxamide (188) was prepared using dimethylcarbamic chloride. MS found for C$_{27}$H$_{35}$N$_9$O$_3$ as (M+H)$^+$ 534.2, (M–H)$^-$ 532.3. UV: λ=268, 277, 305, 336, 372 nm.

Example 154

Synthesis of (R)-5-(3-(3,3-dimethylureido)piperidin-1-yl)-3-(4-(piperidin-4-yl)phenylamino)pyrazine-2-carboxamide (189)

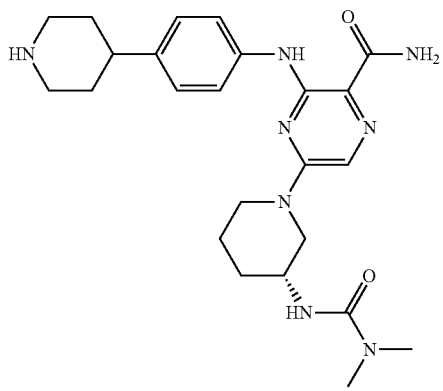

189

In a similar manner as described in Example 134, (R)-5-(3-(3,3-dimethylureido)piperidin-1-yl)-3-(4-(piperidin-4-yl)phenylamino)pyrazine-2-carboxamide (189) was prepared using dimethylcarbamic chloride. MS found for C$_{24}$H$_{34}$N$_8$O$_2$ as (M+H)$^+$ 467.2, (M–H)$^-$ (weak). UV: λ=268, 277, 306, 336, 373 nm.

Example 155

Synthesis of (R)-3-(4-(1-cyclopentylpiperidin-4-yl)phenylamino)-5-(3-(3,3-dimethylureido)piperidin-1-yl)pyrazine-2-carboxamide (190)

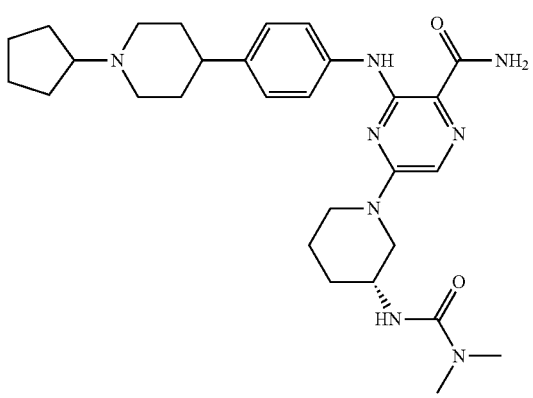

190

In a similar manner as described in Example 135, (R)-3-(4-(1-cyclopentylpiperidin-4-yl)phenylamino)-5-(3-(3,3-dimethylureido)piperidin-1-yl)pyrazine-2-carboxamide (190) was prepared using dimethylcarbamic chloride. MS found for C$_{29}$H$_{42}$N$_8$O$_2$ as (M+H)$^+$ 535.3, (M–H)$^-$ 533.4. UV: λ=268, 277, 306, 336, 373 nm. Proton NMR (CD$_3$OD): δ 7.65 (1H, s), 7.61 (2H, d, J=8.5 Hz), 7.21 (2H, d, J=8.5 Hz), 4.2 (1H, dd, J=13.0; 3.5 Hz), 4.20 (1H, m), 3.77 (1H, m), 3.71 (2H, d, J=12.5 Hz), 3.56 (1H, m), 3.27-3.10 (4H, m), 2.87 (7H, s), 2.25-2.10 (4H, m), 2.05-1.85 (7H, m), 1.80-1.65 (5H, m) ppm.

Example 156

Synthesis of (R,E)-5-((1-(4-(cyclopropyl(methyl)amino)but-2-enoyl)piperidin-3-yl)(methyl)amino)-3-(4-(morpholine-4-carbonyl)phenylamino)pyrazine-2-carboxamide (191)

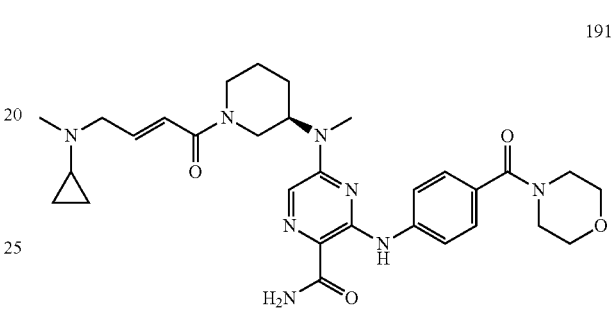

191

In a similar manner as described in Example 75, (R,E)-5-((1-(4-(cyclopropyl(methyl)amino)but-2-enoyl)piperidin-3-yl)(methyl)amino)-3-(4-(morpholine-4-carbonyl)phenylamino)pyrazine-2-carboxamide (191) was prepared using (E)-4-(cyclopropyl(methyl)amino)but-2-enoic acid. MS found for C$_{30}$H$_{40}$N$_8$O$_4$ as (M+H)$^+$ 577.2, (M–H)$^-$ 575.4. UV: λ=274, 281, 313, 344, 369 nm.

Example 157

Synthesis of (R)-5-((1-but-2-ynoylpiperidin-3-yl)(methyl)amino)-3-(4-(morpholine-4-carbonyl)phenylamino)pyrazine-2-carboxamide (192)

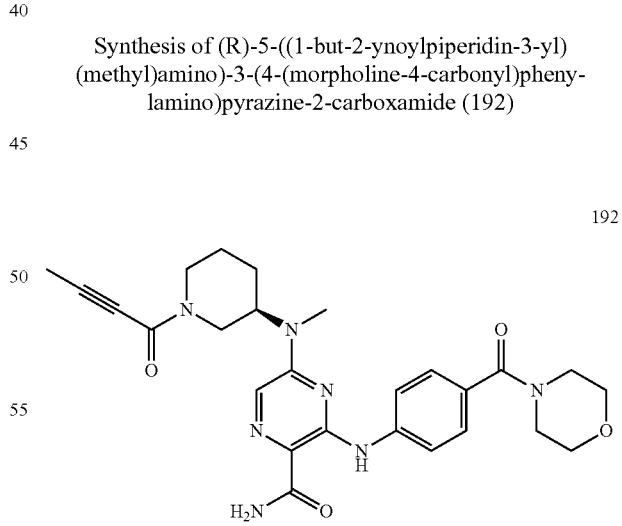

192

In a similar manner as described in Example 75, (R)-5-((1-but-2-ynoylpiperidin-3-yl)(methyl)amino)-3-(4-(morpholine-4-carbonyl)phenylamino)pyrazine-2-carboxamide (192) was prepared using 2-butynoic acid. MS found for C$_{26}$H$_{31}$N$_7$O$_4$ as (M+H)$^+$ 506.2, (M–H)$^-$ 504.3. UV: λ=313, 342, 369 nm.

Example 158

Synthesis of (R,E)-5-((1-(4-(dimethylamino)but-2-enoyl)piperidin-3-yl)(methyl)amino)-3-(4-phenoxyphenylamino)pyrazine-2-carboxamide (193)

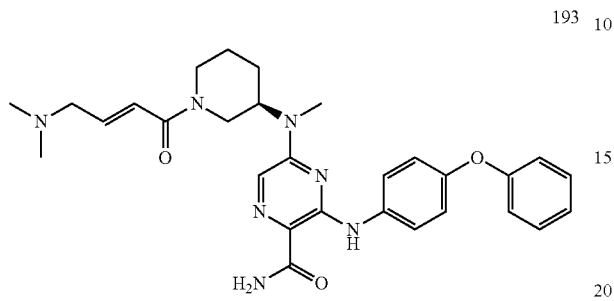

In a similar manner as described in Example 75, (R,E)-5-((1-(4-(dimethylamino)but-2-enoyl)piperidin-3-yl)(methyl)amino)-3-(4-phenoxyphenylamino)pyrazine-2-carboxamide (193) was prepared using 4-phenoxyaniline. MS found for $C_{29}H_{35}N_7O_3$ as $(M+H)^+$ 530.2, $(M-H)^-$ 528.3. UV: $\lambda$=265, 274, 302, 335, 372 nm.

Example 159

Synthesis of (R)-5-(4-cyanophenylamino)-3-(3-(4-ethoxybenzamido)piperidin-1-yl)-1,2,4-triazine-6-carboxamide (194)

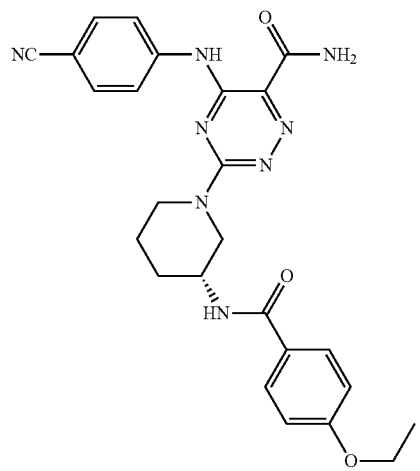

In a similar manner as described in Example 110, (R)-5-(4-cyanophenylamino)-3-(3-(4-ethoxybenzamido)piperidin-1-yl)-1,2,4-triazine-6-carboxamide (194) was prepared using 4-aminobenzonitrile and 4-ethoxybenzoic acid. MS found for $C_{25}H_{26}N_8O_3$ as $(M+H)^+$ 487.1, $(M-H)^-$ 485.3. UV: $\lambda$=275 nm.

Example 160

Synthesis of (R)-3-(4-isopropylphenylamino)-5-(3-(4-methoxybenzamido)piperidin-1-yl)pyrazine-2-carboxamide (195)

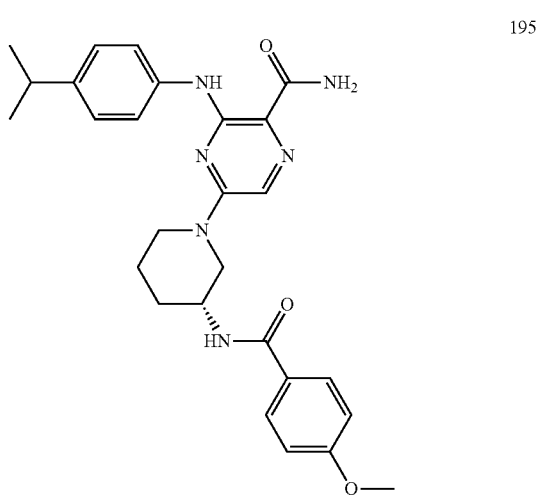 [SMILES: COc1ccc(C(=O)N[C@@H]2CCCN(c3cnc(C(N)=O)c(Nc4ccc(C(C)C)cc4)n3)C2)cc1]

In a similar manner as described in Example 110, (R)-3-(4-isopropylphenylamino)-5-(3-(4-methoxybenzamido)piperidin-1-yl)pyrazine-2-carboxamide (195) was prepared using 4-isopropylaniline. MS found for $C_{27}H_{32}N_6O_3$ as $(M+H)^+$ 489.1, $(M-H)^-$ 487.3. UV: $\lambda$=257, 279, 304, 335, 372 nm.

Example 161

Synthesis of (R)-5-(3-(4-methoxybenzamido)piperidin-1-yl)-3-(4-(1,1-dioxothiomorpholino)phenylamino)pyrazine-2-carboxamide (196)

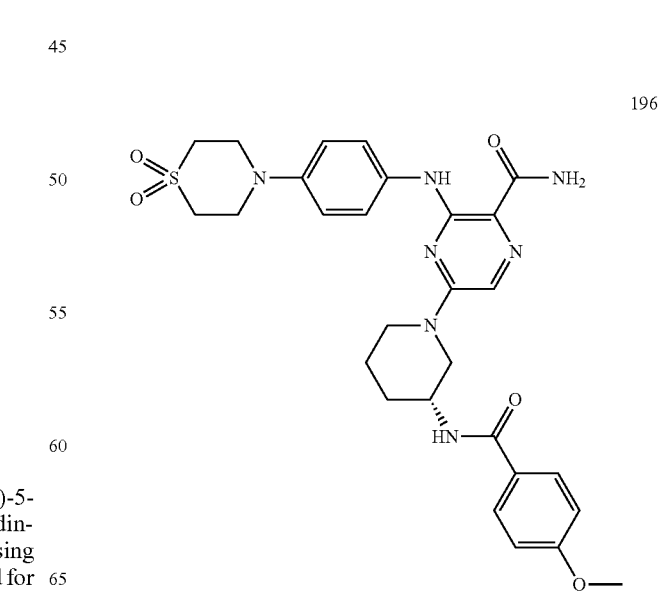

In a similar manner as described in Example 110, (R)-5-(3-(4-methoxybenzamido)piperidin-1-yl)-3-(4-dioxothiomorpholinophenylamino)pyrazine-2-carboxamide (196) was prepared using 4-(1,1-dioxothiomorpholino)aniline. MS found for $C_{28}H_{33}N_7O_5S$ as $(M+H)^+$ 580.1, $(M-H)^-$ 578.2. UV: λ=309, 349, 375 nm.

Example 162

Synthesis of (R)-3-(2-fluoro-4-(piperidin-4-yl)phenylamino)-5-(3-(4-methoxybenzamido)piperidin-1-yl)pyrazine-2-carboxamide (201)

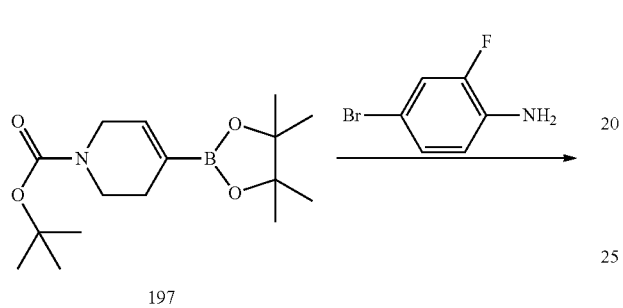

197

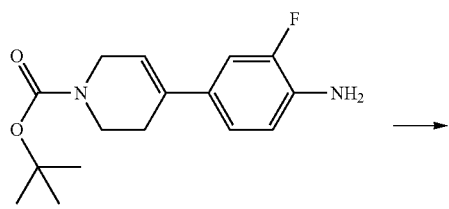

198

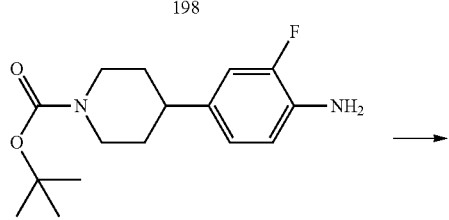

199

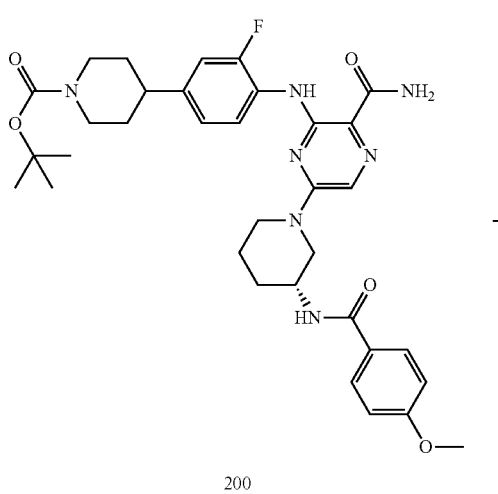

200

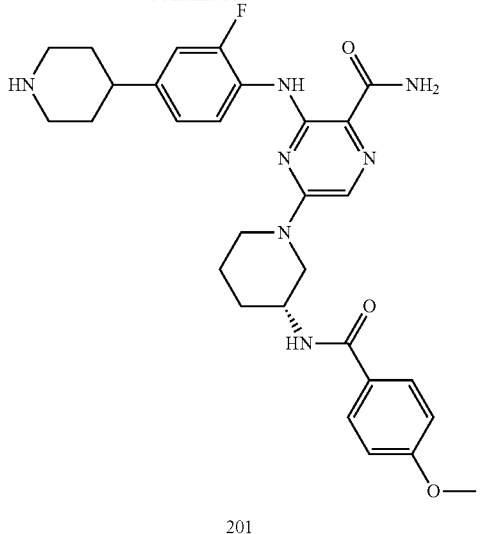 [SMILES: COc1ccc(C(=O)N[C@@H]2CCCN(c3cnc(C(N)=O)c(Nc4ccc(C5CCNCC5)cc4F)n3)C2)cc1]

201 tert-Butyl 4-(4,4,5,5-tetramethyl-1,3,2-dioxaborolan-2-yl)-5,6-dihydropyridine-1(2H)-carboxylate (197, 1.95 g, 6.32 mmol), 4-bromo-2fluoroaniline (1.00 g, 5.26 mmol), Pd(dppf)Cl$_2$.DCM (0.43 g, 0.526 mmol), K$_2$CO$_3$ (1.45 g, 10.5 mmol) were mixed in 40 mL dioxane and 20 mL water. The mixture was degassed with N$_2$ stream for 3 min and stirred at 90° C. in N$_2$ atmosphere for overnight. The mixture was cooled to RT, concentrated in vacuo, diluted with 120 mL EtOAc, washed with water ×2, dried, concentrated, and subjected to silica flash column to isolate tert-butyl 4-(4-amino-3-fluorophenyl)-5,6-dihydropyridine-1(2H)-carboxylate (198, 1.55 g, quantitative yield) using 0 to 25% EtOAc in hexane. It was dissolved in 150 mL iPrOH, and to it was hydrogenated with 10% Pd/C using a balloon for overnight. The mixture was filtered through celite, concentrated in vacuo to afford tert-butyl 4-(4-amino-3-fluorophenyl)piperidine-1-carboxylate (199) in quantitative yield.

In a similar manner as described in Example 110, (R)-tert-butyl 4-(4-(3-carbamoyl-6-(3-(4-methoxybenzamido)piperidin-1-yl)pyrazin-2-ylamino)-3-fluorophenyl)piperidine-1-carboxylate (200) was prepared using tert-butyl 4-(4-amino-3-fluorophenyl)piperidine-1-carboxylate. It was treated with 1:1 TFA/DCM at RT for 30 min, and (R)-3-(2-fluoro-4-(piperidin-4-yl)phenylamino)-5-(3-(4-methoxybenzamido)piperidin-1-yl)pyrazine-2-carboxamide (201) was isolated as HCl salt using reverse phase prep HPLC using 5 mM HCl (aq) and neat MeCN as mobile phases. MS found for $C_{29}H_{34}FN_7O_3$ as $(M+H)^+$ 548.2, $(M-H)^-$ 546.3. UV: λ=257, 280, 306, 334, 369 nm. Proton NMR (CD$_3$OD): δ 8.34 (1H, m), 7.79 (2H, d, J=9.0 Hz), 7.72 (1H, s), 7.03 (1H, d, J=12.5 Hz), 6.99 (2H, d, J=8.5 Hz), 6.96 (1H, d, J=9.5 Hz), 4.46 (1H, m), 4.18 (1H, m), 4.12 (1H, m), 3.86 (3H, m), 3.45 (1H, s), 3.42 (1H, s), 3.25 (2H, m), 3.08 (2H, m), 2.80 (1H, m), 2.11 (1H, m), 2.01-1.94 (3H, m), 1.81-1.70 (4H, m) ppm.

Example 163

Synthesis of (R)-3-(3-fluoro-4-(piperidin-4-yl)phenylamino)-5-(3-(4-methoxybenzamido)piperidin-1-yl)pyrazine-2-carboxamide (202)

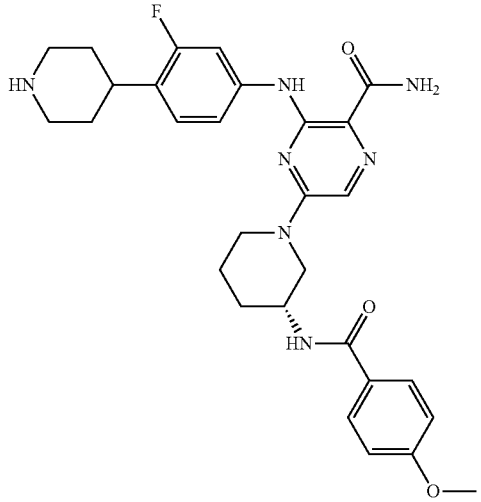

202

In a similar manner as described in Example 162, (R)-3-(3-fluoro-4-(piperidin-4-yl)phenylamino)-5-(3-(4-methoxybenzamido)piperidin-1-yl)pyrazine-2-carboxamide (202) was prepared using 4-bromo-3-fluoroaniline. MS found for $C_{29}H_{34}FN_7O_3$ as (M+H)+ 548.2, (M–H)− 546.3. UV: λ=259, 281, 307, 335, 372 nm NMR (CD$_3$OD): δ 7.78 (2H, d, J=9.0 Hz), 7.71 (1H, s), 7.61 (1H, d, J=13.5 Hz), 7.27 (1H, d, J=8.5 Hz), 7.16 (1H, t, J=8.5 Hz), 6.97 (2H, d, J=8.5 Hz), 4.45 (1H, m), 4.23 (1H, m), 4.10 (1H, m), 3.86 (3H, m), 3.46 (2H, m), 3.30 (2H, m), 3.13-3.06 (3H, m), 2.13 (1H, m), 2.04-1.86 (5H, m), 1.82-1.70 (2H, m) ppm.

Example 164

Synthesis of (R)-5-(3-(4-methoxybenzamido)piperidin-1-yl)-3-(4-(piperidin-1-yl)phenylamino)pyrazine-2-carboxamide (203)

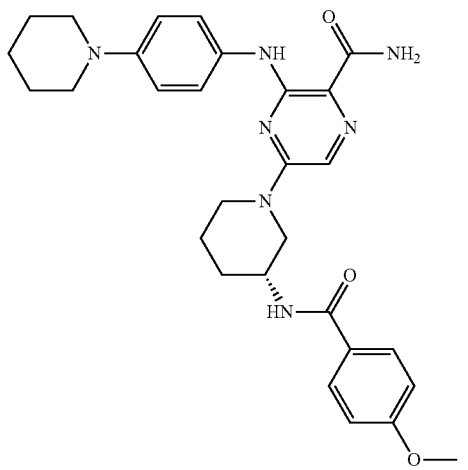

203

In a similar manner as described in Example 110, (R)-5-(3-(4-methoxybenzamido)piperidin-1-yl)-3-(4-(piperidin-1-yl)phenylamino)pyrazine-2-carboxamide (203) was prepared using 4-(piperidin-1-yl)aniline. MS found for $C_{29}H_{35}N_7O_3$ as (M+H)+ 530.4. UV: λ=261, 285, 308, 335, 369 nm NMR (CD$_3$OD): δ 7.83 (4H, m), 7.76 (1H, s), 7.49 (2H, d, J=9.0 Hz), 7.00 (2H, d, J=9.0 Hz), 4.52 (1H, m), 4.17 (1H, m), 4.13 (1H, m), 3.86 (3H, m), 3.46 (2H, m), 3.22 (1H, m), 2.13 (1H, m), 2.01-1.94 (6H, m), 1.84-1.69 (3H, m) ppm.

Example 165

Synthesis of (R)-5-(3-(3,3-dimethylureido)piperidin-1-yl)-3-(4-(1-methylpiperidin-4-yl)phenylamino)pyrazine-2-carboxamide

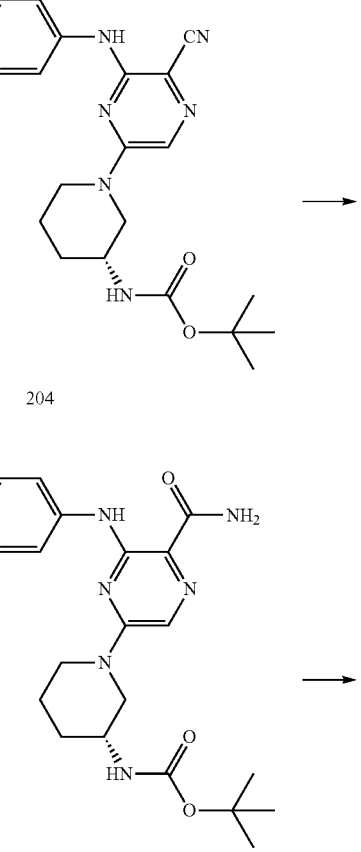

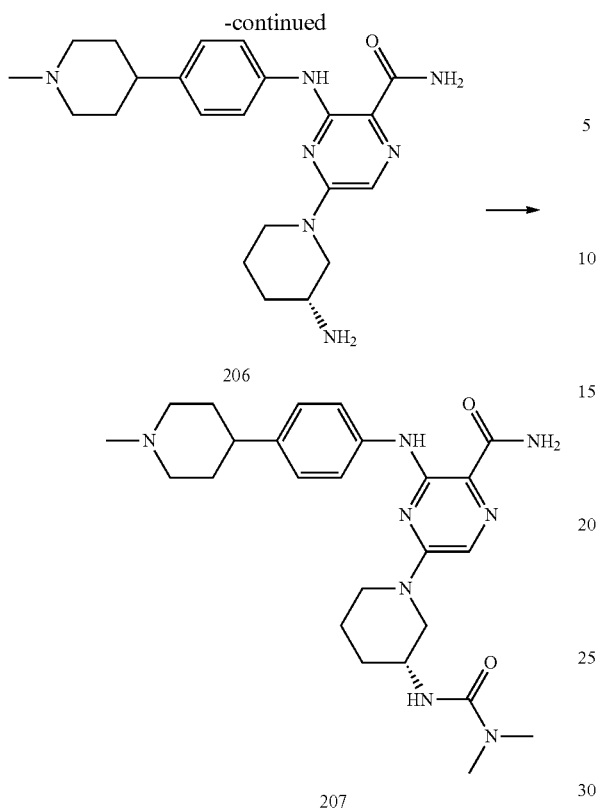

The mixture of (R)-tert-butyl 1-(6-chloro-5-cyanopyrazin-2-yl)piperidin-3-ylcarbamate (87, 240 mg, 0.71 mmol), 4-(1-methylpiperidin-4-yl)aniline (280 mg, 1.42 mmol), fine-powder cesium carbonate (930 mg, 2.84 mmol), Pd(OAc)$_2$ (32 mg, 0.14 mmol), BINAP (88 mg, 0.14 mmol) in 20 mL dioxane was degassed with nitrogen stream for 3 min. It was then stirred in 115° C. bath in nitrogen atmosphere for 2 hours. The mixture was cooled to RT, diluted with 100 mL EtOAc, and filtered. The filtrate was concentrated in vacuo and subjected to silica flash column using 0 to 15% MeOH in chloroform to isolate (R)-tert-butyl 1-(5-cyano-6-(4-(1-methylpiperidin-4-yl)phenylamino)pyrazin-2-yl)piperidin-3-ylcarbamate (204) in >90% yield. It was dissolved in 30 mL MeOH and 3 mL DMSO. To it were added two NaOH solid bead (about 200 mg) and then 1 mL 30% H$_2$O$_2$. The mixture was stirred at RT for 2 hours, diluted with 10 mL MeCN, stirred for 5 min, and concentrated on rotavap. The residue was diluted with 120 mL EtOAc, washed with water, concentrated in vacuo to dryness to give crude (R)-tert-butyl 1-(5-carbamoyl-6-(4-(1-methylpiperidin-4-yl)phenylamino)pyrazin-2-yl)piperidin-3-ylcarbamate (205). It was treated with 40 mL commercial 4N HCl in dioxane for 40 min, and concentrated in vacuo to afford crude (R)-5-(3-aminopiperidin-1-yl)-3-(4-(1-methylpiperidin-4-yl)phenylamino)pyrazine-2-carboxamide (206) hydrochloride. Crude 206 hydrochloride (60 mg, 0.12 mmol) was dissolved in 3 mL DMF. To it were added DIEA (210 µL, 1.2 mmol) and dimethylcarbamoyl chloride (34 µL, 0.36 mmol). The mixture was stirred at RT for 1.5 hour, acidified with 0.3 mL TFA, and directly subjected to reverse phase prep HPLC using 5 mM HCl (aq) and neat MeCN as mobile phases to isolate (R)-5-(3-(3,3-dimethylureido)piperidin-1-yl)-3-(4-O-methylpiperidin-4-yl)phenylamino)pyrazine-2-carboxamide (207) as HCl salt (36 mg). MS found for C$_{25}$H$_{36}$N$_8$O$_2$ as (M+H)$^+$ 481.2, (M–H)$^-$ 479.3. UV: λ=268, 277, 306, 336, 372 nm.

Example 166

Synthesis of (R)-5-(3-(3-ethyl-3-methylureido)piperidin-1-yl)-3-(4-(1-methylpiperidin-4-yl)phenylamino)pyrazine-2-carboxamide

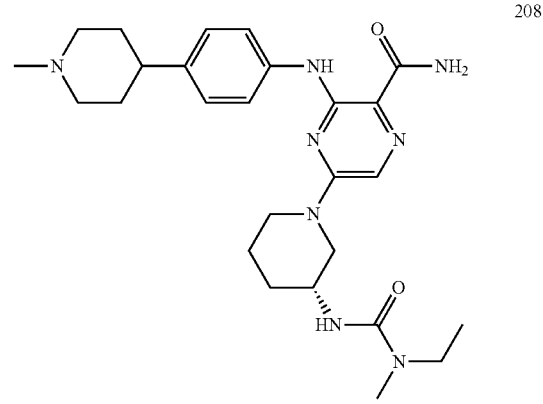 [SMILES: CCN(C)C(=O)N[C@@H]1CCCN(c2cnc(C(N)=O)c(Nc3ccc(C4CCN(C)CC4)cc3)n2)C1]

In a similar manner as described in Example 165, (R)-5-(3-(3-ethyl-3-methylureido)piperidin-1-yl)-3-(4-(1-methylpiperidin-4-yl)phenylamino)pyrazine-2-carboxamide (208) was prepared using ethyl(methyl)carbamic chloride. MS found for C$_{26}$H$_{38}$N$_8$O$_2$ as (M+H)$^+$ 495.2, (M–H)$^-$ 493.3. UV: λ=268, 277, 306, 336, 373 nm.

Example 167

Synthesis of (R)-5-(3-(3,3-diethylureido)piperidin-1-yl)-3-(4-(1-methylpiperidin-4-yl)phenylamino)pyrazine-2-carboxamide

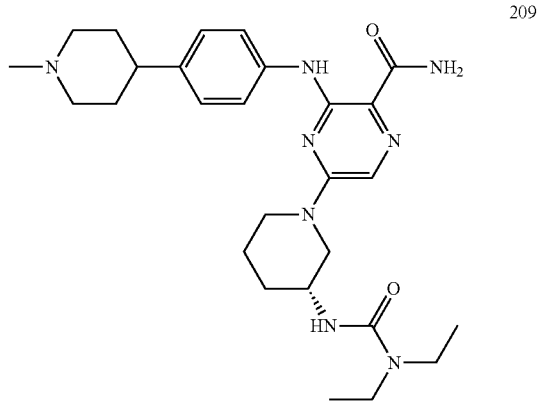 [SMILES: CCN(CC)C(=O)N[C@@H]1CCCN(c2cnc(C(N)=O)c(Nc3ccc(C4CCN(C)CC4)cc3)n2)C1]

In a similar manner as described in Example 165, (R)-5-(3-(3,3-diethylureido)piperidin-1-yl)-3-(4-(1-methylpiperidin-4-yl)phenylamino)pyrazine-2-carboxamide (209) was

Example 168

Synthesis of (R)-5-(3-(4-fluorobenzamido)piperidin-1-yl)-3-(4-(1-methylpiperidin-4-yl)phenylamino)pyrazine-2-carboxamide prepared using diethylcarbamic chloride. MS found for $C_{27}H_{40}N_8O_2$ as (M+H)$^+$ 509.2, (M–H)$^-$ 507.4. UV: λ=267, 277, 306, 336, 372 nm.

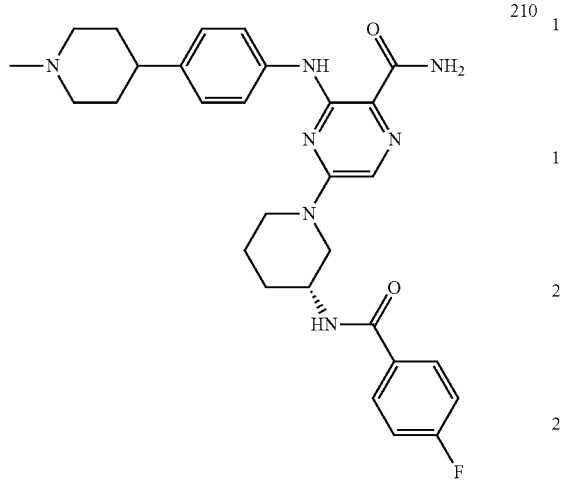

210

In a similar manner as described in Example 165, (R)-5-(3-(4-fluorobenzamido)piperidin-1-yl)-3-(4-(1-methylpiperidin-4-yl)phenylamino)pyrazine-2-carboxamide (210) was prepared using 4-fluorobenzoyl chloride. MS found for $C_{29}H_{34}FN_7O_2$ as (M+H)$^+$ 532.1, (M–H)$^-$ 530.3. UV: λ=266, 276, 305, 336, 372 nm.

Example 169

Synthesis of (R)-5-(3-(4-ethoxybenzamido)piperidin-1-yl)-3-(4-(1-methylpiperidin-4-yl)phenylamino)pyrazine-2-carboxamide

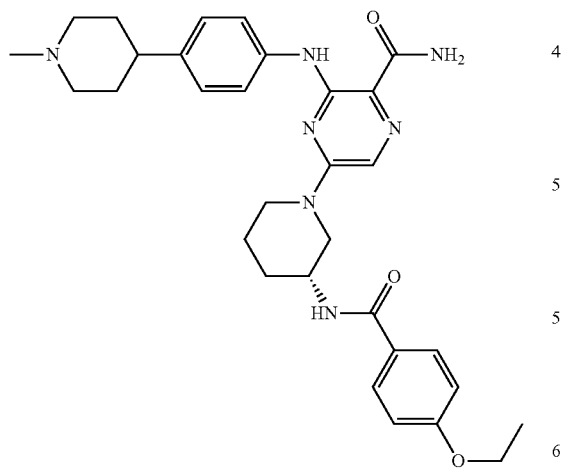

211

In a similar manner as described in Example 165, ((R)-5-(3-(4-ethoxybenzamido)piperidin-1-yl)-3-(4-(1-methylpiperidin-4-yl)phenylamino)pyrazine-2-carboxamide (210) was prepared using 4-ethoxybenzoic acid and PyBOP. MS found for $C_{31}H_{39}N_7O_3$ as (M+H)$^+$ 558.2, (M–H)$^-$ 556.3. UV: λ=259, 280, 305, 336, 372 nm.

Example 170

Synthesis of (R)-3-(4-(1-(dimethylcarbamoyl)piperidin-4-yl)phenylamino)-5-(3-(3,3-dimethylureido)piperidin-1-yl)pyrazine-2-carboxamide

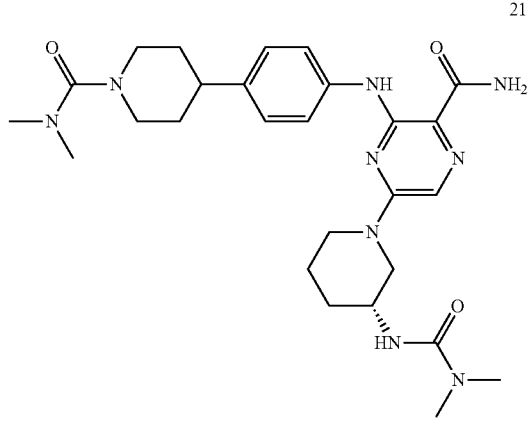

212

(R)-5-(3-(3,3-Dimethylureido)piperidin-1-yl)-3-(4-(piperidin-4-yl)phenylamino)pyrazine-2-carboxamide (189) TFA salt (115 mg, 0.20 mmol) was dissolved in 4 mL NMP. To it were added DIEA (350 µL, 2.0 mmol) and then dimethylcarbamoyl chloride (55 µL, 0.60 mmol). The mixture was stirred at RT for 30 min, quenched with 0.5 mL TFA, and directly subjected to reverse phase prep HPLC using 5 mM HCl (aq) and neat MeCN as mobile phases to isolate (R)-3-(4-(1-(dimethylcarbamoyl)piperidin-4-yl)phenylamino)-5-(3-(3,3-dimethylureido)piperidin-1-yl)pyrazine-2-carboxamide (207) as HCl salt (90 mg). MS found for $C_{27}H_{39}N_9O_3$ as (M+H)$^+$ 538.7, (M–H)$^-$ 536.3. UV: λ=267, 276, 305, 336, 373 nm. Proton NMR (CD$_3$OD): δ 7.62 (1H, s), 7.55 (2H, d, J=8.5 Hz), 7.17 (2H, d, J=8.5 Hz), 4.33 (1H, m), 4.20 (1H, m), 3.80-3.73 (3H, m), 3.19 (1H, m), 3.09 (1H, m), 2.93 (2H, m), 2.89 (6H, s), 2.88 (6H, s), 2.67 (1H, m) 2.02 (1H, m), 1.88-1.82 (3H, m), 1.72-1.62 (4H, m) ppm.

Example 171

Synthesis of (R)-3-(4-(1-(cyclopropanecarbonyl)piperidin-4-yl)phenylamino)-5-(3-(3,3-dimethylureido)piperidin-1-yl)pyrazine-2-carboxamide

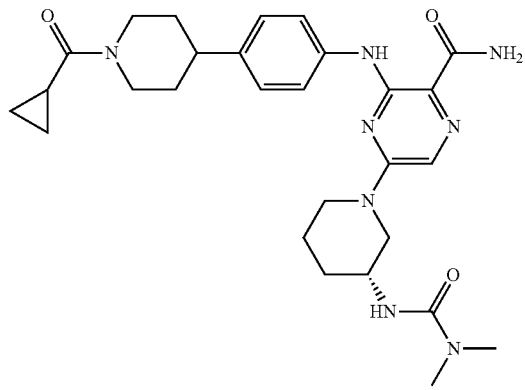

213

In a similar manner as described in Example 170, (R)-3-(4-(1-(cyclopropanecarbonyl)piperidin-4-yl)phenylamino)-5-(3-(3,3-dimethylureido)piperidin-1-yl)pyrazine-2-carboxamide (213) was prepared using cyclopropanecarbonyl chloride. MS found for $C_{28}H_{38}N_8O_3$ as $(M+H)^+$ 535.7, $(M-H)^-$ 533.3. UV: λ=268, 277, 305, 336, 372 nm. Proton NMR (CD$_3$OD): δ 7.62 (1H, s), 7.56 (2H, d, J=8.5 Hz), 7.18 (2H, d, J=8.5 Hz), 4.65 (1H, m), 4.46 (1H, m), 4.35 (1H, m), 4.20 (1H, m), 3.76 (1H, m), 3.28 (1H, m), 3.17 (1H, m), 3.08 (1H, m), 2.88 (6H, s), 2.79 (1H, m), 2.75 (1H, m), 2.02 (2H, m), 1.96 (1H, m), 1.87 (2H, m), 1.70-1.55 (4H, m), 0.89 (2H, m), 0.82 (2H, m) ppm.

Example 172

Synthesis of (R)-5-(3-(3,3-dimethylureido)piperidin-1-yl)-3-(4-(1-(methylsulfonyl)piperidin-4-yl)phenylamino)pyrazine-2-carboxamide

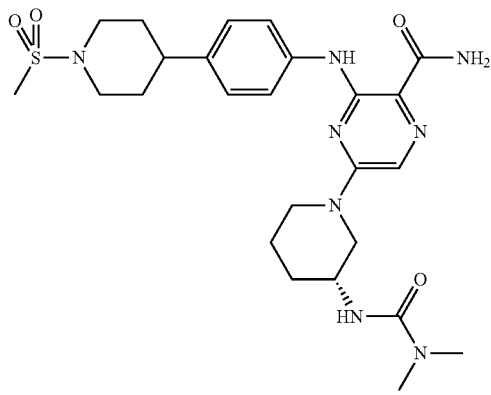

214

In a similar manner as described in Example 170, (R)-5-(3-(3,3-dimethylureido)piperidin-1-yl)-3-(4-(1-(methylsulfonyl)piperidin-4-yl)phenylamino)pyrazine-2-carboxamide (214) was prepared using methanesulfonyl chloride. MS found for $C_{25}H_{36}N_8O_4S$ as $(M+H)^+$ 545.6, $(M-H)^-$ 543.2. UV: λ=268, 276, 305, 336, 372 nm. Proton NMR (CD$_3$OD): δ 7.63 (1H, s), 7.56 (2H, d, J=8.5 Hz), 7.19 (2H, d, J=8.5 Hz), 4.35 (1H, m), 4.21 (1H, m), 3.84 (2H, m), 3.76 (1H, m), 3.20 (1H, m), 3.10 (1H, m), 2.89 (6H, s), 2.86 (3H, s), 2.85-2.80 (2H, m), 2.64 (1H, m), 2.05 (1H, m), 1.96 (1H, m), 1.88 (1H, m), 1.78 (2H, m), 1.66 (2H, m) ppm.

Example 173

Synthesis of (R)-3-(4-(1-(N,N-dimethylsulfamoyl)piperidin-4-yl)phenylamino)-5-(3-(3,3-dimethylureido)piperidin-1-yl)pyrazine-2-carboxamide

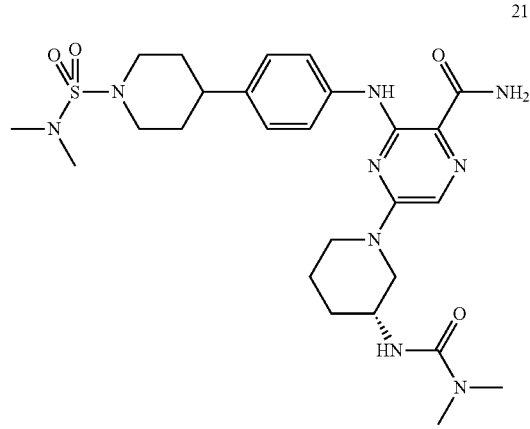

215

In a similar manner as described in Example 170, (R)-3-(4-(1-(N,N-dimethylsulfamoyl)piperidin-4-yl)phenylamino)-5-(3-(3,3-dimethylureido)piperidin-1-yl)pyrazine-2-carboxamide (215) was prepared using dimethylsulfamoyl chloride. MS found for $C_{26}H_{39}N_9O_4S$ as $(M+H)^+$ 571.8, $(M-H)^-$ 569.3. UV: λ=266, 276, 305, 335, 373 nm.

Example 174

Synthesis of (R)-5-(3-(3,3-dimethylureido)piperidin-1-yl)-3-(4-(1-(pyridin-2-yl)piperidin-4-yl)phenylamino)pyrazine-2-carboxamide

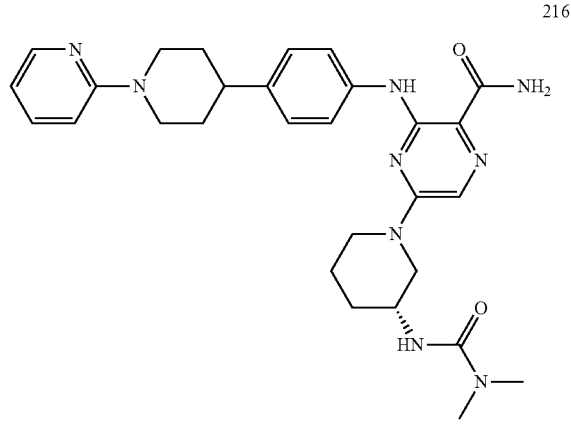 [SMILES: CN(C)C(=O)N[C@@H]1CCCN(c2cnc(C(N)=O)c(Nc3ccc(C4CCN(c5ccccn5)CC4)cc3)n2)C1]

216

(R)-5-(3-(3,3-Dimethylureido)piperidin-1-yl)-3-(4-(piperidin-4-yl)phenylamino)pyrazine-2-carboxamide (189) HCl salt (44 mg, 0.082 mmol) was dissolved in 4 mL NMP in a sealed tube. To it were added DIEA (150 μL, 0.82 mmol) and then 2-fluoropyridine (35 μL, 0.41 mmol). The mixture was stirred at 120° C. for 3 hours, quenched with 0.5 mL TFA, and directly subjected to reverse phase prep HPLC using 5 mM HCl (aq) and neat MeCN as mobile phases to isolate (R)-5-(3-(3,3-dimethylureido)piperidin-1-yl)-3-(4-(1-(pyridin-2-yl)piperidin-4-yl)phenylamino)pyrazine-2-carboxamide (216) as HCl salt. MS found for $C_{29}H_{37}N_9O_2$ as $(M+H)^+$ 544.4. UV: λ=307, 344, 370 nm.

Example 175

Synthesis of (R)-3-(4-(1-cyclobutylpiperidin-4-yl)phenylamino)-5-(3-(3,3-dimethylureido)piperidin-1-yl)pyrazine-2-carboxamide

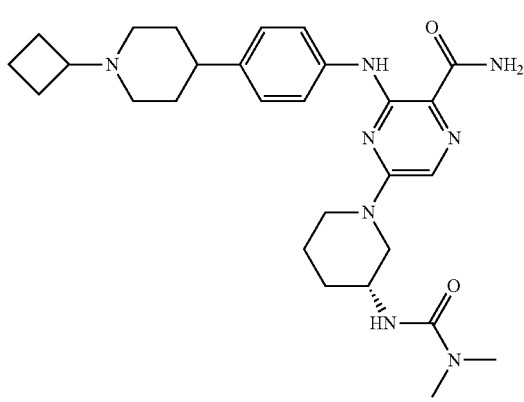

217

(R)-5-(3-(3,3-Dimethylureido)piperidin-1-yl)-3-(4-(piperidin-4-yl)phenylamino)pyrazine-2-carboxamide (189) TFA salt (115 mg, 0.20 mmol) was dissolved in 10 mL dioxane and 10 mL 1,2-dichloroethane (DCE) with DIEA (175 µL, 1.0 mmol). To it was added cyclobutanone (450 µL, 6.0 mmol), and the mixture was stirred at RT for overnight. To it were added HOAc (112 µL, 2.0 mmol) and then $NaBH(OAc)_3$ (212 mg, 1.0 mmol). The mixture was stirred at RT for 2 hours, diluted with 10 mL MeOH, concentrated in vacuo, acidified with 0.5 mL TFA, and directly subjected to reverse phase prep HPLC using 5 mM HCl (aq) and neat MeCN as mobile phases to isolate (R)-3-(4-(1-cyclobutylpiperidin-4-yl)phenylamino)-5-(3-(3,3-dimethylureido)piperidin-1-yl)pyrazine-2-carboxamide (217) as HCl salt (73 mg). MS found for $C_{28}H_{40}N_8O_2$ as $(M+H)^+$ 521.7, $(M-H)^-$ 519.3. UV: λ=268, 277, 306, 336, 373 nm. Proton NMR ($CD_3OD$): δ 7.65 (1H, s), 7.61 (2H, d, J=8.5 Hz), 7.21 (2H, d, J=8.5 Hz), 4.29 (1H, m), 4.20 (1H, m), 3.78 (1H, m), 3.70 (1H, m), 3.60 (1H, s), 3.57 (1H, s), 3.30-3.20 (2H, m), 2.92 (2H, m), 2.87 (6H, s), 2.86 (1H, m), 2.37 (2H, m), 2.27 (2H, m), 2.14 (2H, m), 2.03 (1H, m), 1.90 (5H, m), 1.67 (2H, m) ppm.

Example 176

Synthesis of (R)-5-(3-(3,3-dimethylureido)piperidin-1-yl)-3-(4-(1-(tetrahydro-2H-pyran-4-yl)piperidin-4-yl)phenylamino)pyrazine-2-carboxamide

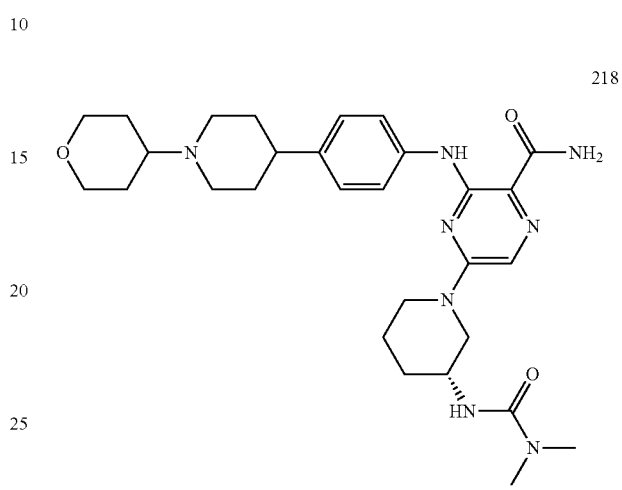

218

In a similar manner as described in Example 175, (R)-5-(3-(3,3-dimethylureido)piperidin-1-yl)-3-(4-(1-(tetrahydro-2H-pyran-4-yl)piperidin-4-yl)phenylamino)pyrazine-2-carboxamide (218) was prepared using dihydro-2H-pyran-4(3H)-one. MS found for $C_{29}H_{42}N_8O_3$ as $(M+H)^+$ 551.5. UV: λ=268, 277, 306, 336, 373 nm. Compound 219, (R)-5-(3-(3,3-dimethylureido)piperidin-1-yl)-3-(4-(1-(2-(2-hydroxyethoxyl)ethyl)piperidin-4-yl)phenylamino)pyrazine-2-carboxamide, was also found and isolated as a by-product.

Example 177

Synthesis of (R)-5-(3-(3,3-dimethylureido)piperidin-1-yl)-3-(4-(1-(2-(2-hydroxyethoxyl)ethyl)piperidin-4-yl)phenylamino)pyrazine-2-carboxamide

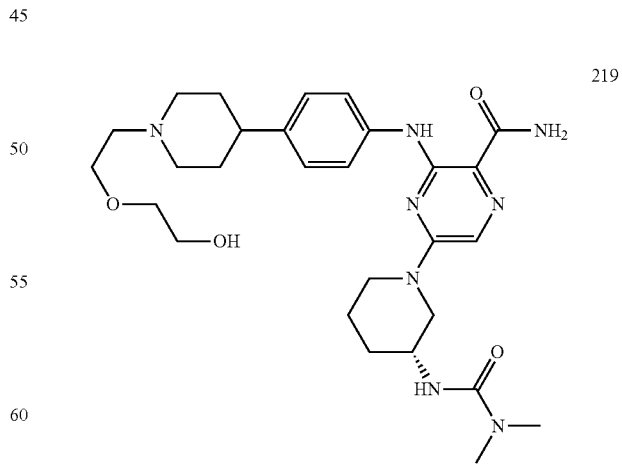

219

(R)-5-(3-(3,3-Dimethylureido)piperidin-1-yl)-3-(4-(1-(2-(2-hydroxyethoxyl)ethyl)piperidin-4-yl)phenylamino)pyrazine-2-carboxamide (219) was found and isolated as a by-product in the final step for the preparation of (R)-5-(3-(3,3- dimethylureido)piperidin-1-yl)-3-(4-(1-(tetrahydro-2H-pyran-4-yl)piperidin-4-yl)phenylamino)pyrazine-2-carboxamide (218). MS found for $C_{28}H_{42}N_8O_4$ as $(M+H)^+$ 555.6, $(M-H)^-$ 553.3. UV: λ=268, 277, 306, 336, 373 nm.

Example 178

Synthesis of (R)-5-(3-(3,3-dimethylureido)piperidin-1-yl)-3-(4-(1-(oxetan-3-yl)piperidin-4-yl)phenylamino)pyrazine-2-carboxamide

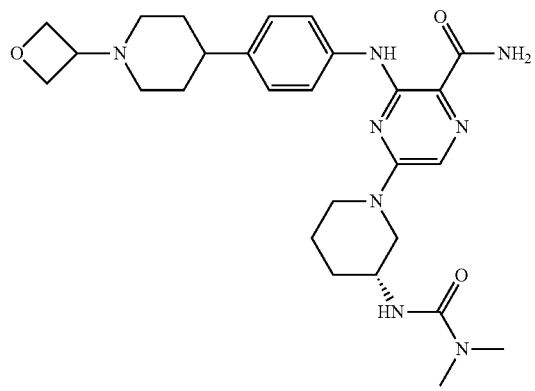

220

In a similar manner as described in Example 175, (R)-5-(3-(3,3-dimethylureido)piperidin-1-yl)-3-(4-(1-(oxetan-3-yl)piperidin-4-yl)phenylamino)pyrazine-2-carboxamide (220) was prepared using 3-oxetanone. MS found for $C_{27}H_{38}N_8O_3$ as $(M+H)^+$ 523.8, $(M-H)^-$ 521.3. UV: λ=268, 277, 306, 336, 373 nm. Proton NMR (CD$_3$OD): δ 7.63 (1H, s), 7.56 (2H, d, J=8.5 Hz), 7.19 (2H, d, J=8.5 Hz), 4.75 (2H, t, J=7.0 Hz), 4.68 (2H, t, J=6.5 Hz), 4.31 (1H, m), 4.21 (1H, m), 3.74 (2H, m), 3.22 (1H, m), 3.16 (1H, m), 3.05 (2H, m), 2.88 (6H, s), 2.60 (1H, m), 2.21 (2H, m), 2.02 (1H, m), 1.94-1.78 (5H, m), 1.64 (2H, m) ppm.

Example 179

Synthesis of (R)-5-(3-(3,3-dimethylureido)piperidin-1-yl)-3-(4-fluorophenylamino)pyrazine-2-carboxamide

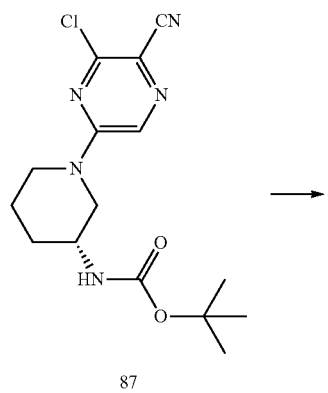

87

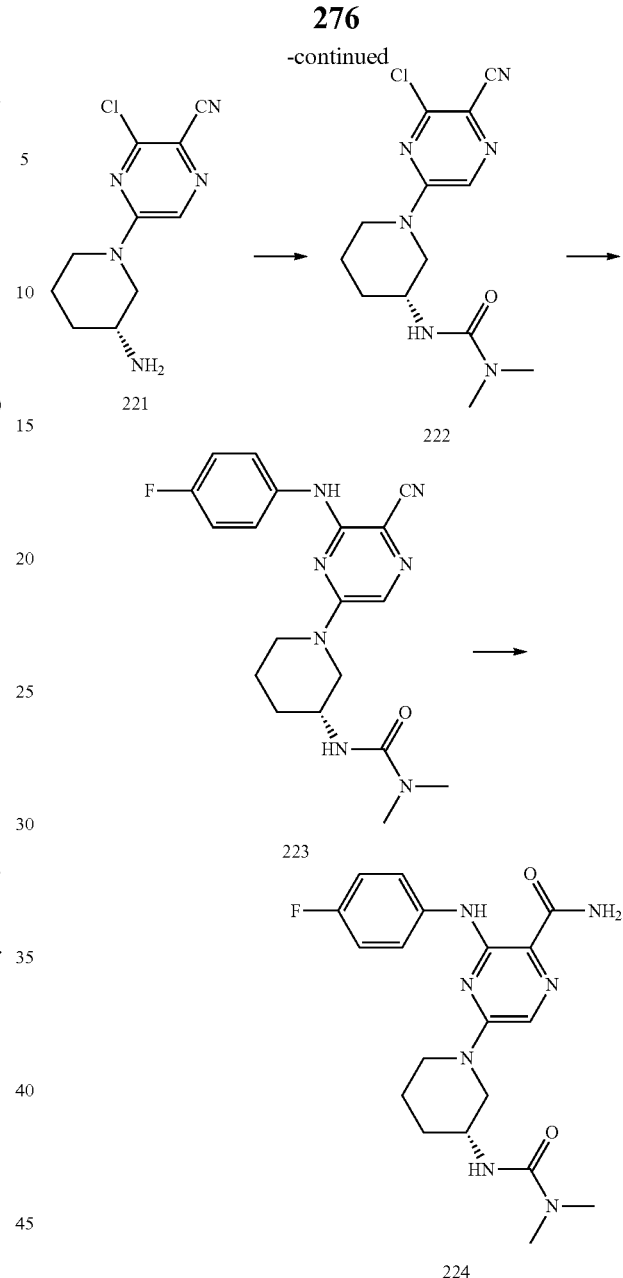

(R)-tert-Butyl 1-(6-chloro-5-cyanopyrazin-2-yl)piperidin-3-ylcarbamate (87, 2.00 g, 5.93 mmol) was treated with 25 mL commercial 4N HCl in dioxane at RT for 2 hours. It was concentrated in vacuo to afford crude (R)-5-(3-aminopiperidin-1-yl)-3-chloropyrazine-2-carbonitrile (221) hydrochloride as white solid. It was dissolved in 10 mL DMF and 50 mL dioxane. To it were added DIEA (8.25 mL, 47.4 mmol) and then dropwise dimethylcarbamoyl chloride (1.64 mL, 17.8 mmol). The mixture was stirred at RT for 3 hours. It was concentrated in vacuo, diluted with 200 mL EtOAc, washed with water ×2, dried, concentrated in vacuo, subjected to silica flash column using 0 to 4% MeOH in DCM to isolate (R)-3-(1-(6-chloro-5-cyanopyrazin-2-yl)piperidin-3-yl)-1,1-dimethylurea (222) (1.47 g, 80%) as a white solid.

(R)-3-(1-(6-chloro-5-cyanopyrazin-2-yl)piperidin-3-yl)-1,1-dimethylurea (222, 40 mg, 0.13 mmol), 4-fluoroaniline (29 mg, 0.26 mmol), fine-powder cesium carbonate (170 mg, 0.52 mmol), Pd(OAc)$_2$ (10 mg, 0.04 mmol), BINAP (25 mg, 0.04 mmol) in 15 mL dioxane was degassed with nitrogen stream for 3 mM It was then stirred in 115° C. bath in nitrogen atmosphere for 1 hour. The mixture was cooled to RT, diluted with 60 mL EtOAc, and filtered. The filtrate was concentrated in vacuo and subjected to silica flash column using 0 to 7% MeOH in chloroform to isolate (R)-3-(1-(5-cyano-6-(4-fluorophenylamino)pyrazin-2-yl)piperidin-3-yl)-1,1-dimethylurea (223). It was dissolved in 10 mL MeOH and 2 mL DMSO. To it were added one NaOH solid bead (about 100 mg) and then 0.5 mL 30% $H_2O_2$. The mixture was stirred at RT for 1.5 hour, diluted with 10 mL MeCN, stirred for 5 mM, concentrated in vacuo, acidified with 0.2 mL TFA, and directly subjected to reverse phase prep HPLC using 5 mM HCl (aq) and neat MeCN as mobile phases to isolate (R)-5-(3-(3,3-dimethylureido)piperidin-1-yl)-3-(4-fluorophenylamino)pyrazine-2-carboxamide (224) as HCl salt (40 mg, 76%). MS found for $C_{19}H_{24}FN_7O_2$ as $(M+H)^+$ 402.1, $(M-H)^-$ 400.1. UV: λ=264, 274, 300, 331, 372 nm. Proton NMR (CD$_3$OD): δ 7.63 (1H, s), 7.59 (2H, m), 7.02 (2H, t, J=9.0 Hz), 4.34 (1H, m), 4.19 (1H, m), 3.74 (1H, m), 3.17 (1H, m), 3.05 (1H, m), 2.89 (6H, s), 2.02 (1H, m), 1.86 (1H, m), 1.70-1.61 (2H, m) ppm.

Example 180

Synthesis of (R)-5-(3-(3,3-dimethylureido)piperidin-1-yl)-3-(phenylamino)pyrazine-2-carboxamide

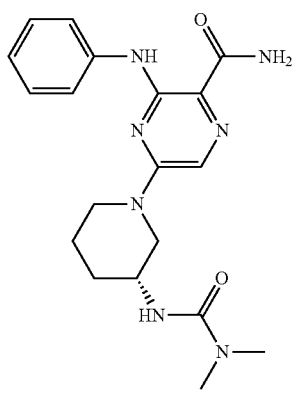

225

In a similar manner as described in Example 179, (R)-5-(3-(3,3-dimethylureido)piperidin-1-yl)-3-(phenylamino)pyrazine-2-carboxamide (225) was prepared using aniline. MS found for $C_{19}H_{25}N_7O_2$ as $(M+H)^+$ 384.4, $(M-H)^-$ 382.1. UV: λ=266, 276, 306, 333, 372 nm. Proton NMR (CD$_3$OD): δ 7.64 (1H, s), 7.60 (2H, d, J=8.0 Hz), 7.28 (2H, t, J=8.5 Hz), 6.98 (1H, t, J=7.5 Hz), 4.32 (1H, m), 4.21 (1H, m), 3.75 (1H, m), 3.20 (1H, m), 3.13 (1H, m), 2.88 (6H, s), 2.02 (1H, m), 1.86 (1H, m), 1.70-1.60 (2H, m) ppm.

Example 181

Synthesis of (R)-3-(4-chlorophenylamino)-5-(3-(3,3-dimethylureido)piperidin-1-yl)pyrazine-2-carboxamide

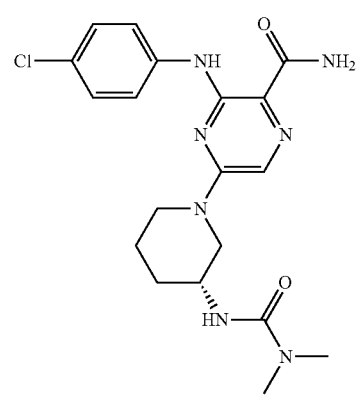

226

In a similar manner as described in Example 179, (R)-3-(4-chlorophenylamino)-5-(3-(3,3-dimethylureido)piperidin-1-yl)pyrazine-2-carboxamide (226) was prepared using 4-chloroaniline. MS found for $C_{19}H_{24}ClN_7O_2$ as $(M+H)^+$ 418.1 (chloro pattern), $(M-H)^-$ 416.1 (chloro pattern). UV: λ=269, 278, 306, 335, 370 nm. Proton NMR (CD$_3$OD): δ 7.65 (1H, s), 7.60 (2H, d, J=9.0 Hz), 7.26 (2H, d, J=9.0 Hz), 4.37 (1H, m), 4.19 (1H, m), 3.75 (1H, m), 3.19 (1H, m), 3.05 (1H, m), 2.89 (6H, s), 2.02 (1H, m), 1.87 (1H, m), 1.70-1.60 (2H, m) ppm.

Example 182

Synthesis of (R)-3-(4-chloro-3-methoxyphenylamino)-5-(3-(3,3-dimethylureido)piperidin-1-yl)pyrazine-2-carboxamide

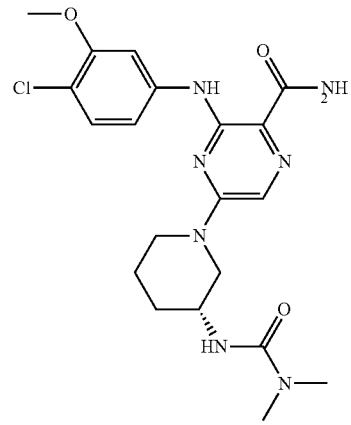

227

In a similar manner as described in Example 179, (R)-3-(4-chloro-3-methoxyphenylamino)-5-(3-(3,3-dimethylureido)piperidin-1-yl)pyrazine-2-carboxamide (227) was prepared using 4-chloro-3-methoxyaniline. MS found for $C_{20}H_{26}ClN_7O_3$ as $(M+H)^+$ 448.1 (chloro pattern), $(M-H)^-$ 446.1 (chloro pattern). UV: $\lambda$=267, 277, 308, 339, 373 nm.

Example 183

Synthesis of (R)-5-(3-(3,3-dimethylureido)piperidin-1-yl)-3-(3-methoxy-4-methylphenylamino)pyrazine-2-carboxamide

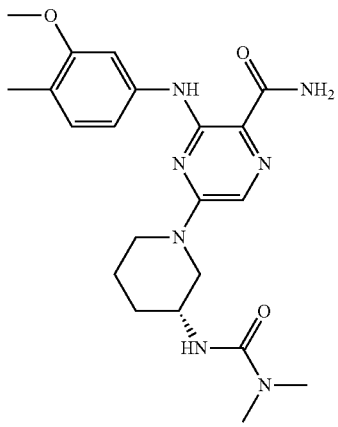

228

In a similar manner as described in Example 179, (R)-5-(3-(3,3-dimethylureido)piperidin-1-yl)-3-(3-methoxy-4-methylphenylamino)pyrazine-2-carboxamide (228) was prepared using 3-methoxy-4-toluidine. MS found for $C_{21}H_{29}N_7O_3$ as $(M+H)^+$ 428.3. UV: $\lambda$=267, 277, 308, 339, 373 nm.

Example 184

Synthesis of (R)-5-(3-(3,3-dimethylureido)piperidin-1-yl)-3-(5-fluoro-6-methylpyridin-2-ylamino)pyrazine-2-carboxamide

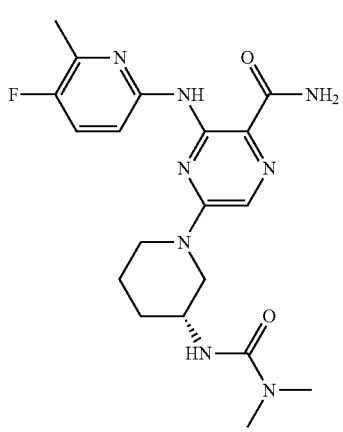

229

In a similar manner as described in Example 179, (R)-5-(3-(3,3-dimethylureido)piperidin-1-yl)-3-(5-fluoro-6-methylpyridin-2-ylamino)pyrazine-2-carboxamide (229) was prepared using 2-amino-5-fluoro-6-methylpyridine. MS found for $C_{19}H_{25}FN_8O_2$ as $(M+H)^+$ 417.4, $(M-H)^-$ 415.1. UV: $\lambda$=268, 271, 296, 303, 311, 334, 366 nm.

Example 185

Synthesis of (R)-5-(3-(3,3-dimethylureido)piperidin-1-yl)-3-(1-methyl-2-oxo-1,2-dihydropyridin-4-ylamino)pyrazine-2-carboxamide

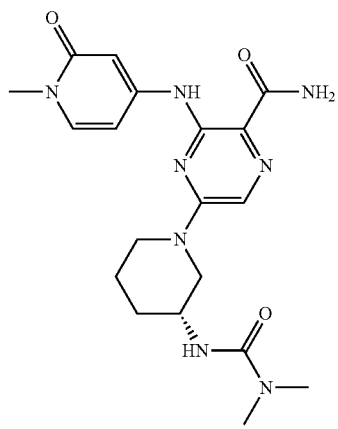

230

In a similar manner as described in Example 179, (R)-5-(3-(3,3-dimethylureido)piperidin-1-yl)-3-(1-methyl-2-oxo-1,2-dihydropyridin-4-ylamino)pyrazine-2-carboxamide (230) was prepared using 4-amino-1-methylpyridin-2(1H)-one. MS found for $C_{19}H_{26}N_8O_3$ as $(M+H)^+$ 415.2, $(M-H)^-$ 413.2. UV: $\lambda$=279, 291, 315, 344, 364 nm.

Example 186

Synthesis of (R)-5-(3-(3,3-dimethylureido)piperidin-1-yl)-3-(1-methyl-6-oxo-1,6-dihydropyridin-3-ylamino)pyrazine-2-carboxamide

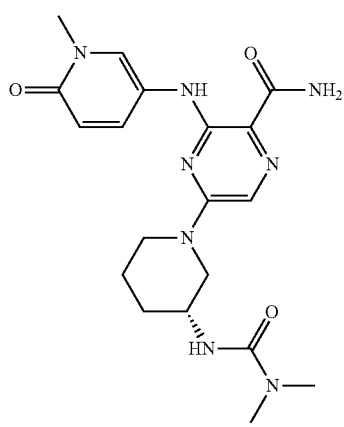

231

In a similar manner as described in Example 179, (R)-5-(3-(3,3-dimethylureido)piperidin-1-yl)-3-(1-methyl-6-oxo-1,6-dihydropyridin-3-ylamino)pyrazine-2-carboxamide (231) was prepared using 5-amino-1-methylpyridin-2(1H)- one. MS found for $C_{19}H_{26}N_8O_3$ as $(M+H)^+$ 415.2, $(M-H)^-$ 413.1. UV: λ=300, 335, 369 nm.

Example 187

Synthesis of (R)-5-(3-(3,3-dimethylureido)piperidin-1-yl)-3-(3-methylisothiazol-5-ylamino)pyrazine-2-carboxamide

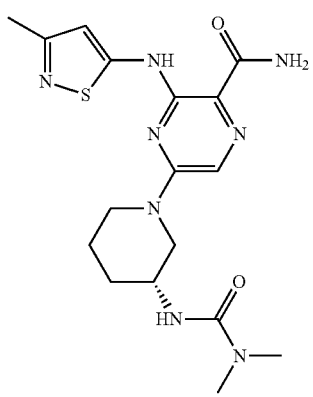

232

In a similar manner as described in Example 179, (R)-5-(3-(3,3-dimethylureido)piperidin-1-yl)-3-(3-methylisothiazol-5-ylamino)pyrazine-2-carboxamide (232) was prepared using 5-amino-3-methylisothiazole hydrochloride. MS found for $C_{17}H_{24}N_8O_2S$ as $(M+H)^+$ 405.3, $(M-H)^-$ 403.1. UV: λ=280, 286, 315, 344, 368 nm. Proton NMR (CD₃OD): δ 7.91 (1H, s), 6.92 (1H, s), 4.45 (1H, m), 4.38 (1H, m), 3.80 (1H, m), 3.33 (1H, m), 3.21 (1H, m), 2.90 (6H, s), 2.49 (3H,$), 2.08 (1H, m), 1.97 (1H, m), 1.74 (2H, m) ppm.

Example 188

Synthesis of (R)-5-(3-(3,3-dimethylureido)piperidin-1-yl)-3-(4-isopropoxyphenylamino)pyrazine-2-carboxamide

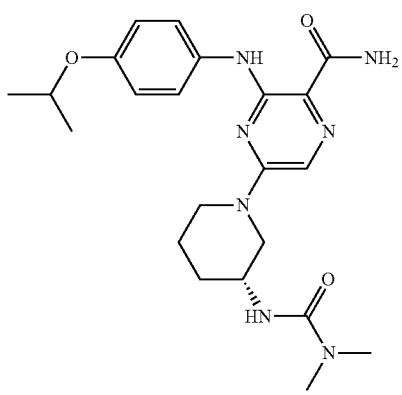

233

In a similar manner as described in Example 179, (R)-5-(3-(3,3-dimethylureido)piperidin-1-yl)-3-(4-isopropoxyphenylamino)pyrazine-2-carboxamide (233) was prepared using 4-isopropoxyaniline. MS found for $C_{22}H_{31}N_7O_3$ as $(M+H)^+$ 442.4, $(M-H)^-$ 440.2. UV: λ=269, 275, 304, 339, 373 nm. Proton NMR (CD₃OD): δ 7.59 (1H, s), 7.48 (2H, d, J=9.0 Hz), 6.85 (2H, d, J=9.0 Hz), 4.52 (1H, m), 4.32 (1H, m), 4.18 (1H, m), 3.74 (1H, m), 3.18 (1H, m), 3.09 (1H, m), 2.88 (6H, s), 2.02 (1H, m), 1.85 (1H, m), 1.67 (2H, m), 1.30 (6H, d, J=6.0 Hz) ppm.

Example 189

Synthesis of (R)-3-(4-(cyclopentyloxy)phenylamino)-5-(3-(3,3-dimethylureido)piperidin-1-yl)pyrazine-2-carboxamide

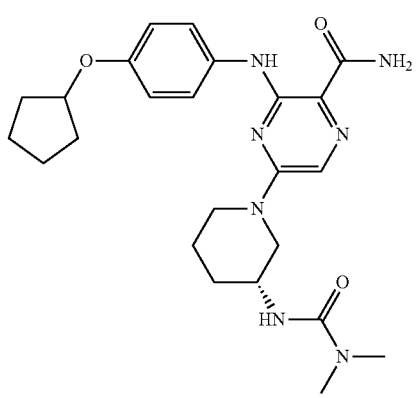

234

In a similar manner as described in Example 179, (R)-3-(4-(cyclopentyloxy)phenylamino)-5-(3-(3,3-dimethylureido)piperidin-1-yl)pyrazine-2-carboxamide (234) was prepared using 4-cyclopentoxyaniline. MS found for $C_{24}H_{33}N_7O_3$ as $(M+H)^+$ 468.4. UV: λ=270, 276, 304, 340, 373 nm.

Example 190

Synthesis of (R)-5-(3-(3,3-dimethylureido)piperidin-1-yl)-3-(4-(2-methoxyethoxyl)phenylamino)pyrazine-2-carboxamide

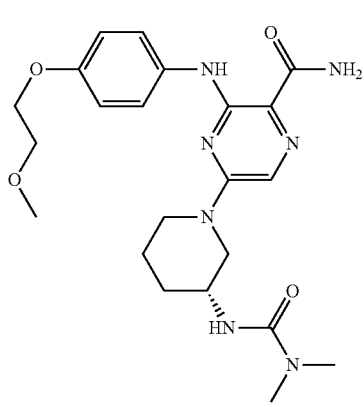

235

In a similar manner as described in Example 179, (R)-5-(3-(3,3-dimethylureido)piperidin-1-yl)-3-(4-(2-methoxyethoxyl)phenylamino)pyrazine-2-carboxamide (235) was prepared using 4-(2-methoxyethoxy)aniline. MS found for C$_{22}$H$_{31}$N$_7$O$_4$ as (M+H)$^+$ 458.2, (M−H)$^−$ 456.2. UV: λ=270, 275, 303, 339, 373 nm.

Example 191

Synthesis of (R)-3-(4-(2-(dimethylamino)ethoxy)phenylamino)-5-(3-(3,3-dimethylureido)piperidin-1-yl)pyrazine-2-carboxamide

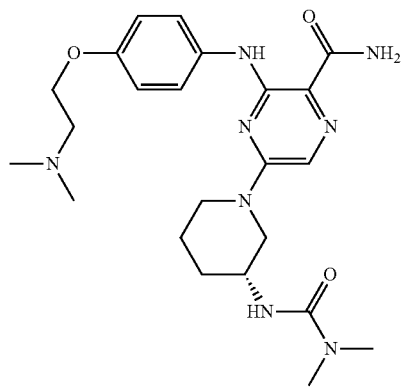

236

In a similar manner as described in Example 179, (R)-3-(4-(2-(dimethylamino)ethoxy)phenylamino)-5-(3-(3,3-dimethylureido)piperidin-1-yl)pyrazine-2-carboxamide (236) was prepared using 4-(2-(dimethylamino)ethoxy)aniline. MS found for C$_{23}$H$_{34}$N$_8$O$_3$ as (M+H)$^+$ 471.3. UV: λ=270, 275, 304, 337, 373 nm.

Example 192

Synthesis of (R)-5-(3-(3,3-dimethylureido)piperidin-1-yl)-3-(4-nitrophenylamino)pyrazine-2-carboxamide

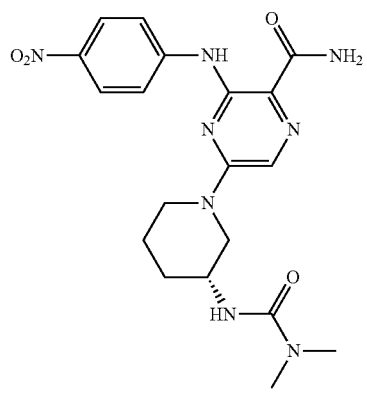

237

In a similar manner as described in Example 179, (R)-5-(3-(3,3-dimethylureido)piperidin-1-yl)-3-(4-nitrophenylamino)pyrazine-2-carboxamide (237) was prepared using 4-nitroaniline. MS found for C$_{19}$H$_{24}$N$_8$O$_4$ as (M+H)$^+$ 429.1, (M−H)$^−$ 427.1. UV: λ=283, 308, 359 nm. Proton NMR (CD$_3$OD): δ 8.20 (2H, d, J=9.5 Hz), 7.85 (2H, d, J=9.0 Hz), 7.77 (1H, s), 4.53 (1H, m), 4.22 (1H, m), 3.78 (1H, m), 3.21 (1H, m), 3.01 (1H, m), 2.93 (6H, s), 2.05 (1H, m), 1.93 (1H, m), 1.68 (2H, m) ppm.

Example 193

Synthesis of (R)-3-(4-((dimethylamino)methyl)phenylamino)-5-(3-(3,3-dimethylureido)piperidin-1-yl)pyrazine-2-carboxamide

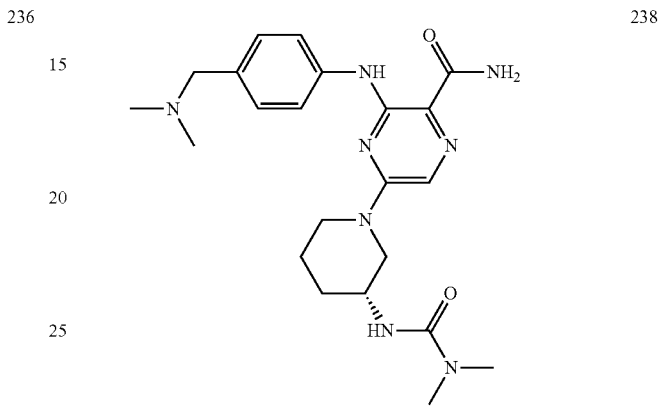

238

In a similar manner as described in Example 179, (R)-3-(4-((dimethylamino)methyl)phenylamino)-5-(3-(3,3-dimethylureido)piperidin-1-yl)pyrazine-2-carboxamide (238) was prepared using 4-((dimethylamino)methyl)aniline. MS found for C$_{22}$H$_{32}$N$_8$O$_2$ as (M+H)$^+$ 441.3. UV: λ=271, 282, 310, 337, 372 nm.

Example 194

Synthesis of (R)-3-(4-(dimethylcarbamoyl)phenylamino)-5-(3-(3,3-dimethylureido)piperidin-1-yl)pyrazine-2-carboxamide

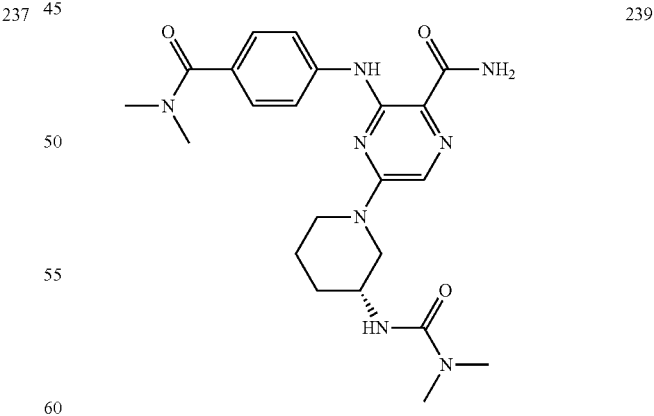

239

In a similar manner as described in Example 179, (R)-3-(4-(dimethylcarbamoyl)phenylamino)-5-(3-(3,3-dimethylureido)piperidin-1-yl)pyrazine-2-carboxamide (239) was prepared using 4-amino-N,N-dimethylbenzamide. MS found for C$_{22}$H$_{30}$N$_8$O$_3$ as (M+H)$^+$ 455.6, (M−H)$^−$ 453.2. UV: λ=278, 288, 312, 343, 372 nm. Proton NMR (CD$_3$OD): δ 7.73

(2H, d, J=9.0 Hz), 7.70 (1H, s), 7.42 (2H, d, J=8.5 Hz), 4.38 (1H, m), 4.23 (1H, m), 3.76 (1H, m), 3.20 (1H, m), 3.09 (7H, s), 2.89 (6H, s), 2.03 (1H, m), 1.89 (1H, m), 1.69 (2H, m) ppm.

Example 195

Synthesis of (R)-5-(3-(3,3-dimethylureido)piperidin-1-yl)-3-(4-(pyrrolidine-1-carbonyl)phenylamino)pyrazine-2-carboxamide

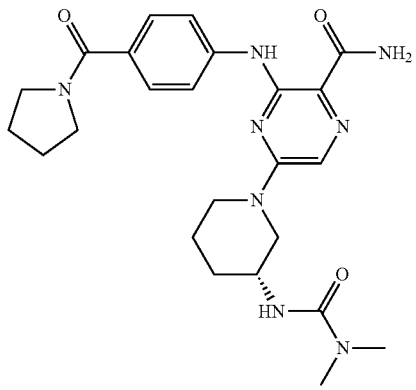

240

In a similar manner as described in Example 179, (R)-5-(3-(3,3-dimethylureido)piperidin-1-yl)-3-(4-(pyrrolidine-1-carbonyl)phenylamino)pyrazine-2-carboxamide (240) was prepared using (4-aminophenyl)(pyrrolidin-1-yl)methanone. MS found for $C_{24}H_{32}N_8O_3$ as (M+H)$^+$ 481.5, (M−H)$^−$ 479.2. UV: λ=280, 286, 315, 345, 370 nm.

Example 196

Synthesis of (R)-5-(3-(3,3-dimethylureido)piperidin-1-yl)-3-(4-(pyridin-2-ylcarbamoyl)phenylamino)pyrazine-2-carboxamide

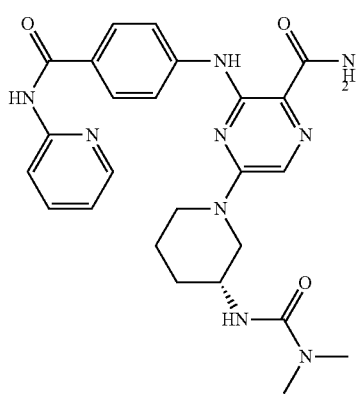

241

In a similar manner as described in Example 179, (R)-5-(3-(3,3-dimethylureido)piperidin-1-yl)-3-(4-(pyridin-2-ylcarbamoyl)phenylamino)pyrazine-2-carboxamide (241) was prepared using 4-amino-N-(pyridin-2-yl)benzamide. MS found for $C_{25}H_{29}N_9O_3$ as (M+H)$^+$ 504.2, (M−H)$^−$ 502.2. UV: λ=288, 299, 343 nm.

Example 197

Synthesis of (R)-3-(4-(2-cyanopropan-2-yl)phenylamino)-5-(3-(3,3-dimethylureido)piperidin-1-yl)pyrazine-2-carboxamide

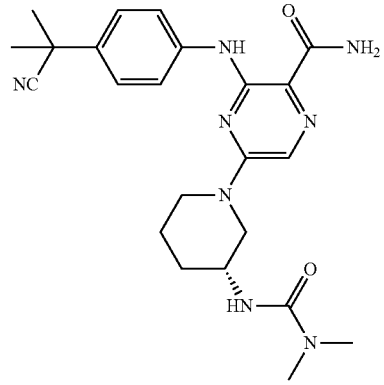

242

In a similar manner as described in Example 179, (R)-3-(4-(2-cyanopropan-2-yl)phenylamino)-5-(3-(3,3-dimethylureido)piperidin-1-yl)pyrazine-2-carboxamide (242) was prepared using 2-(4-aminophenyl)-2-methylpropanenitrile. MS found for $C_{23}H_{30}N_8O_2$ as (M+H)$^+$ 451.5, (M−H)$^−$ 449.2. UV: λ=268, 278, 306, 335, 372 nm. Proton NMR (CD$_3$OD): δ 7.69 (2H, d, J=9.0 Hz), 7.66 (1H, s), 7.44 (2H, d, J=9.0 Hz), 4.43 (1H, m), 4.21 (1H, m), 3.77 (1H, m), 3.19 (1H, m), 3.05 (7H, s), 2.90 (6H, s), 2.03 (1H, m), 1.89 (1H, m), 1.71 (6H, s), 1.66 (2H, m) ppm. In the final step, (R)-3-(4-(1-amino-2-methyl-1-oxopropan-2-yl)phenylamino)-5-(3-(3,3-dimethylureido)piperidin-1-yl)pyrazine-2-carboxamide (243) was also found and isolated as the main by-product.

Example 198

Synthesis of (R)-3-(4-(1-amino-2-methyl-1-oxopropan-2-yl)phenylamino)-5-(3-(3,3-dimethylureido)piperidin-1-yl)pyrazine-2-carboxamide

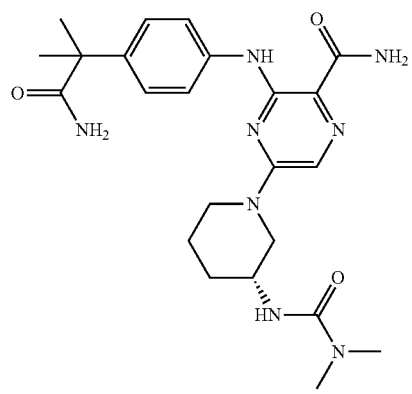

243

(R)-3-(4-(1-Amino-2-methyl-1-oxopropan-2-yl)phenylamino)-5-(3-(3,3-dimethylureido)piperidin-1-yl)pyrazine-2-carboxamide (243) was found and isolated as the main by-product in the final step during preparation of (R)-3-(4-(2-cyanopropan-2-yl)phenylamino)-5-(3-(3,3-dimethylureido)piperidin-1-yl)pyrazine-2-carboxamide (242). MS found for C$_{23}$H$_{32}$N$_8$O$_3$ as (M+H)$^+$ 469.4, (M–H)$^-$ 467.2. UV: 269, 278, 307, 336, 372 nm. Proton NMR (CD$_3$OD): δ 7.63 (1H, s), 7.61 (2H, d, J=8.5 Hz), 7.33 (2H, d, J=9.0 Hz), 4.40 (1H, m), 4.22 (1H, m), 3.76 (1H, m), 3.18 (1H, m), 3.05 (7H, s), 2.90 (6H, s), 2.02 (1H, m), 1.88 (1H, m), 1.68 (2H, m), 1.54 (6H, s) ppm.

Example 199

Synthesis of (R)-3-(4-(1-cyanocyclopropyl)phenylamino)-5-(3-(3,3-dimethylureido)piperidin-1-yl)pyrazine-2-carboxamide

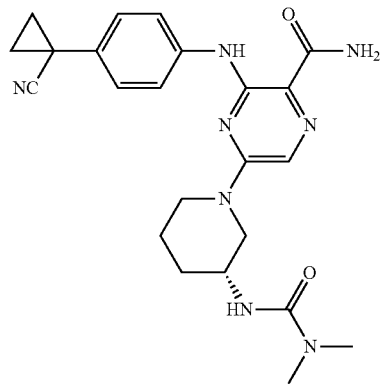

244

In a similar manner as described in Example 179, (R)-3-(4-(1-cyanocyclopropyl)phenylamino)-5-(3-(3,3-dimethylureido)piperidin-1-yl)pyrazine-2-carboxamide (244) was prepared using 1-(4-aminophenyl)cyclopropanecarbonitrile. MS found for C$_{23}$H$_{28}$N$_8$O$_2$ as (M+H)$^+$ 449.4, (M–H)$^-$ 447.1. UV: λ=270, 279, 308, 337, 372 nm. Proton NMR (CD$_3$OD): δ 7.65 (1H, s), 7.64 (2H, d, J=9.0 Hz), 7.26 (2H, d, J=9.0 Hz), 4.41 (1H, m), 4.20 (1H, m), 3.76 (1H, m), 3.18 (1H, m), 3.05 (1H, m), 2.91 (6H, s), 2.03 (1H, m), 1.88 (1H, m), 1.66 (4H, m), 1.43 (2H, m) ppm. In the final step, (R)-3-(4-(1-carbamoylcyclopropyl)phenylamino)-5-(3-(3,3-dimethylureido)piperidin-1-yl)pyrazine-2-carboxamide (245) was also found and isolated as the main by-product.

Example 200

Synthesis of (R)-3-(4-(1-carbamoylcyclopropyl)phenylamino)-5-(3-(3,3-dimethylureido)piperidin-1-yl)pyrazine-2-carboxamide

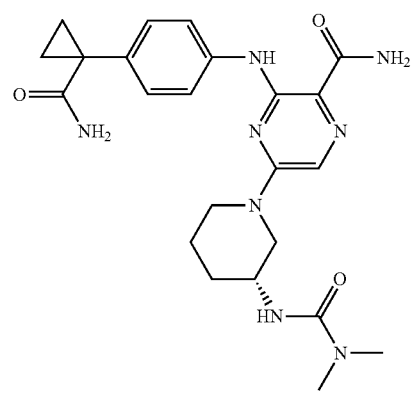

245

(R)-3-(4-(1-Carbamoylcyclopropyl)phenylamino)-5-(3-(3,3-dimethylureido)piperidin-1-yl)pyrazine-2-carboxamide (243) was found and isolated as the main by-product in the final step during preparation of (R)-3-(4-(1-cyanocyclopropyl)phenylamino)-5-(3-(3,3-dimethylureido)piperidin-1-yl)pyrazine-2-carboxamide (244). MS found for C$_{23}$H$_{30}$N$_8$O$_3$ as (M+H)$^+$ 467.3, (M–H)$^-$ 465.2. UV: 270, 279, 307, 336, 372 nm. Proton NMR (CD$_3$OD): δ 7.66 (1H, s), 7.66 (2H, d, J=9.0 Hz), 7.35 (2H, d, J=8.5 Hz), 4.43 (1H, m), 4.23 (1H, m), 3.76 (1H, m), 3.19 (1H, m), 3.05 (1H, s), 2.90 (6H, s), 2.03 (1H, m), 1.89 (1H, m), 1.66 (2H, m), 1.49 (2H, m), 1.08 (2H, m) ppm.

Example 201

Synthesis of (R)-3-(4-(1-(aminomethyl)cyclopropyl)phenylamino)-5-(3-(3,3-dimethylureido)piperidin-1-yl)pyrazine-2-carboxamide

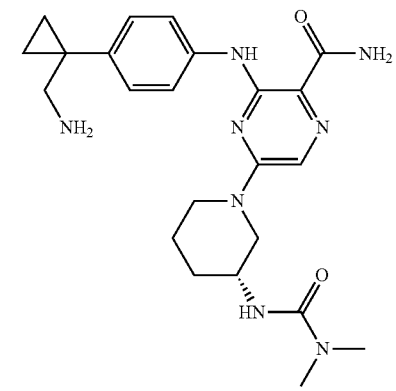

246

(R)-3-(4-(1-Cyanocyclopropyl)phenylamino)-5-(3-(3,3-dimethylureido)piperidin-1-yl)pyrazine-2-carboxamide (244, 25 mg, 0.05 mmol) was dissolved in 5 mL MeOH. To it were added CoCl$_2$ (20 mg, 0.15 mmol) and then NaBH$_4$ (19 mg, 0.5 mmol). The mixture immediately turned black. It was stirred at RT for 15 min, and quenched with 1 mL MeCN and 0.5 mL TFA. The mixture was stirred at RT for 10 min, filtered, and directly subjected to reverse phase prep HPLC using 5 mM HCl (aq) and neat MeCN as mobile phases to isolate (R)-3-(4-(1-(aminomethyl)cyclopropyl)phenylamino)-5-(3-(3,3-dimethylureido)piperidin-1-yl)pyrazine-2-carboxamide (246) as HCl salt. MS found for C$_{23}$H$_{32}$N$_8$O$_2$ as (M+H)$^+$ 453.3. UV: λ=269, 278, 307, 336, 373 nm.

Example 202

Synthesis of (R)-3-(4-(1-(dimethylcarbamoyl)cyclopropyl)phenylamino)-5-(3-(3,3-dimethylureido)piperidin-1-yl)pyrazine-2-carboxamide

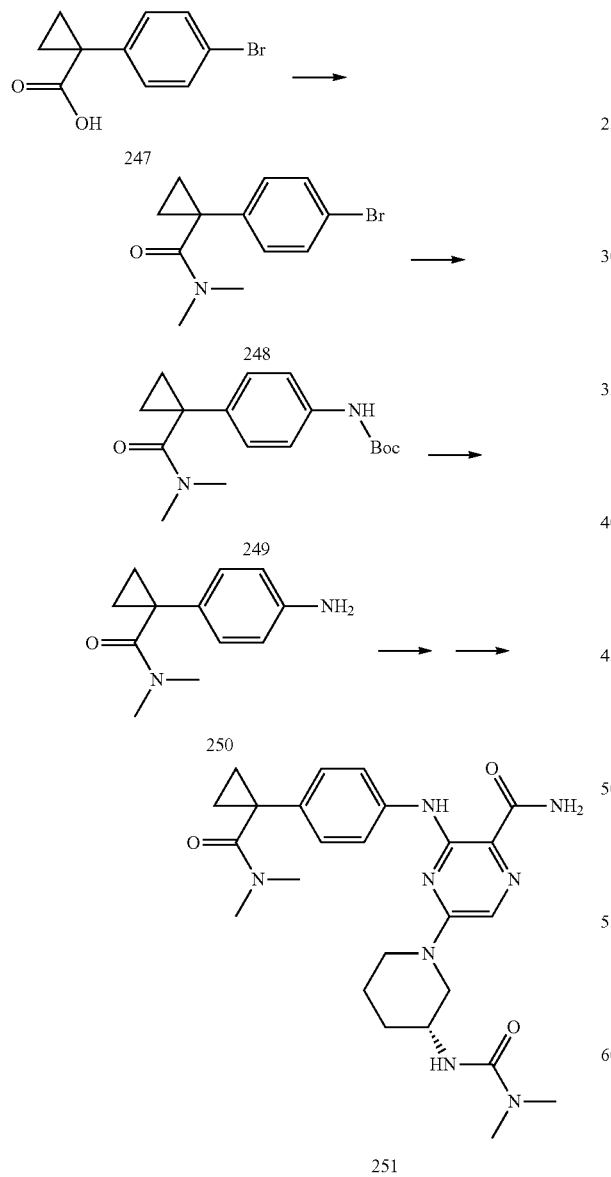

1-(4-Bromophenyl)cyclopropanecarboxylic acid (247, 1.00 g, 4.15 mmol) was dissolved in 10 mL DMF and 90 mL dioxane. To it were added dimethylamine (2M in THF, 10.4 mL, 20.7 mmol) and then PyBOP (4.32 g, 8.30 mmol). The mixture was stirred at RT for 2 hours, concentrated in vacuo, diluted with 100 mL EtOAc, washed with water ×3, dried, concentrated in vacuo, and subjected to silica flash column using 0 to 3% MeOH in DCM to isolate 1-(4-bromophenyl)-N,N-dimethylcyclopropanecarboxamide (248) in quantitative yield. It was dissolved in 100 mL dioxane. To the solution were added tert-butyl carbamate (2.91 g, 24.9 mmol), Pd$_2$(dba)$_3$ (760 mg, 0.83 mmol), XantPhos (1.44 g, 2.49 mmol), fine-powder cesium carbonate (8.12 g, 24.9 mmol). The mixture was degassed using N$_2$ stream for 5 min, and stirred under N$_2$ atmosphere at 115° C. for 2 days. It was cooled to RT, concentrated in vacuo, diluted with 200 mL EtOAc, washed with water ×3, dried, concentrated, and subjected to silica flash column to isolate tert-butyl 4-(1-(dimethylcarbamoyl)cyclopropyl)phenylcarbamate (249, 600 mg). It was treated with 20 mL commercial 4N HCl in dioxane at RT for 1.5 hour. The mixture was concentrated in vacuo to dryness to give 1-(4-aminophenyl)-N,N-dimethylcyclopropanecarboxamide (250) as HCl salt.

In a similar manner as described in Example 179, (R)-3-(4-(1-(dimethylcarbamoyl)cyclopropyl)phenylamino)-5-(3-(3,3-dimethylureido)piperidin-1-yl)pyrazine-2-carboxamide (251) was prepared using 1-(4-aminophenyl)-N,N-dimethylcyclopropanecarboxamide (250). MS found for C$_{25}$H$_{34}$N$_8$O$_3$ as (M+H)$^+$ 495.4, (M−H)$^-$ 493.2. UV: λ=271, 279, 308, 338, 372 nm. Proton NMR (CD$_3$OD): δ 7.64 (1H, s), 7.59 (2H, d, J=8.5 Hz), 7.11 (2H, d, J=8.5 Hz), 4.37 (1H, m), 4.20 (1H, m), 3.75 (1H, m), 3.19 (1H, m), 3.07 (1H, s), 2.96 (6H, s), 2.89 (6H, s), 2.03 (1H, m), 1.87 (1H, m), 1.67 (2H, m), 1.33 (2H, m), 1.20 (2H, m) ppm.

Example 203

Synthesis of (R)-3-(4-(1-cyanocyclopentyl)phenylamino)-5-(3-(3,3-dimethylureido)piperidin-1-yl)pyrazine-2-carboxamide

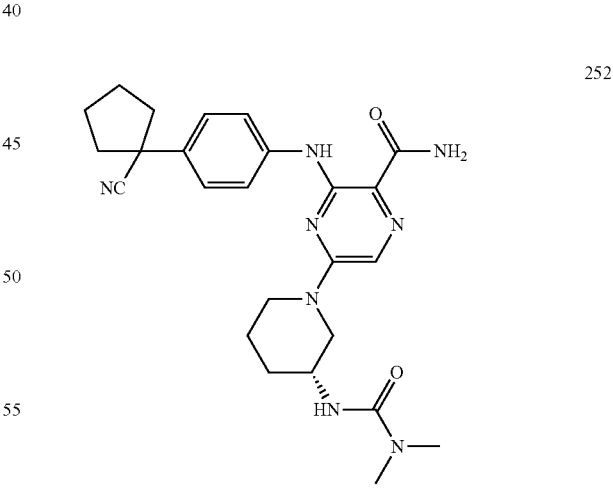

In a similar manner as described in Example 179, (R)-3-(4-(1-cyanocyclopentyl)phenylamino)-5-(3-(3,3-dimethylureido)piperidin-1-yl)pyrazine-2-carboxamide (252) was prepared using 1-(4-aminophenyl)cyclopentanecarbonitrile. MS found for C$_{25}$H$_{32}$N$_8$O$_2$ as (M+H)$^+$ 477.5, (M−H)$^-$ 475.2. UV: λ=269, 279, 307, 335, 373 nm. Proton NMR (CD$_3$OD): δ 7.68 (2H, d, J=8.5 Hz), 7.66 (1H, s), 7.42 (2H, d, J=8.5 Hz), 4.42 (1H, m), 4.21 (1H, m), 3.76 (1H, m), 3.19 (1H, m), 3.06

(1H, m), 2.90 (6H, s), 2.42 (2H, m), 2.13 (2H, m), 2.04-1.97 (5H, m), 1.88 (1H, m), 1.67 (2H, m) ppm.

Example 204

Synthesis of (R)-3-(4-(1-(aminomethyl)cyclopentyl)phenylamino)-5-(3-(3,3-dimethylureido)piperidin-1-yl)pyrazine-2-carboxamide

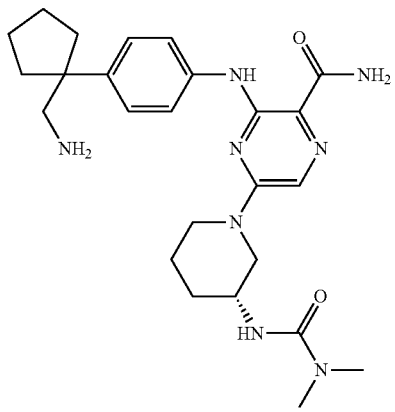

253

In a similar manner as described in Example 201, (R)-3-(4-(1-(aminomethyl)cyclopentyl)phenylamino)-5-(3-(3,3-dimethylureido)piperidin-1-yl)pyrazine-2-carboxamide (253) was prepared using (R)-3-(4-(1-cyanocyclopentyl)phenylamino)-5-(3-(3,3-dimethylureido)piperidin-1-yl)pyrazine-2-carboxamide (252). MS found for $C_{25}H_{36}N_8O_2$ as $(M+H)^+$ 481.3. UV: λ=269, 278, 307, 336, 372 nm.

Example 205

Synthesis of (R)-5-(3-(3,3-dimethylureido)piperidin-1-yl)-3-(4-(1,1-dioxothiomorpholino)phenylamino)pyrazine-2-carboxamide

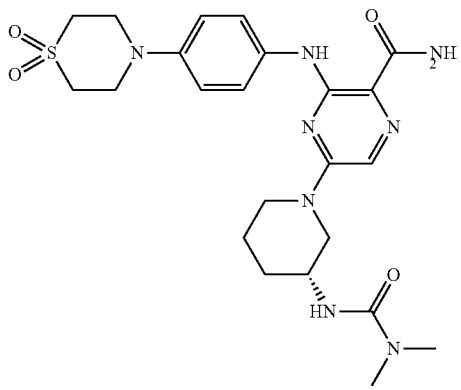

254

In a similar manner as described in Example 179, (R)-5-(3-(3,3-dimethylureido)piperidin-1-yl)-3-(4-(1,1-dioxothiomorpholino)phenylamino)pyrazine-2-carboxamide (254) was prepared using 4-(1,1-dioxothiomorpholino)aniline. MS found for $C_{23}H_{32}N_8O_4S$ as $(M+H)^+$ 517.4, $(M-H)^-$ 515.2. UV: λ=310, 349, 374 nm.

Example 206

Synthesis of (R)-3-(4-(1-cyclopropylpiperidin-4-yl)phenylamino)-5-(3-(3,3-dimethylureido)piperidin-1-yl)pyrazine-2-carboxamide

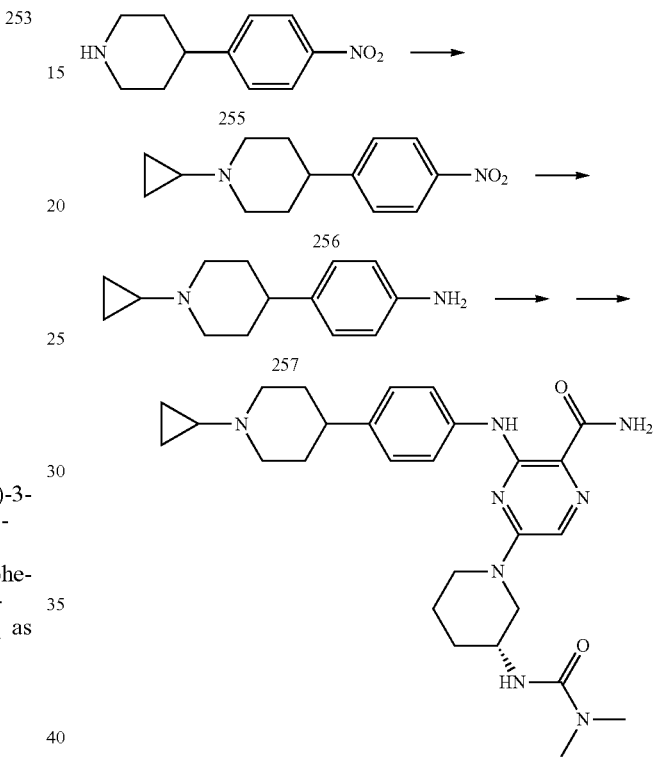

4-(4-Nitrophenyl)piperidine (1.00 g, 4.85 mmol) was dissolved in 80 mL MeOH and 2 mL HOAc. To it was added (1-ethoxycycloproxy)trimethylsilane, and the mixture was stirred at RT for 40 min To it was then added NaBH₃CN (1.83 g, 29.0 mmol), and the mixture was stirred in 65° C. bath for overnight. It was concentrated in vacuo to dryness, diluted with 120 mL EtOAc, washed with 1N NaOH and water ×2, dried, concentrated in vacuo, and subjected to silica flash column using 0 to 4% MeOh in DCM to isolate 1-cyclopropyl-4-(4-nitrophenyl)piperidine (256). It was dissolved in 50 mL EtOAc. To it was added 10% Pd/C (0.5 g), and the mixture was hydrogenated using a H₂ balloon at RT for overnight. The mixture was filtered through celite, and concentrated in vacuo to give 4-(1-cyclopropylpiperidin-4-yl)aniline (257) (960 mg, 91% overall) as a white solid.

In a similar manner as described in Example 179, (R)-3-(4-(1-cyclopropylpiperidin-4-yl)phenylamino)-5-(3-(3,3-dimethylureido)piperidin-1-yl)pyrazine-2-carboxamide (258) was prepared using 4-(1-cyclopropylpiperidin-4-yl)aniline (257). MS found for $C_{27}H_{38}N_8O_2$ as $(M+H)^+$ 507.7, $(M-H)^-$ 505.3. UV: λ=268, 277, 306, 336, 373 nm. Proton NMR (CD₃OD): δ 7.65 (1H, s), 7.61 (2H, d, J=8.5 Hz), 7.20 (2H, d, J=8.5 Hz), 4.29 (1H, m), 4.20 (1H, m), 3.75 (3H, m), 3.33 (1H, m), 3.24 (1H, m), 3.19 (1H, m), 2.92-2.80 (8H, m), 2.14 (2H, m), 2.03 (1H, m), 1.96-1.83 (3H, m), 1.66 (2H, m), 1.02 (4H, m) ppm.

Example 207

Synthesis of (R)-5-(3-(3,3-dimethylureido)piperidin-1-yl)-3-(4-(1-ethylpiperidin-4-yl)phenylamino)pyrazine-2-carboxamide

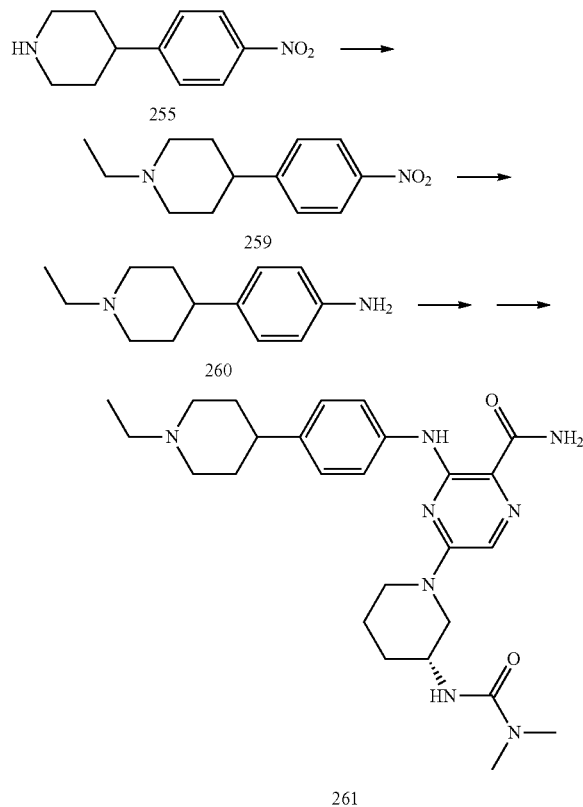

4-(4-Nitrophenyl)piperidine (255, 500 mg g, 2.4 mmol) was dissolved in 30 mL MeCN. To it were added DIEA (830 µL, 4.8 mmol) and then EtOTf (460 µL, 3.6 mmol). The mixture was stirred at RT for 10 min, and to it was added 0.5 mL morpholine. It was concentrated in vacuo and subjected to silica flash column using 0 to 7% MeOh in DCM to isolate 1-ethyl-4-(4-nitrophenyl)piperidine (259). It was dissolved in 40 mL EtOAc. To it was added 10% Pd/C (0.3 g), and the mixture was hydrogenated using a $H_2$ balloon at RT for overnight. The mixture was filtered through celite, and concentrated in vacuo to give 4-(1-ethylpiperidin-4-yl)aniline (260) (410 mg, 83% overall) as a white solid.

In a similar manner as described in Example 179, (R)-5-(3-(3,3-dimethylureido)piperidin-1-yl)-3-(4-(1-ethylpiperidin-4-yl)phenylamino)pyrazine-2-carboxamide (261) was prepared using 4-(1-ethylpiperidin-4-yl)aniline (260). MS found for $C_{26}H_{38}N_8O_2$ as $(M+H)^+$ 495.6, $(M-H)^-$ 493.2. UV: λ=268, 277, 306, 336, 373 nm. Proton NMR (CD$_3$OD): δ 7.63 (1H, s), 7.59 (2H, d, J=8.5 Hz), 7.20 (2H, d, J=8.5 Hz), 4.29 (1H, m), 4.21 (1H, m), 3.76 (1H, m), 3.67 (2H, m), 3.22-3.05 (6H, m), 2.89 (6H, s), 2.84 (1H, m), 2.12 (2H, m), 2.00 (3H, m), 1.87 (1H, m), 1.68 (2H, m), 1.40 (3H, t, J=7.0 Hz) ppm.

Example 208

Synthesis of (R)-5-(3-(3,3-dimethylureido)piperidin-1-yl)-3-(4-(1-isopropylpiperidin-4-yl)phenylamino)pyrazine-2-carboxamide

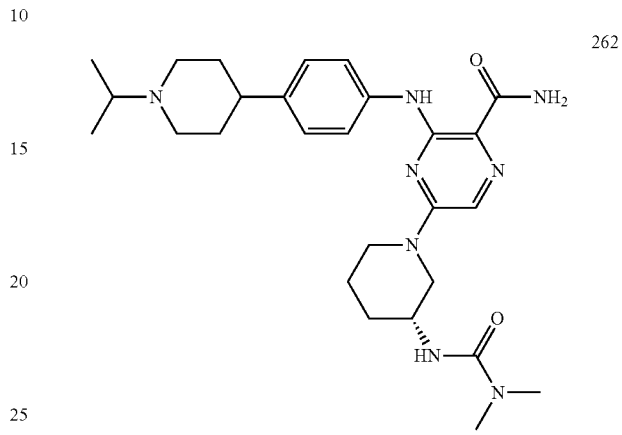

In a similar manner as described in Example 207, (R)-5-(3-(3,3-dimethylureido)piperidin-1-yl)-3-(4-(1-isopropylpiperidin-4-yl)phenylamino)pyrazine-2-carboxamide (262) was prepared using 2-iodopropane and cesium carbonate to alkylate 4-(4-nitrophenyl)piperidine (255) in a sealed tube at 80° C. for overnight. MS found for $C_{27}H_{40}N_8O_2$ as $(M+H)^+$ 509.7, $(M-H)^-$ 507.3. UV: λ=268, 277, 306, 336, 373 nm. Proton NMR (CD$_3$OD): δ 7.64 (1H, s), 7.59 (2H, d, J=8.5 Hz), 7.21 (2H, d, J=8.5 Hz), 4.29 (1H, m), 4.21 (1H, m), 3.75 (1H, m), 3.56 (3H, m), 3.24-3.12 (4H, m), 2.88 (6H, s), 2.85 (1H, m), 2.13 (2H, m), 2.05 (3H, m), 1.86 (1H, m), 1.67 (2H, m), 1.39 (6H, d, J=7.0 Hz) ppm. In the final step, (R)-4-(4-(3-carbamoyl-6-(3-(3,3-dimethylureido)piperidin-1-yl)pyrazin-2-ylamino)phenyl)-1-isopropylpiperidine 1-oxide (263) was also found and isolated as a by-product.

Example 209

Synthesis of (R)-4-(4-(3-carbamoyl-6-(3-(3,3-dimethylureido)piperidin-1-yl)pyrazin-2-ylamino)phenyl)-1-isopropylpiperidine 1-oxide

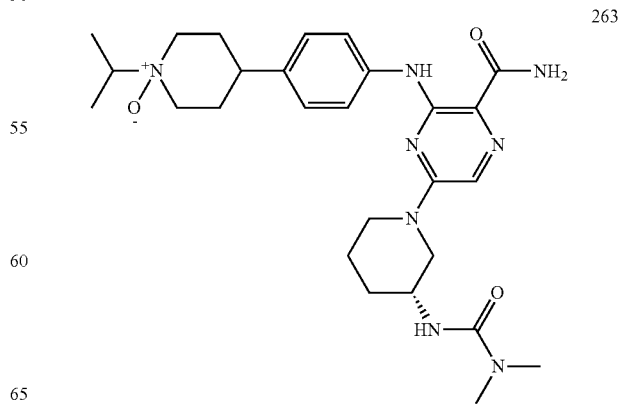

(R)-4-(4-(3-Carbamoyl-6-(3-(3,3-dimethylureido)piperidin-1-yl)pyrazin-2-ylamino)phenyl)-1-isopropylpiperidine 1-oxide (263) was found and isolated as a by-product in the final step during the preparation of (R)-5-(3-(3,3-dimethylureido)piperidin-1-yl)-3-(4-(1-isopropylpiperidin-4-yl)phenylamino)pyrazine-2-carboxamide (262). MS found for $C_{27}H_{40}N_8O_3$ as $(M+H)^+$ 525.4. UV: $\lambda$=268, 277, 306, 336, 373 nm.

Example 210

Synthesis of (R)-3-(4-(1-cyclohexylpiperidin-4-yl)phenylamino)-5-(3-(3,3-dimethylureido)piperidin-1-yl)pyrazine-2-carboxamide

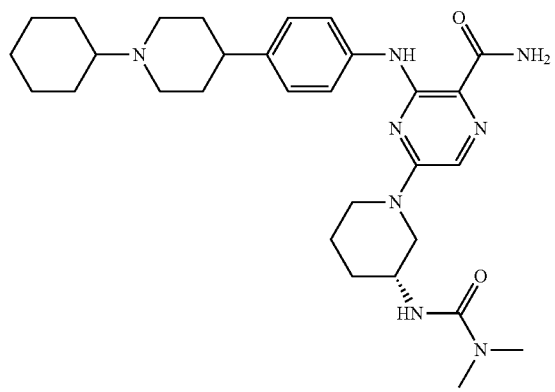

264

In a similar manner as described in Example 179, (R)-3-(4-(1-cyclohexylpiperidin-4-yl)phenylamino)-5-(3-(3,3-dimethylureido)piperidin-1-yl)pyrazine-2-carboxamide (264) was prepared using 4-(1-cyclohexylpiperidin-4-yl)aniline. MS found for $C_{30}H_{44}N_8O_2$ as $(M+H)^+$ 549.9, $(M-H)^-$ 547.4. UV: $\lambda$=268, 277, 306, 336, 373 nm. Proton NMR (CD$_3$OD): δ 7.65 (1H, s), 7.60 (2H, d, J=8.5 Hz), 7.20 (2H, d, J=8.5 Hz), 4.29 (1H, m), 4.21 (1H, m), 3.76 (1H, m), 3.60 (1H, s), 3.57 (1H, s), 3.24-3.15 (5H, m), 2.86 (6H, s), 2.84 (1H, m), 2.14 (4H, m), 2.03-1.95 (5H, m), 1.87 (1H, m), 1.75-1.65 (3H, m), 1.54 (2H, m), 1.43 (2H, m), 1.24 (1H, m) ppm.

Example 211

Synthesis of (R)-5-(3-(3,3-dimethylureido)piperidin-1-yl)-3-(4-(1-phenylpiperidin-4-yl)phenylamino)pyrazine-2-carboxamide

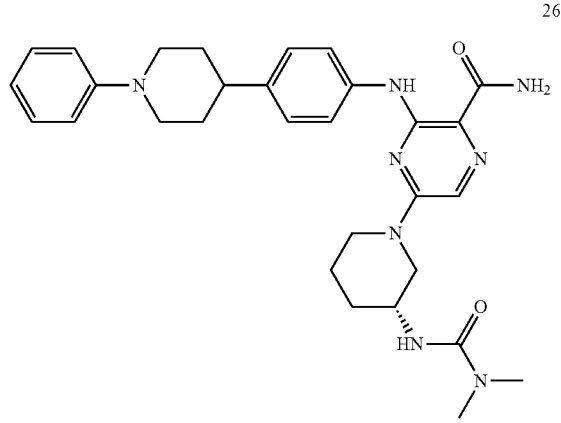

265

In a similar manner as described in Example 179, (R)-5-(3-(3,3-dimethylureido)piperidin-1-yl)-3-(4-(1-phenylpiperidin-4-yl)phenylamino)pyrazine-2-carboxamide (265) was prepared using 4-(1-phenylpiperidin-4-yl)aniline. MS found for $C_{30}H_{38}N_8O_2$ as $(M+H)^+$ 543.9, $(M-H)^-$ 541.3. UV: $\lambda$=267, 278, 306, 336, 372 nm. Proton NMR (CD$_3$OD): δ 7.72 (2H, d, J=8.0 Hz), 7.65-7.62 (5H, m), 7.57 (1H, t, J=7.0 Hz), 7.28 (2H, d, J=8.5 Hz), 4.31 (1H, m), 4.22 (1H, m), 3.80-3.75 (5H, m), 3.23 (1H, m), 3.16 (1H, m), 3.04 (1H, m), 2.89 (6H, s), 2.23 (4H, m), 2.03 (1H, m), 1.88 (1H, m), 1.74-1.64 (2H, m) ppm.

Example 212

Synthesis of (R)-3-(4-cyclohexylphenylamino)-5-(3-(3,3-dimethylureido)piperidin-1-yl)pyrazine-2-carboxamide

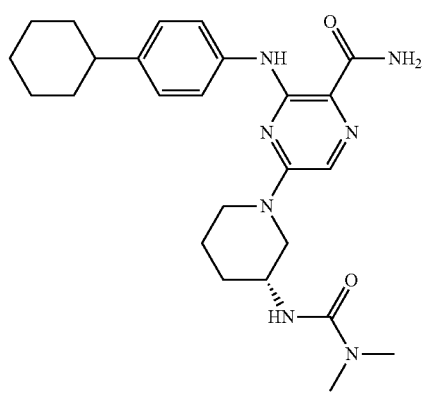

266

In a similar manner as described in Example 179, (R)-3-(4-cyclohexylphenylamino)-5-(3-(3,3-dimethylureido)piperidin-1-yl)pyrazine-2-carboxamide (266) was prepared using 4-cyclohexylaniline. MS found for $C_{25}H_{35}N_7O_2$ as $(M+H)^+$ 466.5. UV: $\lambda$=267, 276, 305, 336, 373 nm.

Example 213

Synthesis of (R)-3-(2-chloro-4-(piperidin-4-yl)phenylamino)-5-(3-(3,3-dimethylureido)piperidin-1-yl)pyrazine-2-carboxamide

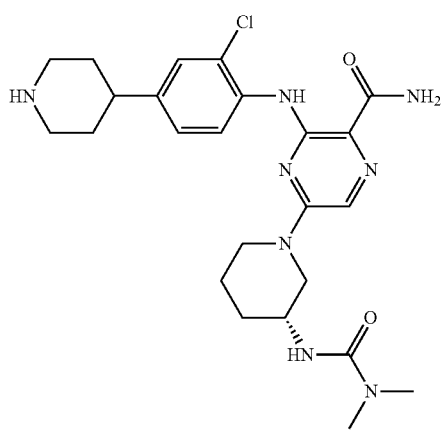

267

In a similar manner as described in Example 162, (R)-3-(2-chloro-4-(piperidin-4-yl)phenylamino)-5-(3-(3,3-dimethylureido)piperidin-1-yl)pyrazine-2-carboxamide (267) was prepared. MS found for C$_{24}$H$_{33}$ClN$_8$O$_2$ as (M+H)$^+$ 501.2 (chloro pattern). UV: λ=309, 344, 388 nm.

Example 214

Synthesis of (R)-3-(4-(4-cyclopropylpiperazin-1-yl)phenylamino)-5-(3-(3,3-dimethylureido)piperidin-1-yl)pyrazine-2-carboxamide

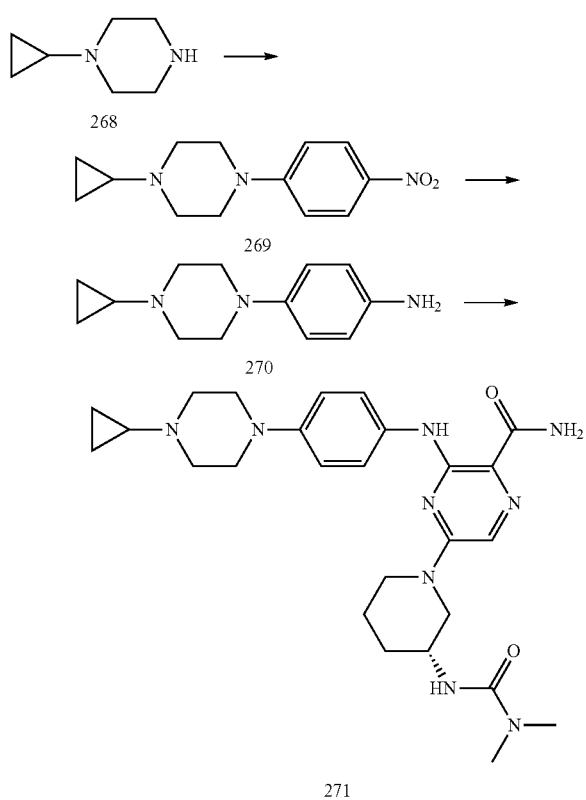

1-Cyclopropylpiperazine (268, 1.76 g, 14.0 mmol) was dissolved in 15 mL DMF. To it were added 1-fluoro-4-nitrobenzene (1.00 g, 7.0 mmol) and DIEA (1.24 mL, 7.0 mmol). The mixture was stirred at 90° C. for overnight, cooled to RT, diluted with EtOAc, washed with water ×2, dried, concentrated in vacuo, subjected to silica flash column using 0 to 40% EtOAc in DCM to isolate 1-cyclopropyl-4-(4-nitrophenyl)piperazine (269). It was dissolved in 2:1 EtOAc/MeOH (80 mL/40 mL), and to it were added 40 μL 6N HCl and 10% Pd/C (0.5 g). The mixture was stirred at RT for overnight under a hydrogen balloon. It was filtered through celite, concentrated in vacuo to dryness to afford 4-(4-cyclopropylpiperazin-1-yl)aniline hydrochloride (270, 1.30 g, 73% overall) as an off-white solid.

In a similar manner as described in Example 179, (R)-3-(4-(4-cyclopropylpiperazin-1-yl)phenylamino)-5-(3-(3,3-dimethylureido)piperidin-1-yl)pyrazine-2-carboxamide (271) was prepared using 4-(4-cyclopropylpiperazin-1-yl)aniline hydrochloride (270). MS found for C$_{26}$H$_{37}$N$_9$O$_2$ as (M+H)$^+$ 508.5. UV: λ=309, 346, 375 nm. Proton NMR (CD$_3$OD): δ 7.58 (3H, m), 7.03 (2H, m), 4.28 (1H, m), 4.19 (1H, m), 3.76 (2H, m), 3.65-3.50 (5H, m), 3.20 (1H, m), 3.15 (1H, m), 2.96 (2H, m), 2.93 (7H, s), 2.02 (1H, m), 1.86 (1H, m), 1.69 (2H, m), 1.09-1.00 (4H, m) ppm.

Example 215

Synthesis of (R)-3-(4-(4-cyclopentylpiperazin-1-yl)phenylamino)-5-(3-(3,3-dimethylureido)piperidin-1-yl)pyrazine-2-carboxamide

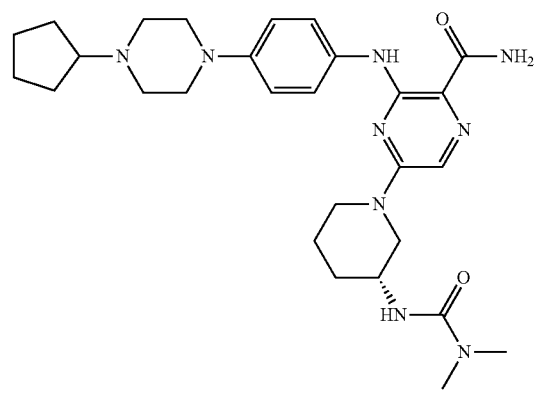

In a similar manner as described in Example 214, (R)-3-(4-(4-cyclopentylpiperazin-1-yl)phenylamino)-5-(3-(3,3-dimethylureido)piperidin-1-yl)pyrazine-2-carboxamide (272) was prepared using 1-cyclopentylpiperazine. MS found for C$_{28}$H$_{41}$N$_9$O$_2$ as (M+H)$^+$ 536.3. UV: λ=309, 347, 374 nm.

Example 216

Synthesis of (R)-3-(1-cyclopropyl-1H-pyrazol-4-ylamino)-5-(3-(3,3-dimethylureido)piperidin-1-yl)pyrazine-2-carboxamide

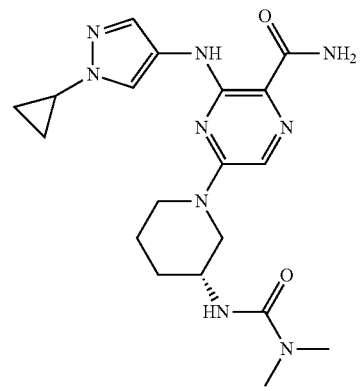

In a similar manner as described in Example 179, (R)-3-(1-cyclopropyl-1H-pyrazol-4-ylamino)-5-(3-(3,3-dimethylureido)piperidin-1-yl)pyrazine-2-carboxamide (273) was prepared using 1-cyclopropyl-1H-pyrazol-4-amine. MS found for C$_{19}$H$_{27}$N$_9$O$_2$ as (M+H)$^+$ 414.4, (M−H)$^-$ 412.2. UV: λ=254, 270, 298, 331, 376 nm. Proton NMR (CD$_3$OD): δ 7.97 (1H, s), 7.59 (1H, s), 7.55 (1H, s), 4.38 (1H, m), 4.19 (1H, m), 3.76 (1H, m), 3.63 (1H, m), 3.21 (1H, m), 3.10 (1H, m), 2.87 (6H, s), 2.03 (1H, m), 1.87 (1H, m), 1.67 (2H, m), 1.06 (2H, m), 0.99 (2H, m) ppm.

Example 217

Synthesis of (R)-3-(1-cyclopentyl-1H-pyrazol-4-ylamino)-5-(3-(3,3-dimethylureido)piperidin-1-yl)pyrazine-2-carboxamide

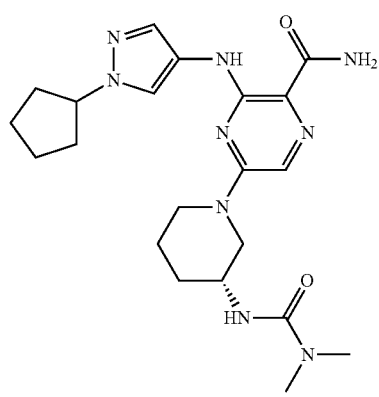

274

In a similar manner as described in Example 179, (R)-3-(1-cyclopentyl-1H-pyrazol-4-ylamino)-5-(3-(3,3-dimethylureido)piperidin-1-yl)pyrazine-2-carboxamide (274) was prepared using 1-cyclopentyl-1H-pyrazol-4-amine. MS found for $C_{21}H_{31}N_9O_2$ as $(M+H)^+$ 442.5, $(M-H)^-$ 440.2. UV: $\lambda$=254, 270, 298, 332, 375 nm. Proton NMR (CD$_3$OD): δ 8.05 (1H, s), 7.60 (1H, s), 7.59 (1H, s), 4.71 (1H, m), 4.40 (1H, m), 4.19 (1H, m), 3.76 (1H, m), 3.21 (1H, m), 3.11 (1H, m), 2.87 (6H, s), 2.16 (2H, m), 2.04-1.96 (3H, m), 1.87 (3H, m), 1.74 (2H, m), 1 (2H, m) ppm.

Example 218

Synthesis of (R)-3-(1-(1-cyclopentylpiperidin-4-yl)-1H-pyrazol-4-ylamino)-5-(3-(3,3-dimethylureido)piperidin-1-yl)pyrazine-2-carboxamide

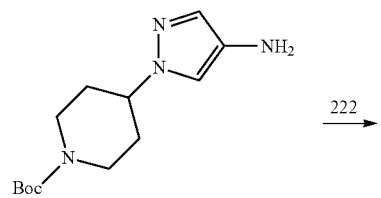

275

-continued

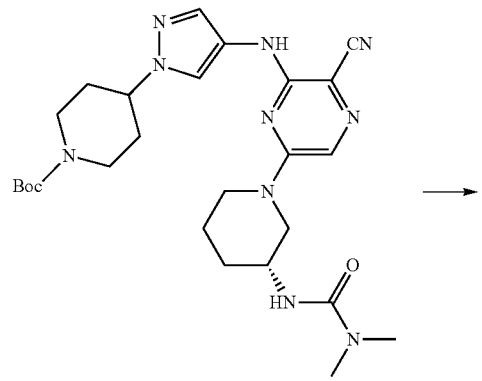

276

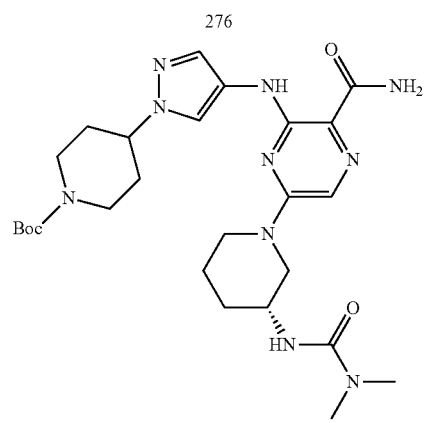

277

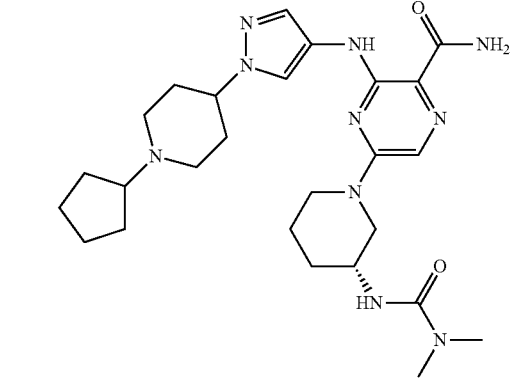

278

279

The mixture of (R)-3-(1-(6-chloro-5-cyanopyrazin-2-yl)piperidin-3-yl)-1,1-dimethylurea (222, 330 mg, 1.07 mmol), tert-butyl 4-(4-amino-1H-pyrazol-1-yl)piperidine-1-carboxylate (275, 426 mg, 1.60 mmol), fine-powder cesium carbonate (1.05 g, 3.21 mmol), Pd(OAc)$_2$ (72 mg, 0.32 mmol), BINAP (200 mg, 0.32 mmol) in 60 mL dioxane was degassed with nitrogen stream for 3 min. It was then stirred in 115° C. bath in nitrogen atmosphere for 2 hours. The mixture was cooled to RT, diluted with 60 mL EtOAc, and filtered. The filtrate was concentrated in vacuo and subjected to silica flash column using 0 to 6% MeOH in chloroform to isolate (R)-tert-butyl 4-(4-(3-cyano-6-(3-(3,3-dimethylureido)piperidin-1-yl)pyrazin-2-ylamino)-1H-pyrazol-1-yl)piperidine-1-carboxylate (276). It was dissolved in 20 mL MeOH and 4 mL DMSO. To it were added one NaOH solid bead (about 100 mg) and then 0.5 mL 30% H$_2$O$_2$. The mixture was stirred at RT for 2 hours, diluted with 10 mL MeCN, stirred for 5 min, concentrated in vacuo, diluted with EtOAc 150 mL, washed with water ×3, dried, concentrated in vacuo to afford crude (R)-tert-butyl 4-(4-(3-carbamoyl-6-(3-(3,3-dimethylureido)piperidin-1-yl)pyrazin-2-ylamino)-1H-pyrazol-1-yl)piperidine-1-carboxylate (277).

Crude (R)-tert-butyl 4-(4-(3-carbamoyl-6-(3-(3,3-dimethylureido)piperidin-1-yl)pyrazin-2-ylamino)-1H-pyrazol-1-yl)piperidine-1-carboxylate (277, 108 mg, 0.19 mmol) was treated with 2:1 DCM/TFA at RT for 1 hour and concentrated in vacuo to get (R)-5-(3-(3,3-dimethylureido)piperidin-1-yl)-3-(1-(piperidin-4-yl)-1H-pyrazol-4-ylamino)pyrazine-2-carboxamide (278) TFA salt. It was dissolved in 10 mL DCE and 2 mL NMP. To it were added DIEA (330 µL, 1.9 mmol) and cyclopentanone (480 mg, 5.7 mmol). The mixture was stirred at RT for 5 hours, and to it were added HOAc (220 µL, 3.8 mmol) and NaBH(OAc)$_3$ (240 mg, 1.14 mmol). The mixture was stirred at RT for overnight. It was diluted with 10 mL MeOH, concentrated in vacuo, acidified with 0.3 mL TFA, and directly subjected to reverse phase prep HPLC using 5 mM HCl (aq) and neat MeCN as mobile phases to isolate (R)-3-(1-(1-cyclopentylpiperidin-4-yl)-1H-pyrazol-4-ylamino)-5-(3-(3,3-dimethylureido)piperidin-1-yl)pyrazine-2-carboxamide (279) as HCl salt (45 mg, 45%). MS found for C$_{26}$H$_{40}$N$_{10}$O$_2$ as (M+H)$^+$ 525.6, (M–H)$^-$ 523.3. UV: λ=254, 270, 297, 331, 374 nm.

Example 219

Synthesis of (R)-3-(1-(1-(cyclopropanecarbonyl)piperidin-4-yl)-1H-pyrazol-4-ylamino)-5-(3-(3,3-dimethylureido)piperidin-1-yl)pyrazine-2-carboxamide

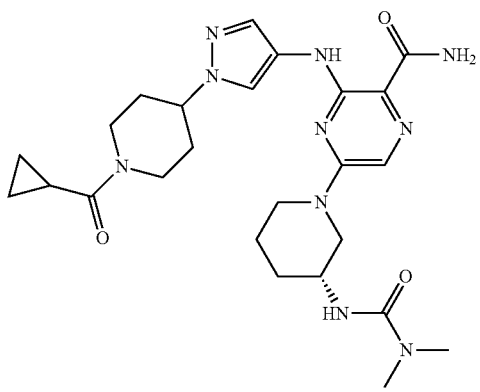

280

Crude (R)-tert-butyl 4-(4-(3-carbamoyl-6-(3-(3,3-dimethylureido)piperidin-1-yl)pyrazin-2-ylamino)-1H-pyrazol-1-yl)piperidine-1-carboxylate (277, 72 mg, 0.13 mmol) was treated with 2:1 DCM/TFA at RT for 1 hour and concentrated in vacuo to get (R)-5-(3-(3,3-dimethylureido)piperidin-1-yl)-3-(1-(piperidin-4-yl)-1H-pyrazol-4-ylamino)pyrazine-2-carboxamide (278) TFA salt. It was dissolved in 4 mL NMP. To it were added DIEA (230 µL, 1.3 mmol) and cyclopropanecarbobyl chloride (41 mg, 0.39 mmol). The mixture was stirred at RT for 2 hours, acidified with 0.5 mL TFA, and directly subjected to reverse phase prep HPLC using 5 mM HCl (aq) and neat MeCN as mobile phases to isolate (R)-3-(1-(1-(cyclopropanecarbonyl)piperidin-4-yl)-1H-pyrazol-4-ylamino)-5-(3-(3,3-dimethylureido)piperidin-1-yl)pyrazine-2-carboxamide (280) as HCl salt (32 mg, 47%). MS found for C$_{25}$H$_{36}$N$_{10}$O$_3$ as (M+H)$^+$ 525.5, (M–H)$^-$ 523.3. UV: λ=253, 269, 298, 331, 374 nm.

In a similar manner as described in Example 179, (R)-3-(4-cyclohexylphenylamino)-5-(3-(3,3-dimethylureido)piperidin-1-yl)pyrazine-2-carboxamide (266) was prepared using 4-cyclohexylaniline. MS found for C$_{25}$H$_{35}$N$_7$O$_2$ as (M+H)$^+$ 466.5. UV: λ=267, 276, 305, 336, 373 nm.

Example 220

Synthesis of (R)-3-(1-(1-cyclopentylazetidin-3-yl)-1H-pyrazol-4-ylamino)-5-(3-(3,3-dimethylureido)piperidin-1-yl)pyrazine-2-carboxamide

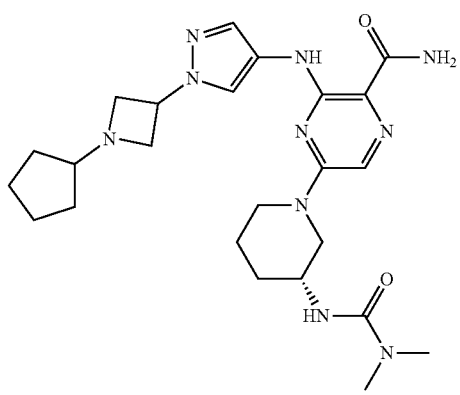

281

In a similar manner as described in Example 218, (R)-3-(1-(1-cyclopentylazetidin-3-yl)-1H-pyrazol-4-ylamino)-5-(3-(3,3-dimethylureido)piperidin-1-yl)pyrazine-2-carboxamide (281) was prepared using tert-butyl 3-(4-amino-1H- pyrazol-1-yl)azetidine-1-carboxylate. MS found for $C_{24}H_{36}N_{10}O_2$ as $(M+H)^+$ 497.4, $(M-H)^-$ 495.2. UV: $\lambda$=253, 269, 298, 330, 372 nm.

Example 221

Synthesis of (R)-5-(3-(3,3-dimethylureido)piperidin-1-yl)-3-(4-(4-methylpiperidin-4-yl)phenylamino)pyrazine-2-carboxamide (289)

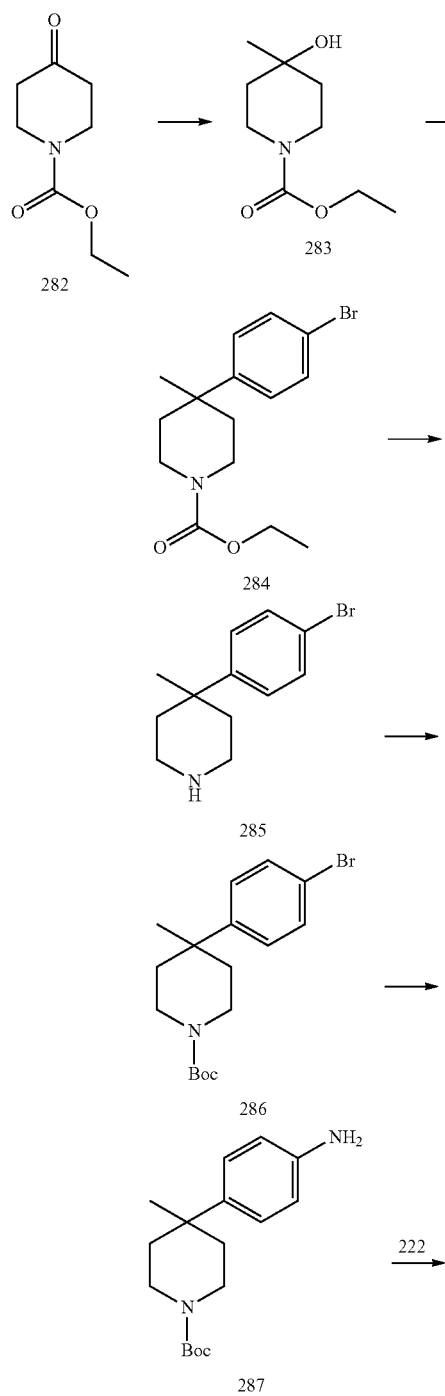

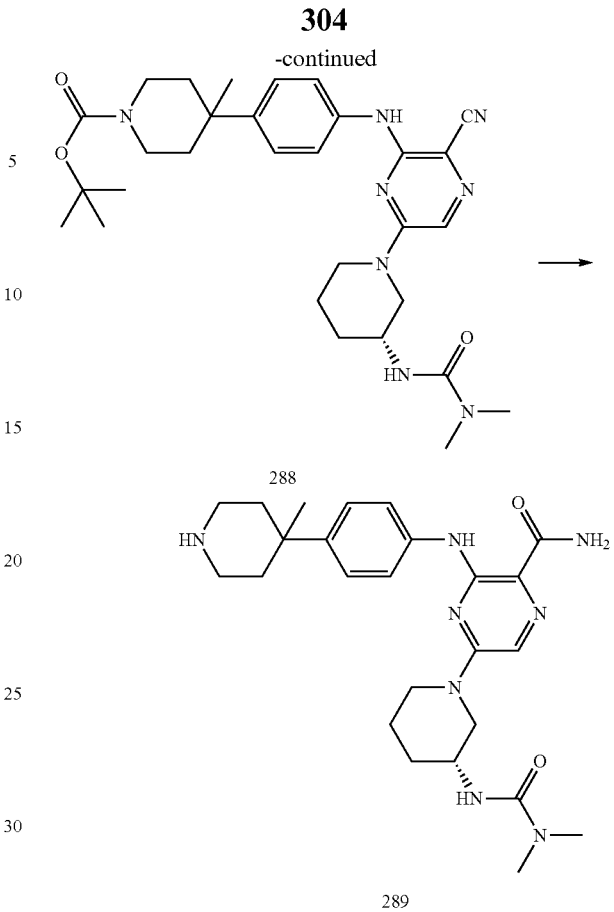

At −30° C. and under $N_2$ atmosphere, to a solution of ethyl 4-oxopiperidine-1-carboxylate (282) (6.0 g, 35.1 mmol) in anhydrous $Et_2O$ (100 mL) was added MeMgBr (3.0 M, 14 mL, 42.1 mmol). The resulting mixture was stirred at 0° C. for 2 hours before being quenched with aqueous $NH_4Cl$ solution. The mixture was extracted with DCM (30 mL×3). The combined organic layers were washed with brine, dried over $Na_2SO_4$, concentrated in vacuo and subjected to silica flash column chromatography using 0 to 50% EtOAc in PE (petroleum ether) to isolate ethyl 4-hydroxy-4-methylpiperidine-1-carboxylate (283) (4 g, 61%) as an oil.

At 0° C. under $N_2$ atmosphere, to a solution of ethyl 4-hydroxy-4-methylpiperidine-1-carboxylate (283) (2.4 g, 12.8 mmol) in bromobenzene (20.1 g, 128 mmol) was added trifluoromethanesulfonic acid (19.2 g, 128 mmol). The resulting mixture was stirred at RT for 3 hours before being poured onto ice. The mixture was basified with 1N NaOH and extracted with DCM (20 mL×3). The combined organic layers were washed with brine, dried, concentrated in vacuo and subjected to silica flash column using 0 to 20% EtOAc in PE to give ethyl 4-(4-bromophenyl)-4-methylpiperidine-1-carboxylate (284) (3.4 g, 81%) as a light yellow oil.

To a solution of ethyl 4-(4-bromophenyl)-4-methylpiperidine-1-carboxylate (284) (5.36 g, 16 mmol) in EtOH (75 mL) was added KOH (17.9 g, 320 mmol). The resulting mixture was stirred at 80° C. for overnight before being cooled down to RT. The solvent was removed and the residue was partitioned in water (30 mL) and DCM (20 mL). The layers were separated and the aqueous layer was extracted with DCM (10 mL×5). The combined organic layers were washed with brine, dried, and concentrated in vacuo to give crude 4-(4-bromophenyl)-4-methylpiperidine (285) in quantitative yield, which was used directly in next step without further purification.

To a solution of 4-(4-bromophenyl)-4-methylpiperidine (285) (4.1 g, 16 mmol) in DCM (20 mL) was added (BOC)$_2$O (5.7 g, 26 mmol). The resulting mixture was stirred at RT for 30 min before being diluted with water (10 mL). The mixture was extracted with DCM (10 mL×2). The combine organic layers were washed with brine, dried, concentrated in vacuo, and subjected to silica flash column using 0 to 20% EtOAc in PE to give tert-butyl 4-(4-bromophenyl)-4-methylpiperidine-1-carboxylate (286) (5 g, 88%) as colorless oil.

A sealed tube was charged with tert-butyl 4-(4-bromophenyl)-4-methylpiperidine-1-carboxylate (286) (2.6 g, 7.37 mmol), (dicyclohexylphosphino)biphenyl (65 mg, 0.18 mmol), Pd$_2$(dba)$_3$ (68 mg, 0.074 mmol) and LiHMDS (1M, 14.7 mL, 14.7 mmol) in anhydrous THF (15 mL). The resulting mixture was purged with N$_2$ stream and stirred in 65° C. bath for overnight. After being cooled to RT, the mixture was diluted with water (10 mL) and extracted with DCM (5 mL×3). The combined organic layers were washed with brine, dried, concentrated in vacuo, and subjected to silica flash column chromatography using 0 to 30% EtOAc in PE to afford tert-butyl 4-(4-aminophenyl)-4-methylpiperidine-1-carboxylate (287) (750 mg, 36%) as a white solid. Proton NMR (CDCl$_3$): δ 7.13 (2H, d, J=8.5 Hz), 6.69 (2H, d, J=8.5 Hz), 3.67-3.57 (2H, m), 3.54-3.44 (2H, m), 3.43-3.33 (2H, m), 2.03 (2H, s), 1.67-1.61 (2H, m), 1.47 (9H, s), 1.22 (3H, s) ppm.

The mixture of 3-((2R,3R)-1-(6-chloro-5-cyanopyrazin-2-yl)-2-methylpiperidin-3-yl)-1,1-dimethylurea (222) (250 mg, 0.81 mmol), tert-butyl 4-(4-aminophenyl)-4-methylpiperidine-1-carboxylate (287) (400 mg, 1.22 mmol), fine-powder cesium carbonate (800 mg, 2.43 mmol), Pd(OAc)$_2$ (55 mg, 0.24 mmol), BINAP (150 mg, 0.24 mmol) in 30 mL dioxane was degassed with nitrogen stream for 3 mM It was then stirred in 115° C. bath in nitrogen atmosphere for 2 hours. The mixture was cooled to RT, diluted with 100 mL EtOAc, and filtered using ChemGlass OP-6602-12 disposable funnel. The filtrate was concentrated in vacuo and subjected to silica flash column using 0 to 8% MeOH in DCM to isolate (R)-tert-butyl 4-(4-(3-cyano-6-(3-(3,3-dimethylureido)piperidin-1-yl)pyrazin-2-ylamino)phenyl)-4-methylpiperidine-1-carboxylate (288). It was dissolved in 10 mL MeOH and 3 mL DMSO. To it were added one NaOH solid bead (about 100 mg) and then 1 mL 30% H$_2$O$_2$. The mixture was stirred at RT for overnight, diluted with 10 mL MeCN, stirred for 5 min, and concentrated on rotavap. The residue was diluted with 150 mL EtOAc, washed with water ×3, dried, and subjected to silica flash column using 0 to 10% MeOH in DCM to isolate (R)-tert-butyl 4-(4-(3-carbamoyl-6-(3-(3,3-dimethylureido)piperidin-1-yl)pyrazin-2-ylamino)phenyl)-4-methylpiperidine-1-carboxylate. It was treated with 20 mL commercial 4N HCl in dioxane at RT for 45 mM, and concentrated to dryness to give crude (R)-5-(3-(3,3-dimethylureido)piperidin-1-yl)-3-(4-(4-methylpiperidin-4-yl)phenylamino)pyrazine-2-carboxamide (289) as HCl salt. It was subjected to reverse phase prep HPLC using 5 mM HCl (aq) and neat MeCN as mobile phases for purification. MS found for C$_{25}$H$_{36}$N$_8$O$_2$ as (M+H)$^+$ 481.3. UV: λ=268, 277, 306, 336, 373 nm.

Example 222

Synthesis of (R)-3-(4-(1-cyclopentyl-4-methylpiperidin-4-yl)phenylamino)-5-(3-(3,3-dimethylureido)piperidin-1-yl)pyrazine-2-carboxamide

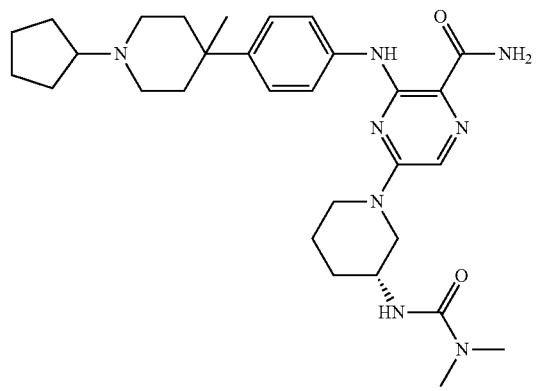

290

(R)-5-(3-(3,3-Dimethylureido)piperidin-1-yl)-3-(4-(4-methylpiperidin-4-yl)phenylamino)pyrazine-2-carboxamide (289) (190 mg, 0.4 mmol) was dissolved in 20 mL DCE and 20 mL dioxane. To it were added DIEA (350 μL, 2.0 mmol) and cyclopentanone (710 μL, 8.0 mmol). The mixture was stirred at RT for 2 hours, and to it were added HOAc (250 μL, 4.0 mmol) and NaBH(OAc)$_3$ (430 mg, 2.0 mmol). The mixture was stirred at RT for 1.5 hour. It was diluted with 10 mL MeOH, concentrated in vacuo, acidified with 0.5 mL TFA, and directly subjected to reverse phase prep HPLC using 5 mM HCl (aq) and neat MeCN as mobile phases to isolate (R)-3-(4-(1-cyclopentyl-4-methylpiperidin-4-yl)phenylamino)-5-(3-(3,3-dimethylureido)piperidin-1-yl)pyrazine-2-carboxamide (290) as HCl salt (82 mg, 37%). MS found for C$_{30}$H$_{44}$N$_8$O$_2$ as (M+H)$^+$ 549.6. UV: λ=268, 278, 306, 336, 373 nm. Proton NMR (CD$_3$OD): δ 7.71-7.63 (3H, m), 7.36-7.33 (2H, m), 4.38-4.32 (1H, m), 4.22 (1H, m), 3.77 (1H, m), 3.66-3.50 (2H, m), 3.28-3.10 (2H, m), 2.89 (6H, s), 2.86-2.80 (2H, m), 2.64 (1H, m), 2.23-1.62 (16H, m), 1.42-1.26 (3H, s) ppm.

Example 223

Synthesis of (R)-3-(4-(1-(dimethylcarbamoyl)-4-methylpiperidin-4-yl)phenylamino)-5-(3-(3,3-dimethylureido)piperidin-1-yl)pyrazine-2-carboxamide

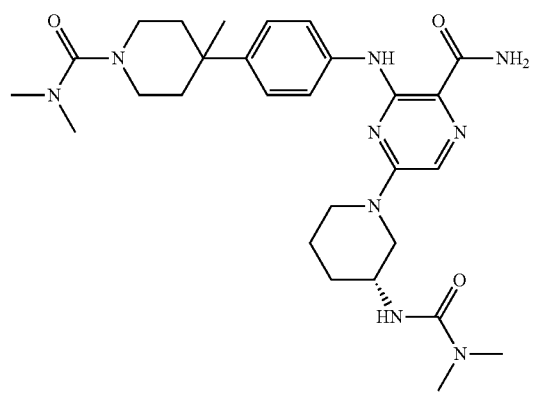

291

(R)-5-(3-(3,3-Dimethylureido)piperidin-1-yl)-3-(4-(4-methylpiperidin-4-yl)phenylamino)pyrazine-2-carboxamide (289) (90 mg, 0.2 mmol) was dissolved in 4 mL NMP. To it were added DIEA (350 μL, 2.0 mmol) and then dimethylcarbamoyl chloride (55 μL, 0.6 mmol). The mixture was stirred at RT for 30 min, quenched with 0.5 mL TFA, and directly subjected to reverse phase prep HPLC using 5 mM HCl (aq) and neat MeCN as mobile phases to isolate (R)-3-(4-(1-(dimethylcarbamoyl)-4-methylpiperidin-4-yl)phenylamino)-5-(3-(3,3-dimethylureido)piperidin-1-yl)pyrazine-2-carboxamide (291) as HCl salt (61 mg, 55%). MS found for $C_{28}H_{41}N_9O_3$ as $(M+H)^+$ 552.4, $(M-H)^-$ 550.3. UV: λ=268, 277, 305, 336, 372 nm Proton NMR (CD$_3$OD): δ 7.63 (1H, s), 7.61 (2H, d, J=8.5 Hz), 7.32 (2H, d, J=8.5 Hz), 4.37 (1H, m), 4.21 (1H, m), 3.77 (1H, m), 3.37-3.31 (2H, m), 3.21-3.15 (3H, m), 3.10 (1H, m), 2.88 (6H, s), 2.83 (6H, s), 2.15 (2H, m), 2.02 (1H, m), 1.87 (1H, m), 1.75-1.63 (4H, m), 1.26 (3H, s) ppm.

Example 224

Synthesis of (R)-5-(3-(3,3-dimethylureido)piperidin-1-yl)-3-(4-(4-methyl-1-propionylpiperidin-4-yl)phenylamino)pyrazine-2-carboxamide

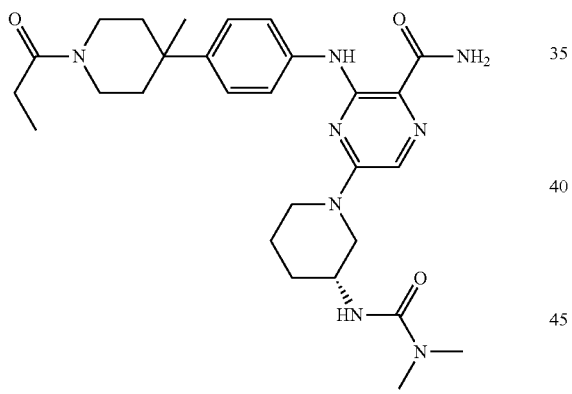

292

In a similar manner as described in Example 223, (R)-5-(3-(3,3-dimethylureido)piperidin-1-yl)-3-(4-(4-methyl-1-propionylpiperidin-4-yl)phenylamino)pyrazine-2-carboxamide (292) was prepared using propionyl chloride. MS found for $C_{28}H_{40}N_8O_3$ as $(M+H)^+$ 537.4, $(M-H)^-$ 535.3. UV: λ=268, 277, 306, 336, 372 nm Proton NMR (CD$_3$OD): δ 7.63 (1H, s), 7.62 (2H, d, J=8.5 Hz), 7.33 (2H, d, J=8.5 Hz), 4.37 (1H, m), 4.20 (1H, m), 3.81-3.77 (2H, m), 3.62 (1H, m), 3.40 (2H, m), 3.20 (1H, m), 3.10 (1H, m), 2.88 (6H, s), 2.42 (2H, m), 2.20-2.11 (2H, m), 2.03 (1H, m), 1.88 (1H, m), 1.73 (1H, m), 1.71-1.61 (3H, m), 1.27 (3H, s), 1.11 (3H, t, J=7.5 Hz) ppm.

Example 225

Synthesis of (R)-3-(4-(1-cyclopentylpiperidin-4-yl)phenylamino)-5-(3-(1,3,3-trimethylureido)piperidin-1-yl)pyrazine-2-carboxamide

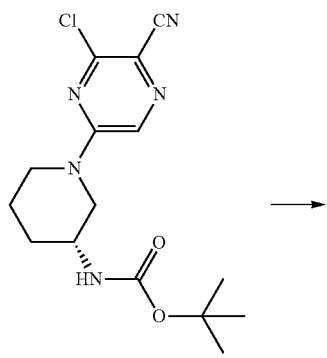

87

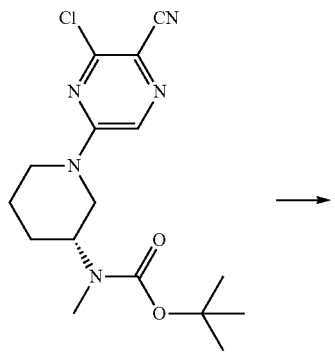

293

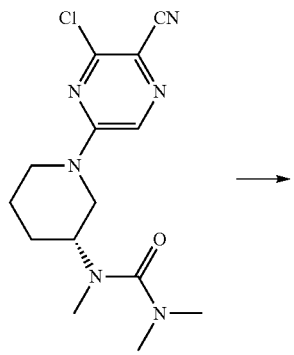

294

309
-continued

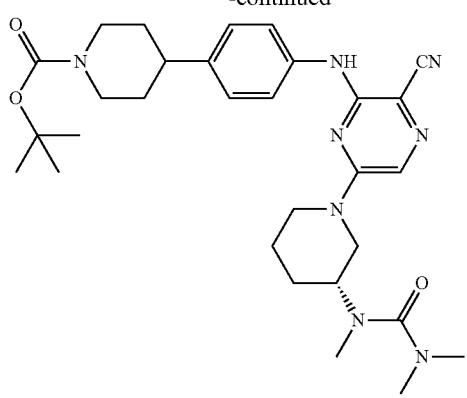

295

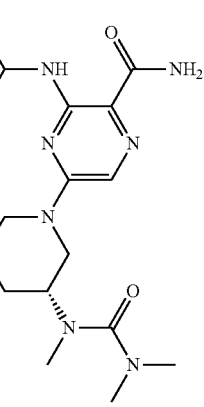

296

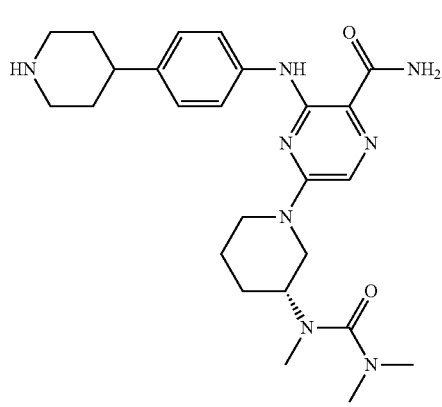

297

310
-continued

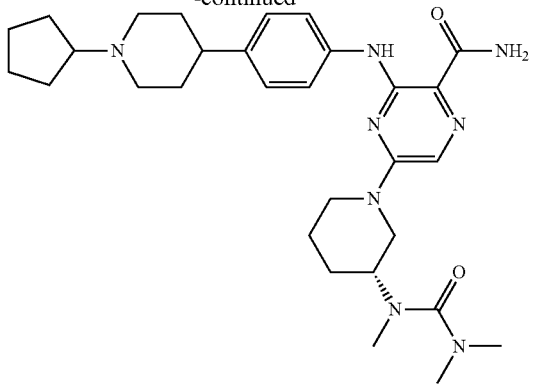

298

(R)-tert-Butyl 1-(6-chloro-5-cyanopyrazin-2-yl)piperidin-3-ylcarbamate (87, 550 mg, 1.63 mmol) was dissolved in 20 mL DMF. To it was added NaH (60% in mineral oil, 98 mg, 2.45 mmol). The mixture was stirred at RT for 30 min, and then iodomethane (305 µL, 4.89 mmol) was added. It was stirred for 1.5 hour, diluted with 120 mL EtOAc, washed with water ×3, dried, concentrated, and subjected to flash column using 0 to 50% EtOAc in hexane to isolate (R)-tert-butyl 1-(6-chloro-5-cyanopyrazin-2-yl)piperidin-3-yl(methyl)carbamate (293). It was treated with 20 mL commercial 4N HCl in dioxane at RT for 1 hour, and the mixture was concentrated in vacuo to dryness. It was dissolved in 5 mL DMF and 15 mL dioxane. To it were added DIEA (1.45 mL, 8.15 mmol) and then dimethylcarbamoyl chloride (300 µL, 3.26 mmol). The mixture was stirred at RT for overnight, diluted with 120 mL EtOAc, washed with water ×2, dried, concentrated, and subjected to silica flash column using 0 to 5% MeOH in DCM to isolate (R)-1-(1-(6-chloro-5-cyanopyrazin-2-yl)piperidin-3-yl)-1,3,3-trimethylurea (294, 490 mg, 93% overall) as a white solid.

The mixture of (R)-1-(1-(6-chloro-5-cyanopyrazin-2-yl)piperidin-3-yl)-1,3,3-trimethylurea (294, 390 mg, 1.21 mmol), tert-butyl 4-(4-aminophenyl)piperidine-1-carboxylate (670 mg, 2.42 mmol), fine-powder cesium carbonate (1600 mg, 4.84 mmol), Pd(OAc)$_2$ (134 mg, 0.60 mmol), BINAP (374 mg, 0.60 mmol) in 60 mL dioxane was degassed with nitrogen stream for 5 min. It was then stirred in 115° C. bath in nitrogen atmosphere for 2 hours. The mixture was cooled to RT, diluted with 120 mL EtOAc, and filtered. The filtrate was concentrated in vacuo and subjected to silica flash column using 20 to 100% EtOAc in DCM to isolate (R)-tert-butyl 4-(4-(3-cyano-6-(3-(1,3,3-trimethylureido)piperidin-1-yl)pyrazin-2-ylamino)phenyl)piperidine-1-carboxylate (295) in >80% yield. It was dissolved in 40 mL MeOH and 10 mL DMSO. To it were added two NaOH solid bead (about 200 mg) and then 2 mL 30% H$_2$O$_2$. The mixture was stirred at RT for 3 hours, diluted with 10 mL MeCN, stirred for 5 min, and concentrated on rotavap. The residue was diluted with 120 mL EtOAc, washed with water ×2, concentrated, and subjected to silica flash column using 0 to 7% MeOh in DCM to give crude (R)-tert-butyl 4-(4-(3-carbamoyl-6-(3-(1,3,3-trimethylureido)piperidin-1-yl)pyrazin-2-ylamino)phenyl)piperidine-1-carboxylate (296). It was treated with 30 mL commercial 4N HCl in dioxane for 90 min, and concentrated in vacuo to afford crude (R)-3-(4-(piperidin-4-yl)phenylamino)-5-(3-(1,3,3-trimethylureido)piperidin-1-yl)pyrazine-2-carboxamide (297) hydrochloride.

Crude (R)-3-(4-(piperidin-4-yl)phenylamino)-5-(3-(1,3,3-trimethylureido)piperidin-1-yl)pyrazine-2-carboxamide (297) (100 mg, 0.18 mmol) was dissolved in 10 mL DCE and 10 mL dioxane. To it were added DIEA (160 μL, 0.90 mmol) and cyclopentanone (320 μL, 3.60 mmol). The mixture was stirred at RT for 2 hours, and to it were added HOAc (100 μL, 1.8 mmol) and NaBH(OAc)$_3$ (190 mg, 0.90 mmol). The mixture was stirred at RT for overnight. It was diluted with 10 mL MeOH, concentrated in vacuo, acidified with 0.5 mL TFA, and directly subjected to reverse phase prep HPLC using 5 mM HCl (aq) and neat MeCN as mobile phases to isolate (R)-3-(4-(1-cyclopentylpiperidin-4-yl)phenylamino)-5-(3-(1,3,3-trimethylureido)piperidin-1-yl)pyrazine-2-carboxamide (298) as HCl salt (29 mg, 29%). MS found for $C_{30}H_{44}N_8O_2$ as (M+H)$^+$ 549.6. UV: λ=269, 276, 306, 335, 373 nm. Proton NMR (CD$_3$OD): δ 7.64 (1H, s), 7.57 (2H, d, J=8.5 Hz), 7.21 (2H, d, J=8.5 Hz), 4.53 (1H, m), 4.35 (1H, m), 3.72 (1H, s), 3.70 (1H, s), 3.56 (2H, m), 3.20 (1H, m), 3.13 (2H, m), 3.00 (1H, m), 2.85 (1H, m), 2.83 (3H, s), 2.77 (6H, s), 2.21 (2H, m), 2.12 (2H, m), 2.03-1.65 (12H, m) ppm.

Example 226

Synthesis of (R)-3-(4-(1-(dimethylcarbamoyl)piperidin-4-yl)phenylamino)-5-(3-(1,3,3-trimethylureido)piperidin-1-yl)pyrazine-2-carboxamide

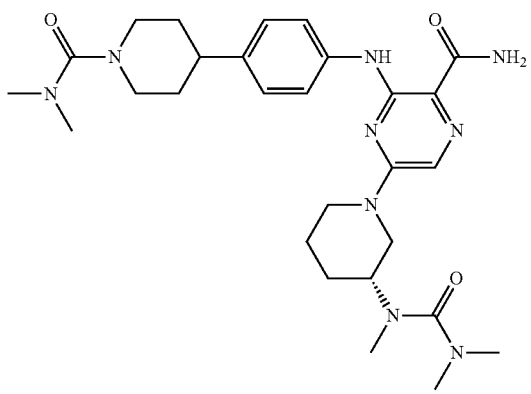

299

In a similar manner as described in Example 223, (R)-3-(4-(1-(dimethylcarbamoyl)piperidin-4-yl)phenylamino)-5-(3-(1,3,3-trimethylureido)piperidin-1-yl)pyrazine-2-carboxamide (299) was prepared using (R)-3-(4-(piperidin-4-yl)phenylamino)-5-(3-(1,3,3-trimethylureido)piperidin-1-yl)pyrazine-2-carboxamide (297). MS found for $C_{28}H_{41}N_9O_3$ as (M+H)$^+$ 552.5. UV: λ=268, 276, 305, 336, 373 nm. Proton NMR (CD$_3$OD): δ 7.61 (1H, s), 7.53 (2H, d, J=8.5 Hz), 7.17 (2H, d, J=8.5 Hz), 4.54 (1H, m), 4.34 (1H, m), 3.80 (1H, s), 3.77 (1H, s), 3.58 (1H, m), 3.17 (1H, m), 2.98 (1H, m), 2.93 (2H, m), 2.87 (6H, s), 2.82 (3H, s), 2.78 (6H, s), 2.65 (1H, m), 2.42 (2H, m), 1.98-1.63 (8H, m) ppm.

Example 227

Synthesis of (R)-3-(4-(1-propionylpiperidin-4-yl)phenylamino)-5-(3-(1,3,3-trimethylureido)piperidin-1-yl)pyrazine-2-carboxamide

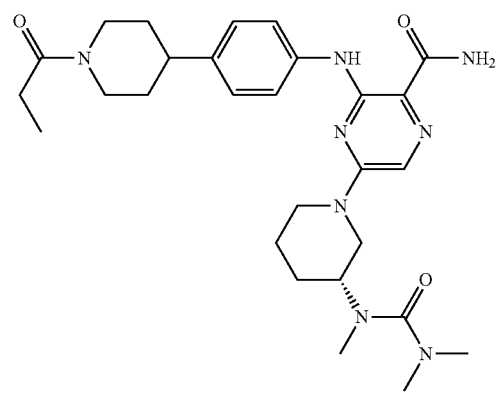

300

In a similar manner as described in Example 226, (R)-3-(4-(1-propionylpiperidin-4-yl)phenylamino)-5-(3-(1,3,3-trimethylureido)piperidin-1-yl)pyrazine-2-carboxamide (300) was prepared using propionyl chloride. MS found for $C_{28}H_{40}N_8O_3$ as (M+H)$^+$ 537.5. UV: λ=268, 276, 305, 336, 373 nm.

Example 228

Synthesis of (R)-3-(4-(1-(methylsulfonyl)piperidin-4-yl)phenylamino)-5-(3-(1,3,3-trimethylureido)piperidin-1-yl)pyrazine-2-carboxamide

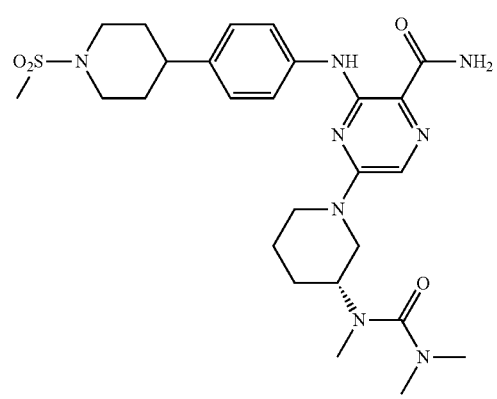

301

In a similar manner as described in Example 226, (R)-3-(4-(1-(methylsulfonyl)piperidin-4-yl)phenylamino)-5-(3-(1,3,3-trimethylureido)piperidin-1-yl)pyrazine-2-carboxamide (301) was prepared using methanesulfonyl chloride. MS found for $C_{26}H_{38}N_8O_4S$ as $(M+H)^+$ 559.4. UV: $\lambda$=268, 277, 305, 336, 372 nm.

Example 229

Synthesis of (R)-3-(4-(1,1-dioxothiomorpholino)phenylamino)-5-(3-(1,3,3-trimethylureido)piperidin-1-yl)pyrazine-2-carboxamide

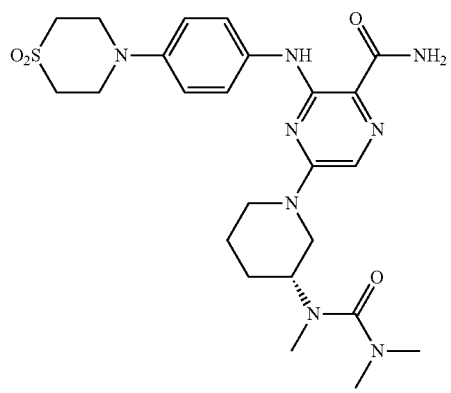

302

In a similar manner as described in Example 226, (R)-3-(4-(1,1-dioxothiomorpholino)phenylamino)-5-(3-(1,3,3-trimethylureido)piperidin-1-yl)pyrazine-2-carboxamide (302) was prepared using 4-(1,1-dioxothiomorpholino)aniline. MS found for $C_{24}H_{34}N_8O_4S$ as $(M+H)^+$ 531.1, $(M-H)^-$ 529.3. UV: $\lambda$=310, 348, 373 nm. Proton NMR (CD$_3$OD): δ 7.61 (1H, s), 7.52 (2H, d, J=9.0 Hz), 7.01 (2H, d, J=9.0 Hz), 4.54 (1H, m), 4.34 (1H, m), 3.77 (4H, m), 3.56 (1H, m), 3.20 (1H, m), 3.16 (4H, m), 2.99 (1H, m), 2.82 (3H, s), 2.78 (6H, s), 2.01-1.88 (3H, m), 1.65 (1H, m) ppm.

Example 230

Synthesis of 5-((2R,3R)-3-amino-2-methylpiperidin-1-yl)-3-(4-(1-cyclopentylpiperidin-4-yl)phenylamino)pyrazine-2-carboxamide

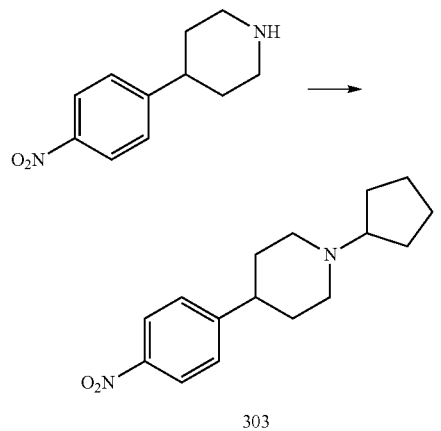

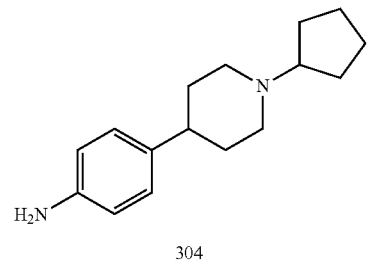

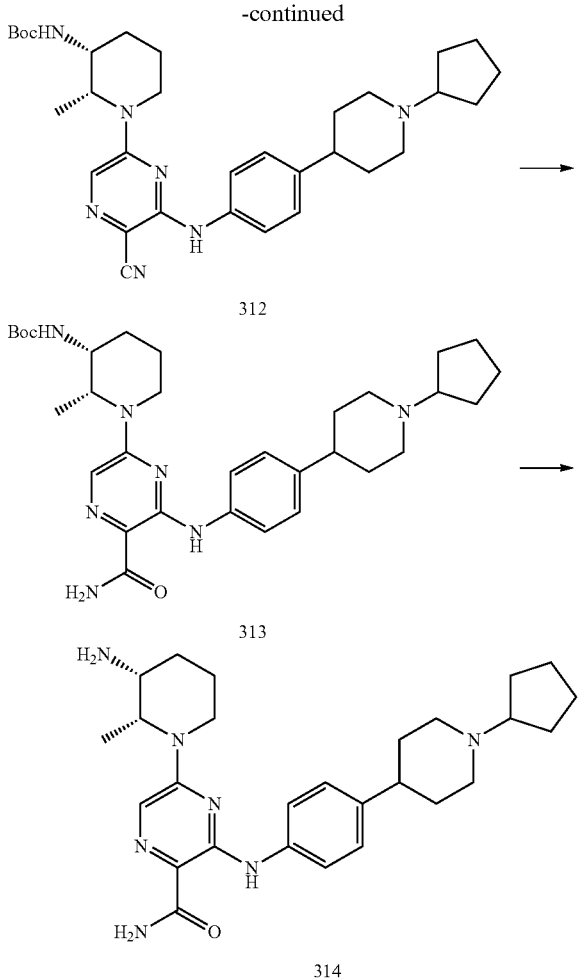

4-(4-Nitrophenyl)piperidine (5 g, 24 mmol) was dissolved in MeOH (240 mL). To the solution were added cyclopentanone (6.5 mL, 73 mmol) and acetic acid (3 mL). The mixture was stirred for 1 hour, and then NaBH₃CN (6.1 g, 97 mmol) was added. The mixture was stirred at room temperature for 12 hours. The solvent was removed under reduced pressure, and the residue was suspended in EtOAc. The organic suspension was washed with 1N NaOH (aq), water and brine, dried, concentrated and purified by flash column chromatography (MeOH/DCM) to obtain 1-cyclopentyl-4-(4-nitrophenyl)piperidine (303) (6.5 g, 24 mmol, 100% yield).

1-Cyclopentyl-4-(4-nitrophenyl)piperidine (303) (6.5 g, 24 mmol) was dissolved in IPA (70 mL) and 2M HCl (aq) (18 mL), and 10% Pd/C (2 g) was added. The resulting mixture was agitated on Parr shaker under 50 psi hydrogen for 18 hours. The reaction mixture was filtered through celite, and the solvent was removed under reduced pressure to give 4-(1-cyclopentylpiperidin-4-yl)aniline hydrochloride (304) (4.0 g, 14 mmol, 60% yield).

To a 1-liter round bottom flask were added (R)-5-(benzyloxycarbonylamino)-2-(tert-butoxycarbonylamino)pentanoic acid (10 g, 27 mmol), N-methoxy-N-methylamine-HCl (5.3 g, 55 mmol), PyBOP (21 g, 41 mmol), and MeCN (400 mL). DIEA (19 mL, 110 mmol) was added and the reaction was allowed to stir at room temperature for 12 hours. The solvent was removed under reduced pressure and the residue was suspended in EtOAc and washed with 1N NaOH (aq) (×3) then 2N HCl (aq) (×2), then saturated NaHCO₃ (aq) (×1), then brine (×1). The product was then purified by column chromatography (EtOAc/hexanes) to give N-methoxy-N-methyl-(R)-5-(benzyloxycarbonylamino)-2-(tert-butoxycarbonylamino)pentanamide (305) (10.9 g, 26.7 mmol, 99% yield) as a clear oil.

N-Methoxy-N-methyl-(R)-5-(Benzyloxycarbonylamino)-2-(tert-butoxycarbonylamino)-pentanamide (305) (10 g, 24 mmol) was dissolved in THF (250 mL) and the solution was cooled to −30° C. in a dry-ice acetone bath. MeMgBr (3M in Et₂O, 123 mL, 369 mmol) was added drop-wise over 30 minutes. The bath temperature was slowly allowed to increase to 0° C. and then was maintained at 0° C. until TLC showed no further reaction progress (~80-90% complete). Saturated NH₄Cl (aq) was then slowly added to the reaction mixture at 0° C. and the THF was removed under reduced pressure. The resulting aqueous solution was then extracted with EtOAc and the extracts were washed with water and then brine. The residue was then purified by column chromatography (EtOAc/hexanes) to give (R)-6-(benzyloxycarbonylamino)-3-(tert-butoxycarbonylamino)-2-hexanone (306), (6.5 g, 18 mmol, 75% yield).

(R)-6-(Benzyloxycarbonylamino)-3-(tert-butoxycarbonylamino)-2-hexanone (306) (14.3 g, 39.3 mmol) was divided in 2 equal batches and each batch was dissolved in IPA (70 mL), combined with 10% Pd/C (5.5 g), and hydrogenated on a Parr shaker at 50 psi pressure for 12 hours. The batches were combined, filtered through celite and concentrated in vacuo to give (R)-tert-butyl 2-methylpiperidin-3-ylcarbamate (307), (8.2 g, 38 mmol, 97% yield) as a clear oil.

(R)-tert-Butyl 2-methylpiperidin-3-ylcarbamate (307) (8.2 g, 38 mmol) was suspended in a solution of DCM (500 mL) and DIEA (13.4 mL, 76.9 mmol). Benzyl chloroformate (6.6 mL, 46 mmol) was then added drop-wise over 5 minutes and the reaction was stirred at 0° C. for 30 minutes. Water was then added and the mixture was allowed to come to room temperature and stirred for 30 minutes. The organic phase was separated, washed with 1M HCl (aq), saturated NaHCO₃ (aq), and brine. On TLC, the trans-isomer (309) displayed a higher silica R$_f$ value than the cis isomer (308). The two diastereomers were separated by silica flash column chromatography (EtOAc/hexanes). The mixed fractions from the first purification were combined and subjected to a second purification. After two purifications, (2R,3R)-benzyl 3-(tert-butoxycarbonylamino)-2-methylpiperidine-1-carboxylate (308) (2.5 g, 7.2 mmol, 19% yield) and (2S,3R)-benzyl 3-(tert-butoxycarbonylamino)-2-methylpiperidine-1-carboxylate (309) (8 g, 23 mmol, 61% yield) were obtained.

(2R,3R)-Benzyl 3-(tert-butoxycarbonylamino)-2-methylpiperidine-1-carboxylate (308) (1.7 g, 4.9 mmol) was dissolved in IPA (20 mL). 10% Pd/C (1 g) was added and the mixture was hydrogenated on a Parr shaker at 50 psi pressure for 12 hours. The reaction mixture was filtered through celite, and the solvent was removed under reduced pressure to give tert-butyl (2R,3R)-2-methylpiperidin-3-ylcarbamate (310), (1.1 g, 5.1 mmol, 100% yield).

tert-Butyl (2R,3R)-2-methylpiperidin-3-ylcarbamate (310) (1.1 g, 5.1 mmol) was dissolved in THF (20 mL). To the stirred solution was added DIEA (1.34 mL, 7.7 mmol), followed by 3,5-dichloropyrazine-2-carbonitrile (1.07 g, 6.2 mmol). The reaction was stirred at room temperature for 1 hour. An additional amount of 3,5-dichloropyrazine-2-carbonitrile (200 mg, 1.2 mmol) was added, and the reaction was stirred for another hour. The solvent was removed under reduced pressure, and the residue was suspended in EtOAc. The organic mixture was washed with 1N HCl (aq), saturated NaHCO₃(aq) and brine, dried, and concentrated in vacuo. The residue was then purified by silica flash column chromatography (EtOAc/hexanes) to give tert-butyl (2R,3R)-1-(6-chloro-5-cyanopyrazin-2-yl)-2-methylpiperidin-3-ylcarbamate (311), (1.54 g, 4.38 mmol, 86% yield).

tert-Butyl (2R,3R)-1-(6-chloro-5-cyanopyrazin-2-yl)-2-methylpiperidin-3-ylcarbamate (311) (390 mg, 1.1 mmol), 4-(1-cyclopentylpiperidin-4-yl)aniline HCl salt (304) (406 mg, 1.7 mmol), fine-powder Cs₂CO₃ (1.1 g, 3.3 mmol), BINAP (207 mg, 0.33 mmol), and Pd(OAc)₂ (75 mg, 0.33 mmol) were combined and suspended in dioxane (30 mL) and water (1 mL). The mixture was sparged with nitrogen stream for 10 minutes, and then stirred under nitrogen atmosphere in 115° C. oil bath for 5 hours. The mixture was cooled to RT, diluted with EtOAc (100 mL), stirred, filtered and concentrated under reduced pressure. The resulting residue was subjected to silica flash column chromatography (MeOH/DCM) to give tert-butyl (2R,3R)-1-(5-cyano-6-(4-(1-cyclopentylpiperidin-4-yl)phenylamino)pyrazin-2-yl)-2-methylpiperidin-3-ylcarbamate (312) (430 mg, 0.74 mmol, 68% yield).

tert-Butyl (2R,3R)-1-(5-cyano-6-(4-(1-cyclopentylpiperidin-4-yl)phenylamino)pyrazin-2-yl)-2-methylpiperidin-3-ylcarbamate (312) (430 mg, 0.74 mmol) was dissolved in MeOH (25 mL), DMSO (4.4 mL), and TEA (0.22 mL, 1.6 mmol). The solution was cooled to 0° C., and a pre-mixed solution of 30% H₂O₂ (175 µL, 1.5 mmol) and 4N NaOH (384 µL, 1.5 mmol) was added. The reaction was stirred for 1 hour at 0° C. An additional amount of the pre-mixed solution 30% H₂O₂ (175 µL, 1.5 mmol) and 4N NaOH (384 µL, 1.5 mmol) was added, and the reaction was stirred for an additional hour at 0° C. MeCN (10 mL) was then added and the solution was stirred for 10 minutes at room temperature. The solvents were removed under reduced pressure, and the residue was subjected to silica flash column chromatography (MeOH/DCM) to give tert-butyl (2R,3R)-1-(5-carbamoyl-6-(4-(1-cyclopentylpiperidin-4-yl)phenylamino)pyrazin-2-yl)-2-methylpiperidin-3-ylcarbamate (313) (430 mg, 0.74 mmol, 97% yield).

tert-Butyl (2R,3R)-1-(5-carbamoyl-6-(4-(1-cyclopentylpiperidin-4-yl)phenylamino)pyrazin-2-yl)-2-methylpiperidin-3-ylcarbamate (313) (430 mg, 0.74 mmol) was treated in DCM (20 mL) and TFA (7 mL) at room temperature for 2 hours. The mixture was concentrated in vacuo, dissolved in MeOH/water, and subjected to reverse phase prep HPLC using 5 mM HCl in water and neat MeCN as mobile phases to isolate 5-((2R,3R)-3-amino-2-methylpiperidin-1-yl)-3-(4-(1-cyclopentylpiperidin-4-yl)phenylamino)pyrazine-2-carboxamide (314) as HCl salt. LC-MS (ESI): m/z (M+1) 478.5. UV: λ=264, 274, 304, 335, 372 nm. Proton NMR (CD₃OD): δ 7.66 (1H, s), 7.58 (2H, d, J=8.5 Hz), 7.27 (2H, d, J=8.5 Hz), 5.03 (1H, m), 4.32 (1H, d, J=11.0 Hz), 3.72 (2H, d, J=10.0 Hz), 3.56 (1H, m), 3.45 (1H, m), 3.14 (2H, m), 3.11 (1H, m), 2.88 (1H, m), 2.22-1.70 (16H, m), 1.32 (3H, d, J=7.0 Hz) ppm.

Example 231

Synthesis of 5-((2S,3R)-3-amino-2-methylpiperidin-1-yl)-3-(4-(1-cyclopentylpiperidin-4-yl)phenylamino)pyrazine-2-carboxamide

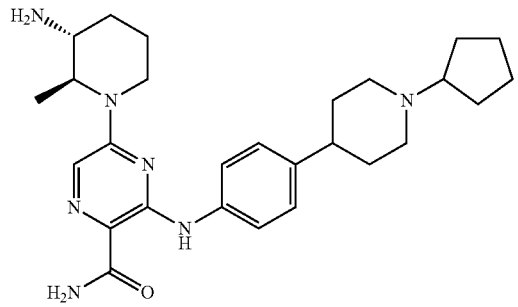

315

The title compound, 5-((2S,3R)-3-amino-2-methylpiperidin-1-yl)-3-(4-(1-cyclopentylpiperidin-4-yl)phenylamino)pyrazine-2-carboxamide (315), was prepared by the same synthetic scheme illustrated for Example 230 using (2S,3R)-benzyl 3-(tert-butoxycarbonylamino)-2-methylpiperidine-1-carboxylate (309). It was isolated as HCl salt using reverse phase prep HPLC. LC-MS (ESI): m/z (M+1) 478.4. UV: λ=263, 272, 304, 334, 370 nm Proton NMR (CD₃OD): δ 7.70 (1H, s), 7.59 (2H, d, J=9.0 Hz), 7.26 (2H, d, J=8.5 Hz), 4.89 (1H, m), 4.30 (1H, d, J=13.5 Hz), 3.72 (2H, d, J=10.0 Hz), 3.56 (2H, m), 3.25 (1H, m), 3.14 (2H, m), 2.89 (1H, m), 2.24-1.71 (16H, m), 1.39 (3H, d, J=7.0 Hz) ppm.

Example 232

Synthesis of 3-(4-(1-cyclopentylpiperidin-4-yl)phenylamino)-5-((2R,3R)-3-(3,3-dimethylureido)-2-methylpiperidin-1-yl)pyrazine-2-carboxamide

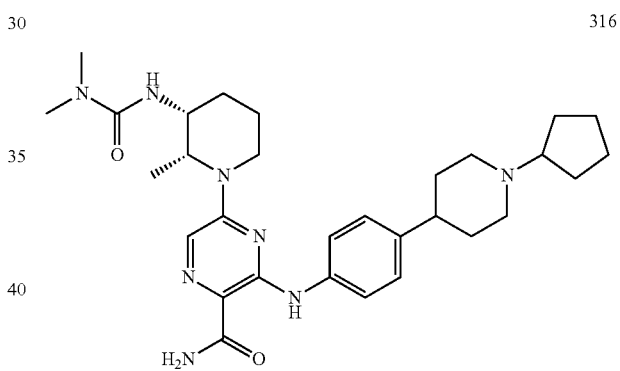

316

5-((2R,3R)-3-Amino-2-methylpiperidin-1-yl)-3-(4-(1-cyclopentylpiperidin-4-yl)phenylamino)pyrazine-2-carboxamide (314) (15 mg, 0.027 mmol, HCL salt) was dissolved in 3 mL NMP and stirred at RT. To it were added DIEA (47 µL, 0.27 mmol) and then dimethylcarbamoyl chloride (15 µL, 0.162 mmol). The mixture was stirred for 1 hour, quenched with TFA (0.1 mL), and directly subjected to reverse phase prep HPLC to isolate 3-(4-(1-cyclopentylpiperidin-4-yl)phenylamino)-5-((2R,3R)-3-(3,3-dimethylureido)-2-methylpiperidin-1-yl)pyrazine-2-carboxamide (316) as HCl salt (14 mg). LC-MS (ESI): m/z (M+1) 549.8. UV: λ=268, 277, 306, 336, 373 nm. Proton NMR (CD₃OD): δ 7.65 (1H, s), 7.61 (2H, d, J=8.5 Hz), 7.21 (2H, d, J=8.5 Hz), 4.98 (1H, m), 4.35 (1H, m), 3.87 (1H, m), 3.71 (2H, d, J=12.5 Hz), 3.54 (1H, m), 3.13 (2H, m), 3.04 (1H, m), 3.02 (6H, s), 2.85 (1H, m), 2.23

(2H, m), 2.14 (2H, m), 1.97 (2H, m), 1.88 (4H, m), 1.79-1.64 (5H, m), 1.17 (3H, d, J=7.0 Hz) ppm.

Example 233

Synthesis of 3-(4-(1-cyclopentylpiperidin-4-yl)phenylamino)-5-((2S,3R)-3-(3,3-dimethylureido)-2-methylpiperidin-1-yl)pyrazine-2-carboxamide

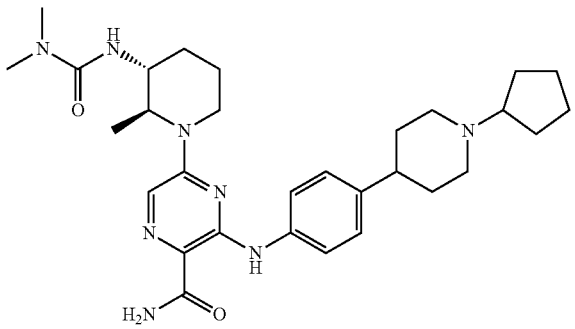

317

The title compound, 3-(4-(1-cyclopentylpiperidin-4-yl)phenylamino)-5-((2S,3R)-3-(3,3-dimethylureido)-2-methylpiperidin-1-yl)pyrazine-2-carboxamide (317), was prepared by the same synthetic scheme illustrated for Example 232 using 5-((2S,3R)-3-amino-2-methylpiperidin-1-yl)-3-(4-(1-cyclopentylpiperidin-4-yl)phenylamino)pyrazine-2-carboxamide (315). LC-MS (ESI): m/z (M+1) 549.8. UV: λ=268, 277, 306, 336, 373 nm.

Example 234

Synthesis of 5-((2R,3R)-3-benzamido-2-methylpiperidin-1-yl)-3-(4-(1-cyclopentylpiperidin-4-yl)phenylamino)pyrazine-2-carboxamide

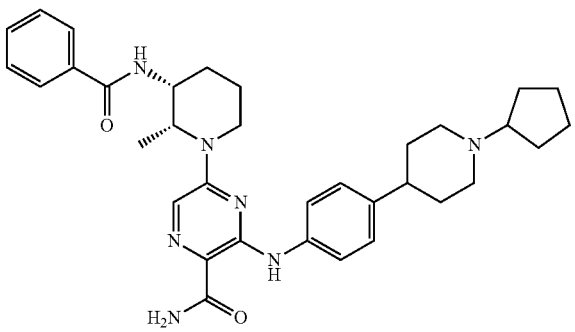

318

The title compound, 5-((2R,3R)-3-benzamido-2-methylpiperidin-1-yl)-3-(4-(1-cyclopentylpiperidin-4-yl)phenylamino)pyrazine-2-carboxamide (318), was prepared by the same synthetic method illustrated for Example 232 using benzoyl chloride. LC-MS (ESI): m/z (M+1) 582.8. UV: λ=268, 276, 304, 334, 372 nm. Proton NMR (CD$_3$OD): δ 7.88 (2H, d, J=8.5 Hz), 7.66 (1H, s), 7.61 (2H, d, J=8.0 Hz), 7.58 (1H, d, J=7.5 Hz), 7.52 (2H, t, J=7.5 Hz), 7.17 (2H, d, J=8.0 Hz), 5.24 (1H, m), 4.25 (1H, m), 4.21 (1H, m), 3.62 (2H, m), 3.54 (1H, m), 3.15 (1H, m), 3.07 (2H, m), 2.80 (1H, m), 2.20 (2H, m), 2.04 (3H, m), 1.97 (1H, m), 1.85 (5H, m), 1.74 (5H, m), 1.21 (3H, d, J=7.0 Hz) ppm.

Example 235

Synthesis of 5-((2S,3R)-3-benzamido-2-methylpiperidin-1-yl)-3-(4-(1-cyclopentylpiperidin-4-yl)phenylamino)pyrazine-2-carboxamide

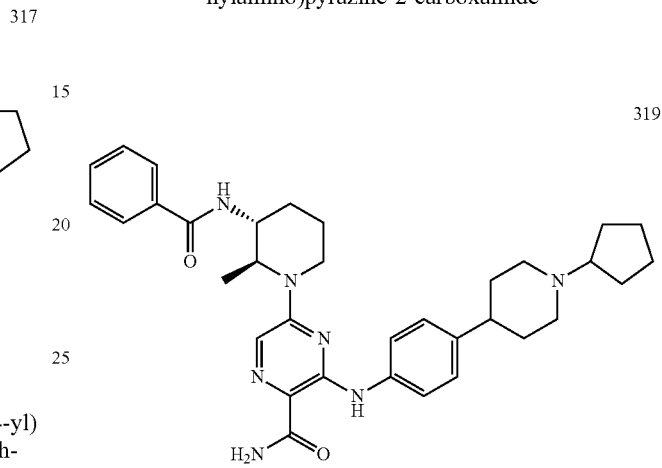

319

The title compound, 5-((2S,3R)-3-benzamido-2-methylpiperidin-1-yl)-3-(4-(1-cyclopentylpiperidin-4-yl)phenylamino)pyrazine-2-carboxamide (319), was prepared by the same synthetic method illustrated for Example 233 using benzoyl chloride. LC-MS (ESI): m/z (M+1) 582.9. UV: λ=267, 277, 306, 336, 373 nm.

Example 236

Synthesis of 3-(4-(1-cyclobutylpiperidin-4-yl)phenylamino)-5-((2R,3R)-3-(3,3-dimethylureido)-2-ethylpiperidin-1-yl)pyrazine-2-carboxamide

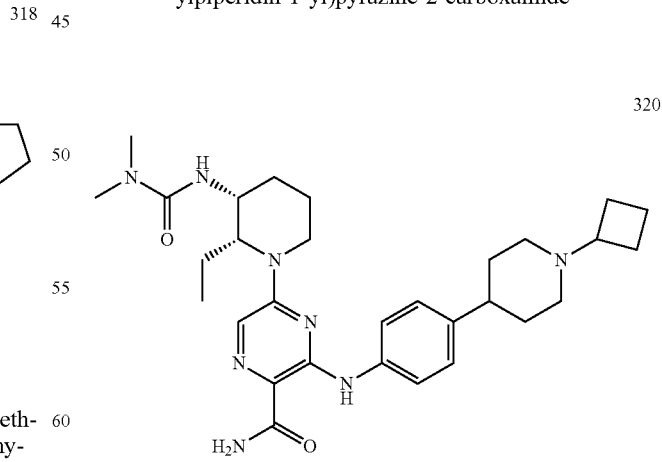

320

The title compound, 3-(4-(1-cyclobutylpiperidin-4-yl)phenylamino)-5-((2R,3R)-3-(3,3-dimethylureido)-2-ethylpiperidin-1-yl)pyrazine-2-carboxamide (320), was prepared by the same synthetic scheme illustrated for Example 232 using commercial EtMgBr reagent and cyclobutanone. LC-MS (ESI): m/z (M+1) 549.6. UV: λ=269, 280, 307, 337, 373 nm.

Example 237

Synthesis of 3-(4-(1-cyclopropylpiperidin-4-yl)phenylamino)-5-((2R,3R)-3-(3,3-dimethylureido)-2-methylpiperidin-1-yl)pyrazine-2-carboxamide

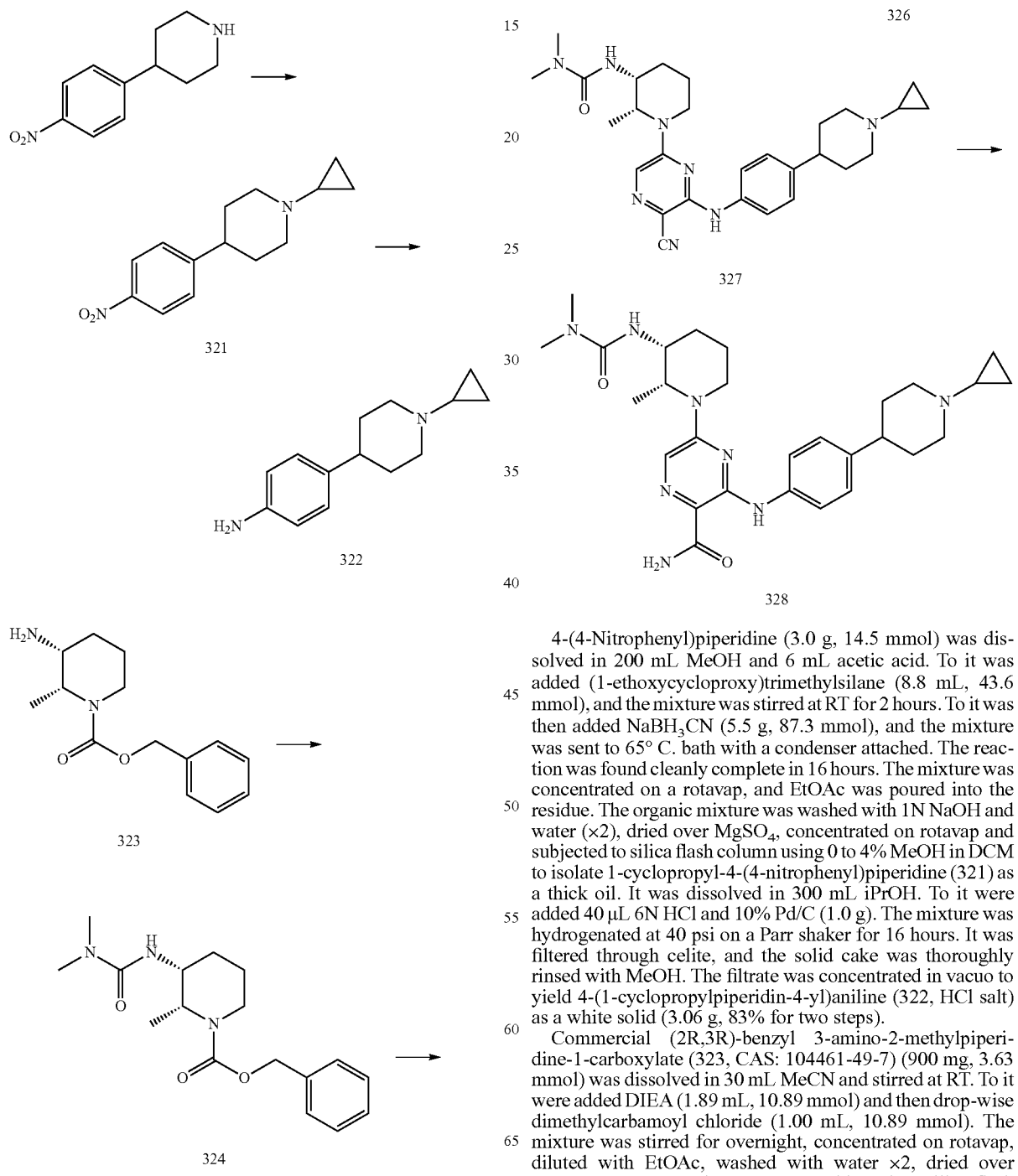

4-(4-Nitrophenyl)piperidine (3.0 g, 14.5 mmol) was dissolved in 200 mL MeOH and 6 mL acetic acid. To it was added (1-ethoxycycloproxy)trimethylsilane (8.8 mL, 43.6 mmol), and the mixture was stirred at RT for 2 hours. To it was then added NaBH₃CN (5.5 g, 87.3 mmol), and the mixture was sent to 65° C. bath with a condenser attached. The reaction was found cleanly complete in 16 hours. The mixture was concentrated on a rotavap, and EtOAc was poured into the residue. The organic mixture was washed with 1N NaOH and water (×2), dried over MgSO₄, concentrated on rotavap and subjected to silica flash column using 0 to 4% MeOH in DCM to isolate 1-cyclopropyl-4-(4-nitrophenyl)piperidine (321) as a thick oil. It was dissolved in 300 mL iPrOH. To it were added 40 μL 6N HCl and 10% Pd/C (1.0 g). The mixture was hydrogenated at 40 psi on a Parr shaker for 16 hours. It was filtered through celite, and the solid cake was thoroughly rinsed with MeOH. The filtrate was concentrated in vacuo to yield 4-(1-cyclopropylpiperidin-4-yl)aniline (322, HCl salt) as a white solid (3.06 g, 83% for two steps).

Commercial (2R,3R)-benzyl 3-amino-2-methylpiperidine-1-carboxylate (323, CAS: 104461-49-7) (900 mg, 3.63 mmol) was dissolved in 30 mL MeCN and stirred at RT. To it were added DIEA (1.89 mL, 10.89 mmol) and then drop-wise dimethylcarbamoyl chloride (1.00 mL, 10.89 mmol). The mixture was stirred for overnight, concentrated on rotavap, diluted with EtOAc, washed with water ×2, dried over MgSO₄, concentrated on rotavap, subjected to silica flash column using 0 to 4% MeOH in DCM to give (2R,3R)-benzyl 3-(3,3-dimethylureido)-2-methylpiperidine-1-carboxylate (324). It was dissolved in 100 mL iPrOH, and subjected to hydrogenation at 35 psi on Parr shaker with 10% Pd/C (1.0 g) for overnight. The mixture was filtered through celite, and the filtrate was concentrated in vacuo to afford 1,1-dimethyl-3-((2R,3R)-2-methylpiperidin-3-yl)urea (325) as a thick oil. It was dissolved in 30 mL dry DMF. To it were added 3,5-dichloropyrazine-2-carbonitrile (630 mg, 3.6 mmol) and then DIEA (1.25 mL, 7.2 mmol). The mixture was stirred at RT for overnight. It was diluted with 300 mL EtOAc, washed with water ×3, dried over $MgSO_4$, concentrated on rotavap, and subjected to silica flash column with 0 to 4% MeOH in DCM to isolate 3-((2R,3R)-1-(6-chloro-5-cyanopyrazin-2-yl)-2-methylpiperidin-3-yl)-1,1-dimethylurea (326) (850 mg, 73% overall yield for three steps).

The mixture of 3-((2R,3R)-1-(6-chloro-5-cyanopyrazin-2-yl)-2-methylpiperidin-3-yl)-1,1-dimethylurea (326) (80 mg, 0.25 mmol), 4-(1-cyclopropylpiperidin-4-yl)aniline (322, HCl salt, 76 mg, 0.30 mmol), fine-powder cesium carbonate (326 mg, 1.00 mmol), $Pd(OAc)_2$ (18 mg, 0.08 mmol), BINAP (50 mg, 0.08 mmol) in 15 mL dioxane was degassed with nitrogen stream for 3 min. It was then stirred in 115° C. bath in nitrogen atmosphere for 3 hours. The mixture was cooled to RT, diluted with 100 mL EtOAc, and filtered using ChemGlass OP-6602-12 disposable funnel. The filtrate was concentrated in vacuo and subjected to silica flash column using 0 to 5% MeOH in DCM to isolate 3-((2R,3R)-1-(5-cyano-6-(4-(1-cyclopropylpiperidin-4-yl)phenylamino)pyrazin-2-yl)-2-methylpiperidin-3-yl)-1,1-dimethylurea (327). It was dissolved in 10 mL MeOH and 2 mL DMSO. To it were added 100 μL $Et_3N$, 100 mg powder cesium carbonate, and then 0.5 mL 30% $H_2O_2$. The mixture was stirred at RT for 1.5 hour, diluted with 10 mL MeCN, stirred for 5 mM, concentrated on rotavap. The residue was treated with 0.3 mL TFA, and directly subjected to reverse phase prep HPLC using 5 mM HCl (aq) and neat MeCN as mobile phases to isolate 3-(4-(1-cyclopropylpiperidin-4-yl)phenylamino)-5-((2R,3R)-3-(3,3-dimethylureido)-2-methylpiperidin-1-yl)pyrazine-2-carboxamide (328) as HCl salt (76 mg, 58% yield). LC-MS (ESI): m/z (M+1) 521.8. UV: λ=268, 277, 306, 336, 372 nm. Proton NMR ($CD_3OD$): δ 7.64 (1H, s), 7.61 (2H, d, J=8.5 Hz), 7.20 (2H, d, J=8.5 Hz), 4.98 (1H, m), 4.34 (1H, m), 3.87 (1H, m), 3.77 (1H, s), 3.74 (1H, s), 3.34 (2H, m), 3.02 (1H, m), 2.95 (6H, s), 2.90 (1H, m), 2.85 (1H, m), 2.15 (2H, m), 1.95-1.65 (6H, m), 1.17 (3H, d, J=7.0 Hz), 1.02 (4H, m) ppm.

Example 238

Synthesis of 3-(4-(1-cyclobutylpiperidin-4-yl)phenylamino)-5-((2R,3R)-3-(3,3-dimethylureido)-2-methylpiperidin-1-yl)pyrazine-2-carboxamide (329)

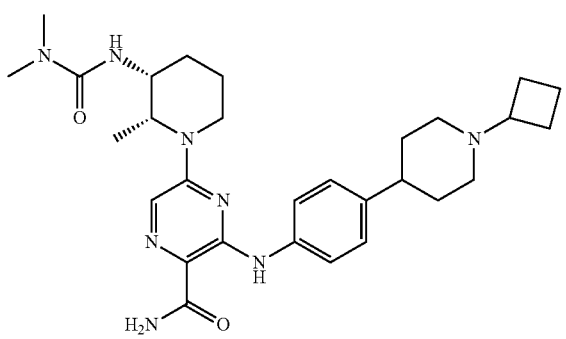

329

The title compound, 3-(4-(1-cyclobutylpiperidin-4-yl) phenylamino)-5-((2R,3R)-3-(3,3-dimethylureido)-2-methylpiperidin-1-yl)pyrazine-2-carboxamide (329), was prepared by the same synthetic scheme illustrated for Example 237 using cyclobutanone. LC-MS (ESI): m/z (M+1) 535.8. UV: λ=268, 277, 306, 336, 372 nm. Proton NMR ($CD_3OD$): δ 7.64 (1H, s), 7.61 (2H, d, J=8.5 Hz), 7.20 (2H, d, J=8.5 Hz), 4.97 (1H, m), 4.35 (1H, m), 3.87 (1H, m), 3.68 (1H, m), 3.59 (1H, s), 3.56 (1H, s), 3.04 (1H, m), 2.96 (6H, s), 2.92 (2H, m), 2.84 (1H, m), 2.37 (2H, m), 2.30 (2H, m), 2.13 (2H, m), 1.95-1.90 (6H, m), 1.73 (1H, m), 1.66 (1H, m), 1.17 (3H, d, J=7.0 Hz) ppm.

Example 239

Synthesis of 5-((2R,3R)-3-(3,3-dimethylureido)-2-methylpiperidin-1-yl)-3-(4-(1-(trifluoromethyl)cyclopropyl)phenylamino)pyrazine-2-carboxamide

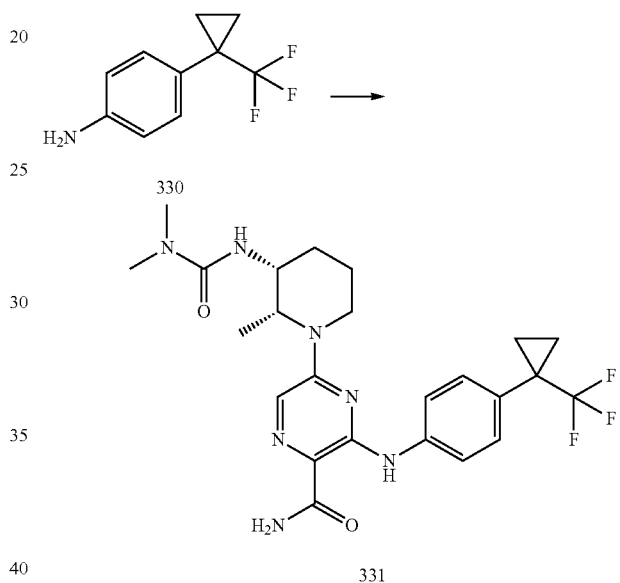

1-Bromo-4-(1-(trifluoromethyl)cyclopropyl)benzene (1.00 g, 3.77 mmol) was mixed with tert-butyl carbamate (1.77 g, 15.1 mmol), $Pd_2(dba)_3$ (350 mg, 0.38 mmol), Xant-Phos (650 mg, 1.13 mmol), fine-powder cesium carbonate (7.40 g, 22.6 mmol) in 80 mL dioxane. The mixture was degassed using nitrogen stream for 5 min, and stirred in 115° C. bath under nitrogen atmosphere for 7 hours. It was cooled to RT, diluted with 200 mL EtOAc, well stirred, filtered using ChemGlass OP-6602-12 disposable funnel, concentrated in vacuo, and subjected to silica flash column using 0 to 1% MeOH in DCM to isolate tert-butyl 4-(1-(trifluoromethyl) cyclopropyl)phenylcarbamate. It was treated with 1:1 DCM/TFA (10 mL/10 mL) at RT for 10 min, concentrated in vacuo, taken into chloroform, washed with 1N NaOH (aq) and water, dried, concentrated and subjected to silica flash column to isolate 4-(1-(trifluoromethyl)cyclopropyl)aniline (330) (300 mg, 40%).

The title compound, 5-((2R,3R)-3-(3,3-dimethylureido)-2-methylpiperidin-1-yl)-3-(4-(1-(trifluoromethyl)cyclopropyl)phenylamino)pyrazine-2-carboxamide (331), was prepared using the same synthetic scheme illustrated for Example 237 using 4-(1-(trifluoromethyl)cyclopropyl) aniline (330). LC-MS (ESI): m/z (M+1) 506.5. UV: λ=269, 279, 307, 334, 372 nm. Proton NMR ($CD_3OD$): δ 7.64 (1H, s), 7.63 (2H, d, J=8.5 Hz), 7.39 (2H, d, J=8.5 Hz), 5.05 (1H, m), 4.29 (1H, m), 3.88 (1H, m), 3.06 (1H, m), 2.96 (6H, s), 1.89 (2H, m), 1.74 (1H, m), 1.67 (1H, m), 1.31 (2H, m), 1.16 (3H, d, J=7.0 Hz), 1.04 (2H, m) ppm.

Example 240

Synthesis of 3-(4-(1-cyanocyclopropyl)phenylamino)-5-((2R,3R)-3-(3,3-dimethylureido)-2-methylpiperidin-1-yl)pyrazine-2-carboxamide

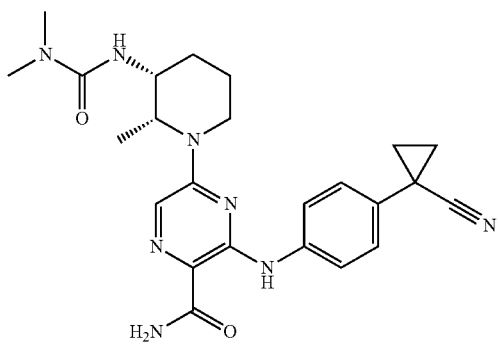

332

The title compound, 3-(4-(1-cyanocyclopropyl)phenylamino)-5-((2R,3R)-3-(3,3-dimethylureido)-2-methylpiperidin-1-yl)pyrazine-2-carboxamide (332), was prepared by the same synthetic scheme illustrated for Example 237 using 1-(4-aminophenyl)cyclopropanecarbonitrile. LC-MS (ESI): m/z (M+1) 463.4. UV: λ=270, 280, 308, 336, 372 nm. Proton NMR (CD₃OD): δ 7.66 (2H, d, J=8, 5 Hz), 7.64 (1H, s), 7.27 (2H, d, J=8.5 Hz), 5.08 (1H, m), 4.27 (1H, m), 3.88 (1H, m), 3.07 (1H, m), 2.97 (6H, s), 1.90 (2H, m), 1.76 (1H, m), 1.67 (3H, m), 1.43 (2H, m), 1.16 (3H, d, J=7.0 Hz) ppm. Compound 333, 3-(4-(1-carbamoylcyclopropyl)phenylamino)-5-((2R,3R)-3-(3,3-dimethylureido)-2-methylpiperidin-1-yl) pyrazine-2-carboxamide, was also found and isolated as a major by-product in the final step.

Example 241

Synthesis of 3-(4-(1-carbamoylcyclopropyl)phenylamino)-5-((2R,3R)-3-(3,3-dimethylureido)-2-methylpiperidin-1-yl)pyrazine-2-carboxamide

333

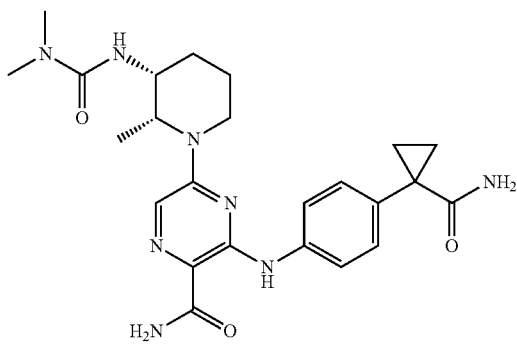

The title compound, 3-(4-(1-carbamoylcyclopropyl)phenylamino)-5-((2R,3R)-3-(3,3-dimethylureido)-2-methylpiperidin-1-yl)pyrazine-2-carboxamide (333), was found and isolated as a major by-product in the final step during the preparation of 3-(4-(1-cyanocyclopropyl)phenylamino)-5-((2R,3R)-3-(3,3-dimethylureido)-2-methylpiperidin-1-yl) pyrazine-2-carboxamide (332). LC-MS (ESI): m/z (M+1) 481.3. UV: λ=270, 279, 307, 336, 372 nm. Proton NMR (CD₃OD): δ 7.67 (2H, d, J=8, 5 Hz), 7.64 (1H, s), 7.36 (2H, d, J=8.5 Hz), 5.08 (1H, m), 4.27 (1H, m), 3.87 (1H, m), 3.07 (1H, m), 2.96 (6H, s), 1.90 (1H, m), 1.86 (1H, m), 1.75 (1H, m), 1.66 (1H, m), 1.48 (2H, m), 1.16 (3H, d, J=7.0 Hz), 1.06 (2H, m) ppm.

Example 242

Synthesis of 5-((2R,3R)-3-(3,3-dimethylureido)-2-methylpiperidin-1-yl)-3-(3-methylisothiazol-5-ylamino)pyrazine-2-carboxamide

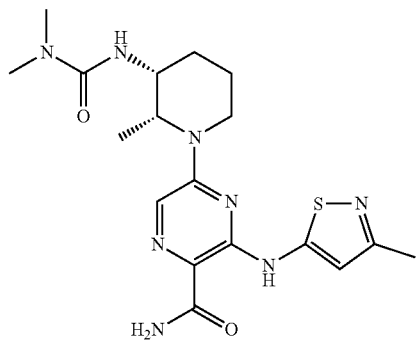

334

The title compound, 5-((2R,3R)-3-(3,3-dimethylureido)-2-methylpiperidin-1-yl)-3-(3-methylisothiazol-5-ylamino) pyrazine-2-carboxamide (334), was prepared by the same synthetic scheme illustrated for Example 237 using 5-amino-3-methylisothiazole hydrochloride. LC-MS (ESI): m/z (M+1) 419.5. UV: λ=279, 287, 315, 343, 368 nm. Proton NMR (CD₃OD): δ 7.88 (1H, s), 6.89 (1H, s), 5.05 (1H, m), 4.44 (1H, m), 3.91 (1H, m), 3.22 (1H, m), 2.95 (6H, s), 2.47 (3H, s), 1.99-1.90 (2H, m), 1.80-1.72 (2H, m), 1.27 (3H, d, J=7.0 Hz) ppm.

Example 243

Synthesis of 5-((2R,3R)-3-(3,3-dimethylureido)-2-methylpiperidin-1-yl)-3-(4-isopropoxyphenylamino) pyrazine-2-carboxamide

335

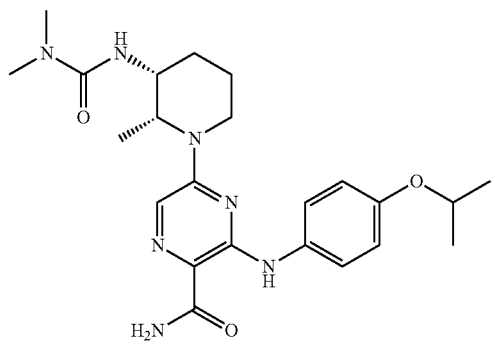

The title compound, 5-((2R,3R)-3-(3,3-dimethylureido)-2-methylpiperidin-1-yl)-3-(4-isopropoxyphenylamino)pyrazine-2-carboxamide (335), was prepared by the same synthetic scheme illustrated for Example 237 using 4-isopropoxyaniline. LC-MS (ESI): m/z (M+1) 456.3. UV: λ=269, 275, 304, 339, 373 nm. Proton NMR (CD₃OD): δ 7.58 (1H, s), 7.49 (2H, d, J=9.0 Hz), 6.85 (2H, d, J=9.0 Hz), 4.97 (1H, m), 4.52 (1H, m), 4.30 (1H, m), 3.86 (1H, m), 3.01 (1H, m), 2.95 (6H, s), 1.87 (2H, m), 1.72 (1H, m), 1.63 (1H, m), 1.30 (6H, d, J=6.5 Hz), 1.14 (3H, d, J=7.0 Hz) ppm.

Example 244

Synthesis of 5-((2R,3R)-3-(3,3-dimethylureido)-2-methylpiperidin-1-yl)-3-(4-(methylsulfonyl)phenylamino)pyrazine-2-carboxamide

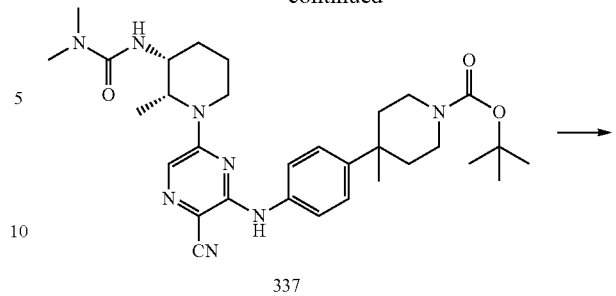

336

The title compound, 5-((2R,3R)-3-(3,3-dimethylureido)-2-methylpiperidin-1-yl)-3-(4-(methylsulfonyl)phenylamino)pyrazine-2-carboxamide (336), was prepared by the same synthetic scheme illustrated for Example 237 using 4-methylsulfonylaniline. LC-MS (ESI): m/z (M+1) 476.2. UV: λ=280, 293, 319, 346, 367 nm.

Example 245

Synthesis of 3-(4-(1-cyclopentyl-4-methylpiperidin-4-yl)phenylamino)-5-((2R,3R)-3-(3,3-dimethylureido)-2-methylpiperidin-1-yl)pyrazine-2-carboxamide

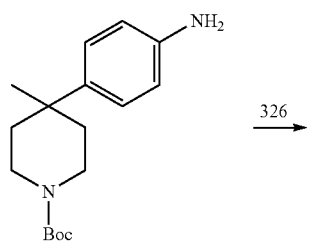

287

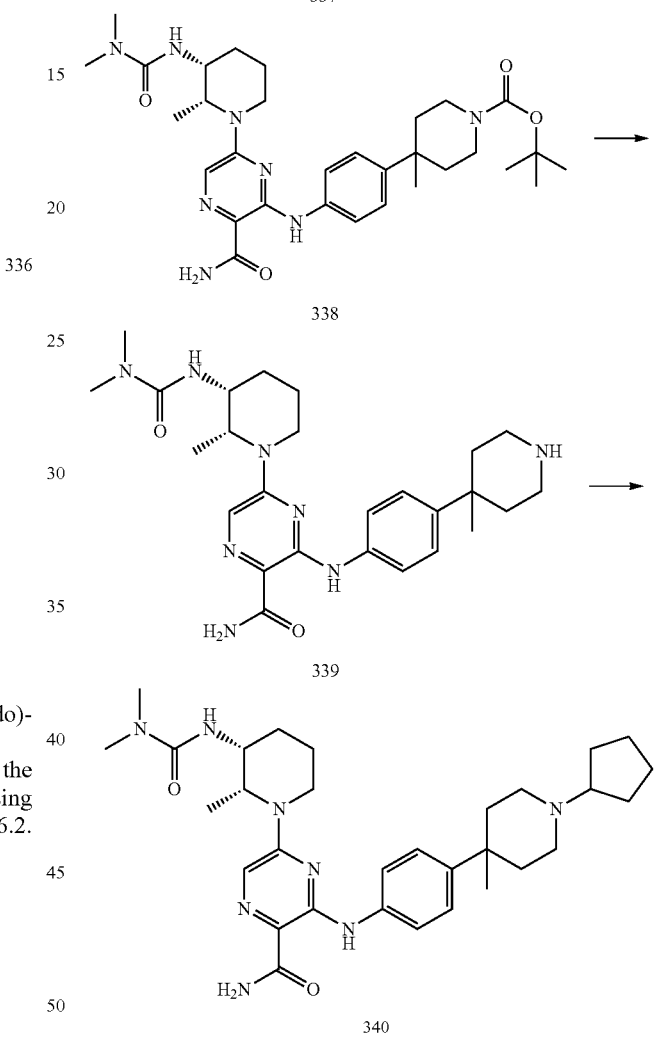

The mixture of 3-((2R,3R)-1-(6-chloro-5-cyanopyrazin-2-yl)-2-methylpiperidin-3-yl)-1,1-dimethylurea (326) (300 mg, 0.93 mmol), tert-butyl 4-(4-aminophenyl)-4-methylpiperidine-1-carboxylate (287) (325 mg, 1.12 mmol), fine-powder cesium carbonate (1300 mg, 4.00 mmol), Pd(OAc)₂ (67 mg, 0.30 mmol), BINAP (190 mg, 0.30 mmol) in 45 mL dioxane was degassed with nitrogen stream for 3 min. It was then stirred in 115° C. bath in nitrogen atmosphere for 3 hours. The mixture was cooled to RT, diluted with 150 mL EtOAc, and filtered using ChemGlass OP-6602-12 disposable funnel. The filtrate was concentrated in vacuo and subjected to silica flash column using 0 to 5% MeOH in DCM to isolate tert-butyl 4-(4-(3-cyano-6-((2R,3R)-3-(3,3-dimethylureido)-2- methylpiperidin-1-yl)pyrazin-2-ylamino)phenyl)-4-methylpiperidine-1-carboxylate (337). It was dissolved in 20 mL MeOH and 4 mL DMSO. To it were added one NaOH solid bead (about 100 mg) and then 1 mL 30% $H_2O_2$. The mixture was stirred at RT for 1 hour, diluted with 10 mL MeCN, stirred for 5 min, and concentrated on rotavap. The residue was diluted with 150 mL EtOAc, washed with water (×2), dried, and subjected to silica flash column using 0 to 5% MeOH in DCM to isolate tert-butyl 4-(4-(3-carbamoyl-6-((2R,3R)-3-(3,3-dimethylureido)-2-methylpiperidin-1-yl) pyrazin-2-ylamino)phenyl)-4-methylpiperidine-1-carboxylate (338). It was treated with 2:1 DCM and TFA (10 mL/5 mL) at RT for 30 min and concentrated to dryness to give crude 5-((2R,3R)-3-(3,3-dimethylureido)-2-methylpiperidin-1-yl)-3-(4-(4-methylpiperidin-4-yl)phenylamino)pyrazine-2-carboxamide (339) as TFA salt. Half of this salt was dissolved in 10 mL 1,2-dichloroethane (DCE) and 2 mL NMP. To it were added DIEA (700 μL, 4.0 mmol) and cyclopentanone (1.06 mL, 12.0 mmol). The mixture was stirred at RT for 2 hours. To it were then added acetic acid (450 μL, 8.0 mmol) and then NaBH(OAc)$_3$ (510 mg, 2.4 mmol). The mixture was stirred at RT for overnight, diluted with 20 mL MeOH, concentrated in vacuo, acidified with TFA (1 mL). and directly subjected to reverse phase prep HPLC using 5 mM HCl (aq) and neat MeCN as mobile phases to isolate 3-(4-(1-cyclopentyl-4-methylpiperidin-4-yl)phenylamino)-5-((2R,3R)-3-(3,3-dimethylureido)-2-methylpiperidin-1-yl) pyrazine-2-carboxamide (340) as HCl salt (142 mg, 54% overall yield for 4 steps). LC-MS (ESI): m/z (M+1) 564.0. UV: λ=268, 278, 306, 336, 372 nm. Proton NMR (CD$_3$OD): δ 7.73-7.63 (3H, m), 7.34 (2H, m), 5.05 (1H, m), 4.33 (1H, m), 3.87 (1H, m), 3.64-3.50 (2H, m), 3.06 (1H, m), 2.96 (6H, s), 2.89-2.63 (3H, m), 2.23-2.09 (4H, m), 2.01-1.91 (4H, m), 1.89-1.62 (8H, m), 1.41-1.27 (3H, s), 1.17 (3H, d, J=7.0 Hz) ppm.

Example 246

Synthesis of 3-(4-(1-cyclobutyl-4-methylpiperidin-4-yl)phenylamino)-5-((2R,3R)-3-(3,3-dimethylureido)-2-methylpiperidin-1-yl)pyrazine-2-carboxamide

341

The title compound, 3-(4-(1-cyclobutyl-4-methylpiperidin-4-yl)phenylamino)-5-((2R,3R)-3-(3,3-dimethylureido)-2-methylpiperidin-1-yl)pyrazine-2-carboxamide (341), was prepared by the same synthetic scheme illustrated for Example 245 using cyclobutanone. LC-MS (ESI): m/z (M+1) 549.9. UV: λ=268, 278, 306, 336, 372 nm. Proton NMR (CD$_3$OD): δ 7.72-7.64 (3H, m), 7.34 (2H, m), 5.06 (1H, m), 4.33 (1H, m), 3.88 (1H, m), 3.51-3.35 (2H, m), 3.12-3.04 (1H, m), 2.95 (6H, s), 2.70-2.61 (3H, m), 2.40-2.11 (6H, m), 1.93-1.64 (8H, m), 1.40-1.27 (3H, s), 1.17 (3H, d, J=6.5 Hz) ppm.

Example 247

Synthesis of 3-(4-(1-cyclopropyl-4-methylpiperidin-4-yl)phenylamino)-5-((2R,3R)-3-(3,3-dimethylureido)-2-methylpiperidin-1-yl)pyrazine-2-carboxamide

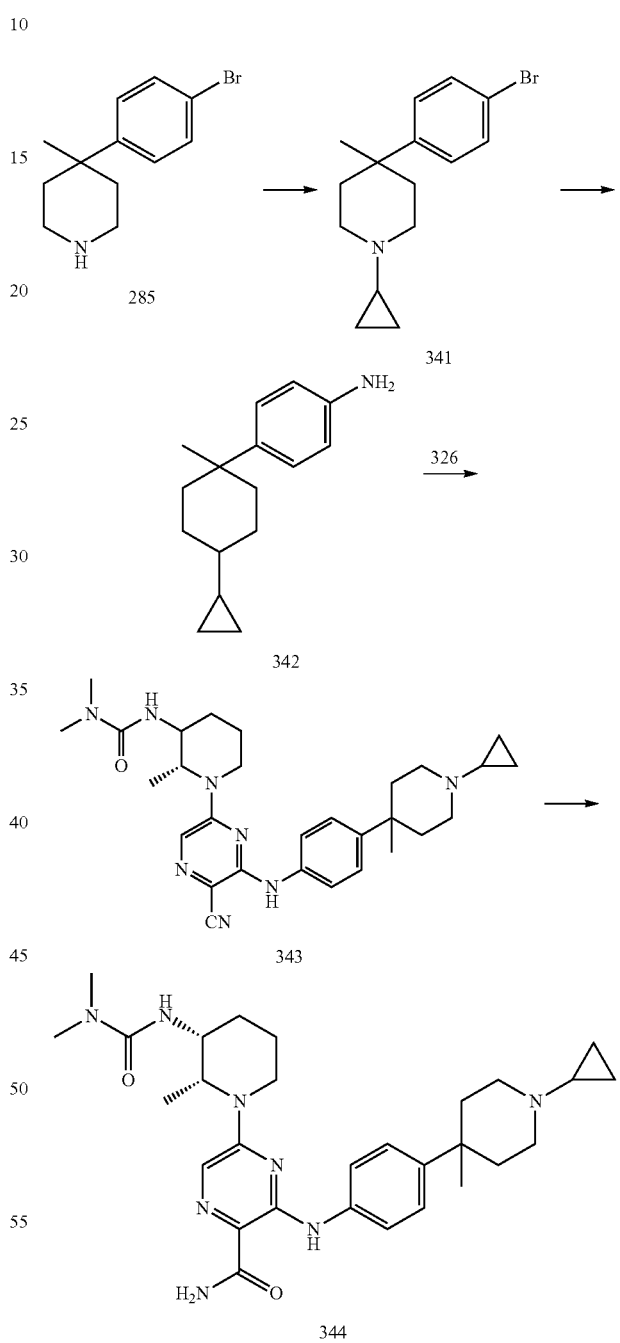

344

To a solution of 4-(4-bromophenyl)-4-methylpiperidine (285) (10.5 g, 41.3 mmol), (1-ethoxycyclopropoxy)trimethylsilane (18.0 g, 103.6 mmol) and NaBH$_3$CN (12.46 g, 198.1 mmol) in MeOH (100 mL) was added acetic acid (0.5 mL). The resulting mixture was stirred at 90° C. under N$_2$ atmosphere for 2 hours. After the reaction was cooled down to RT, the solvent was removed in vacuo, and the residue was partitioned in aqueous NaHCO₃ (200 mL) and DCM (200 mL). The layers was separated, the aqueous was extracted with DCM (50 mL×3). The combined organic layers were washed with brine, dried, concentrated and subjected to silica flash column chromatography using 0 to 5% EtOAc in PE to afford 4-(4-bromophenyl)-1-cyclopropyl-4-methylpiperidine (341) (8 g, 66%) as an oil.

To a suspended of 4-(4-bromophenyl)-1-cyclopropyl-4-methylpiperidine (341) (16.0 g, 54.5 mmol), (dicyclohexylphosphino)biphenyl (1.9 g, 5.4 mmol) and Pd₂(dba)₃ (2.5 g, 27.2 mmol) in anhydrous THF (100 mL) was added LiHMDS (1M, 109 mL, 109 mmol). The resulting mixture was purged with N₂ and then stirred at 60° C. for overnight under N₂ atmosphere. After cooled down to RT, the mixture was diluted with water (100 mL) and extracted with DCM (50 mL×3). The combined organic layers were washed with brine, dried, concentrated and subjected to silica flash column chromatography using 0 to 50% EtOAc in PE to give 4-(1-cyclopropyl-4-methylpiperidin-4-yl)aniline (342) (5 g, 40%) as a white solid. Proton NMR (CDCl3): δ 7.16 (2H, d, J=8.5 Hz), 6.69 (2H, d, J=8.6 Hz), 3.58 (2H, s), 2.82-2.65 (2H, m), 2.64-2.49 (2H, m), 2.14-2.04 (2H, m), 1.77-1.65 (2H, m), 1.21 (3H, s), 0.96-0.82 (1H, m), 0.56-0.28 (4H, m) ppm.

The mixture of 3-((2R,3R)-1-(6-chloro-5-cyanopyrazin-2-yl)-2-methylpiperidin-3-yl)-1,1-dimethylurea (326) (75 mg, 0.23 mmol), 4-(1-cyclopropyl-4-methylpiperidin-4-yl)aniline (342) (65 mg, 0.28 mmol), fine-powder cesium carbonate (230 mg, 0.70 mmol), Pd(OAc)₂ (16 mg, 0.07 mmol), BINAP (44 mg, 0.07 mmol) in 20 mL dioxane was degassed with nitrogen stream for 3 min. It was then stirred in 115° C. bath in nitrogen atmosphere for 2 hours. The mixture was cooled to RT, diluted with 100 mL EtOAc, and filtered using ChemGlass OP-6602-12 disposable funnel. The filtrate was concentrated in vacuo and subjected to silica flash column using 0 to 10% MeOH in DCM to isolate 3-((2R,3R)-1-(5-cyano-6-(4-(1-cyclopropyl-4-methylpiperidin-4-yl)phenylamino)pyrazin-2-yl)-2-methylpiperidin-3-yl)-1,1-dimethylurea (343). It was dissolved in 10 mL MeOH and 2 mL DMSO. To it were added fine-powder cesium carbonate (50 mg), DIEA (60 μL), and then 0.5 mL 30% H₂O₂. The mixture was stirred at RT for 30 min, diluted with 10 mL MeCN, stirred for 5 min, and concentrated on rotavap. The residue was acidified with TFA (0.5 mL) and directly subjected to reverse phase prep HPLC using 5 mM HCl (aq) and neat MeCN as mobile phases to isolate 3-(4-(1-cyclopropyl-4-methylpiperidin-4-yl)phenylamino)-5-((2R,3R)-3-(3,3-dimethylureido)-2-methylpiperidin-1-yl)pyrazine-2-carboxamide (344) as HCl salt (68 mg, 55% overall yield for 2 steps). LC-MS (ESI): m/z (M+1) 535.9. UV: λ=268, 278, 306, 336, 372 nm. Proton NMR (CD₃OD): δ 7.74-7.64 (3H, m), 7.38-7.33 (2H, m), 5.08 (1H, m), 4.33 (1H, m), 3.88 (1H, m), 3.62-3.47 (2H, m), 3.05 (2H, m), 2.96 (6H, s), 2.70-2.64 (2H, m), 2.20-2.12 (2H, m), 1.91-1.86 (4H, m), 1.75 (1H, m), 1.66 (1H, m), 1.45-1.26 (3H, s), 1.17 (3H, d, J=7.0 Hz), 1.02-0.89 (4H, m) ppm.

Example 248

Synthesis of 3-(4-(1-cyanocyclopentyl)phenylamino)-5-((2R,3R)-3-(3,3-dimethylureido)-2-methylpiperidin-1-yl)pyrazine-2-carboxamide

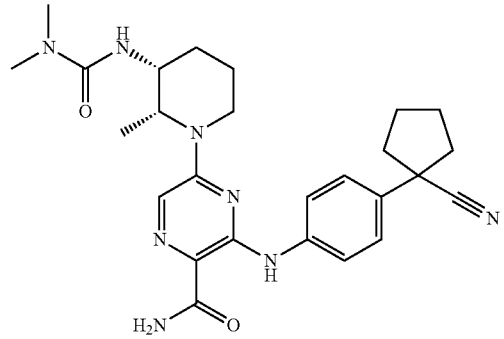

345

The title compound, 3-(4-(1-cyanocyclopentyl)phenylamino)-5-((2R,3R)-3-(3,3-dimethylureido)-2-methylpiperidin-1-yl)pyrazine-2-carboxamide (345), was prepared by the same synthetic scheme illustrated for Example 247 using 1-(4-aminophenyl)cyclopentanecarbonitrile. LC-MS (ESI): m/z (M+1) 491.6. UV: λ=269, 279, 307, 335, 372 nm. Proton NMR (CD₃OD): δ 7.69 (2H, d, J=8, 5 Hz), 7.64 (1H, s), 7.42 (2H, d, J=8.5 Hz), 5.08 (1H, m), 4.28 (1H, m), 3.88 (1H, m), 3.07 (1H, m), 2.96 (6H, s), 2.42 (2H, m), 2.12 (2H, m), 1.99 (4H, m), 1.90 (2H, m), 1.73 (1H, m), 1.66 (1H, m), 1.16 (3H, d, J=7.0 Hz) ppm. Compound 346, 3-(4-(1-carbamoylcyclopentyl)phenylamino)-5-((2R,3R)-3-(3,3-dimethylureido)-2-methylpiperidin-1-yl)pyrazine-2-carboxamide, was also found and isolated as a major by-product in the final step.

Example 249

Synthesis of 3-(4-(1-carbamoylcyclopentyl)phenylamino)-5-((2R,3R)-3-(3,3-dimethylureido)-2-methylpiperidin-1-yl)pyrazine-2-carboxamide

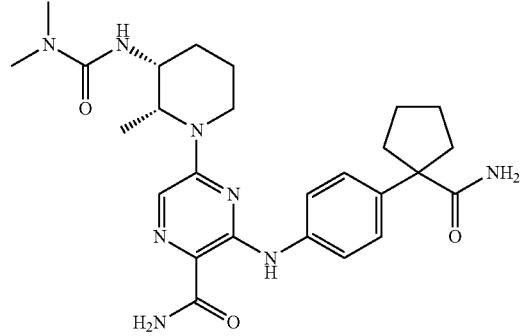

346

The title compound, 3-(4-(1-carbamoylcyclopentyl)phenylamino)-5-((2R,3R)-3-(3,3-dimethylureido)-2-methylpiperidin-1-yl)pyrazine-2-carboxamide (346), was found and isolated as a major by-product in the final step during the preparation of 3-(4-(1-cyanocyclopentyl)phenylamino)-5-((2R,3R)-3-(3,3-dimethylureido)-2-methylpiperidin-1-yl)pyrazine-2-carboxamide (345). LC-MS (ESI): m/z (M+1) 509.5. UV: λ=270, 278, 307, 336, 372 nm.

Example 250

Synthesis of 3-(4-(4-cyano-1-cyclopentylpiperidin-4-yl)phenylamino)-5-((2R,3R)-3-(3,3-dimethylureido)-2-methylpiperidin-1-yl)pyrazine-2-carboxamide (54)

cooled to RT, diluted with EtOAc 200 mL and filtered. The filtrate was concentrated in vacuo and subjected to silica flash column using 0 to 30% MeOH in DCM to afford tert-butyl 4-(4-cyanopiperidin-4-yl)phenylcarbamate (348, 230 mg, 39%).

Compound 348 (230 mg, 0.77 mmol) was dissolved in 20 mL MeOH and 1 mL HOAc. To the solution was added cyclopentanone (280 μL, 3.08 mmol) and the mixture was stirred at RT for 2.5 hours. Then NaBH$_3$CN (290 mg, 4.62 mmol) was added, and the mixture was stirred at RT for overnight. It was concentrated in vacuo, diluted with EtOAc 150 mL, washed with 1N NaOH and water, dried, concentrated in vacuo to dryness to give crude tert-butyl 4-(4-cyano-1-cyclopentylpiperidin-4-yl)phenylcarbamate (349, 280 mg, 98%). It was treated with 4N HCl in dioxane at RT for 4 hours

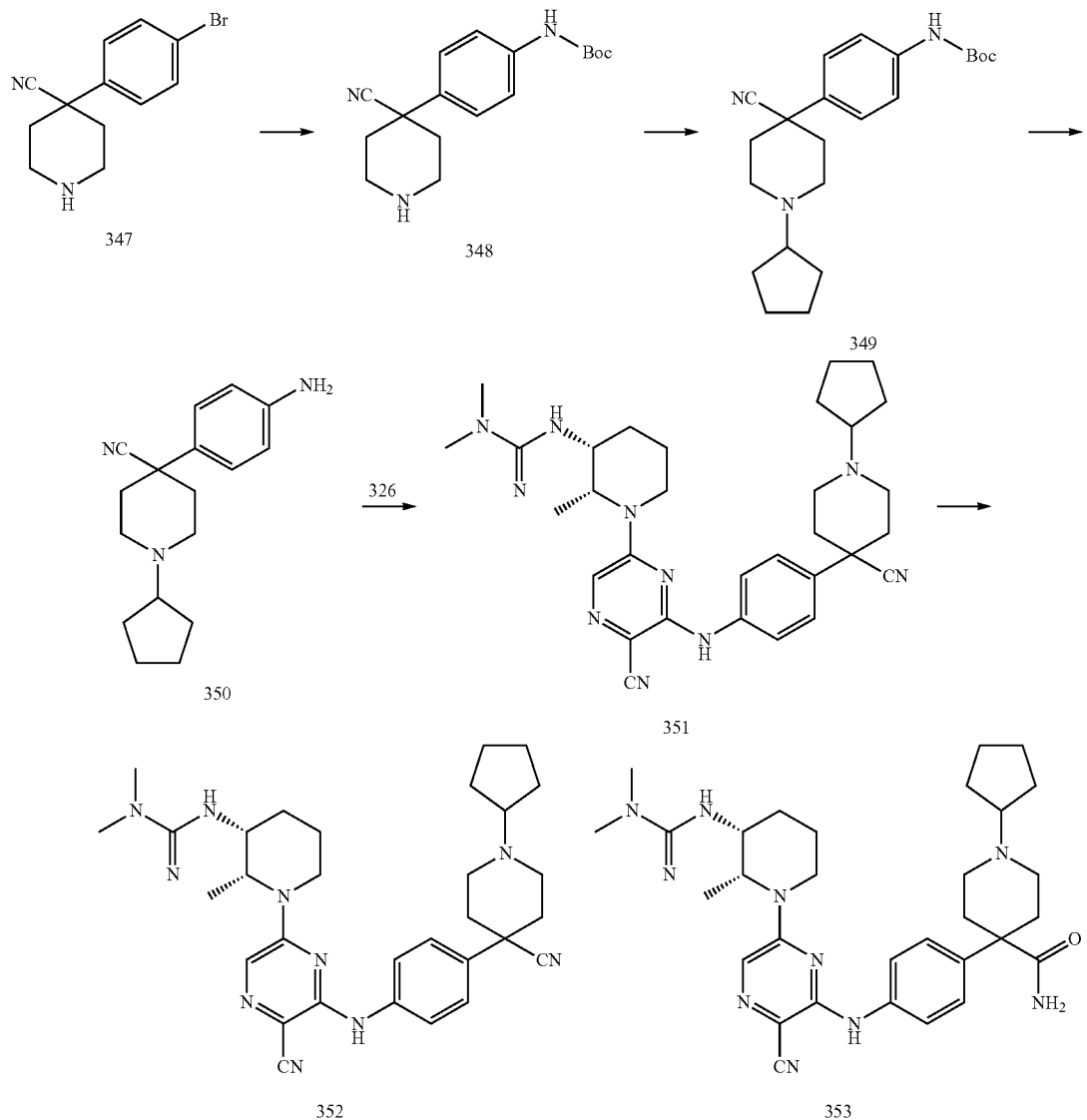

The mixture of 4-(4-bromophenyl)piperidine-4-carbonitrile (347, 520 mg, 1.96 mmol), tert-butyl carbamate (460 mg, 3.92 mmol), Pd$_2$(dba)$_3$ (180 mg, 0.20 mmol), XantPhos (350 mg, 0.60 mmol), fine-powder Cs$_2$CO$_3$ (1.96 g, 6.0 mmol) in 30 mL dioxane was degassed using N$_2$ stream for 5 min and stirred in 115° C. bath in N$_2$ atmosphere for overnight. It was and concentrated in vacuo to dryness to give 4-(4-aminophenyl)-1-cyclopentylpiperidine-4-carbonitrile hydrochloride (350, 250 mg, quantitative yield).

The mixture of 3-((2R,3R)-1-(6-chloro-5-cyanopyrazin-2-yl)-2-methylpiperidin-3-yl)-1,1-dimethylurea (326) (100 mg, 0.31 mmol), 4-(4-aminophenyl)-1-cyclopentylpiperidine-4-carbonitrile hydrochloride (350) (114 mg, 0.37 mmol), fine-powder cesium carbonate (400 mg, 1.24 mmol), Pd(OAc)$_2$ (22 mg, 0.1 mmol), BINAP (62 mg, 0.1 mmol) in 20 mL dioxane was degassed with nitrogen stream for 3 min. It was then stirred in 115° C. bath in nitrogen atmosphere for 2.5 hours. The mixture was cooled to RT, diluted with 100 mL EtOAc, and filtered. The filtrate was concentrated in vacuo and subjected to silica flash column using 0 to 10% MeOH in chloroform to isolate 3-((2R,3R)-1-(5-cyano-6-(4-(4-cyano-1-cyclopentylpiperidin-4-yl)phenylamino)pyrazin-2-yl)-2-methylpiperidin-3-yl)-1,1-dimethylurea (351). It was dissolved in 10 mL MeOH and 1 mL DMSO. To it were added one NaOH solid bead (about 100 mg), DIEA (60 µL), and then 1 mL 30% H$_2$O$_2$. The mixture was stirred at RT for 1 hour, diluted with 10 mL MeCN, stirred for 5 min, and concentrated on rotavap. The residue was acidified with TFA (0.5 mL) and directly subjected to reverse phase prep HPLC using 5 mM HCl (aq) and neat MeCN as mobile phases to isolate 3-(4-(4-cyano-1-cyclopentylpiperidin-4-yl)phenylamino)-5-((2R,3R)-3-(3,3-dimethylureido)-2-methylpiperidin-1-yl)pyrazine-2-carboxamide (352) as HCl salt (22 mg). LC-MS (ESI): adz (M+1) 574.6. UV: λ=270, 281, 309, 336, 371 nm. Proton NMR (CD$_3$OD): δ 7.78 (2H, d, J=9.0 Hz), 7.67 (1H, s), 7.49 (2H, d, J=8.5 Hz), 5.09 (1H, m), 4.28 (1H, m), 3.88 (3H, m), 3.69 (1H, m), 3.36 (2H, m), 3.09 (1H, m), 2.97 (6H, s), 2.51 (2H, m), 2.40 (2H, m), 2.26 (2H, m), 1.89 (4H, m), 1.86-1.66 (6H, m), 1.17 (3H, d, J=6.5 Hz) ppm. Compound 353, 3-(4-(4-carbamoyl-1-cyclopentylpiperidin-4-yl)phenylamino)-5-((2R,3R)-3-(3,3-dimethylureido)-2-methylpiperidin-1-yl)pyrazine-2-carboxamide, was also found and isolated as a major by-product in the final step.

Example 251

Synthesis of 3-(4-(4-carbamoyl-1-cyclopentylpiperidin-4-yl)phenylamino)-5-((2R,3R)-3-(3,3-dimethylureido)-2-methylpiperidin-1-yl)pyrazine-2-carboxamide

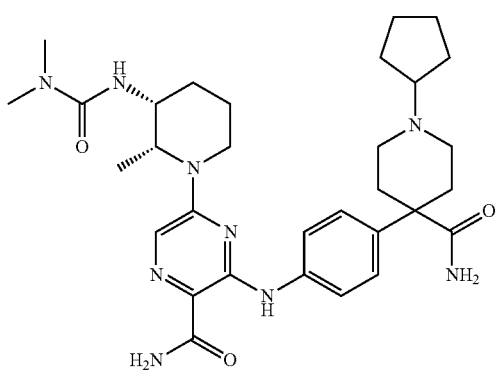

353

The title compound, 3-(4-(4-carbamoyl-1-cyclopentylpiperidin-4-yl)phenylamino)-5-((2R,3R)-3-(3,3-dimethylureido)-2-methylpiperidin-1-yl)pyrazine-2-carboxamide (353, 15 mg), was found and isolated as HCl salt as a major by-product in the final step during the preparation of 3-(4-(4-cyano-1-cyclopentylpiperidin-4-yl)phenylamino)-5-((2R,3R)-3-(3,3-dimethylureido)-2-methylpiperidin-1-yl)pyrazine-2-carboxamide (352). LC-MS (ESI): m/z (M+1) 592.7. UV: λ=271, 281, 309, 337, 372 nm. Proton NMR (CD$_3$OD): δ 7.82-7.71 (2H, d, J=8.5 Hz), 7.65 (1H, s), 7.46-7.35 (2H, d, J=8.5 Hz), 5.06 (1H, m), 4.30 (1H, m), 3.88 (1H, m), 3.69 (1H, m), 3.56 (1H, m), 3.20 (1H, m), 3.08 (1H, m), 2.96 (6H, s), 2.83 (2H, m), 2.39-2.22 (2H, m), 2.04 (2H, m), 1.87 (4H, m), 1.76-1.63 (6H, m), 1.17 (3H, d, J=6.5 Hz) ppm.

Example 252

Synthesis of 5-((2R,3R)-2-methyl-3-(3-methyl-2-oxoimidazolidin-1-yl)piperidin-1-yl)-3-(4-(4-methylpiperidin-4-yl)phenylamino)pyrazine-2-carboxamide

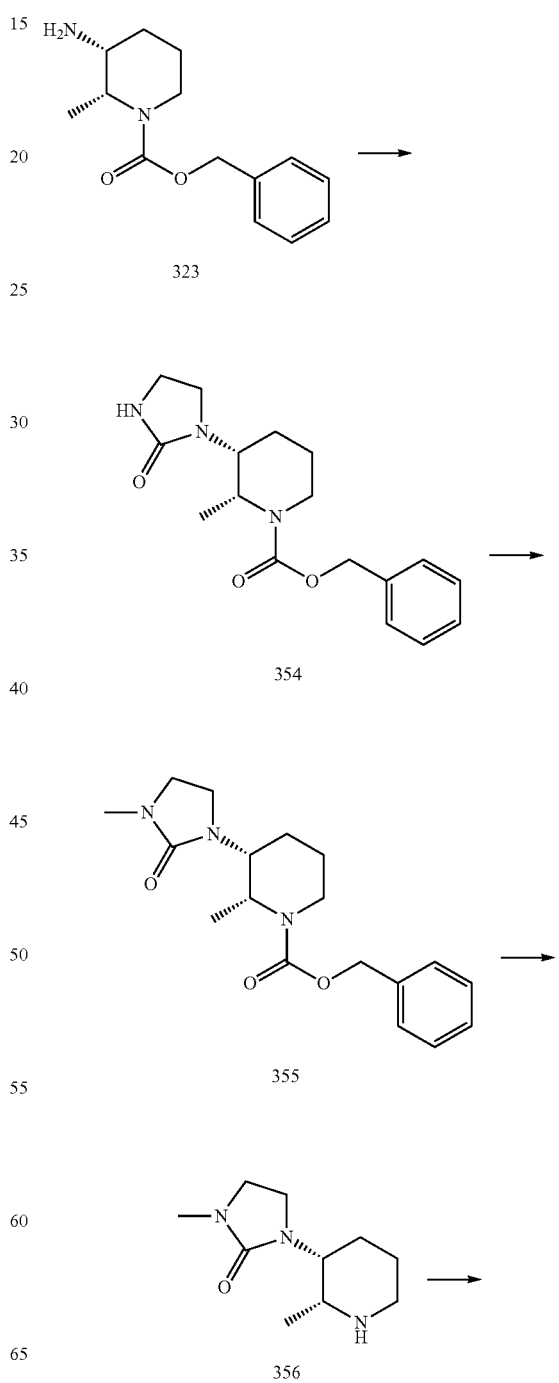

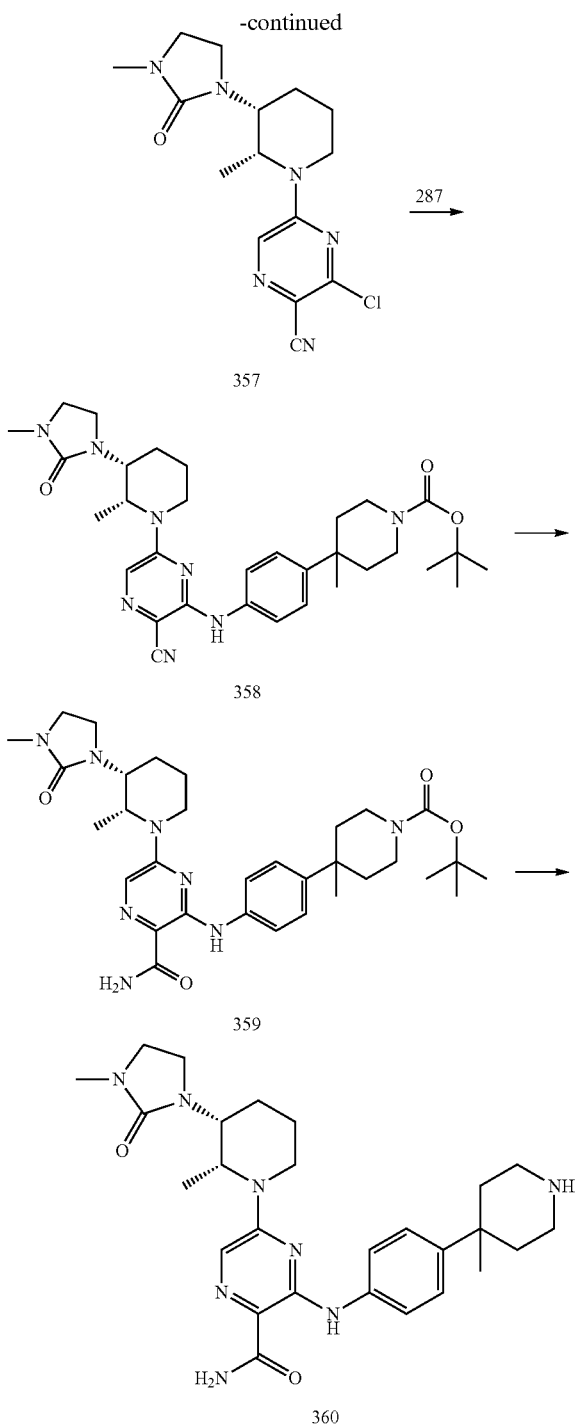

357

358

359

360

(2R,3R)-Benzyl 3-amino-2-methylpiperidine-1-carboxylate (323, 610 mg, 2.46 mmol) was dissolved in 10 mL dry THF. To it was added 2-chloroethyl isocyante (210 µL, 2.46 mmol), and the mixture was stirred at RT for 2 hours. To it was added NaH (60% in mineral oil, 120 mg, 2.95 mmol) and the mixture was stirred for overnight. Another batch of NaH (120 mg, 2.95 mmol) was then added to drive the cyclization to completion in overnight. The mixture was diluted with 150 mL EtOAc and 50 mL water. The organic phase was separated, washed with water, dried, concentrated in vacuo, and subjected to silica flash column using 0 to 4% MeOH in DCM to isolate (2R,3R)-benzyl 2-methyl-3-(2-oxoimidazolidin-1-yl)piperidine-1-carboxylate (354, 490 mg, 63%) as a white solid.

Compound 354 (490 mg, 1.55 mmol) was dissolved in 15 mL dry THF. It was treated with NaH (60% in mineral oil, 125 mg, 3.1 mmol) for 15 min at RT. To the mixture was then added iodomethane (200 µL, 3.1 mmol). The mixture was stirred at RT for 1.5 hour, diluted with 150 mL EtOAc and 50 water. The organic phase was separated, washed with water, dried, concentrated, and subjected to silica flash column using 0 to 4% MeOH in DCM to isolate (2R,3R)-benzyl 2-methyl-3-(3-methyl-2-oxoimidazolidin-1-yl)piperidine-1-carboxylate (355, 470 mg, 92%). It was dissolved in 100 mL iPrOH. To it was added 10% Pd/C (0.5 g), and the mixture was hydrogenated at 40 psi on a Parr shaker for overnight. The mixture was filtered through celite and concentrated in vacuo to give 1-methyl-3-((2R,3R)-2-methylpiperidin-3-yl)imidazolidin-2-one (356) as a white solid in quantitative yield.

Compound 356 from above was dissolved in 10 mL DMF. To it were added 3,5-dichloropyrazine-2-carbonitrile (250 mg, 1.42 mmol) and DIEA (500 µL, 2.84 mmol). The mixture was stirred at RT for 2 hours, diluted with 150 mL EtOAc, washed with water ×3, dried, concentrated in vacuo, and subjected to silica flash column using 0 to 3% MeOH in DCM to isolate 3-chloro-5-((2R,3R)-2-methyl-3-(3-methyl-2-oxoimidazolidin-1-yl)piperidin-1-yl)pyrazine-2-carbonitrile (357, 200 mg, 42% yield).

The mixture of 3-chloro-5-((2R,3R)-2-methyl-3-(3-methyl-2-oxoimidazolidin-1-yl)piperidin-1-yl)pyrazine-2-carbonitrile (357) (100 mg, 0.60 mmol), tert-butyl 4-(4-aminophenyl)-4-methylpiperidine-1-carboxylate (287) (175 mg, 0.60 mmol), fine-powder cesium carbonate (590 mg, 1.80 mmol), Pd(OAc)$_2$ (45 mg, 0.2 mmol), BINAP (125 mg, 0.2 mmol) in 30 mL dioxane was degassed with nitrogen stream for 3 min. It was then stirred in 115° C. bath in nitrogen atmosphere for 70 min. The mixture was cooled to RT, diluted with 120 mL EtOAc, and filtered. The filtrate was concentrated in vacuo and subjected to silica flash column using 0 to 4% MeOH in chloroform to isolate tert-butyl 4-(4-(3-cyano-6-((2R,3R)-2-methyl-3-(3-methyl-2-oxoimidazolidin-1-yl)piperidin-1-yl)pyrazin-2-ylamino)phenyl)-4-methylpiperidine-1-carboxylate (358). It was dissolved in 10 mL MeOH and 2 mL DMSO. To it were added fine-powder Cs$_2$CO$_3$ (50 mg) and then 1 mL 30% H$_2$O$_2$. The mixture was stirred at RT for 30 min, diluted with 10 mL MeCN, stirred for 5 min, and concentrated on rotavap. The residue was diluted with 150 mL EtOAc, washed with water ×3, dried, concentrated in vacuo, and subjected to silica flash column using 0 to 4% MeOH in DCM to isolate tert-butyl 4-(4-(3-carbamoyl-6-((2R,3R)-2-methyl-3-(3-methyl-2-oxoimidazolidin-1-yl)piperidin-1-yl)pyrazin-2-ylamino)phenyl)-4-methylpiperidine-1-carboxylate (359). It was treated with 2:1 DCM/TFA (12 mL/6 mL) at RT for 30 min. The mixture was concentrated in vacuo. One third of the residue was dissolved in MeOH/water and directly subjected to reverse phase prep HPLC using 5 mM HCl (aq) and neat MeCN as mobile phases to isolate 5-((2R,3R)-2-methyl-3-(3-methyl-2-oxoimidazolidin-1-yl)piperidin-1-yl)-3-(4-(4-methylpiperidin-4-yl)phenylamino)pyrazine-2-carboxamide (360) as HCl salt (65 mg). LC-MS (ESI): m/z (M+1) 507.8. UV: λ=268, 277, 306, 336, 372 nm. Proton NMR (CD$_3$OD): δ 7.68 (2H, d, J=9.0 Hz), 7.62 (1H, s), 7.35 (2H, d, J=8.5 Hz), 5.11 (1H, m), 4.28 (1H, m), 3.89 (1H, m), 3.53 (2H, m), 3.38 (2H, m), 3.30 (2H, m), 3.06 (3H, m), 2.81 (3H, s), 2.42 (2H, m), 2.03 (1H, m), 1.95 (3H, m), 1.83 (1H, m), 1.68 (1H, m), 1.31 (3H, s), 1.21 (3H, d, J=7.0 Hz) ppm.

Example 253

Synthesis of 3-(4-(1-cyclopentyl-4-methylpiperidin-4-yl)phenylamino)-5-((2R,3R)-2-methyl-3-(3-methyl-2-oxoimidazolidin-1-yl)piperidin-1-yl)pyrazine-2-carboxamide

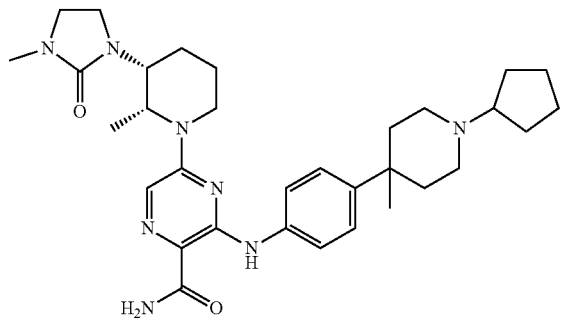

361

A crude TFA salt of 5-((2R,3R)-2-methyl-3-(3-methyl-2-oxoimidazolidin-1-yl)piperidin-1-yl)-3-(4-(4-methylpiperidin-4-yl)phenylamino)pyrazine-2-carboxamide (360) (0.2 mmol) was dissolved in 10 mL DCE and 2 mL NMP. To it were added DIEA (350 µL, 2.0 mmol) and cyclopentanone (530 µL, 6.0 mmol). The mixture was stirred at RT for 2.5 hours. To it were then added HOAc (230 µL, 4.0 mmol) and NaBH(OAc)$_3$ (260 mg, 1.2 mmol). The mixture was stirred at RT for 1.5 hour, diluted with 10 mL MeOH, stirred, concentrated in vacuo, acidified with 0.6 mL TFA, and directly subjected to reverse phase prep HPLC using 5 mM HCl (aq) and neat MeCN as mobile phases to isolate 3-(4-(1-cyclopentyl-4-methylpiperidin-4-yl)phenylamino)-5-((2R,3R)-2-methyl-3-(3-methyl-2-oxoimidazolidin-1-yl)piperidin-1-yl)pyrazine-2-carboxamide (361) as HCl salt (80 mg). LC-MS (ESI): m/z (M+1) 575.9. UV: λ=268, 277, 306, 336, 372 nm. Proton NMR (CD$_3$OD): δ 7.72-7.62 (3H, m), 7.35 (2H, m), 5.12 (1H, m), 4.29 (1H, m), 3.89 (1H, m), 3.65-3.45 (4H, m), 3.40-3.37 (2H, m), 3.09 (1H, m), 2.88 (1H, m), 2.81 (3H, s), 2.65 (2H, m), 2.23-1.62 (16H, m), 1.42-1.27 (3H, s), 1.21 (3H, d, J=7.0 Hz) ppm.

Example 254

Synthesis of 3-(4-(1-cyclobutyl-4-methylpiperidin-4-yl)phenylamino)-5-((2R,3R)-2-methyl-3-(3-methyl-2-oxoimidazolidin-1-yl)piperidin-1-yl)pyrazine-2-carboxamide

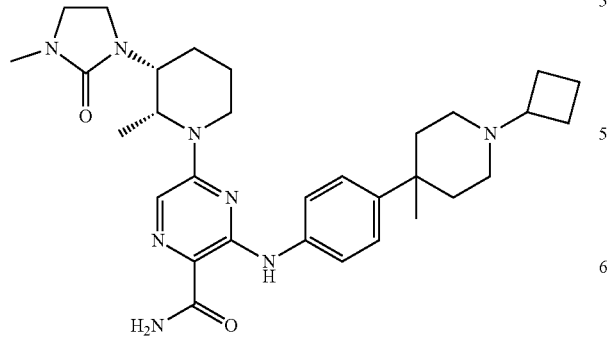

362

The title compound, 3-(4-(1-cyclobutyl-4-methylpiperidin-4-yl)phenylamino)-5-((2R,3R)-2-methyl-3-(3-methyl-2-oxoimidazolidin-1-yl)piperidin-1-yl)pyrazine-2-carboxamide (362), was prepared by the same synthetic scheme illustrated for Example 20 using cyclobutanone. LC-MS (ESI): m/z (M+1) 575.9. UV: λ=268, 277, 306, 336, 372 nm.

Example 255

Synthesis of 3-(4-(4-methyl-1-propionylpiperidin-4-yl)phenylamino)-5-((2R,3R)-2-methyl-3-(3-methyl-2-oxoimidazolidin-1-yl)piperidin-1-yl)pyrazine-2-carboxamide

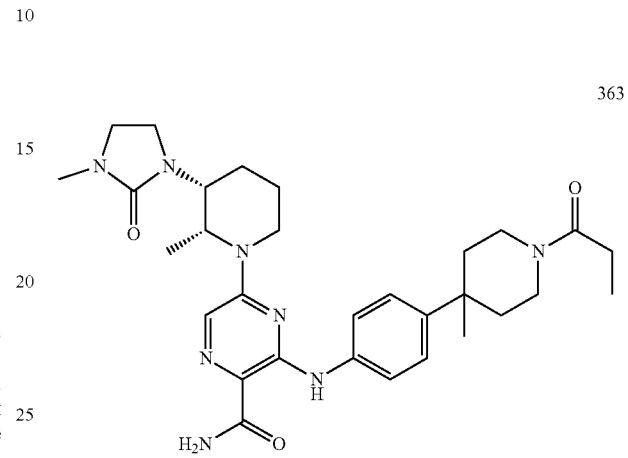

363

5-((2R,3R)-2-Methyl-3-(3-methyl-2-oxoimidazolidin-1-yl)piperidin-1-yl)-3-(4-(4-methylpiperidin-4-yl)phenylamino)pyrazine-2-carboxamide hydrochloride (360) (50 mg, 0.092 mmol) was dissolved in 3 mL NMP. To it were added DIEA (160 µL, 0.92 mmol) and propionyl chloride (32 µL, 0.36 mmol). The mixture was stirred at RT for 20 min, quenched with 0.5 mL TFA, and directly subjected to reverse phase prep HPLC using 5 mM HCl (aq) and neat MeCN as mobile phases to isolate 3-(4-(4-methyl-1-propionylpiperidin-4-yl)phenylamino)-5-((2R,3R)-2-methyl-3-(3-methyl-2-oxoimidazolidin-1-yl)piperidin-1-yl)pyrazine-2-carboxamide (363) as HCl salt (46 mg). LC-MS (ESI): m/z (M+1) 563.7. UV: λ=268, 277, 305, 335, 372 nm. Proton NMR (CD$_3$OD): δ 7.62 (2H, d, J=9.0 Hz), 7.61 (1H, s), 7.34 (2H, d, J=9.0 Hz), 5.10 (1H, m), 4.28 (1H, m), 3.89 (1H, m), 3.80 (1H, m), 3.62 (1H, m), 3.51 (2H, m), 3.45-3.35 (4H, m), 3.08 (1H, m), 2.81 (3H, d, J=4.0 Hz), 2.41 (2H, m), 2.15 (2H, m), 2.05-1.65 (6H, m), 1.28 (3H, s), 1.20 (3H, t, J=7.0 Hz), 1.11 (3H, t, J=7.5 Hz) ppm.

Example 256

Synthesis of (R)-3-(4-(1-cyclopentylpiperidin-4-yl)phenylamino)-5-(3-(3-methyl-2-oxoimidazolidin-1-yl)piperidin-1-yl)pyrazine-2-carboxamide

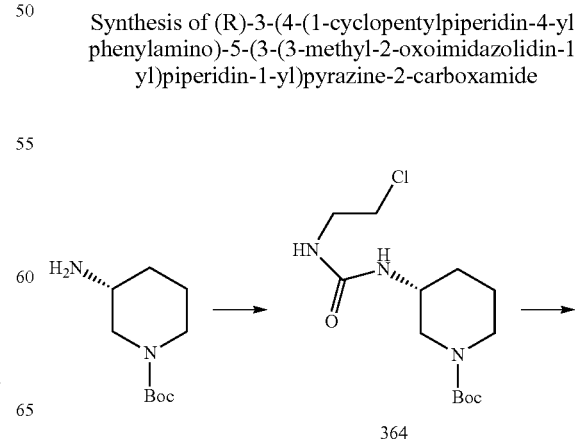

364

-continued

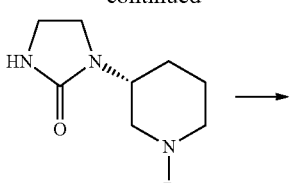
365

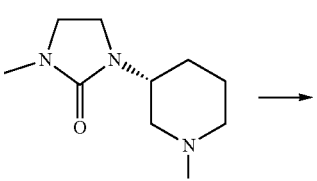
366

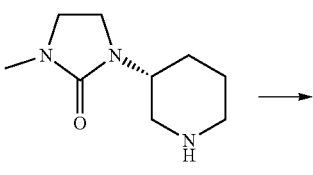
367

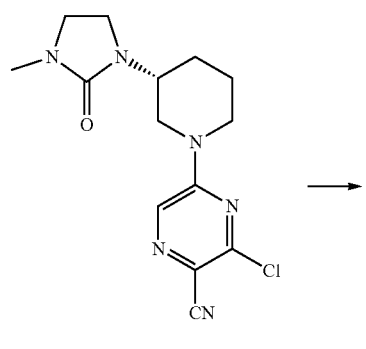
368

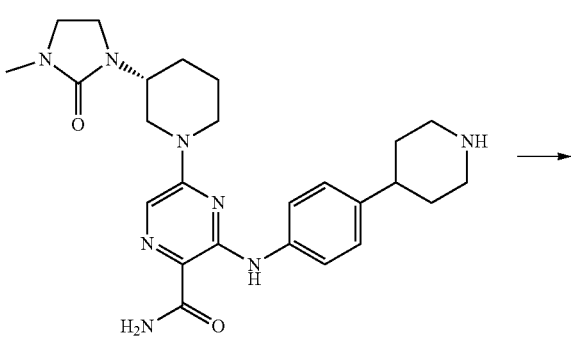
369

-continued

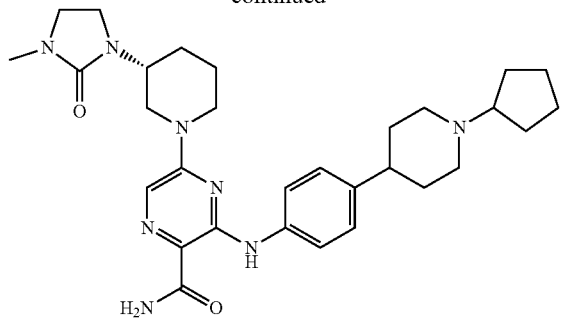
370

To a solution of (R)-tert-butyl 3-aminopiperidine-1-carboxylate (50 g, 250 mmol) and Et₃N (50.5 g, 500 mmol) in DCM (500 mL) was added 2-chloroethyl isocyanate (31.65 g, 300 mmol) dropwise. The resulting mixture was stirred at RT for 4 hours before being quenched with water (100 mL). The layers were separated and the organic layer was washed with brine, dried, concentrated, and subjected to silica flash column using 0 to 50% EA in to isolate (R)-tert-butyl 3-(3-(2-chloroethyl)ureido)piperidine-1-carboxylate (364) (63.6 g, 81.5%) as a colorless oil. At 0° C., to a solution of (R)-tert-butyl 3-(3-(2-chloroethyl)ureido)piperidine-1-carboxylate (364, 31.0 g, 102 mmol) in anhydrous THF (350 mL) was added NaH (60% in mineral oil, 4.82 g, 122 mmol) in small portions slowly. The resulting mixture was stirred at RT for 6 hours before being quenched with water (50 mL). The layers were separated and the aqueous was extracted with DCM (20 mL×3). The combined organic layers were washed with brine, dried, concentrated and subjected to silica flash column using 0 to 5% MeOH in DCM to isolate (R)-tert-butyl 3-(2-oxoimidazolidin-1-yl)piperidine-1-carboxylate (365) (25.4 g, 93%) as a white solid. At 0° C., to a solution of (R)-tert-butyl 3-(2-oxoimidazolidin-1-yl)piperidine-1-carboxylate (365) (16.2 g, 60.2 mmol) in anhydrous THF (160 mL) was added NaH (60%, 3.6 g, 90.3 mmol) in small portions. The resulting mixture was stirred at RT for 30 min, cooled back to 0° C., and then iodomethane (12.9 g, 90.3 mmol) was added dropwise. After the addition, the mixture was stirred at RT for 3 hours. The reaction was quenched with water and extracted with DCM (50 mL×2). The combined organic layers were washed with brined, dried, concentrated, and purified by silica flash column using 0 to 3% MeOH in DCM to get (R)-tert-butyl 3-(3-methyl-2-oxoimidazolidin-1-yl)piperidine-1-carboxylate (366) (13.0 g, 74%) as a light yellow oil. (R)-tert-butyl 3-(3-methyl-2-oxoimidazolidin-1-yl)piperidine-1-carboxylate (366) (3.5 g, 12.37 mmol) was treated with 40 mL commercial 4N HCl in dioxane at RT for 2 hours. The solvent was removed in vacuo, and the residue was basified to pH 9 with ammonium hydroxide. The solvent was then removed in vacuo, and the residue was subjected to silica flash column using 0 to 10% MeOH in DCM to isolate (R)-1-methyl-3-(piperidin-3-yl)imidazolidin-2-one (367) (1.2 g, 53%) as an oil. LC-MS (ESI): m/z (M+1) 184.2. Proton NMR (CDCl₃): δ 3.95-3.83 (2H, m), 3.75 (1H, s), 3.39-3.26 (5H, m), 3.08-2.97 (1H, m), 2.93-2.79 (1H, m), 2.78 (3H, s), 1.94-1.86 (2H, m), 1.82-1.56 (2H, m), 1.48-1.21 (1H, m) ppm.

The title compound, (R)-3-(4-(1-cyclopentylpiperidin-4-yl)phenylamino)-5-(3-(3-methyl-2-oxoimidazolidin-1-yl)piperidin-1-yl)pyrazine-2-carboxamide (370), was prepared by the same synthetic scheme illustrated for Example 252 and Example 253 using (R)-1-methyl-3-(piperidin-3-yl)imidazolidin-2-one (367) via intermediates (R)-3-chloro-5-(3-(3-methyl-2-oxoimidazolidin-1-yl)piperidin-1-yl)pyrazine-2-carbonitrile (368) and (R)-5-(3-(3-methyl-2-oxoimidazolidin-1-yl)piperidin-1-yl)-3-(4-(piperidin-4-yl)phenylamino)pyrazine-2-carboxamide (369). LC-MS (ESI): m/z (M+1) 547.5. UV: λ=268, 276, 305, 336, 373 nm. Proton NMR (CD$_3$OD): δ 7.65 (1H, s), 7.59 (2H, d, J=8.5 Hz), 7.20 (2H, d, J=8.5 Hz), 4.41-4.36 (2H, m), 3.78-3.71 (3H, m), 3.56 (1H, m), 3.50-3.42 (2H, m), 3.38-3.31 (2H, m), 3.19-3.11 (3H, m), 3.03 (1H, m), 2.87 (1H, m), 2.81 (3H, s), 2.22 (2H, m), 2.15 (2H, m), 1.96-1.84 (7H, m), 1.77-1.67 (5H, m) ppm.

Example 257

Synthesis of (R)-3-(4-(1-ethylpiperidin-4-yl)phenylamino)-5-(3-(3-methyl-2-oxoimidazolidin-1-yl)piperidin-1-yl)pyrazine-2-carboxamide

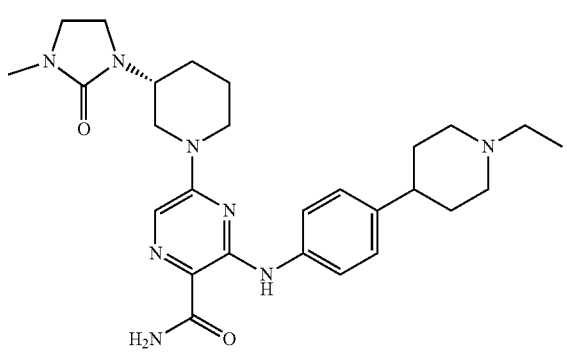

371

The title compound, (R)-3-(4-(1-ethylpiperidin-4-yl)phenylamino)-5-(3-(3-methyl-2-oxoimidazolidin-1-yl)piperidin-1-yl)pyrazine-2-carboxamide (371), was prepared by the same synthetic scheme illustrated for Example 256 using aldehyde. LC-MS (ESI): m/z (M+1) 507.4. UV: λ=268, 276, 305, 336, 372 nm.

Example 258

Synthesis of (R)-3-(4-(1-cyclobutylpiperidin-4-yl)phenylamino)-5-(3-(3-methyl-2-oxoimidazolidin-1-yl)piperidin-1-yl)pyrazine-2-carboxamide

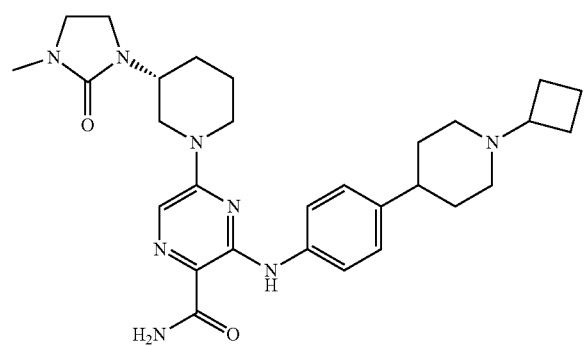

372

The title compound, (R)-3-(4-(1-cyclobutylpiperidin-4-yl)phenylamino)-5-(3-(3-methyl-2-oxoimidazolidin-1-yl)piperidin-1-yl)pyrazine-2-carboxamide (372), was prepared by the same synthetic scheme illustrated for Example 256 using cyclobutanone. LC-MS (ESI): m/z (M+1) 533.8. UV: λ=268, 276, 305, 335, 372 nm. Proton NMR (CD$_3$OD): δ 7.63 (1H, s), 7.58 (2H, d, J=8.5 Hz), 7.19 (2H, d, J=8.5 Hz), 4.40-4.34 (2H, m), 3.76 (1H, m), 3.68 (1H, m), 3.59 (1H, s), 3.56 (1H, s), 3.47 (1H, m), 3.42 (1H, m), 3.36 (2H, m), 3.14 (1H, m), 3.01 (1H, m), 2.92-2.87 (2H, m), 2.81 (3H, s), 2.37 (2H, m), 2.32 (2H, m), 2.12 (2H, m), 1.95-1.85 (7H, m), 1.66 (1H, m) ppm.

Example 259

Synthesis of (R)-3-(4-(1-cyclopropylpiperidin-4-yl)phenylamino)-5-(3-(3-methyl-2-oxoimidazolidin-1-yl)piperidin-1-yl)pyrazine-2-carboxamide

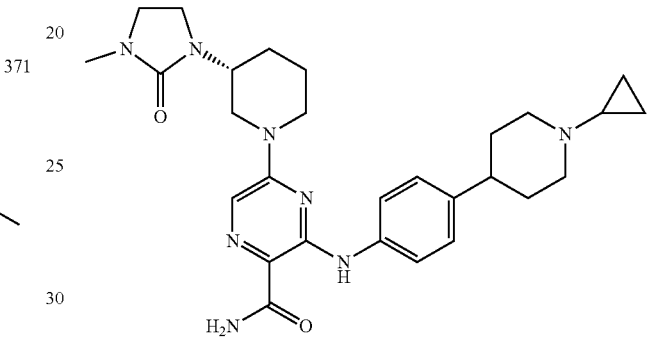

373

The title compound, (R)-3-(4-(1-cyclopropylpiperidin-4-yl)phenylamino)-5-(3-(3-methyl-2-oxoimidazolidin-1-yl)piperidin-1-yl)pyrazine-2-carboxamide (373), was prepared by the same synthetic scheme illustrated for Example 256 using 4-(1-cyclopropylpiperidin-4-yl)aniline (322) hydrochloride. LC-MS (ESI): m/z (M+1) 519.2. UV: λ=268, 276, 305, 336, 373 nm. Proton NMR (CD$_3$OD): δ 7.64 (1H, s), 7.59 (2H, d, J=8.5 Hz), 7.19 (2H, d, J=8.5 Hz), 4.40-4.35 (2H, m), 3.77 (3H, m), 3.48 (1H, m), 3.44 (1H, m), 3.37 (2H, m), 3.17 (1H, m), 3.02 (1H, m), 2.92-2.85 (2H, m), 2.80 (3H, s), 2.14 (2H, m), 1.95-1.85 (5H, m), 1.66 (1H, m), 1.02 (4H, m) ppm.

Example 260

Synthesis of (R)-5-(3-(3-methyl-2-oxoimidazolidin-1-yl)piperidin-1-yl)-3-(4-(1,1-dioxothiomorpholino)phenylamino)pyrazine-2-carboxamide

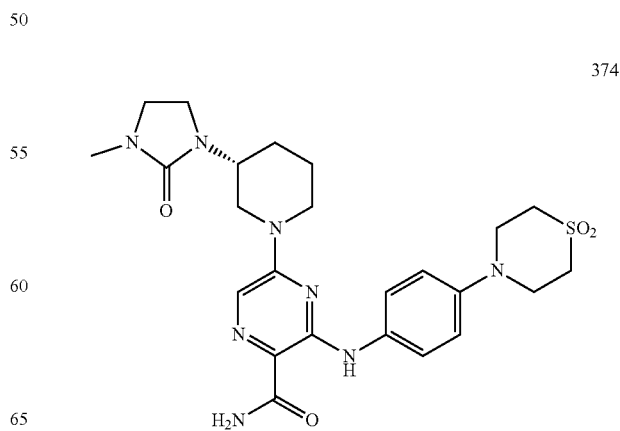

374

The title compound, (R)-5-(3-(3-methyl-2-oxoimidazolidin-1-yl)piperidin-1-yl)-3-(4-(1,1-dioxothiomorpholino)phenylamino)pyrazine-2-carboxamide (374), was prepared by the same synthetic scheme illustrated for Example 256 using 4-(1,1-dioxothiomorpholino)aniline. LC-MS (ESI): m/z (M+1) 529.3. UV: λ=309, 348, 374 nm. Proton NMR (CD₃OD): δ 7.60 (1H, s), 7.52 (2H, d, J=8.5 Hz), 7.01 (2H, d, J=8.5 Hz), 4.43 (1H, m), 4.33 (1H, m), 3.78 (5H, m), 3.47-3.33 (4H, m), 3.17 (4H, m), 3.08 (1H, m), 3.00 (1H, m), 2.81 (3H, s), 1.97-1.83 (3H, m), 1.66 (1H, m) ppm.

Example 261

Synthesis of (R)-5-(3-(3-methyl-2-oxoimidazolidin-1-yl)piperidin-1-yl)-3-(phenylamino)pyrazine-2-carboxamide

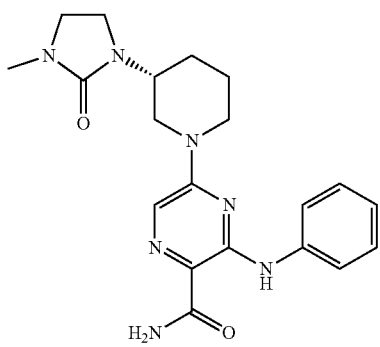

375

The title compound, (R)-5-(3-(3-methyl-2-oxoimidazolidin-1-yl)piperidin-1-yl)-3-(phenylamino)pyrazine-2-carboxamide (375), was prepared by the same synthetic scheme illustrated for Example 256 using aniline. LC-MS (ESI): m/z (M+1) 396.3. UV: λ=265, 275, 303, 333, 372 nm. Proton NMR (CD₃OD): δ 7.63 (1H, s), 7.59 (2H, d, J=7.5 Hz), 7.27 (2H, t, J=7.5 Hz), 6.98 (1H, t, J=7.5 Hz), 4.42 (1H, m), 4.36 (1H, m), 3.75 (1H, m), 3.47-3.41 (2H, m), 3.37-3.32 (2H, m), 3.12 (1H, m), 3.00 (1H, m), 2.80 (3H, s), 1.95-1.83 (3H, m), 1.67 (1H, m) ppm Example 262

Synthesis of (R)-5-(3-(3-methyl-2-oxoimidazolidin-1-yl)piperidin-1-yl)-3-(4-(1-(trifluoromethyl)cyclopropyl)phenylamino)pyrazine-2-carboxamide

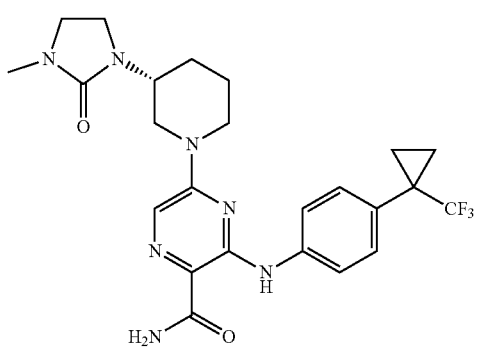

376

The title compound, (R)-5-(3-(3-methyl-2-oxoimidazolidin-1-yl)piperidin-1-yl)-3-(4-(1-(trifluoromethyl)cyclopropyl)phenylamino)pyrazine-2-carboxamide (376), was prepared by the same synthetic scheme illustrated for Example 256 using 4-(1-(trifluoromethyl)cyclopropyl)aniline (330). LC-MS (ESI): m/z (M+1) 504.5. UV: λ=268, 278, 306, 334, 372 nm. Proton NMR (CD₃OD): δ 7.64 (1H, s), 7.60 (2H, d, J=8.5 Hz), 7.38 (2H, d, J=8.5 Hz), 4.47 (1H, m), 4.32 (1H, m), 3.77 (1H, m), 3.48-3.40 (2H, m), 3.47-3.34 (2H, m), 3.08 (1H, m), 3.01 (1H, m), 2.82 (3H, s), 1.96-1.82 (3H, m), 1.68 (1H, m), 1.31 (2H, m), 1.05 (2H, m) ppm.

Example 263

Synthesis of (R)-3-(4-(1-cyclopropyl-4-methylpiperidin-4-yl)phenylamino)-5-(3-(3-methyl-2-oxoimidazolidin-1-yl)piperidin-1-yl)pyrazine-2-carboxamide

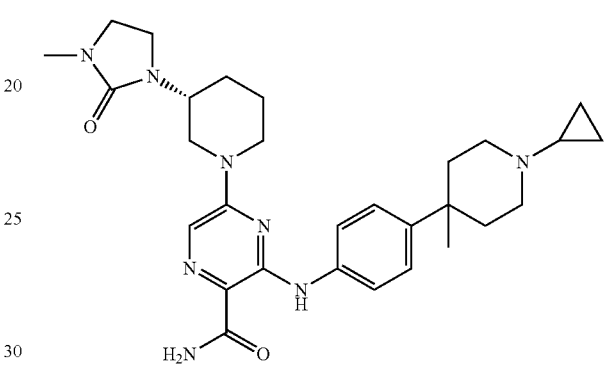

377

The title compound, (R)-3-(4-(1-cyclopropyl-4-methylpiperidin-4-yl)phenylamino)-5-(3-(3-methyl-2-oxoimidazolidin-1-yl)piperidin-1-yl)pyrazine-2-carboxamide (377), was prepared by the same synthetic scheme illustrated for Example 256 using 4-(1-cyclopropyl-4-methylpiperidin-4-yl)aniline (342). LC-MS (ESI): m/z (M+1) 533.7. UV: λ=269, 277, 306, 335, 372 nm.

Example 264

Synthesis of (R)-3-(4-(1-isopropyl-4-methylpiperidin-4-yl)phenylamino)-5-(3-(3-methyl-2-oxoimidazolidin-1-yl)piperidin-1-yl)pyrazine-2-carboxamide

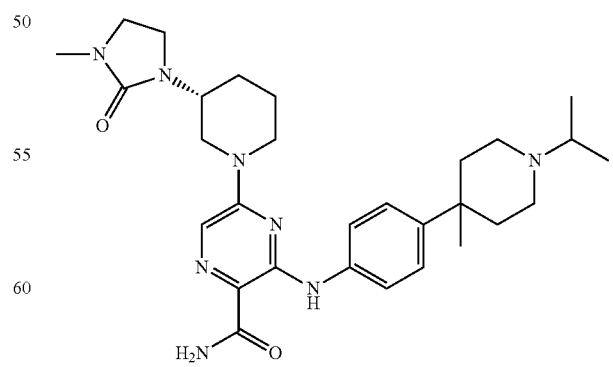

378

The title compound, (R)-3-(4-(1-isopropyl-4-methylpiperidin-4-yl)phenylamino)-5-(3-(3-methyl-2-oxoimidazolidin-1-yl)piperidin-1-yl)pyrazine-2-carboxamide (378), was prepared by the same synthetic scheme illustrated for Example 256 using tert-butyl 4-(4-aminophenyl)-4-methylpiperidine-1-carboxylate (287) and acetone. LC-MS (ESI): m/z (M+1) 535.9. UV: λ=269, 277, 306, 336, 372 nm.

Example 265

Synthesis of (R)-3-(4-(4-methyl-1-(oxetan-3-yl)piperidin-4-yl)phenylamino)-5-(3-(3-methyl-2-oxoimidazolidin-1-yl)piperidin-1-yl)pyrazine-2-carboxamide

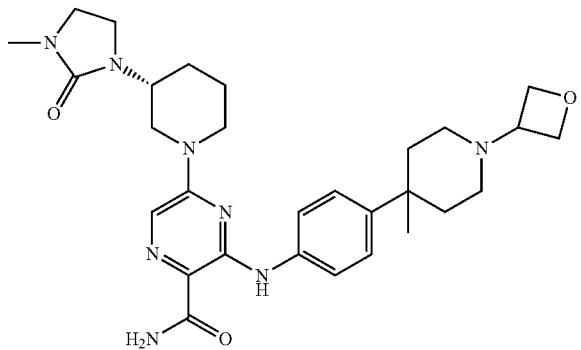

379

The title compound, (R)-3-(4-(4-methyl-1-(oxetan-3-yl) piperidin-4-yl)phenylamino)-5-(3-(3-methyl-2-oxoimidazolidin-1-yl)piperidin-1-yl)pyrazine-2-carboxamide (379), was prepared by the same synthetic scheme illustrated for Example 256 using tert-butyl 4-(4-aminophenyl)-4-methylpiperidine-1-carboxylate (287) and oxetan-3-one. LC-MS (ESI): m/z (M+1) 549.8. UV: λ=269, 277, 306, 336, 372 nm. Proton NMR (CD$_3$OD): δ 7.64 (1H, s), 7.57 (2H, d, J=8.5 Hz), 7.29 (2H, d, J=8.5 Hz), 4.67 (2H, t, J=7.0 Hz), 4.60 (2H, t, J=6.5 Hz), 4.46 (1H, m), 4.34 (1H, m), 3.76 (1H, m), 3.50 (1H, m), 3.47 (1H, m), 3.42 (1H, m), 3.35 (2H, m), 3.08 (1H, m), 3.00 (1H, m), 2.80 (3H, s), 2.32 (2H, m), 2.21 (2H, m), 1.95-1.65 (4H, m), 1.23 (3H, s) ppm.

Example 266

Synthesis of (R)-3-(4-(1-cyclobutyl-4-methylpiperidin-4-yl)phenylamino)-5-(3-(3-methyl-2-oxoimidazolidin-1-yl)piperidin-1-yl)pyrazine-2-carboxamide

380

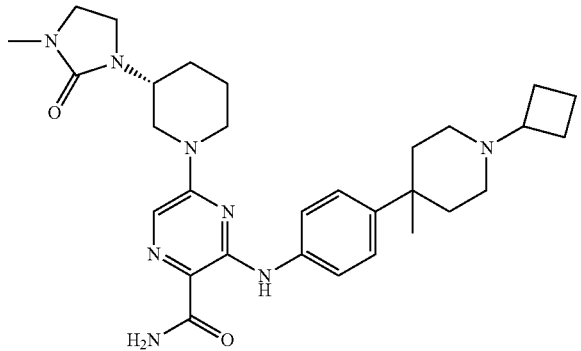

The title compound, (R)-3-(4-(1-cyclobutyl-4-methylpiperidin-4-yl)phenylamino)-5-(3-(3-methyl-2-oxoimidazolidin-1-yl)piperidin-1-yl)pyrazine-2-carboxamide (379), was prepared by the same synthetic scheme illustrated for Example 256 using tert-butyl 4-(4-aminophenyl)-4-methylpiperidine-1-carboxylate (287) and cyclobutanone. LC-MS (ESI): m/z (M+1) 547.9. UV: λ=268, 277, 306, 336, 372 nm. Proton NMR (CD$_3$OD): δ 7.69-7.61 (3H, m), 7.34-7.32 (2H, m), 4.48-4.43 (1H, m), 4.38-4.35 (1H, m), 3.79 (1H, m), 3.50-3.35 (6H, m), 3.16-3.02 (3H, m), 2.80 (3H, s), 2.67-2.64 (2H, m), 2.42-1.65 (14H, m), 1.40-1.27 (3H, s) ppm.

Example 267

Synthesis of (R)-3-(4-(1-cyclopentyl-4-methylpiperidin-4-yl)phenylamino)-5-(3-(3-methyl-2-oxoimidazolidin-1-yl)piperidin-1-yl)pyrazine-2-carboxamide

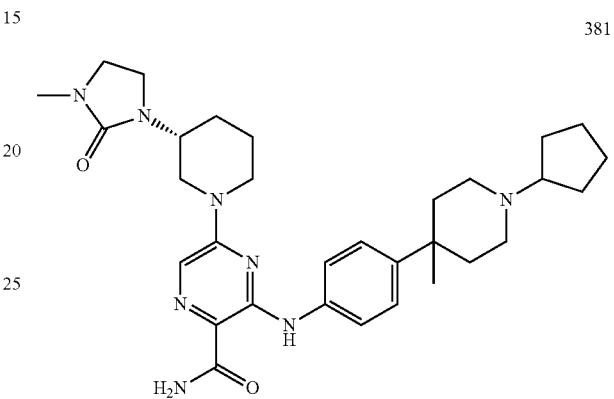

381

The title compound, (R)-3-(4-(1-cyclopentyl-4-methylpiperidin-4-yl)phenylamino)-5-(3-(3-methyl-2-oxoimidazolidin-1-yl)piperidin-1-yl)pyrazine-2-carboxamide (381), was prepared by the same synthetic scheme illustrated for Example 256 using tert-butyl 4-(4-aminophenyl)-4-methylpiperidine-1-carboxylate (287) and cyclopentanone. LC-MS (ESI): m/z (M+1) 561.9. UV: λ=268, 277, 306, 336, 372 nm. Proton NMR (CD$_3$OD): δ 7.69-7.61 (3H, m), 7.34-7.32 (2H, m), 4.47-4.43 (1H, m), 4.38-4.35 (1H, m), 3.79 (1H, m), 3.55-3.35 (6H, m), 3.16-2.82 (3H, m), 2.80 (3H, s), 2.66-2.63 (2H, m), 2.25-1.60 (16H, m), 1.42-1.27 (3H, s) ppm.

Example 268

Synthesis of (R)-3-(4-(1-formyl-4-methylpiperidin-4-yl)phenylamino)-5-(3-(3-methyl-2-oxoimidazolidin-1-yl)piperidin-1-yl)pyrazine-2-carboxamide

382

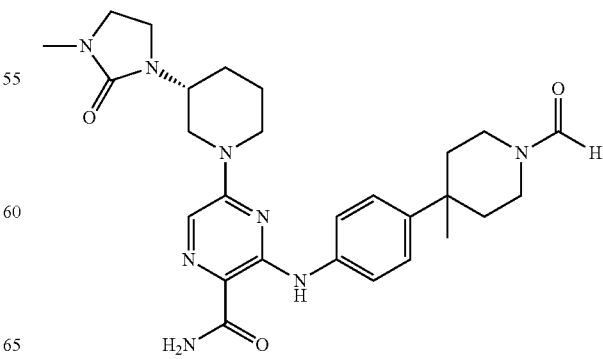

The title compound, (R)-3-(4-(1-formyl-4-methylpiperidin-4-yl)phenylamino)-5-(3-(3-methyl-2-oxoimidazolidin-1-yl)piperidin-1-yl)pyrazine-2-carboxamide (382), was prepared by the same synthetic scheme illustrated for Example 255 using (R)-5-(3-(3-methyl-2-oxoimidazolidin-1-yl)piperidin-1-yl)-3-(4-(piperidin-4-yl)phenylamino)pyrazine-2-carboxamide (369), formic acid and PyBOP. LC-MS (ESI): m/z (M+1) 521.5. UV: λ=268, 276, 305, 335, 372 nm.

Example 269

Synthesis of (R)-3-(4-(4-methyl-1-propionylpiperidin-4-yl)phenylamino)-5-(3-(3-methyl-2-oxoimidazolidin-1-yl)piperidin-1-yl)pyrazine-2-carboxamide

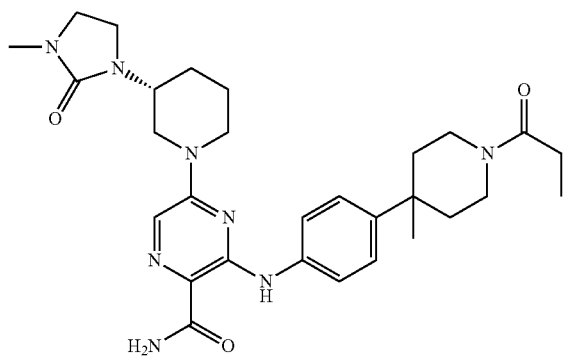

383

The title compound, (R)-3-(4-(4-methyl-1-propionylpiperidin-4-yl)phenylamino)-5-(3-(3-methyl-2-oxoimidazolidin-1-yl)piperidin-1-yl)pyrazine-2-carboxamide (383), was prepared by the same synthetic scheme illustrated for Example 255 using (R)-5-(3-(3-methyl-2-oxoimidazolidin-1-yl)piperidin-1-yl)-3-(4-(piperidin-4-yl)phenylamino)pyrazine-2-carboxamide (369). LC-MS (ESI): m/z (M+1) 549.7. UV: λ=268, 276, 305, 335, 372 nm. Proton NMR (CD$_3$OD): δ 7.64 (1H, s), 7.59 (2H, d, J=8.5 Hz), 7.32 (2H, d, J=8.5 Hz), 4.48 (1H, m), 4.34 (1H, m), 3.78 (1H, m), 3.63 (1H, m), 3.47-3.33 (7H, m), 3.12-2.99 (2H, m), 2.81 (3H, s), 2.41 (2H, m), 2.20-2.10 (2H, m), 1.96-1.65 (6H, m), 1.27 (3H, s), 1.11 (3H, t, J=7.5 Hz) ppm.

Example 270

Synthesis of (R)-3-(4-(1-(cyclopropanecarbonyl)-4-methylpiperidin-4-yl)phenylamino)-5-(3-(3-methyl-2-oxoimidazolidin-1-yl)piperidin-1-yl)pyrazine-2-carboxamide

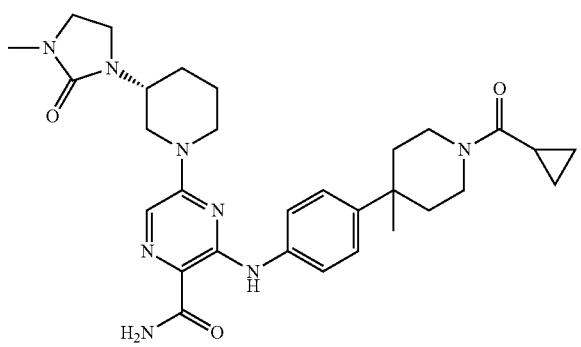

384

The title compound, (R)-3-(4-(1-(cyclopropanecarbonyl)-4-methylpiperidin-4-yl)phenylamino)-5-(3-(3-methyl-2-oxoimidazolidin-1-yl)piperidin-1-yl)pyrazine-2-carboxamide (384), was prepared by the same synthetic scheme illustrated for Example 255 using (R)-5-(3-(3-methyl-2-oxoimidazolidin-1-yl)piperidin-1-yl)-3-(4-(piperidin-4-yl)phenylamino)pyrazine-2-carboxamide (369) and cyclopropanecarbonyl chloride. LC-MS (ESI): ink (M+1) 561.7. UV: λ=268, 276, 305, 335, 372 nm. Proton NMR (CD$_3$OD): δ 7.64 (1H, s), 7.59 (2H, d, J=8.5 Hz), 7.33 (2H, d, J=9.0 Hz), 4.48 (1H, m), 4.34 (1H, m), 3.88 (1H, m), 3.78 (2H, m), 3.61 (1H, m), 3.47-3.34 (5H, m), 3.12-2.98 (2H, m), 2.81 (3H, s), 2.21 (1H, m), 2.12 (1H, m), 1.97-1.65 (6H, m), 1.29 (3H, s), 0.88-0.78 (4H, m) ppm.

Example 271

Synthesis of (R)-3-(4-(4-cyano-1-cyclopentylpiperidin-4-yl)phenylamino)-5-(3-(3-methyl-2-oxoimidazolidin-1-yl)piperidin-1-yl)pyrazine-2-carboxamide

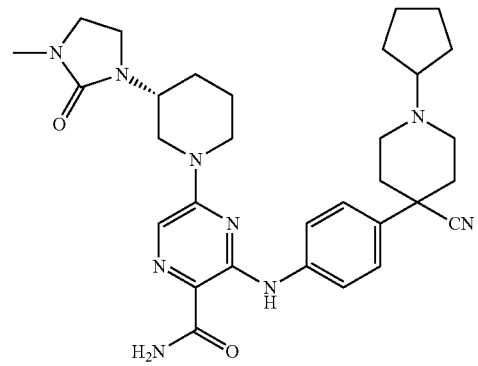

385

The title compound, (R)-3-(4-(4-cyano-1-cyclopentylpiperidin-4-yl)phenylamino)-5-(3-(3-methyl-2-oxoimidazolidin-1-yl)piperidin-1-yl)pyrazine-2-carboxamide (385), was prepared by the same synthetic scheme illustrated for Example 256 using 4-(4-aminophenyl)-1-cyclopentylpiperidine-4-carbonitrile hydrochloride (350). LC-MS (ESI): m/z (M+1) 572.8. UV: λ=270, 280, 308, 336, 372 nm. Proton NMR (CD$_3$OD): δ 7.77 (2H, d, J=8.5 Hz), 7.66 (1H, s), 7.47 (2H, d, J=8.5 Hz), 4.47 (1H, m), 4.33 (1H, m), 3.88 (1H, s), 3.85 (1H, s), 3.76 (1H, m), 3.68 (1H, m), 3.47-3.34 (6H, m), 3.10 (1H, m), 3.05 (1H, m), 2.82 (3H, s), 2.52-2.40 (4H, m), 2.25 (2H, m), 1.95-1.65 (10H, m) ppm. Compound 386, (R)-3-(4-(4-carbamoyl-1-cyclopentylpiperidin-4-yl)phenylamino)-5-(3-(3-methyl-2-oxoimidazolidin-1-yl)piperidin-1-yl)pyrazine-2-carboxamide, was also found and isolated as a major by-product in the final step.

Example 272

Synthesis of (R)-3-(4-(4-carbamoyl-1-cyclopentylpiperidin-4-yl)phenylamino)-5-(3-(3-methyl-2-oxoimidazolidin-1-yl)piperidin-1-yl)pyrazine-2-carboxamide

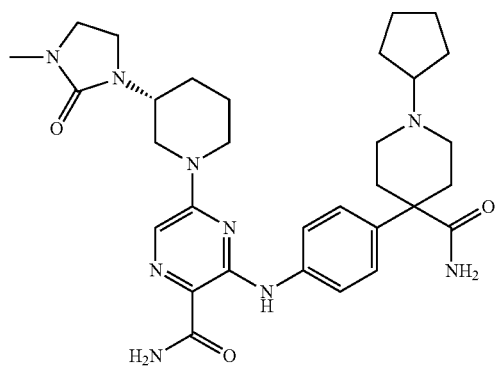

386

The title compound, (R)-3-(4-(4-carbamoyl-1-cyclopentylpiperidin-4-yl)phenylamino)-5-(3-(3-methyl-2-oxoimidazolidin-1-yl)piperidin-1-yl)pyrazine-2-carboxamide (386), was found and isolated as a major by-product in the final step during the preparation of (R)-3-(4-(4-cyano-1-cyclopentylpiperidin-4-yl)phenylamino)-5-(3-(3-methyl-2-oxoimidazolidin-1-yl)piperidin-1-yl)pyrazine-2-carboxamide (385). LC-MS (ESI): m/z (M+1) 590.5. UV: λ=271, 280, 309, 337, 372 nm.

Example 273

Synthesis of (R)-3-(4-(4-cyano-1-cyclobutylpiperidin-4-yl)phenylamino)-5-(3-(3-methyl-2-oxoimidazolidin-1-yl)piperidin-1-yl)pyrazine-2-carboxamide

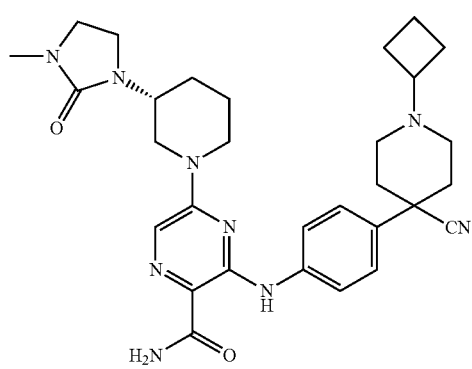

387

The title compound, (R)-3-(4-(4-cyano-1-cyclobutylpiperidin-4-yl)phenylamino)-5-(3-(3-methyl-2-oxoimidazolidin-1-yl)piperidin-1-yl)pyrazine-2-carboxamide (387), was prepared by the same synthetic scheme illustrated for Example 271 using cyclobutanone. LC-MS (ESI): m/z (M+1) 558.8. UV: λ=270, 279, 308, 336, 370 nm. Proton NMR (CD$_3$OD): δ 7.74 (2H, d, J=8.5 Hz), 7.68 (1H, s), 7.48 (2H, d, J=9.0 Hz), 4.49 (1H, m), 4.34 (1H, m), 3.86 (1H, m), 3.78 (1H, m), 3.73 (2H, m), 3.49-3.35 (4H, m), 3.20-3.02 (4H, m), 2.82 (3H, s), 2.52-2.32 (8H, m), 1.95-1.66 (6H, m) ppm.

Example 274

Synthesis of (R)-3-(4-(1-cyclopentylpiperidin-4-yl)phenylamino)-5-(3-(2-oxoimidazolidin-1-yl)piperidin-1-yl)pyrazine-2-carboxamide

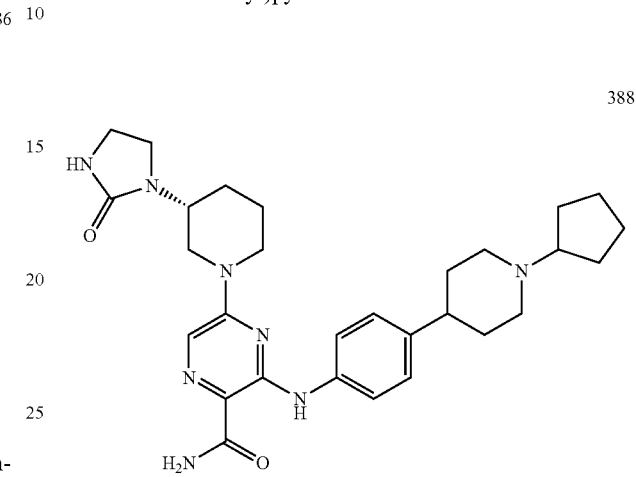

388

The title compound, (R)-3-(4-(1-cyclopentylpiperidin-4-yl)phenylamino)-5-(3-(2-oxoimidazolidin-1-yl)piperidin-1-yl)pyrazine-2-carboxamide (388), was prepared by the same synthetic scheme illustrated for Example 256 using (R)-tert-butyl 3-(2-oxoimidazolidin-1-yl)piperidine-1-carboxylate (365) without methylation by iodomethane and sodium hydride. LC-MS (ESI): m/z (M+1) 533.8. UV: λ=268, 276, 305, 335, 372 nm. Proton NMR (CD$_3$OD): δ 7.64 (1H, s), 7.58 (2H, d, J=8.5 Hz), 7.21 (2H, d, J=8.5 Hz), 4.43 (1H, m), 4.36 (1H, m), 3.77 (1H, m), 3.72 (1H, s), 3.70 (1H, s), 3.59-3.52 (3H, m), 3.42 (2H, m), 3.13 (3H, m), 3.01 (1H, m), 2.86 (1H, m), 2.21 (2H, m), 2.13 (2H, m), 1.97-1.64 (12H, m) ppm.

Example 275

Synthesis of (R)-3-(4-(1-cyclopentylpiperidin-4-yl)phenylamino)-5-(3-(3-ethyl-2-oxoimidazolidin-1-yl)piperidin-1-yl)pyrazine-2-carboxamide

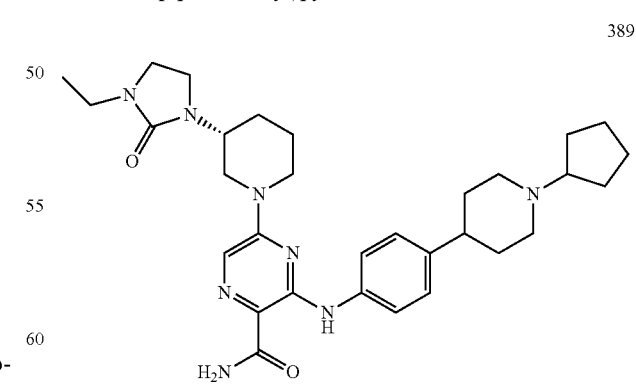

389

The title compound, (R)-3-(4-(1-cyclopentylpiperidin-4-yl)phenylamino)-5-(3-(3-ethyl-2-oxoimidazolidin-1-yl)piperidin-1-yl)pyrazine-2-carboxamide (389), was prepared by the same synthetic scheme illustrated for Example 256 using iodoethane. LC-MS (ESI): m/z (M+1) 561.8. UV: λ=268, 276, 305, 335, 372 nm. Proton NMR (CD$_3$OD): δ 7.64 (1H, s), 7.59 (2H, d, J=8.5 Hz), 7.20 (2H, d, J=9.0 Hz), 4.38 (2H, m), 3.77 (1H, m), 3.73 (1H, s), 3.70 (1H, s), 3.51 (1H, m), 3.48 (1H, m), 3.44 (1H, m), 3.38 (2H, m), 3.27 (2H, q, J=7.0 Hz), 3.17 (1H, m), 3.14 (2H, m), 3.02 (1H, m), 2.85 (1H, m), 2.22 (2H, m), 2.14 (2H, m), 1.98-1.66 (12H, m), 1.14 (3H, t, J=7.0 Hz) ppm.

Example 276

Synthesis of (R)-3-(4-(1-cyclopropyl-4-methylpiperidin-4-yl)phenylamino)-5-(3-(3-ethyl-2-oxoimidazolidin-1-yl)piperidin-1-yl)pyrazine-2-carboxamide

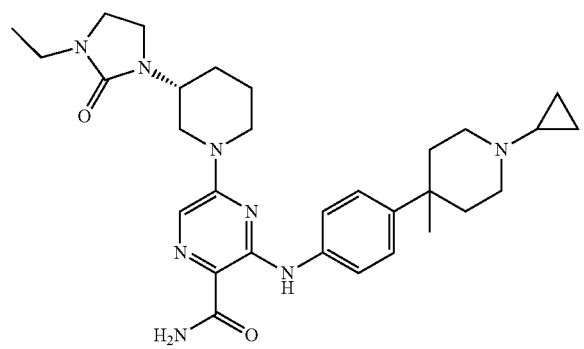

390

The title compound, (R)-3-(4-(1-cyclopropyl-4-methylpiperidin-4-yl)phenylamino)-5-(3-(3-ethyl-2-oxoimidazolidin-1-yl)piperidin-1-yl)pyrazine-2-carboxamide (390), was prepared by the same synthetic scheme illustrated for Example 275 using 4-(1-cyclopropyl-4-methylpiperidin-4-yl)aniline (342). LC-MS (ESI): m/z (M+1) 547.5. UV: λ=269, 277, 306, 336, 372 nm. Proton NMR (CD$_3$OD): δ 7.70-7.62 (3H, m), 7.36-7.32 (2H, m), 4.47-4.35 (2H, m), 3.78 (1H, m), 3.61-3.37 (6H, m), 3.27 (2H, q, J=7.0 Hz), 3.16-2.99 (3H, m), 2.69-2.62 (2H, m), 2.16-1.66 (8H, m), 1.44-1.26 (3H, s), 1.14 (3H, t, J=7.5 Hz), 1.02-0.87 (4H, m) ppm.

Example 277

Synthesis of (R)-3-(4-(1-cyclopentylpiperidin-4-yl)phenylamino)-5-(3-(3-cyclopropyl-2-oxoimidazolidin-1-yl)piperidin-1-yl)pyrazine-2-carboxamide

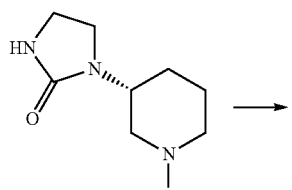

365

-continued

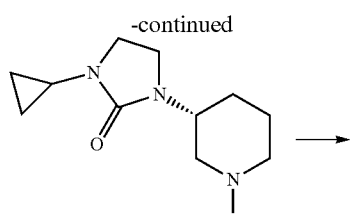

391

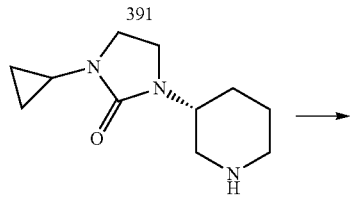

392

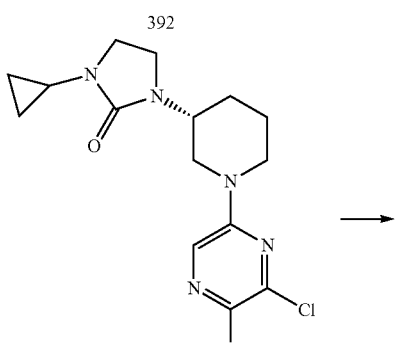

393

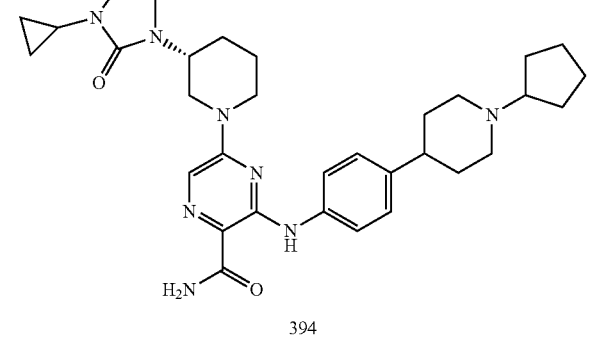

394

To a solution of (R)-tert-butyl 3-(2-oxoimidazolidin-1-yl)piperidine-1-carboxylate (365) (10.0 g, 31.17 mmol), cyclopropylboronic acid (6.39 g, 74.35 mmol) and pyridine (8.82 g, 111.5 mmol) in anhydrous DMF (100 mL) was added Cu(OAc)$_2$ (6.75 g, 37.17 mmol). The resulting mixture was stirred at 40° C. under O$_2$ atmosphere (balloon) for 48 hours. After quenched with NH$_3$.H$_2$O (10 mL), the mixture was diluted with water (50 mL) and extracted with EtOAc (100 mL×3). The organic layers were combined, washed with brine, dried, concentrated, and subjected to silica flash column chromatography using 0 to 70% EtOAc in PE to isolate (R)-tert-butyl 3-(3-cyclopropyl-2-oxoimidazolidin-1-yl)piperidine-1-carboxylate (391) (2.6 g, 23%) as a light yellow oil.

(R)-tert-Butyl 3-(3-cyclopropyl-2-oxoimidazolidin-1-yl)piperidine-1-carboxylate (391) (3.0 g, 9.7 mmol) was treated with commercial 4N HCl in dioxane at RT to afford (R)-1-cyclopropyl-3-(piperidin-3-yl)imidazolidin-2-one hydrochloride (392) (2.05 g, 86%) as a light brown solid after concentration in vacuo. Proton NMR (DMSO-d$_6$): δ 9.37 (1H, s), 8.99 (1H, s), 3.89-3.82 (1H, m), 3.64-3.57 (1H, m), 3.28-3.18 (4H, m), 3.11-3.03 (1H, m), 2.97-2.87 (1H, m), 2.77-2.67 (1H, m), 2.44-2.29 (1H, m), 1.89-1.80 (1H, m), 1.75-1.64 (3H, m), 0.81-0.36 (4H, m) ppm.

The title compound, (R)-3-(4-(1-cyclopentylpiperidin-4-yl)phenylamino)-5-(3-(3-cyclopropyl-2-oxoimidazolidin-1-yl)piperidin-1-yl)pyrazine-2-carboxamide (394), was prepared by the same synthetic scheme illustrated for Example 252 using (R)-1-cyclopropyl-3-(piperidin-3-yl)imidazolidin-2-one hydrochloride (392) and 4-(1-cyclopentylpiperidin-4-yl)aniline hydrochloride (304) via intermediates (R)-3-chloro-5-(3-(3-cyclopropyl-2-oxoimidazolidin-1-yl)piperidin-1-yl)pyrazine-2-carbonitrile (393). LC-MS (ESI): m/z (M+1) 573.7. UV: λ=268, 277, 305, 335, 372 nm.

Example 278

Synthesis of (R)-3-(4-(1-cyclobutylpiperidin-4-yl)phenylamino)-5-(3-(3-cyclopropyl-2-oxoimidazolidin-1-yl)piperidin-1-yl)pyrazine-2-carboxamide

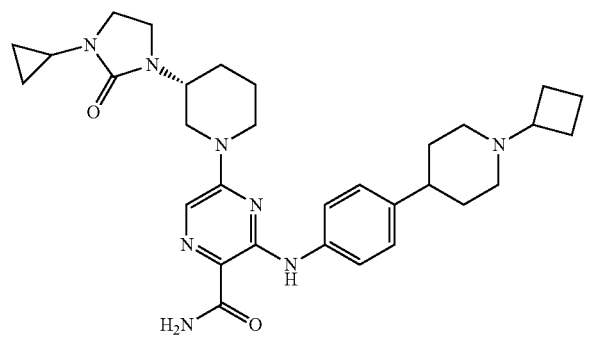

395

The title compound, (R)-3-(4-(1-cyclobutylpiperidin-4-yl)phenylamino)-5-(3-(3-cyclopropyl-2-oxoimidazolidin-1-yl)piperidin-1-yl)pyrazine-2-carboxamide (395), was prepared by the same synthetic scheme illustrated for Example 277 using 4-(1-cyclobutylpiperidin-4-yl)aniline hydrochloride. LC-MS (ESI): m/z (M+1) 559.9. UV: λ=268, 276, 305, 336, 372 nm Proton NMR (CD$_3$OD): δ 7.64 (1H, s), 7.59 (2H, d, J=8.5 Hz), 7.21 (2H, d, J=8.5 Hz), 4.37 (2H, m), 3.78 (1H, m), 3.71 (1H, m), 3.59 (1H, s), 3.57 (1H, s), 3.43 (1H, m), 3.36 (3H, m), 3.15 (1H, m), 3.01 (1H, m), 2.92 (2H, m), 2.84 (1H, m), 2.40 (3H, m), 2.29 (2H, m), 2.14 (2H, m), 1.97-1.65 (8H, m), 0.72-0.66 (4H, m) ppm.

Example 279

Synthesis of (R)-5-(3-(3-cyclopropyl-2-oxoimidazolidin-1-yl)piperidin-1-yl)-3-(4-(1-cyclopropyl-4-methylpiperidin-4-yl)phenylamino)pyrazine-2-carboxamide

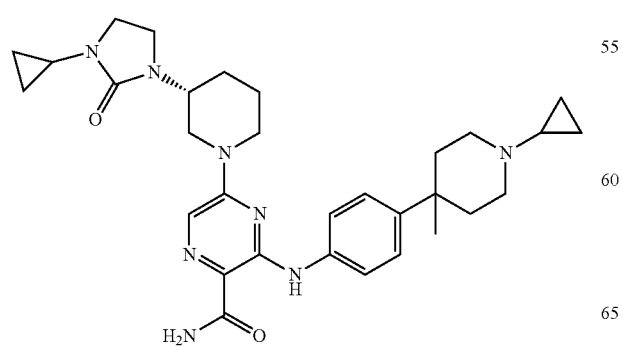

396

The title compound, (R)-5-(3-(3-cyclopropyl-2-oxoimidazolidin-1-yl)piperidin-1-yl)-3-(4-(1-cyclopropyl-4-methylpiperidin-4-yl)phenylamino)pyrazine-2-carboxamide (396), was prepared by the same synthetic scheme illustrated for Example 277 using 4-(1-cyclopropyl-4-methylpiperidin-4-yl)aniline (342). LC-MS (ESI): m/z (M+1) 559.8. UV: λ=268, 277, 306, 336, 372 nm. Proton NMR (CD$_3$OD): δ 7.71-7.61 (3H, m), 7.38-7.32 (2H, m), 4.45-4.35 (2H, m), 3.79 (1H, m), 3.60-3.36 (7H, m), 3.16-2.99 (3H, m), 2.70-2.64 (2H, m), 2.41 (1H, m), 2.19-1.66 (7H, m), 1.45-1.26 (3H, s), 1.02-0.87 (4H, m), 0.72-0.67 (4H, m) ppm.

Example 280

Synthesis of (R)-5-(3-(3-(3-chlorophenyl)-2-oxoimidazolidin-1-yl)piperidin-1-yl)-3-(4-(1-cyclopentylpiperidin-4-yl)phenylamino)pyrazine-2-carboxamide

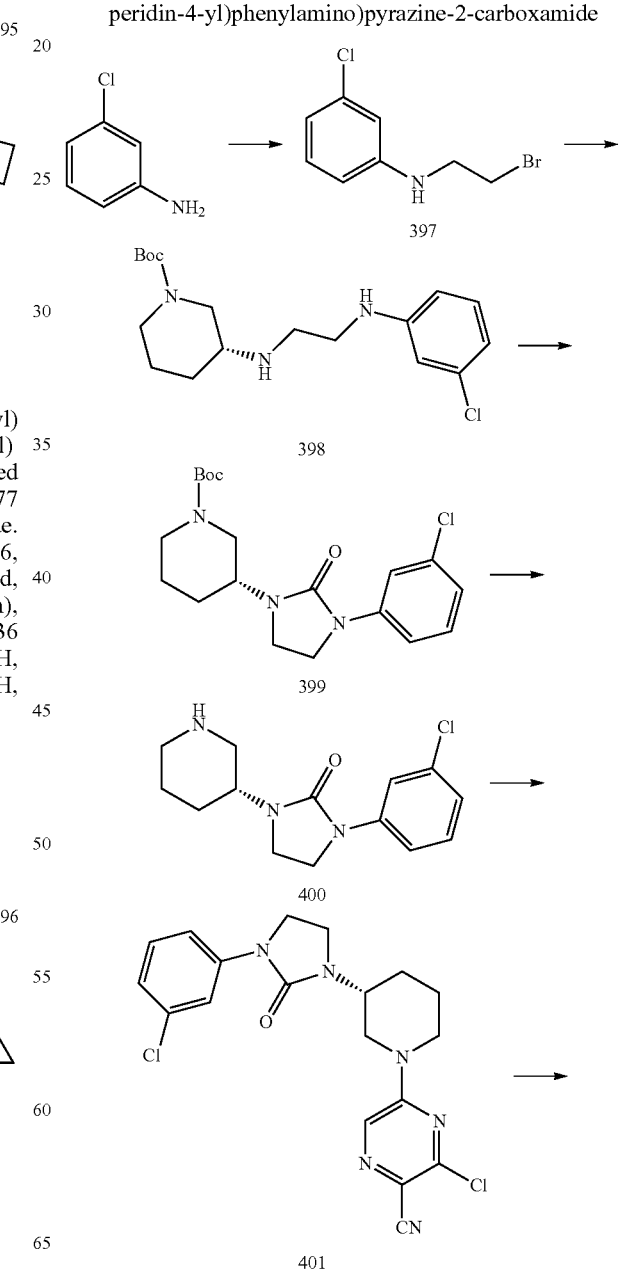

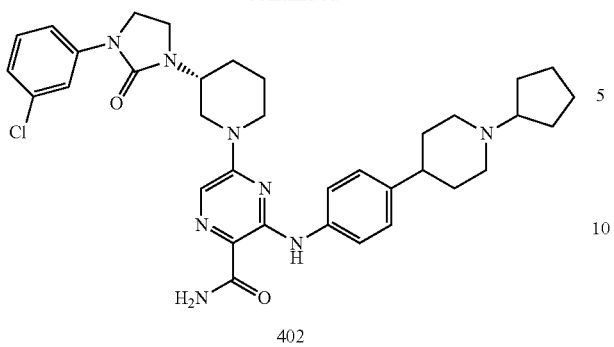

402

A mixture of 3-chloroaniline (50 g, 0.39 mol) and 1,2-dibromoethane (73 g, 0.39 mol) in MeCN (500 mL) was heated at 80° C. for 2 days. The reaction mixture was concentrated on rotavap and subjected to silica flash column chromatography using 0 to 30% EtOAc in PE to isolate N-(2-bromoethyl)-3-chloroaniline (397) (9.0 g, 10%) as a yellow solid. To a solution of N-(2-bromoethyl)-3-chloroaniline (397) (9.0 g, 38.46 mmol) and (R)-tert-butyl 3-aminopiperidine-1-carboxylate (7.74 g, 38.46 mmol) in THF (100 mL) was added DIEA (14.88 g, 115.38 mmol). The resulting mixture was stirred at 70° C. for 2 days. It was partitioned in EtOAc (50 mL) and water (50 mL). The layers were separated and the aqueous was extracted with EtOAC (50 mL×3). The combined organic layer was washed with brine, dried, concentrated and subjected to silica flash column chromatography using 0 to 5% MeOH in DCM to isolated (R)-tert-butyl 3-(2-(3-chlorophenylamino)ethylamino)piperidine-1-carboxylate (398) (10.1 g, 74.4%) as a white solid.

In ice bath and under $N_2$ atmosphere, to a stirred solution of (R)-tert-butyl 3-(2-(3-chlorophenylamino)ethylamino)piperidine-1-carboxylate (398) (10.1 g, 28.37 mmol) and $Et_3N$ (3.01 g, 29.8 mmol) in anhydrous DCM (300 mL) was added a solution of triphosgene (2.95 g, 9.93 mmol) in DCM (100 mL) dropwise. The resulting mixture was stirred in ice bath for 1 hour, and quenched with $NaHCO_3$ (aq.) (1M, 50 mL). The mixture was extracted with DCM (100 mL×3). The combined organic layer was washed with brine, dried, concentrated and subjected to silica flash column chromatography using 0 to 5% MeOH in DCM to isolate (R)-tert-butyl 3-(3-(3-chlorophenyl)-2-oxoimidazolidin-1-yl)piperidine-1-carboxylate (399) (4 g, 37%) as a white solid. It was treated with 40 mL commercial 4N HCl in dioxane to give (R)-1-(3-chlorophenyl)-3-(piperidin-3-yl)imidazolidin-2-one hydrochloride (400) (3.3 g, quant.) as a white solid. Proton NMR (DMSO-$d_6$): δ 9.26 (1H, s), 8.93 (1H, s), 7.77 (1H, t, J=2.0 Hz), 7.47-7.40 (1H, m), 7.35 (1H, t, J=8.1 Hz), 7.06 (1H, dd, J=7.9, 1.1 Hz), 4.10-3.94 (1H, m), 3.89-3.76 (2H, m), 3.48 (2H, t, J=8.5 Hz), 3.25-3.14 (2H, m), 3.06-2.97 (1H, m), 2.82-2.72 (1H, m), 1.95-1.86 (1H, m), 1.83-1.68 (3H, m) ppm.

The title compound, (R)-5-(3-(3-(3-chlorophenyl)-2-oxoimidazolidin-1-yl)piperidin-1-yl)-3-(4-(1-cyclopentylpiperidin-4-yl)phenylamino)pyrazine-2-carboxamide (402), was prepared by the same synthetic scheme illustrated for Example 252 using (R)-1-(3-chlorophenyl)-3-(piperidin-3-yl)imidazolidin-2-one hydrochloride (400) and 4-(1-cyclopentylpiperidin-4-yl)aniline hydrochloride (304) via intermediates (R)-3-chloro-5-(3-(3-(3-chlorophenyl)-2-oxoimidazolidin-1-yl)piperidin-1-yl)pyrazine-2-carbonitrile (401). LC-MS (ESI): m/z (M+1) 644.4. UV: λ=255, 276, 304, 335, 372 nm.

Example 281

Synthesis of 3-(4-(1-cyclopentylpiperidin-4-yl)phenylamino)-5-((2R,3R)-2-methyl-3-(3-methyl-2-oxotetrahydropyrimidin-1(2H)-yl)piperidin-1-yl)pyrazine-2-carboxamide

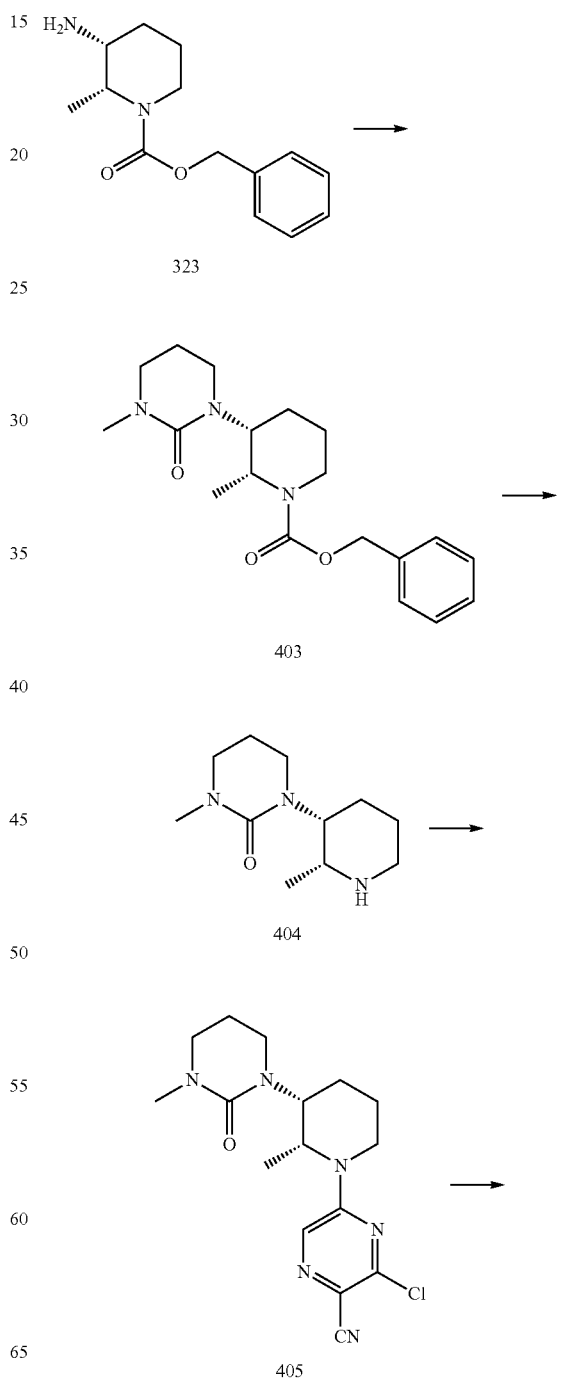

323

403

404

405

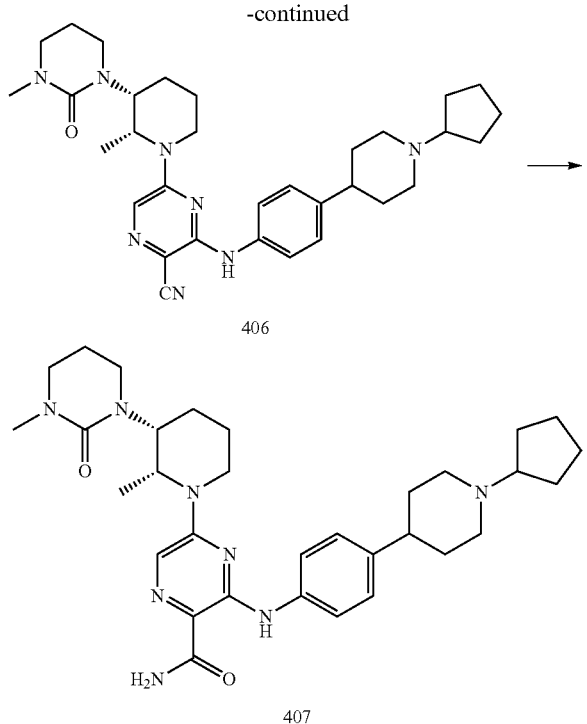

406

407

(2R,3R)-Benzyl 3-amino-2-methylpiperidine-1-carboxylate (323, 270 mg, 1.09 mmol) was dissolved in 10 mL dry THF. To it was added 3-chloropropyl isocyante (112 μL, 1.09 mmol), and the mixture was stirred at RT for 3 hours. To it was added NaH (60% in mineral oil, 87 mg, 2.18 mmol) and the mixture was stirred for overnight. Another batch of NaH (87 mg, 2.18 mmol) was then added to drive the cyclization to completion in 4 hours. To the mixture was added iodomethane (540 μL, 8.64 mmol), and it was stirred at RT for overnight. It was diluted with 120 mL EtOAc and 30 mL water. The organic phase was separated, washed with water, dried, concentrated and subjected to silica flash column with 0 to 4% MeOH in DCM to isolate (2R,3R)-benzyl 2-methyl-3-(3-methyl-2-oxotetrahydropyrimidin-1(2H)-yl)piperidine-1-carboxylate (403) (350 mg, 93%) as a thick oil. It was dissolved in 100 mL MeOH, and with 10% Pd/C (0.5 g) it was hydrogenated at 40 psi on a Parr shaker for overnight. The mixture was filtered through celite, and the filtrate was concentrated in vacuo to afford 1-methyl-3-((2R,3R)-2-methylpiperidin-3-yl)tetrahydropyrimidin-2(1H)-one (404).

1-Methyl-3-((2R,3R)-2-methylpiperidin-3-yl)tetrahydropyrimidin-2(1H)-one (404, 120 mg, 0.55 mmol) was dissolved in 10 mL DMF. To it were added 3,5-dichloropyrazine-2-carbonitrile (175 mg, 1.0 mmol) and DIEA (350 μL, 2.0 mmol). The mixture was stirred at RT for 30 mM, diluted with 150 mL EtOAc, washed with water ×3, dried, concentrated in vacuo, and subjected to silica flash column using 0 to 3.5% MeOH in DCM to isolate 3-chloro-5-((2R,3R)-2-methyl-3-(3-methyl-2-oxotetrahydropyrimidin-1(2H)-yl)piperidin-1-yl)pyrazine-2-carbonitrile (405, 60 mg, 31% yield).

The mixture of 3-chloro-5-((2R,3R)-2-methyl-3-(3-methyl-2-oxotetrahydropyrimidin-1(2H)-yl)piperidin-1-yl)pyrazine-2-carbonitrile (405) (60 mg, 0.17 mmol), 4-(1-cyclopentylpiperidin-4-yl)aniline hydrochloride (304) (58 mg, 0.21 mmol), fine-powder cesium carbonate (230 mg, 0.68 mmol), Pd(OAc)₂(11 mg, 0.05 mmol), BINAP (31 mg, 0.05 mmol) in 15 mL dioxane was degassed with nitrogen stream for 3 min. It was then stirred in 115° C. bath in nitrogen atmosphere for 1 hour. The mixture was cooled to RT, diluted with 100 mL EtOAc, and filtered. The filtrate was concentrated in vacuo and subjected to silica flash column using 0 to 10% MeOH in chloroform to isolate 3-(4-(1-cyclopentylpiperidin-4-yl)phenylamino)-5-((2R,3R)-2-methyl-3-(3-methyl-2-oxotetrahydropyrimidin-1(2H)-yl)piperidin-1-yl)pyrazine-2-carbonitrile (406). It was dissolved in 10 mL MeOH and 2 mL DMSO. To it were added one NaOH solid bead (about 100 mg), Et₃N (60 μL), and then 0.5 mL 30% H₂O₂. The mixture was stirred at RT for 30 min, diluted with 10 mL MeCN, stirred for 5 min, and concentrated on rotavap. The residue was diluted with 150 mL EtOAc, washed with water ×3, dried, concentrated in vacuo, acidified with 0.2 mL TFA, and directly subjected to reverse phase prep HPLC using 5 mM HCl (aq) and neat MeCN as mobile phases to isolate 3-(4-(1-cyclopentylpiperidin-4-yl)phenylamino)-5-((2R,3R)-2-methyl-3-(3-methyl-2-oxotetrahydropyrimidin-1(2H)-yl)piperidin-1-yl)pyrazine-2-carboxamide (407) as HCl salt (58 mg, 59%). LC-MS (ESI): m/z (M+1) 575.8. UV: λ=268, 277, 306, 336, 372 nm. Proton NMR (CD₃OD): δ 7.64 (1H, s), 7.61 (2H, d, J=8.5 Hz), 7.20 (2H, d, J=8.5 Hz), 4.93 (1H, m), 4.56-4.30 (3H, m), 3.71 (2H, m), 3.55 (1H, m), 3.38 (3H, m), 3.13 (2H, m), 3.06 (1H, m), 2.97 (3H, s), 2.84 (1H, m), 2.25-1.65 (18H, m), 1.20 (3H, d, J=6.5 Hz) ppm.

Example 282

Synthesis of (R)-3-(4-(1-cyclopentylpiperidin-4-yl)phenylamino)-5-(3-(3-methyl-2-oxotetrahydropyrimidin-1(2H)-yl)piperidin-1-yl)pyrazine-2-carboxamide

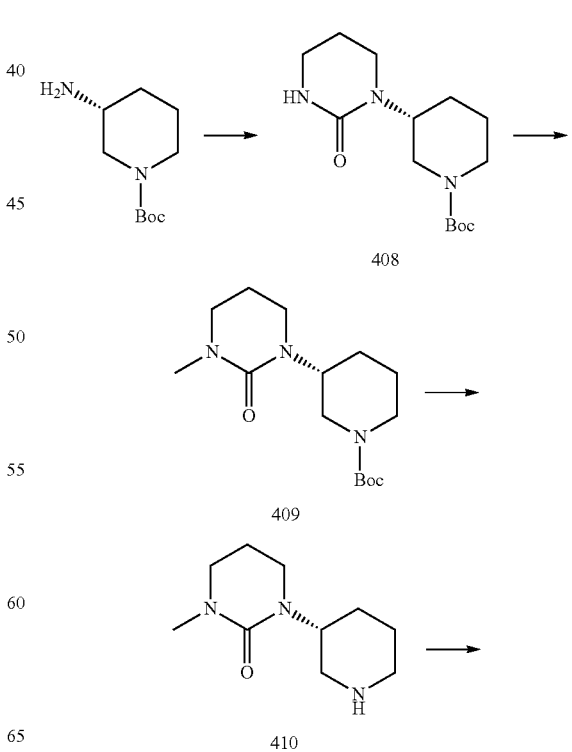

408

409

410

-continued

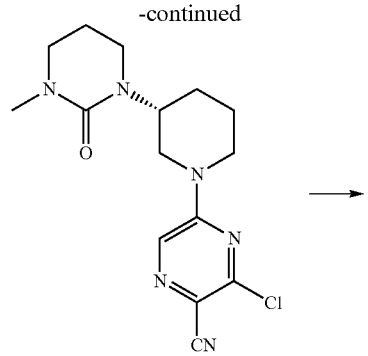

411

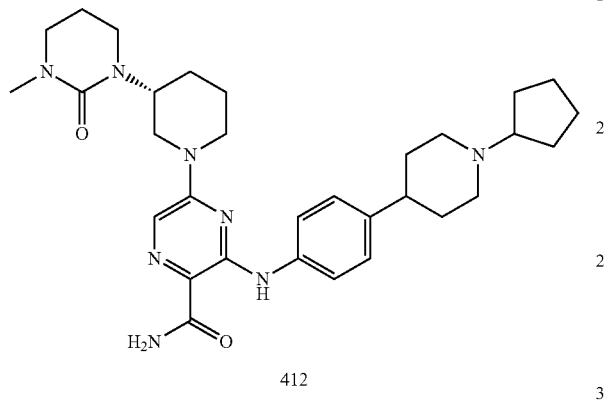

412

(R)-tert-Butyl 3-aminopiperidine-1-carboxylate (1.28 g, 6.4 mmol) was dissolved in 15 mL dry THF. To it was added 3-chloropropyl isocyante (660 µL, 6.4 mmol), and the mixture was stirred at RT for 3 hours. To it was added NaH (60% in mineral oil, 310 mg, 7.68 mmol) and the mixture was stirred for overnight. Another batch of NaH (310 mg, 7.68 mmol) was then added to drive the cyclization to completion, The mixture was diluted with 200 mL EtOAc, washed with water, dried, concentrated and subjected to silica flash column using 0 to 5% MeOh in DCM to isolate (R)-tert-butyl 3-(2-oxotetrahydropyrimidin-1(2H)-yl)piperidine-1-carboxylate (408) (1.53 g, 84%) as a white solid. It was dissolved in 50 mL dry THF. To the solution was added NaH (440 mg, 10.80 mmol), and the mixture was stirred for 15 min at RT. Then iodomethane (680 µL, 10.80 mmol) was added, and it was stirred at RT for overnight. It was diluted with 200 mL EtOAc and 30 mL water. The organic phase was separated, washed with water, dried, concentrated and subjected to silica flash column with 0 to 4% MeOH in DCM to isolate (R)-tert-butyl 3-(3-methyl-2-oxotetrahydropyrimidin-1(2H)-yl)piperidine-1-carboxylate (409) (1.52 g, 95%) as a white solid. It was treated with 20 mL commercial 4N HCl in dioxane at RT for 30 min to yield (R)-1-methyl-3-(piperidin-3-yl)tetrahydropyrimidin-2(1H)-one hydrochloride (410) (1.27 g) as a white solid after evaporation in vacuo to dryness.

The title compound, (R)-3-(4-(1-cyclopentylpiperidin-4-yl)phenylamino)-5-(3-(3-methyl-2-oxotetrahydropyrimidin-1(2H)-yl)piperidin-1-yl)pyrazine-2-carboxamide (412), was prepared by the same synthetic scheme illustrated for Example 281 using (R)-1-methyl-3-(piperidin-3-yl)tetrahydropyrimidin-2(1H)-one hydrochloride (410) and 4-(1-cyclopentylpiperidin-4-yl)aniline hydrochloride (304) via intermediates (R)-3-chloro-5-(3-(3-methyl-2-oxotetrahydropyrimidin-1(2H)-yl)piperidin-1-yl)pyrazine-2-carbonitrile (411). LC-MS (ESI): m/z (M+1) 561.9. UV: λ=268, 277, 305, 336, 372 nm. Proton NMR (CD₃OD): δ 7.64 (1H, s), 7.59 (2H, d, J=8.5 Hz), 7.18 (2H, d, J=8.5 Hz), 4.44 (1H, m), 4.35 (1H, m), 4.26 (1H, m), 3.72 (1H, s), 3.69 (1H, s), 3.54 (1H, m), 3.40-3.32 (4H, m), 3.14-3.06 (3H, m), 2.96 (3H, s), 2.92-2.82 (2H, m), 2.20 (2H, m), 2.12 (2H, m), 2.00-1.65 (14H, m) ppm.

Example 283

Synthesis of (R)-3-(4-(1-cyclopentyl-4-methylpiperidin-4-yl)phenylamino)-5-(3-(3-methyl-2-oxotetrahydropyrimidin-1(2H)-yl)piperidin-1-yl)pyrazine-2-carboxamide

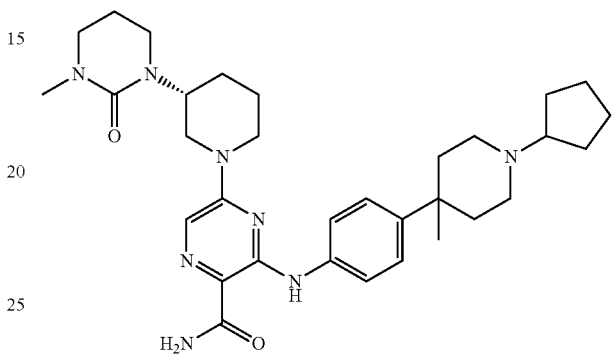

413

The title compound, (R)-3-(4-(1-cyclopentyl-4-methylpiperidin-4-yl)phenylamino)-5-(3-(3-methyl-2-oxotetrahydropyrimidin-1(2H)-yl)piperidin-1-yl)pyrazine-2-carboxamide (413), was prepared by the same synthetic scheme illustrated for Example 282 using (R)-3-chloro-5-(3-(3-methyl-2-oxotetrahydropyrimidin-1(2H)-yl)piperidin-1-yl)pyrazine-2-carbonitrile (411) and 4-(1-cyclopentyl-4-methylpiperidin-4-yl)aniline hydrochloride. LC-MS (ESI): m/z (M+1) 575.9. UV: λ=269, 277, 306, 336, 372 nm. Proton NMR (CD₃OD): δ 7.70-7.61 (3H, m), 7.34-7.31 (2H, m), 4.46 (1H, m), 4.38 (1H, m), 4.29 (1H, m), 3.67-3.50 (2H, m), 3.40-3.32 (4H, m), 3.10 (1H, m), 2.96 (3H, s), 2.93-2.82 (3H, m), 2.64 (1H, m), 2.24-1.62 (18H, m), 1.42-1.27 (3H, s) ppm.

Example 284

Synthesis of (R)-3-(4-(1-cyclopropylpiperidin-4-yl)phenylamino)-5-(3-(3-methyl-2-oxotetrahydropyrimidin-1(2H)-yl)piperidin-1-yl)pyrazine-2-carboxamide

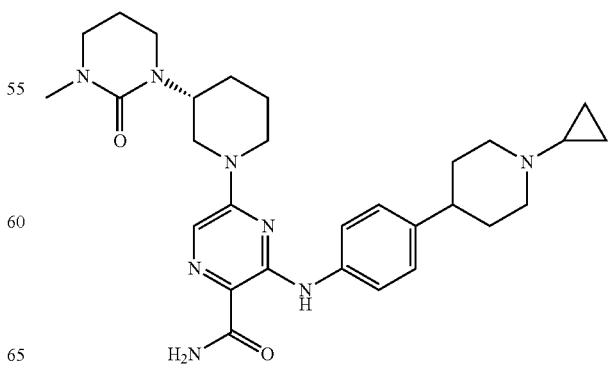

414

The title compound, (R)-3-(4-(1-cyclopropylpiperidin-4-yl)phenylamino)-5-(3-(3-methyl-2-oxotetrahydropyrimidin-1(2H)-yl)piperidin-1-yl)pyrazine-2-carboxamide (414), was prepared by the same synthetic scheme illustrated for Example 282 using (R)-3-chloro-5-(3-(3-methyl-2-oxotetrahydropyrimidin-1(2H)-yl)piperidin-1-yl)pyrazine-2-carbonitrile (411) and 4-(1-cyclopropylpiperidin-4-yl)aniline (322) hydrochloride. LC-MS (ESI): m/z (M+1) 533.7. UV: λ=269, 277, 305, 335, 372 nm. Proton NMR (CD$_3$OD): δ 7.64 (1H, s), 7.57 (2H, d, J=8.5 Hz), 7.17 (2H, d, J=8.5 Hz), 4.43 (1H, m), 4.33 (1H, m), 4.24 (1H, m), 3.76 (1H, s), 3.73 (1H, s), 3.48-3.32 (5H, m), 3.08 (1H, m), 2.95 (3H, s), 2.93-2.81 (3H, m), 2.10 (2H, m), 2.03-1.95 (4H, m), 1.90-1.85 (3H, m), 1.65 (1H, m), 1.11-0.98 (4H, m) ppm.

Example 285

Synthesis of (R)-3-(4-(1-cyclopropyl-4-methylpiperidin-4-yl)phenylamino)-5-(3-(3-methyl-2-oxotetrahydropyrimidin-1(2H)-yl)piperidin-1-yl)pyrazine-2-carboxamide

415

The title compound, (R)-3-(4-(1-cyclopropyl-4-methylpiperidin-4-yl)phenylamino)-5-(3-(3-methyl-2-oxotetrahydropyrimidin-1(2H)-yl)piperidin-1-yl)pyrazine-2-carboxamide (415), was prepared by the same synthetic scheme illustrated for Example 282 using (R)-3-chloro-5-(3-(3-methyl-2-oxotetrahydropyrimidin-1(2H)-yl)piperidin-1-yl)pyrazine-2-carbonitrile (411) and 4-(1-cyclopropyl-4-methylpiperidin-4-yl)aniline (342). LC-MS (ESI): m/z (M+1) 547.8. UV: λ=269, 277, 306, 336, 372 nm. Proton NMR (CD$_3$OD): δ 7.70-7.60 (3H, m), 7.35-7.31 (2H, m), 4.47-4.36 (2H, m), 4.29 (1H, m), 3.64-3.47 (3H, m), 3.37-3.32 (3H, m), 3.11-3.05 (2H, m), 2.96 (3H, s), 2.93 (1H, m), 2.70-2.62 (2H, m), 2.16 (2H, m), 2.00-1.85 (7H, m), 1.67 (1H, m), 1.44-1.26 (3H, s), 1.03-0.87 (4H, m) ppm.

Example 286

Preparation of 3-(4-(1-cyclopentylpiperidin-4-yl)phenylamino)-5-((3aR,7aR)-dihydro-1H-pyrrolo[3,2-b]pyridin-4(2H,5H,6H,7H,7aH)-yl)pyrazine-2-carboxamide

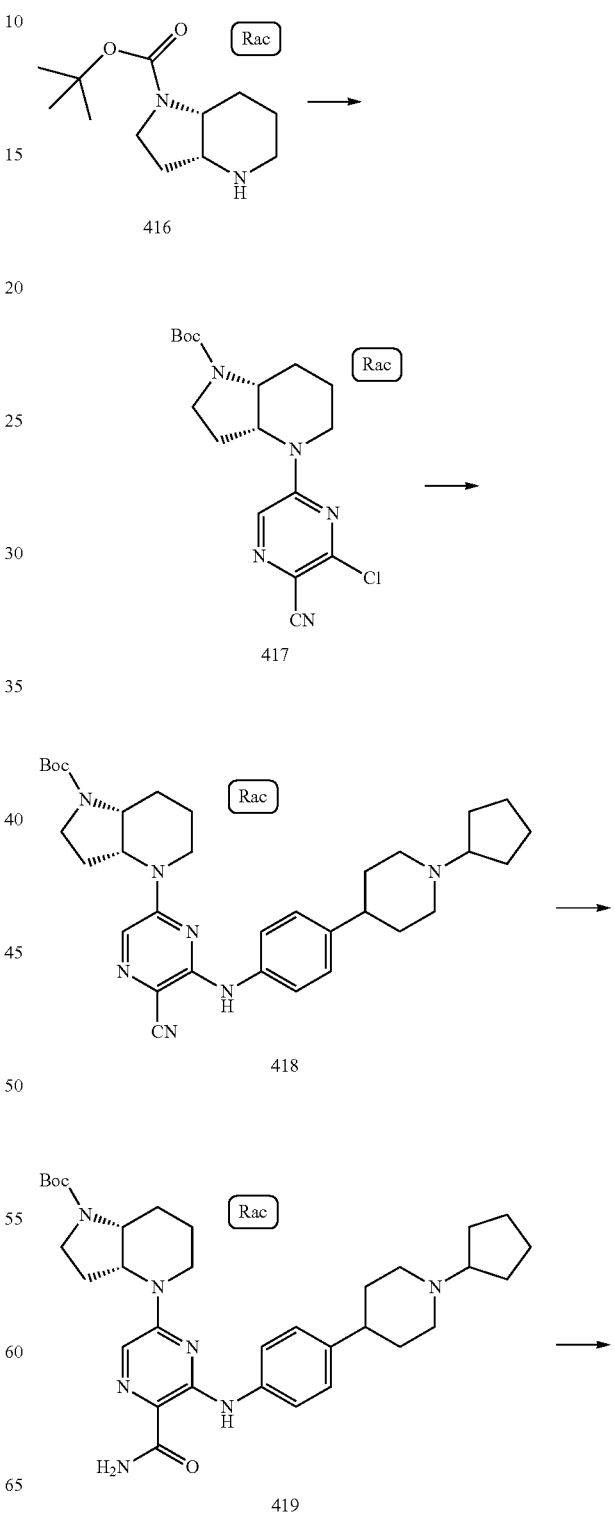

-continued

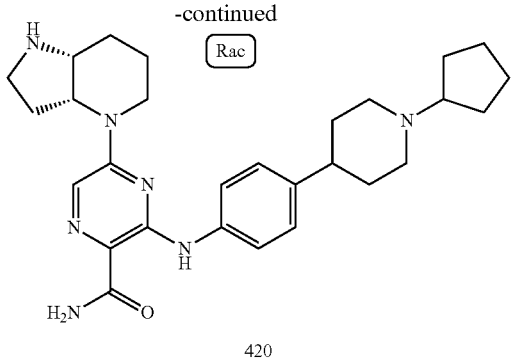

420

Commercial (3aR,7aR)-tert-butyl octahydro-1H-pyrrolo[3,2-b]pyridine-1-carboxylate (416, CAS: 1251010-63-5, 476 mg, 2.1 mmol) was dissolved in 15 mL DMF. To it were added 3,5-dichloropyrazine-2-carbonitrile (340 mg, 1.9 mmol) and DIEA (500 μL, 2.9 mmol). The mixture was stirred at RT for 3.5 hours, diluted with 100 mL EtOAc, washed with water ×3, dried, concentrated in vacuo, and subjected to silica flash column using 0 to 3% MeOH in DCM to isolate (3aR,7aR)-tert-butyl 4-(6-chloro-5-cyanopyrazin-2-yl)octahydro-1H-pyrrolo[3,2-b]pyridine-1-carboxylate (417, 670 mg, 88%) as a white solid.

The mixture of (3aR,7aR)-tert-butyl 4-(6-chloro-5-cyanopyrazin-2-yl)octahydro-1H-pyrrolo[3,2-b]pyridine-1-carboxylate (417) (400 mg, 1.10 mmol), 4-(1-cyclopentylpiperidin-4-yl)aniline hydrochloride (304) (340 mg, 1.21 mmol), fine-powder cesium carbonate (1.08 g, 3.30 mmol), Pd(OAc)$_2$ (74 mg, 0.33 mmol), BINAP (206 mg, 0.33 mmol) in 40 mL dioxane was degassed with nitrogen stream for 3 min. It was then stirred in 115° C. bath in nitrogen atmosphere for 1.5 hour. The mixture was cooled to RT, diluted with 150 mL EtOAc, and filtered. The filtrate was concentrated in vacuo and subjected to silica flash column using 0 to 6% MeOH in DCM to isolate (3aR,7aR)-tert-butyl 4-(5-cyano-6-(4-(1-cyclopentylpiperidin-4-yl)phenylamino)pyrazin-2-yl)octahydro-1H-pyrrolo[3,2-b]pyridine-1-carboxylate (418) (480 mg, 76%). It was dissolved in 25 mL MeOH and 2 mL DMSO. To it were added fine-powder Cs$_2$CO$_3$ (100 mg) and then 1 mL 30% H$_2$O$_2$. The mixture was stirred at RT for 1 hour, diluted with 10 mL MeCN, stirred for 5 min, and concentrated on rotavap. The residue was diluted with 150 mL EtOAc, washed with water ×2, concentrated in vacuo to give crude (3aR,7aR)-tert-butyl 4-(5-carbamoyl-6-(4-(1-cyclopentylpiperidin-4-yl)phenylamino)pyrazin-2-yl)octahydro-1H-pyrrolo[3,2-b]pyridine-1-carboxylate (419). It was treated with 1:1 TFA/DCM at RT for 5 min, concentrated in vacuo, and subjected to reverse phase prep HPLC using 5 mM HCl (aq) and neat MeCN as mobile phases to isolate 3-(4-(1-cyclopentylpiperidin-4-yl)phenylamino)-5-((3aR,7aR)-dihydro-1H-pyrrolo[3,2-b]pyridin-4(2H,5H,6H,7H,7aH)-yl)pyrazine-2-carboxamide (420) as HCl salt. LC-MS (ESI): m/z (M+1) 490.4. UV: λ=263, 272, 303, 334, 370 nm. Proton NMR (CD$_3$OD): δ 7.68 (1H, s), 7.57 (2H, d, J=8.5 Hz), 7.30 (2H, d, J=9.0 Hz), 5.16 (1H, m), 4.21 (1H, m), 3.85 (1H, m), 3.72 (2H, d, J=13.0 Hz), 3.58 (2H, m), 3.42 (1H, m), 3.12 (3H, m), 2.89 (1H, m), 2.35 (1H, m), 2.20 (2H, m), 2.14-1.71 (15H, m) ppm.

Example 287

Preparation of (3aR,7aR)-4-(5-carbamoyl-6-(4-(1-cyclopentylpiperidin-4-yl)phenylamino)pyrazin-2-yl)-N,N-dimethyloctahydro-1H-pyrrolo[3,2-b]pyridine-1-carboxamide

421

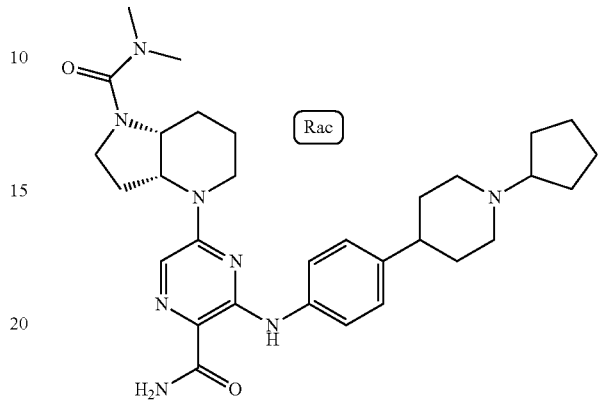

3-(4-(1-Cyclopentylpiperidin-4-yl)phenylamino)-5-((3aR,7aR)-dihydro-1H-pyrrolo[3,2-b]pyridin-4(2H,5H,6H,7H,7aH)-yl)pyrazine-2-carboxamide (420) (82 mg, 0.16 mmol) was dissolved in 3 mL NMP. To it were added DIEA (290 μL, 1.68 mmol) and then dimethylcarbamoyl chloride (62 μL, 0.67 mmol). The mixture was stirred at RT for 2 hours, quenched with 0.5 mL TFA, and subjected to reverse phase prep HPLC using 5 mM HCl (aq) and neat MeCN as mobile phases to isolate (3aR,7aR)-4-(5-carbamoyl-6-(4-(1-cyclopentylpiperidin-4-yl)phenylamino)pyrazin-2-yl)-N,N-dimethyloctahydro-1H-pyrrolo[3,2-b]pyridine-1-carboxamide (421) as HCl salt (61 mg, 64%). LC-MS (ESI): m/z (M+1) 561.9. UV: λ=267, 275, 304, 334, 372 nm. Proton NMR (CD$_3$OD): δ 7.64 (1H, m), 7.59 (2H, d, J=7.5 Hz), 7.20 (2H, d, J=8.0 Hz), 4.18 (2H, m), 3.71 (3H, m), 3.61-3.56 (2H, m), 3.44 (1H, m), 3.13 (3H, m), 2.90 (7H, s), 2.21 (3H, m), 2.15 (2H, m), 2.07 (1H, m), 1.95 (3H, m), 1.87 (3H, m), 1.73 (4H, m), 1.61 (2H, m) ppm.

Example 288

Preparation of 3-(4-(1-cyclopentylpiperidin-4-yl)phenylamino)-5-((3aR,7aR)-1-(cyclopropanecarbonyl)dihydro-1H-pyrrolo[3,2-b]pyridin-4(2H,5H,6H,7H,7aH)-yl)pyrazine-2-carboxamide

422

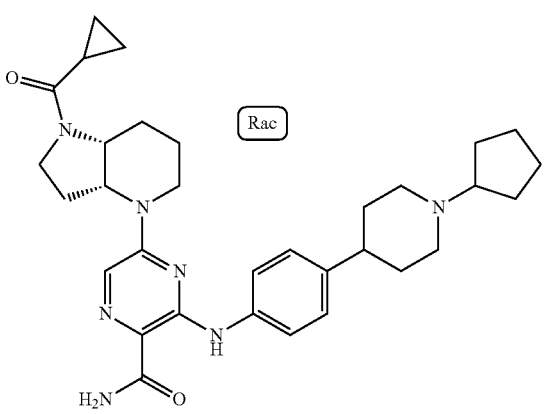

3-(4-(1-Cyclopentylpiperidin-4-yl)phenylamino)-5-((3aR,7aR)-dihydro-1H-pyrrolo[3,2-b]pyridin-4(2H,5H,6H,7H,7aH)-yl)pyrazine-2-carboxamide (420) (82 mg, 0.16 mmol) was dissolved in 3 mL NMP. To it were added DIEA (290 µL, 1.68 mmol) and then cyclopropanecarbonyl chloride (61 µL, 0.67 mmol). The mixture was stirred at RT for 2 hours, quenched with 0.5 mL TFA, and subjected to reverse phase prep HPLC using 5 mM HCl (aq) and neat MeCN as mobile phases to isolate 3-(4-(1-cyclopentylpiperidin-4-yl)phenylamino)-5-((3aR,7aR)-1-(cyclopropanecarbonyl)dihydro-1H-pyrrolo[3,2-b]pyridin-4(2H,5H,6H,7H,7aH)-yl)pyrazine-2-carboxamide (422) as HCl salt (58 mg, 62%). LC-MS (ESI): m/z (M+1) 558.8. UV: λ=266, 274, 304, 334, 372 nm.

Example 289

Preparation of (4aR,8aR)-5-(5-carbamoyl-6-(4-(1-cyclopentylpiperidin-4-yl)phenylamino)pyrazin-2-yl)-N,N-dimethyloctahydro-1,5-naphthyridine-1(2H)-carboxamide

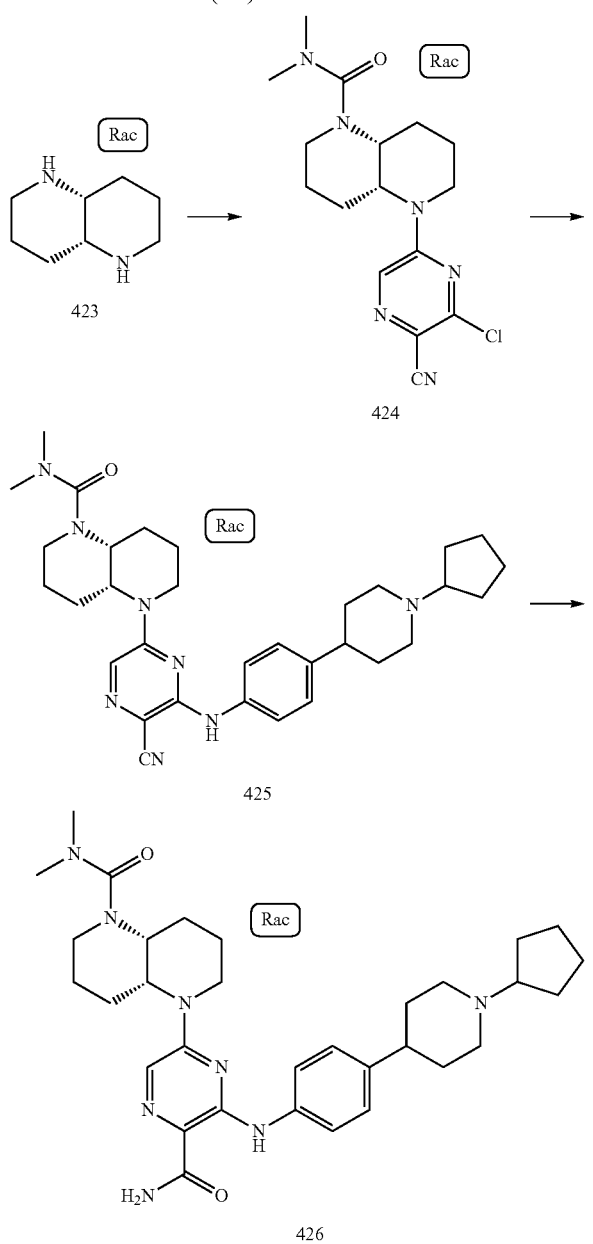

Commercial (4aR,8aR)-decahydro-1,5-naphthyridine (423, 120 mg, 0.86 mmol) was dissolved in 2 mL NMP. To it were added DIEA (150 µL, 0.86 mmol) and then 3,5-dichloropyrazine-2-carbonitrile (150 mg, 0.86 mmol). The mixture was stirred at RT for 1.5 hour, and to it were added DIEA (450 µL, 2.58 mmol) and dimethylcarbamoyl chloride (240 µL, 2.58 mmol). The mixture was stirred at RT for overnight. It was diluted with 100 mL EtOAc, washed with water ×2, dried, concentrated in vacuo, and subjected to silica flash column using 0 to 3% MeOH in DCM to isolate (4aR,8aR)-5-(6-chloro-5-cyanopyrazin-2-yl)-N,N-dimethyloctahydro-1,5-naphthyridine-1(2H)-carboxamide (424, 56 mg, 19%). It was mixed with 4-(1-cyclopentylpiperidin-4-yl)aniline hydrochloride (304) (90 mg, 0.32 mmol), fine-powder cesium carbonate (210 mg, 0.64 mmol), Pd(OAc)$_2$ (11 mg, 0.05 mmol), BINAP (31 mg, 0.05 mmol) in 15 mL dioxane. The mixture was degassed with nitrogen stream for 3 min. It was then stirred in 115° C. bath in nitrogen atmosphere for 1.5 hour. The mixture was cooled to RT, diluted with 100 mL EtOAc, and filtered. The filtrate was concentrated in vacuo and subjected to silica flash column using 0 to 11% MeOH in DCM to isolate (4aR,8aR)-5-(5-cyano-6-(4-(1-cyclopentylpiperidin-4-yl)phenylamino)pyrazin-2-yl)-N,N-dimethyloctahydro-1,5-naphthyridine-1(2H)-carboxamide (425). It was dissolved in 10 mL MeOH and 2 mL DMSO. To it were added one NaOH solid bead (about 100 mg), Et$_3$N (60 µL) and then 0.5 mL 30% H$_2$O$_2$. The mixture was stirred at RT for 30 min, diluted with 10 mL MeCN, stirred for 5 min, and concentrated, acidified with 0.3 mL TFA, and subjected to reverse phase prep HPLC using 5 mM HCl (aq) and neat MeCN as mobile phases to isolate (4aR,8aR)-5-(5-carbamoyl-6-(4-(1-cyclopentylpiperidin-4-yl)phenylamino)pyrazin-2-yl)-N,N-dimethyloctahydro-1,5-naphthyridine-1(2H)-carboxamide (426) as HCl salt (23 mg). LC-MS (ESI): m/z (M+1) 575.8. UV: λ=269, 276, 305, 335, 372 nm.

Example 290

Synthesis of 3-(4-(1-cyclopentylpiperidin-4-yl)phenylamino)-5-((3R,4R)-3-(3,3-dimethylureido)-4-methylpiperidin-1-yl)pyrazine-2-carboxamide

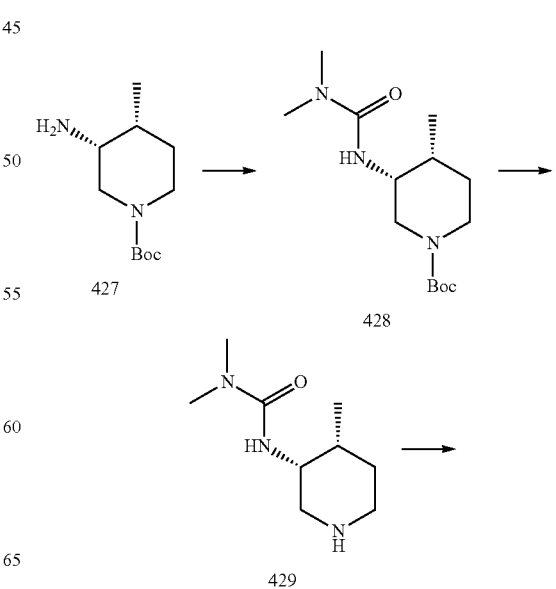

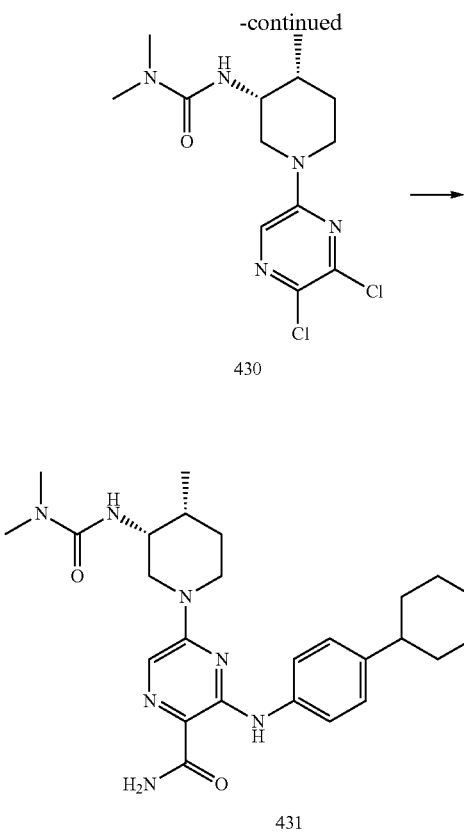

430

431

Commercial (3R,4R)-tert-butyl 3-amino-4-methylpiperidine-1-carboxylate (427, 250 mg, 1.16 mmol) was dissolved in 10 mL dry THF. To it were added DIEA (610 µL, 3.50 mmol) and dimethylcarbamoyl chloride (214 µL, 2.32 mmol). The mixture was stirred at RT for 2 hours, diluted with 100 mL EtOAc, washed with water ×3, dried, concentrated, and subjected to silica flash column using 0 to 5% MeOh in DCM to isolate (3R,4R)-tert-butyl 3-(3,3-dimethylureido)-4-methylpiperidine-1-carboxylate (428, 350 mg) in quantitative yield as a white solid. It was treated with 15 mL commercial 4N HCkl in dioxane at RT for 40 min to yield 1,1-dimethyl-3-((3R,4R)-4-methylpiperidin-3-yl)urea hydrochloride (429).

The title compound, 3-(4-(1-cyclopentylpiperidin-4-yl)phenylamino)-5-((3R,4R)-3-(3,3-dimethylureido)-4-methylpiperidin-1-yl)pyrazine-2-carboxamide (431), was prepared by the same synthetic scheme illustrated for Example 282 using 1,1-dimethyl-34(3R,4R)-4-methylpiperidin-3-yl)urea hydrochloride (429) and 4-(1-cyclopentylpiperidin-4-yl)aniline hydrochloride (304) via intermediate 3-((3R,4R)-1-(6-chloro-5-cyanopyrazin-2-yl)-4-methylpiperidin-3-yl)-1,1-dimethylurea (430). LC-MS (ESI): m/z (M+1) 549.9. UV: λ=268, 278, 306, 336, 373 nm. Proton NMR (CD₃OD): δ 7.61 (1H, s), 7.58 (2H, d, J=8.5 Hz), 7.22 (2H, d, J=8.5 Hz), 4.61 (1H, m), 4.33 (1H, m), 4.07 (1H, m), 3.73 (1H, s), 3.71 (1H, s), 3.56 (1H, m), 3.20-3.09 (4H m), 2.87 (1H, m), 2.70 (6H, s), 2.23 (2H, m), 2.15 (2H, m), 2.08-1.61 (11H, m), 0.99 (3H, d, J=6.5 Hz) ppm.

Example 291

Synthesis of 3-(4-(1-cyclopentylpiperidin-4-yl)phenylamino)-5-((3aR,7aR)-tetrahydro-1H-pyrrolo[2,3-c]pyridin-6(2H,7H,7aH)-yl)pyrazine-2-carboxamide

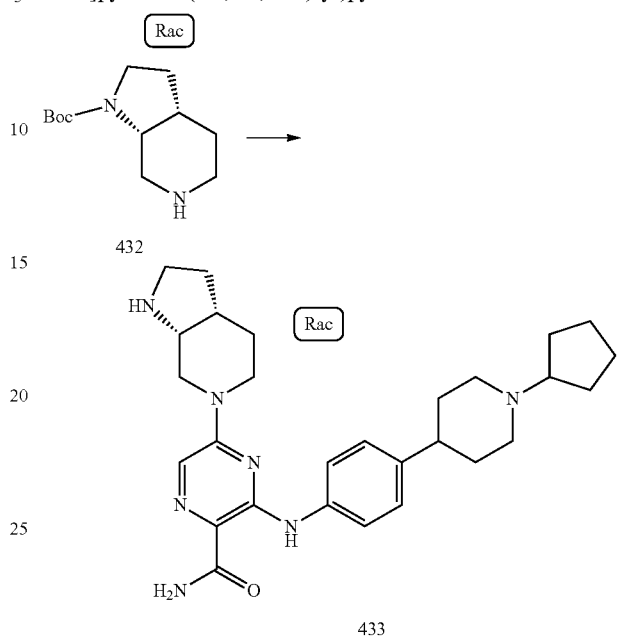

432

433

The title compound, 3-(4-(1-cyclopentylpiperidin-4-yl)phenylamino)-5-((3aR,7aR)-tetrahydro-1H-pyrrolo[2,3-c]pyridin-6(2H,7H,7aH)-yl)pyrazine-2-carboxamide (433), was prepared by the same synthetic scheme illustrated for Example 286 using commercial racemic (3aS,7aR)-tert-butyl octahydro-1H-pyrrolo[2,3-c]pyridine-1-carboxylate (432). LC-MS (ESI): m/z (M+1) 490.4. UV: λ=262, 272, 303, 334, 370 nm. Proton NMR (CD₃OD): δ 7.67 (1H, s), 7.59 (2H, d, J=8.5 Hz), 7.28 (2H, d, J=8.5 Hz), 4.50 (1H, dd, J=14.5; 8.0 Hz), 4.12 (1H, dt, J=13.0; 5.0 Hz), 3.87 (1H, m), 3.78 (1H, dd, J=15.0; 4.0 Hz), 3.73 (1H, s), 3.71 (1H, s), 3.56 (1H, m), 3.45-3.32 (3H, m), 3.14 (2H, m), 2.88 (1H, m), 2.66 (1H, m), 2.29 (1H, m), 2.21 (2H, m), 2.14-1.96 (6H, m), 1.88 (2H, m), 1.81 (2H, m), 1.72 (2H, m), 1.62 (1H, m) ppm.

Example 292

Synthesis of (3aS,7aR)-6-(5-carbamoyl-6-(4-(1-cyclopentylpiperidin-4-yl)phenylamino)pyrazin-2-yl)-N,N-dimethyloctahydro-1H-pyrrolo[2,3-c]pyridine-1-carboxamide

434

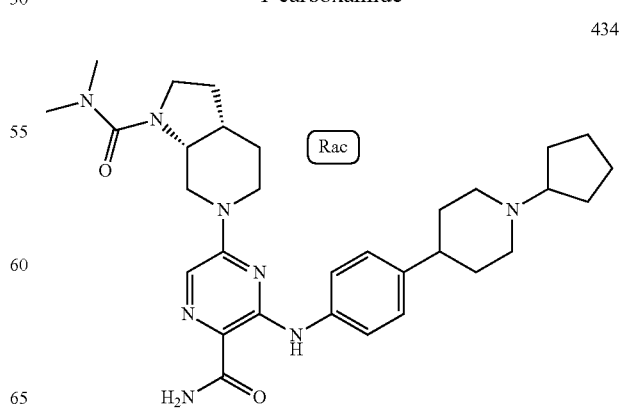

The title compound, (3aS,7aR)-6-(5-carbamoyl-6-(4-(1-cyclopentylpiperidin-4-yl)phenylamino)pyrazin-2-yl)-N,N-dimethyloctahydro-1H-pyrrolo[2,3-c]pyridine-1-carboxamide (434), was prepared by the same synthetic scheme illustrated for Example 287 using racemic 3-(4-(1-cyclopentylpiperidin-4-yl)phenylamino)-5-((3aR,7aR)-tetrahydro-1H-pyrrolo[2,3-c]pyridin-6(2H,7H,7aH)-yl)pyrazine-2-carboxamide (433). LC-MS (ESI): m/z (M+1) 561.9. UV: λ=268, 279, 307, 336, 373 nm. Proton NMR (CD$_3$OD): δ 7.60 (2H, d, J=8.5 Hz), 7.50 (1H, s), 7.24 (2H, d, J=8.5 Hz), 4.75 (1H, m), 4.35 (1H, m), 3.96 (1H, m), 3.73 (1H, s), 3.70 (1H, s), 3.56 (1H, m), 3.43 (1H, m), 3.15-3.12 (4H, m), 2.86 (1H, m), 2.53 (7H, s), 2.25-2.14 (4H, m), 1.99-1.87 (6H, m), 1.78-1.72 (5H, m), 1.62 (1H, m) ppm.

Example 293

Synthesis of 3-(4-(1-cyclopentylpiperidin-4-yl)phenylamino)-5-((3aS,7aR)-1-(cyclopropanecarbonyl)tetrahydro-1H-pyrrolo[2,3-c]pyridin-6(2H,7H,7aH)-yl)pyrazine-2-carboxamide

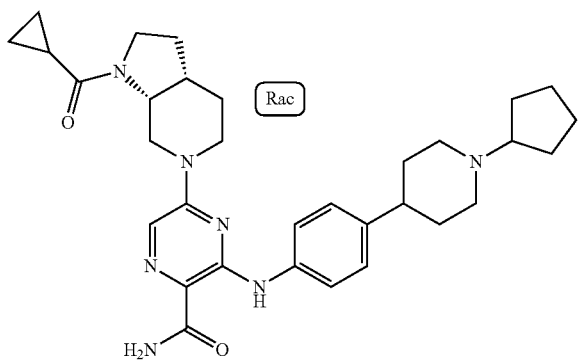

435

The title compound, 3-(4-(1-cyclopentylpiperidin-4-yl)phenylamino)-5-((3aS,7aR)-1-(cyclopropanecarbonyl)tetrahydro-1H-pyrrolo[2,3-c]pyridin-6(2H,7H,7aH)-yl)pyrazine-2-carboxamide (435), was prepared by the same synthetic scheme illustrated for Example 288 using racemic 3-(4-(1-cyclopentylpiperidin-4-yl)phenylamino)-5-((3aR,7aR)-tetrahydro-1H-pyrrolo[2,3-c]pyridin-6(2H,7H,7aH)-yl)pyrazine-2-carboxamide (433). LC-MS (ESI): m/z (M+1) 558.8. UV: λ=267, 277, 306, 336, 372 nm.

Example 294

Synthesis of (R)-5-(3-aminopiperidin-1-yl)-3-(4-(1-cyclopentylpiperidin-4-yl)phenylamino)pyrazine-2-carboxamide

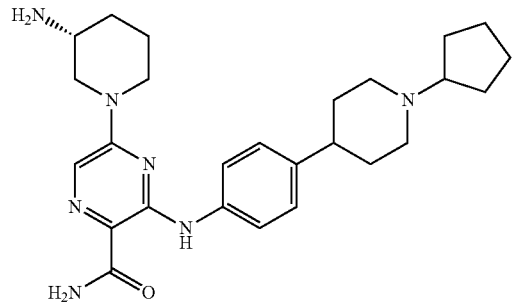

436

The title compound, (R)-5-(3-aminopiperidin-1-yl)-3-(4-(1-cyclopentylpiperidin-4-yl)phenylamino)pyrazine-2-carboxamide (436), was prepared by the same synthetic scheme illustrated for (R)-5-(3-aminopiperidin-1-yl)-3-(4-(1-methylpiperidin-4-yl)phenylamino)pyrazine-2-carboxamide (206) hydrochloride, shown in Example 165 using 4-(1-cyclopentylpiperidin-4-yl)aniline hydrochloride (304). LC-MS (ESI): m/z (M+1) 464.3. UV: λ=263, 273, 304, 335, 372 nm. Proton NMR (CD$_3$OD): δ 7.68 (1H, s), 7.59 (2H, d, J=9.0 Hz), 7.26 (2H, d, J=8.5 Hz), 4.25 (1H, dd, J=13.0; 3.0 Hz), 4.01 (1H, dt, J=9.0; 4.5 Hz), 3.72 (2H, d, J=10.0 Hz), 3.58-3.54 (2H, m), 3.45 (2H, m), 3.14 (2H, m), 2.89 (1H, m), 2.22-1.71 (16H, m) ppm.

Example 295

Synthesis of (R)-3-(4-(1-cyclopentylpiperidin-4-yl)phenylamino)-5-(3-formamidopiperidin-1-yl)pyrazine-2-carboxamide

437

(R)-5-(3-Aminopiperidin-1-yl)-3-(4-(1-cyclopentylpiperidin-4-yl)phenylamino)pyrazine-2-carboxamide (436) (50 mg, 0.1 mmol) was dissolved in 4 mL DMF. To it were added formic acid (20 μL, 0.5 mmol), DIEA (180 μL, 1.0 mmol) and then PyBOP (105 mg, 0.2 mmol). The mixture was stirred at RT for 2 hours, quenched with 0.3 mL TFA, and directly subjected to reverse phase preparative HPLC using 5 mM HCl (aq) and nest MeCN to isolate the title compound, (R)-3-(4-(1-cyclopentylpiperidin-4-yl)phenylamino)-5-(3-formamidopiperidin-1-yl)pyrazine-2-carboxamide (437), as HCl salt (24 mg). LC-MS (ESI): m/z (M+1) 492.7. UV: λ=267, 276, 305, 335, 372 nm. Proton NMR (CD$_3$OD): δ 8.06 (1H, s), 7.65 (1H, s), 7.58 (2H, d, J=8.5 Hz), 7.21 (2H, d, J=8.5 Hz), 4.19 (1H, m), 4.01 (1H, m), 3.93 (1H, m), 3.71 (2H, d, J=12.0 Hz), 3.54 (1H, m), 3.46 (1H, m), 3.38 (1H, m), 3.12 (2H, m), 2.86 (1H, m), 2.22-1.66 (16H, m) ppm.

Example 296

Synthesis of (R)-3-(4-(1-cyclopentylpiperidin-4-yl)phenylamino)-5-(3-propionamidopiperidin-1-yl)pyrazine-2-carboxamide

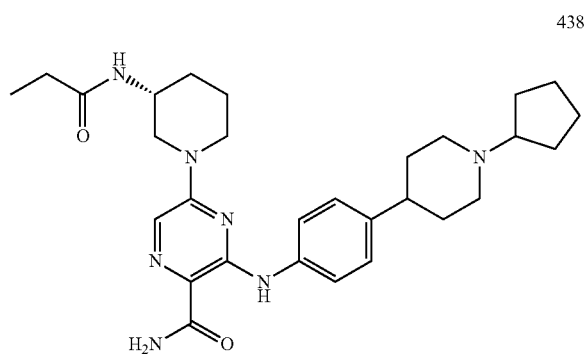 [SMILES: CCC(=O)N[C@@H]1CCCN(c2cnc(C(N)=O)c(Nc3ccc(C4CCN(C5CCCC5)CC4)cc3)n2)C1]

438

(R)-5-(3-Aminopiperidin-1-yl)-3-(4-(1-cyclopentylpiperidin-4-yl)phenylamino)pyrazine-2-carboxamide (436) (40 mg, 0.075 mmol) was dissolved in 3 mL NMP. To it were added DIEA (80 μL, 0.45 mmol) and then propionyl chloride (20 μL, 0.23 mmol). The mixture was stirred at RT for 30 min, quenched with 0.3 mL TFA, and directly subjected to reverse phase preparative HPLC using 5 mM HCl (aq) and nest MeCN to isolate the title compound, (R)-3-(4-(1-cyclopentylpiperidin-4-yl)phenylamino)-5-(3-propionamidopiperidin-1-yl)pyrazine-2-carboxamide (438), as HCl salt (23 mg). LC-MS (ESI): m/z (M+1) 520.6. UV: λ=267, 276, 305, 335, 372 nm. Proton NMR (CD$_3$OD): δ 7.62 (1H, s), 7.59 (2H, d, J=8.5 Hz), 7.21 (2H, d, J=8.5 Hz), 4.19 (1H, m), 4.01 (1H, m), 3.91 (1H, m), 3.72 (2H, d, J=12.0 Hz), 3.55 (1H, m), 3.42 (1H, m), 3.38 (1H, m), 3.12 (2H, m), 2.86 (1H, m), 2.22-1.64 (18H, m), 1.12 (3H, t, J=7.5 Hz) ppm.

Example 297

Synthesis of (R)-3-(4-(1-cyclopentylpiperidin-4-yl)phenylamino)-5-(3-(3-ethyl-3-methylureido)piperidin-1-yl)pyrazine-2-carboxamide

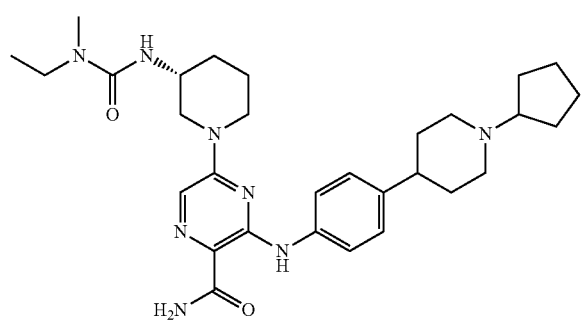

439

The title compound, (R)-3-(4-(1-cyclopentylpiperidin-4-yl)phenylamino)-5-(3-(3-ethyl-3-methylureido)piperidin-1-yl)pyrazine-2-carboxamide (436), was prepared by the same synthetic scheme illustrated for Example 296 using N-ethyl-N-methylcarbamoyl chloride. LC-MS (ESI): m/z (M+1) 549.6. UV: λ=268, 277, 306, 336, 373 nm. Proton NMR (CD$_3$OD): δ 7.65 (1H, s), 7.61 (2H, d, J=9.0 Hz), 7.21 (2H, d, J=8.5 Hz), 4.28 (1H, m), 4.19 (1H, m), 3.78 (1H, m), 3.71 (2H, d, J=12.5 Hz), 3.56 (1H, m), 3.44 (1H, m), 3.26-3.16 (3H, m), 3.12 (2H, m), 2.86 (1H, m), 2.84 (3H, s), 2.24-1.63 (18H, m), 1.08 (3H, t, J=7.0 Hz) ppm.

Example 298

Synthesis of (R)-ethyl 1-(5-carbamoyl-6-(4-(1-cyclopentylpiperidin-4-yl)phenylamino)pyrazin-2-yl)piperidin-3-ylcarbamate

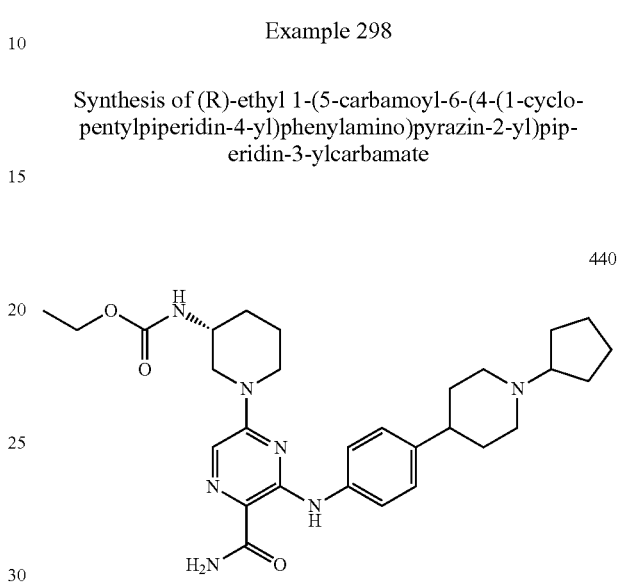

440

The title compound, (R)-ethyl 1-(5-carbamoyl-6-(4-(1-cyclopentylpiperidin-4-yl)phenylamino)pyrazin-2-yl)piperidin-3-ylcarbamate (440), was prepared by the same synthetic scheme illustrated for Example 296 using ethyl chloroformate. LC-MS (ESI): m/z (M+1) 536.8. UV: λ=267, 276, 305, 335, 373 nm.

Example 299

Synthesis of (R)-3-(4-(1-cyclopentylpiperidin-4-yl)phenylamino)-5-(3-(cyclopropanecarboxamido)piperidin-1-yl)pyrazine-2-carboxamide

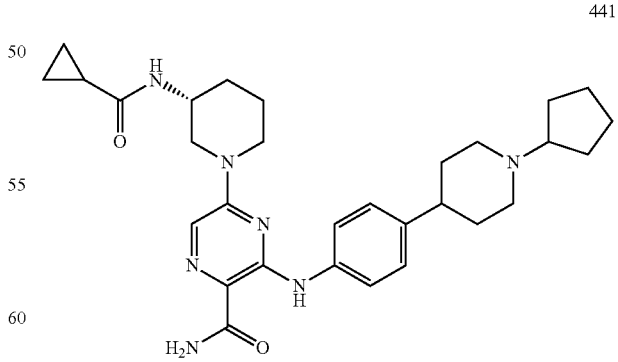

441

The title compound, (R)-3-(4-(1-cyclopentylpiperidin-4-yl)phenylamino)-5-(3-(cyclopropanecarboxamido)piperidin-1-yl)pyrazine-2-carboxamide (441), was prepared by the same synthetic scheme illustrated for Example 296 using cyclopropanecarbonyl chloride. LC-MS (ESI): m/z (M+1) 532.8. UV: λ=267, 277, 306, 336, 372 nm.

Example 300

Synthesis of (R)-3-(4-(1-cyclopentylpiperidin-4-yl)phenylamino)-5-(3-(methylsulfonamido)piperidin-1-yl)pyrazine-2-carboxamide

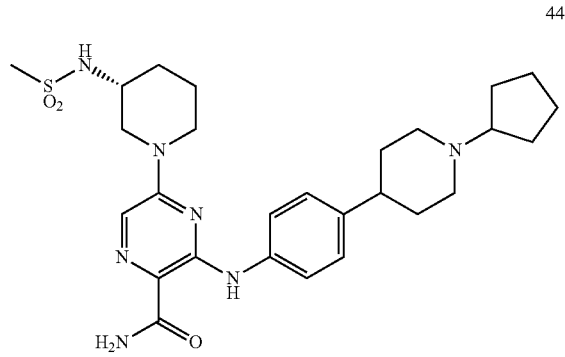

442

The title compound, (R)-3-(4-(1-cyclopentylpiperidin-4-yl)phenylamino)-5-(3-(methylsulfonamido)piperidin-1-yl)pyrazine-2-carboxamide (442), was prepared by the same synthetic scheme illustrated for Example 296 using methanesulfonyl chloride. LC-MS (ESI): m/z (M+1) 542.9. UV: λ=266, 275, 304, 335, 372 nm. Proton NMR (CD$_3$OD): δ 7.63 (1H, s), 7.60 (2H, d, J=9.0 Hz), 7.24 (2H, d, J=8.5 Hz), 4.55 (1H, m), 4.09 (1H, m), 3.70 (2H, d, J=12.5 Hz), 3.55 (1H, m), 3.43 (1H, m), 3.20 (1H, m), 3.14-3.06 (3H, m), 2.93 (3H, s), 2.86 (1H, m), 2.24-1.61 918H, m) ppm.

Example 301

Synthesis of (R)-3-(4-(1-cyclopentylpiperidin-4-yl)phenylamino)-5-(3-(ethylsulfonamido)piperidin-1-yl)pyrazine-2-carboxamide

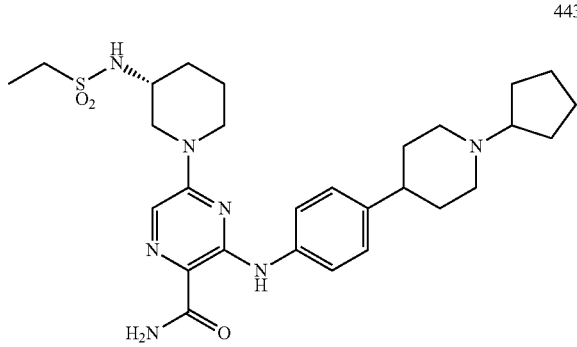 [SMILES: CCS(=O)(=O)N[C@@H]1CCCN(c2cnc(C(N)=O)c(Nc3ccc(C4CCN(C5CCCC5)CC4)cc3)n2)C1]

443

The title compound, (R)-3-(4-(1-cyclopentylpiperidin-4-yl)phenylamino)-5-(3-(ethylsulfonamido)piperidin-1-yl)pyrazine-2-carboxamide (443), was prepared by the same synthetic scheme illustrated for Example 296 using ethanesulfonyl chloride. LC-MS (ESI): m/z (M+1) 556.9. UV: λ=266, 276, 305, 335, 372 nm.

Example 302

Synthesis of (R)-3-(4-(1-cyclopentylpiperidin-4-yl)phenylamino)-5-(3-(N,N-dimethylsulfamoylamino)piperidin-1-yl)pyrazine-2-carboxamide

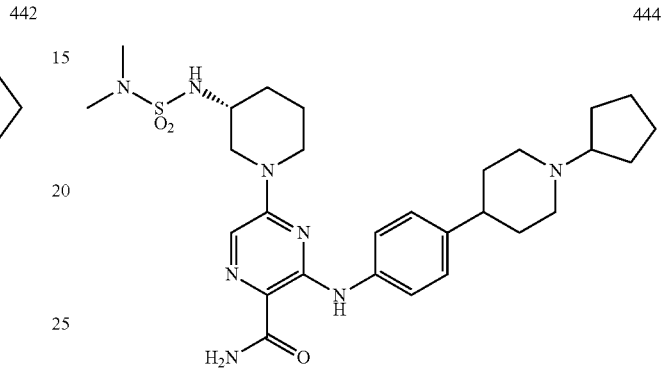

444

The title compound, (R)-3-(4-(1-cyclopentylpiperidin-4-yl)phenylamino)-5-(3-(N,N-dimethylsulfamoylamino)piperidin-1-yl)pyrazine-2-carboxamide (444), was prepared by the same synthetic scheme illustrated for Example 296 using dimethylsulfamoyl chloride. LC-MS (ESI): m/z (M+1) 571.8. UV: λ=266, 276, 305, 335, 373 nm.

Example 303

Synthesis of (R)-5-(3-benzamidopiperidin-1-yl)-3-(4-(1-cyclopentylpiperidin-4-yl)phenylamino)pyrazine-2-carboxamide

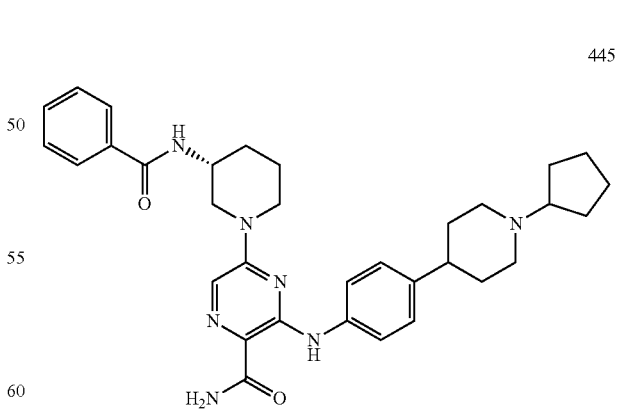

445

The title compound, (R)-5-(3-benzamidopiperidin-1-yl)-3-(4-(1-cyclopentylpiperidin-4-yl)phenylamino)pyrazine-2-carboxamide (445), was prepared by the same synthetic scheme illustrated for Example 296 using benzoyl chloride. LC-MS (ESI): m/z (M+1) 568.9. UV: λ=267, 276, 305, 335, 372 nm.

Example 304

Synthesis of (R)-3-(4-(1-cyclopentylpiperidin-4-yl)phenylamino)-5-(3-(nicotinamido)piperidin-1-yl)pyrazine-2-carboxamide

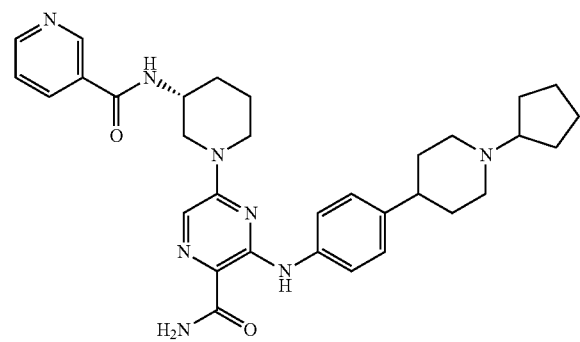

446

The title compound, (R)-3-(4-(1-cyclopentylpiperidin-4-yl)phenylamino)-5-(3-(nicotinamido)piperidin-1-yl)pyrazine-2-carboxamide (446), was prepared by the same synthetic scheme illustrated for Example 295 using nicotinic acid. LC-MS (ESI): m/z (M+1) 569.6. UV: λ=265, 277, 305, 336, 373 nm. Proton NMR (CD$_3$OD): δ 9.13 (1H, s), 8.91 (1H, d, J=5.5 Hz), 8.74 (1H, d, J=8.0 Hz), 8.03 (1H, dd, J=8.0; 5.5 Hz), 7.67 (1H, s), 7.58 (2H, d, J=8.5 Hz), 7.19 (2H, d, J=8.5 Hz), 4.35 (1H, dd, J=13.0; 3.5 Hz), 4.17 (1H, m), 4.13 (1H, m), 3.69 (2H, d, J=12.5 Hz), 3.57-3.47 (2H, m), 3.42 (1H, m), 3.11 (2H, td, J=12.5; 2.5 Hz), 2.84 (1H, tt, J=12.5; 3.5 Hz), 2.23-1.71 (18H, m) ppm.

Example 305

Synthesis of (R)-3-(4-(1-cyclopentylpiperidin-4-yl)phenylamino)-5-(3-(5-fluoronicotinamido)piperidin-1-yl)pyrazine-2-carboxamide

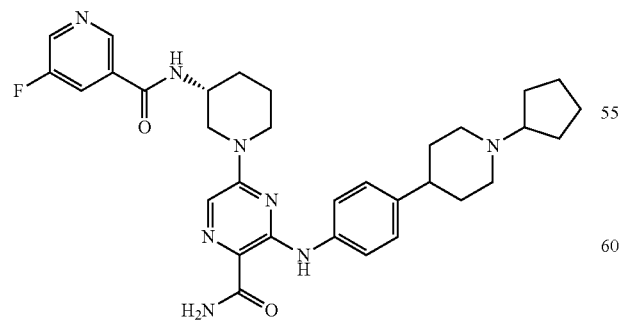

447

The title compound, (R)-3-(4-(1-cyclopentylpiperidin-4-yl)phenylamino)-5-(3-(5-fluoronicotinamido)piperidin-1-yl)pyrazine-2-carboxamide (447), was prepared by the same synthetic scheme illustrated for Example 295 using 5-fluoronicotinic acid. LC-MS (ESI): m/z (M+1) 587.9. UV: λ=268, 278, 305, 336, 373 nm. Proton NMR (CD$_3$OD): δ 8.85 (1H, s), 8.71 (1H, d, J=3.0 Hz), 8.08 (1H, m), 7.67 (1H, s), 7.58 (2H, d, J=8.5 Hz), 7.18 (2H, d, J=8.5 Hz), 4.39 (1H, dd, J=13.0; 3.5 Hz), 4.16 (1H, m), 4.12 (1H, m), 3.69 (2H, d, J=11.5 Hz), 3.54 (1H, m), 3.46-3.37 (2H, m), 3.11 (2H, td, J=12.5; 2.5 Hz), 2.82 (1H, tt, J=12.5; 3.5 Hz), 2.25-1.70 (18H, m) ppm.

Example 306

Synthesis of (R)-3-(4-(1-cyclopentylpiperidin-4-yl)phenylamino)-5-(3-(2-oxopyrrolidin-1-yl)piperidin-1-yl)pyrazine-2-carboxamide

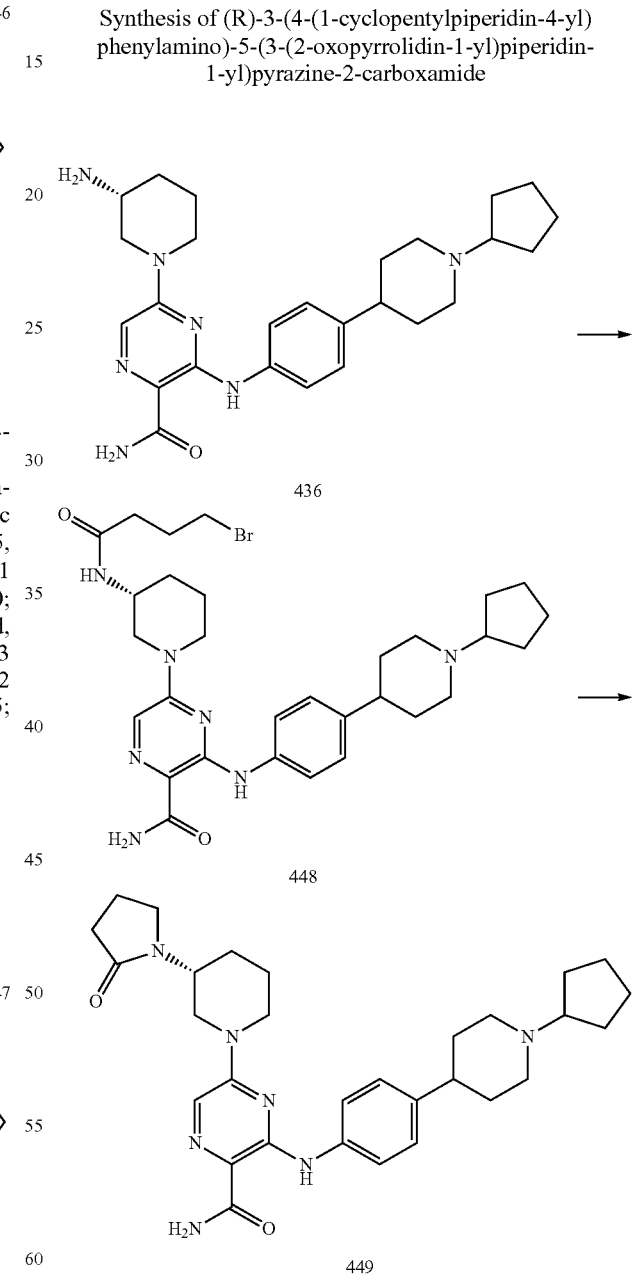

(R)-5-(3-Aminopiperidin-1-yl)-3-(4-(1-cyclopentylpiperidin-4-yl)phenylamino)pyrazine-2-carboxamide (436) (50 mg, 0.1 mmol) was dissolved in 4 mL DMF. To it were added DIEA (180 μL, 1.0 mmol) and then 4-bromobutyryl chloride (56 mg, 0.3 mmol). The mixture was stirred at RT for 1.5 hours, diluted with 60 mL EtOAc, washed with water ×3, dried, concentrated in vacuo to afford crude (R)-5-(3-(4-bromobutanamido)piperidin-1-yl)-3-(4-(1-cyclopentylpiperidin-4-yl)phenylamino)pyrazine-2-carboxamide (448). It was dissolved in 3 mL dry DMF and the solution was stirred at RT. To it was added NaH (60%, 30 mg), and the mixture was stirred for 1 hour. It was quenched with 0.5 mL TFA, and directly subjected to reverse phase preparative HPLC using 5 mM HCl (aq) and nest MeCN to isolate the title compound, (R)-3-(4-(1-cyclopentylpiperidin-4-yl)phenylamino)-5-(3-(2-oxopyrrolidin-1-yl)piperidin-1-yl)pyrazine-2-carboxamide (449), as HCl salt (7 mg). LC-MS (ESI): m/z (M+1) 532.6. UV: λ=267, 275, 305, 335, 373 nm.

Example 307

Synthesis of (R)-3-(4-(1-cyclopentylpiperidin-4-yl)phenylamino)-5-(3-(1-oxoisoindolin-2-yl)piperidin-1-yl)pyrazine-2-carboxamide

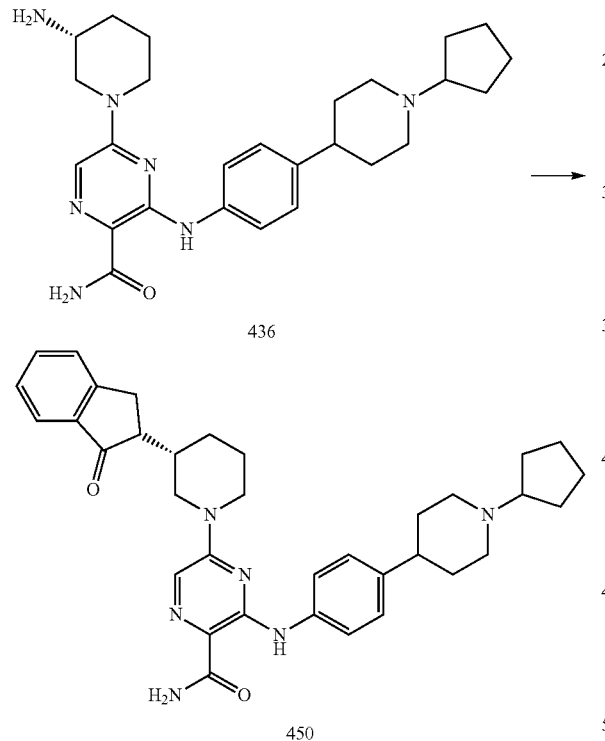

(R)-5-(3-Aminopiperidin-1-yl)-3-(4-(1-cyclopentylpiperidin-4-yl)phenylamino)pyrazine-2-carboxamide (436) (50 mg, 0.1 mmol) was dissolved in 4 mL DMF. To it were added DIEA (180 µL, 1.0 mmol) and then methyl 2-bromomethylbenzoate (46 mg, 0.2 mmol) at RT. The reaction temperature was raised to 60° C. and the mixture was stirred for overnight. It was cooled to RT, quenched with 0.5 mL TFA, and directly subjected to reverse phase preparative HPLC using 5 mM HCl (aq) and nest MeCN to isolate the title compound, (R)-3-(4-(1-cyclopentylpiperidin-4-yl)phenylamino)-5-(3-(1-oxoisoindolin-2-yl)piperidin-1-yl)pyrazine-2-carboxamide (450), as HCl salt (19 mg). LC-MS (ESI): m/z (M+1) 580.8. UV: λ=269, 275, 304, 335, 372 nm. Proton NMR (CD₃OD): δ 7.84 (1H, d, J=7.5 Hz), 7.69 (1H, s), 7.66-7.58 (2H, m), 7.56-7.52 (3H, m), 7.12 (2H, d, J=8.5 Hz), 4.67-4.57 (3H, m), 4.40-4.30 (2H, m), 3.64 (2H, m), 3.55 (1H, m), 3.27-3.06 (4H, m), 2.76 (1H, m), 2.24-1.72 (18H, m) ppm.

Example 308

Synthesis of (R)-5-(3-aminopiperidin-1-yl)-3-(4-(1-cyclopropylpiperidin-4-yl)phenylamino)pyrazine-2-carboxamide

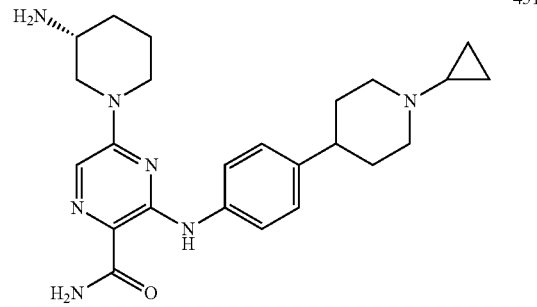

The title compound, (R)-5-(3-aminopiperidin-1-yl)-3-(4-(1-cyclopropylpiperidin-4-yl)phenylamino)pyrazine-2-carboxamide (451), was prepared by the same synthetic scheme illustrated for (R)-5-(3-aminopiperidin-1-yl)-3-(4-(1-methylpiperidin-4-yl)phenylamino)pyrazine-2-carboxamide (206) hydrochloride, shown in Example 165 using 4-(1-cyclopropylpiperidin-4-yl)aniline (322) hydrochloride. LC-MS (ESI): m/z (M+1) 436.2. UV: λ=263, 272, 304, 335, 372 nm. Proton NMR (CD₃OD): δ 7.69 (1H, s), 7.58 (2H, d, J=8.5 Hz), 7.26 (2H, d, J=8.5 Hz), 4.26 (1H, dd, J=13.0; 3.5 Hz), 4.01 (1H, m), 3.75 (2H, d, J=12.5 Hz), 3.54 (1H, m), 3.48 (1H, m), 3.44 (1H, m), 3.35 (2H, m), 2.89 (1H, m), 2.84 (1H, m), 2.20-1.70 (8H, m), 1.10 (2H, m), 0.98 (2H, m) ppm.

Example 309

Synthesis of 3-(4-(1-cyclopropylpiperidin-4-yl)phenylamino)-5-((3R)-3-(spiro[3.3]heptane-2-carboxamido)piperidin-1-yl)pyrazine-2-carboxamide

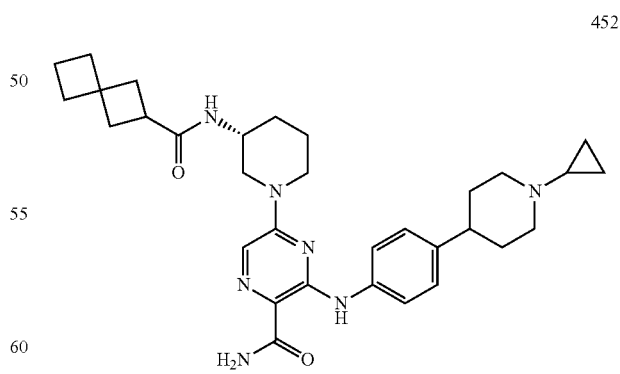

The title compound, 3-(4-(1-cyclopropylpiperidin-4-yl)phenylamino)-54(3R)-3-(spiro[3.3]heptane-2-carboxamido)piperidin-1-yl)pyrazine-2-carboxamide (452), was prepared by the same synthetic scheme illustrated for Example 295 using (R)-5-(3-aminopiperidin-1-yl)-3-(4-(1-cyclopropylpi-

Example 310

Synthesis of (R)-5-(3-(cyclopentanecarboxamido)piperidin-1-yl)-3-(4-(1-cyclopropylpiperidin-4-yl)phenylamino)pyrazine-2-carboxamide

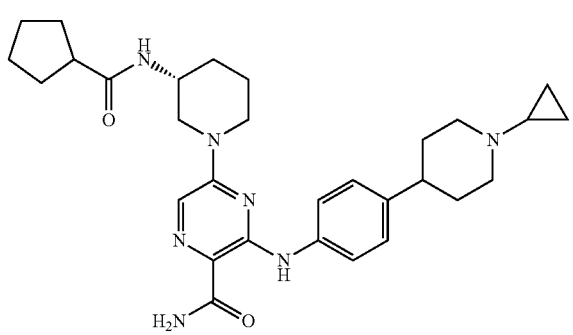

453

The title compound, (R)-5-(3-(cyclopentanecarboxamido)piperidin-1-yl)-3-(4-(1-cyclopropylpiperidin-4-yl)phenylamino)pyrazine-2-carboxamide (453), was prepared by the same synthetic scheme illustrated for Example 295 using (R)-5-(3-aminopiperidin-1-yl)-3-(4-(1-cyclopropylpiperidin-4-yl)phenylamino)pyrazine-2-carboxamide (451) and cyclopentanecarboxylic acid. LC-MS (ESI): m/z (M+1) 532.8. UV: λ=267, 277, 306, 336, 372 nm. Proton NMR (CD$_3$OD): δ 7.61 (1H, s), 7.58 (2H, d, J=8.5 Hz), 7.20 (2H, d, J=8.5 Hz), 4.15 (1H, dd, J=13.0; 3.0 Hz), 3.98 (1H, m), 3.89 (1H, m), 3.76 (2H, d, J=12.5 Hz), 3.44-3.34 (3H, m), 2.88-2.81 (2H, m), 2.62 (1H, m), 2.13 (2H, m), 2.02-1.55 (15H, m), 1.07-0.98 (4H, m) ppm.

Example 311

Synthesis of (R)-5-(3-(4-chlorobenzamido)piperidin-1-yl)-3-(4-(1-cyclopropylpiperidin-4-yl)phenylamino)pyrazine-2-carboxamide

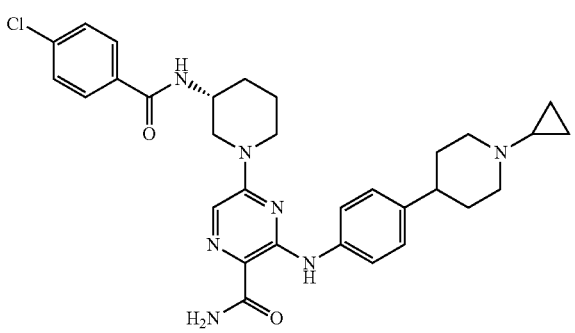

454

The title compound, (R)-5-(3-(4-chlorobenzamido)piperidin-1-yl)-3-(4-(1-cyclopropylpiperidin-4-yl)phenylamino)pyrazine-2-carboxamide (454), was prepared by the same synthetic scheme illustrated for Example 295 using (R)-5-(3-aminopiperidin-1-yl)-3-(4-(1-cyclopropylpiperidin-4-yl)phenylamino)pyrazine-2-carboxamide (451) and 4-chlorobenzoic acid. LC-MS (ESI): m/z (M+1) 574.2 (chloro pattern). UV: λ=265, 276, 305, 335, 372 nm.

Example 312

Synthesis of (R)-5-(3-(3-chlorobenzamido)piperidin-1-yl)-3-(4-(1-cyclopropylpiperidin-4-yl)phenylamino)pyrazine-2-carboxamide

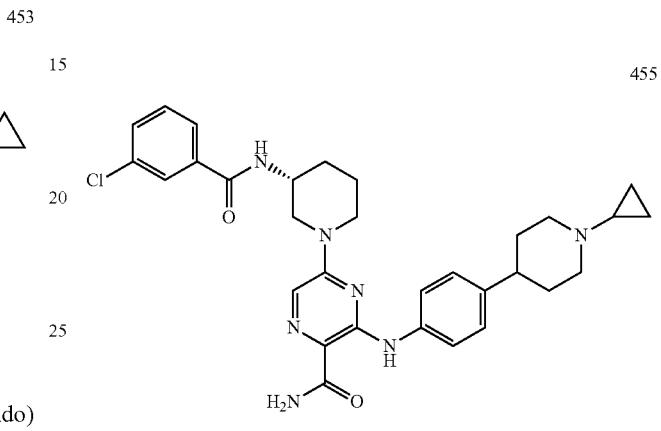

455

The title compound, (R)-5-(3-(3-chlorobenzamido)piperidin-1-yl)-3-(4-(1-cyclopropylpiperidin-4-yl)phenylamino)pyrazine-2-carboxamide (455), was prepared by the same synthetic scheme illustrated for Example 295 using (R)-5-(3-aminopiperidin-1-yl)-3-(4-(1-cyclopropylpiperidin-4-yl)phenylamino)pyrazine-2-carboxamide (451) and 3-chlorobenzoic acid. LC-MS (ESI): m/z (M+1) 574.2 (chloro pattern). UV: λ=305, 336, 373 nm.

Example 313

Synthesis of (R)-5-(3-(5-chloronicotinamido)piperidin-1-yl)-3-(4-(1-cyclopropylpiperidin-4-yl)phenylamino)pyrazine-2-carboxamide

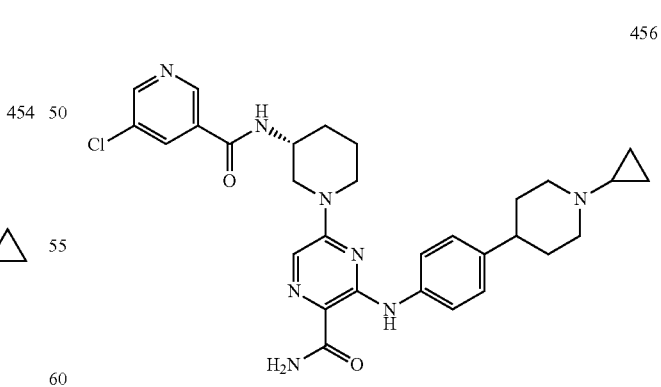

456

The title compound, (R)-5-(3-(5-chloronicotinamido)piperidin-1-yl)-3-(4-(1-cyclopropylpiperidin-4-yl)phenylamino)pyrazine-2-carboxamide (455), was prepared by the same synthetic scheme illustrated for Example 295 using (R)-5-(3-aminopiperidin-1-yl)-3-(4-(1-cyclopropylpiperidin-4-yl)phenylamino)pyrazine-2-carboxamide (451) and 5-chloronicotinic acid. LC-MS (ESI): m/z (M+1) 575.2 (chloro pattern). UV: λ=269, 275, 305, 336, 373 nm Proton NMR (CD$_3$OD): δ 8.45 (1H, d, J=2.0 Hz), 8.75 (1H, d, J=2.5 Hz), 8.21 (1H, t, J=2.0 Hz), 7.67 (1H, s), 7.57 (2H, d, J=8.5 Hz), 7.17 (2H, d, J=8.5 Hz), 4.33 (1H, dd, J=13.5; 3.5 Hz), 4.16 (1H, m), 4.05 (1H, m), 3.73 (2H, d, J=11.0 Hz), 3.52 (1H, dd, J=13.0; 8.0 Hz), 3.47-3.43 (2H, m), 3.33 (1H, m), 2.87-2.81 (2H, m), 2.17-1.70 (8H, m), 1.04-0.98 (4H, m) ppm.

Example 314

Synthesis of (R)-5-(3-(5-chlorothiophene-2-carboxamido)piperidin-1-yl)-3-(4-(1-cyclopropylpiperidin-4-yl)phenylamino)pyrazine-2-carboxamide

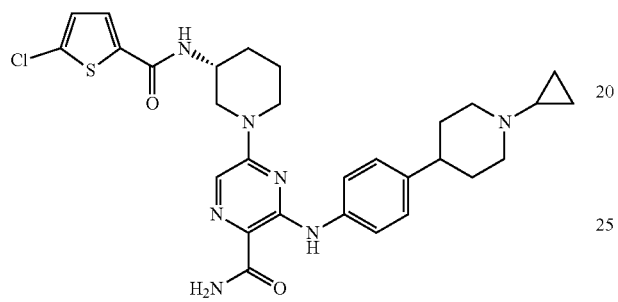

457

The title compound, (R)-5-(3-(5-chlorothiophene-2-carboxamido)piperidin-1-yl)-3-(4-(1-cyclopropylpiperidin-4-yl)phenylamino)pyrazine-2-carboxamide (457), was prepared by the same synthetic scheme illustrated for Example 295 using (R)-5-(3-aminopiperidin-1-yl)-3-(4-(1-cyclopropylpiperidin-4-yl)phenylamino)pyrazine-2-carboxamide (451) and 5-chlorothiophenecarboxylic acid. LC-MS (ESI): m/z (M+1) 580.2 (chloro pattern). UV: λ=265, 276, 305, 335, 372 nm. Proton NMR (CD$_3$OD): δ 7.66 (1H, s), 7.57 (2H, d, J=8.5 Hz), 7.54 (1H, d, J=4.5 Hz), 7.17 (2H, d, J=8.0 Hz), 7.04 (1H, d, J=4.0 Hz), 4.52 (1H, m), 4.18 (1H, m), 4.06 (1H, m), 3.69 (2H, m), 3.25 (2H, m), 3.15 (2H, m), 2.84 (2H, m), 2.14-1.70 (8H, m), 1.02-0.98 (4H, m) ppm.

Example 315

Synthesis of (R)-5-(3-(benzo[b]thiophene-2-carboxamido)piperidin-1-yl)-3-(4-(1-cyclopropylpiperidin-4-yl)phenylamino)pyrazine-2-carboxamide

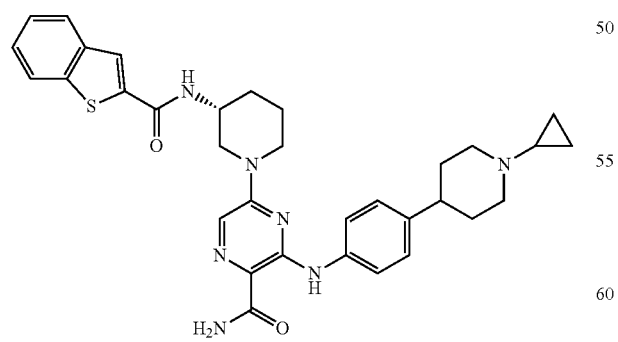

458

The title compound, (R)-5-(3-(benzo[b]thiophene-2-carboxamido)piperidin-1-yl)-3-(4-(1-cyclopropylpiperidin-4-yl)phenylamino)pyrazine-2-carboxamide (458), was prepared by the same synthetic scheme illustrated for Example 295 using (R)-5-(3-aminopiperidin-1-yl)-3-(4-(1-cyclopropylpiperidin-4-yl)phenylamino)pyrazine-2-carboxamide (451) and 2-benzothiophenecarboxylic acid. LC-MS (ESI): m/z (M+1) 596.8. UV: λ=301, 336, 372 nm.

Example 316

Synthesis of (R)-3-(4-(1-cyclopropylpiperidin-4-yl)phenylamino)-5-(3-(4,5,6,7-tetrahydrobenzo[b]thiophene-2-carboxamido)piperidin-1-yl)pyrazine-2-carboxamide

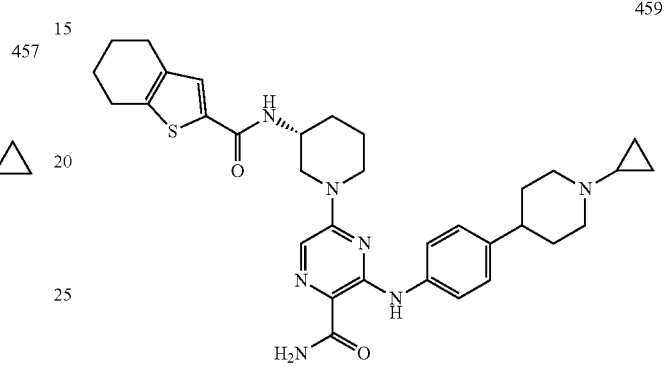

459

The title compound, (R)-3-(4-(1-cyclopropylpiperidin-4-yl)phenylamino)-5-(3-(4,5,6,7-tetrahydrobenzo[b]thiophene-2-carboxamido)piperidin-1-yl)pyrazine-2-carboxamide (459), was prepared by the same synthetic scheme illustrated for Example 295 using (R)-5-(3-aminopiperidin-1-yl)-3-(4-(1-cyclopropylpiperidin-4-yl)phenylamino)pyrazine-2-carboxamide (451) and 4,5,6,7-tetrahydrobenzo[b]thiophene-2-carboxylic acid. LC-MS (ESI): m/z (M+1) 601.0. UV: λ=268, 272, 302, 336, 373 nm. Proton NMR (CD$_3$OD): δ 7.65 (1H, s), 7.57 (2H, d, J=8.5 Hz), 7.31 (1H, s), 7.18 (2H, d, J=8.5 Hz), 4.42 (1H, m), 4.17 (1H, m), 4.04 (1H, m), 3.71 (2H, d, J=11.5 Hz), 3.24 (4H, m), 2.86-2.78 (4H, m), 2.61 (2H, m), 2.10-1.67 (12H, m), 1.04-0.98 (4H, m) ppm.

Example 317

Synthesis of (R)-5-(3-(2-naphthamido)piperidin-1-yl)-3-(4-(1-cyclopropylpiperidin-4-yl)phenylamino)pyrazine-2-carboxamide

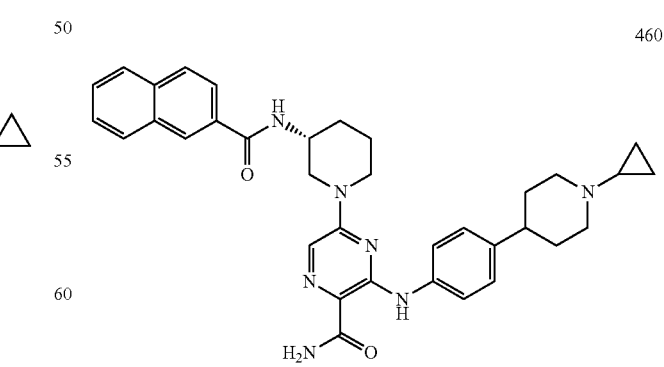

460

The title compound, (R)-5-(3-(2-naphthamido)piperidin-1-yl)-3-(4-(1-cyclopropylpiperidin-4-yl)phenylamino)pyrazine-2-carboxamide (460), was prepared by the same synthetic scheme illustrated for Example 295 using (R)-5-(3- aminopiperidin-1-yl)-3-(4-(1-cyclopropylpiperidin-4-yl) phenylamino)pyrazine-2-carboxamide (451) and 2-naphthalenecarboxylic acid. LC-MS (ESI): m/z (M+1) 590.8. UV: λ=270, 274, 304, 337, 372 nm.

Example 318

Synthesis of (R)-5-(3-biphenyl-4-ylcarboxamidopiperidin-1-yl)-3-(4-(1-cyclopropylpiperidin-4-yl)phenylamino)pyrazine-2-carboxamide

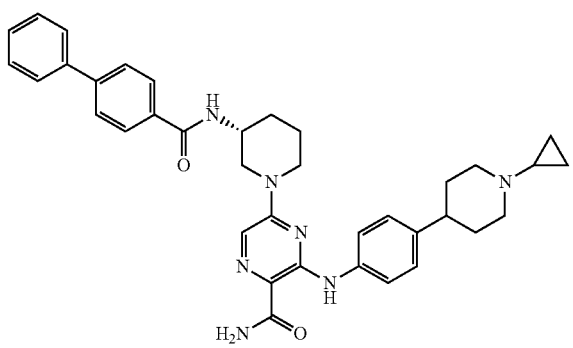

461

The title compound, (R)-5-(3-biphenyl-4-ylcarboxamidopiperidin-1-yl)-3-(4-(1-cyclopropylpiperidin-4-yl)phenylamino)pyrazine-2-carboxamide (461), was prepared by the same synthetic scheme illustrated for Example 295 using (R)-5-(3-aminopiperidin-1-yl)-3-(4-(1-cyclopropylpiperidin-4-yl)phenylamino)pyrazine-2-carboxamide (451) and biphenyl-4-carboxylic acid. LC-MS (ESI): m/z (M+1) 616.8. UV: λ=268, 289, 299, 335, 373 nm.

Example 319

Synthesis of (R)-3-(4-(1-cyclopropylpiperidin-4-yl) phenylamino)-5-(3-(6-phenylnicotinamido)piperidin-1-yl)pyrazine-2-carboxamide

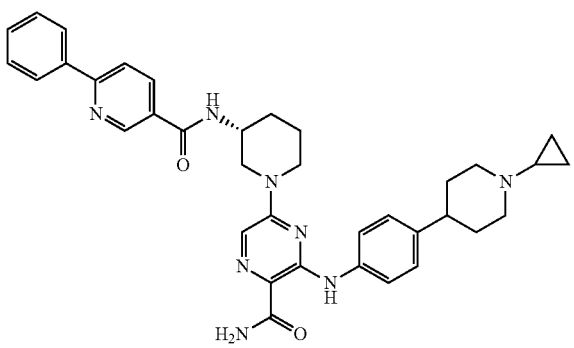

462

The title compound, (R)-3-(4-(1-cyclopropylpiperidin-4-yl)phenylamino)-5-(3-(6-phenylnicotinamido)piperidin-1-yl)pyrazine-2-carboxamide (462), was prepared by the same synthetic scheme illustrated for Example 295 using (R)-5-(3-aminopiperidin-1-yl)-3-(4-(1-cyclopropylpiperidin-4-yl) phenylamino)pyrazine-2-carboxamide (451) and 6-phenylnicotinic acid. LC-MS (ESI): m/z (M+1) 617.5. UV: λ=265, 272, 300, 336, 372 nm.

Example 320

Synthesis of (R)-3-(4-(1-cyclopentylpiperidin-4-yl) phenylamino)-5-(3-(4-fluorobenzamido)piperidin-1-yl)pyrazine-2-carboxamide

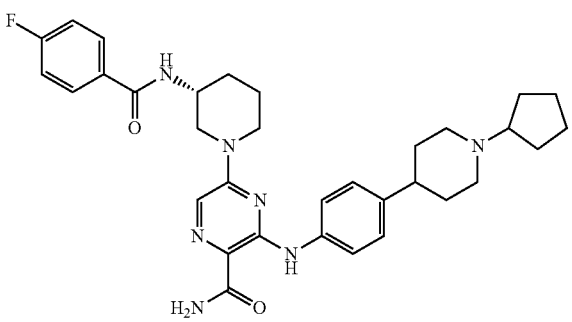

463

The title compound, (R)-3-(4-(1-cyclopentylpiperidin-4-yl)phenylamino)-5-(3-(4-fluorobenzamido)piperidin-1-yl) pyrazine-2-carboxamide (463), was prepared by the same synthetic scheme illustrated for Example 296 using 4-fluorobenzoyl chloride. LC-MS (ESI): m/z (M+1) 586.6. UV: λ=267, 276, 305, 335, 372 nm. Proton NMR (CD$_3$OD): δ 7.85 (2H, dd, J=9.0; 5.5 Hz), 7.68 (1H, s), 7.59 (2H, d, J=8.5 Hz), 7.21-7.15 (4H, m), 4.57 (1H, m), 4.44 (1H, m), 4.18-4.11 (2H, m), 3.63 (2H, m), 3.53 (1H, m), 3.07 (2H, m), 2.79 (2H, m), 2.21-1.72 (16H, m) ppm.

Example 321

Synthesis of (R)-5-(3-(3-methyl-3-phenylureido) piperidin-1-yl)-3-(phenylamino)pyrazine-2-carboxamide

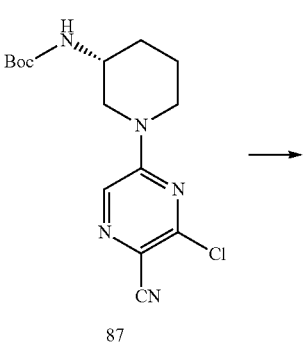

87

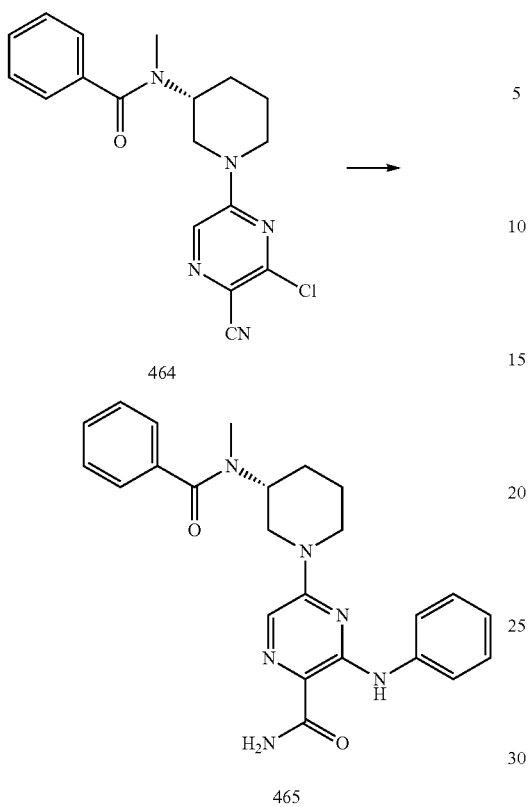

464

465

The title compound, (R)-5-(3-(3-methyl-3-phenylureido) piperidin-1-yl)-3-(phenylamino)pyrazine-2-carboxamide (465), was prepared by the same synthetic scheme illustrated for Example 179 using N-methyl-N-phenylcarbamoyl chloride and aniline via intermediate (R)-3-(1-(6-chloro-5-cyanopyrazin-2-yl)piperidin-3-yl)-1-methyl-1-phenylurea (464). LC-MS (ESI): m/z (M+1) 446.3. UV: λ=264, 277, 305, 334, 372 nm.

Example 322

Synthesis of (R)-5-(3-(3-(3-chloro-5-(trifluoromethyl)phenyl)-3-methylureido)piperidin-1-yl)-3-(4-fluorophenylamino)pyrazine-2-carboxamide

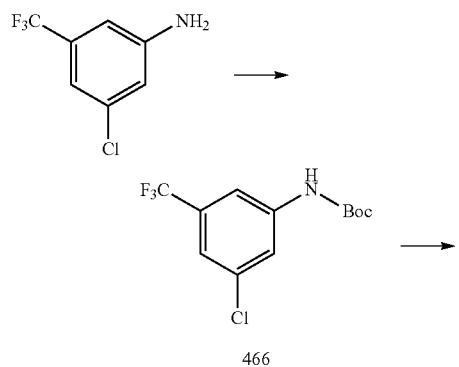

466

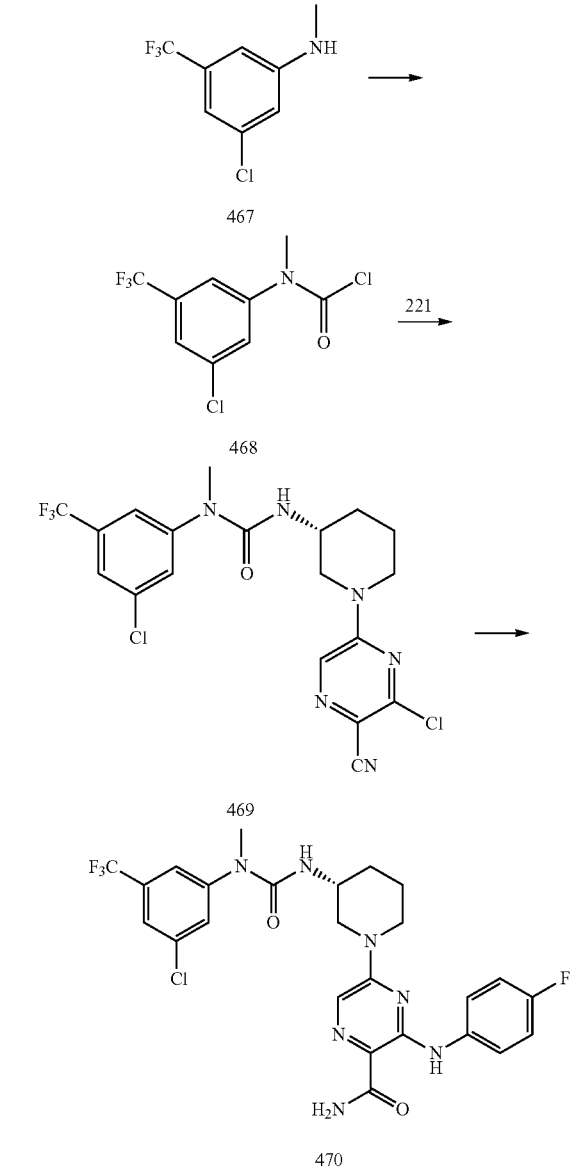

467

468

469

470

3-Chloro-5-trifluoromethylaniline (3.66 g, 18.7 mmol) was dissolved in 70 mL THF and stirred in an ice bath. To it were added Boc₂O (4.48 g, 20.6 mmol) and DMAP (2.51 g, 20.6 mmol). The mixture was stirred for overnight, and was concentrated in vacuo. The residue was taken into 200 mL EtOAc, washed with water ×3, dried, rotavaped, and subjected to silica flash column using 1% MeOH in DCM to get tert-butyl 3-chloro-5-(trifluoromethyl)phenylcarbamate (466, 3.37 g, 61%) as a white solid. It was dissolved in 100 mL dry THF and treated with NaH (60% in mineral oil, 910 mg, 22.8 mmol) at RT for 15 min and then iodomethane (1.42 mL, 22.8 mmol) was added. The mixture was stirred for overnight, concentrated, taken into 200 mL EtOAc, washed with water ×2, dried, concentrated, and subjected to silica flash column using 0 to 5% EtOAc in DCM to isolate the methylation product as an oil. It was treated with 1:1 TFA/DCM (10 mL/10 mL) at RT for 3 hours, concentrated in vacuo, taken into 200 mL EtAOc and 50 mL 1N NaOH. The organic phase was separated, washed with water, dried, subjected to silica flash column with 1% MeOH in DCM to isolate 3-chloro-N-methyl-5-(trifluoromethyl)aniline (467, 1.76 g, 53%) as an oil.

3-Chloro-N-methyl-5-(trifluoromethyl)aniline (467, 1.24 g, 5.9 mmol) was dissolved in 15 mL dry toluene. To it was added Et₃N (1.1 mL, 7.9 mmol), and the mixture was stirred in ice bath. To it was drop-wise added a pre-made solution of triphosgene (2.46 g, 8.3 mmol) in 7.5 mL dry toluene. The mixture was then stirred in ice bath for 3 hours. EtOAc (120 mL) and water (50 mL) were then poured into the mixture, and the organic phase was separated. It was washed with saturated NaHCO₃ (aq) solution, dried, concentrated in vacuo to afford crude 3-chloro-5-(trifluoromethyl)phenyl(methyl) carbamic chloride (468) as an oil.

(R)-tert-Butyl 1-(6-chloro-5-cyanopyrazin-2-yl)piperidin-3-ylcarbamate (87, 950 mg, 2.8 mmol) was treated with 2:1 DCM/TFA (20 mL/10 mL) at RT for 20 min. The mixture was concentrated in vacuo to dryness as crude (R)-5-(3-aminopiperidin-1-yl)-3-chloropyrazine-2-carbonitrile (221, TFA salt). It was dissolved in 18 mL DMF. To it were added DIEA (3.9 mL, 22.4 mmol) and then the crude 468 (estimated 5.9 mmol) prepared. The mixture was stirred at RT for 1.5 hour, diluted with 120 mL EtOAc, washed with water and saturated NaHCO₃ (aq) solution, dried, concentrated and subjected to silica flash column using 0 to 3.5% MeOH in DCM to isolate (R)-1-(3-chloro-5-(trifluoromethyl)phenyl)-3-(1-(6-chloro-5-cyanopyrazin-2-yl)piperidin-3-yl)-1-methylurea (469) in quantitative yield.

The title compound, (R)-5-(3-(3-(3-chloro-5-(trifluoromethyl)phenyl)-3-methylureido)piperidin-1-yl)-3-(4-fluorophenylamino)pyrazine-2-carboxamide (470), was prepared by the same synthetic scheme illustrated for Example 179 using (R)-1-(3-chloro-5-(trifluoromethyl)phenyl)-3-(1-(6-chloro-5-cyanopyrazin-2-yl)piperidin-3-yl)-1-methylurea (469) and 4-fluoroaniline. LC-MS (ESI): m/z (M+1) 566.1 (chloro pattern). UV: λ=261, 275, 300, 332, 372 nm. Proton NMR (CD₃OD): δ 7.61 (1H, s), 7.59-7.56 (2H, m), 7.49-7.47 (3H, m), 7.02-6.99 (2H, m), 4.09 (1H, dd, J=13.0; 3.0 Hz), 3.90 (1H, m), 3.85 (1H, m), 3.49-3.42 (2H, m), 3.24 (3H, s), 1.98 (1H, m), 1.75 (2H, m), 1.64 (1H, m) ppm.

Example 323

Synthesis of (R)-5-(3-(3-(3-chloro-5-(trifluoromethyl)phenyl)-3-methylureido)piperidin-1-yl)-3-(4-(1-cyanocyclopropyl)phenylamino)pyrazine-2-carboxamide The title compound, (R)-5-(3-(3-(3-chloro-5-(trifluoromethyl)phenyl)-3-methylureido)piperidin-1-yl)-3-(4-(1-cyanocyclopropyl)phenylamino)pyrazine-2-carboxamide (471), was prepared by the same synthetic scheme illustrated for Example 322 using 1-(4-aminophenyl)cyclopropanecarbonitrile. LC-MS (ESI): m/z (M+1) 613.2 (chloro pattern). UV: λ=267, 282, 308, 337, 376 nm. Proton NMR (CD₃OD): δ 7.65-7.63 (3H m), 7.49-7.46 (3H, m), 7.27 (2H, d, J=9.0 Hz), 4.12 (1H, dd, J=12.5; 2.5 Hz), 3.89 (2H, m), 3.54-3.45 (2H, m), 3.25 (3H, s), 1.99 (1H, m), 1.81-1.64 (5H, m), 1.39 (2H, m) ppm. In the final step, compound (R)-3-(4-(1-carbamoylcyclopropyl)phenylamino)-5-(3-(3-(3-chloro-5-(trifluoromethyl)phenyl)-3-methylureido)piperidin-1-yl)pyrazine-2-carboxamide (472) was found as a by-product and isolated as HCl salt.

Example 324

Synthesis of (R)-3-(4-(1-carbamoylcyclopropyl)phenylamino)-5-(3-(3-(3-chloro-5-(trifluoromethyl)phenyl)-3-methylureido)piperidin-1-yl)pyrazine-2-carboxamide

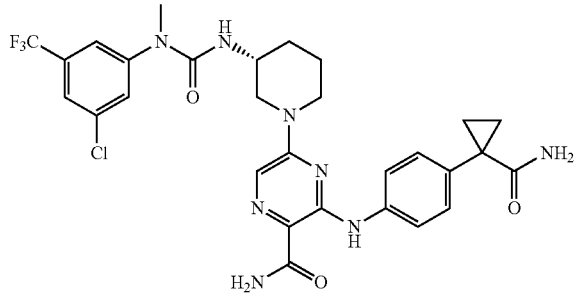

472

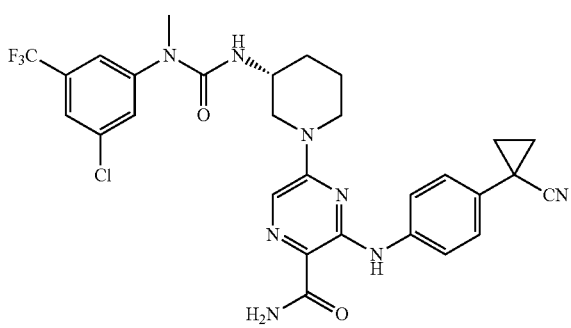

471

The title compound, (R)-3-(4-(1-carbamoylcyclopropyl)phenylamino)-5-(3-(3-(3-chloro-5-(trifluoromethyl)phenyl)-3-methylureido)piperidin-1-yl)pyrazine-2-carboxamide (472), was found and isolated as a by-product in the final step during the preparation of (R)-5-(3-(3-(3-chloro-5-(trifluoromethyl)phenyl)-3-methylureido)piperidin-1-yl)-3-(4-(1-cyanocyclopropyl)phenylamino)pyrazine-2-carboxamide (471). LC-MS (ESI): m/z (M+1) 631.2 (chloro pattern). UV: λ=267, 280, 308, 337, 373 nm.

Example 325

Synthesis of (R)—N-(1-(5-carbamoyl-6-(4-(tetrahydro-2H-pyran-4-yl)phenylamino)pyrazin-2-yl)piperidin-3-yl)imidazo[1,2-a]pyridine-6-carboxamide

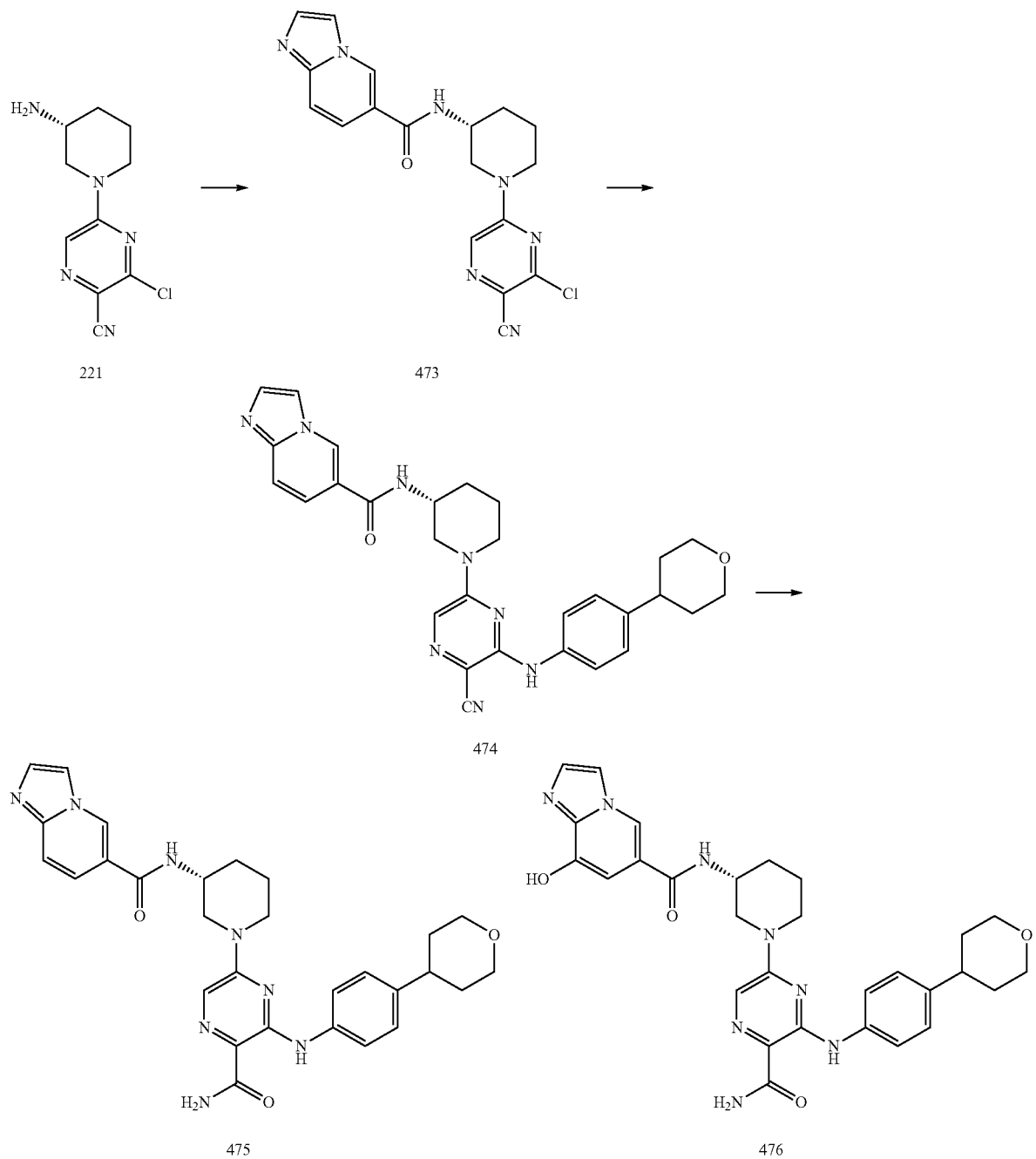

(R)-5-(3-Aminopiperidin-1-yl)-3-chloropyrazine-2-carbonitrile (221, HCl salt, 350 mg, 1.28 mmol) was dissolved in 10 mL DMF. To it were added imidazo[1,2-a]pyridine-6-carboxylic acid (310 mg, 1.92 mmol), DIEA (890 µL, 5.12 mmol) and then PyBOP (1.00 g, 1.92 mmol). The mixture was stirred at RT for 1 hour, diluted with 100 mL EtOAc, washed with water ×3, dried, concentrated, and subjected to silica flash column using 0 to 7% MeOH in DCM to isolate (R)—N-(1-(6-chloro-5-cyanopyrazin-2-yl)piperidin-3-yl)imidazo[1,2-a]pyridine-6-carboxamide (473). Compound 473 (75 mg, 0.20 mmol) was mixed with 4-(tetrahydro-2H-pyran-4-yl)aniline (106 mg, 0.60 mmol), fine-powder cesium carbonate (326 mg, 1.00 mmol), palladium acetate (22 mg, 0.10 mmol), BINAP (62 mg, 0.10 mmol) in 15 mL dioxane.

The mixture was degassed using nitrogen stream for 3 min, and stirred in nitrogen atmosphere at 115° C. for 1 hour. It was cooled to RT, diluted with 50 mL EtOAc, stirred and filtered. The filtrate was concentrated and subjected to silica flash column using 0 to 11% MeOH in DCM to isolate (R)—N-(1-(5-cyano-6-(4-(tetrahydro-2H-pyran-4-yl)phenylamino)pyrazin-2-yl)piperidin-3-yl)imidazo[1,2-a]pyridine-6-carboxamide (474). It was dissolved in 10 mL MeOH and 3 mL DMSO. To it were added one NaOH solid bead (about 100 mg) and 1 mL 30% H$_2$O$_2$. The mixture was stirred at RT for 1.5 hour, quenched with 5 mL MeCN, stirred, concentrated, acidified with 0.3 mL TFA, and directly subjected to reverse phase prep HPLC using 5 mM HCl (aq) and neat MeCN as mobile phases to isolate the title compound, (R)—N—O-(5-carbamoyl-6-(4-(tetrahydro-2H-pyran-4-yl)phenylamino)pyrazin-2-yl)piperidin-3-yl)imidazo[1,2-a]pyridine-6-carboxamide (475) (24 mg) as HCl salt, and also the by-product, (R)—N—O-(5-carbamoyl-6-(4-(tetrahydro-2H-pyran-4-yl)phenylamino)pyrazin-2-yl)piperidin-3-yl)-5-hydroxyimidazo[1,2-a]pyridine-6-carboxamide (476) (15 mg) as HCl salt. For compound 475, LC-MS (ESI): m/z (M+1) 541.3. UV: λ=304, 336, 373 nm. Proton NMR (CD$_3$OD): δ 9.26 (1H, s), 8.30 (2H, m), 8.14 (1H, d, J=2.0 Hz), 7.99 (1H, d, J=9.5 Hz), 7.66 (1H, s), 7.51 (2H, d, J=9.0 Hz), 7.11 (2H, d, J=9.0 Hz), 4.41 (1H, m), 4.21 (1H, m), 4.10 (1H, m), 3.92 (2H, m), 3.44 (4H, m), 2.66 (1H, m), 2.16 (1H, m), 1.97 (1H, m), 1.84 (1H, m), 1.76 (1H, m), 1.62 (3H, m), 1.56 (1H, m) ppm.

Example 326

Synthesis of (R)—N-(1-(5-carbamoyl-6-(4-(tetrahydro-2H-pyran-4-yl)phenylamino)pyrazin-2-yl)piperidin-3-yl)-5-hydroxyimidazo[1,2-a]pyridine-6-carboxamide

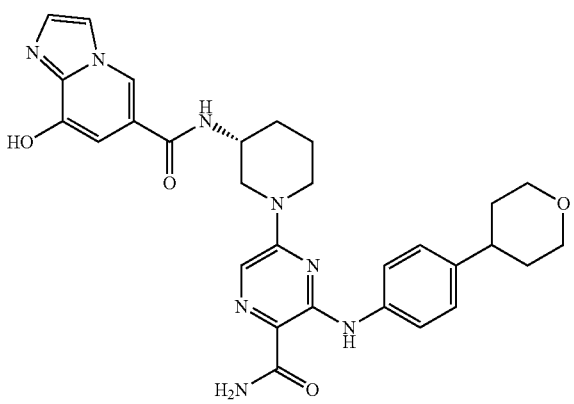

476

The title compound, (R)—N-(1-(5-carbamoyl-6-(4-(tetrahydro-2H-pyran-4-yl)phenylamino)pyrazin-2-yl)piperidin-3-yl)-5-hydroxyimidazo[1,2-a]pyridine-6-carboxamide (476), was found and isolated as by-product during the preparation of (R)—N-(1-(5-cyano-6-(4-(tetrahydro-2H-pyran-4-yl)phenylamino)pyrazin-2-yl)piperidin-3-yl)imidazo[1,2-a]pyridine-6-carboxamide (474) in the final step. LC-MS (ESI): m/z (M+1) 557.3. UV: λ=309, 358, 373 nm. Proton NMR (CD$_3$OD): δ 8.28 (1H, d, J=9.0 Hz), 7.83 (1H, d, J=2.5 Hz), 7.60 (1H, s), 7.55 (1H, d, J=2.5 Hz), 7.49 (2H, d, J=9.0 Hz), 7.10 (2H, d, J=8.5 Hz), 6.58 (1H, d, J=9.5 Hz), 4.21 (1H, m), 4.17 (1H, m), 3.95 (2H, m), 3.83 (1H, m), 3.67 (1H, m), 3.61 (1H, m), 3.49 (2H, m), 2.66 (1H, m), 2.14 (1H, m), 1.96 (1H, m), 1.83-1.60 (6H, m) ppm.

Example 327

Synthesis of (R)-3-(4-(1-cyclopentylpiperidin-4-yl)phenylamino)-5-(3-(3,3-dimethylureido)azepan-1-yl)pyrazine-2-carboxamide

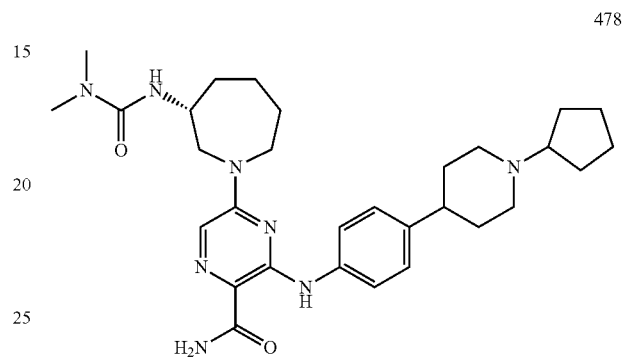

478

The title compound, (R)-3-(4-(1-cyclopentylpiperidin-4-yl)phenylamino)-5-(3-(3,3-dimethylureido)azepan-1-yl)pyrazine-2-carboxamide (478), was prepared by the same synthetic scheme illustrated for Example 286 and Example 287 using (R)-3-Boc-aminoazepane. LC-MS (ESI): m/z (M+1) 549.8. UV: λ=267, 278, 306, 336, 373 nm. Proton NMR (CD$_3$OD): δ 7.70-7.63 (3H, m), 7.19 (2H, d, J=8.5 Hz), 4.02 (2H, m), 3.71 (2H, d, J=12.5 Hz), 3.57-3.53 (2H, m), 3.15-3.11 (2H, m), 2.88-2.78 (9H, m), 2.23 (2H, m), 2.13 (2H, m), 2.05-1.93 (4H, m), 1.89-1.59 (9H, m), 1.43 (1H, m) ppm.

Example 328

Synthesis of (R)-3-(4-(1-cyclopentylpiperidin-4-yl)phenylamino)-5-(3-(cyclopropanecarboxamido)azepan-1-yl)pyrazine-2-carboxamide

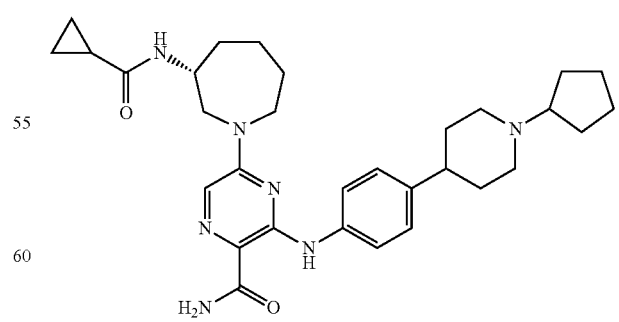

479

The title compound, (R)-3-(4-(1-cyclopentylpiperidin-4-yl)phenylamino)-5-(3-(cyclopropanecarboxamido)azepan-1-yl)pyrazine-2-carboxamide (479), was prepared by the same synthetic scheme illustrated for Example 286 and Example 288 using (R)-3-Boc-aminoazepane. LC-MS (ESI): m/z (M+1) 546.9.

Example 329

Synthesis of (R)-5-(4-(1-cyclopentylpiperidin-4-yl)phenylamino)-3-(3-(3,3-dimethylureido)piperidin-1-yl)-1,2,4-triazine-6-carboxamide

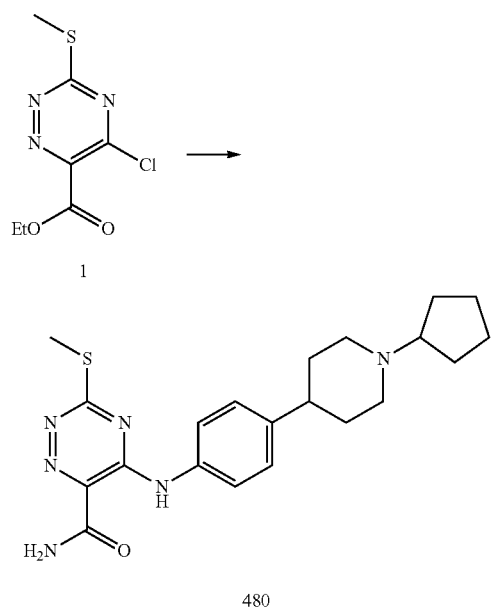

480

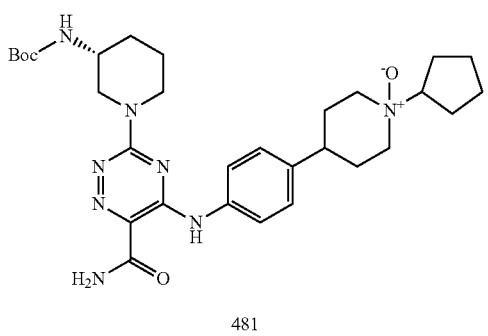

481

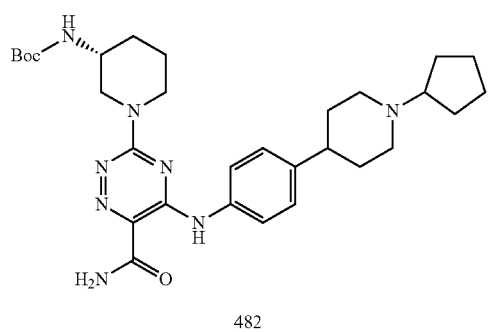

482

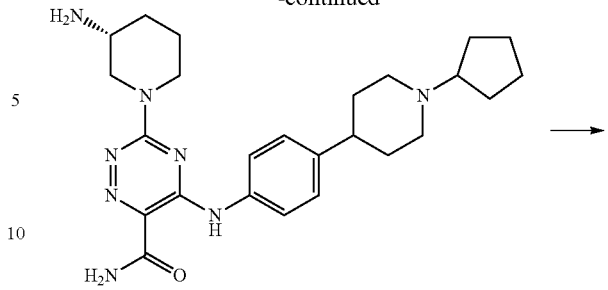

483

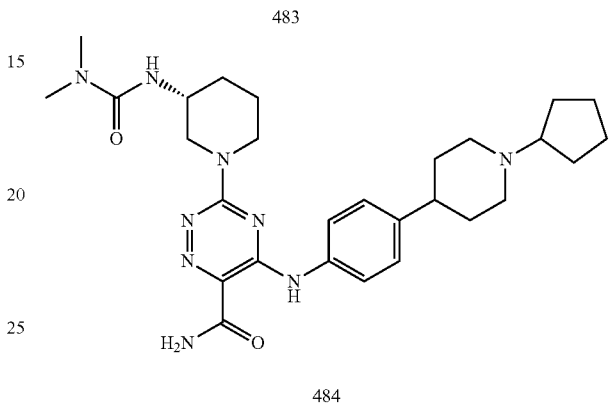

484

To ethyl 5-chloro-3-(methylthio)-1,2,4-triazine-6-carboxylate (1) (120 mg, 0.50 mmol) in acetonitrile (10 mL) was added 4-(1-cyclopentylpiperidin-4-yl)aniline hydrochloride (304) (140 mg, 0.50 mmol) and then DIEA (180 μL, 1.0 mmol). The mixture was stirred at RT for 30 min. To the mixture was then added ammonia (7.0 N solution in methanol, 15 mL). The mixture turned cloudy in 10 min and then into a suspension. The mixture was stirred for 2 hours, concentrated in vacuo to ½ of the volume, and the solid was isolated by filtration. It was washed with cold acetonitrile (10 mL×2) and then washed with hexane (10 mL×3). The solid was dried in a vacuum oven to afford 5-(4-(1-cyclopentylpiperidin-4-yl)phenylamino)-3-(methylthio)-1,2,4-triazine-6-carboxamide (480) (170 mg, 0.41 mmol, 82% yield) in high purity. It was dissolved in 10 mL NMP. To it was added dry mCPBA (77% strength, 320 mg, 1.44 mmol). The mixture was stirred at RT for 2 hours. To the mixture was added DIEA (720 μL, 4.10 mmol) and (R)-(3-BOC-amino)piperidine (3) (170 mg, 0.82 mmol). The mixture was stirred at 80° C. for 2 hours. The mixture was cooled to RT, diluted with water 30 mL, extracted with EtOAc 25 mL×5. The combined organic extract phase was washed with brine, dried, concentrated and subjected to silica flash column using 0 to 40% MeOH in DCM to isolate (R)-4-(4-(3-(3-(tert-butoxycarbonylamino)piperidin-1-yl)-6-carbamoyl-1,2,4-triazin-5-ylamino)phenyl)-1-cyclopentylpiperidine 1-oxide (481). It was dissolved in 10 mL dry MeCN and 3 mL NMP. To the stirred solution was added bis(pinacolato)diborane (100 mg, 0.39 mmol). The mixture was stirred at RT for 10 min, quenched with 5 mL MeOH, stirred for 30 min, concentrated and subjected to silica flash column using 0 to 15% MeOH in DCM to isolate (R)-tert-butyl 1-(6-carbamoyl-5-(4-(1-cyclopentylpiperidin-4-yl)phenylamino)-1,2,4-triazin-3-yl)piperidin-3-ylcarbamate (482) (160 mg, 69% yield for 2 steps). It was treated with 20 mL commercial 4N HCl in dioxane at RT for 1.5 hour to give (R)-3-(3-aminopiperidin-1-yl)-5-(4-(1-cyclopentylpiperidin-4-yl)phenylamino)-1,2,4-triazine-6-carboxamide hydrochloride (483) in quantitative yield. Compound 483 (88 mg, 0.19 mmol) was dissolved in 5 mL NMP. To it were added DIEA (330 µL, 1.9 mmol) and then dimethylcarbamoyl chloride (70 µL, 0.76 mmol). The mixture was stirred at RT for 1.5 hour, quenched with 0.5 mL TFA, and directly subjected to reverse phase prep HPLC using 5 mM HCl (aq) and neat MeCN as mobile phases to isolate the title compound, (R)-5-(4-(1-cyclopentylpiperidin-4-yl)phenylamino)-3-(3-(3,3-dimethylureido)piperidin-1-yl)-1,2,4-triazine-6-carboxamide (484), as HCl salt (49 mg). LC-MS (ESI): m/z (M+1) 536.3. UV: λ=260 nm.

Example 330

Synthesis of (R)-5-(4-(1-cyclopentylpiperidin-4-yl)phenylamino)-3-(3-propionamidopiperidin-1-yl)-1,2,4-triazine-6-carboxamide

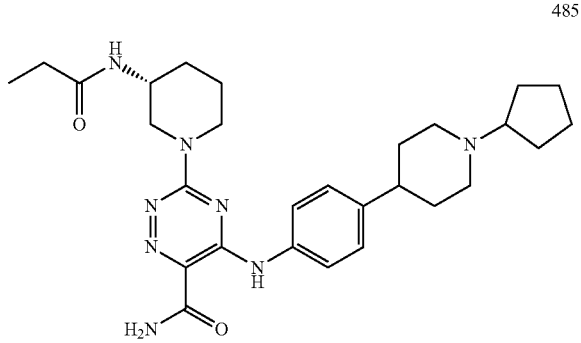 [SMILES: CCC(=O)N[C@@H]1CCCN(c2nnc(C(N)=O)c(Nc3ccc(C4CCN(C5CCCC5)CC4)cc3)n2)C1]

485

The title compound, (R)-5-(4-(1-cyclopentylpiperidin-4-yl)phenylamino)-3-(3-propionamidopiperidin-1-yl)-1,2,4-triazine-6-carboxamide (485), was prepared by the same synthetic scheme illustrated for Example 329 using (R)-3-(3-aminopiperidin-1-yl)-5-(4-(1-cyclopentylpiperidin-4-yl)phenylamino)-1,2,4-triazine-6-carboxamide hydrochloride (483) and propionyl chloride. LC-MS (ESI): m/z (M+1) 521.4. UV: λ=260 nm. Proton NMR (CD$_3$OD): δ 7.70 (2H, d, J=8.5 Hz), 7.37 (2H, d, J=8.5 Hz), 4.28 (1H, dd, J=13.0; 3.5 Hz), 3.99 (1H, m), 3.73 (2H, d, J=12.5 Hz), 3.59-3.54 (2H, m), 3.47-3.44 (2H, m), 3.17-3.13 (2H, m), 2.95 (1H, m), 2.25-2.14 (6H, m), 2.06-1.95 (4H, m), 1.88 (2H, m), 1.80-1.68 (6H, m), 1.11 (3H, t, J=7.5 Hz) ppm.

Example 331

Synthesis of (R)-5-(4-(4-cyclopentylpiperazin-1-yl)phenylamino)-3-(3-(4-methoxybenzamido)piperidin-1-yl)-1,2,4-triazine-6-carboxamide

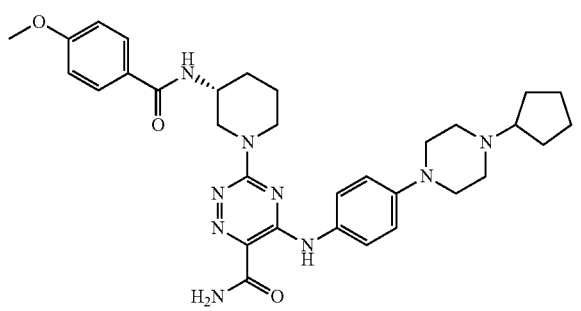

486

The title compound, (R)-5-(4-(4-cyclopentylpiperazin-1-yl)phenylamino)-3-(3-(4-methoxybenzamido)piperidin-1-yl)-1,2,4-triazine-6-carboxamide (486), was prepared by the same synthetic scheme illustrated for Example 330 using 4-methoxybenzoyl chloride and 4-(4-cyclopentylpiperazin-1-yl)aniline. LC-MS (ESI): m/z (M+1) 600.2. UV: λ=251 nm.

Example 332

Synthesis of (R)-5-(4-(4-(dimethylcarbamoyl)piperidin-1-yl)phenylamino)-3-(3-(4-methoxybenzamido)piperidin-1-yl)-1,2,4-triazine-6-carboxamide

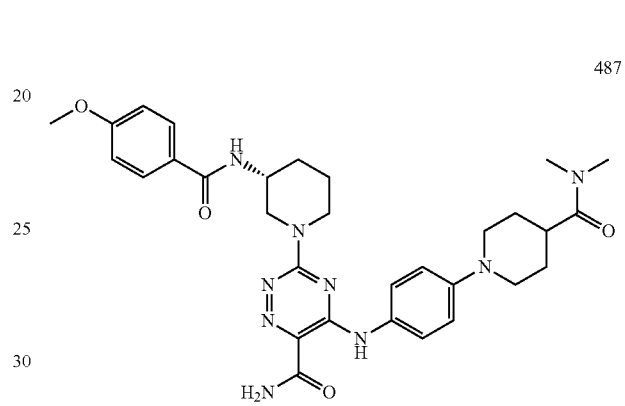

487

The title compound, (R)-5-(4-(4-(dimethylcarbamoyl)piperidin-1-yl)phenylamino)-3-(3-(4-methoxybenzamido)piperidin-1-yl)-1,2,4-triazine-6-carboxamide (487), was prepared by the same synthetic scheme illustrated for Example 330 using 1-(4-aminophenyl)-N,N-dimethylpiperidine-4-carboxamide and 4-methoxybenzoyl chloride. LC-MS (ESI): m/z (M+1) 602.2. UV: λ=259 nm.

Example 333

Synthesis of (R)-5-(4-(4-(dimethylcarbamoyl)piperidin-1-yl)phenylamino)-3-(3-(4-methoxybenzamido)piperidin-1-yl)-1,2,4-triazine-6-carboxamide

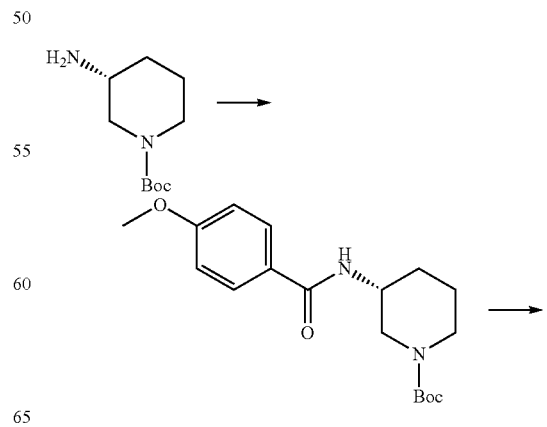

488

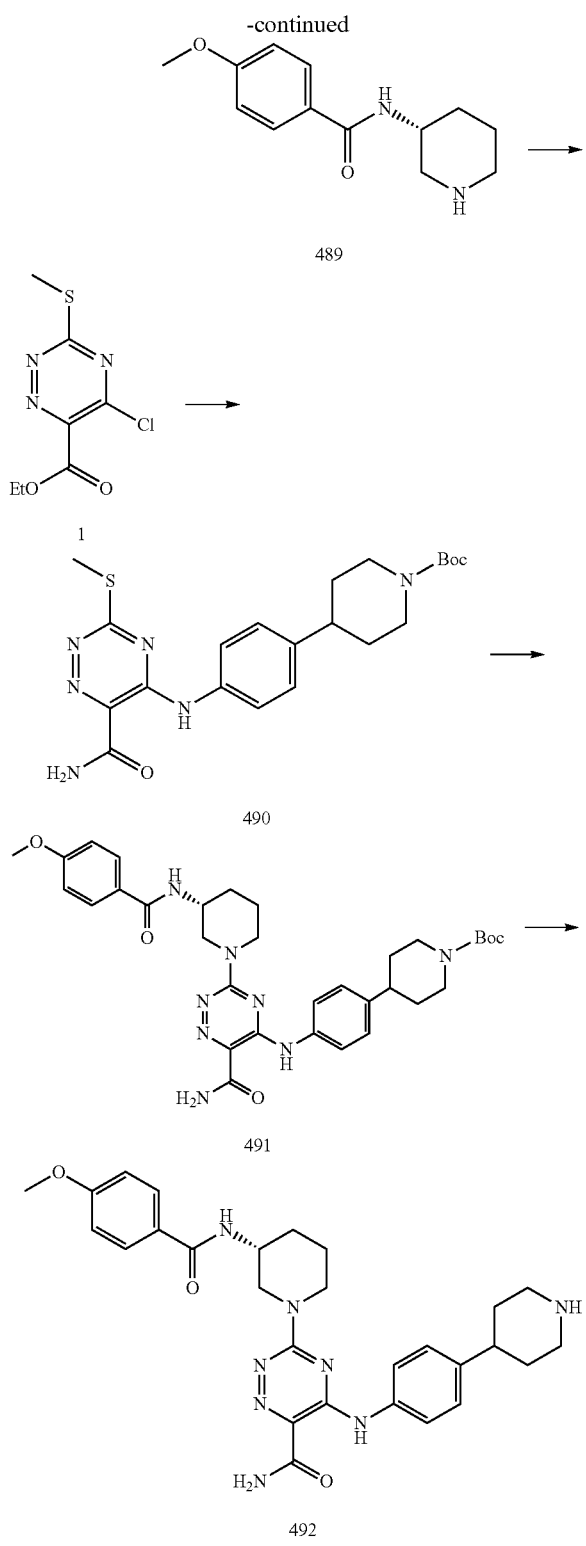

methoxybenzamido)piperidine-1-carboxylate (488) in quantitative yield. Compound 488 (1.86 g, 5.56 mmol) was treated with 30 mL commercial 4N HCl in dioxane at RT for 15 min, giving (R)-4-methoxy-N-(piperidin-3-yl)benzamide hydrochloride (489) in quantitative yield as a white solid.

To ethyl 5-chloro-3-(methylthio)-1,2,4-triazine-6-carboxylate (1) (1.20 g, 5.15 mmol) in acetonitrile (40 mL) was added tert-butyl 4-(4-aminophenyl)piperidine-1-carboxylate (2.14 g, 7.73 mmol) and then DIEA (1350 μL, 7.73 mmol). The mixture was stirred at RT for 1 hour. To the mixture was then added ammonia (7.0 N solution in methanol, 30 mL). The mixture turned cloudy in 10 min and then into a suspension. The mixture was stirred for 8 hours, and the solid was isolated by filtration. It was washed with cold acetonitrile (10 mL×2) and then washed with hexane (10 mL×3). The solid was dried in a vacuum oven to afford tert-butyl 4-(4-(6-carbamoyl-3-(methylthio)-1,2,4-triazin-5-ylamino)phenyl)piperidine-1-carboxylate (490) (1.82 g, 79% yield) in high purity. Compound 490 (600 mg, 1.35 mmol) was dissolved in 20 mL NMP. To it were added dry mCPBA (77% strength, 840 mg, 3.38 mmol). The mixture was stirred at RT for 1 hour. To the mixture was added DIEA (2.10 mL, 12.1 mmol) and (R)-4-methoxy-N-(piperidin-3-yl)benzamide hydrochloride (489) (550 mg, 2.03 mmol). The mixture was stirred at 70° C. for 30 min. The mixture was cooled to RT, diluted with 200 mL chloroform, washed with 1N NaOH (aq) ×2 and water, dried, concentrated in vacuo to dryness for crude (R)-tert-butyl 4-(4-(6-carbamoyl-3-(3-(4-methoxybenzamido)piperidin-1-yl)-1,2,4-triazin-5-ylamino)phenyl)piperidine-1-carboxylate (491) (740 mg, 87%). It was treated with 35 mL commercial 4N HCl in dioxane at RT for 45 min. The mixture was concentrated in vacuo to dryness to afford crude (R)-3-(3-(4-methoxybenzamido)piperidin-1-yl)-5-(4-(piperidin-4-yl)phenylamino)-1,2,4-triazine-6-carboxamide (492). A small amount of crude 492 was purified using reverse phase prep HPLC to isolate as HCl salt. LC-MS (ESI): m/z (M+1) 531.1. UV: λ=255 nm.

Example 334

Synthesis of (R)-5-(4-(1-cyclopentylpiperidin-4-yl)phenylamino)-3-(3-(4-methoxybenzamido)piperidin-1-yl)-1,2,4-triazine-6-carboxamide

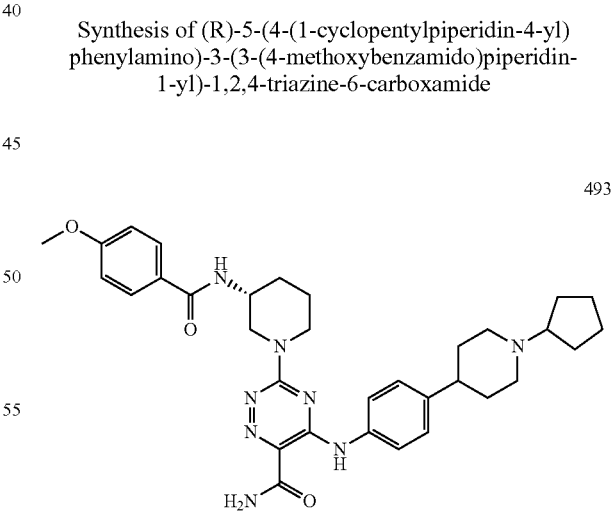

The title compound, (R)-5-(4-(1-cyclopentylpiperidin-4-yl)phenylamino)-3-(3-(4-methoxybenzamido)piperidin-1-yl)-1,2,4-triazine-6-carboxamide (493), was prepared by the same synthetic scheme illustrated for Example 256 using (R)-3-(3-(4-methoxybenzamido)piperidin-1-yl)-5-(4-(piperidin-4-yl)phenylamino)-1,2,4-triazine-6-carboxamide (492). LC-MS (ESI): m/z (M+1) 599.2. UV: λ=257 nm.

(R)-tert-Butyl 3-aminopiperidine-1-carboxylate (1.70 g, 8.5 mmol) was mixed with p-anisic acid (1.42 g, 9.35 mmol) in 5 mL DMF and 25 mL dioxane. The mixture was stirred at RT, and to it were added DIEA (2.07 mL, 11.9 mmol) and then PyBOP (4.86 g, 9.35 mmol). The mixture was stirred at RT for 3 hours, diluted with 150 mL EtOAc, washed with water 60 mL×3, dried, concentrated, subjected to silica flash column using 0 to 20% EtOAc in DCM to isolate (R)-tert-butyl 3-(4-

Example 335

Synthesis of (R)-5-(4-(piperidin-4-yl)phenylamino)-3-(3-(piperidine-1-carboxamido)piperidin-1-yl)-1,2,4-triazine-6-carboxamide

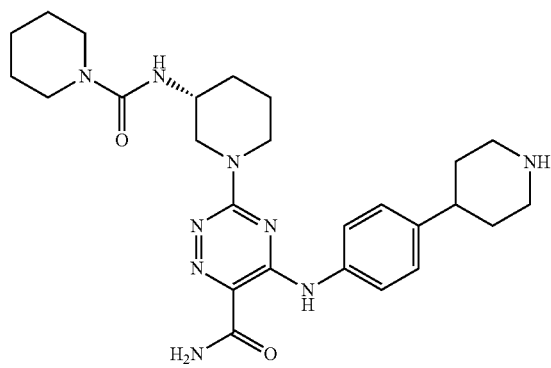

494

The title compound, (R)-5-(4-(piperidin-4-yl)phenylamino)-3-(3-(piperidine-1-carboxamido)piperidin-1-yl)-1,2,4-triazine-6-carboxamide (494), was prepared by the same synthetic scheme illustrated for Example 333 using piperidine-1-carbonyl chloride to replace p-anisic acid/PyBOP. LC-MS (ESI): m/z (M+1) 508.2. UV: λ=261 nm.

Example 336

Synthesis of (R)-5-(4-(1-cyclopentylpiperidin-4-yl)phenylamino)-3-(3-(piperidine-1-carboxamido)piperidin-1-yl)-1,2,4-triazine-6-carboxamide

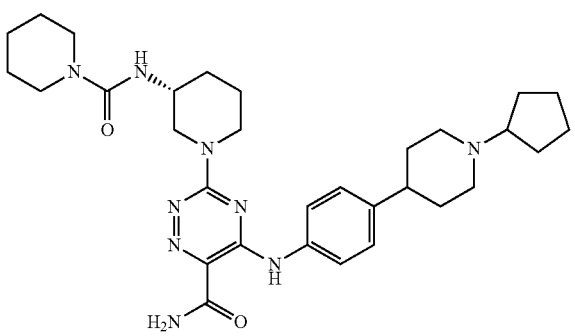

495

The title compound, (R)-5-(4-(1-cyclopentylpiperidin-4-yl)phenylamino)-3-(3-(piperidine-1-carboxamido)piperidin-1-yl)-1,2,4-triazine-6-carboxamide (493), was prepared by the same synthetic scheme illustrated for Example 256 using (R)-5-(4-(piperidin-4-yl)phenylamino)-3-(3-(piperidine-1-carboxamido)piperidin-1-yl)-1,2,4-triazine-6-carboxamide (494). LC-MS (ESI): m/z (M+1) 576.3. UV: λ=265, 323, 337 nm.

Example 337

(R)-5-(4-(1-formylpiperidin-4-yl)phenylamino)-3-(3-(piperidine-1-carboxamido)piperidin-1-yl)-1,2,4-triazine-6-carboxamide

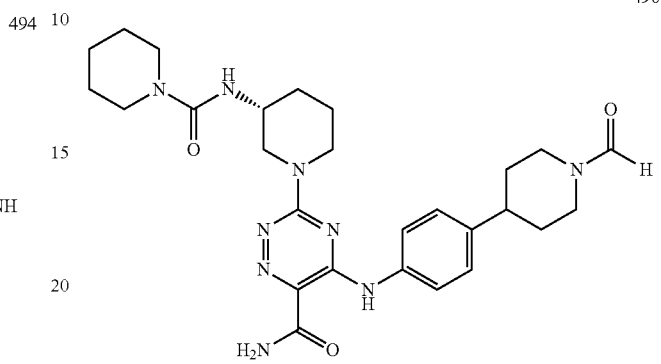

496

(R)-5-(4-(Piperidin-4-yl)phenylamino)-3-(3-(piperidine-1-carboxamido)piperidin-1-yl)-1,2,4-triazine-6-carboxamide hydrochloride (494) (60 mg, 0.11 mmol) was dissolved in 3 mL DMF. To it were added formic acid (25 mg, 0.55 mmol), DIEA (200 μL, 1.10 mmol) and then PyBOP (115 mg, 0.22 mmol). The mixture was stirred at RT for 1 hour, quenched with 0.3 mL TFA, and directly subjected to reverse phase prep HPLC to isolate the title compound, (R)-5-(4-(1-formylpiperidin-4-yl)phenylamino)-3-(3-(piperidine-1-carboxamido)piperidin-1-yl)-1,2,4-triazine-6-carboxamide (496), as HCl salt (37 mg). LC-MS (ESI): m/z (M+1) 536.2. UV: λ=261, 329, 337 nm.

Example 338

(R)-5-(4-(1-acetylpiperidin-4-yl)phenylamino)-3-(3-(piperidine-1-carboxamido)piperidin-1-yl)-1,2,4-triazine-6-carboxamide

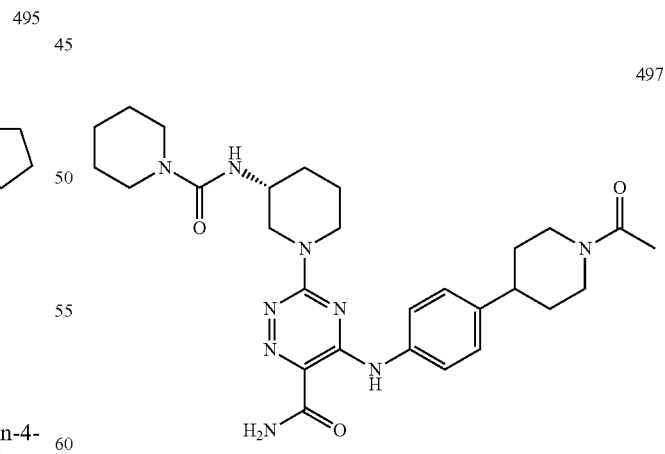

497

(R)-5-(4-(Piperidin-4-yl)phenylamino)-3-(3-(piperidine-1-carboxamido)piperidin-1-yl)-1,2,4-triazine-6-carboxamide hydrochloride (494) (70 mg, 0.13 mmol) was dissolved in 4 mL DMF. To it were added DIEA (230 μL, 1.30 mmol) and then acetic anhydride (37 μL, 0.39 mmol). The mixture was stirred at RT for 1 hour, quenched with 0.3 mL TFA, and directly subjected to reverse phase prep HPLC to isolate the title compound, (R)-5-(4-(1-acetylpiperidin-4-yl)phenylamino)-3-(3-(piperidine-1-carboxamido)piperidin-1-yl)-1,2,4-triazine-6-carboxamide (497), as HCl salt (47 mg). LC-MS (ESI): m/z (M+1) 550.3. UV: λ=261, 329, 337 nm.

Example 339

(R)-3-(3-(piperidine-1-carboxamido)piperidin-1-yl)-5-(4-(1-propionylpiperidin-4-yl)phenylamino)-1,2,4-triazine-6-carboxamide

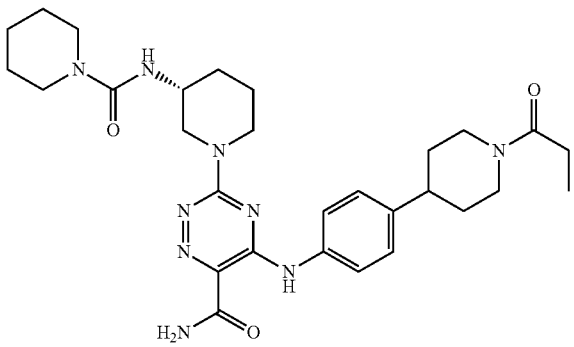

498

(R)-5-(4-(Piperidin-4-yl)phenylamino)-3-(3-(piperidine-1-carboxamido)piperidin-1-yl)-1,2,4-triazine-6-carboxamide hydrochloride (494) (70 mg, 0.13 mmol) was dissolved in 4 mL DMF. To it were added DIEA (230 μL, 1.30 mmol) and then propionyl chloride (36 μL, 0.39 mmol). The mixture was stirred at RT for 1 hour, quenched with 0.3 mL TFA, and directly subjected to reverse phase prep HPLC to isolate the title compound, (R)-3-(3-(piperidine-1-carboxamido)piperidin-1-yl)-5-(4-(1-propionylpiperidin-4-yl)phenylamino)-1,2,4-triazine-6-carboxamide (498), as HCl salt (45 mg). LC-MS (ESI): m/z (M+1) 564.3. UV: λ=263, 329, 338 nm.

Example 340

(R)-3-(3-(piperidine-1-carboxamido)piperidin-1-yl)-5-(4-(1-propionylpiperidin-4-yl)phenylamino)-1,2,4-triazine-6-carboxamide

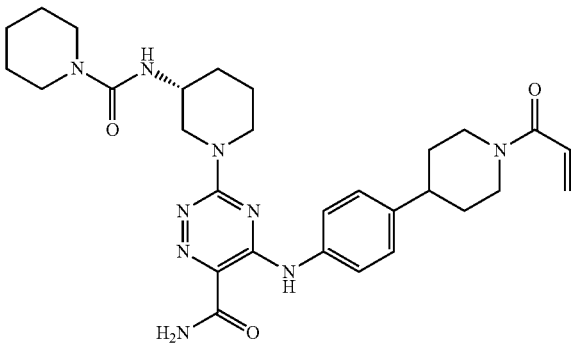

499

(R)-5-(4-(Piperidin-4-yl)phenylamino)-3-(3-(piperidine-1-carboxamido)piperidin-1-yl)-1,2,4-triazine-6-carboxamide hydrochloride (494) (60 mg, 0.11 mmol) was dissolved in 3 mL DMF. To it were added DIEA (190 μL, 1.10 mmol) and then acryloyl chloride (30 mg, 0.33 mmol). The mixture was stirred at RT for 20 min, quenched with 0.3 mL TFA, and directly subjected to reverse phase prep HPLC to isolate the title compound, (R)-3-(3-(piperidine-1-carboxamido)piperidin-1-yl)-5-(4-(1-propionylpiperidin-4-yl)phenylamino)-1,2,4-triazine-6-carboxamide (499), as HCl salt (35 mg). LC-MS (ESI): m/z (M+1) 562.3. UV: λ=258, 329, 337 nm.

Example 341

(R)-5-(4-(1-(2-cyanoacetyl)piperidin-4-yl)phenylamino)-3-(3-(piperidine-1-carboxamido)piperidin-1-yl)-1,2,4-triazine-6-carboxamide

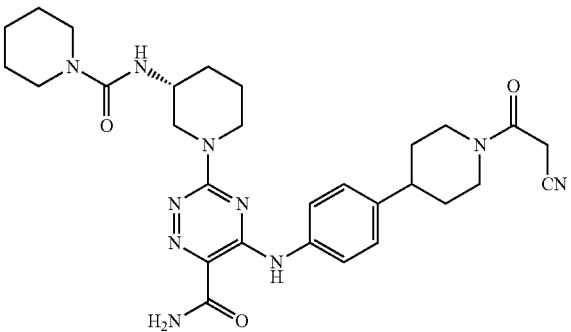

500

(R)-5-(4-(Piperidin-4-yl)phenylamino)-3-(3-(piperidine-1-carboxamido)piperidin-1-yl)-1,2,4-triazine-6-carboxamide hydrochloride (494) (75 mg, 0.14 mmol) was dissolved in 4 mL DMF. To it were added 2-cyanoacetic acid (36 mg, 0.42 mmol), DIEA (250 μL, 1.40 mmol) and then PyBOP (150 mg, 0.28 mmol). The mixture was stirred at RT for 45 min, quenched with 0.3 mL TFA, and directly subjected to reverse phase prep HPLC to isolate the title compound, (R)-5-(4-(1-(2-cyanoacetyl)piperidin-4-yl)phenylamino)-3-(3-(piperidine-1-carboxamido)piperidin-1-yl)-1,2,4-triazine-6-carboxamide (500), as HCl salt (76 mg). LC-MS (ESI): m/z (M+1) 575.3. UV: λ=262, 329, 337 nm.

Example 342

(R)-5-(4-(N,N-dimethylcarbamimidoyl)phenylamino)-3-(3-(4-ethoxybenzamido)piperidin-1-yl)-1,2,4-triazine-6-carboxamide

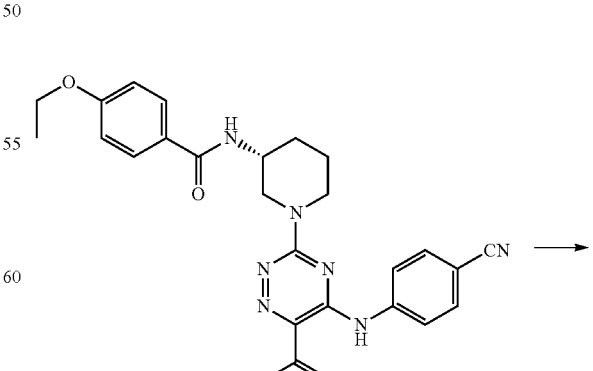

194

-continued

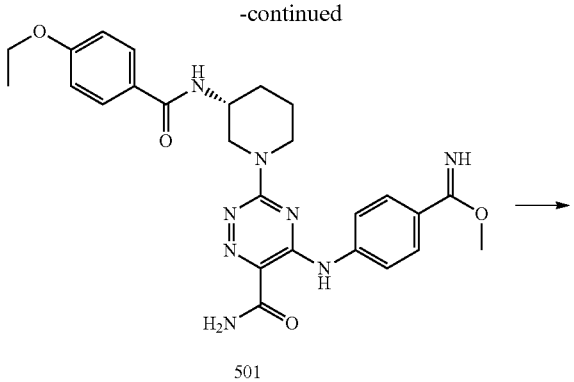

501

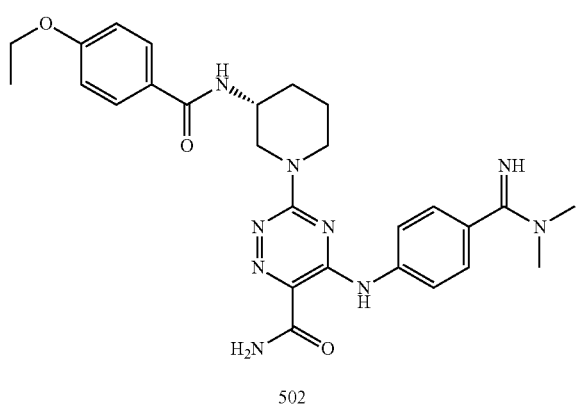

502

(R)-5-(4-Cyanophenylamino)-3-(3-(4-ethoxybenzamido)piperidin-1-yl)-1,2,4-triazine-6-carboxamide (194) (90 mg, 0.18 mmol) was dissolved in 25 mL dry MeOH. It was chilled in an ice bath, and was then charged with HCl gas from a lecture bottle using a long needle to bubble the gas into the bottom of the solution until saturation reached. The resulting mixture was stirred at RT for overnight, and was placed back to the ice bath for repeated HCl gas charging till saturation. The resulting mixture was stirred for another overnight, and concentrated in vacuo to dryness to afford crude (R)-methyl 4-(6-carbamoyl-3-(3-(4-ethoxybenzamido)piperidin-1-yl)-1,2,4-triazin-5-ylamino)benzimidate (501). It was dissolved in 15 mL dry MeOH. To it was added dimethylamine (2M in THF, 1.0 mL). The mixture was sent to 60° C. bath and stirred for 1 hour. It was cooled to RT, concentrated in vacuo, acidified with 0.3 mL TFA, and directly subjected to reverse phase prep HPLC using 5 mM HCl (aq) and next MeCN as mobile phases to isolate the title compound, (R)-5-(4-(N,N-dimethylcarbamimidoyl)phenylamino)-3-(3-(4-ethoxybenzamido)piperidin-1-yl)-1,2,4-triazine-6-carboxamide (502), as HCl salt (59 mg). LC-MS (ESI): m/z (M+1) 532.2. UV: λ=267 nm.

Example 343

Synthesis of (R)-3-(3-(4-ethoxybenzamido)piperidin-1-yl)-5-(4-(imino(pyrrolidin-1-yl)methyl)phenylamino)-1,2,4-triazine-6-carboxamide

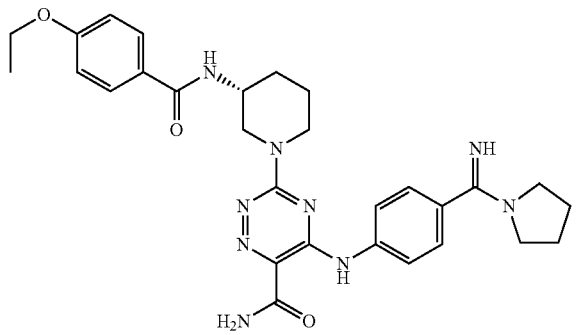

503

The title compound, (R)-3-(3-(4-ethoxybenzamido)piperidin-1-yl)-5-(4-(imino(pyrrolidin-1-yl)methyl)phenylamino)-1,2,4-triazine-6-carboxamide (503), was prepared by the same synthetic scheme illustrated for Example 342 using pyrrolidine. LC-MS (ESI): m/z (M+1) 558.2. UV: λ=268 nm.

Example 344

Synthesis of (R)-3-(3-(4-ethoxybenzamido)piperidin-1-yl)-5-(4-(1-methyl-4,5-dihydro-1H-imidazol-2-yl)phenylamino)-1,2,4-triazine-6-carboxamide

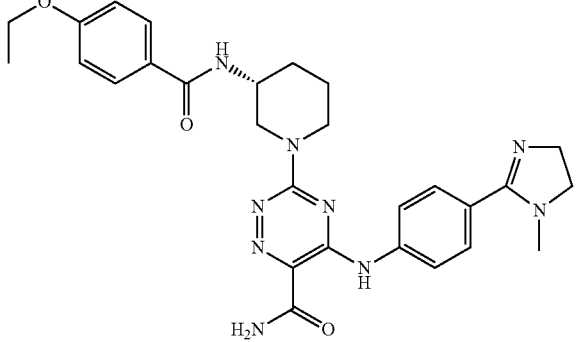

504

The title compound, (R)-3-(3-(4-ethoxybenzamido)piperidin-1-yl)-5-(4-(1-methyl-4,5-dihydro-1H-imidazol-2-yl)phenylamino)-1,2,4-triazine-6-carboxamide (504), was prepared by the same synthetic scheme illustrated for Example 342 using N-methylethylenediamine. LC-MS (ESI): m/z (M+1) 532.2. UV: λ=267 nm.

Example 345

(R)-3-(1-but-2-ynoylpyrrolidin-3-ylamino)-5-(4-(morpholine-4-carbonyl)phenylamino)-1,2,4-triazine-6-carboxamide

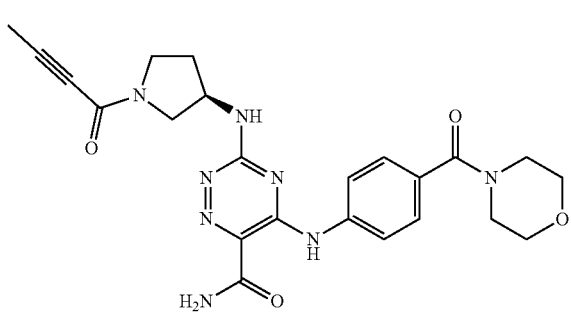

505

To a solution of (R)-5-(4-(morpholine-4-carbonyl)phenylamino)-3-(pyrrolidin-3-ylamino)-1,2,4-triazine-6-carboxamide (83) (90 mg, 0.22 mmol) in NMP (4 mL) were 2-butynoic acid (55 mg, 0.66 mmol), DIEA (380 µL, 2.2 mmol) and then PyBOP (230 mg, 0.44 mmol). The mixture was stirred at RT for 30 min, quenched with TFA (0.6 mL), diluted with 2 mL water, and subjected to reverse phase preparative HPLC using 0.1% formic acid in water and neat MeCN to isolate the title compound, (R)-3-(1-but-2-ynoylpyrrolidin-3-ylamino)-5-(4-(morpholine-4-carbonyl)phenylamino)-1,2,4-triazine-6-carboxamide (505) as formic acid salt. LC-MS (ESI): m/z (M+1) 479.1. UV: λ=280 nm. Proton NMR (CD$_3$OD): δ 7.87 (2H, m), 7.47 (2H, m), 4.56 (1H, m), 4.07 (1H, m), 3.88-3.77 (2H, m), 3.75-3.44 (9H, m), 2.37 (1H, m), 2.15 (1H, m), 2.05 (3H, s) ppm.

Example 346

Synthesis of 3-(4-(2-methoxyethoxyl)phenylamino)-5-((R)-3-(3-((S)-1-phenylethyl)ureido)piperidin-1-yl)pyrazine-2-carboxamide

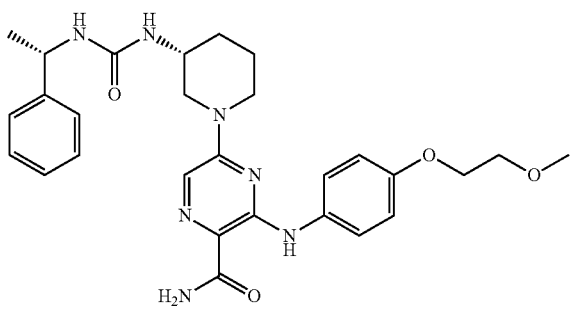

506

To a solution of (R)-5-(3-(3,3-dimethylureido)piperidin-1-yl)-3-(4-(2-methoxyethoxyl)phenylamino)pyrazine-2-carboxamide (235) (14 mg, 0.03 mmol) in 1 mL NMP in a sealed tube added (S)-(−)-1-phenylethylamine (50 µL). The mixture was stirred in 100° C. bath for overnight. It was acidified with 0.5 mL TFA, and subjected to reverse phase preparative HPLC using 5 mM HCl (aq) and neat MeCN to isolate the title compound, 3-(4-(2-methoxyethoxyl)phenylamino)-5-((R)-3-(3-((S)-1-phenylethyl)ureido)piperidin-1-yl)pyrazine-2-carboxamide (506) as HCl salt (9.5 mg). LC-MS (ESI): m/z (M+1) 534.2. UV: λ=268, 276, 304, 339, 375 nm.

Example 347

Synthesis of 3-(4-(2-methoxyethoxyl)phenylamino)-5-((R)-3-(3-((R)-1-phenylethyl)ureido)piperidin-1-yl)pyrazine-2-carboxamide

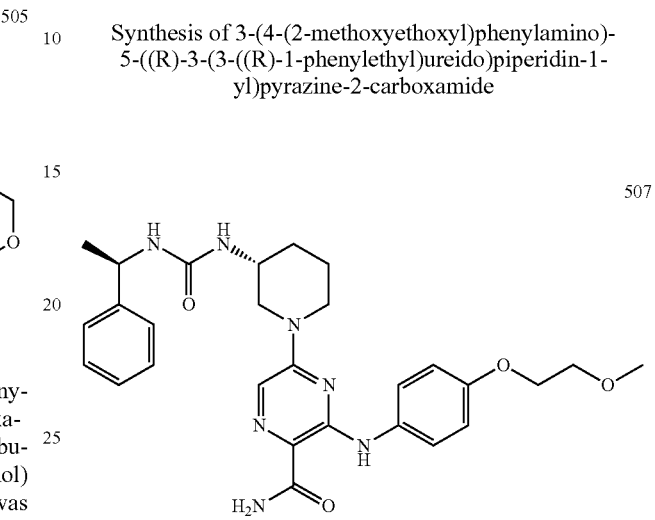

507

The title compound, 3-(4-(2-methoxyethoxyl)phenylamino)-5-((R)-3-(3-((R)-1-phenylethyl)ureido)piperidin-1-yl)pyrazine-2-carboxamide (507), was prepared by the same synthetic scheme illustrated for Example 346 using (R)-(+)-1-phenylethylamine. LC-MS (ESI): m/z (M+1) 534.3. UV: λ=268, 276, 304, 338, 373 nm.

Example 348

Synthesis of (R)-3-(5-carbamoyl-6-(3-methylisothiazol-5-ylamino)pyrazin-2-ylamino)-N,N-dimethylazepane-1-carboxamide

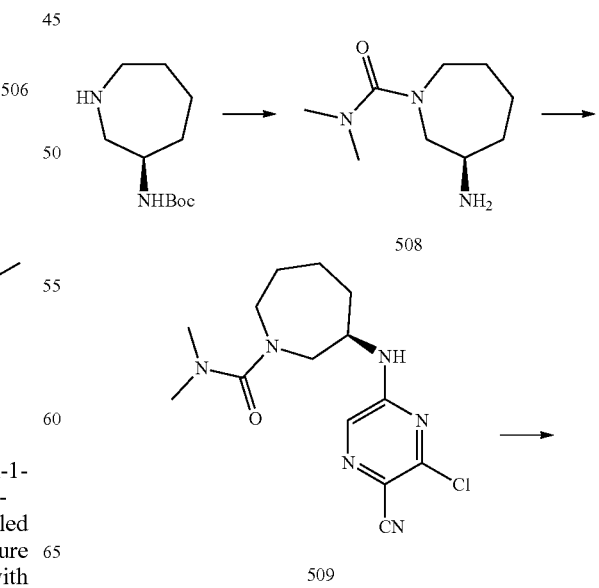

508

509

-continued

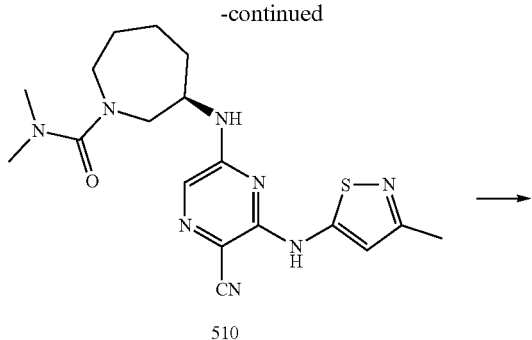

510

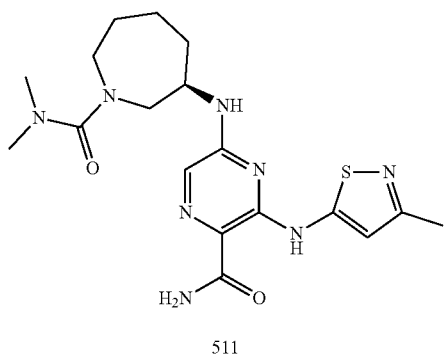

511

(R)-tert-Butyl-azepan-3-ylcarbamate (250 mg, 1.17 mmol) was dissolved in DMF (0.5 mL), and DIEA (0.41 mL, 2.3 mmol). Dimethylcarbamoyl chloride (0.16 mL, 1.8 mmol) was then added and the reaction was stirred at RT for 1 hour. An additional aliquot of dimethylcarbamoyl chloride (0.16 mL, 1.8 mmol), DIEA (0.41 mL, 2.3 mmol), and DMF (0.5 mL) were added and the reaction was stirred for 6 hours. The solution was diluted with water (1 mL) and the solvents were removed under reduced pressure. The residue was dissolved in a mixture of EtOAc and H₂O and the aqueous layer was extracted with EtOAc (×2). The organic extracts were combined, washed with brine, dried, and concentrated. The crude material (300 mg) was dissolved in HCl/dioxane (4 M, 2 mL) and stirred at RT for 1 hour. The solid that formed during the reaction was removed by filtration, suspended in EtOAc, and washed with 1 M NaOH (aq). The aqueous solution was then extracted with EtOAc (×3) and the combined organic extracts were washed with brine, dried, and concentrated to give (R)-3-amino-N,N-dimethylazepane-1-carboxamide (508) (~200 mg crude).

(R)-3-Amino-N,N-dimethylazepane-1-carboxamide (508) (~200 mg crude) was dissolved in THF (7 mL), and DIEA (0.30 mL, 1.7 mmol) was added, followed by 3,5-dichloropyrazine-2-carbonitrile (100 mg, 0.57 mmol). The reaction was stirred at RT for 12 hours. The solvents were removed under reduced pressure, and the residue was purified by silica column chromatography (MeOH, DCM) to give (R)-3-(6-chloro-5-cyanopyrazin-2-ylamino)-N,N-dimethylazepane-1-carboxamide (509) (53 mg, 0.16 mmol, 14% yield over 3 steps).

(R)-3-(6-Chloro-5-cyanopyrazin-2-ylamino)-N,N-dimethylazepane-1-carboxamide (509) (53 mg, 0.16 mmol) was combined with 3-methylisothiazol-5-amine hydrochloride (45 mg, 0.39 mmol), Pd(OAc)₂ (14 mg, 0.062 mmol), BINAP (36 mg, 0.058 mmol), and Cs₂CO₃ (196 mg, 0.601 mmol). The solids were suspended in dioxane (10 mL degassed for 10 minutes with Nitrogen sparge) and the resulting suspension was stirred at 115° C. for 4 hours. The reaction mixture was cooled to RT, filtered, and purified by prep-TLC (EtOAc/DCM) to give (R)-3-(5-cyano-6-(3-methylisothiazol-5-ylamino)pyrazin-2-ylamino)-N,N-dimethylazepane-1-carboxamide (510) (20 mg, 0.050 mmol, 31% yield).

(R)-3-(5-Cyano-6-(3-methylisothiazol-5-ylamino) pyrazin-2-ylamino)-N,N-dimethylazepane-1-carboxamide (510) (20 mg, 0.050 mmol) was dissolved in 5 mL TFA, and the solution was heated to 80° C. Concentrated H₂SO₄ (7 drops) was added dropwise, and the reaction was allowed to stir for 30 min Additional H₂SO₄ (15 drops) was added dropwise and the reaction was allowed to stir for 30 minutes. The reaction was cooled to RT, and diluted with 2 mL water and 2 mL methanol. The mixture was then directly subjected to reverse phase preparative HPLC using 5 mM HCl (aq) and neat MeCN as mobile phases, and lyophilized to give (R)-3-(5-carbamoyl-6-(3-methylisothiazol-5-ylamino)pyrazin-2-ylamino)-N,N-dimethylazepane-1-carboxamide (511) (16 mg, 0.038 mmol, 76% yield). LC-MS (ESI): m/z (M+1) 419.6. Proton NMR (DMSO-d₆): δ 12.27 (1H, s), 8.05 (1H, s), 7.81 (1H, s), 7.48-7.44 (2H, m), 6.85 (1H, s), 4.46 (1H, m), 3.35 (4H, m), 2.70 (6H, s), 2.30 (3H, s), 2.02 (1H, m), 1.79 (2H, m), 1.70 (1H, m), 1.57 (2H, m) ppm.

Example 349

Synthesis of (R)-3-(4-(1-cyclopentylpiperidin-4-yl) phenylamino)-5-(3-(cyclopropanecarboxamido)-2-methylpiperidin-1-yl)pyrazine-2-carboxamide

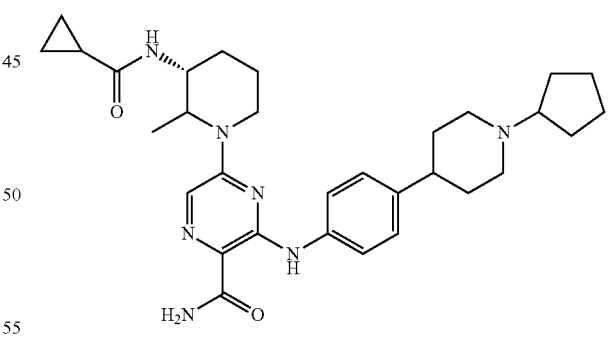

512

The title compound, (R)-3-(4-(1-cyclopentylpiperidin-4-yl)phenylamino)-5-(3-(cyclopropanecarboxamido)-2-methylpiperidin-1-yl)pyrazine-2-carboxamide (512), was prepared by the same synthetic scheme illustrated for Example 234 using (R)-tert-butyl 2-methylpiperidin-3-ylcarbamate (307) and cyclopropanecarbonyl chloride. LC-MS (ESI): m/z (M+1) 546.8. UV: λ=268, 277, 306, 335, 372 nm.

Example 350

Synthesis of (R)-3-(cyclopropylamino)-5-(3-(3-methyl-3-phenylureido)piperidin-1-yl)pyrazine-2-carboxamide

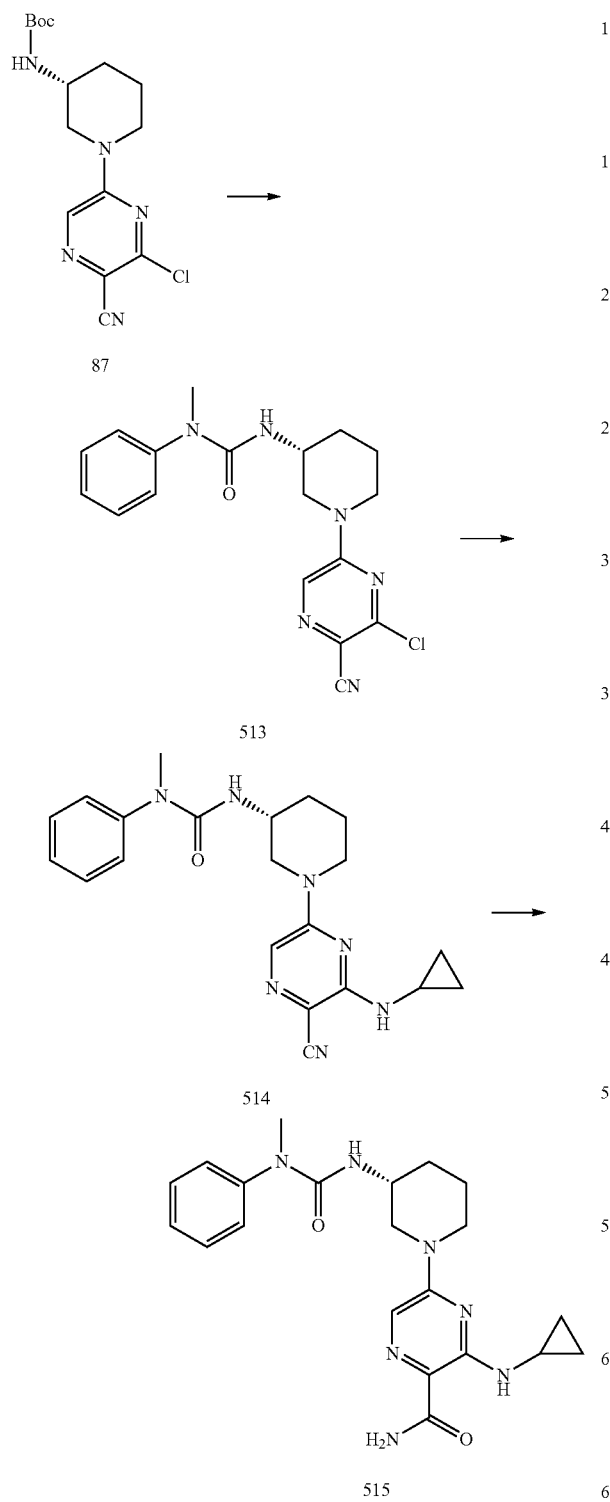

(R)-tert-Butyl 1-(6-chloro-5-cyanopyrazin-2-yl)piperidin-3-ylcarbamate (87, 400 mg, 1.20 mmol) was treated with 10 mL 4N HCl in dioxane for 2 hours. The mixture was concentrated in vacuo to dryness. It was dissolved in 3 mL DMF/15 mL dioxane. To it were added DIEA (2.09 mL, 12 mmol) and then N-methyl-N-phenylcarbamoyl chloride (610 mg, 3.6 mmol). The mixture was stirred for 3 hours, diluted with 100 mL EtOAc, washed with water ×3, dried, concentrated and subjected to flash column with 0 to 4% MeOH in DCM to isolate (R)-3-(1-(6-chloro-5-cyanopyrazin-2-yl)piperidin-3-yl)-1-methyl-1-phenylurea (513, 530 mg) in quantitative yield.

(R)-3-(1-(6-Chloro-5-cyanopyrazin-2-yl)piperidin-3-yl)-1-methyl-1-phenylurea (513, 100 mg) was dissolved in 4 mL DMSO in a sealed tube. To it was added cyclopropylamine (210 μL, 3 mmol) and the mixture was stirred in 70° C. bath for 16 hours. It was diluted with 60 mL EtOAc, washed with water ×2, concentrated in vacuo to afford crude (R)-3-(1-(5-cyano-6-(cyclopropylamino)pyrazin-2-yl)piperidin-3-yl)-1-methyl-1-phenylurea (514). It was dissolved in 4 mL MeOH and 2 mL DMSO. To it were added one NaOH solid pellet (about 50-100 mg) and then 0.5 mL 30% $H_2O_2$. The mixture was stirred at RT for 45 min, diluted with 10 mL MeCN, stirred for 5 min, concentrated on rotavap. The residue was treated with 0.3 mL TFA, and directly subjected to reverse phase prep HPLC using 5 mM HCl (aq) and neat MeCN as mobile phases to isolate (R)-3-(cyclopropylamino)-5-(3-(3-methyl-3-phenylureido)piperidin-1-yl)pyrazine-2-carboxamide (515) as HCl salt (74 mg, 67% yield). LC-MS (ESI): m/z (M+1) 410.3. UV: λ=283, 317, 369 nm.

Example 351

Synthesis of (R)-3-(cyclopentylamino)-5-(3-(3-methyl-3-phenylureido)piperidin-1-yl)pyrazine-2-carboxamide

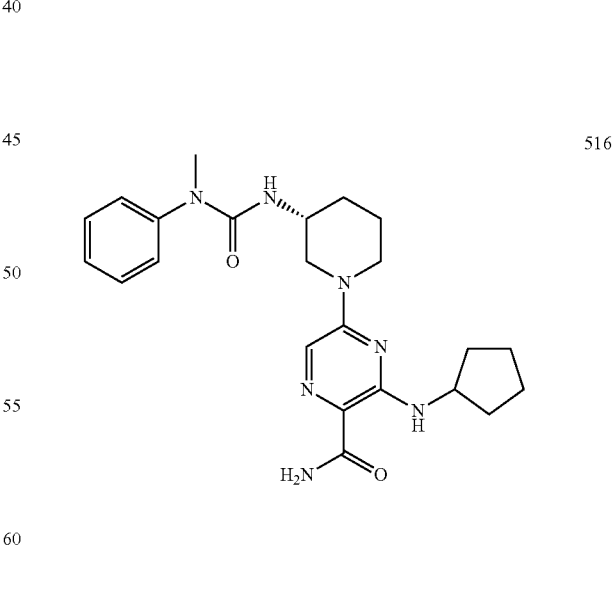

The title compound, (R)-3-(cyclopentylamino)-5-(3-(3-methyl-3-phenylureido)piperidin-1-yl)pyrazine-2-carboxamide (516), was prepared by the same synthetic scheme illustrated for Example 350 using cyclopentylamine. It was

Example 352

Synthesis of (R)-5-(3-(3-(3-chloro-5-(trifluoromethyl)phenyl)-3-methylureido)piperidin-1-yl)-3-(cyclopropylamino)pyrazine-2-carboxamide

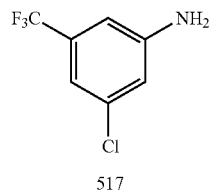

517

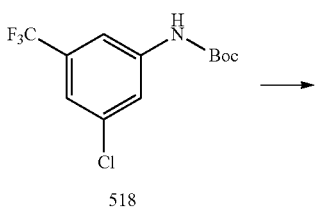

518

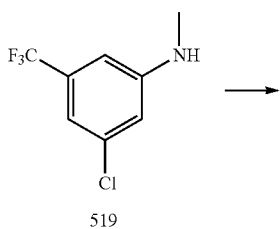

519

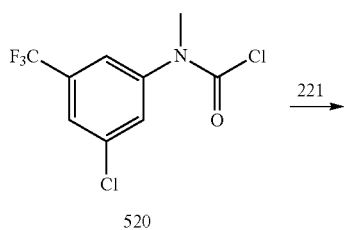

520

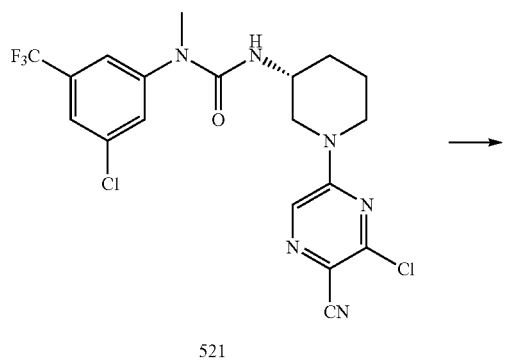

521

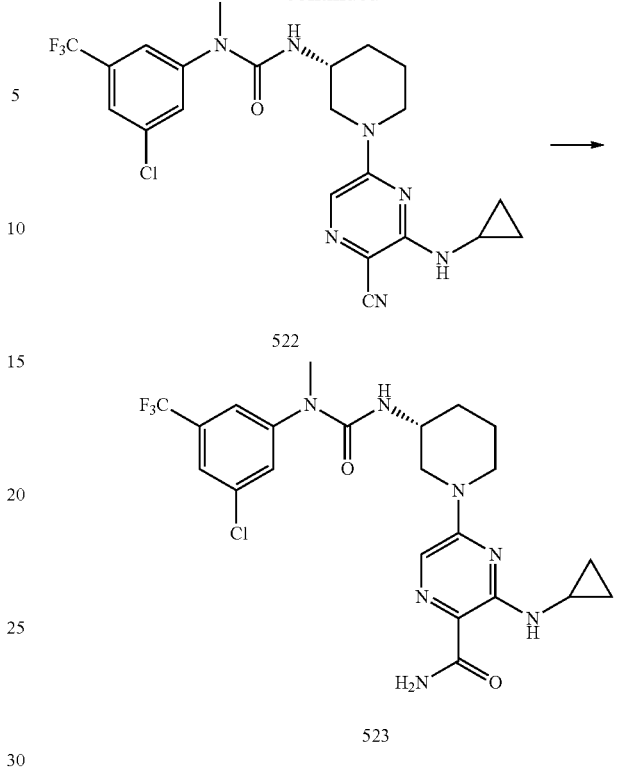

3-Chloro-5-trifluoromethylaniline (517, 3.66 g, 18.7 mmol) was dissolved in 70 mL THF and stirred in an ice bath. To it were added BoC₂O (4.48 g, 20.6 mmol) and DMAP (2.51 g, 20.6 mmol). The mixture was stirred for overnight, and was concentrated in vacuo. The residue was taken into 200 mL EtOAc, washed with water ×3, dried, rotavaped, and subjected to silica flash column using 1% MeOH in DCM to get tert-butyl 3-chloro-5-(trifluoromethyl)phenylcarbamate (518, 3.37 g, 61%) as a white solid. It was dissolved in 100 mL dry THF and treated with NaH (60% in mineral oil, 910 mg, 22.8 mmol) at RT for 15 min and then iodomethane (1.42 mL, 22.8 mmol) was added. The mixture was stirred for overnight, concentrated, taken into 200 mL EtOAc, washed with water ×2, dried, concentrated, and subjected to silica flash column using 0 to 5% EtOAc in DCM to isolate the methylation product as an oil. It was treated with 1:1 TFA/DCM (10 mL/10 mL) at RT for 3 hours, concentrated in vacuo, taken into 200 mL EtAOc and 50 mL 1N NaOH. The organic phase was separated, washed with water, dried, subjected to silica flash column with 1% MeOH in DCM to isolate 3-chloro-N-methyl-5-(trifluoromethyl)aniline (519, 1.76 g, 53%) as an oil.

3-Chloro-N-methyl-5-(trifluoromethyl)aniline (519, 1.24 g, 5.9 mmol) was dissolved in 15 mL dry toluene. To it was added Et₃N (1.1 mL, 7.9 mmol), and the mixture was stirred in ice bath. To it was drop-wise added a pre-made solution of triphosgene (2.46 g, 8.3 mmol) in 7.5 mL dry toluene. The mixture was then stirred in ice bath for 3 hours. EtOAc (120 mL) and water (50 mL) were then poured into the mixture, and the organic phase was separated. It was washed with saturated NaHCO₃ (aq) solution, dried, concentrated in vacuo to afford crude 3-chloro-5-(trifluoromethyl)phenyl(methyl) carbamic chloride (520) as an oil.

(R)-tert-Butyl 1-(6-chloro-5-cyanopyrazin-2-yl)piperidin-3-ylcarbamate (87, 950 mg, 2.8 mmol) was treated with 2:1 DCM/TFA (20 mL/10 mL) at RT for 20 min. The mixture was concentrated in vacuo to dryness as crude (R)-5-(3-aminopiperidin-1-yl)-3-chloropyrazine-2-carbonitrile (221, TFA salt). It was dissolved in 18 mL DMF. To it were added DIEA (3.9 mL, 22.4 mmol) and then the crude 520 (estimated 5.9 mmol) prepared. The mixture was stirred at RT for 1.5 hour, diluted with 120 mL EtOAc, washed with water and saturated NaHCO$_3$ (aq) solution, dried, concentrated and subjected to silica flash column using 0 to 3.5% MeOH in DCM to isolate (R)-1-(3-chloro-5-(trifluoromethyl)phenyl)-3-(1-(6-chloro-5-cyanopyrazin-2-yl)piperidin-3-yl)-1-methylurea (521) in quantitative yield.

(R)-1-(3-Chloro-5-(trifluoromethyl)phenyl)-3-(1-(6-chloro-5-cyanopyrazin-2-yl)piperidin-3-yl)-1-methylurea (521, 50 mg, 0.10 mmol) was dissolved in 2 mL NMP in a sealed tube. To it was added cyclopropylamine (210 µL, 3.0 mmol), and the mixture was stirred in 70° C. bath for overnight. It was diluted with 50 mL EtOAc, washed with saturated NH$_4$Cl (aq) solution and water ×2, concentrated in vacuo to give crude (R)-1-(3-chloro-5-(trifluoromethyl)phenyl)-3-(1-(5-cyano-6-(cyclopropylamino)pyrazin-2-yl)piperidin-3-yl)-1-methylurea (522). It was dissolved in 10 mL MeOH and 2 mL DMSO. To it were added one NaOH solid pellet (about 50-100 mg) and then 0.5 mL 30% H$_2$O$_2$. The mixture was stirred at RT for 1 hour, diluted with 10 mL MeCN, stirred for 5 min, concentrated on rotavap. The residue was treated with 0.3 mL TFA, and directly subjected to reverse phase prep HPLC using 5 mM HCl (aq) and neat MeCN as mobile phases to isolate (R)-5-(3-(3-(3-chloro-5-(trifluoromethyl)phenyl)-3-methylureido)piperidin-1-yl)-3-(cyclopropylamino)pyrazine-2-carboxamide (523 as HCl salt (32 mg, 62% yield). LC-MS (ESI): m/z (M+1) 512.2 (chloro pattern). UV: λ=282, 318, 369 nm. Proton NMR (CD$_3$OD): δ 7.53 (1H, m), 7.51 (1H, broad s), 7.48 (1H, broad s), 7.46 (1H, s), 3.98 (1H, dd, J=13.5; 3.5 Hz), 3.90 (1H, m), 3.81 (1H, m), 3.66 (1H, m), 3.52 (1H, m), 3.25 (3H, s), 2.71 (1H, m), 1.96 (1H, m), 1.78 (2H, m), 1.62 (1H, m), 0.76 (2H, m), 0.45 (2H, m) ppm.

Example 353

Synthesis of (R)-5-(3-(3-(3-chloro-5-(trifluoromethyl)phenyl)-3-methylureido)piperidin-1-yl)-3-(tetrahydro-2H-pyran-4-ylamino)pyrazine-2-carboxamide

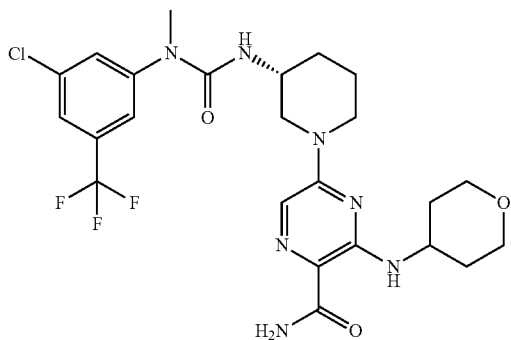

525

The title compound, (R)-5-(3-(3-(3-chloro-5-(trifluoromethyl)phenyl)-3-methylureido)piperidin-1-yl)-3-(tetrahydro-2H-pyran-4-ylamino)pyrazine-2-carboxamide (525), was prepared by the same synthetic scheme illustrated for Example 352 using tetrahydro-2H-pyran-4-amine. It was isolated as HCl salt using reverse phase prep HPLC. LC-MS (ESI): m/z (M+1) 556.2 (chloro pattern). UV: λ=281, 317, 369 nm.

Example 354

Synthesis of (R)-5-(3-(3-(tetrahydro-2H-pyran-4-yl)ureido)piperidin-1-yl)-3-(tetrahydro-2H-pyran-4-ylamino)pyrazine-2-carboxamide

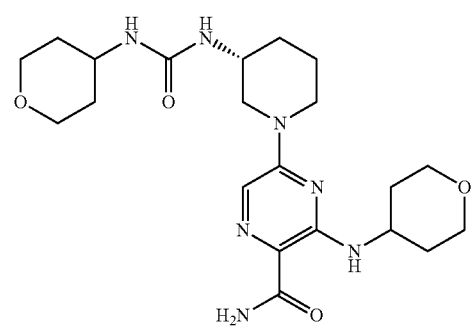

526

The title compound, (R)-5-(3-(3-(tetrahydro-2H-pyran-4-yl)ureido)piperidin-1-yl)-3-(tetrahydro-2H-pyran-4-ylamino)pyrazine-2-carboxamide (526), was found and isolated as a major by-product during the final step of the preparation of (R)-5-(3-(3-(3-chloro-5-(trifluoromethyl)phenyl)-3-methylureido)piperidin-1-yl)-3-(tetrahydro-2H-pyran-4-ylamino)pyrazine-2-carboxamide (525). It was isolated as HCl salt using reverse phase prep HPLC. LC-MS (ESI): m/z (M+1) 448.3. UV: λ=281, 317, 369 nm.

Example 355a

Btk In Vitro Inhibitory Activity (Method A)

The Btk IC$_{50}$s of compounds disclosed herein is determined in both a cellular kinase assay and in a cellular functional assay of BCR-induced calcium flux as described below.

Btk kinase activity is determined using a time-resolved fluorescence resonance energy transfer (TR-FRET) methodology. Measurements are performed in a reaction volume of 50 µL using 96-well assay plates. Kinase enzyme, inhibitor, ATP (at the K$_m$ for the kinase), and 1 µM peptide substrate (Biotin-AVLESEEELYSSARQ-NH$_2$) are incubated in a reaction buffer composed of 20 mM Tris, 50 mM NaCl, MgCl$_2$ (5-25 mM depending on the kinase), MnCl$_2$ (0-10 mM), 1 mM DTT, 0.1 mM EDTA, 0.01% bovine serum albumin, 0.005% Tween-20, and 10% DMSO at pH 7.4 for one hour. The reaction is quenched by the addition of 1.2 equivalents of EDTA (relative to divalent cation) in 25 µL of 1× Lance buffer (Perkin-Elmer). Streptavidin-APC (Perkin-Elmer) and Eu-labeled p-Tyr100 antibody (Perkin-Elmer) in 1× Lance buffer are added in a 25 µL volume to give final concentrations of 100 nM and 2.5 nM, respectively, and the mixture is allowed to incubate for one hour. The TR-FRET signal is measured on a multimode plate reader with an excitation wavelength (λ$_{Ex}$) of 330 nm and detection wavelengths (λ$_{Em}$) of 615 and 665 nm. Activity is determined by the ratio of the fluorescence at 665 nm to that at 615 nm. For each compound, enzyme activity is measured at various concentrations of compound. Negative control reactions are performed in the absence of inhibitor in replicates of six, and two no-enzyme controls are used to determine baseline fluorescence levels Inhibition constants, $K_i(app)$, were obtained using the program BatchK$_i$ (Kuzmic et al. (2000), *Anal. Biochem.* 286:45-50). IC$_{50}$s are obtained according to the equation:

$$IC_{50} = \{Ki(app)/(1+[ATP]/K_m^{ATP})\} + [E]_{total}\frac{1}{2};$$

For all kinases, $[ATP] = K_m^{ATP}$, $[Btk]_{total}1 = 0.5$ nM and $[Lck]_{total}1 = 6$ nM.

Example 355b

Btk In Vitro Inhibitory Activity (Method B)

Kinase activity is measured in vitro using electrophoretic mobility shift assay. The kinase reactions are assembled in a total volume of 25 μL in 384 well plates. The reactions comprise: BTK enzyme (1 nM, N-terminal His6-tagged, recombinant, full-length, human BTK purified from baculovirus Sf21 insect cell system), inhibitor, ATP (16 μM, the apparent K$_m$ for the kinase), fluorescently labeled peptide substrate (1 μM, FAM-GEEPLYWSFPAKKK-NH2) in a reaction buffer composed of 100 mM HEPES, pH7.5, 5 mM MgCl$_2$ 1 mM DTT, 0.1% bovine serum albumin, 0.01% Triton X-100, and 1% DMSO. The reaction is incubated for one hour and is quenched by the addition of 45 μL of termination buffer (100 mM HEPES, pH7.5, 0.01% Triton X-100, 30 mM EDTA). The terminated reactions are analyzed using 12 channel LabChip® 3000 microfluidic detection instrument (Caliper Life Sciences). The enzymatic phosphorylation of the peptide results in a change in net charge, enabling electrophoretic separation of product from substrate peptide. As substrate and product peptides are separated, two peaks of fluorescence are observed. Change in the relative fluorescence intensity of the substrate and product peaks is the parameter measured, reflecting enzyme activity. In the presence of an inhibitor, the ratio between product and substrate is altered: the signal of the product decreases, while the signal of the substrate increases.

Activity in each sample is determined as the product to sum ratio (PSR): P/(S+P), where P is the peak height of the product peptide and S is the peak height of the substrate peptide. For each compound, enzyme activity is measured at various concentrations (12 concentrations of compound spaced by 3× dilution intervals). Negative control samples (0%-inhibition in the absence of inhibitor) and positive control samples (100%-inhibition, in the presence of 20 mM EDTA) are assembled in replicates of four and are used to calculate %-inhibition values for each inhibitor at each concentration. Percent inhibition (P$_{inh}$) is determined using following equation:

$$P_{inh} = (PSR_{0\%} - PSR_{inh})/(PSR_{0\%} - PSR_{100\%}) * 100,$$

where PSR$_{inh}$ is the product sum ratio in the presence of inhibitor, PSR$_{0\%}$ is the average product sum ration in the absence of inhibitor and PSR$_{100\%}$ is the average product sum ratio in 100%-inhibition control samples;

The IC50 values of inhibitors are determined by 4 parameter sigmoidal dose-response model fitting of the inhibition curves (P$_{inh}$ versus inhibitor concentration) using XLfit 4 software.

Example 355c

Btk In Vitro Inhibitory Activity (Method C)

Human Btk kinase (Genbank accession # NP_000052) was purified from insect cells as a full-length construct containing a N-terminal 6×-His tag. Btk kinase activity was determined using a radiometric filter binding assay. Measurements are performed in a low μL reaction volume 384-well assay plates. BTK enzyme (8 nM final in reaction), inhibitor (at requested doses), and 0.2 mg/mL peptide substrate (Poly-Glu-Tyr, 4:1 ratio) are incubated in a reaction buffer composed of 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO for 15 min. followed by addition of 1 μM ATP to start the assay. Kinase reactions are carried out for 120 min. at room temperature. The reaction was stopped by spotting of reaction sample onto P81 cationic exchange paper (Whatman). Unbound phosphate was removed by extensive washing of filters in 0.75% Phosphoric acid. After subtraction of background derived from control reactions containing inactive enzyme (via addition of saturating EDTA), kinase activity data for each dose of compound tested was expressed as the percent of remaining kinase activity in test samples compared to vehicle (dimethyl sulfoxide) reactions. IC$_{50}$ values and curve fits were obtained using Prism (GraphPad Software).

The degree of Btk inhibition was determined using one of the methods outlined in Example 355a, 355b and 355c.

TABLE 1

BTK IC$_{50}$ Values for Exemplary Compounds of the Invention

| Example # | BTK IC$_{50}$ |
|---|---|
| 1 | D |
| 2 | A |
| 3 | B |
| 4 | A |
| 5 | A |
| 6 | A |
| 7 | B |
| 8 | A |
| 9 | A |
| 10 | A |
| 11 | A |
| 12 | A |
| 13 | B |
| 14 | A |
| 15 | B |
| 16 | A |
| 17 | A |
| 18 | B |
| 19 | A |
| 20 | B |
| 21 | B |
| 22 | A |
| 23 | B |
| 24 | B |
| 25 | B |
| 26 | B |
| 27 | B |
| 28 | B |
| 29 | B |
| 30 | B |
| 31 | B |
| 32 | B |
| 33 | B |
| 34 | B |
| 35 | B |
| 36 | B |
| 37 | B |
| 38 | B |
| 39 | B |
| 40 | B |
| 41 | A |
| 42 | C |
| 43 | C |
| 44 | B |
| 45 | C |
| 46 | B |

TABLE 1-continued

BTK IC$_{50}$ Values for Exemplary Compounds of the Invention

| Example # | BTK IC$_{50}$ |
|---|---|
| 47 | A |
| 48 | C |
| 49 | C |
| 50 | C |
| 51 | C |
| 52 | C |
| 53 | D |
| 54 | D |
| 55 | A |
| 56 | C |
| 57 | C |
| 58 | B |
| 59 | B |
| 60 | C |
| 61 | D |
| 62 | B |
| 63 | A |
| 64 | A |
| 65 | A |
| 66 | A |
| 67 | A |
| 68 | C |
| 69 | B |
| 70 | A |
| 71 | B |
| 72 | A |
| 73 | A |
| 74 | A |
| 75 | A |
| 76 | C |
| 77 | B |
| 78 | A |
| 79 | B |
| 80 | B |
| 81 | B |
| 82 | B |
| 83 | C |
| 84 | B |
| 85 | B |
| 86 | A |
| 87 | B |
| 88 | A |
| 89 | A |
| 90 | B |
| 91 | B |
| 92 | A |
| 93 | A |
| 94 | A |
| 95 | B |
| 96 | B |
| 97 | B |
| 98 | B |
| 99 | A |
| 100 | A |
| 101 | A |
| 102 | A |
| 103 | A |
| 104 | B |
| 105 | A |
| 106 | A |
| 107 | A |
| 108 | C |
| 109 | C |
| 110 | B |
| 111 | B |
| 112 | B |
| 113 | B |
| 114 | C |
| 115 | A |
| 116 | B |
| 117 | A |
| 118 | B |
| 119 | B |
| 120 | B |
| 121 | B |
| 122 | A |
| 123 | A |
| 124 | A |
| 125 | A |
| 126 | A |
| 127 | B |
| 128 | A |
| 129 | A |
| 130 | A |
| 131 | A |
| 132 | A |
| 133 | A |
| 134 | A |
| 135 | A |
| 136 | B |
| 137 | B |
| 138 | A |
| 139 | A |
| 140 | A |
| 141 | A |
| 142 | B |
| 143 | B |
| 144 | A |
| 145 | A |
| 146 | B |
| 147 | A |
| 148 | A |
| 149 | B |
| 150 | A |
| 151 | A |
| 152 | A |
| 153 | A |
| 154 | A |
| 155 | A |
| 156 | A |
| 157 | A |
| 158 | A |
| 159 | C |
| 160 | B |
| 161 | A |
| 162 | A |
| 163 | A |
| 164 | A |
| 165 | A |
| 166 | A |
| 167 | A |
| 168 | A |
| 169 | A |
| 170 | A |
| 171 | A |
| 172 | A |
| 173 | B |
| 174 | B |
| 175 | A |
| 176 | A |
| 177 | A |
| 178 | A |
| 179 | B |
| 180 | C |
| 181 | B |
| 182 | C |
| 183 | C |
| 184 | D |
| 185 | C |
| 186 | B |
| 187 | B |
| 188 | A |
| 189 | B |
| 190 | B |
| 191 | B |
| 192 | B |
| 193 | B |
| 194 | A |
| 195 | A |
| 196 | B |

TABLE 1-continued

BTK IC$_{50}$ Values for Exemplary Compounds of the Invention

| Example # | BTK IC$_{50}$ |
|---|---|
| 197 | A |
| 198 | B |
| 199 | A |
| 200 | A |
| 201 | B |
| 202 | A |
| 203 | A |
| 204 | B |
| 205 | B |
| 206 | A |
| 207 | B |
| 208 | A |
| 209 | B |
| 210 | A |
| 211 | B |
| 212 | C |
| 213 | B |
| 214 | A |
| 215 | A |
| 216 | B |
| 217 | B |
| 218 | A |
| 219 | B |
| 220 | B |
| 221 | A |
| 222 | A |
| 223 | A |
| 224 | A |
| 225 | A |
| 226 | B |
| 227 | B |
| 228 | B |
| 229 | B |
| 230 | B |
| 231 | C |
| 232 | A |
| 233 | C |
| 234 | A |
| 235 | C |
| 236 | A |
| 237 | A |
| 238 | A |
| 239 | A |
| 240 | A |
| 241 | A |
| 242 | A |
| 243 | A |
| 244 | A |
| 245 | A |
| 246 | A |
| 247 | A |
| 248 | A |
| 249 | A |
| 250 | A |
| 251 | A |
| 252 | A |
| 253 | A |
| 254 | A |
| 255 | A |
| 256 | A |
| 257 | A |
| 258 | A |
| 259 | A |
| 260 | A |
| 261 | B |
| 262 | B |
| 263 | A |
| 264 | A |
| 265 | A |
| 266 | A |
| 267 | A |
| 268 | A |
| 269 | A |
| 270 | A |
| 271 | A |
| 272 | A |
| 273 | A |
| 274 | A |
| 275 | A |
| 276 | A |
| 277 | A |
| 278 | A |
| 279 | A |
| 280 | A |
| 281 | A |
| 282 | A |
| 283 | A |
| 284 | A |
| 285 | A |
| 286 | B |
| 287 | B |
| 288 | B |
| 289 | B |
| 290 | B |
| 291 | C |
| 292 | B |
| 293 | B |
| 294 | C |
| 295 | A |
| 296 | A |
| 297 | A |
| 298 | A |
| 299 | A |
| 300 | B |
| 301 | B |
| 302 | B |
| 303 | A |
| 304 | A |
| 305 | A |
| 306 | A |
| 307 | A |
| 308 | C |
| 309 | C |
| 310 | B |
| 311 | A |
| 312 | A |
| 313 | A |
| 314 | B |
| 315 | B |
| 316 | A |
| 317 | B |
| 318 | B |
| 319 | A |
| 320 | A |
| 321 | C |
| 322 | C |
| 323 | C |
| 324 | B |
| 325 | A |
| 326 | A |
| 327 | A |
| 328 | A |
| 329 | A |
| 330 | A |
| 331 | A |
| 332 | A |
| 333 | A |
| 334 | A |
| 335 | A |
| 336 | A |
| 337 | A |
| 338 | A |
| 339 | A |
| 340 | A |
| 341 | A |
| 342 | B |
| 343 | A |
| 344 | B |
| 345 | A |
| 346 | B |

TABLE 1-continued

BTK IC$_{50}$ Values for Exemplary Compounds of the Invention

| Example # | BTK IC$_{50}$ |
|---|---|
| 347 | B |
| 348 | B |
| 349 | A |
| 350 | D |
| 351 | D |
| 352 | D |
| 353 | D |
| 354 | D |

IC$_{50}$: A≤10 nM; 10 nM<B≤100 nM; 100 nM<C≤1 µM; 1 µM<D≤10 µM; E>10 µM

Example 356

Inhibition of a Panel of Kinases

The degree of inhibition of a panel of kinases is determined using the in vitro HotSpot kinase assay (purified enzymes, $^{33}$P-ATP, an appropriate substrate and 1 uM ATP).

TABLE 2

IC$_{50}$ Values for Exemplary Compounds of the Invention

| Compd ID | Btk (IC$_{50}$) | Btk C481S (IC$_{50}$) | EGFR (IC$_{50}$) | LCK (IC$_{50}$) | JAK3 (IC$_{50}$) |
|---|---|---|---|---|---|
| 47 | A | N/A | E | A | N/A |
| 48 | C | N/A | E | E | N/A |
| 55 | B | N/A | E | A | N/A |
| 70 | A | C | B | C | A |
| 74 | A | N/A | C | C | B |
| 75 | A | N/A | D | C | D |
| 78 | A | N/A | D | C | N/A |
| 79 | B | N/A | N/A | C | N/A |
| 80 | B | N/A | N/A | C | N/A |
| 81 | B | N/A | C | N/A | D |
| 82 | B | N/A | N/A | C | D |
| 83 | C | N/A | N/A | D | C |
| 84 | B | N/A | E | D | N/A |
| 85 | B | N/A | D | C | N/A |
| 86 | A | N/A | E | C | N/A |
| 87 | B | N/A | E | C | N/A |
| 88 | A | N/A | N/A | C | N/A |
| 89 | A | N/A | N/A | C | N/A |
| 90 | B | N/A | N/A | C | N/A |
| 91 | B | N/A | N/A | C | N/A |
| 92 | A | N/A | N/A | C | C |
| 93 | A | N/A | N/A | C | C |
| 94 | A | N/A | N/A | C | C |
| 95 | B | N/A | N/A | C | C |
| 97 | B | N/A | N/A | C | C |
| 98 | B | N/A | N/A | C | C |
| 99 | A | N/A | D | D | C |
| 100 | A | N/A | N/A | C | C |
| 101 | A | N/A | N/A | D | N/A |
| 102 | A | N/A | N/A | C | C |
| 103 | B | N/A | N/A | D | C |
| 104 | B | N/A | E | C | N/A |
| 105 | A | N/A | D | B | C |
| 106 | A | N/A | C | B | C |
| 107 | A | N/A | D | B | D |
| 108 | C | N/A | N/A | D | E |
| 109 | C | N/A | N/A | D | E |
| 110 | B | N/A | E | E | E |
| 111 | B | N/A | N/A | E | E |
| 112 | B | N/A | E | E | E |
| 113 | B | N/A | N/A | E | E |
| 114 | C | N/A | N/A | E | E |
| 115 | A | N/A | N/A | N/A | C |
| 117 | A | N/A | N/A | E | C |
| 118 | B | N/A | N/A | D | C |
| 119 | B | N/A | N/A | C | C |
| 120 | B | N/A | E | E | E |
| 121 | B | N/A | E | E | E |
| 122 | A | N/A | N/A | E | C |
| 123 | A | N/A | N/A | D | C |
| 124 | B | N/A | E | E | E |
| 125 | A | N/A | N/A | D | D |
| 126 | B | N/A | N/A | D | C |
| 127 | B | N/A | N/A | E | C |
| 128 | A | N/A | N/A | D | C |
| 129 | A | N/A | E | C | C |
| 130 | A | N/A | D | C | C |
| 131 | A | A | C | B | B |
| 132 | A | N/A | C | B | B |
| 133 | A | B | E | C | C |
| 134 | A | N/A | N/A | B | B |
| 135 | A | A | N/A | B | B |
| 136 | B | N/A | N/A | D | E |
| 137 | B | N/A | N/A | D | E |
| 138 | A | N/A | N/A | D | C |
| 139 | A | B | E | E | C |
| 140 | A | N/A | N/A | C | E |
| 141 | A | B | N/A | E | E |
| 142 | B | N/A | E | N/A | D |
| 143 | B | N/A | N/A | E | E |
| 144 | A | A | N/A | C | B |
| 145 | A | N/A | N/A | D | C |
| 146 | B | N/A | N/A | C | N/A |
| 147 | A | N/A | N/A | C | N/A |
| 148 | A | N/A | D | C | C |
| 149 | B | N/A | C | N/A | D |
| 150 | A | N/A | D | C | C |
| 151 | A | B | D | C | C |
| 152 | A | B | D | C | C |
| 153 | A | B | D | C | C |
| 154 | A | B | D | C | C |
| 155 | A | B | D | B | B |
| 156 | A | N/A | D | C | D |
| 157 | A | N/A | D | C | C |
| 159 | C | N/A | E | E | E |
| 161 | A | N/A | N/A | E | C |
| 162 | B | N/A | N/A | C | D |
| 163 | A | N/A | N/A | B | C |
| 164 | A | N/A | N/A | E | D |
| 165 | A | N/A | C | B | C |
| 166 | A | N/A | D | C | C |
| 167 | A | N/A | D | C | C |
| 168 | A | N/A | C | B | C |
| 170 | A | B | D | D | C |
| 171 | A | B | D | C | C |
| 172 | A | B | D | C | C |
| 173 | B | B | N/A | N/A | B |
| 174 | B | B | D | C | C |
| 175 | A | B | D | C | B |
| 176 | A | B | D | C | C |
| 177 | A | B | C | C | C |
| 178 | A | B | D | C | C |
| 179 | B | C | N/A | N/A | D |
| 182 | C | D | N/A | N/A | E |
| 183 | C | D | N/A | N/A | E |
| 184 | C | D | E | E | E |
| 185 | C | C | E | D | D |
| 186 | B | C | N/A | E | D |
| 187 | B | B | N/A | C | C |
| 188 | A | B | N/A | D | C |
| 189 | B | B | D | D | C |
| 190 | B | C | N/A | D | D |
| 191 | B | B | N/A | C | C |
| 192 | B | C | N/A | D | D |
| 193 | B | B | D | C | C |
| 194 | A | B | D | D | C |
| 195 | A | B | D | D | C |
| 196 | B | C | N/A | N/A | C |
| 197 | A | B | N/A | N/A | C |

TABLE 2-continued

IC$_{50}$ Values for Exemplary Compounds of the Invention

| Compd ID | Btk (IC$_{50}$) | Btk C481S (IC$_{50}$) | EGFR (IC$_{50}$) | LCK (IC$_{50}$) | JAK3 (IC$_{50}$) |
|---|---|---|---|---|---|
| 198 | B | B | N/A | N/A | C |
| 199 | A | B | N/A | C | C |
| 200 | A | B | N/A | C | C |
| 201 | B | B | E | C | D |
| 202 | A | B | D | C | C |
| 203 | A | B | N/A | N/A | C |
| 204 | B | B | D | C | D |
| 205 | B | N/A | N/A | C | C |
| 206 | A | B | C | C | C |
| 207 | B | B | D | C | C |
| 208 | A | B | D | C | C |
| 210 | A | B | D | C | B |
| 211 | B | C | E | E | C |
| 212 | C | C | N/A | N/A | D |
| 213 | B | B | N/A | N/A | B |
| 214 | A | B | N/A | N/A | C |
| 215 | A | B | N/A | N/A | C |
| 216 | B | B | E | D | D |
| 217 | B | B | E | C | D |
| 218 | A | B | D | B | C |
| 219 | B | B | D | C | C |
| 220 | B | B | D | C | C |
| 221 | A | A | D | B | C |
| 222 | A | A | N/A | N/A | B |
| 223 | A | B | N/A | N/A | C |
| 224 | A | A | N/A | N/A | C |
| 225 | B | N/A | N/A | C | C |
| 226 | B | N/A | N/A | C | C |
| 227 | B | N/A | N/A | C | C |
| 228 | B | N/A | N/A | E | C |
| 229 | B | N/A | N/A | D | C |
| 230 | B | B | N/A | N/A | B |
| 231 | C | C | N/A | N/A | C |
| 232 | A | A | C | B | B |
| 233 | C | C | E | C | C |
| 234 | A | A | N/A | N/A | B |
| 235 | C | C | N/A | N/A | C |
| 236 | A | B | C | B | B |
| 237 | A | A | N/A | N/A | C |
| 238 | A | A | N/A | B | B |
| 239 | A | B | N/A | C | C |
| 240 | A | A | C | C | C |
| 241 | A | A | D | C | C |
| 242 | A | A | N/A | C | C |
| 243 | A | B | N/A | C | C |
| 244 | A | A | N/A | C | C |
| 245 | A | A | C | B | B |
| 246 | A | A | C | B | B |
| 247 | A | A | C | B | B |
| 248 | A | A | N/A | N/A | C |
| 249 | A | A | N/A | N/A | C |
| 250 | A | A | N/A | A | B |
| 251 | A | A | N/A | A | B |
| 252 | A | A | N/A | A | B |
| 253 | A | A | B | A | B |
| 254 | A | A | N/A | A | B |
| 255 | A | A | N/A | B | B |
| 256 | A | A | C | B | B |
| 257 | A | N/A | N/A | N/A | B |
| 258 | A | B | N/A | B | B |
| 259 | A | B | N/A | B | B |
| 260 | A | A | N/A | C | B |
| 261 | B | B | N/A | D | D |
| 261 | B | C | N/A | D | C |
| 263 | A | A | D | B | B |
| 264 | A | A | D | B | B |
| 265 | A | A | C | B | B |
| 266 | A | A | C | B | B |
| 267 | A | A | C | B | B |
| 268 | A | A | C | C | B |
| 269 | A | A | C | C | B |
| 270 | A | A | C | C | C |
| 271 | A | A | N/A | B | B |
| 272 | A | A | N/A | B | B |
| 273 | A | A | N/A | B | B |
| 274 | A | A | N/A | B | B |
| 275 | A | A | D | B | B |
| 276 | A | A | D | B | C |
| 277 | A | B | N/A | B | B |
| 278 | A | B | N/A | B | B |
| 279 | A | B | N/A | B | B |
| 280 | A | A | N/A | A | B |
| 281 | A | A | C | B | B |
| 282 | A | A | N/A | B | B |
| 283 | A | A | C | B | B |
| 284 | A | A | C | B | B |
| 285 | A | A | D | B | B |
| 286 | B | B | N/A | B | B |
| 287 | B | B | N/A | B | B |
| 288 | B | B | N/A | B | B |
| 289 | B | B | D | B | C |
| 290 | B | C | N/A | C | D |
| 291 | C | C | N/A | B | B |
| 292 | B | C | N/A | C | C |
| 293 | B | B | N/A | B | B |
| 294 | C | C | C | B | B |
| 295 | A | B | C | B | B |
| 296 | A | B | N/A | B | B |
| 297 | A | N/A | N/A | N/A | C |
| 298 | A | B | C | C | B |
| 299 | A | A | D | C | B |
| 300 | B | B | C | B | B |
| 302 | B | B | N/A | N/A | C |
| 303 | A | A | C | B | B |
| 304 | A | A | N/A | B | B |
| 305 | A | A | C | B | B |
| 306 | A | A | C | B | B |
| 307 | A | A | D | B | B |
| 308 | C | C | N/A | N/A | C |
| 309 | C | C | N/A | N/A | D |
| 310 | B | B | N/A | N/A | C |
| 311 | A | B | N/A | N/A | E |
| 312 | A | B | N/A | N/A | C |
| 313 | A | A | N/A | N/A | B |
| 314 | B | C | N/A | N/A | E |
| 315 | B | B | N/A | N/A | E |
| 316 | A | A | N/A | N/A | E |
| 317 | B | B | N/A | N/A | E |
| 318 | B | C | N/A | N/A | E |
| 319 | A | B | N/A | N/A | E |
| 320 | A | A | N/A | B | B |
| 321 | C | E | N/A | N/A | E |
| 322 | C | E | D | D | E |
| 323 | C | C | E | D | E |
| 324 | B | B | E | C | E |
| 325 | A | N/A | N/A | C | B |
| 326 | A | N/A | N/A | D | C |
| 327 | A | A | C | B | A |
| 328 | A | B | C | B | A |
| 329 | A | B | N/A | B | B |
| 330 | A | B | N/A | B | B |
| 336 | A | N/A | C | C | B |
| 337 | A | N/A | D | C | B |
| 338 | A | N/A | D | C | B |
| 339 | A | N/A | D | C | B |
| 341 | B | N/A | D | C | C |
| 342 | B | N/A | D | D | C |
| 343 | A | N/A | D | C | C |
| 344 | B | N/A | D | C | C |
| 345 | A | C | D | C | C |

IC$_{50}$: A ≤ 10 nM; 10 nM < B ≤ 100 nM; 100 nM < C ≤ 1 µM; 1 µM < D ≤ 10 µM; E > 10 µM

Example 357

Pharmaceutical Compositions

The compositions described below are presented with a compound of Formula (IA), Formula (I), Formula (Ia), Formula (II), Formula (III), Formula (IV), Formula (Va)-(Vh), or Formula (VIa)-(VIb) for illustrative purposes.

Example 357a

Parenteral Composition

To prepare a parenteral pharmaceutical composition suitable for administration by injection, 100 mg of a water-soluble salt of a compound of Formula (IA), Formula (I), Formula (Ia), Formula (II), Formula (III), Formula (IV), Formula (Va)-(Vh), or Formula (VIa)-(VIb) is dissolved in DMSO and then mixed with 10 mL of 0.9% sterile saline. The mixture is incorporated into a dosage unit form suitable for administration by injection.

Example 357b

Oral Composition

To prepare a pharmaceutical composition for oral delivery, 100 mg of a compound of Formula (IA), Formula (I), Formula (Ia), Formula (II), Formula (III), Formula (IV), Formula (Va)-(Vh), or Formula (VIa)-(VIb) is mixed with 750 mg of starch. The mixture is incorporated into an oral dosage unit for, such as a hard gelatin capsule, which is suitable for oral administration.

Example 357c

Sublingual (Hard Lozenge) Composition

To prepare a pharmaceutical composition for buccal delivery, such as a hard lozenge, mix 100 mg of a compound of Formula (IA), Formula (I), Formula (Ia), Formula (II), Formula (III), Formula (IV), Formula (Va)-(Vh), or Formula (VIa)-(VIb) with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 357d

Inhalation Composition

To prepare a pharmaceutical composition for inhalation delivery, 20 mg of a compound of Formula (IA), Formula (I), Formula (Ia), Formula (II), Formula (III), Formula (IV), Formula (Va)-(Vh), or Formula (VIa)-(VIb) is mixed with 50 mg of anhydrous citric acid and 100 mL of 0.9% sodium chloride solution. The mixture is incorporated into an inhalation delivery unit, such as a nebulizer, which is suitable for inhalation administration.

Example 357e

Rectal Gel Composition

To prepare a pharmaceutical composition for rectal delivery, 100 mg of a compound of Formula (IA), Formula (I), Formula (Ia), Formula (II), Formula (III), Formula (IV), Formula (Va)-(Vh), or Formula (VIa)-(VIb) is mixed with 2.5 g of methylcellulose (1500 mPa), 100 mg of methylparaben, 5 g of glycerin and 100 mL of purified water. The resulting gel mixture is then incorporated into rectal delivery units, such as syringes, which are suitable for rectal administration.

Example 357f

Topical Gel Composition

To prepare a pharmaceutical topical gel composition, 100 mg of a compound of Formula (IA), Formula (I), Formula (Ia), Formula (II), Formula (III), Formula (IV), Formula (Va)-(Vh), or Formula (VIa)-(VIb) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 357g

Ophthalmic Solution Composition

To prepare a pharmaceutical ophthalmic solution composition, 100 mg of a compound of Formula (IA), Formula (I), Formula (Ia), Formula (II), Formula (III), Formula (IV), Formula (Va)-(Vh), or Formula (VIa)-(VIb) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 358

Clinical Trial of the Safety and Efficacy of a Compound of Formula (IA), Formula (I), Formula (Ia), Formula (II), Formula (III), Formula (IV), Formula (Va)-(Vh), or Formula (VIa)-(VIb) in Rheumatoid Arthritis Patients The purpose of this study is to determine the safety and efficacy of a compound of Formula (IA), Formula (I), Formula (Ia), Formula (II), Formula (III), Formula (IV), Formula (Va)-(Vh), or Formula (VIa)-(VIb) in patients with rheumatoid arthritis.

Inclusion Criteria
    Adult males/Females aged 18~80 years.
    Patients who are taking NSAIDs for the treatment of rheumatoid arthritis.
    Patients who belong to ACR functional class 1, 2, 3.

Exclusion Criteria
    Patients who belong to ACR functional class 4.
    Patients who are hypersensitive to clinical trial medicines or excipient.
    Patients who have experience of Cerebrovascular bleeding, bleeding disorder.

Study Design
    Allocation: Randomized, placebo-controlled.
    Intervention Model: Single Group Assignment.
    Masking: Double Blind (Subject, Caregiver).
    Primary Purpose: Supportive Care.

Primary Outcome Measures
    Changes in '100 mm pain VAS' value from baseline [Time Frame: −14, 0, 14, 28, 42 day] [Designated as safety issue: No].
    Determine PK of an orally administered compound of Formula (IA), Formula (I), Formula (Ia), Formula (II), Formula (III), Formula (IV), Formula (Va)-(Vh), or Formula (VIa)-(VIb).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of Formula (IA) having the structure:

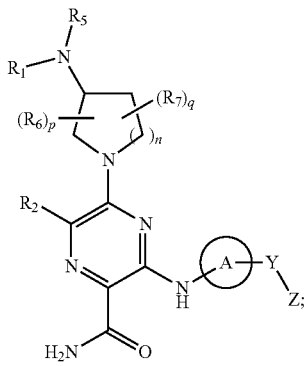

Formula (IA)

wherein:
ring A is substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;

Y is optionally present and when present is —$CH_2O$—, —$OCH_2$—, —$OCH_2CH_2O$—, —O—, —$N(R_3)$—, —C(O)—, —$N(R_3)C(O)$—, —$C(O)N(R_3)$—, —$N(R_3)C(O)N(R_3)$—, —S(O)—, —$S(O)_2$—, —$N(R_3)S(O)_2$—, —$S(O)_2N(R_3)$—, —C(=NH)—, —$C(=NH)N(R_3)$—, —$C(=NH)N(R_3)$—, or substituted or unsubstituted $C_1$-$C_4$alkylene;

Z is optionally present and when present is substituted or unsubstituted $C_1$-$C_3$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;

$R_1$ is —C(O)$R_4$, —C(O)C(O)$R_4$, —C(O)N($R_3$)($R_4$), or —S(O)$_2R_4$;

each $R_2$ is independently H, substituted or unsubstituted $C_1$-$C_4$alkyl, —CN, or halogen;

each $R_3$ is independently is H, or substituted or unsubstituted $C_1$-$C_4$alkyl;

each $R_4$ is independently H, substituted or unsubstituted $C_1$-$C_6$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;

$R_5$ is H, substituted or unsubstituted $C_1$-$C_4$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl; or $R_1$ and $R_5$ together with the nitrogen atom to which they are attached are combined to form a substituted or unsubstituted $C_2$-$C_9$heterocycloalkyl ring;

each $R_6$ is independently halogen, —CN, —OH, —$NH_2$, substituted or unsubstituted $C_1$-$C_4$alkoxy, substituted or unsubstituted $C_1$-$C_4$alkyl, substituted or unsubstituted $C_3$-$C_6$cycloalkyl, substituted or unsubstituted $C_2$-$C_6$heterocycloalkyl, or —N($R_3$)$_2$;

or $R_1$ and $R_6$ are combined to form a substituted or unsubstituted $C_2$-$C_9$heterocycloalkyl ring;

each $R_7$ is independently halogen, —CN, —OH, —$NH_2$, substituted or unsubstituted $C_1$-$C_4$alkoxy, substituted or unsubstituted $C_1$-$C_4$alkyl, substituted or unsubstituted $C_3$-$C_6$cycloalkyl, substituted or unsubstituted $C_2$-$C_6$heterocycloalkyl, or —N($R_3$)$_2$;

n is 0-3;
p is 0-3; and
q is 0-3;

or a pharmaceutically acceptable solvate, or pharmaceutically acceptable salt thereof;

provided that when n is 0; then each of p and q is independently 0, 1, or 2.

2. A compound of Formula (I) having the structure:

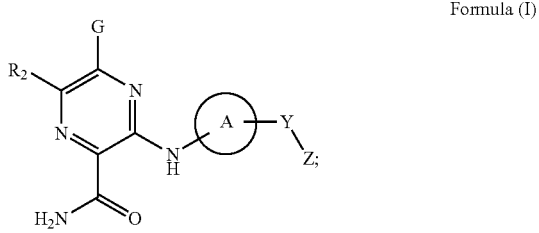

Formula (I)

wherein:
ring A is substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;

Y is optionally present and when present is —$CH_2O$—, —$OCH_2$—, —$OCH_2CH_2O$—, —O—, —$N(R_3)$—, —C(O)—, —$N(R_3)C(O)$—, —$C(O)N(R_3)$—, —$N(R_3)C(O)N(R_3)$—, —S(O)—, —$S(O)_2$—, —$N(R_3)S(O)_2$—, —$S(O)_2N(R_3)$—, —C(=NH)—, —$C(=NH)N(R_3)$—, —$C(=NH)N(R_3)$—, or substituted or unsubstituted $C_1$-$C_4$alkylene;

Z is optionally present and when present is substituted or unsubstituted $C_1$-$C_3$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;

G is

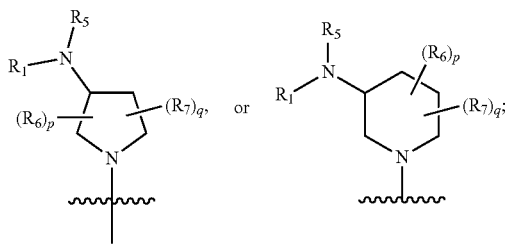

$R_1$ is —C(O)($R_4$), —C(O)N($R_3$)($R_4$), or —S(O)$_2R_4$;
each $R_2$ is independently H, —CN, or halogen;
each $R_3$ is independently is H, or substituted or unsubstituted $C_1$-$C_4$alkyl;
each $R_4$ is independently H, substituted or unsubstituted $C_1$-$C_6$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl;

$R_5$ is H, substituted or unsubstituted $C_1$-$C_4$alkyl, substituted or unsubstituted $C_3$-$C_6$cycloalkyl, substituted or unsubstituted $C_2$-$C_7$heterocycloalkyl, substituted or unsubstituted $C_6$-$C_{12}$aryl, or substituted or unsubstituted $C_1$-$C_{12}$heteroaryl; or $R_1$ and $R_5$ together with the nitrogen atom to which they are attached are combined to form a substituted or unsubstituted $C_2$-$C_9$heterocycloalkyl ring;

each $R_6$ is independently halogen, —CN, —OH, —NH$_2$, substituted or unsubstituted $C_1$-$C_4$alkoxy, substituted or unsubstituted $C_1$-$C_4$alkyl, substituted or unsubstituted $C_3$-$C_6$cycloalkyl, substituted or unsubstituted $C_2$-$C_6$heterocycloalkyl, or —N(R$_3$)$_2$; or $R_1$ and $R_6$ are combined to form a substituted or unsubstituted $C_2$-$C_9$heterocycloalkyl ring;

each $R_7$ is independently halogen, —CN, —OH, —NH$_2$, substituted or unsubstituted $C_1$-$C_4$alkoxy, substituted or unsubstituted $C_1$-$C_4$alkyl, substituted or unsubstituted $C_3$-$C_6$cycloalkyl, substituted or unsubstituted $C_2$-$C_6$heterocycloalkyl, or —N(R$_3$)$_2$;

p is 0-3; and q is 0-3;

or a pharmaceutically acceptable solvate, or pharmaceutically acceptable salt thereof.

3. The compound of claim 1, wherein the compound is of the structure

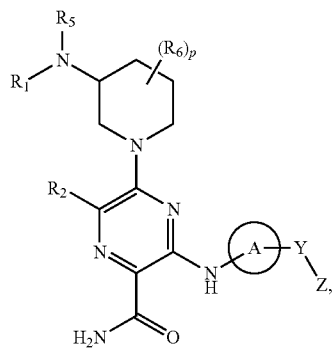

or a pharmaceutically acceptable solvate, or pharmaceutically acceptable salt thereof.

4. The compound of claim 3, wherein the compound is of the structure:

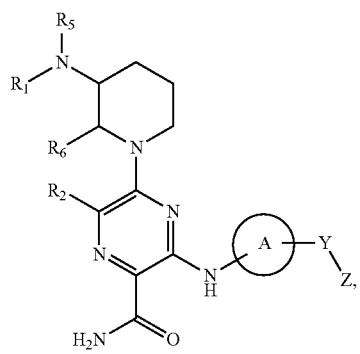

or a pharmaceutically acceptable solvate, or pharmaceutically acceptable salt thereof.

5. The compound according to claim 2, wherein the compound is of Formula (IV) having the structure:

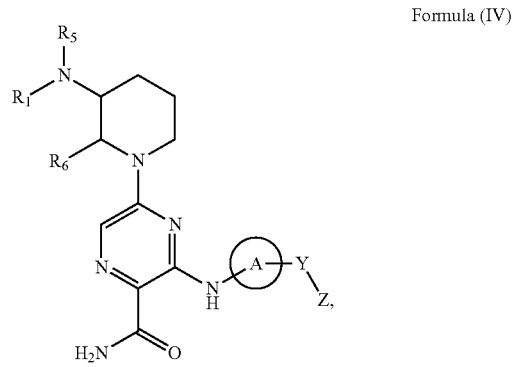

Formula (IV)

or a pharmaceutically acceptable solvate, or pharmaceutically acceptable salt thereof.

6. The compound of claim 5, wherein $R_6$ is Me.

7. The compound of claim 5, wherein ring A is phenyl.

8. The compound of claim 5, wherein Y is absent, —CH$_2$O—, —OCH$_2$—, —O—, —N(R$_3$)—, —C(O)—, —N(R$_3$)C(O)—, —C(O)N(R$_3$)—, or substituted or unsubstituted $C_1$-$C_4$alkylene.

9. The compound of claim 5, wherein Z is substituted or unsubstituted $C_2$-$C_7$heterocycloalkyl, substituted or unsubstituted $C_6$-$C_{12}$aryl, or substituted or unsubstituted $C_1$-$C_{12}$heteroaryl.

10. The compound of claim 5, wherein $R_1$ is —C(O)R$_4$.

11. The compound of claim 10, wherein $R_4$ is substituted or unsubstituted $C_6$-$C_{12}$aryl, or substituted or unsubstituted $C_1$-$C_{12}$heteroaryl.

12. The compound of claim 5, wherein ring A is substituted or unsubstituted $C_1$-$C_{12}$heteroaryl.

13. The compound of claim 12, wherein ring A is pyridyl, pyrazolyl, thiazolyl, isothiazolyl, oxazolyl, or isoxazolyl.

14. The compound of claim 5, wherein $R_1$ is —C(O)N(R$_3$)(R$_4$).

15. The compound of claim 5, wherein $R_1$ is —C(O)N(R$_3$)(R$_4$) and $R_4$ is H, or substituted or unsubstituted $C_1$-$C_6$alkyl.

16. The compound of claim 5, wherein $R_1$ and $R_5$ together with the nitrogen atom to which they are attached are combined to form a substituted or unsubstituted $C_2$-$C_9$heterocycloalkyl ring.

17. A compound selected from the group consisting of
5-[(3R)-3-(4-tert-butylbenzamido)piperidin-1-yl]-3-{[4-(morpholine-4-carbonyl)phenyl]amino}pyrazine-2-carboxamide;
5-[(3R)-3-(4-tert-butylbenzamido)piperidin-1-yl]-3-{[4-(1-methylpiperidin-4-yl)phenyl]amino}pyrazine-2-carboxamide;
5-[(3R)-3-(4-tert-butylbenzamido)piperidin-1-yl]-3-{[4-(4-methylpiperazin-1-yl)phenyl]amino}pyrazine-2-carboxamide;
3-{[4-(1-methylpiperidin-4-yl)phenyl]amino}-5-[(3R)-3-[(piperidine-1-carbonyl)amino]piperidin-1-yl]pyrazine-2-carboxamide;
3-{[4-(4-methylpiperazin-1-yl)phenyl]amino}-5-[(3R)-3-[(piperidine-1-carbonyl)amino]piperidin-1-yl]pyrazine-2-carboxamide;

5-[(3R)-3-(4-methoxybenzamido)piperidin-1-yl]-3-{[4-(1-propanoylpiperidin-4-yl)phenyl]amino}pyrazine-2-carboxamide;

3-({4-[1-(cyanomethyl)piperidin-4-yl]phenyl}amino)-5-[(3R)-3-(4-methoxybenzamido)piperidin-1-yl]pyrazine-2-carboxamide;

5-[(3R)-3-(4-methoxybenzamido)piperidin-1-yl]-3-({4-[1-(2,2,2-trifluoroethyl)piperidin-4-yl]phenyl}amino)pyrazine-2-carboxamide;

3-{[3-fluoro-4-(morpholin-4-yl)phenyl]amino}-5-[(3R)-3-(4-methoxybenzamido)piperidin-1-yl]pyrazine-2-carboxamide;

5-[(3R)-3-(4-methoxybenzamido)piperidin-1-yl]-3-{[4-(3-oxomorpholin-4-yl)phenyl]amino}pyrazine-2-carboxamide;

5-[(3R)-3-(4-methoxybenzamido)piperidin-1-yl]-3-[(3-methyl-1,2-thiazol-5-yl)amino]pyrazine-2-carboxamide;

3-({4-[2-(dimethylamino)ethoxy]phenyl}amino)-5-[(3R)-3-(4-methoxybenzamido)piperidin-1-yl]pyrazine-2-carboxamide;

(R)-2-(4-(3-carbamoyl-6-(3-(4-methoxybenzamido)piperidin-1-yl)pyrazin-2-ylamino)phenoxy)-N,N-dimethylethanamine oxide;

3-{[4-(dimethylcarbamoyl)phenyl]amino}-5-[(3R)-3-(4-methoxybenzamido)piperidin-1-yl]pyrazine-2-carboxamide;

3-({4-[4-(dimethylcarbamoyl)piperidin-1-yl]phenyl}amino)-5-[(3R)-3-(4-methoxybenzamido)piperidin-1-yl]pyrazine-2-carboxamide;

5-[(3R)-3-(4-methoxybenzamido)piperidin-1-yl]-3-({4-[1-(propan-2-yl)piperidin-4-yl]phenyl}amino)pyrazine-2-carboxamide;

3-{[4-(1-cyclopentylpiperidin-4-yl)phenyl]amino}-5-[(3R)-3-(4-methoxybenzamido)piperidin-1-yl]pyrazine-2-carboxamide;

3-{[4-(1-formylpiperidin-4-yl)phenyl]amino}-5-[(3R)-3-(4-methoxybenzamido)piperidin-1-yl]pyrazine-2-carboxamide;

5-[(3R)-3-(4-methoxybenzamido)piperidin-1-yl]-3-{[4-(morpholin-4-yl)phenyl]amino}pyrazine-2-carboxamide;

3-[(6-ethoxypyridin-3-yl)amino]-5-[(3R)-3-(4-methoxybenzamido)piperidin-1-yl]pyrazine-2-carboxamide;

3-[(4-methanesulfonylphenyl)amino]-5-[(3R)-3-(4-methoxybenzamido)piperidin-1-yl]pyrazine-2-carboxamide;

5-[(3R)-3-(4-methoxybenzamido)piperidin-1-yl]-3-{[4-(2-oxo-1,2-dihydropyridin-1-yl)phenyl]amino}pyrazine-2-carboxamide;

3-{[4-(1-methanesulfonylpiperidin-4-yl)phenyl]amino}-5-[(3R)-3-(4-methoxybenzamido)piperidin-1-yl]pyrazine-2-carboxamide;

3-({4-[1-(2-cyanoacetyl)piperidin-4-yl]phenyl}amino)-5-[(3R)-3-(4-methoxybenzamido)piperidin-1-yl]pyrazine-2-carboxamide;

3-[(4-methanesulfonylphenyl)amino]-5-[(3R)-3-[(piperidine-1-carbonyl)amino]piperidin-1-yl]pyrazine-2-carboxamide;

3-{[4-(2-ethoxyethoxy)phenyl]amino}-5-[(3R)-3-(4-methoxybenzamido)piperidin-1-yl]pyrazine-2-carboxamide;

3-[(4-ethoxyphenyl)amino]-5-[(3R)-3-(4-methoxybenzamido)piperidin-1-yl]pyrazine-2-carboxamide;

5-[(3R)-3-(4-methoxybenzamido)piperidin-1-yl]-3-{[4-(oxan-4-yl)phenyl]amino}pyrazine-2-carboxamide;

5-[(3R)-3-(4-methoxybenzamido)piperidin-1-yl]-3-{[4-(2-oxopiperidin-1-yl)phenyl]amino}pyrazine-2-carboxamide;

3-({4-[1-(dimethylcarbamoyl)piperidin-4-yl]phenyl}amino)-5-[(3R)-3-(4-methoxybenzamido)piperidin-1-yl]pyrazine-2-carboxamide;

5-[(3R)-3-[(piperidine-1-carbonyl)amino]piperidin-1-yl]-3-{[4-(1-propanoylpiperidin-4-yl)phenyl]amino}pyrazine-2-carboxamide;

3-{[4-(1-acetylpiperidin-4-yl)phenyl]amino}-5-[(3R)-3-(4-methoxybenzamido)piperidin-1-yl]pyrazine-2-carboxamide;

3-{[4-(1-formylpiperidin-4-yl)phenyl]amino}-5-[(3R)-3-[(piperidine-1-carbonyl)amino]piperidin-1-yl]pyrazine-2-carboxamide;

5-[(3R)-3-(4-methoxybenzamido)piperidin-1-yl]-3-{[4-(1-methylpiperidin-4-yl)phenyl]amino}pyrazine-2-carboxamide;

5-[(3R)-3-(4-methoxybenzamido)piperidin-1-yl]-3-{[6-(morpholin-4-yl)pyridin-3-yl]amino}pyrazine-2-carboxamide;

5-[(3R)-3-(4-methoxybenzamido)piperidin-1-yl]-3-[(quinolin-6-yl)amino]pyrazine-2-carboxamide;

3-[(1,3-benzothiazol-6-yl)amino]-5-[(3R)-3-(4-methoxybenzamido)piperidin-1-yl]pyrazine-2-carboxamide;

5-[(3R)-3-(4-methoxybenzamido)piperidin-1-yl]-3-[(4-methoxyphenyl)amino]pyrazine-2-carboxamide;

5-[(3R)-3-(4-methoxybenzamido)piperidin-1-yl]-3-{[4-(2-methoxyethoxy)phenyl]amino}pyrazine-2-carboxamide;

3-({4-[1-(2-cyanoacetyl)piperidin-4-yl]phenyl}amino)-5-[(3R)-3-[(piperidine-1-carbonyl)amino]piperidin-1-yl]pyrazine-2-carboxamide;

5-[(3R)-3-[(dimethylcarbamoyl)amino]piperidin-1-yl]-3-[(4-methanesulfonylphenyl)amino]pyrazine-2-carboxamide;

3-({4-[1-(2-cyanoacetyl)piperidin-4-yl]phenyl}amino)-5-[(3R)-3-[(dimethylcarbamoyl)amino]piperidin-1-yl]pyrazine-2-carboxamide;

3-{[4-(1-cyclopentylpiperidin-4-yl)phenyl]amino}-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-{[4-(piperidin-4-yl)phenyl]amino}pyrazine-2-carboxamide;

5-[(3R)-3-[(dimethylcarbamoyl)amino]piperidin-1-yl]-3-{[4-(1-propanoylpiperidin-4-yl)phenyl]amino}pyrazine-2-carboxamide;

3-{[4-(1-ethylpiperidin-4-yl)phenyl]amino}-5-[(3R)-3-(4-methoxybenzamido)piperidin-1-yl]pyrazine-2-carboxamide;

3-{[4-(1-cyclopropylpiperidin-4-yl)phenyl]amino}-5-[(3R)-3-(4-methoxybenzamido)piperidin-1-yl]pyrazine-2-carboxamide;

5-[(3R)-3-[(dimethylcarbamoyl)amino]piperidin-1-yl]-3-{[4-(1-methylpiperidin-4-yl)phenyl]amino}pyrazine-2-carboxamide;

5-[(3R)-3-{[ethyl(methyl)carbamoyl]amino}piperidin-1-yl]-3-{[4-(1-methylpiperidin-4-yl)phenyl]amino}pyrazine-2-carboxamide;

5-[(3R)-3-[(diethylcarbamoyl)amino]piperidin-1-yl]-3-{[4-(1-methylpiperidin-4-yl)phenyl]amino}pyrazine-2-carboxamide;

5-[(3R)-3-(4-fluorobenzamido)piperidin-1-yl]-3-{[4-(1-methylpiperidin-4-yl)phenyl]amino}pyrazine-2-carboxamide;

5-[(3R)-3-(4-ethoxybenzamido)piperidin-1-yl]-3-{[4-(1-methylpiperidin-4-yl)phenyl]amino}pyrazine-2-carboxamide;

5-[(3R)-3-(4-methoxybenzamido)piperidin-1-yl]-3-{[4-(propan-2-yl)phenyl]amino}pyrazine-2-carboxamide;

3-{[4-(1,1-dioxo-1$\lambda^6$-thiomorpholin-4-yl)phenyl]amino}-5-[(3R)-3-(4-methoxybenzamido)piperidin-1-yl]pyrazine-2-carboxamide;

5-[(3R)-3-[(dimethylcarbamoyl)(methyl)amino]piperidin-1-yl]-3-{[4-(1,1-dioxo-1$\lambda^6$-thiomorpholin-4-yl)phenyl]amino}pyrazine-2-carboxamide;

3-{[2-fluoro-4-(piperidin-4-yl)phenyl]amino}-5-[(3R)-3-(4-methoxybenzamido)piperidin-1-yl]pyrazine-2-carboxamide;

3-{[3-fluoro-4-(piperidin-4-yl)phenyl]amino}-5-[(3R)-3-(4-methoxybenzamido)piperidin-1-yl]pyrazine-2-carboxamide;

5-[(3R)-3-[(dimethylcarbamoyl)(methyl)amino]piperidin-1-yl]-3-{[4-(1-propanoylpiperidin-4-yl)phenyl]amino}pyrazine-2-carboxamide;

5-[(3R)-3-[(dimethylcarbamoyl)(methyl)amino]piperidin-1-yl]-3-({4-[1-(dimethylcarbamoyl)piperidin-4-yl]phenyl}amino)pyrazine-2-carboxamide;

5-[(3R)-3-[(dimethylcarbamoyl)(methyl)amino]piperidin-1-yl]-3-{[4-(1-methanesulfonylpiperidin-4-yl)phenyl]amino}pyrazine-2-carboxamide;

3-{[4-(1-cyclopentylpiperidin-4-yl)phenyl]amino}-5-[(3R)-3-[(dimethylcarbamoyl)(methyl)amino]piperidin-1-yl]pyrazine-2-carboxamide;

3-{[4-(1,1-dioxo-1$\lambda^6$-thiomorpholin-4-yl)phenyl]amino}-5-[(3R)-3-(3-methyl-2-oxoimidazolidin-1-yl)piperidin-1-yl]pyrazine-2-carboxamide;

5-[(3R)-3-{imidazo[1,2-a]pyridine-6-amido}piperidin-1-yl]-3-{[4-(oxan-4-yl)phenyl]amino}pyrazine-2-carboxamide;

5-[(3R)-3-{5-hydroxyimidazo[1,2-a]pyridine-6-amido}piperidin-1-yl]-3-{[4-(oxan-4-yl)phenyl]amino}pyrazine-2-carboxamide;

5-[(3R)-3-(4-methoxybenzamido)piperidin-1-yl]-3-{[4-(piperidin-1-yl)phenyl]amino}pyrazine-2-carboxamide;

3-{[4-(1-cyclopropylpiperidin-4-yl)phenyl]amino}-5-[(3R)-3-(3-methyl-2-oxoimidazolidin-1-yl)piperidin-1-yl]pyrazine-2-carboxamide;

5-[(3R)-3-[(dimethylcarbamoyl)amino]piperidin-1-yl]-3-{[4-(1,1-dioxo-1$\lambda^6$-thiomorpholin-4-yl)phenyl]amino}pyrazine-2-carboxamide;

3-{[4-(1-cyclopentylpiperidin-4-yl)phenyl]amino}-5-[(3R)-3-(3-methyl-2-oxoimidazolidin-1-yl)piperidin-1-yl]pyrazine-2-carboxamide;

3-{[4-(1-ethylpiperidin-4-yl)phenyl]amino}-5-[(3R)-3-(3-methyl-2-oxoimidazolidin-1-yl)piperidin-1-yl]pyrazine-2-carboxamide;

3-{[4-(1-cyclopentylpiperidin-4-yl)phenyl]amino}-5-[(3R)-3-{[ethyl(methyl)carbamoyl]amino}piperidin-1-yl]pyrazine-2-carboxamide;

3-{[4-(1-cyclopentylpiperidin-4-yl)phenyl]amino}-5-[(3R)-3-propanamidopiperidin-1-yl]pyrazine-2-carboxamide;

3-{[4-(1-cyclopentylpiperidin-4-yl)phenyl]amino}-5-[(3R)-3-(4-fluorobenzamido)piperidin-1-yl]pyrazine-2-carboxamide;

5-[(3R)-3-[(dimethylcarbamoyl)amino]piperidin-1-yl]-3-(phenylamino)pyrazine-2-carboxamide;

5-[(3R)-3-[(dimethylcarbamoyl)amino]piperidin-1-yl]-3-{[4-(4-methylpiperidin-4-yl)phenyl]amino}pyrazine-2-carboxamide;

5-[(3R)-3-[(dimethylcarbamoyl)amino]piperidin-1-yl]-3-{[4-(1-ethylpiperidin-4-yl)phenyl]amino}pyrazine-2-carboxamide;

3-{[4-(1-cyclopropylpiperidin-4-yl)phenyl]amino}-5-[(3R)-3-[(dimethylcarbamoyl)amino]piperidin-1-yl]pyrazine-2-carboxamide;

3-[(4-chlorophenyl)amino]-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-({4-[1-(propan-2-yl)piperidin-4-yl]phenyl}amino)pyrazine-2-carboxamide;

4-[4-({3-carbamoyl-6-[(3R)-3-[(dimethylcarbamoyl)amino]piperidin-1-yl]pyrazin-2-yl}amino)phenyl]-1-(propan-2-yl)piperidin-1-ium-1-olate;

3-[(4-chloro-3-methoxyphenyl)amino]-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-[(3-methoxy-4-methylphenyl)amino]pyrazine-2-carboxamide;

5-[(3R)-3-[(dimethylcarbamoyl)amino]piperidin-1-yl]-3-{[4-(4-methyl-1-propanoylpiperidin-4-yl)phenyl]amino}pyrazine-2-carboxamide;

3-({4-[1-(dimethylcarbamoyl)-4-methylpiperidin-4-yl]phenyl}amino)-5-[(3R)-3-[(dimethylcarbamoyl)amino]piperidin-1-yl]pyrazine-2-carboxamide;

3-{[4-(1-cyclopentyl-4-methylpiperidin-4-yl)phenyl]amino}-5-[(3R)-3-[(dimethylcarbamoyl)amino]piperidin-1-yl]pyrazine-2-carboxamide;

3-{[4-(4-cyclopropylpiperazin-1-yl)phenyl]amino}-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-[(4-fluorophenyl)amino]pyrazine-2-carboxamide;

3-{[4-(4-cyclopentylpiperazin-1-yl)phenyl]amino}-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-({4-[(pyridin-2-yl)carbamoyl]phenyl}amino)pyrazine-2-carboxamide;

5-[(3R)-3-{[methyl(phenyl)carbamoyl]amino}piperidin-1-yl]-3-(phenylamino)pyrazine-2-carboxamide;

3-{[2-chloro-4-(piperidin-4-yl)phenyl]amino}-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-({4-[1-(dimethylcarbamoyl)piperidin-4-yl]phenyl}amino)pyrazine-2-carboxamide;

3-{[4-(1-cyclobutylpiperidin-4-yl)phenyl]amino}-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-({4-[1-(oxan-4-yl)piperidin-4-yl]phenyl}amino)pyrazine-2-carboxamide;

5-[(3R)-3-[(dimethylcarbamoyl)amino]piperidin-1-yl]-3-[(4-{1-[2-(2-hydroxyethoxy)ethyl]piperidin-4-yl}phenyl)amino]pyrazine-2-carboxamide;

3-{[4-(1-cyclopropanecarbonylpiperidin-4-yl)phenyl]amino}-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-{[4-(1-methanesulfonylpiperidin-4-yl)phenyl]amino}pyrazine-2-carboxamide;

ethyl N-[(3R)-1-(5-carbamoyl-6-{[4-(1-cyclopentylpiperidin-4-yl)phenyl]amino}pyrazin-2-yl)piperidin-3-yl]carbamate;

5-[(3R)-3-[(dimethylcarbamoyl)amino]piperidin-1-yl]-3-[(5-fluoro-6-methylpyridin-2-yl)amino]pyrazine-2-carboxamide;

5-[(3R)-3-[(dimethylcarbamoyl)amino]piperidin-1-yl]-3-({4-[1-(pyridin-2-yl)piperidin-4-yl]phenyl}amino)pyrazine-2-carboxamide;

5-[(3R)-3-[(dimethylcarbamoyl)amino]piperidin-1-yl]-3-{[4-(dimethylcarbamoyl)phenyl]amino}pyrazine-2-carboxamide;

5-[(3R)-3-[(dimethylcarbamoyl)amino]piperidin-1-yl]-3-{[4-(pyrrolidine-1-carbonyl)phenyl]amino}pyrazine-2-carboxamide;

5-[(3R)-3-[(dimethylcarbamoyl)amino]piperidin-1-yl]-3-{[4-(1-phenylpiperidin-4-yl)phenyl]amino}pyrazine-2-carboxamide;

3-{[4-(1-cyclohexylpiperidin-4-yl)phenyl]amino}-5-[(3R)-3-[(dimethylcarbamoyl)amino]piperidin-1-yl]pyrazine-2-carboxamide;

5-[(3R)-3-aminopiperidin-1-yl]-3-{[4-(1-cyclopentylpiperidin-4-yl)phenyl]amino}pyrazine-2-carboxamide;

3-{[4-(1-cyclopentylpiperidin-4-yl)phenyl]amino}-5-[(3R)-3-formamidopiperidin-1-yl]pyrazine-2-carboxamide;

3-{[4-(1-cyclopentylpiperidin-4-yl)phenyl]amino}-5-[(3R)-3-methanesulfonamidopiperidin-1-yl]pyrazine-2-carboxamide;

3-{[4-(1-cyclopentylpiperidin-4-yl)phenyl]amino}-5-[(3R)-3-ethanesulfonamidopiperidin-1-yl]pyrazine-2-carboxamide;

5-[(3R)-3-benzamidopiperidin-1-yl]-3-{[4-(1-cyclopentylpiperidin-4-yl)phenyl]amino}pyrazine-2-carboxamide;

3-{[4-(1-cyclopentylpiperidin-4-yl)phenyl]amino}-5-[(3R)-3-(pyridine-3-amido)piperidin-1-yl]pyrazine-2-carboxamide;

3-{[4-(1-cyclopentylpiperidin-4-yl)phenyl]amino}-5-[(3R)-3-(5-fluoropyridine-3-amido)piperidin-1-yl]pyrazine-2-carboxamide;

3-{[4-(1-cyclopentylpiperidin-4-yl)phenyl]amino}-5-[(3R)-3-(1-oxo-2,3-dihydro-1H-isoindol-2-yl)piperidin-1-yl]pyrazine-2-carboxamide;

3-{[4-(1-cyclopentylpiperidin-4-yl)phenyl]amino}-5-[(3R)-3-(2-oxopyrrolidin-1-yl)piperidin-1-yl]pyrazine-2-carboxamide;

3-{[4-(1-cyclopentylpiperidin-4-yl)phenyl]amino}-5-[(3R)-3-cyclopropaneamidopiperidin-1-yl]pyrazine-2-carboxamide;

5-[(3R)-3-[(dimethylcarbamoyl)amino]piperidin-1-yl]-3-({4-[1-(oxetan-3-yl)piperidin-4-yl]phenyl}amino)pyrazine-2-carboxamide;

3-{[4-(1-cyclopentylpiperidin-4-yl)phenyl]amino}-5-[(3R)-3-(3-ethyl-2-oxoimidazolidin-1-yl)piperidin-1-yl]pyrazine-2-carboxamide;

3-{[4-(1-cyclopentylpiperidin-4-yl)phenyl]amino}-5-[(2R,3R)-3-[(dimethylcarbamoyl)amino]-2-methylpiperidin-1-yl]pyrazine-2-carboxamide;

3-{[4-(1-cyclopentylpiperidin-4-yl)phenyl]amino}-5-[(2S,3R)-3-[(dimethylcarbamoyl)amino]-2-methylpiperidin-1-yl]pyrazine-2-carboxamide;

3-({4-[4-methyl-1-(propan-2-yl)piperidin-4-yl]phenyl}amino)-5-[(3R)-3-(3-methyl-2-oxoimidazolidin-1-yl)piperidin-1-yl]pyrazine-2-carboxamide;

3-{[4-(1-cyclopropyl-4-methylpiperidin-4-yl)phenyl]amino}-5-[(3R)-3-(3-methyl-2-oxoimidazolidin-1-yl)piperidin-1-yl]pyrazine-2-carboxamide;

3-({4-[4-methyl-1-(oxetan-3-yl)piperidin-4-yl]phenyl}amino)-5-[(3R)-3-(3-methyl-2-oxoimidazolidin-1-yl)piperidin-1-yl]pyrazine-2-carboxamide;

3-{[4-(1-cyclobutyl-4-methylpiperidin-4-yl)phenyl]amino}-5-[(3R)-3-(3-methyl-2-oxoimidazolidin-1-yl)piperidin-1-yl]pyrazine-2-carboxamide;

3-{[4-(1-cyclopentyl-4-methylpiperidin-4-yl)phenyl]amino}-5-[(3R)-3-(3-methyl-2-oxoimidazolidin-1-yl)piperidin-1-yl]pyrazine-2-carboxamide;

3-{[4-(1-formyl-4-methylpiperidin-4-yl)phenyl]amino}-5-[(3R)-3-(3-methyl-2-oxoimidazolidin-1-yl)piperidin-1-yl]pyrazine-2-carboxamide;

3-{[4-(4-methyl-1-propanoylpiperidin-4-yl)phenyl]amino}-5-[(3R)-3-(3-methyl-2-oxoimidazolidin-1-yl)piperidin-1-yl]pyrazine-2-carboxamide;

3-{[4-(1-cyclopropanecarbonyl-4-methylpiperidin-4-yl)phenyl]amino}-5-[(3R)-3-(3-methyl-2-oxoimidazolidin-1-yl)piperidin-1-yl]pyrazine-2-carboxamide;

3-{[4-(1-cyclopentylpiperidin-4-yl)phenyl]amino}-5-[(3R)-3-[(dimethylsulfamoyl)amino]piperidin-1-yl]pyrazine-2-carboxamide;

5-[(3R)-3-[(dimethylcarbamoyl)amino]piperidin-1-yl]-3-({4-[1-(dimethylsulfamoyl)piperidin-4-yl]phenyl}amino)pyrazine-2-carboxamide;

5-[(2R,3R)-3-amino-2-methylpiperidin-1-yl]-3-{[4-(1-cyclopentylpiperidin-4-yl)phenyl]amino}pyrazine-2-carboxamide;

5-[(2S,3R)-3-amino-2-methylpiperidin-1-yl]-3-{[4-(1-cyclopentylpiperidin-4-yl)phenyl]amino}pyrazine-2-carboxamide;

5-[(3R)-3-aminopiperidin-1-yl]-3-{[4-(1-cyclopropylpiperidin-4-yl)phenyl]amino}pyrazine-2-carboxamide;

3-[(4-cyclohexylphenyl)amino]-5-[(3R)-3-[(dimethylcarbamoyl)amino]piperidin-1-yl]pyrazine-2-carboxamide;

3-{[4-(1-cyanocyclopentyl)phenyl]amino}-5-[(3R)-3-[(dimethylcarbamoyl)amino]piperidin-1-yl]pyrazine-2-carboxamide;

3-{[4-(1-cyclopropylpiperidin-4-yl)phenyl]amino}-5-[(3R)-3-{spiro[3.3]heptane-2-amido}piperidin-1-yl]pyrazine-2-carboxamide;

3-{[4-(1-cyclopropylpiperidin-4-yl)phenyl]amino}-5-[(3R)-3-(4-phenylbenzamido)piperidin-1-yl]pyrazine-2-carboxamide;

3-{[4-(1-cyclopropylpiperidin-4-yl)phenyl]amino}-5-[(3R)-3-(6-phenylpyridine-3-amido)piperidin-1-yl]pyrazine-2-carboxamide;

5-[(2R,3R)-3-benzamido-2-methylpiperidin-1-yl]-3-{[4-(1-cyclopentylpiperidin-4-yl)phenyl]amino}pyrazine-2-carboxamide;

5-[(2S,3R)-3-benzamido-2-methylpiperidin-1-yl]-3-{[4-(1-cyclopentylpiperidin-4-yl)phenyl]amino}pyrazine-2-carboxamide;

5-[(3R)-3-(1-benzothiophene-2-amido)piperidin-1-yl]-3-{[4-(1-cyclopropylpiperidin-4-yl)phenyl]amino}pyrazine-2-carboxamide;

5-[(3R)-3-(3-chlorobenzamido)piperidin-1-yl]-3-{[4-(1-cyclopropylpiperidin-4-yl)phenyl]amino}pyrazine-2-carboxamide;

5-[(3R)-3-(4-chlorobenzamido)piperidin-1-yl]-3-{[4-(1-cyclopropylpiperidin-4-yl)phenyl]amino}pyrazine-2-carboxamide;

5-[(3R)-3-(5-chlorothiophene-2-amido)piperidin-1-yl]-3-{[4-(1-cyclopropylpiperidin-4-yl)phenyl]amino}pyrazine-2-carboxamide;

5-[(3R)-3-cyclopentaneamidopiperidin-1-yl]-3-{[4-(1-cyclopropylpiperidin-4-yl)phenyl]amino}pyrazine-2-carboxamide;

3-{[4-(1-cyclopropylpiperidin-4-yl)phenyl]amino}-5-[(3R)-3-(4,5,6,7-tetrahydro-1-benzothiophene-2-amido)piperidin-1-yl]pyrazine-2-carboxamide;

5-[(3R)-3-(5-chloropyridine-3-amido)piperidin-1-yl]-3-{[4-(1-cyclopropylpiperidin-4-yl)phenyl]amino}pyrazine-2-carboxamide;

3-{[4-(1-cyclopropylpiperidin-4-yl)phenyl]amino}-5-[(3R)-3-(naphthalene-2-amido)piperidin-1-yl]pyrazine-2-carboxamide;

3-{[4-(1-cyclopropylpiperidin-4-yl)phenyl]amino}-5-[(2R,3R)-3-[(dimethylcarbamoyl)amino]-2-methylpiperidin-1-yl]pyrazine-2-carboxamide;

3-{[4-(1-cyclobutyl-4-methylpiperidin-4-yl)phenyl]amino}-5-[(2R,3R)-3-[(dimethylcarbamoyl)amino]-2-methylpiperidin-1-yl]pyrazine-2-carboxamide;

3-{[4-(1-cyclopentyl-4-methylpiperidin-4-yl)phenyl]amino}-5-[(2R,3R)-3-[(dimethylcarbamoyl)amino]-2-methylpiperidin-1-yl]pyrazine-2-carboxamide;

3-{[4-(1-cyano-1-methylethyl)phenyl]amino}-5-[(3R)-3-[(dimethylcarbamoyl)amino]piperidin-1-yl]pyrazine-2-carboxamide;

3-{[4-(1-carbamoyl-1-methylethyl)phenyl]amino}-5-[(3R)-3-[(dimethylcarbamoyl)amino]piperidin-1-yl]pyrazine-2-carboxamide;

3-{[4-(1-cyanocyclopentyl)phenyl]amino}-5-[(2R,3R)-3-[(dimethylcarbamoyl)amino]-2-methylpiperidin-1-yl]pyrazine-2-carboxamide;

3-{[4-(1-carbamoylcyclopentyl)phenyl]amino}-5-[(2R,3R)-3-[(dimethylcarbamoyl)amino]-2-methylpiperidin-1-yl]pyrazine-2-carboxamide;

3-{[4-(4-cyano-1-cyclopentylpiperidin-4-yl)phenyl]amino}-5-[(3R)-3-(3-methyl-2-oxoimidazolidin-1-yl)piperidin-1-yl]pyrazine-2-carboxamide;

3-{[4-(4-carbamoyl-1-cyclopentylpiperidin-4-yl)phenyl]amino}-5-[(3R)-3-(3-methyl-2-oxoimidazolidin-1-yl)piperidin-1-yl]pyrazine-2-carboxamide;

5-[(3aR,7aR)-1-(dimethylcarbamoyl)-octahydro-1H-pyrrolo[3,2-b]pyridin-4-yl]-3-{[4-(1-cyclopentylpiperidin-4-yl)phenyl]amino}pyrazine-2-carboxamide;

5-[(3aR,7aR)-1-cyclopropanecarbonyl-octahydro-1H-pyrrolo[3,2-b]pyridin-4-yl]-3-{[4-(1-cyclopentylpiperidin-4-yl)phenyl]amino}pyrazine-2-carboxamide;

3-{[4-(1-cyanocyclopropyl)phenyl]amino}-5-[(3R)-3-[(dimethylcarbamoyl)amino]piperidin-1-yl]pyrazine-2-carboxamide;

3-{[4-(1-carbamoylcyclopropyl)phenyl]amino}-5-[(3R)-3-[(dimethylcarbamoyl)amino]piperidin-1-yl]pyrazine-2-carboxamide;

3-{[4-(4-cyano-1-cyclobutylpiperidin-4-yl)phenyl]amino}-5-[(3R)-3-(3-methyl-2-oxoimidazolidin-1-yl)piperidin-1-yl]pyrazine-2-carboxamide;

5-[(3aR,7aR)-octahydro-1H-pyrrolo[3,2-b]pyridin-4-yl]-3-{[4-(1-cyclopentylpiperidin-4-yl)phenyl]amino}pyrazine-2-carboxamide;

3-{[4-(1-cyclobutylpiperidin-4-yl)phenyl]amino}-5-[(3R)-3-(3-methyl-2-oxoimidazolidin-1-yl)piperidin-1-yl]pyrazine-2-carboxamide;

5-[(3R)-3-[3-(3-chlorophenyl)-2-oxoimidazolidin-1-yl]piperidin-1-yl]-3-{[4-(1-cyclopentylpiperidin-4-yl)phenyl]amino}pyrazine-2-carboxamide;

5-[(2R,3R)-2-methyl-3-(3-methyl-2-oxoimidazolidin-1-yl)piperidin-1-yl]-3-{[4-(4-methylpiperidin-4-yl)phenyl]amino}pyrazine-2-carboxamide;

3-{[4-(1-cyclobutyl-4-methylpiperidin-4-yl)phenyl]amino}-5-[(2R,3R)-2-methyl-3-(3-methyl-2-oxoimidazolidin-1-yl)piperidin-1-yl]pyrazine-2-carboxamide;

3-{[4-(1-cyclopentyl-4-methylpiperidin-4-yl)phenyl]amino}-5-[(2R,3R)-2-methyl-3-(3-methyl-2-oxoimidazolidin-1-yl)piperidin-1-yl]pyrazine-2-carboxamide;

5-[(3R)-3-(3-methyl-2-oxoimidazolidin-1-yl)piperidin-1-yl]-3-(phenylamino)pyrazine-2-carboxamide;

5-[(3R)-3-(3-methyl-2-oxoimidazolidin-1-yl)piperidin-1-yl]-3-({4-[1-(trifluoromethyl)cyclopropyl]phenyl}amino)pyrazine-2-carboxamide;

5-[(3aR,7aR)-octahydro-1H-pyrrolo[2,3-c]pyridin-6-yl]-3-{[4-(1-cyclopentylpiperidin-4-yl)phenyl]amino}pyrazine-2-carboxamide;

3-{[4-(1-cyclopentylpiperidin-4-yl)phenyl]amino}-5-[(3R)-3-(3-methyl-2-oxo-1,3-diazinan-1-yl)piperidin-1-yl]pyrazine-2-carboxamide;

3-{[4-(1-cyclopropyl-4-methylpiperidin-4-yl)phenyl]amino}-5-[(2R,3R)-3-[(dimethylcarbamoyl)amino]-2-methylpiperidin-1-yl]pyrazine-2-carboxamide;

3-{[4-(1-cyclopentylpiperidin-4-yl)phenyl]amino}-5-[(3R,4R)-3-[(dimethylcarbamoyl)amino]-4-methylpiperidin-1-yl]pyrazine-2-carboxamide;

5-[(3aS,7aR)-1-(dimethylcarbamoyl)-octahydro-1H-pyrrolo[2,3-c]pyridin-6-yl]-3-{[4-(1-cyclopentylpiperidin-4-yl)phenyl]amino}pyrazine-2-carboxamide;

5-[(3aS,7aR)-1-cyclopropanecarbonyl-octahydro-1H-pyrrolo[2,3-c]pyridin-6-yl]-3-{[4-(1-cyclopentylpiperidin-4-yl)phenyl]amino}pyrazine-2-carboxamide;

3-{[4-(1-cyclobutylpiperidin-4-yl)phenyl]amino}-5-[(2R,3R)-3-[(dimethylcarbamoyl)amino]-2-methylpiperidin-1-yl]pyrazine-2-carboxamide;

3-{[4-(4-methyl-1-propanoylpiperidin-4-yl)phenyl]amino}-5-[(2R,3R)-2-methyl-3-(3-methyl-2-oxoimidazolidin-1-yl)piperidin-1-yl]pyrazine-2-carboxamide;

3-{[4-(1-cyclopentylpiperidin-4-yl)phenyl]amino}-5-[(3R)-3-(2-oxoimidazolidin-1-yl)piperidin-1-yl]pyrazine-2-carboxamide;

3-{[4-(1-cyclopentylpiperidin-4-yl)phenyl]amino}-5-[(3R)-3-(3-cyclopropyl-2-oxoimidazolidin-1-yl)piperidin-1-yl]pyrazine-2-carboxamide;

5-[(3R)-3-(3-cyclopropyl-2-oxoimidazolidin-1-yl)piperidin-1-yl]-3-{[4-(1-cyclopropyl-4-methylpiperidin-4-yl)phenyl]amino}pyrazine-2-carboxamide;

3-{[4-(1-cyclobutylpiperidin-4-yl)phenyl]amino}-5-[(3R)-3-(3-cyclopropyl-2-oxoimidazolidin-1-yl)piperidin-1-yl]pyrazine-2-carboxamide;

3-{[4-(4-cyano-1-cyclopentylpiperidin-4-yl)phenyl]amino}-5-[(2R,3R)-3-[(dimethylcarbamoyl)amino]-2-methylpiperidin-1-yl]pyrazine-2-carboxamide;

3-{[4-(4-carbamoyl-1-cyclopentylpiperidin-4-yl)phenyl]amino}-5-[(2R,3R)-3-[(dimethylcarbamoyl)amino]-2-methylpiperidin-1-yl]pyrazine-2-carboxamide;

5-[(2R,3R)-3-[(dimethylcarbamoyl)amino]-2-methylpiperidin-1-yl]-3-({4-[1-(trifluoromethyl)cyclopropyl]phenyl}amino)pyrazine-2-carboxamide;

3-{[4-(1-cyanocyclopropyl)phenyl]amino}-5-[(2R,3R)-3-[(dimethylcarbamoyl)amino]-2-methylpiperidin-1-yl]pyrazine-2-carboxamide;

3-{[4-(1-carbamoylcyclopropyl)phenyl]amino}-5-[(2R,3R)-3-[(dimethylcarbamoyl)amino]-2-methylpiperidin-1-yl]pyrazine-2-carboxamide;

3-({4-[1-(aminomethyl)cyclopentyl]phenyl}amino)-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-({4-[1-(dimethylcarbamoyl)cyclopropyl]phenyl}amino)pyrazine-2-carboxamide;

5-[(3R)-3-({[3-chloro-5-(trifluoromethyl)phenyl](methyl)carbamoyl}amino)piperidin-1-yl]-3-[(4-fluorophenyl)amino]pyrazine-2-carboxamide;

5-[(3R)-3-({[3-chloro-5-(trifluoromethyl)phenyl](methyl)carbamoyl}amino)piperidin-1-yl]-3-{[4-(1-cyanocyclopropyl)phenyl]amino}pyrazine-2-carboxamide;

3-{[4-(1-carbamoylcyclopropyl)phenyl]amino}-5-[(3R)-3-({[3-chloro-5-(trifluoromethyl)phenyl](methyl)carbamoyl}amino)piperidin-1-yl]pyrazine-2-carboxamide;

3-{[4-(1-cyclopropylpiperidin-4-yl)phenyl]amino}-5-[(3R)-3-(3-methyl-2-oxo-1,3-diazinan-1-yl)piperidin-1-yl]pyrazine-2-carboxamide;

3-{[4-(1-cyclopropyl-4-methylpiperidin-4-yl)phenyl]amino}-5-[(3R)-3-(3-methyl-2-oxo-1,3-diazinan-1-yl)piperidin-1-yl]pyrazine-2-carboxamide;

3-[(1-cyclopropyl-1H-pyrazol-4-yl)amino]-5-[(3R)-3-[(dimethylcarbamoyl)amino]piperidin-1-yl]pyrazine-2-carboxamide;

3-[(1-cyclopentyl-1H-pyrazol-4-yl)amino]-5-[(3R)-3-[(dimethylcarbamoyl)amino]piperidin-1-yl]pyrazine-2-carboxamide;

3-{[4-(1-cyclopentyl-4-methylpiperidin-4-yl)phenyl]amino}-5-[(3R)-3-(3-methyl-2-oxo-1,3-diazinan-1-yl)piperidin-1-yl]pyrazine-2-carboxamide;

3-{[4-(1-cyclopropyl-4-methylpiperidin-4-yl)phenyl]amino}-5-[(3R)-3-(3-ethyl-2-oxoimidazolidin-1-yl)piperidin-1-yl]pyrazine-2-carboxamide;

3-{[4-(1-cyclopentylpiperidin-4-yl)phenyl]amino}-5-[(2R,3R)-2-methyl-3-(3-methyl-2-oxo-1,3-diazinan-1-yl)piperidin-1-yl]pyrazine-2-carboxamide;

3-({4-[1-(aminomethyl)cyclopropyl]phenyl}amino)-5-[(3R)-3-[(dimethylcarbamoyl)amino]piperidin-1-yl]pyrazine-2-carboxamide;

3-({4-[(dimethylamino)methyl]phenyl}amino)-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-[(1-methyl-2-oxo-1,2-dihydropyridin-4-yl)amino]pyrazine-2-carboxamide;

3-{[4-(1-cyclopentylpiperidin-4-yl)phenyl]amino}-5-[(3R)-3-[(dimethylcarbamoyl)amino]azepan-1-yl]pyrazine-2-carboxamide;

3-{[4-(1-cyclopentylpiperidin-4-yl)phenyl]amino}-5-[(3R)-3-cyclopropaneamidoazepan-1-yl]pyrazine-2-carboxamide;

3-{[1-(1-cyclopentylazetidin-3-yl)-1H-pyrazol-4-yl]amino}-5-[(3R)-3-[(dimethylcarbamoyl)amino]piperidin-1-yl]pyrazine-2-carboxamide;

3-{[1-(1-cyclopentylpiperidin-4-yl)-1H-pyrazol-4-yl]amino}-5-[(3R)-3-[(dimethylcarbamoyl)amino]piperidin-1-yl]pyrazine-2-carboxamide;

3-{[1-(1-cyclopropanecarbonylpiperidin-4-yl)-1H-pyrazol-4-yl]amino}-5-[(3R)-3-[(dimethylcarbamoyl)amino]piperidin-1-yl]pyrazine-2-carboxamide;

(4aR,8aR)-5-(5-carbamoyl-6-{[4-(1-cyclopentylpiperidin-4-yl)phenyl]amino}pyrazin-2-yl)-N,N-dimethyl-decahydro-1,5-naphthyridine-1-carboxamide;

5-[(3R)-3-[(dimethylcarbamoyl)amino]piperidin-1-yl]-3-[(3-methyl-1,2-thiazol-5-yl)amino]pyrazine-2-carboxamide;

5-[(3R)-3-[(dimethylcarbamoyl)amino]piperidin-1-yl]-3-[(1-methyl-6-oxo-1,6-dihydropyridin-3-yl)amino]pyrazine-2-carboxamide;

5-[(3R)-3-[(dimethylcarbamoyl)amino]piperidin-1-yl]-3-{[4-(propan-2-yloxy)phenyl]amino}pyrazine-2-carboxamide;

5-[(3R)-3-[(dimethylcarbamoyl)amino]piperidin-1-yl]-3-{[4-(2-methoxyethoxy)phenyl]amino}pyrazine-2-carboxamide;

3-({4-[2-(dimethylamino)ethoxy]phenyl}amino)-5-[(3R)-3-[(dimethylcarbamoyl)amino]piperidin-1-yl]pyrazine-2-carboxamide;

5-[(3R)-3-[(dimethylcarbamoyl)amino]piperidin-1-yl]-3-[(4-nitrophenyl)amino]pyrazine-2-carboxamide;

3-{[4-(1-cyclobutylpiperidin-4-yl)phenyl]amino}-5-[(2R,3R)-3-[(dimethylcarbamoyl)amino]-2-ethylpiperidin-1-yl]pyrazine-2-carboxamide;

3-{[4-(cyclopentyloxy)phenyl]amino}-5-[(3R)-3-[(dimethylcarbamoyl)amino]piperidin-1-yl]pyrazine-2-carboxamide;

5-[(2R,3R)-3-[(dimethylcarbamoyl)amino]-2-methylpiperidin-1-yl]-3-[(3-methyl-1,2-thiazol-5-yl)amino]pyrazine-2-carboxamide;

5-[(2R,3R)-3-[(dimethylcarbamoyl)amino]-2-methylpiperidin-1-yl]-3-{[4-(propan-2-yloxy)phenyl]amino}pyrazine-2-carboxamide;

5-[(2R,3R)-3-[(dimethylcarbamoyl)amino]-2-methylpiperidin-1-yl]-3-[(4-methanesulfonylphenyl)amino]pyrazine-2-carboxamide;

3-(4-(2-methoxyethoxy)phenylamino)-5-((R)-3-(3-((S)-1-phenylethyl)ureido)piperidin-1-yl)pyrazine-2-carboxamide;

3-(4-(2-methoxyethoxy)phenylamino)-5-((R)-3-(3-((R)-1-phenylethyl)ureido)piperidin-1-yl)pyrazine-2-carboxamide;

(R)-3-(4-(1-cyclopentylpiperidin-4-yl)phenylamino)-5-(3-(cyclopropanecarboxamido)-2-methylpiperidin-1-yl)pyrazine-2-carboxamide;

(R)-3-(cyclopropylamino)-5-(3-(3-methyl-3-phenylureido)piperidin-1-yl)pyrazine-2-carboxamide;

(R)-3-(cyclopentylamino)-5-(3-(3-methyl-3-phenylureido)piperidin-1-yl)pyrazine-2-carboxamide;

(R)-5-(3-(3-(3-chloro-5-(trifluoromethyl)phenyl)-3-methylureido)piperidin-1-yl)-3-(cyclopropylamino)pyrazine-2-carboxamide;

(R)-5-(3-(3-(3-chloro-5-(trifluoromethyl)phenyl)-3-methylureido)piperidin-1-yl)-3-(tetrahydro-2H-pyran-4-ylamino)pyrazine-2-carboxamide; and (R)-5-(3-(3-(tetrahydro-2H-pyran-4-yl)ureido)piperidin-1-yl)-3-(tetrahydro-2H-pyran-4-ylamino)pyrazine-2-carboxamide;

or a pharmaceutically acceptable solvate or pharmaceutically acceptable salt thereof.

18. A pharmaceutical composition comprising a therapeutically effective amount of a compound of claim 1, and a pharmaceutically acceptable excipient.

19. The compound of claim 1, wherein $R_1$ is —C(O)$R_4$, —C(O)N($R_3$)($R_4$), or —S(O)$_2R_4$.

20. The compound of claim 2, wherein $R_1$ is —C(O)$R_4$ or —C(O)N($R_3$)($R_4$).

* * * * *